US012239711B2

(12) United States Patent
Crew et al.

(10) Patent No.: US 12,239,711 B2
(45) Date of Patent: Mar. 4, 2025

(54) CEREBLON LIGANDS AND BIFUNCTIONAL COMPOUNDS COMPRISING THE SAME

(71) Applicant: Arvinas Operations, Inc., New Haven, CT (US)

(72) Inventors: Andrew P. Crew, Chester, CT (US); Craig M. Crews, New Haven, CT (US); Hanqing Dong, Madison, CT (US); Keith R. Hornberger, Southbury, CT (US); Yimin Qian, Plainsboro, NJ (US); Lawrence B. Snyder, Killingworth, CT (US); Jing Wang, Milford, CT (US)

(73) Assignee: Arvinas Operations, Inc., New Haven, CT (US)

( * ) Notice: Subject to any disclaimer, the term of this patent is extended or adjusted under 35 U.S.C. 154(b) by 0 days.

(21) Appl. No.: 17/571,018

(22) Filed: Jan. 7, 2022

(65) Prior Publication Data

US 2023/0082997 A1 Mar. 16, 2023

Related U.S. Application Data

(63) Continuation of application No. 15/953,108, filed on Apr. 13, 2018, now abandoned, which is a continuation-in-part of application No. 14/792,414, filed on Jul. 6, 2015, now abandoned, which is a continuation-in-part of application No. 14/686,640, filed on Apr. 14, 2015, now abandoned.

(60) Provisional application No. 62/171,090, filed on Jun. 4, 2015, provisional application No. 61/979,351, filed on Apr. 14, 2014.

(51) Int. Cl.
| | | |
|---|---|---|
| C07D 401/04 | (2006.01) | |
| A61K 31/437 | (2006.01) | |
| A61K 31/496 | (2006.01) | |
| A61K 31/497 | (2006.01) | |
| A61K 31/501 | (2006.01) | |
| A61K 31/506 | (2006.01) | |
| A61K 31/551 | (2006.01) | |
| A61K 45/06 | (2006.01) | |
| A61K 47/54 | (2017.01) | |
| A61K 47/55 | (2017.01) | |
| A61P 35/00 | (2006.01) | |
| C07D 401/14 | (2006.01) | |
| C07D 471/04 | (2006.01) | |

(52) U.S. Cl.
CPC ............ *A61K 47/55* (2017.08); *A61K 31/437* (2013.01); *A61K 31/496* (2013.01); *A61K 31/497* (2013.01); *A61K 31/501* (2013.01); *A61K 31/506* (2013.01); *A61K 31/551* (2013.01); *A61K 45/06* (2013.01); *A61K 47/545* (2017.08); *A61P 35/00* (2018.01); *C07D 401/04* (2013.01); *C07D 401/14* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 4,160,452 | A | 7/1979 | Theeuwes |
| 4,256,108 | A | 3/1981 | Theeuwes |
| 4,265,874 | A | 5/1981 | Bonsen et al. |
| 4,522,811 | A | 6/1985 | Eppstein et al. |
| 5,007,790 | A | 4/1991 | Shell |
| 5,169,645 | A | 12/1992 | Shukla et al. |
| 5,292,638 | A | 3/1994 | Benz et al. |
| 5,492,922 | A | 2/1996 | Palkowitz |
| 5,582,837 | A | 12/1996 | Shell |
| 5,681,835 | A | 10/1997 | Willson |
| 5,681,858 | A | 10/1997 | Stevens et al. |
| 5,877,219 | A | 3/1999 | Willson |
| 5,972,389 | A | 10/1999 | Shell et al. |
| 6,207,716 | B1 | 3/2001 | Willson |
| 6,268,391 | B1 | 7/2001 | Dickerson et al. |

(Continued)

FOREIGN PATENT DOCUMENTS

| | | |
|---|---|---|
| CN | 1844118 A | 10/2006 |
| CN | 102477033 A | 5/2012 |

(Continued)

OTHER PUBLICATIONS

Lai et al (Nat Rev Drug Discov 16(2):101-114, 2017) (Year: 2017).*

(Continued)

*Primary Examiner* — Craig D Ricci
(74) *Attorney, Agent, or Firm* — McCarter & English, LLP; Michael J. DeGrazia; James M. Alburger

(57) ABSTRACT

The description relates to cereblon E3 ligase binding compounds, including bifunctional compounds comprising the same, which find utility as modulators of targeted ubiquitination, especially inhibitors of a variety of polypeptides and other proteins which are degraded and/or otherwise inhibited by bifunctional compounds according to the present disclosure. In particular, the description provides compounds, which contain on one end a ligand which binds to the cereblon E3 ubiquitin ligase and on the other end a moiety which binds a target protein such that the target protein is placed in proximity to the ubiquitin ligase to effect degradation (and inhibition) of that protein. Compounds can be synthesized that exhibit a broad range of pharmacological activities consistent with the degradation/inhibition of targeted polypeptides of nearly any type.

1 Claim, 1 Drawing Sheet

(56) References Cited

U.S. PATENT DOCUMENTS

| | | |
|---|---|---|
| 6,303,618 B1 | 10/2001 | Griffin et al. |
| 6,306,663 B1 | 10/2001 | Kenten et al. |
| 6,316,003 B1 | 11/2001 | Frankel et al. |
| 6,323,219 B1 | 11/2001 | Costanzo |
| 6,340,475 B2 | 1/2002 | Shell et al. |
| 6,451,808 B1 | 9/2002 | Cowles |
| 6,488,962 B1 | 12/2002 | Berner et al. |
| 6,559,280 B2 | 5/2003 | Kenten et al. |
| 6,670,348 B1 | 12/2003 | Rosen et al. |
| 7,041,298 B2 | 5/2006 | Deshaies et al. |
| 7,074,620 B2 | 7/2006 | Kenten et al. |
| 7,132,438 B2 | 11/2006 | Frenkel et al. |
| 7,208,157 B2 | 4/2007 | Dashaies et al. |
| 7,244,851 B2 | 7/2007 | Cohen et al. |
| 7,273,920 B2 | 9/2007 | Kenten et al. |
| 7,294,748 B2 | 11/2007 | Poole et al. |
| 7,345,081 B2 | 3/2008 | Cohen et al. |
| 7,390,784 B2 | 6/2008 | Briesewitz et al. |
| 7,419,975 B2 | 9/2008 | Palermo et al. |
| 7,517,906 B2 | 4/2009 | Condon et al. |
| 7,683,160 B2 | 3/2010 | Eckhardt et al. |
| 7,915,293 B2 | 3/2011 | Ramesh et al. |
| 8,106,191 B2 | 1/2012 | Holt et al. |
| 8,716,315 B2 | 5/2014 | Figg et al. |
| 9,500,653 B2 | 11/2016 | Crews et al. |
| 9,632,089 B2 | 4/2017 | Crews et al. |
| 9,694,084 B2 | 7/2017 | Bradner et al. |
| 9,750,816 B2 | 9/2017 | Bradner et al. |
| 9,770,512 B2 | 9/2017 | Bradner et al. |
| 9,821,068 B2 | 11/2017 | Bradner et al. |
| 9,938,264 B2 | 4/2018 | Crews et al. |
| 10,584,101 B2 | 3/2020 | Crew et al. |
| 10,604,506 B2 | 3/2020 | Crew et al. |
| 10,647,698 B2 | 5/2020 | Crew et al. |
| 10,723,717 B2 | 7/2020 | Crew et al. |
| 10,730,870 B2 | 8/2020 | Crew et al. |
| 10,844,021 B2 | 11/2020 | Crew et al. |
| 10,899,742 B1 | 1/2021 | Crew et al. |
| 11,065,231 B2 | 7/2021 | Crew et al. |
| 11,173,211 B2 | 11/2021 | Crew et al. |
| 11,236,051 B2 | 2/2022 | Crew et al. |
| 11,597,720 B2 | 3/2023 | Qian et al. |
| 11,952,347 B2 | 4/2024 | Crew et al. |
| 11,964,945 B2 | 4/2024 | Crew et al. |
| 12,043,612 B2 | 7/2024 | Allan et al. |
| 2002/0051820 A1 | 5/2002 | Shell et al. |
| 2003/0039688 A1 | 2/2003 | Shell et al. |
| 2003/0044466 A1 | 3/2003 | Markey et al. |
| 2003/0104053 A1 | 6/2003 | Gusler et al. |
| 2003/0104062 A1 | 6/2003 | Berner et al. |
| 2003/0133927 A1 | 7/2003 | DeFeo-Jones et al. |
| 2003/0147952 A1 | 8/2003 | Lim et al. |
| 2004/0053324 A1 | 3/2004 | Wong et al. |
| 2004/0114258 A1 | 6/2004 | Harris, III et al. |
| 2004/0163138 A1 | 8/2004 | Reed et al. |
| 2005/0019813 A1 | 1/2005 | Conaway et al. |
| 2005/0215550 A1 | 9/2005 | Tang et al. |
| 2006/0128632 A1 | 6/2006 | Sharma et al. |
| 2006/0149073 A1 | 7/2006 | Tanaka et al. |
| 2006/0258719 A1 | 11/2006 | Combs et al. |
| 2007/0099844 A1 | 5/2007 | Prendergast et al. |
| 2007/0099954 A1 | 5/2007 | Gomtsyan et al. |
| 2007/0105907 A1 | 5/2007 | Prendergast et al. |
| 2007/0149572 A1 | 6/2007 | Ballentine et al. |
| 2007/0173524 A1 | 7/2007 | Prendergast et al. |
| 2007/0254933 A1 | 11/2007 | Jung et al. |
| 2007/0281907 A1 | 12/2007 | Watkins |
| 2008/0051432 A1 | 2/2008 | Zhang |
| 2008/0108564 A1 | 5/2008 | Holmes et al. |
| 2008/0153837 A1 | 6/2008 | Mailliet et al. |
| 2008/0214501 A1 | 9/2008 | Pan et al. |
| 2008/0219929 A1 | 9/2008 | Wischik et al. |
| 2008/0269140 A1 | 10/2008 | Wang et al. |
| 2009/0035362 A1 | 2/2009 | Shih et al. |
| 2009/0054358 A1 | 2/2009 | Small et al. |
| 2009/0298843 A1 | 12/2009 | Kloog et al. |
| 2010/0048517 A1 | 2/2010 | Hu et al. |
| 2010/0056524 A1 | 3/2010 | McIver et al. |
| 2010/0076066 A1 | 3/2010 | Prendergast et al. |
| 2010/0113549 A1 | 5/2010 | Block et al. |
| 2010/0203012 A1 | 8/2010 | Laurent et al. |
| 2010/0286127 A1 | 11/2010 | Miyoshi et al. |
| 2011/0195043 A1 | 8/2011 | Sun et al. |
| 2011/0269793 A1 | 11/2011 | Maccioni |
| 2012/0270800 A1 | 10/2012 | Verdine et al. |
| 2013/0274259 A1 | 10/2013 | Zhang et al. |
| 2014/0066625 A1 | 3/2014 | Mautino et al. |
| 2014/0088143 A1 | 3/2014 | Jain |
| 2014/0161720 A1 | 6/2014 | Garkavtsev et al. |
| 2014/0194404 A1 | 7/2014 | McElroy et al. |
| 2014/0235629 A1 | 8/2014 | Bartberger et al. |
| 2014/0243372 A1 | 8/2014 | Rew |
| 2014/0256700 A1 | 9/2014 | Poss et al. |
| 2014/0296243 A1 | 10/2014 | Albrecht et al. |
| 2014/0302523 A1 | 10/2014 | Crews et al. |
| 2014/0329799 A1 | 11/2014 | Seganish et al. |
| 2014/0329800 A1 | 11/2014 | Gao et al. |
| 2014/0356322 A1 | 12/2014 | Crews et al. |
| 2014/0371206 A1 | 12/2014 | Albrecht et al. |
| 2015/0011532 A1 | 1/2015 | Paidi et al. |
| 2015/0045339 A1 | 2/2015 | Takasaki et al. |
| 2015/0045347 A1 | 2/2015 | Dodd et al. |
| 2015/0119421 A1 | 4/2015 | Jain |
| 2015/0119435 A1 | 4/2015 | Crews et al. |
| 2015/0133451 A1 | 5/2015 | Yoshida et al. |
| 2015/0133674 A1 | 5/2015 | Tao et al. |
| 2015/0141402 A1 | 5/2015 | Behenna et al. |
| 2015/0141470 A1 | 5/2015 | Garraway et al. |
| 2015/0148342 A1 | 5/2015 | Yue et al. |
| 2015/0191464 A1 | 7/2015 | Santella et al. |
| 2015/0218126 A1 | 8/2015 | Gore et al. |
| 2015/0256700 A1 | 9/2015 | Sakai |
| 2015/0259288 A1 | 9/2015 | Nam et al. |
| 2015/0274708 A1 | 10/2015 | Seganish et al. |
| 2015/0284405 A1 | 10/2015 | Trzupek et al. |
| 2015/0291562 A1* | 10/2015 | Crew ............... A61P 35/02 435/375 |
| 2015/0329525 A1 | 11/2015 | Crosignani et al. |
| 2015/0344473 A1 | 12/2015 | Du et al. |
| 2015/0352206 A1 | 12/2015 | Gajewski et al. |
| 2016/0002265 A1 | 1/2016 | Jenkins et al. |
| 2016/0022619 A1 | 1/2016 | Balog et al. |
| 2016/0022642 A1 | 1/2016 | Crews et al. |
| 2016/0045627 A1 | 2/2016 | Crew et al. |
| 2016/0058872 A1 | 3/2016 | Crew et al. |
| 2016/0075711 A1 | 3/2016 | Sherer |
| 2016/0083375 A1 | 3/2016 | Paidi et al. |
| 2016/0136230 A1 | 5/2016 | Campos et al. |
| 2016/0137595 A1 | 5/2016 | Markwalder et al. |
| 2016/0137652 A1 | 5/2016 | Beck et al. |
| 2016/0137653 A1 | 5/2016 | Beck et al. |
| 2016/0143870 A1 | 5/2016 | Markwalder et al. |
| 2016/0168152 A1 | 6/2016 | Li et al. |
| 2016/0176864 A1 | 6/2016 | Norris et al. |
| 2016/0176916 A1 | 6/2016 | Bradner et al. |
| 2016/0200674 A1 | 7/2016 | Markwalder et al. |
| 2016/0214972 A1 | 7/2016 | Jin et al. |
| 2016/0235730 A1 | 8/2016 | Bradner et al. |
| 2016/0235731 A1 | 8/2016 | Bradner et al. |
| 2016/0243247 A1 | 8/2016 | Bradner et al. |
| 2016/0272639 A1 | 9/2016 | Crew et al. |
| 2016/0297822 A1 | 10/2016 | Yang et al. |
| 2016/0303109 A1 | 10/2016 | Jain |
| 2016/0326151 A1 | 11/2016 | Gummadi et al. |
| 2016/0333009 A1 | 11/2016 | Bartlett et al. |
| 2016/0368911 A1 | 12/2016 | Campos et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0204093 A1 | 7/2017 | Chan et al. |
| 2017/0209446 A1 | 7/2017 | Altman et al. |
| 2017/0217981 A1 | 8/2017 | Altman et al. |
| 2017/0247388 A1 | 8/2017 | Altman et al. |

(56) References Cited

U.S. PATENT DOCUMENTS

| | | |
|---|---|---|
| 2017/0275297 A1 | 9/2017 | Altman et al. |
| 2017/0281784 A1 | 10/2017 | Wang et al. |
| 2017/0307614 A1 | 10/2017 | Crews et al. |
| 2017/0327469 A1 | 11/2017 | Crew et al. |
| 2018/0015087 A1 | 1/2018 | Liu et al. |
| 2018/0072711 A1 | 3/2018 | Crew et al. |
| 2018/0099940 A1 | 4/2018 | Crew et al. |
| 2018/0125821 A1 | 5/2018 | Crew et al. |
| 2018/0147202 A1 | 5/2018 | Crew et al. |
| 2018/0155322 A1 | 6/2018 | Crew et al. |
| 2018/0177750 A1 | 6/2018 | Crew et al. |
| 2018/0179183 A1 | 6/2018 | Crew et al. |
| 2018/0186785 A1 | 7/2018 | Crews et al. |
| 2018/0193470 A1 | 7/2018 | Crew et al. |
| 2018/0215731 A1 | 8/2018 | Crew et al. |
| 2018/0228907 A1 | 8/2018 | Crew et al. |
| 2018/0237418 A1 | 8/2018 | Crew et al. |
| 2018/0256586 A1 | 9/2018 | Crew et al. |
| 2018/0346461 A1 | 12/2018 | Crew et al. |
| 2018/0353501 A1 | 12/2018 | Crew et al. |
| 2019/0151295 A1 | 5/2019 | Crew et al. |
| 2019/0192514 A1 | 6/2019 | Crew et al. |
| 2019/0233433 A1 | 8/2019 | Crews et al. |
| 2019/0276459 A1 | 9/2019 | Crews et al. |
| 2019/0315732 A1 | 10/2019 | Crew et al. |
| 2020/0038513 A1 | 2/2020 | Crews et al. |
| 2020/0085793 A1 | 3/2020 | Crew et al. |
| 2020/0121684 A1 | 4/2020 | Crews et al. |
| 2020/0129627 A1 | 4/2020 | Crew et al. |
| 2020/0155689 A1 | 5/2020 | Crew et al. |
| 2020/0155690 A1 | 5/2020 | Crew et al. |
| 2020/0297725 A1 | 9/2020 | Crews et al. |
| 2020/0325130 A1 | 10/2020 | Crews et al. |
| 2021/0040044 A1 | 2/2021 | Crew et al. |
| 2021/0060008 A1 | 3/2021 | Chen et al. |
| 2021/0113557 A1 | 4/2021 | Crew et al. |
| 2021/0139458 A1 | 5/2021 | Crew et al. |
| 2021/0171470 A1 | 6/2021 | Crew et al. |
| 2021/0315856 A1 | 10/2021 | Crew et al. |
| 2021/0353621 A1 | 11/2021 | Peck et al. |
| 2022/0089570 A1 | 3/2022 | Crew et al. |
| 2022/0184078 A1 | 6/2022 | Chirnomas et al. |
| 2023/0128132 A1 | 4/2023 | Crew et al. |
| 2023/0331681 A1 | 10/2023 | Berlin et al. |
| 2024/0066032 A1 | 2/2024 | Chirnomas |

FOREIGN PATENT DOCUMENTS

| | | |
|---|---|---|
| CN | 103159736 A | 6/2013 |
| CN | 103688176 A | 3/2014 |
| CN | 110741004 A | 1/2020 |
| EP | 0805147 A1 | 11/1997 |
| EP | 2985285 A1 | 2/2016 |
| EP | 3634960 A1 | 4/2020 |
| EP | 3652329 A1 | 5/2020 |
| EP | 3672949 A1 | 7/2020 |
| EP | 3689868 A1 | 8/2020 |
| JP | 2004523561 A | 8/2004 |
| JP | 2004525889 A | 8/2004 |
| JP | 2010502627 A | 1/2010 |
| JP | 2012532929 A | 12/2012 |
| JP | 2013528206 A | 7/2013 |
| KR | 20050059180 A | 6/2005 |
| RU | 2008112221 A | 10/2009 |
| RU | 2418800 C2 | 5/2011 |
| RU | 2448101 C2 | 4/2012 |
| RU | 2011121567 A | 12/2012 |
| RU | 2012138709 A | 3/2014 |
| WO | WO-9011757 A1 | 10/1990 |
| WO | WO-9318755 A1 | 9/1993 |
| WO | WO-9730034 A1 | 8/1997 |
| WO | WO-9742216 A1 | 11/1997 |
| WO | WO-9747285 A1 | 12/1997 |
| WO | WO-9803502 A1 | 1/1998 |
| WO | WO-9811879 A1 | 3/1998 |
| WO | WO-9818493 A2 | 5/1998 |
| WO | WO-9845287 A1 | 10/1998 |
| WO | WO-9855107 A1 | 12/1998 |
| WO | WO-9902175 A1 | 1/1999 |
| WO | WO-9913077 A2 | 3/1999 |
| WO | WO-9915521 A1 | 4/1999 |
| WO | WO-0022110 A2 | 4/2000 |
| WO | WO-0050445 A1 | 8/2000 |
| WO | WO-0066119 A1 | 11/2000 |
| WO | WO-0128593 A2 | 4/2001 |
| WO | WO-0132217 A2 | 5/2001 |
| WO | WO-0156544 A2 | 8/2001 |
| WO | WO-0175145 A2 | 10/2001 |
| WO | WO-0197783 A1 | 12/2001 |
| WO | WO-0200617 A2 | 1/2002 |
| WO | WO-0222577 A2 | 3/2002 |
| WO | WO-0232416 A2 | 4/2002 |
| WO | WO-02059106 A1 | 8/2002 |
| WO | WO-02066512 A1 | 8/2002 |
| WO | WO-02076986 A1 | 10/2002 |
| WO | WO-02080926 A1 | 10/2002 |
| WO | WO-02096404 A1 | 12/2002 |
| WO | WO-02100845 A1 | 12/2002 |
| WO | WO-03013541 A1 | 2/2003 |
| WO | WO-03035029 A1 | 5/2003 |
| WO | WO-03035039 A1 | 5/2003 |
| WO | WO-03035040 A1 | 5/2003 |
| WO | WO-03035041 A1 | 5/2003 |
| WO | WO-03035177 A2 | 5/2003 |
| WO | WO-03057820 A2 | 7/2003 |
| WO | WO-2004028516 A2 | 4/2004 |
| WO | WO-2004100868 A2 | 11/2004 |
| WO | WO-2005016326 A2 | 2/2005 |
| WO | WO-2005118588 A1 | 12/2005 |
| WO | WO-2006069063 A1 | 6/2006 |
| WO | WO-2006113942 A2 | 10/2006 |
| WO | WO-2007022638 A1 | 3/2007 |
| WO | WO-2007101347 A1 | 9/2007 |
| WO | WO-2007106670 A2 | 9/2007 |
| WO | WO-2007125405 A2 | 11/2007 |
| WO | WO-2007129195 A2 | 11/2007 |
| WO | WO-2007130626 A2 | 11/2007 |
| WO | WO-2008011392 A2 | 1/2008 |
| WO | WO-2008014236 A1 | 1/2008 |
| WO | WO-2008027542 A2 | 3/2008 |
| WO | WO-2008067495 A2 | 6/2008 |
| WO | WO-2008109727 A1 | 9/2008 |
| WO | WO-2008109731 A2 | 9/2008 |
| WO | WO-2008115663 A1 | 9/2008 |
| WO | WO-2008128121 A1 | 10/2008 |
| WO | WO-2008128171 A2 | 10/2008 |
| WO | WO-2008134679 A1 | 11/2008 |
| WO | WO-2009015254 A1 | 1/2009 |
| WO | WO-2009060292 A2 | 5/2009 |
| WO | WO-2010053732 A1 | 5/2010 |
| WO | WO-2010107485 A1 | 9/2010 |
| WO | WO-2010141805 A1 | 12/2010 |
| WO | WO-2011005510 A2 | 1/2011 |
| WO | WO-2011008260 A2 | 1/2011 |
| WO | WO-2011043371 A1 | 4/2011 |
| WO | WO-2011082007 A2 | 7/2011 |
| WO | WO-2011119565 A1 | 9/2011 |
| WO | WO-2011143660 A2 | 11/2011 |
| WO | WO-2011143669 A2 | 11/2011 |
| WO | WO-2011160016 A2 | 12/2011 |
| WO | WO-2012003281 A2 | 1/2012 |
| WO | WO-2012007375 A1 | 1/2012 |
| WO | WO-2012009649 A1 | 1/2012 |
| WO | WO-2012040389 A2 | 3/2012 |
| WO | WO-2012040527 A2 | 3/2012 |
| WO | WO-2012054110 A2 | 4/2012 |
| WO | WO-2012061299 A1 | 5/2012 |
| WO | WO-2012078559 A2 | 6/2012 |
| WO | WO-2012090104 A1 | 7/2012 |
| WO | WO-2012142498 A2 | 10/2012 |
| WO | WO-2013006821 A1 | 1/2013 |
| WO | WO-2013042137 A1 | 3/2013 |
| WO | WO-2013071035 A1 | 5/2013 |
| WO | WO-2013071039 A1 | 5/2013 |

(56) References Cited

FOREIGN PATENT DOCUMENTS

| | | | |
|---|---|---|---|
| WO | WO 2013/106643 * | 7/2013 | ............ C07K 19/00 |
| WO | WO-2013106535 A1 | 7/2013 | |
| WO | WO-2013106646 A2 | 7/2013 | |
| WO | WO-2013170147 A1 | 11/2013 | |
| WO | WO-2013175417 A1 | 11/2013 | |
| WO | WO-2013178570 A1 | 12/2013 | |
| WO | WO-2014001356 A1 | 1/2014 | |
| WO | WO-2014011712 A1 | 1/2014 | |
| WO | WO-2014020502 A2 | 2/2014 | |
| WO | WO-2014025759 A1 | 2/2014 | |
| WO | WO-2014038606 A1 | 3/2014 | |
| WO | WO-2014047024 A1 | 3/2014 | |
| WO | WO-2014055461 A1 | 4/2014 | |
| WO | WO-2014058691 A1 | 4/2014 | |
| WO | WO-2014074658 A1 | 5/2014 | |
| WO | WO-2014100065 A1 | 6/2014 | |
| WO | WO-2014100071 A2 | 6/2014 | |
| WO | WO-2014107713 A1 | 7/2014 | |
| WO | WO-2014108452 A1 | 7/2014 | |
| WO | WO-2014123418 A1 | 8/2014 | |
| WO | WO-2014128111 A1 | 8/2014 | |
| WO | WO-2014134201 A1 | 9/2014 | |
| WO | WO-2014151863 A1 | 9/2014 | |
| WO | WO-2015000867 A1 | 1/2015 | |
| WO | WO-2015000868 A1 | 1/2015 | |
| WO | WO-2015006524 A1 | 1/2015 | |
| WO | WO-2015011084 A1 | 1/2015 | |
| WO | WO-2015015318 A2 | 2/2015 | |
| WO | WO-2015022332 A1 | 2/2015 | |
| WO | WO-2015067770 A1 | 5/2015 | |
| WO | WO-2015074064 A2 | 5/2015 | |
| WO | WO-2015104688 A1 | 7/2015 | |
| WO | WO-2015160845 A2 | 10/2015 | |
| WO | WO-2015175632 A1 | 11/2015 | |
| WO | WO-2015195863 A1 | 12/2015 | |
| WO | WO-2016011390 A1 | 1/2016 | |
| WO | WO-2016050821 A1 | 4/2016 | |
| WO | WO-2016053769 A1 | 4/2016 | |
| WO | WO-2016053770 A1 | 4/2016 | |
| WO | WO-2016053771 A1 | 4/2016 | |
| WO | WO-2016053772 A1 | 4/2016 | |
| WO | WO-2016069578 A1 | 5/2016 | |
| WO | WO-2016105518 A1 | 6/2016 | |
| WO | WO-2016118666 A1 | 7/2016 | |
| WO | WO-2016138114 A1 | 9/2016 | |
| WO | WO-2016144844 A1 | 9/2016 | |
| WO | WO-2016144846 A1 | 9/2016 | |
| WO | WO-2016144847 A1 | 9/2016 | |
| WO | WO-2016144848 A1 | 9/2016 | |
| WO | WO-2016144849 A1 | 9/2016 | |
| WO | WO-2016146985 A1 | 9/2016 | |
| WO | WO-2016169989 A1 | 10/2016 | |
| WO | WO-2016172134 A2 | 10/2016 | |
| WO | WO-2016197032 A1 | 12/2016 | |
| WO | WO-2016197114 A1 | 12/2016 | |
| WO | WO-2016201328 A1 | 12/2016 | |
| WO | WO-2017011590 A1 | 1/2017 | |
| WO | WO-2017024318 A1 | 2/2017 | |
| WO | WO-2017030814 A1 | 2/2017 | |
| WO | WO-2017046036 A1 | 3/2017 | |
| WO | WO-2017079267 A1 | 5/2017 | |
| WO | WO-2017197051 A1 | 11/2017 | |
| WO | WO-2017197056 A1 | 11/2017 | |
| WO | WO-2018052945 A1 | 3/2018 | |
| WO | WO-2018052949 A1 | 3/2018 | |
| WO | WO-2018119448 A1 | 6/2018 | |
| WO | WO-2018226542 A1 | 12/2018 | |
| WO | WO-2019014429 A1 | 1/2019 | |
| WO | WO-2019038717 A1 | 2/2019 | |
| WO | WO-2019042444 A1 | 3/2019 | |
| WO | WO-2019148055 A1 | 8/2019 | |
| WO | WO-2019199816 A1 | 10/2019 | |

OTHER PUBLICATIONS

Shih et al (J Chemical Information and Modeling 51:398-407, 2011) (Year: 2011).*
Edelmann et al (Expert Revies in Molecular Medicine 13(e35):17 pages, 2011) (Year: 2011).*
Abella, J.V., et al., "Met/Hepatocyte growth factor receptor ubiquitination suppresses transformation and is required for Hrs Phosphorylation", Mol Cell Biol, Nov. 2005, 25(21), 9632-9645.
Abraham R.T., "Phosphatidylinositol 3-kinase Related Kinases," Current Opinion in Immunology, Jun. 1996, vol. 8, No. 3, pp. 412-418.
Agashe, V. R., et al., "Initial hydrophobic collapse in the folding of barstar", Nature, Oct. 26, 1995, 377, 754-757.
Aghajanyy, M., et al., "Chemical genetics of TOR identified an SCF family E3 ubiquitin ligase inhibitor", Nature Biotechnology, Jul. 2010, 28(7), 738-742.
Ahn, D., et al., "HIF-1α Peptide Derivatives with modifications at the hydroxyproline residue as activators of HIF-1α", Bioorganic & Medicinal Chemistry Letters (2009); 19(15): 4403-4405.
Albrecht, B. K., et al., "Identification of a benzoisoxazoloazepine inhibitor (CPI-0610) of the bromodomain and extra-terminal (BET) family as a candidate for human clinical trials", Journal of Medicinal Chemistry (2016); 59: 1330-1339.
Allan, G. F., et al., "Therapeutic androgen receptor ligands", Nuclear Receptor Signaling (2003); 1(1): 1-4.
Anido, J., et al., "ZD1839, a specific epidermal growth factor receptor (EGFR) tyrosine kinase inhibitor, induces the formation of inactive EGFR/HER2 and EGFR/HER3 heterodimers and prevents heregulin signaling in HER2-overexpressing breast cancer cells", Clinical Cancer Research, Apr. 2003, 9, 1274-1283.).
Ardecky R.J., et al., "Design, Synthesis and Evaluation of Inhibitor of Apoptosis Protein (IAP) Antagonists That Are Highly Selective for the BIR2 Domain of XIAP," Bioorganic & Medicinal Chemistry, Jul. 15, 2013, vol. 23, No. 14, pp. 4253-4257.
Ariza, M., et al., "Tau positron emission tomography (PET) imaging: past, present, and future", Journal of Medicinal Chemistry (2015); 58(11): 4365-4382.
Arya, A. K. et al., "Nutlin-3, the small-molecule inhibitor of MDM2, promotes senescence and radiosensitises laryngeal carcinoma cells harbouring wild-type p53," British Journal of Cancer, 2010, 103, 186-195.
Asangani, I. A., et al., "Therapeutic Targeting of BET Bromodomain Proteins in Castration-Resistant Prostate Cancer", Nature (2014); 510: 278-282.
Asano M., et al., "Design, Stereoselective Synthesis, and Biological Evaluation of Novel Tri-Cyclic Compounds as Inhibitor of Apoptosis Proteins (IAP) Antagonists," Bioorganic & Medicinal Chemistry, Sep. 15, 2013, vol. 21, No. 18, pp. 5725-5737.
Asaoka, Y., et al., "Gastric cancer cell line Hs746T harbors a splice site mutation of c-Met causing juxtamembrane domain deletion", Biochem Biophys Res Commun, 2010, 394 (4), 1042-1046.
Ashby, M.N., "CaaX converting enzymes", Current Opinion in Lipidology., 1998, 9(2), 99-102.
[Author Unknown] "Cancer" Medline Plus Trusted Health Information for You [online] www.nlm.nih.gov/medlineplus/cancer.html (Jul. 6, 2007); 10 pages.
Banaszynski, L. A. et al. "A Rapid, Reversible, and Tunable Method to Regulate Protein Function in Living Cells Using Synthetic Small Molecules", Cell, Sep. 8, 2006, 126 (5), 995-1004.
Banaszynski, L. A. et al., "Chemical control of protein stability and function in living mice", Nature Medicine, Oct. 2008, 14(10), 1123-1127.
Baratta, M. G., et al., "An in-tumor genetic screen reveals that the BET bromodomain protein, BRD4, is a potential therapeutic target in ovarian carcinoma", PNAS (2015); 112: 232-237.
Bargagna-Mohan, P., et al., "Use of Protacs as molecular probes of angiogenesis", Bioorganic & Medicinal Chemistry Letters (2005); 15(11): 2724-2727.
Barker AJ, et al. Studies leading to the identification of ZD1839 (IRESSA): an orally active, selective epidermal growth factor receptor tyrosine kinase inhibitor targeted to the treatment of cancer. Bioorganic & medicinal chemistry letters 11, 1911-1914 (2001).

(56) References Cited

OTHER PUBLICATIONS

Battista, M. J., et al., "Fulvestrant for the treatment of endometrial cancer." Expert Opinion on Investigational Drugs (2016); 25(4): 475-483.
Beck, S. et al., "Fluorophore-assisted light inactivation: A high-throughput tool for direct target validation of proteins", Proteomics, 2002, 2 (3), 247-255.
Belikov, V.G, "Pharmaceutical Chemistry. Chapter 2.6 Relationship between the chemical structure, properties of substances and their effect on the body", MEDpress-inform (2007); pp. 27-29; 14 pages with English translation.
Belkina, A. C., et al., "BET domain co-regulators in obesity, inflammation and cancer", Nature Reviews Cancer (2012); 12(7): 465-477.
Belshaw, P.J., et al., "Controlling protein association and subcellular localization with a synthetic ligand that induces heterodimerization of proteins." Proc. Natl. Acad. Sci. USA (1996); 93: 4604-4607.
Berge, S. M., et al., "Pharmaceutical salts", Journal of Pharmaceutical Sciences (1977); 66(1): 1-19.
Birchmeier, C., et al., "Met, metastasis, motility and more", Nat Rev Mol Cell Biol, Dec. 2003, 4, 915-925.
Blond-Elguindi, S. et al., "Affinity panning of a library of peptides displayed on bacteriophages reveals the binding specificity of BiP", Cell, Nov. 19, 1993, 75, 717-728.
Boi, M., et al., "The BET Bromodomain inhibitor OTX015 Affects pathogenetic Pathways in Preclinical B-cell Tumor Models and synergizes with Targeted Drugs", Clinical Cancer Research (2015); 21(7): 1628-1638.
Boitano, A. E., et al., "Aryl Hydrocarbon Receptor Antagonists Promote the Expansion of Human Hematopoietic Stem Cells", Science (2010); 329: 1345-1348.
Bolen, J. B., et al., "Leukocyte protein tyrosine kinases: potential targets for drug discovery", Annual review of Immunology., 1997, 15, 371-404.
Bondeson, D. P., et al., "Catalytic in vivo protein knockdown by small-molecule Protacs", Nature Chemical Biology (2015); 11(8): 611-617.
Bondeson, D. P., et al., "Lessons in Protac design from selective degradation with a promiscuous warhead", Cell Chemical Biology (2018); 25(1): 78-87.
Bondeson, D. P., et al., "Targeted Protein Degradation by Small Molecules", Annual Review of Pharmacology and Toxicology (2017); 57: 107-123.
Borchardt, A., et al., "Small Molecule-dependent genetic selection in stochastic nanodroplets as a means of detecting protein-ligand interactions on a large scale", Chem. Bio., 1997, 4, 961-968.
Bos, J. L., "ras oncogenes in human cancer: a review", Cancer Res., 1989, 49, 4682-4689.
Bradbury, R. H., et al., "Small-molecule androgen receptor downregulators as an approach to treatment of advanced prostate cancer", Bioorganic & Medicinal Chemistry Letters (2011); 21: 5442-5445.
Braun, et al., "Quantitative analysis of bifunctional molecules", Biochemistry, 2004, 43, 5406-5413.
Brekken, R.A. et al., "Selective inhibition of Vascular Endothelial Growth Factor (VEGF) Receptor 2 (KDR/FIk-1) activity by a monoclonal Anti-VEGF antibody blocks tumor growth in mice", Cancer Res., 2000, 60, 5117-5124.
Briscoe, C. P. et al., "The orphan G protein-coupled receptor GPR40 is activated by medium and long chain fatty acids", J Biol Chem, Mar. 28, 2003, 278(13), 11303-11311.
Brodt, et al., "Inhibition of the type I insulin-like growth factor receptor expression and signaling: novel strategies for antimetastatic therapy", Biochemical Pharmacology, 2000, 60,1101-1107.
Brough, P. A., et al., "4,5-Diarylisoxazole HSP90 Chaperone Inhibitors: Potential Therapeutic Agents for the Treatment of Cancer", Journal of Medicinal Chemistry (2008); 51(2): 196-218.
Buckley, D. L., et al., "HaloProtacs: use of small molecule Protacs to induce degradation of HaloTag fusion proteins", ACS Chemical Biology (2015); 10(8): 1831-1837.

Buckley, D. L et al., "Small-Molecule Inhibitors of the Interaction between the E3 Ligase VHL and HIF1α," Angew, Chem. Int. Ed. Engl. 51:11463-11467 (2012).
Buckley, D. L., et al., "Targeting the von Hippel-Lindau E3 ubiquitin ligase using small molecules to disrupt the VHL/HIF-1α interaction", Journal of the American Chemical Society (2012); 134(10): 4465-4468.
Burke P.J., et al., "Design, Synthesis and Biological Evaluation of Doxorubicin-Formaldehyde Conjugates Targeted to Breast Cancer Cells," Journal of Medicinal Chemistry, Jan. 24, 2004, vol. 47, No. 5, pp. 1193-1206.
Burslem, G. M., et al., "Small-Molecule Modulation of Protein Homeostasis", Chemical Reviews (2017); 117(17): 11269-11301.
Burslem, G. M., et al., "The Advantages of Targeted Protein Degradation Over Inhibition: An RTK Case Study", Cell Chemical Biology (2018); 25(1): 67-77.
Caballero, J., et al., "Investigation of the Differences in Activity between Hydroxycycloalkyl N1 Substituted Pyrazole Derivatives As Inhibitors of B-Rat Kinase by Using Docking, Molecular Dynamics, QM/MM, and Fragment-Based De Novo Design: Study of Binding Mode of Diastereomer Compounds", Journal of Chemical Information and Modeling, val. 51, No. 11, Nov. 28, 2011, pp. 2920-2931.
Caira, M. R., "Crystalline Polymorphism of Organic Compounds", Topics in Current Chemistry (Jan. 1, 1998); 198:163-208.
Calloway, N.T., et al., "Optimized fluorescent trimethoprim derivatives for in vivo protein labeling", ChemBioChem., 2007, 8, 767-774.
Canman, C.E., et al., "The role of ATM in DNA damage responses and cancer", Oncogene, 1998, 17(25) 3301-3308.
Capitosti, S. M., et al., "Thalidomide analogues demonstrate dual inhibition of both angiogenesis and prostate cancer", Bioorganic & Medicinal Chemistry (2004); 12(2): 327-336.
Carlson, et al., "Selection of small-molecule mediators of the RNA regulation of PKR, the RNA-Dependent Protein Kinase", Chembiochem, 2002, 3(9), 859-865.
Carmony, K. C., et al., "Protac-induced proteolytic targeting", Methods in Molecular Biology (2012); 832: 627-638.
Ceribelli, M., et al., "Blockade of oncogenic IKB kinase activity in diffuse large B-cell lymphoma by bromodomain and extraterminal domain protein inhibitors", PNAS (2014); 111(31): 11365-11370.
Chan, K., et al., "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (IBET726) BET Inhibitor Scaffolds", Journal of Medicinal Chemistry (Jun. 8, 2018) ; 61(2): 504-513.
Chang, Y., et al., "Structural basis for G9a-like protein lysine methyltransferase inhibition by BIX-01294", Nature Structural & Molecular Biology (2009); 16(3): 312-317.
Chapuy, B., et al., "Discovery and characterization of super-enhancer-associated dependencies in diffuse large B cell lymphoma", Cancer Cell (2013); 24: 777-790.
CHEMBL256713, PubChem National Center for Biotechnology Information, 2009, PubChem Compound Database; CID-44449334, https://pubchem.ncbi.nlm.nih.gov/compound/44449334, 1-12.
CHEMEXPER.Com Catalog pages: "Fluorescein sodium 518-47-8 Catalog of Chemical Suppliers,", Retrieved from the internet on May 12, 2016: URL: https://www.chemexper.comichemicals/supplier/cas/518-47-8+Fluorescein+sodium.html.
CHEMEXPER.Com (Marco Engeler): "Anthracene," 2016, XP055272008, Retrieved from the Internet on May 12, 2016: URL: http://www.chemexper.com/searchResult.shtm17format=ccd2013%2Cccd&target=structure&options=brandqtyoffercrm&searchValue=1201278tsearch Template=rn.value%3D%22%3F%22&Search=Search.
Chéne P., et al., "Inhibiting the p53-MDM2 Interaction: An Important Target for Cancer Therapy," Nature Reviews Cancer, Feb. 2003, vol. 3, pp. 102-109.
Choi, H. Y., et al., "Curcumin interrupts the interaction between the androgen receptor and Wnt/β-catenin signaling pathway in LNCaP prostate cancer cells", Prostate Cancer and Prostatic Diseases (2010); 13(4): 343-349.

(56) References Cited

OTHER PUBLICATIONS

Chou et al., "Quantitative analysis of dose-effect relationships: the combined effects of multiple drugs or enzyme inhibitors", Advances in Enzyme Regulation, vol. 22, p. 27-55 (1984).
Chung, C., et al., "Discovery and Characterization of Small Molecule Inhibitors of the BET Family Bromodomains", Journal of Medicinal Chemistry (2011); 54(11): 3827-3838.
Churcher, I., "Protac-Induced Protein Degradation in Drug Discovery: Breaking the Rules or Just Making New Ones?", Journal of Medicinal Chemistry (2018); 61(2): 444-452.
CID16125106—"4-(4-aminophenyl)-1H-indazol-3-amine", (2007) National Center for Biotechnology Information. PubChem Compound Database; CID=16125106, https://pubchem.ncbi.nlm.nih.gov/compound/16125106.
CID21042819, National Center for Biotechnology Information. PubChem Compound Database; CID=21042819, https://pubchem.ncbi.nlm.nih.gov/compound/21042819 (accessed Feb. 7, 2016).
Ciechanover, A. et al., "Ubiquitin-mediated proteolysis: biological regulation via destruction", BioEssays, 2000, 22, 442-451.
Clarkson, T. et al. (Sep. 1998) "Redesigning an FKBP-ligand interface to generate chemical dimerizers with novel specificity", Proc Natl Acad Sci, 95(18): 10437-10442.
Cohen F., et al., "Antagonists of Inhibitors of Apoptosis Proteins Based on Thiazole Amide Isosteres," Bioorganic & Medicinal Chemistry Letters, Apr. 1, 2010, vol. 20, No. 7, pp. 2229-2233.
Cohen F., et al., "Orally Bioavailable Antagonists of Inhibitor of Apoptosis Proteins Based on an Azabicyclooctane Scaffold," Journal of Medicinal Chemistry, Mar. 26, 2009, vol. 52, No. 6, pp. 1723-1730.
Collins MA., et al., "Kras as a key oncogene and therapeutic target in pancreatic cancer", Frontiers in Physiol. Jan. 21, 2014, 4(407), 1-8.
Connor C.E., et al., "Circumventing Tamoxifen Resistance in Breast Cancers Using Antiestrogens That Induce Unique Conformational Changes in the Estrogen Receptor," Cancer Research, Apr. 1, 2001, vol. 61, pp. 2917-2922.
Contino-Pepin, C., et al., "Preliminary biological evaluations of new thalidomide analogues for multiple sclerosis application", Bioorganic & Medicinal Chemistry Letters (2009); 19(3): 878-881.
Corson, T. W., et al., "Design and applications of bifunctional small molecules: why two heads are better than one", ACS Chemical Biology (2008); 3(11): 677-692.
Crew, A. P., et al., "Identification and Characterization of Von Hippel-Lindau-Recruiting Proteolysis Targeting Chimeras (Protacs) of TANK-Binding Kinase 1", Journal of Medicinal Chemistry (2018); 61(2): 583-598.
Crews, C. M., "Targeting the undruggable proteome: the small molecules of my dreams", Chemistry & Biology (2010); 17(6): 551-555.
Cromm, P. M., et al., "Targeted protein degradation: from chemical biology to drug discovery", Cell chemical Biology (2017); 24(9): 1181-1190.
Cyrus, K., et al., "Impact of linker length on the activity of PROTACs", Molecular BioSystems (2011); 7(2): 359-364.
Cyrus, K., et al., "Jostling for position: Optimizing linker location in the design of estrogen receptor-targeting Protacs", ChemMedChem (2010); 5(7): 979-985.
Cyrus, K., et al., "Two-Headed Protac: An Effective New Tool for Targeted Protein Degradation", Chembiochem (2010); 11(11): 1531-1534.
Dassonville, O., et al., "EGFR targeting therapies: Monoclonal antibodies versus tyrosine kinase inhibitors similarities and differences", Critical Reviews in Oncology/Hematology, 2007, 62, 53-61.
Database STN, CAS Registry No. 1004933-70-3, "2-Pyrrolidinecarboxamide, N-(4-bromo-2-fluorophenyl)-4-hydroxy-1-(2-naphthalenylsulfonyl)-, (2S,4R)-", Chemical Abstracts Service, American Chemical Society; entered Feb. 2, 20081; 1 page.
Database STN, CAS Registry No. 1542127-97-8, "4,7, 10, 13-Tetraoxa-16-azaheneicosanamide, N-[4-[3-(4-amino-1,3-dihydro-1,3-dioxo-2H-isoindol-2-yl)-2,6-dioxo-3-piperidinyl]butyl]-21-[(3aS,4S,6aR)-hexahydro-2-oxo-1H-thieno[3,4-d]imidazol-4-yl]-17-oxo-", Chemical Abstracts Service, American Chemical Society; entered Feb. 11, 2014, 4 Pages.
Database STN, CAS Registry No. 155180-53-3, "Benzonitrile, 4-[3-(4-hydroxybutyl)-4,4-dimethyl-5-oxo-2-thioxo-1-imidazolidinyl]-2-(trifluoromethyl)-", Chemical Abstracts Service, American Chemical Society; entered May 19, 1994; 1 page.
Database STN, CAS Registry No. 155255-73-5, "Benzonitrile, 4-[4,4-dimethyl-2,5-dioxo-3-[4-(triphenylmethoxy)butyl]-1-imidazolidinyl]-2-(trifluoromethyl)-", Chemical Abstracts Service, American Chemical Society; entered May 24, 1994; 1 page.
Database STN, CAS Registry No. 186040-53-9, "Benzenepropanoic acid, β-(benzoylamino)-α-hydroxy-,(2aR,4S,4aS,6R,9S,11S,12S,12aR,12bS)-6,12b-bis(acetyloxy)-12-(benzoyloxy)-4-[[[2-[3-[4-cyano-3-(trifluoromethyl)phenyl]-5,5-dimethyl-4-oxo-2-thioxo-1-imidazolidinyl]ethyl]amino]carbonyl]oxy]-2a,3,4,4a,5,6,9,10,11,12,12a, 12b-dodecahydro-11-hydroxy-4a,8,13,13-tetramethyl-5-oxo-7, 11-methano-1H-cyclodeca[3,4]benz[1,2-b]oxet-9-ylester, (αR,βS)-", Chemical Abstracts Service, American Chemical Society; entered Feb. 13, 1997; 2 pages.
Database STN, CAS Registry No. 186798-71-0, "Glycinamide, N-[[(triphenylmethyl)thio]acetyl]glycyl-N-[2-[3-[4-cyano-3-(trifluoromethyl)phenyl]-5,5-dimethyl-4-oxo-2-thioxo-1-imidazolidinyl]ethyl]-", Chemical Abstracts Service, American Chemical Society; entered Mar. 7, 1997; 1 page.
Database STN, CAS Registry No. 186798-85-6, "Benzenepropanamide, N-[2-[3-[4-cyano-3-(trifluoromethyl)phenyl]-5,5-dimethyl-4-oxo-2-thioxo-1-imidazolidinyl]ethyl]-4-hydroxy-3,5-diiodo-", Chemical Abstracts Service, American Chemical Society; entered Mar. 7, 1997; 1 page.
Database STN, CAS Registry No. 534612-78-7, "Benzonitrile, 4-[3-[5-[4-[2-[2-(2- methoxyethoxy)ethoxy]ethyl]sulfonyl]-1-piperazinyl]pentyl]-4,4-dimethyl-5-oxo-2-thioxo-1-imidazolidinyl]-2-(trifluoromethyl)-", Chemical Abstracts Service, American Chemical Society; entered Jun. 20, 2003; 1 page.
Database STN, CAS Registry No. 871986-52-6, "2-Pyrrolidinecarboxamide, N-[(1S)-3-[(3aR,6aS)-5-(2,6-dimethylbenzoyl)hexahydropyrrolo[3,4-c]pyrrol-2(1H)-yl]-1-phenylpropyl]-1-(2-furanylcarbonyl)-4-hydroxy-", Chemical Abstracts Service, American Chemical Society; entered Jan. 1, 20066; 1 page.
Dawson, M. A., et al., "Inhibition of BET recruitment to chromatin as an effective treatment for MLL-fusion leukemia", Nature (Oct. 2, 2011); 478; 529-533.
Dejarnette, J. B et al., "Specific requirement for CD3ε in T cell development", Proc Natl Acad Sci USA, Dec. 1998, 95, 14909-14914.
Delmore, J. E., et al., "BET Bromodomain inhibition as a therapeutic strategy to target c-Myc", Cell (2011); 146: 904-917.
Deroo, B.J., et al., "Estrogen receptors and human disease", Journal of Clinical Investigation (2006); 116(3): 561-570.
Deshaies, R.J., "SCF and Cullin/RING H2-based ubiquitin ligases", Annu. Rev. Cell Dev. Biol., 1999, 15, 435-467.
Di, J., et al., "Reactivation of p53 by inhibiting Mdm2 E3 Ligase: a novel antitumor approach", Current Cancer Drug Targets (2011); 11(8): 987-994.
Ding, et al. "Discovery of RG7388, a potent and selective p53-MDM2 inhibitor in clinical development." J Med Chem. Jul. 25, 2013; 56(14):5979-83. doi: 10.1021/jm400487c.
Dixon, S. J., et al., "Identifying druggable disease-modifying gene products", Current Opinion in Chemical Biology (2009); 13(5-6): 549-555.
Douglass, E.F., et al., "A Comprehensive Mathematical Model for Three-Body Binding Equilibria", J Am Chem Soc, Apr. 24, 2013, 135(16), 6092-6099.
Drilon, A., "MET Exon 14 Alterations in Lung Cancer: Exon Skipping Extends Half-Life", Clinical Cancer Research, Jun. 15, 2016, 22(12), 2832-2834.
Dvorin, J.D., et al. "A Plant-Like Kinase in Plasmodium falciparum Regulates Parasite Egress from Erythrocytes", Science, May 14, 2010, 328, 910-912.
Elofsson, et al., "Towards subunit-specific proteasome inhibitors: synthesis and evaluation of peptide α', β'-epoxyketones", Chem Biol, 1999, 6(11), 811-822.

(56) References Cited

OTHER PUBLICATIONS

El-Shami, et al., "FLT3 inhibitors in acute myeloid leukemia", Expert Rev. Hematol., 2008, 1(2) 153-160.
Engleman, J.A., et al., "MET Amplification Leads to Gefitinib Resistance in Lung Cancer by Activating ERBB3 Signaling", Science, May 18, 2007, 316, 1039-1043.
Fang, H., et al., "Study of 202 Natural, Synthetic, and Environmental Chemicals for Binding to the Androgen Receptor," Chem. Res Toxicol., 2003, 16, 1338-1358.
Felici, et al., "β-Cyclodextrin-Appended giant amphiphile: aggregation to vesicle polymersomes and immobilizations of enzymes", Chem. Eur. J., 2008, 14, 9914-9920.
Field, S.D., et al., "Selective Downregulation of JAK2 and JAK3 by an ATP-Competitive pan-JAK Inhibitor", ACS Chem Biol, 2017, 12, 1183-1187.
Filippakopoulos, P., et al., "Selective inhibition of BET bromodomains", Nature (Dec. 23, 2010); 468: 1067-1073.
Finlay et al., "Discovery of a Potent and Selective EGFR Inhibitor (AZD9291) of Both Sensitizing and T790M Resistance Mutations That Spares the Wild Type Form of the Receptor," Journal of Medicinal Chemistry 57(20):8249-8267 (2014).
Finnin, M. S., et al., "Structures of a histone deacetylase homologue bound to the TSA and SAHA inhibitors," Nature (Sep. 1999), vol. 401, pp. 188-193.
Fischer, E. S., et al., "Structure of the DDB1-CRBN E3 Ubiquitin ligase in complex with thalidomide", Nature (2014); 512(7512): 49-53.
Flygare J.A., et al., "Small-Molecule Pan-IAP Antagonists: A Patent Review," Expert Opinion on Therapeutic Patents, Feb. 2010, vol. 20, No. 2, pp. 251-267.
Forastiere, et al., "Use of Paclitaxel (TAXOL®) in squamous cell carcinoma of the head and neck", Sem. Oncol., Aug. 1993, 20(4 Supp. 3), 56-60.
Früchtel, et al., "Organic Chemistry on Solid Supports", Agnew. Chem. Int. Ed. Engl., 1996, 35, 17-42.
French, C. A., et al., "BRD-NUT oncoproteins: a family of closely related nuclear proteins that block epithelial differentiation and maintain the growth of carcinoma cells", Oncogene (2008); 27: 2237-2242.
Fung, S. P. S., "Structure Guided Discovery of Inhibitors of Indoleamine, 2,3-dioxygenase (IDO1)", University of Auckland (2015); 1-244.
Gabay, M., et al., "MYC Activation is a hallmark of cancer initiation and maintenance", Cold Spring Harbor Perspectives In Medicine (2014); 4(a014241): 1-14.
Gadd, M. S., et al., "Structural basis of Protac cooperative recognition for selective protein degradation", Nature Chemical Biology (2017); 13(5): 514-521.
Galdeano, C., et al., "Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities", Journal of Medicinal Chemistry (2014); 57(20): 8657-8663.
Gangjee, A., et al., "The contribution of a 2—amino group on receptor tyrosine kinase inhibition and antiangiogenic activity in 4—anilinosubstituted pyrrolo[2,3-d] pyrimidines", Bioorganic & Medicinal Chemistry Letters (2010); 20(10): 3177-3181.
GenBank: AAV70825. 1, "HT2 [Expression vector pHT2]" Dec. 1, 2004 http://www.ncbi.nlm.nih.gov/protein/AAV70825.1—1 page.
GenBank: ADN27525.1, "HaloTag protein [HaloTag control vector]" Sep. 21, 2010 http://www.ncbi.nlm.nih.gov/protein/ADN27525. 1—1 page.
Gething, M. J. "Role and regulation of the ER chaperone BiP", Semin Cell Dev Biol, 1999, 10, 465-472.
Gheradi, E., et al., "Targeting MET in cancer: rationale and progress", Nat Rev Cancer, Feb. 2012, 12, 89-103.
Gies, E. et al., "Niclosamide prevents the formation of large ubiquitin-containing aggregates caused by proteasome inhibition", PLoS One, 2010, 5(12), e14410, 1-12.
Goldstein, N. et al., Biological Efficacy of a Chimeric Antibody to the Epidermal Growth Factor Receptor in A Human Tumor Xenograft Model, Clinical Cancer Research, 1995, vol. 1, pp. 1311-1318.
Golub, T. R., et al., "Molecular classification of cancer: class discovery and class prediction by gene expression monitoring", Science (1991); 286: 531-537.
Goode, et al., "Identification of Promiscuous Small Molecule Activators in High-Throughput Enzyme Activation Screens", J. Med. Chem. 2008, 51, 2346-2349.
Gosink, M., et al., "Redirecting the specificity of ubiquitination by modifying ubiquitin-conjugating enzymes", Proceedings of the National Academy of Sciences (1995); 92(20): 9117-9121.
Graves, L., et al., "The dynamic nature of the kinome", Biochemical Journal, Feb. 15, 2013, 450(1), 1-17.
Green, M.C et al., "Monoclonal antibody therapy for solid tumors", Cancer Treat. Rev., 2000, 26, 269-286.
Griffith, E., et al., "Methionine aminopeptidase (type 2) is the common target for angiogenesis inhibitors AGM-1470 and ovalicin", Chem. Biol., 1997, 4(6), 461-471.
Gschwind, A., "The discovery of receptor tyrosine kinases: targets for cancer therapy," Nat Rev Cancer (2004); 4: 361-370.
Gu et al., "Protacs: An Emerging Targeting Technique for Protein Degradation in Drug Discovery," BioEssays 2018, 40, 1700247, 11 pages.
Guo, C., et al., "Design of oxobenzimidazoles and oxindoles as novel androgen receptor antagonists", Bioorganic & Medicinal Chemistry Letters (2012); 22: 2572-2578.
Guo, C., et al., "Discovery of Aryloxy Tetramethylcyclobutanes as Novel Androgen Receptor Antagonists", Journal of Medicinal Chemistry (2011); 54: 7693-7704.
Gustafson, J. L., et al., "Small-molecule-mediated degradation of the androgen receptor through hydrophobic tagging", Angewandte Chemie (2015); 54: 9659-9662.
Hallman, K., et al., "The effects of turmeric (curcumin) on tumor suppressor protein (p53) and estrogen receptor (ERα) in breast cancer cells", Breast Cancer: Targets and Therapy (2017): 153-161.
Han D-H., et al., "Relationship between Estrogen Receptor-Binding and Estrogenic Activities of Environmental Estrogens and Suppression by Flavonoids," Bioscience Biotechnology Biochemistry, Feb. 4, 2002, vol. 66, No. 7, pp. 1479-1487.
Hanan, et al., "Discovery of selective and noncovalent diaminopyrimidine-based inhibitors of epidermal growth factor receptor containing the T790M resistance mutation", J. Med Chem., 2014, 57, 10176-10191.
Hanisak, et al., "Efforts toward the optimization of a bi-aryl class of potent IRAK4 inhibitors", Bioorg Med Chem Lett, 2016, 26, 4250-4255.
Hatakeyama, et al., "Ubiquitin-dependent degradation of IκBα is mediated by a ubiquitin ligase Skp1/ Cul 1/ F-box protein FWD1", Pnas USA, Mar. 1999, 96, 3859-3863.
Haupt, et al al. "Mdm2 promotes the rapid degradation of p53." Nature 387, 296-299 (1997).
Heinlein, C. A., et al., "Androgen receptor in prostate cancer", Endocrine Reviews (2004); 25(2): 276-308.
Heinlein, C. A., et al., "The roles of androgen receptors and androgen-binding proteins in nongenomic androgen actions", Molecular Endocrinology (2002); 16(10): 2181-2187.
Heldring, et al. "Estrogen Receptors: How Do They Signal and What are Their Targets." Physiological Reviews (2007), vol. 87, pp. 905-931.
Hennessy, et al. "Discovery of aminopiperidine-based Smac mimetics as IAP antagonists." Bioorg. Med. Chem. Lett., 22(4), 1690-1694 (2012).
Herm-Götz, A. et al., "Rapid control of protein level in the apicomplexan Toxoplasma gondii", Nat Methods, Dec. 2007, 4(12), 1003-1005.
Hewings, D. S., et al., "3,5-Dimethylisoxazoles Act As Acetyllysine-mimetic Bromodomain", Journal of Medicinal Chemistry (Oct. 13, 2011); 54(19): 6761-6770.
Hines, J., et al., "Posttranslational protein knockdown coupled to receptor tyrosine kinase activation with phosphoProtacs", Proceedings of the National Academy of Sciences (2013); 110(22): 8942-8947.

(56) References Cited

OTHER PUBLICATIONS

Hird, et al. "Structure-based design and synthesis of tricyclic IAP (Inhibitors of Apoptosis Proteins) inhibitors." Bioorg. Med. Chem. Lett., 24(7): 1820-1824 (2014).
Hjerpe, R., et al., "Efficient protection and isolation of ubiquitylated proteins using tandem ubiquitin-binding entities", EMBO reports, 2009, 10(11), 1250-1258.
Ho, K. et al., "Discovery of 4-phenyl-2-phenylaminopyridine based TNIK inhibitors", Bioorganic and Medicinal Chemistry Letters, 2013, 23, 569-573.
Hoffmann, J., et al., "Characterization of New Estrogen Receptor Destabilizing Compounds: Effects on Estrogen-Sensitive and Tamoxifen-Resistant Breast Cancer", JNCI Journal of the National Cancer Institute (2004); 96(3); 210-218.
Holford, N., et al., "Understanding the Dos-Effect Relationship: Clinical Application of Pharmacokinetic-Pharmacodynamic Models", Clinical Pharmacokinetics, 1981, 6, 429-453.
Hollstein, et al. "p53 mutations in human cancers", Science 1991, 253:49-53.
Holmes, et al., "Phase II trial of Taxol, an active drug in the treatment of metastatic breast cancer", J. Nat. Cancer Inst., Dec. 18, 1991, 83(24), 1797-1805.
Hon, W., et al., "Structural basis for the recognition of hydroxyproline in HIF-1α by pVHL", Nature (2002); 417(6892): 975-978.
Hong, J. H., et al., "Effect of curcumin on the interaction between androgen receptor and Wnt/β -catenin in LNCaP xenografts", Korean Journal of Urology (2015); 56(9): 656-665.
"Short Course in Molecular Pharmacology" (Kratkiy kurs molekulyarnoy farmakologii), edited by P.V. Sergeev, Moscow, 1975, p. 10.
Huang, H. T., et al., "A Chemoproteomic Approach to Query the Degradable Kinome Using a Multi-kinase Degrader", Cell Chemical Biology (2018); 25(1): 88-99.
Huang, X., et al., "Drugging the undruggables: exploring the ubiquitin system for drug development", Cell Research (2016); 26(4): 484-498.
Hughes, S. J., et al., "Molecular recognition of ternary complexes: a new dimension in the structure-guided design of chemical degraders", Essays in Biochemistry (2017); 61(5): 505-516.
Iqbal, N., "Human Epidermal Growth Factor Receptor 2 (HER2) in Cancers: Overexpression and Therapeutic Implications", Molecular Biology International, 2014, Article ID 852748, 9 pages.
IRAK-1-4 Inhibitor I, PubChem, National Center for Biotechnology Information. PubChem Compound Database; CID-11983295, 2007, https://pubchem.ncbi.nlm.nih.gov/compound/11983295, 1-17.
Ishikawa, T., et al., "Design and synthesis of novel human epidermal growth factor receptor 2 (HER2)/epidermal growth factor receptor (EGFR) dual inhibitors bearing a pyrrolo[3,2-d]pyrimidine scaffold", Journal of Medicinal Chemistry, 2011, 54(23), 8030-8050.
Ito et al., Identification of a primary target of thalidomide teratogenicity, Science, 2010, 327(5971):1345-50 DOI: 10.1126/science. 1177319.
Ivan, M., et al., "HIFα targeted for VHL-mediated destruction by proline hydroxylation: implications for O₂ sensing", Science (2001); 292(5516): 464-468.
Iwamoto et al., "A general chemical method to regulate protein stability in the mammalian central nervous system," Chem Biol. Sep. 24, 2010; 17(9): 981-8.
Jackson, S. P., "DNA-dependent protein kinase", International Journal of Biochemistry and Cell Biology., 1997, 29(7), 935-938.
Jang, E. R., et al., "Targeted Degradation of Proteins by Protacs", Current Protocols in Chemical Biology (2010); 2(2): 71-87.
Janssens, S., et al., "Functional Diversity and Regulation of Different Interleukin-1 Receptor-Associated Kinase (IRAK) Family Members," Mol. Cell., Feb. 2003, 11, 293-302.
Jiang X.R., et al., "Synthesis of 7alpha-Substituted Derivatives of 17Beta-Estradiol," Steroids, May 2006, vol. 71, No. 5, pp. 334-342, (Abstract Only).

Jo, M., et al., "Cross-talk between Epidermal Growth Factor Receptor and c-Met Signal Pathways in Transformed Cells", J Biol Chem, Mar. 24, 2000, 275(12), 8806-8811.
Joffre, C., et al., "A direct role for Met endocytosis in tumorigenesis", Nat Cell Biol., Jul. 2011, 13(7), 827-837 (23 pages total).
Jordan V.C., et al., "A Monohydroxylated Metabolite of Tamoxifen with Potent Antioestrogenic Activity," Journal of Endocrinology, Nov. 1977, vol. 75, pp. 305-316.
Jortzik, et al., "Benzo[b]quinolizinium Derivatives Have a Strong Antimalarial Activity and Inhibit Indoleamine Dioxgenase" Antimicrobial Agents and Chemotherapy, Jan. 2016, 60(1) 115-125.
Jung, M. E., et al., "Structure-activity relationship for thiohydantoin androgen receptor antagonists for castration-resistant prostate cancer (CRPC)", Journal of Medicinal Chemistry (2010); 53(7): 2779-2796.
Kanakaraj, et al. "Defective Interleukin (IL)-18-mediated Natural Killer and T Helper Cell Type 1 Responses in IL-1 Receptor-associated Kinase (IRAK)-deficient Mice", J. Exp. Med., Apr. 5, 1999, 189(7), 1129-1138.
Kanakaraj, et al., "Interleukin (IL)-1 Receptor-associated Kinase (IRAK) Requirement for Optimal Induction of Multiple IL-1 Signaling Pathways and IL-6 Production", J. Exp. Med. Jun. 15, 1998, 187(12), 2073-2079.
Karin, M., et al., "Phosphorylation meets ubiquitination: the control of NF-κB Activity", Annu. Rev. Immunol., 2000, 18, 621-663.
Karlas, A. et al. "Genome-wide RNAi screen identifies human host factors crucial for influenza virus replication", Nature, Feb. 11, 2010, 463, 818-822.
Kawagoe, T, et al. "Essential role of IRAK-4 protein and its kinase activity in Toll-like receptor-mediated immune responses but not in TCR signaling", J. Exp. Med., 2007, 204(5), 1013-1024.
Kearns, C.M et al., "Paclitaxel pharmacokinetics and pharmacodynamics", Seminars in Oncology, 1995, 22(3 Suppl 6), 16-23.
Kermorgant, S., et al., "Protein Kinase C Controls Microtubule-based Traffic but Not Proteasomal Degradation of c-Met", J Biol Chem, Aug. 1, 2003, 278(31), 28921-28929.
Kharkevich, D. A., "Pharmacology/Textbook", 10th edition, (2010); pp. 72-82; 14 pages with English Summary.
Kholodov, L.E., et al., "Clinical Pharmacokinetics" (Klinicheskaya Farmakokinetika), Moscow: Meditsina, 1985, pp. 83-98, 134-138, 160, and 378-380.
Kim, K., et al., "Development and characterization of proteasome inhibitors", Methods Enzymol, 2005, 399, 585-609.
Kim K.S., et al., "Discovery of Tetrahydroisoquinoline-Based Bivalent Heterodimeric IAP Antagonists," Bioorganic & Medicinal Chemistry Letters, Jul. 18, 2014, vol. 24, No. 21, pp. 5022-5029.
Kim, L. S., et al., "Heat shock protein as molecular targets for breast cancer therapeutics", Journal of Breast Cancer (2011); 14(3): 167-174.
Kim, T.W., et al., "A critical role for IRAK4 kinase activity in Toll-like receptor-mediated innate immunity", J. Exp. Med., May 14, 2007, 204(5), 1025-1036.
Kirikoshi, H., et al. "Molecular cloning and characterization of human Frizzled-4 on chromosome 11q14-q21", Biochem Biophys Res Commun., 1999, 264, 955-961.
Kiyoi, "FLT3 inhibitors: recent advances and problems for clinical application", Nagoya J Med, Sci., 2015, 77, 7-17.
Klapproth, K., et al., "Advances in the understanding of MYC-induced lymphomagenesis", British Journal of Hematology (2010); 149: 484-497.
Kummerer, K., "Pharmaceuticals in the Environment", Annual Review of Environment and Resources (2010); 35: 57-75.
Knickelbein K., et al., "Mutant KRAS as a critical determinant of the therapeutic response of colorectal cancer", Genes Dis., Mar. 2015, 2(1), 4-12.
Knott, E. B., "Compounds containing sulphur chromophores. Part I. The action of bases on heterocyclic sulphide quarternary salts", Journal of the Chemical Society (Resumed) (1955); 916-927.
Knott, E. B., et al., Accession No. 1957:56724, "Compounds containing sulfur chromophores. V. Complex cyanines" STN (Nov. 24, 2017); 1 page.
Koch, P. et al., "Inhibitors of c-Jun N-Terminal kinases: an update", Journal of Medicinal Chemistry, 2015, 58, 72-95.

(56) References Cited

OTHER PUBLICATIONS

Koga, F. et al., "Low dose geldanamycin inhibits hepatocyte growth factor-and hypoxia-stimulated invasion of cancer cells", Cell Cycle, Jun. 1, 2007, 6(11), 1393-1402.
Koh, E. Y. et al., "Novel retroviral vectors to facilitate expression screens in mammalian cells", Nucleic Acids Res., 2002, 30(24), e142, 1-7.
Kohl, et al., "Inhibition of farnesyltransferase induces regression of mammary and salivary carcinomas in ras transgenic mice", Nat Med., Aug. 1995, 1(8), 792-797.
Konecny, G. E., et al., "Activity of the Dual Kinase Inhibitor Lapatinib (GW572016) against HER-2-Overexpressing and Trastuzumab-Treated Breast Cancer Cells", Cancer Research (2006); 66(3): 1630-1639.
Kong-Beltran, M., et al., "Somatic Mutations Lead to an Oncogenic Deletion of Met in Lung Cancer", Cancer Research, Jan. 1, 2006, 66(1), 283-289.
Koziczak-Holbro, M, et al., "IRAK-4 kinase activity is required for Interleukin-1 (IL-1) receptor-and toll-like receptor 7-mediated signaling and gene expression", J. Biol. Chem., May 4, 2007, 282(18), 13552-13560.
Krishnan, M. N. et al. "RNA interference screen for human genes associated with West Nile virus infection", Nature, Sep. 11, 2008, 455, 242-245.
Kronke, J., et al., "Lenalidomide causes selective degradation of IKZF1 and IKZF3 in multiple myeloma cells", Science (2014); 343(6168): 301-305.
Kubota, H. "Quality control against misfolded proteins in the cytosol: a network for cell survival", J Biochem, 2009, 146(5), 609-616.
Kuntz, The Importance of Being Me: Magic Methyls, Methyltransferase Inhibitors, and the Discovery of Tazemetostat, Journal of Medicinal Chemistry, 2016, 59, pp. 1556-1564. (Year: 2016).
Kurimchak, A. M., et al.,"Resistance to BET Bromodomain Inhibitors Is Mediated by Kinome Reprogramming in Ovarian Cancer", Cell Reports (2016); 16: 1273-1286.
Kwon, Y., et al., "Bivalent inhibitor of the N-end Rule Pathway", J. Biol. Chem., Jun. 18, 1999, 274(25), 18135-18139.
Lackey, K. et al., "The discovery of potent cRaf1 kinase inhibitors", Bioorganic and Medicinal Chemistry Letters, 2000, 10, 223-226.
Lai, A. C., et al., "Modular PROTAC design for the degradation of oncogenic BCR-ABL", Angewandte Chemie International Edition (2016); 55(2): 807-810.
Lala, P. K., et al., "Role of nitric oxide in tumor progression: lessons from experimental tumors", Cancer and Metastasis Reviews (1998); 17: 91-106.
Lebraud, H., et al., "Protein degradation by in-cell self-assembly of proteolysis targeting chimeras", ACS Central Science (2016); 2(12): 927-934.
Lee, H., et al., "Targeted degradation of the aryl hydrocarbon receptor by the Protac approach: a useful chemical genetic tool", Chembiochem (2007); 8(17): 2058-2062.
Lelais, G., et al., "Discovery of (R, E)-N-(7-Chloro-1-(1-[4-(dimethylamino) but-2-enoyl] azepan-3-yl)-1 H-benzo [d] imidazol-2-yl)-2-methylisonicotinamide (EGF816), a Novel, Potent, and WT Sparing Covalent Inhibitor of Oncogenic (L858R, ex19del) and Resistant (T790M) EGFR Mutants for the Treatment of EGFR Mutant Non-Small-Cell Lung Cancers", Journal of Medicinal Chemistry (2016); 59(14): 6671-6689.
Lemmon, M., et al., "Cell signaling by receptor tyrosine kinases", Cell (2010); 141(7): 1117-1134.
Leu, et al., "HSP70 inhibition by the small-molecule 2-phenylethynesulfonamide impairs protein clearance pathways in tumor cells", Mol. Cancer Res., Jul. 2011, 9(7), 936-947.
Levine, P. M., et al., "Targeting the androgen receptor with steroid conjugates: miniperspective", Journal of Medicinal Chemistry (2014); 57(20): 8224-8237.
Li, et al. "Mutant Cells That do not respond to Interleukin-1 (IL-1) Reveal a Novel Role for IL-1 Receptor-Associated Kinase", Mol. Cell. Biol., Jul. 1999, 19(7), 4643-4652.

Li, S., et al. "IRAK-4: A novel member of the IRAK family with the properties of an IRAK-kinase", Proc. Natl. Acad. Sci. USA, Apr. 16, 2002, 99(8), 5567-5572.
Li, X. et al., "Amino-terminal protein processing in *Saccharomyces cerevisiae* is an essential function that requires two distinct methionine aminopeptidases", Proc. Natl. Acad. Sci. USA, Dec. 1995, 92, 12357-12361.
Li, Y., et al., "Single polymer-drug conjugate carrying two drugs for fixed-dose co-delivery", Medicinal Chemistry (2014); 4(10): 676-683.
Lim, et al."Discovery of 5-Amino-N-(1H-pyrazol-4-yl)pyrazolo[I,5-a]pyrimidine-3-carboxamide inhibitors of IRAK4", ACS Med Chem Lett, 2015, 6, 683-688.
Link, V. et al., "Proteomics of early zebrafish embryos", BMC Dev Biol., 2006, 6(1), 1-9.
Lins, L. et al., "The hydrophobic effect in protein folding", FASEB, 1995, 9(7), 535-540.
Littlejohn, T. K., "Studies on human indoleamie 2,3-dioxygenase (IDO)", Doctor of Philosophy Thesis, Faculty of Sciences, University of Wollongong, 2001, 1-189.
Liu et al. "Structure of Human Methionine Aminopeptidase-2 Complexed with Fumagillin", Science, 1998, vol. 282, p. 1324-1327.
Liu, F., et al., "Discovery of a 2,4-diamino-7-aminoalkoxyquinazoline as a potent and selective inhibitor of histone lysine methyltransferase G9a", Journal of Medicinal Chemistry (2009); 52(24): 7950-7953.
Liu, H., et al., "Bioactivation of the selective estrogen receptor modulator desmethylated arzoxifene to quinoids: 4'-fluoro substitution prevents quinoid formation", Chemical Research in Toxicology (2005); 18: 162-173.
Liu, K., et al., "Design and biological characterization of hybrid compounds of curcumin and thalidomide for multiple myeloma", Organic & Biomolecular Chemistry (2013); 11(29): 4757-4763.
Llinas-Brunet, M., et al., "Discovery of a potent and selective noncovalent linear inhibitor of the hepatitis C virus NS3 protease (BI 201335)", Journal of Medicinal Chemistry (2010); 53(17): 6466-6476.
Loewe et al., arch. Exp. Pathol Pharmaol., 1926, 114, 313-326.
Lopez-Girona, A. E. A., et al., "Cereblon is a direct protein target for immunomodulatory and antiproliferative activities of lenalidomide and pomalidomide", Leukemia (2012); 26(11): 2326-2335.
Los, G. V. et al., "HaloTag: A novel protein labeling technology for cell imaging and protein analysis", ACS Chemical Biology, Jun. 6, 2008, 3(6), 373-382.
Lountos, G. T., et al., "Structural characterization of inhibitor complexes with checkpoint kinase 2 (Chk2), a drug target for cancer therapy", Journal of Structural Biology (2011); 176(3): 292-301.
Loven, J., et al., "Selective Inhibition of Tumor Oncogenes by Disruption of Super Enhancers", Cell (2013); 153: 320-334.
Lu, G., et al., "The myeloma drug lenalidomide promotes the cereblon-dependent destruction of Ikaros proteins", Science (2014); 343(6168): 305-309.
Lu, J., et al., "Hijacking the E3 ubiquitin ligase cereblon to efficiently target BRD4", Chemistry & Biology (2015); 22(6): 755-763.
Lu, N. Z., et al., "International Union of Pharmacology. LXV. The pharmacology and classification of the nuclear receptor superfamily: glucocorticoid, mineralocorticoid, progesterone, and androgen receptors", Pharmacological Reviews (2006); 58(4): 782-797.
Luo, J. et al. "A genome-wide RNAi screen identifies multiple synthetic lethal interactions with the Ras oncogene", Cell, May 29, 2009, 137(5), 835-848.
Lyapina, S.A., et al., "Human CUL1 forms an evolutionarily conserved ubiquitin ligase complex (SCF) with SKP1 and an F-box protein", Proc. Natl. Acad. Sci. USA, Jun. 1998, 95, 7451-7456.
Lye, E. et al., "The role of interleukin 1 receptor-associated Kinase-4 (IRAK-4) kinase activity in IRAK-4-mediated signaling", J. Biol. Chem., Sep. 24, 2004, 279(39), 40653-40658.
Ma Y, et al., "Targeted degradation of KRAS by an engineered ubiquitin ligase suppresses pancreatic cancer cell growth in vitro and in vivo", Mol Cancer Ther., Mar. 2013, 12(3), 1-10.

(56) References Cited

OTHER PUBLICATIONS

Macbeath, G., et al., "Printing small molecules as microarrays and detecting protein-ligand interactions en masse", J. Am. Chem. Soc., 1999, 121, 7967-7968.
Mahalingam D., et al., "Targeting HSP90 for Cancer Therapy," British Journal of Cancer, May 19, 2009, vol. 100, pp. 1523-1529.
Maniaci, C., et al., "Homo-Protacs: bivalent small-molecule dimerizers of the VHL E3 ubiquitin ligase to induce self-degradation", Nature Communications (2017); 8(1): 1-14.
Maniatis, T. "A ubiquitin ligase complex essential for the NF-κB, Wnt/Wingless and Hedgehog signaling pathways", Genes & Development, 1999, 13, 505-510.
Mannhold R., et al., "IAP Antagonists: Promising Candidates for Cancer Therapy," Drug Discovery Today, Mar. 2010, vol. 15, No. 5-6, pp. 210-219.
Margottin, F. et al., "A novel human WD protein, h-βTrCP, that interacts with HIV-1 Vpu connects CD4 to the ER degradation pathway through an F-Box motif", Mol Cell., Mar. 1998, 1, 565-574.
Markman, et al., "Taxol: an important new drug in the management of epithelial ovarian cancer", Yale Journal of Biology and Medicine, 1991, 64, 583-590.
Martin-Kohler, A., et al., "Furo [2,3-d] pyrimidines and Oxazolo [5,4—d] pyrimidines as Inhibitors of Receptor Tyrosine Kinases (RTK)", Helvetica Chimica Acta (2004); 87(4): 956-975.
Martínez-Lacaci, L., et al., "RAS transformation causes sustained activation of epidermal growth factor receptor and elevation of mitogen-activated protein kinase in human mammary epithelial cells", Int. J. Cancer, 2000, 88, 44-52.
Masellis-Smith, A. et al., "CD9-regulated adhesion. Anti-CD9 monoclonal antibody induce pre-B cell adhesion to bone marrow fibroblasts through de novo recognition of fibronectin," J. Immunol., 1994, 152, 2768-2777.
Mashkovsky, M. D., "Medicaments (Doctor's Manual)", 14th Edition, vol. 1., Moscow. (2001), pp. 11; 6 pages with English translation.
Massague, J. et al., "Serine/threonine kinase receptors: mediators of transforming growth factor beta family signals", Cancer Surveys, 1996, 27, 41-64.
Mathias, L. J., et al., "Adamantane-containing polymers", Acs Sym Ser, 1996, 624, 197-207.
McElroy, et al., "Potent and Selective Amidopyrazole Inhibitors of IRAK4 that are Efficacious in a Rodent Model of Inflammation", ACS Med Chem Lett., 2015, 6, 677-682.
McElroy, W.T et al. (2015) "Discovery and hit-to-lead optimization of 2,6-diaminopyrimidine inhibitors of interleukin-1 receptor-associated kinase 4" Bioorg Med Chem Lett, 25(9): 1836-1841.
McGuire W.P., et al., "Taxol: A Unique Antineoplastic Agent With Significant Activity in Advanced Ovarian Epithelial Neoplasms," Annals of Internal Medicine, Aug. 15, 1989, vol. 111, No. 4, pp. 273-279.
Medvedev, et al. "Distinct Mutations in IRAK-4 confer hyporesponsiveness to lipopolysaccharide and interleukin-1 in a patient with recurrent bacterial infections", J. Exp. Med., 2003, 198(4), 521-531.
Mehellou, Y., et al., "Twenty-six years of anti-HIV drug discovery: where do we stand and where do we go?", Journal of Medicinal Chemistry (2010); 53(2): 521-538.
Meng, et al., "Epoxomicin, a Potent and Selective Proteasome Inhibitor, Exhibits In Vivo Anti-Inflammatory Activity," Proc. Natl. Acad. Sci. USA, (Aug. 1999) 96:10403-10408.
Menger, et al, "Self-adhesion among phospholipid vesicles", J. Am. Chem. Soc., 2006, 128, 1414-1415.
Mercurio, et al., "IKK-1 and IKK-2: cytokine-activated IκB kinases essential for NF-κb activation", Science, Oct. 31, 1997, 278, 860-866.
Mertz, J. A., et al., "Targeting MYC dependence in cancer by inhibiting BET bromodomains", PNAS (2011); 108(40): 16669-16674.

Millan, D.S., et al., "Design and Synthesis of Inhaled p38 Inhibitors for the Treatment of Chronic Obstructive Pulmonary Disease", Journal of Medicinal Chemistry (2011); 54(22): 7797-7814.
Min, J., et al., "Structure of an HIF-1α-pVHL complex: hydroxyproline recognition in signaling", Science (2002); 296(5574): 1886-1889.
Miyajima, N., et al., "The HSP90 Inhibitor Ganetespib Synergizes with the MET Kinase Inhibitor Crizotinib in both Crizotinib-Sensitive and -Resistant MET-Driven Tumor Models", Cancer Research, Dec. 1, 2013, 73(23), 7022-7033.
Miyazaki M., et al., "Discovery of DS-5272 as a Promising Candidate: A Potent and Orally Active P53-mdm2 Interaction Inhibitor," Bioorganic & Medicinal Chemistry Letters, May 15, 2015, vol. 23, pp. 2360-2367.
Mohler, M. L., et al., "Androgen receptor antagonists: a patent review (2008-2011)", Expert Opinion on Therapeutic Patents (2012); 22(5): 541-565.
Momand, et al., "The mdm-2 oncogene product forms a complex with the p53 protein and inhibits p53-mediated transactivation", Cell, Jun. 26, 1992, 69, 1237-1245.
Mooradian, A. D., et al., "Biological actions of androgens", Endocrine Reviews (1987); 8(1): 1-28.
Muller, G. W., et al., "Amino-substituted thalidomide analogs: potent inhibitors of TNF-α production", Bioorganic & Medicinal Chemistry Letters (1999); 9(11): 1625-1630.
Murray, A.W., "Cell cycle extracts", Methods Cell Biol., 1991, 36, 581-605.
Nagahara, H., et al., "Transduction of full-length TAT fusion proteins into mammalian cells: TAT-p27Kip1 induces cell migration", Nat. Med., Dec. 1998, 4(12), 1449-1452.
Nakamura, K., et al., "Curcumin down-regulates AR gene expression and activation in prostate cancer cell lines", International Journal of Oncology (2002); 21(4): 825-830.
Nakayama, et al. "Ubiquitin ligases: cell-cycle control and cancer," Nat Rev Cancer. May 2006, 6(5), 369-81.
Nathan, M. R., et al., "A Review of Fulvestrant in Breast Cancer", Oncology and Therapy (2017); 5: 17-29.
Nawaz, et al., "Proteasome-dependent degradation of the human estrogen receptor", PNAS USA, Mar. 1999, 96, 1858-1862.
Ndubaku C., et al., "Antagonism of c-IAP and XIAP Proteins is Required for Efficient Induction of Cell Death by Small-molecule IAP Antagonists," ACS Chemical Biology, Jul. 17, 2009, vol. 4, No. 7, pp. 557-566.
Neklesa, T. K., et al., "Greasy tags for protein removal", Nature (2012); 487(7407): 308-309.
Neklesa, T. K. et al., "Small-molecule hydrophobic tagging-induced degradation of HaloTag fusion proteins". Nat. Chem. Biol., 2012, 7(8), 538-543.
Neklesa, T. K., et al., "Targeted protein degradation by PROTACs", Pharmacology & Therapeutics (2017); 174: 138-144.
Nicodeme, E., et al., "Suppression of inflammation by a synthetic histone mimic", Nature (2010); 468: 1119-1123.
Nikolovska-Coleska Z., et al., "Interaction of a Cyclic, Bivalent Smac Mimetic with the X-linked Inhibitor of Apoptosis Protein," Biochemistry, Sep. 16, 2008, vol. 47, No. 37, pp. 9811-9824.
Nishimura et al., "An auxin-based degron system for the rapid depletion of proteins in nonplant cells," Nat Methods. Dec. 2009;6(12):917-22.
Noel, J. K., et al., "Abstract C244: ' Development of the BET Bromodomain inhibitor OTX015", Molecular Cancer Therapy (2013); 12(11 Suppl); 4 pages.
Office Action issued in RU Application No. 2020136948/20(068122), application filed Apr. 9, 2019, 1-11 (English-Translation).
Ohoka, N., et al., "Sniper (TACC3) induces cytoplasmic vacuolization and sensitizes cancer cells to Bortezomib", Cancer Science (2017); 108(5): 1032-1041.
Oishi, I. et al. "The receptor tyrosine kinase Ror2 is involved in non-canonical Wnt5a/JNK signaling pathway", Genes Cells, 2003, 8, 645-654.
Oliff, A., "Farnesyltransferase inhibitors: targeting the molecular basis of cancer", Biochim Biophys Acta., 1999, 1423, C19-30.

(56) References Cited

OTHER PUBLICATIONS

Oost T.K., et al., "Discovery of Potent Antagonists of the Antiapoptotic Protein XIAP for the Treatment of Cancer," Journal of Medicinal Chemistry, Aug. 26, 2004, vol. 47, pp. 4417-4426.
Organ, S.L., et al., "An overview of the c-MET signaling pathway", Therapeutic Advances in Medical Oncology, 2011, 3, S7-S19.
Ostrand-Rosenberg, S., "Animal models of tumor immunity, immunotherapy and cancer vaccines", Current Opinion in Immunol, 2004, 16, 143-150.
Ostrem JM, et al., "Direct small-molecule inhibitors of KRAS: from structural insights to mechanism-based design", Nat Rev Drug Discov., Nov. 2016, 15, 771-785.
Ottis, P., et al., "Assessing different E3 ligases for small molecule induced protein ubiquitination and degradation", ACS Chemical Biology (2017); 12(10): 2570-2578.
Ottis, P., et al., "Proteolysis-targeting chimeras: induced protein degradation as a therapeutic strategy", ACS Chemical Biology (2017); 12(4): 892-898.
Overington, J. P., et al., "How many drug targets are there?", Nat Rev Drug Discov., Dec. 2006, 5, 993-996.
Pantoliano M.W., et al., High-Density Miniaturized Thermal Shift Assays as a General Strategy for Drug Discovery, Journal of Biomolecular Screening, Dec. 2001, vol. 6, No. 6, pp. 429-440.
Parada, L. F., et al., "Human EJ bladder carcinoma oncogene is homologue of Harvey sarcoma virus ras gene", Nature, Jun. 10, 1982, 297, 474-478.
Patch, R. J., et al., "Identification of diaryl ether-based ligands for estrogen-related receptor a as potential antidiabetic agents", Journal of Medicinal Chemistry (2011); 54(3): 788-808.
Pellinen, T., et al., "Small GTPase Rab21 regulates cell adhesion and controls endosomal traffic of β1-integrins", The Journal of Cell Biology, 2006, 173(5), 767-780.
Pepe, A., et al., "Synthesis and structure-activity relationship studies of novel dihydropyridones as androgen receptor modulators", Journal of Medicinal Chemistry (2013); 56(21): 8280-8297.
Perez H.L., "Discovery of Potent Heterodimeric Antagonists of Inhibitor of Apoptosis Proteins (IAPs) With Sustained Antitumor Activity," Journal of Medicinal Chemistry, Feb. 12, 2015, vol. 58, No. 3, pp. 1556-1562.
Perez-Torres, M., et al., "Epidermal Growth Factor Receptor (EGFR) Antibody Down-regulates Mutant Receptors and Inhibits Tumors Expressing EGFR Mutations", J Biol Chem., Dec. 29, 2006, 281(52), 40183-40192.
Peschard, P., et al., "Mutation of the c-Cbl TKB Domain Binding Site on the Met Receptor Tyrosine Kinase Converts It into a Transforming Protein", Molecular Cell, Nov. 2001, 8, 995-1004.
Pfaff, P., et al., "Reversible Spatiotemporal Control of Induced Protein Degradation, by Bistable Photo PROTACS", ACS Chemical Biology (2019); 5: 1682-1690.
Philip, P.A., et al., "Potential for protein kinase C inhibitors in cancer therapy", Cancer Treatment and Research, Jan. 25, 1995, 78, 3-27.
Picard, et al. "Pyogenic Bacterial Infections in Humans with IRAK-4 Deficiency", Science, Mar. 28, 2003, 299, 2076-2079.
Pillay, V., et al., "The Plasticity of Oncogene Addiction: Implications for Targeted Therapies Directed to Receptor Tyrosine Kinases1. 2", Neoplasia, May 2009, 11(5), 448-458.
Pillon, et al., "Binding of Estrogenic Compounds to Recombinant Estrogen Receptor-α: Application to Environmental Analysis", Environmental Health Perspectives, Mar. 2005, 113(3), 278-284.
Pokrovsky, V.I., "Small Medical Encyclopedia," Medicine, 1996, V5, pp. 90-96, and English translation of relevant portion, 12 pages.
Porteus, M., "Design and testing of zinc finger nucleases for use in mammalian cells", Methods Mol Biol, 2008, 435, 47-61.
Poutiainen, P. K., et al., "Design, synthesis, and biological evaluation of nonsteroidal cycloalkane [d] isoxazole-containing androgen receptor modulators", Journal of Medicinal Chemistry (2012); 55(14): 6316-6327.

Powell, C. E., et al., "Chemically Induced Degradation of Anaplastic Lymphoma Kinase (ALK)", Journal of Medicinal Chemistry (2018); 61: 4249-4255.
Powis, G., et al., "New Molecular Targets for Cancer Chemotherapy", ed., Paul Workman and David Kerr, CRC press, London, 1994, 81-95.
Prakash, et al., "Stereoselective Nucleophilic Trifluoromethylation of N-(tert-Butylsulfinyl)imines by Using Trimethyl (trifluoromethyl)silane", Angew Chem Int Ed Engl., Feb. 2, 2001, 40(3), 589-590 (Abstract).
Pratz, K.W., et al., "A pharmacodynamic study of the FLT3 inhibitor KW-2449 yields insight into the basis for clinical response", Blood, Apr. 23, 2009, 113(17), 3938-3946.
Prior et al., "A Comprehensive Survey of Ras Mutations in Cancer", Cancer Res. (2012), 72(10), p. 2457-2467.
Pruett-Miller, S. M., et al. "Attenuation of Zinc Finger Nuclease Toxicity by Small-Molecule Regulation of Protein Levels", PLoS Genetics., Feb. 2009, 5(2), e1000376, 1-11.
Puissant, A., et al., "Targeting MYCN in neuroblastoma by BET bromodomain inhibition", Cancer Discovery (Mar. 2013); 3: 308-323.
Puppala, D., et al., "Development of an aryl hydrocarbon receptor antagonist using the proteolysis-targeting chimeric molecules approach: a potential tool for chemoprevention", Molecular Pharmacology (2008); 73(4): 1064-1071.
Qin, Z., et al., "Benzothiophene selective estrogen receptor modulators with modulated oxidative activity and receptor affinity", Journal of Medicinal Chemistry (2007); 50: 2682-2692.
Rago, C. et al., "Genetic knockouts and knockins in human somatic cells", Nat Protoc., 2007, 2(11), 2734-2746.
Raina, K., et al., "Chemical Inducers of Targeted Protein Degradation", Journal of Biological Chemistry (2010); 285(15): 11057-11060.
Raina, K., et al., "Protac-induced BET protein degradation as a therapy for castration-resistant prostate cancer", Proceedings of the National Academy of Sciences (2016); 113(26): 7124-7129.
Raina, K., et al., "Targeted protein knockdown using small molecule degraders", Current Opinion in Chemical Biology (2017); 39: 46-53.
Remillard, D., et al., "Degradation of the BAF complex factor BRD9 by heterobifunctional ligands", Angewandte Chemie International Edition (2017); 56(21): 5738-5743.
Rew Y., et al., "Discovery of AM-7209, A Potent and Selective 4-Amidobenzoic Acid Inhibitor of the Mdm2-p53 Interaction," Journal of Medicinal Chemistry, Dec. 26, 2014, vol. 57, No. 24, pp. 10499-10511, DOI: 10.1021/jm501550p.
Robertson, J. F. R., "Fulvestrant (Faslodex)—how to make a good drug better", The Oncologist (2007); 12: 774-784.
Robinson, M. S., et al. "Rapid Inactivation of Proteins by Rapamycin-Induced Rerouting to Mitochondria", Developmental Cell, Feb. 16, 2010, 18, 324-331.
Rodriguez-Gonzalez, A., et al., "Targeting steroid hormone receptors for ubiquitination and degradation in breast and prostate cancer", Oncogene (2008); 27(57): 7201-7211.
Rosania, G. R., et al., "Targeting hyperproliferative disorders with cyclin dependent kinase inhibitors", Expert Opinion on Therapeutic Patents (2000); 10(2): 215-230.
Ross S.J., et al., "Targeting KRAS-dependent tumors with AZD4785, a high-affinity therapeutic antisense oligonucleotide inhibitor of KRAS", Sci Transl. Med., Jun. 14, 2017, 9(eaaI5253), 1-13.
Roth, J. et al., "Nucleo-cytoplasmic shuttling of the hdm2 oncoprotein regulates the levels of the p53 protein via a pathway used by the human immunodeficiency virus rev protein", EMBO J., 1998, 17(2), 554-564.
Rotili, D., et al., "Photoactivable peptides for identifying enzyme-substrate and protein-protein interactions", Chemical Communications (2011); 47(5): 1488-1490.
Roy, A. K., et al., "Regulation of androgen action", Vitamins & Hormones (1998); 55: 309-352.
Ruchelman, A., et al., "Isosteric analogs of lenalidomide and pomalidomide: Synthesis and biological activity", Bioorganic & Medicinal Chemistry Letters (2013); 23(1): 360-365.

(56) References Cited

OTHER PUBLICATIONS

Rusch, M., et al., "Identification of Acyl Protein Thioesterases 1 and 2 as the Cellular Targets of the Ras-Signaling Modulators Palmostatin B amd M", Angewandte Chemie International Edition (2011); 50: 9838-9842.
Russ, A. P. et al., "The druggable genome: an update", Drug Discov Today, Dec. 2005, 10(23/24), 1607-1610.
Russian Office Action for Application No. RU2020136948 dated Sep. 7, 2022, 34 pages.
Sakamoto, K. M., et al., "Development of Protacs to target cancer-promoting proteins for ubiquitination and degradation", Molecular & Cellular Proteomics (2003); 2(12): 1350-1358.
Sakamoto, K. M., et al., "Protacs: Chimeric molecules that target proteins to the Skp1-Cullin-F box complex for ubiquitination and degradation", Proceedings of the National Academy of Sciences (2001); 98(15): 8554-8559.
Salami, J., et al., "Waste disposal—An attractive strategy for cancer therapy", Science (2017); 355(6330): 1163-1167.
Sargent, et al., "Synthesis of the cyclophane tetramethoxyturriane: a derivative of the phenolic cyclophanes of Grevillea striata R. Br.", J. Chem. Soc., Perkin Trans. 1, 1990, 129-132 (Abstract).
Sausville, E.A., "Cyclin-dependent kinase modulators studied at the NCI: pre-clinical and clinical studies", Curr. Med. Chem. Anti-Canc Agents, 2003, 3, 47-56.
Scagliotti, G., et al., "Phase III Multinational, Randomized, Double-Blind, Placebo- Controlled Study of Tivantinib (ARQ 197) Plus Erlotinib Versus Erlotinib Alone in Previously Treated Patients With Locally Advanced or Metastatic Nonsquamous Non-Small-Cell Lung Cancer", Journal of Clinical Oncology (2015); 33(24): 2667-2674.
Scharovsky, et al., "Inhibition of ras oncogene: a novel approach to antineoplastic therapy", Journal of Biomedical Science., 2000, 7, 292-298.
Schenkel, L. B., et al., "Discovery of Potent and Highly Selective Thienopyridine Janus Kinase 2 Inhibitors", Journal of Medicinal Chemistry (2011); 54(24): 8440-8450.
Schiedel, M., et al., "Chemically induced degradation of sirtuin 2 (Sirt2) by a proteolysis targeting chimera (Protac) based on sirtuin rearranging ligands (SirReals)", Journal of Medicinal Chemistry (2018); 61(2): 482-491.
Schneekloth, A. R., et al., "Targeted intracellular protein degradation induced by a small molecule: En route to chemical proteomics", Bioorganic & Medicinal Chemistry Letters (2008); 18(22): 5904-5908.
Schneekloth Jr, J. S., et al., "Chemical genetic control of protein levels: selective in vivo targeted degradation", Journal of the American Chemical Society (2004); 126(12): 3748-3754.
Schrader, E. K., et al. "Making It Easier to Regulate Protein Stability", Chemistry & Biology, Sep. 24, 2010, 17, 917-918.
Schubert, U., et al., "CD4 glycoprotein degradation induced by human immunodeficiency virus type 1 Vpu protein requires the function of proteasomes and the ubiquitin-conjugating pathway", Journal of Virology, Mar. 1998, 72(3), 2280-2288.
Scudellari, M., "The protein slayers", Nature (Mar. 21, 2019); 567: 298-300.
Seganish, et al., "Discovery and Structure Enabled Synthesis of 2,6-Diaminopyrimidin-4-one IRAK4 Inhibitors", ACS Med Chem Lett, 2015, 6, 942-947.
Seganish, "Inhibitors of interleukin-1 receptor-associated kinase 4 (IRAK4): a patent review (2012-2015)", Expert Opin Ther Pat, 2016, 26(8), 917-932.
Sekulić, et al."A direct linkage between the phosphoinositide 3-Kinase-AKT signaling pathway and the mammalian target of rapamycin in mitogen-stimulated and transfomled cells", Cancer Res., Jul. 1, 2000, 60, 3504-3513.
Sequist, L. V., et al., "Randomized Phase II Study of Erlotinib Plus Tivantinib Versus Erlotinib Plus Placebo in Previously Treated Non-Small-Cell Lung Cancer", Journal of Clinical Oncology (2011); 29(24): 3307-3315.

Shangary, S., et al., "Temporal activation of p53 by a specific MDM2 inhibitor is selectively toxic to tumors and leads to complete tumor growth inhabitation", PNAS (2008); 105(10): 3933-3938.
Shi, J., et al., "The mechanisms behind the therapeutic activity of BET bromodomain inhibition", Molecular Cell (2014); 54(5): 728-736.
Shih, C. et al., "Isolation of a transforming sequence from a human bladder carcinoma cell line", Cell, May 1982, 29, 161-169.
Shimamura, et al., "Efficacy of BET bromodomain inhabitation in kras-mutant non- small cell lung cancer", Clinical Cancer Research, Nov. 15, 2013, 19(22), 6183-6192.
Sin, N., et al., "The anti-angiogenic agent fumagillin covalently binds and inhibits the methionine aminopeptidase, MetAP-2", Proc Natl. Acad. Sci. USA, Jun. 1997, 94, 6099-6103.
Sinha, S., et al., "Implications for Src kinases in hematopoiesis: signal transduction therapeutics", Journal of Hematotherapy and Stem Cell Research, 1999, 8, 465-480.
Smithgall, T.E., "SH2 and SH3 domains: potential targets for anti-cancer drug design", Journal of Pharmacological and Toxicological Methods., 1995, 34, 125-132.
So, MK, et al., "HaloTag protein-mediated specific labeling of living cells with quantum dots", Biochemical and Biophysical Research Communications, Sep. 26, 2008, 374(3), 419-423.
Solca, F., et al., "Target binding properties and cellular activity of afatinib (BIBW 2992), an irreversible ErbB family blocker", J Pharmacol Exp Ther., 2012, 343(2), 342-350.
Soucy, T.A, et al., "An inhibitor of NEDD8-activating enzyme as a new approach to treat cancer", Nature, Apr. 2009, 458, 732-736.
Sow, et al., "Synthesis of RGD amphiphilic cyclic peptide as fibrinogen or fibronectin antagonist", Letters in Peptide Science, 1997, 4, 455-461.
Stanton, B. Z., et al., "Chemically induced proximity in biology and medicine", Science (2018); 359(117): 1-11.
Staschke et al., "IRAK4 kinase activity is required for Th17 differentiation and TH17-mediated disease", The Journal of Immunology, 2009, 183(1), 568-577.
Stern, D., "Tyrosine kinase signalling in Breast cancer ErbB family receptor tyrosine kinases", Breast cancer Res., 2000, 2(3), 176-183.
Stewart, S. G., et al., "Efforts toward elucidating Thalidomide's molecular target: an expedient synthesis of the first Thalidomide biotin analogue", Organic & Biomolecular Chemistry (2010); 8(18): 4059-4062.
Stewart S.G., et al., "New Thalidomide Analogues Derived through Sonogashira or Suzuki Reactions and Their TNF Expression Inhibition Profiles," Bioorganic & Medicinal Chemistry, Jan. 15, 2010, vol. 18, No. 2, pp. 650-662.
Stoppler, M. C., "Endometriosis definition and facts", MedicineNet.com [online] http://www.medicinenet.com/endometriosis/article.htm (Retrieved on Apr. 5, 2017); 7 pages.
Stoppler, M. C., "What about surgery for Endometriosis?", MedicineNet.com [online] http://www.medicinenet.com/endometriosis/article.htm (Retrieved on Apr. 5, 2017); 7 pages.
Stuhlmiller, T. J., et al., "Inhibition of Lapatinib-Induced Kinome Reprogramming in ERBB2-Positive Breast Cancer by Targeting BET Family Bromodomains", Cell Reports (2015); 11: 390-404.
Suh, N., et al., "Arzoxifene, a new selective estrogen receptor modulator for chemoprevention of experimental breast cancer", Cancer Research (2001); 61: 8412-8415.
Sun, B., et al., "BET protein proteolysis targeting chimera (Protac) exerts potent lethal activity against mantle cell lymphoma cells", Leukemia (2018); 32: 343-352.
Sun D., et al., "Discovery of AMG 232, A Potent, Selective, and Orally Bioavailable MDM2—p53 Inhibitor in Clinical Development," Journal of Medicinal Chemistry, PubMed PMID: 24456472, Epublication: Feb. 5, 2014, Feb. 27, 2014, vol. 57, No. 4, pp. 1454-1472, DOI: 10.1021/jm401753e.
Suzuki et al. "Severe impairment of interleukin-1 and toll-like receptor signaling in mice lacking IRAK-4", Nature, Apr. 18, 2002, 416, 750-756.
Tae, H.S et al., "Identification of hydrophobic tags for the degradation of stabilized proteins", Chembiochem, Mar. 5, 2012, 13(4), 538-541.

(56) References Cited

OTHER PUBLICATIONS

Takayama, et al., "Detection of cytochrome P450 substrates by using a small-molecule droplet array on an NADH-immobilized solid surface", Chembiochem., Dec. 16, 2011, 12, 2748-2752.
Takeuchi, et al., "Receptor tyrosine kinases and targeted cancer therapeutics", Biol Pharm Bull, 2011, 34(12), 1774-1780.
Tallarida, R.J. and R.B. Raffa (1996) "Testing for synergism over a range of fixed ration drug combinations: replacing the isobologram" Life Sci, 58:23-28.
Thelemann, A., et al., "Phosphotyrosine Signaling Networks in Epidermal Growth Factor Receptor Overexpressing Squamous Carcinoma Cells", Molecular & Cellular Proteomics, 2005, 4(4), 356-376.
Toure, M., et al., "Small-molecule PROTACS: new approaches to protein degradation", Angewandte Chemie International Edition (2016); 55(6): 1966-1973.
Trewartha, D., et al., "Advances in prostate cancer treatment", Nature Reviews, Drug Discovery (2013); 12(11): 823-824.
Tsao, M., et al., "Hepatocyte growth factor is predominantly expressed by the carcinoma cells in non-small-cell lung cancer", Human Pathology, Jan. 2001, 32(1), 57-65.
Tsui, K., et al., "Curcumin blocks the activation of androgen and interlukin-6 on prostate-specific antigen expression in human prostatic carcinoma cells", Journal of Andrology (2008); 29(6): 661-668.
Tsuzuki, N., et al. "Adamantine as a brain-directed drug carrier for poorly absorbed drug. 2. AZT derivatives conjugated with the 1-Adamantine moiety," Journal of Pharmaceutical Sciences., 1994, 83(4), 481-484.
Tumey, et al., "Identification and optimization of indolo[2,3-c]quinolone inhibitors of IRAK4", Bioorg Med Chem Lett, 2014, 24, 2066-2072.
Turk, B. E., et al., "Binding of thalidomide to alpha1-acid glycoprotein may be involved in its inhibition of tumor necrosis factor alpha production", Proceedings of the National Academy of Sciences (1996); 93(15): 7552-7556.
Vahid, F., et al., "The role dietary of bioactive compounds on the regulation of histone acetylases and deacetylases: A review", Gene, 2015, 562, 8-15.
Vallee, F., et al., "Tricyclic Series of Heat Shock Protein 90 (HSP90) Inhibitors Part I: Discovery of Tricyclic Imidazo[4,5-c] Pyridines as Potent Inhibitors of the Hsp90 Molecular Chaperone", Journal of Medicinal Chemistry (2011); 54(20): 7206-7219.
Vamos M., et al., "Expedient Synthesis of Highly Potent Antagonists of Inhibitor of Apoptosis Proteins (IAPs) with Unique Selectivity for ML-IAP," ACS Chemical Biology, Apr. 19, 2013, vol. 8, No. 4, pp. 725-732.
Van Eis, M. J., et al., "2,6-Naphthyridines as potent and selective inhibitors of the novel protein kinase C isozymes", Bioorganic & Medicinal Chemistry Letters (2011); 21(24): 7367-7372.
Van Molle, I., et al., "Dissecting fragment-based lead discovery at the von Hippel-Lindau protein: hypoxia inducible factor 1α protein-protein interface", Chemistry & Biology (2012); 19(10): 1300-1312.
Vassilev, L. T., et al., "In vivo activation of the p53 pathway by small-molecule antagonists of MDM2", Science (Feb. 6, 2004); 303: 844-848.
Vazquez A., et al., "The Genetics of the p53 Pathway, Apoptosis and Cancer Therapy," Nature Reviews Drug Discovery, Dec. 2008, vol. 7, pp. 979-987.
Vlahos et al. "A specific inhibitor of phosphatidylinositol 3-kinase, 2-(4-morpholinyl)-8-phenyl-4H-1-benzopyran-4-one (LY294002)", J. Biol. Chem., Feb. 18, 1994, 269(7), 5241-5248.
Vogelstein, et al., "Surfing the p53 network", Nature, Nov. 16, 2000, 408, 307-310.
Vu, B., et al., "Discovery of RG7112: a small-molecule MDM2 inhibitor in clinical development", ACS Medicinal Chemistry Letters (2013); 4: 466-469.

Wang, C., et al., "Estrogen induces c-myc gene expression via an upstream enhancer activated by the estrogen receptor and the AP-1 transcription factor", Molecular Endocrinology (Sep. 2011); 25(9): 1527-1538.
Wang J., et al., "Discovery of Novel Second Mitochondrial-derived Activator of Caspase Mimetics as Selective Inhibitor or Apoptosis Protein Inhibitors," Journal of Pharmacology and Experimental Therapeutics, May 2014, vol. 349, No. 2, pp. 319-329.
Wang, P., et al., "Use of computational modeling approaches in studying the binding interactions of compounds with human estrogen receptors," Steroids, Jan. 1, 2016, 105, 26-41.
Wang, S., et al., "Cancer cells harboring MET gene amplification activate alternative signaling pathways to escape MET inhibition but remain sensitive to Hsp90 inhibitors", Cell Cycle, Jul. 1, 2009, 8(13), 2050-2056.
Weinmann, H., "Cancer Immunotherapy: Selected Targets and Small-Molecule Modulators", ChemMedChem, 2016, 11, 450-466.
Weisberg, et al. "Discovery and characterization of novel mutant FLT3 kinase inhibitors", Mol Cancer Ther., Sep. 2010, 9(9), 2468-2477.
Weissman, A., "Regulating protein degradation by ubiquitination", Immunology Today, 1997, 18(4), 189-198.
Whitehead, K.A., et al., "Knocking down barriers: advances in siRNA delivery", Nat Rev Drug Discov., Feb. 2009, 8, 129-138.
Wietek C., et al., "IRAK-4: a new drug target in inflammation, sepsis, and autoimmunity", Mol Interv., 2002, 2, 212-215.
Willson, T. M., et al., "3-[4-(1,2-Diphenylbut-1-Enyl)Phenyl]Acrylic Acid: A non-steroidal estrogen with functional selectivity for bone over uterus in rats", Journal of Medicinal Chemistry (1994); 37 (11): 1550-1552.
Winston, J., et al., "A family of mammalian F-box proteins", Curr. Bio., 1999, 9, 1180-1182 (6 pages total).
Winter, G. E., et al., "Phthalimide conjugation as a strategy for in vivo target protein degradation", Science (2015); 348(6241): 1376-1381.
Wislez, M., et al. "Mutations at the splice sites of exon 14 of MET gene: a new target for sarcomatoid carcinomas?", Annals of Translational Medicine, 2016, 4(5), 96, 1-2.
Woo, et al., "Taxol inhibits progression of congenital polycystic kidney disease", Nature, 368, Apr. 21, 1994, 750-753.
Wood K, et al., "Prognostic and predictive value in KRAS in non-small-cell lung cancer. A Review", JAMA Oncol., Jun. 1, 2016, 2(6), 805-12.
Wright, L., et al., "Structure-Activity Relationships in Purine-Based Inhibitor Binding to HSP90 Isoforms", Chemistry & Biology (2004); 11(6): 775-785.
Wu, et al. "The p53-mdm-2 autoregulatory feedback loop", Genes Dev., 1993, 7, 1126-1132.
Wurz, R et al., "Oxopyrido[2,3-d]pyrimidines as covalent L858R/T790M mutant selective epidermal growth factor receptor (EGFR) inhibitors", ACS Medicinal Chemistry Letters, 2015, 6, 987-992.
Wyce, A., et al., "Inhibition of BET bromodomain proteins as a therapeutic approach in prostate cancer", Oncotarget (Dec. 2013); 4(12): 2419-2429.
Xie, T., et al., "Pharmacological targeting of the Pseudokinase Her3", Nat Chem Biol., Dec. 2014, 10(12), 1006-1012.
Xu, A.M., et al., "Receptor Tyrosine Kinase Coactivation Networks in Cancer", Cancer Research, May 15, 2010, 70, 3857-3860.
Xu, S. et al. (2012) "Design, synthesis and biological evaluation of new molecules inhibiting epidermal growth factor receptor threonine 790->methionine790 mutant" Med Chem Commun, 3:1155-1159.
Xu, T. et al., "C5-substituted pyrido[2,3-d]pyrimidin-7-ones as highly specific kinase inhibitors targeting the clinical resistance-related EGFR T790M mutant", Medicinal Chemistry Communications 2015, 6, 1693-1697.
Yamamoto, T., et al., "Ras-Induced transformation and signaling pathway", Journal of Biochemistry, 1999, 126(5), 799-803.
Yang, et al., "Signaling events inducted by lipopolysaccharide-activated toll-like receptor 2", J. Immunol., 1999, 163(2), 639-643.
Yao, et al., BRAF Mutants Evade ERK-Dependent Feedback by Different Mechanisms that Determine Their Sensitivity to Pharmacologic Inhibition, Cancer Cell, Sep. 14, 2015, pp. 370-383.

(56) References Cited

OTHER PUBLICATIONS

Yaron, A., et al., "Identification of the receptor component of the IkBα-ubiquitin ligase", Nature, Bol, Dec. 10, 1998, 396, 590-594.
Yaron, A., et al., "Inhibition of NF-κB cellular function via specific targeting of the IKB-ubiquitin ligase", EMBO J., 1997, 16(21), 6486-6494.
Yasuda, H. et al. (Dec. 2013) "Structural, Biochemical, and Clinical Characterization of Epidermal Growth Factor Receptor (EGFR) Exon 20 Insertion Mutations in Lung Cancer" Sci Transl Med, 5(216):216ra177; DOI: 10.1126/scitranslmed.3007205, 10 pages.
Yeh, E., et al., "Ubiquitin-like proteins: new wines in new bottles", Gene, 2000, 248(1-2), 1-14.
Yeh, J., et al., "The antiangiogenic agent TNP-480 requires p53 and P21CIP/WAF for endothelial cell growth arrest", Proc. Natl. Acad. Sci. USA, 2000, 97(23), 12782-12787.
Yewale, C., et al., "Epidermal growth factor receptor targeting in cancer: A review of trends and strategies", Biomaterials, 2013, 34, 8690-8707.
You, A.J., et al., "A miniaturized arrayed assay format for detecting small molecule-protein interactions in cells", Chem. Biol., 1997, 4(12), 969-975.
Yuan TL, et al., "Development of siRNA payloads to target KRAS-mutant cancer", Cancer Discov., Oct. 2014, 4(10), 1182-1197.
Zengerle, M., et al., "Selective small molecule induced degradation of the BET bromodomain protein BRD4", ACS Chemical Biology (2015); 10(8): 1770-1777.
Zhang, B., et al., "Small-molecule MDM2-p53 inhibitors: recent advances", Future Medicinal Chemistry (2015); 7(5): 631-645.
Zhang, D., et al., "Targeted Degradation of Proteins by Small Molecules: A Novel Tool for Functional Proteomics", Combinatorial Chemistry & High Throughput Screening (2004); 7(7): 689-697.
Zhao, Y., et al., "Small-molecule inhibitors of the MDM2-p53 protein-protein interaction (MDM2 inhibitors) in clinical trials for cancer treatment", Journal of Medicinal Chemistry (2015); 58: 1038-1052.
Zheng, N., et al., "Structure of a c-Cbl-UbcH7 complex: Ring domain function in ubiquitin-protein ligases", Cell, Aug. 18, 2000, 102, 533-539.
Zhong H., et al., "Modulation of Hypoxia-Inducible Factor 1α Expression by the Epidermal Growth Factor/Phosphatidylinositol 3-Kinase/PTEN/AKT/FRAP Pathway in Human Prostate Cancer Cells: Implications for Tumor Angiogenesis and Therapeutics," Cancer Research, Mar. 15, 2000, vol. 60, No. 6, pp. 1541-1545.
Zhou, B., et al., "Discovery of a Small-Molecule Degrader of Bromodomain and Extra-Terminal (BET) Proteins with Picomolar Cellular Potencies and Capable of Achieving Tumor Regression", Journal of Medicinal Chemistry (2018); 61(2): 462-481.
Zhou H., et al., "Targets of Curcumin," Current Drug Targets, Mar. 1, 2011, vol. 12, No. 3, pp. 332-347.
Zhou, P., et al., "Harnessing the ubiquitination machinery to target the degradation of specific cellular proteins", Mol. Cell, Sep. 2000, 6, 751-756.
Zhulenko, V. N., et al., "Pharmacology", Moscow, "KolosS" Publishing House (2008); pp. 34-35; 4 pages with English summary.
Zillhardt, M., et al., "Foretinib (GSK1363089), an Orally Available Multikinase Inhibitor of c-Met and VEGFR-2, Blocks Proliferation, Induces Anoikis, and Impairs Ovarian Cancer Metastasis", Clinical Cancer Research (2011); 17: 4042-4051.
Zuber, J., et al., "RNAi screen identifies Brd4 as a therapeutic target in acute myeloid leukaemia", Nature (2011); 478(7370): 524-528.
ClinicalTrials.gov Identifier: NCT01587703, "A Study to Investigate the Safety, Pharmacokinetics, Pharmacodynamics, and Clinical Activity of GSK525762 in Subjects With NUT Midline Carcinoma (NMC) and Other Cancers" [online] https://clinicaltrials.gov/study/NCT01587703?a=23&tab=history#version-content-panel (First Posted—Apr. 30, 2012, Last Update Posted—Apr. 13, 2015, Access Date—Jul. 17, 2024); 20 pages.
ClinicalTrials.gov Identifier: NCT01713582, "A Dose-finding Study of the Bromodomain (Brd) Inhibitor OTX015/ Birabresib (MK-8628) in Hematologic Malignancies (MK-8628-001)" [online] https://clinicaltrials.gov/study/NCT01713582?tab=history&a=2#version-content-panel (First Posted—Oct. 24, 2012, Last Update Posted—Apr. 1, 2013, Access Date—Jul. 17, 2024); 13 pages.
ClinicalTrials.gov Identifier: NCT01949883, "A Phase 1 Study Evaluating CPI-0610 in Patients With Progressive Lymphoma" [online] https://clinicaltrials.gov/study/NCT01949883?tab=history&a=7#version-content-panel (First Posted—Sep. 25, 2013, Last Update Posted—Feb. 18, 2015, Access Date—Jul. 17, 2024); 13 pages.
ClinicalTrials.gov Identifier: NCT01987362, "A Two Part Study of RO6870810. Dose-Escalation Study in Participants With Advanced Solid Tumors and Expansion Study in Participants With Selected Malignancies" [online] https://clinicaltrials.gov/study/NCT01987362?tab=history&a=7#version-content-panel (First Posted—Nov. 19, 2013, Last Update Posted—Mar. 5, 2015, Access Date—Jul. 17, 2024); 13 pages.
Co-pending U.S. Appl. No. 18/456,718, inventor Crew; Andrew P. et al., filed on Aug. 28, 2023.
Co-pending U.S. Appl. No. 18/747,080, inventor Allan; Laura E. N. et al., filed on Jun. 18, 2024.
Ito, T., et al., "Supporting Online Material for Identification of a Primary Target of Thalidomide Teratogenicity", Science (2010); 327(5971):1345-1350; 29 pages. DOI: 10.1126/science.1177319.

\* cited by examiner

CEREBLON LIGANDS AND BIFUNCTIONAL COMPOUNDS COMPRISING THE SAME

CROSS-REFERENCE TO RELATED APPLICATIONS

This application is a Continuation of U.S. patent application Ser. No. 15/953,108, filed on Apr. 13, 2018, which is a Continuation-in-Part of U.S. patent application Ser. No. 14/792,414, filed on Jul. 6, 2015, which claims the benefit of U.S. Provisional Patent Application 62/171,090, filed on Jun. 4, 2015, and is a Continuation-in-Part of U.S. patent application Ser. No. 14/686,640, filed on Apr. 14, 2015, which claims priority to U.S. Provisional Application Ser. No. 61/979,351, filed on Apr. 14, 2014; all of which are incorporated herein by reference in their entirety.

INCORPORATION BY REFERENCE

U.S. patent application Ser. No. 15/230,354, filed on Aug. 5, 2016, published as U.S. Patent Application Publication No. 2017/0065719; and U.S. patent application Ser. No. 15/801,243, filed on 1 Nov. 2017; and U.S. patent application Ser. No. 15/206,497 filed 11 Jul. 2016; and U.S. patent application Ser. No. 15/209,648 filed 13 Jul. 2016; and U.S. patent application Ser. No. 15/730,728, filed on Oct. 11, 2017, U.S. patent application Ser. No. 15/829,541, filed on Dec. 1, 2017; U.S. patent application Ser. No. 15/881,318, filed on Jan. 26, 2018; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 14/371,956, filed on Jul. 11, 2014, published as U.S. Patent Application Publication No. 2014/0356322; and U.S. patent application Ser. No. 15/074,820, filed on Mar. 18, 2016, published as U.S. Patent Application Publication No. 2016/0272639; and U.S. patent application Ser. No. 15/885,671, filed on 31 Jan. 2018, are incorporated herein by reference in their entirety. Furthermore, all references cited herein are incorporated by reference herein in their entirety.

FIELD OF THE INVENTION

The description provides imide-based compounds, including bifunctional compounds comprising the same, and associated methods of use. The bifunctional compounds are useful as modulators of targeted ubiquitination, especially with respect to a variety of polypeptides and other proteins, which are degraded and/or otherwise inhibited by bifunctional compounds according to the present disclosure.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped.

One E3 ligase with therapeutic potential is the von Hippel-Lindau (VHL) tumor suppressor. VHL comprises the substrate recognition subunit/E3 ligase complex VCB, which includes elongins B and C, and a complex including Cullin-2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. We generated the first small molecule ligands of Von Hippel Lindau (VHL) to the substrate recognition subunit of the E3 ligase, VCB, an important target in cancer, chronic anemia and ischemia, and obtained crystal structures confirming that the compound mimics the binding mode of the transcription factor HIF-1α, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Thalidomide, which has been approved for the treatment of a number of immunological indications, has also been approved for the treatment of certain neoplastic diseases, including multiple myeloma. In addition to multiple myeloma, thalidomide and several of its analogs are also currently under investigation for use in treating a variety of other types of cancer. While the precise mechanism of thalidomide's anti-tumor activity is still emerging, it is known to inhibit angiogenesis. Recent literature discussing the biology of the imides includes Lu et al Science 343, 305 (2014) and Kronke et al Science 343, 301 (2014).

Significantly, thalidomide and its analogs e.g. pomolinamiode and lenalinomide, are known to bind cereblon. These agents bind to cereblon, altering the specificity of the complex to induce the ubiquitination and degradation of Ikaros (IKZF1) and Aiolos (IKZF3), transcription factors essential for multiple myeloma growth. Indeed, higher expression of cereblon has been linked to an increase in efficacy of imide drugs in the treatment of multiple myeloma.

An ongoing need exists in the art for effective treatments for disease, especially hyperplasias and cancers, such as multiple myeloma. However, non-specific effects, and the inability to target and modulate certain classes of proteins altogether, such as transcription factors, remain as obstacles to the development of effective anti-cancer agents. As such, small molecule therapeutic agents that leverage or potentiate cereblon's substrate specificity and, at the same time, are "tunable" such that a wide range of protein classes can be targeted and modulated with specificity would be very useful as a therapeutic.

BRIEF SUMMARY OF THE INVENTION

The present disclosure describes bifunctional compounds which function to recruit endogenous proteins to an E3 Ubiquitin Ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, e.g., multiple myeloma.

As such, in one aspect the disclosure provides novel imide-based compounds as described herein.

In an additional aspect, the disclosure provides bifunctional or PROTAC compounds, which comprise an E3 Ubiquitin Ligase binding moiety (i.e., a ligand for an E3 Ubiquitin Ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein. In a preferred embodiment, the ULM is a cereblon E3 Ubiquitin Ligase binding moiety (i.e., a "CLM"). For example, the structure of the bifunctional compound can be depicted as:

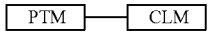

The respective positions of the PTM and CLM moieties as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

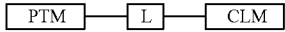

where PTM is a protein/polypeptide targeting moiety, L is a linker, and CLM is a cereblon E3 ubiquitin ligase binding moiety.

In certain preferred embodiments, the E3 Ubiquitin Ligase is cereblon. As such, in certain additional embodiments, the CLM of the bifunctional compound comprises chemistries such as imide, amide, thioamide, thioimide derived moieties. In additional embodiments, the CLM comprises a phthalimido group or an analog or derivative thereof. In still additional embodiments, the CLM comprises a phthalimido-glutarimide group or an analog or derivative thereof. In still other embodiments, the CLM comprises a member of the group consisting of thalidomide, lenalidomide, pomalidomide, and analogs or derivatives thereof.

In certain embodiments, the compounds as described herein comprise multiple CLMs, multiple PTMs, multiple chemical linkers or a combination thereof.

In any aspect or embodiment described herein, the ULM (ubiquitination ligase modulator) can be Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM), or an IAP E3 ubiquitin ligase binding moiety (i.e., a "ILM"). In any aspect or embodiments described herein, the bifunctional compound includes at least one additional E3 ligase binding moiety selected from the group consisting of VLM, VLM', CLM, CLM', MLM, MLM', ILM, ILM', or a combination thereof. For example, there can be at least 1, 2, 3, 4, or 5 additional E3 ligase binding moieties.

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In yet another aspect, the present disclosure provides a method of ubiquitinating/degrading a target protein in a cell. In certain embodiments, the method comprises administering a bifunctional compound as described herein comprising an CLM and a PTM, preferably linked through a linker moiety, as otherwise described herein, wherein the CLM is coupled to the PTM and wherein the CLM recognizes a ubiquitin pathway protein (e.g., an ubiquitin ligase, preferably an E3 ubiquitin ligase such as, e.g., cereblon) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In an additional aspect, the description provides a method for assessing (i.e., determining and/or measuring) a CLM's binding affinity. In certain embodiments, the method comprises providing a test agent or compound of interest, for example, an agent or compound having an imide moiety, e.g., a phthalimido group, phthalimido-glutarimide group, derivatized thalidomide, derivatized lenalidomide or derivatized pomalidomide, and comparing the cereblon binding affinity and/or inhibitory activity of the test agent or compound as compared to an agent or compound known to bind and/or inhibit the activity of cereblon.

In still another aspect, the description provides methods for treating or emeliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present disclosure. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figure 1A:
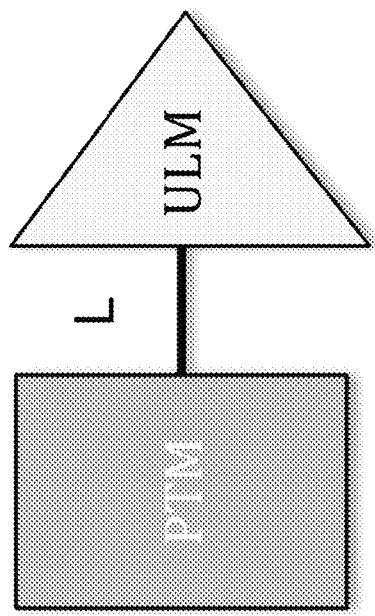
FIGS. 1A and 1B. Illustration of general principle for PROTAC function. (A) Exemplary PROTACs comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. (B) Illustrates the functional use of the PROTACs as described herein. Briefly, the ULM recognizes and binds to a specific E3 Ubiquitin Ligase, and the PTM binds and recruits a target protein bringing it into close proximity to the E3 Ubiquitin Ligase. Typically, the E3 Ubiquitin Ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degration by the proteosomal machinery of the cell.
Figure 1B:
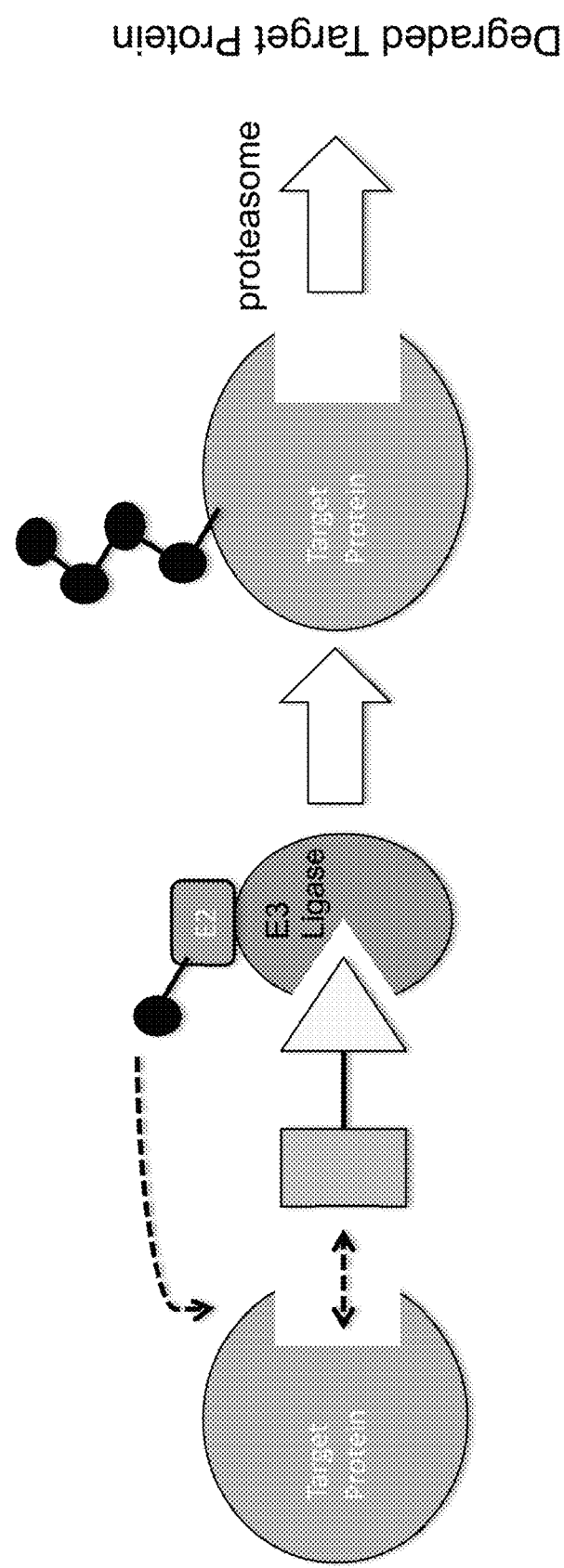

Presently described are compositions and methods that relate to the surprising and unexpected discovery that an E3 Ubiquitin Ligase protein, e.g., cereblon, ubiquitinates a target protein once it and the target protein are placed in proximity by a bifunctional or chimeric construct that binds the E3 Ubiquitin Ligase protein and the target protein. Accordingly the present disclosure provides such compounds and compositions comprising an E3 Ubiquintin Ligase binding moiety ("ULM") coupled to a protein target binding moiety ("PTM"), which result in the ubiquitination of a chosen target protein, which leads to degradation of the target protein by the proteasome (see FIGS. 1A and 1B). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a ubiquitin ligase, such as IAP, VHL, MDM2, or cereblon. The compounds also comprise a moiety that is capable of binding to target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "Ubiquitin Ligase" refers to a family of proteins that facilitate the transfer of ubiquitin to a specific substrate protein, targeting the substrate protein for degradation. For example, cereblon is an E3 Ubiquitin Ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Compounds and Compositions

In one aspect, the description provides compounds comprising an E3 Ubiquitin Ligase binding moiety ("ULM") that is a cereblon E3 Ubiquitin Ligase binding moiety ("CLM"). In one embodiment, the CLM is coupled to a chemical linker (L) according to the structure:

L-CLM    (I)

wherein L is a chemical linker group and CLM is a cereblon E3 Ubiquitin Ligase binding moiety. The number and/or relative positions of the moieties in the compounds illustrated herein is provided by way of example only. As would be understood by the skilled artisan, compounds as described herein can be synthesized with any desired number and/or relative position of the respective functional moieties.

The terms ULM and CLM are used in their inclusive sense unless the context indicates otherwise. For example, the term ULM is inclusive of all ULMs, including those that bind cereblon (i.e., CLMs). Further, the term CLM is inclusive of all possible cereblon E3 Ubiquitin Ligase binding moieties.

In another aspect, the present disclosure provides bifunctional or multifunctional PROTAC compounds useful for regulating protein activity by inducing the degradation of a target protein. In certain embodiments, the compound comprises a CLM coupled, e.g., linked covalently, directly or indirectly, to a moiety that binds a target protein (i.e., protein targeting moiety or "PTM"). In certain embodiments, the CLM and PTM are joined or coupled via a chemical linker (L). The CLM recognizes the cereblon E3 ubiquitin ligase and the PTM recognizes a target protein and the interaction of the respective moieties with their targets facilitates the degradation of the target protein by placing the target protein in proximity to the ubiquitin ligase protein. An exemplary bifunctional compound can be depicted as:

PTM-CLM    (II)

In certain embodiments, the bifunctional compound further comprises a chemical linker ("L"). For example, the bifunctional compound can be depicted as:

PTM-L-CLM    (III)

wherein PTM is a protein/polypeptide targeting moiety, L is a linker, and CLM is a cereblon E3 ligase binding moiety.

In certain embodiments, the compounds as described herein comprise multiple PTMs (targeting the same or different protein targets), multiple CLMs, one or more ULMs (i.e., moieties that bind specifically to another E3 Ubiquitin Ligase, e.g., VHL) or a combination thereof. In any of the aspects of embodiments described herein, the PTMs, CLMs, and ULMs can be coupled directly or via one or more chemical linkers or a combination thereof. In additional embodiments, where a compound has multiple ULMs, the ULMs can be for the same E3 Ubiquintin Ligase or each respective ULM can bind specifically to a different E3 Ubiquitin Ligase. In still further embodiments, where a compound has multiple PTMs, the PTMs can bind the same target protein or each respective PTM can bind specifically to a different target protein.

In another embodiment, the description provides a compound which comprises a plurality of CLMs coupled directly or via a chemical linker moiety (L). For example, a compound having two CLMs can be depicted as:

CLM-CLM or    (IV)

CLM-L-CLM    (V)

In certain embodiments, where the compound comprises multiple CLMs, the CLMs are identical. In additional embodiments, the compound comprising a plurality of CLMs further comprises at least one PTM coupled to a CLM directly or via a chemical linker (L) or both. In certain additional embodiments, the compound comprising a plurality of CLMs further comprises multiple PTMs. In still additional embodiments, the PTMs are the same or, optionally, different. In still further embodiments, wherein the PTMs are different the respective PTMs may bind the same protein target or bind specifically to a different protein target.

In additional embodiments, the description provides a compound comprising at least two different CLMs coupled directly or via a chemical linker (L) or both. For example, such a compound having two different CLMs can be depicted as:

CLM-CLM' or    (VI)

CLM-L-CLM'    (VII)

wherein CLM' indicates a cereblon E3 Ubiquitin Ligase binding moiety that is structurally different from CLM. In certain embodiments, the compound may comprise a plurality of CLMs and/or a plurality of CLM's. In further embodiments, the compound comprising at least two different CLMs, a plurality of CLMs, and/or a plurality of CLM's further comprises at least one PTM coupled to a CLM or a CLM' directly or via a chemical linker or both. In any of the embodiments described herein, a compound comprising at least two different CLMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM or CLM (or ULM' or CLM').

In a preferred embodiment, the CLM comprises a moiety that is a ligand of the cereblon E3 Ubiquitin Ligase (CRBN). In certain embodiments, the CLM comprises a chemotype from the "imide" class of molecules. In certain additional embodiments, the CLM comprises a phthalimido group or an analog or derivative thereof. In still additional embodiments, the CLM comprises a phthalimido-glutarimide group or an analog or derivative thereof. In still other embodiments, the CLM comprises a member of the group consisting of thalidomide, lenalidomide, pomalidomide, and analogs or derivatives thereof.

In additional embodiments, the description provides the compounds as described herein including their enantiomers, diastereomers, solvates and polymorphs, including pharmaceutically acceptable salt forms thereof, e.g., acid and base salt forms.

Exemplary Cereblon Binding and/or Inhibiting Compounds

In one aspect the description provides compounds useful for binding and/or inhibiting cereblon E3 Ubiquitin Ligase binding moiety. In certain embodiments, the compound has a chemical structure that includes at least one of (e.g., the compound has a chemical structure selected from the group consisting of):

Neo-Imide Compounds

In one aspect the description provides compounds useful for binding and/or inhibiting cereblon. In certain embodiments, the compound is selected from the group consisting of chemical structures.

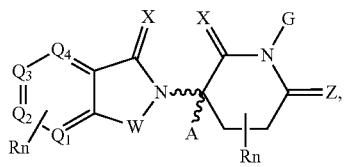
(a1)

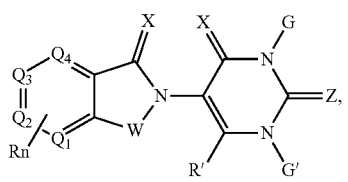
(b)

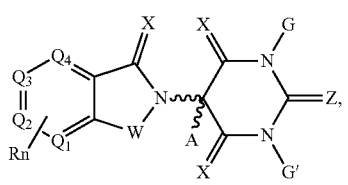
(c)

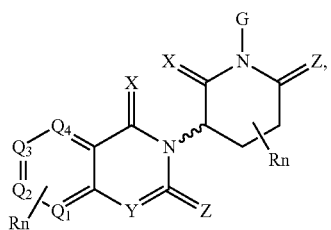
(d1)

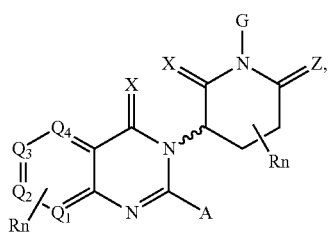
(e)

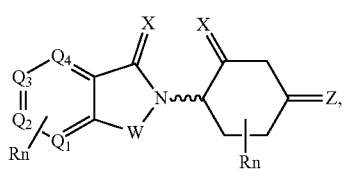
(f)

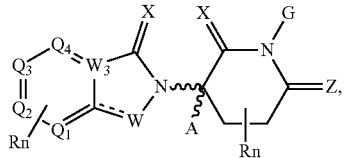
(a2)

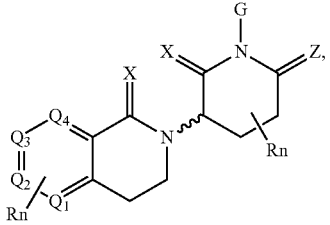
(d2)

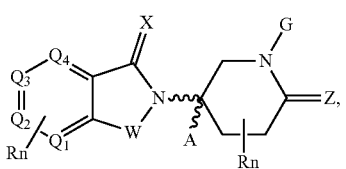
(a3)

wherein:
W of Formulas (a) through (e) is independently selected from the group $CH_2$, CHR, C=O, $SO_2$, NH, cyclopropyl group, cyclobutyl group, and N-alkyl, $W_3$ is selected from C or N;

X of Formulas (a) through (e) is independently selected from the group O, S and $H_2$;

Y of Formulas (a) through (e) is independently selected from the group $CH_2$, —C=CR', NH, N-alkyl, N-aryl, N-hetaryl, N-cycloalkyl, N-heterocyclyl, O, and S;

Z of Formulas (a) through (e) is independently selected from the group O, and S or $H_2$ except that both X and Z cannot be $H_2$;

G and G' of Formulas (a) through (e) are independently selected from the group H, alkyl (linear, branched, optionally substituted), OH, R'OCOOR, R'OCONRR', $CH_2$-heterocyclyl optionally substituted with R', and benzyl optionally substituted with R';

Q1-Q4 of Formulas (a) through (e) represent a carbon C substituted with a group independently selected from R', N or N-oxide;

A of Formulas (a) through (e) is independently selected from the group H, alkyl (linear, branched, optionally substituted), cycloalkyl, Cl and F;

R of Formulas (a) through (e) comprises, but is not limited to: —CONR'R", —OR', —NR'R", —SR', —$SO_2$R', —$SO_2$NR'R", —CR'R"—, —CR'NR'R"—, (—CR'O)$_n$, R", -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R')R", —$SF_5$ and —$OCF_3$ R' and R" of Formulas (a) through (e) are independently selected from a bond, H, alkyl, cycloalkyl, aryl, heteroaryl, heterocyclic, —C(=O)R, heterocyclyl, each of which is optionally substituted;

n' of Formulas (a) through (e) is an integer from 1-10 (e.g., 1-4);

⁓⁓⁓ of Formulas (a) through (e) represents a bond that may be stereospecific ((R) or (S)) or non-stereospecific;

═══ represents a single bond or a double bond;

⁓⁓⁓ represents a bond that may be stereospecific ((R) or (S)) or non-stereospecific; and Rn comprises 1-4 independent functional groups, optionally substituted linear or branched alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted aryl (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted

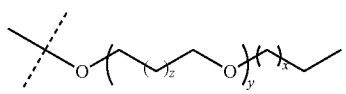

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted

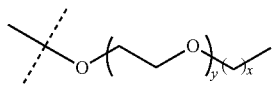

(e.g., optionally substituted with one or more halogen, alkyl, haloalky, fluoroalkyl, cycloalkyl (e.g., a C3-C6 cycloalkyl), or aryl (e.g., C5-C7 aryl)), or atoms; and each of x, y, and z are independently 0, 1, 2, 3, 4, 5, or 6, Exemplary CLMs In any of the compounds described herein, the CLM comprises a chemical structure selected from the group:

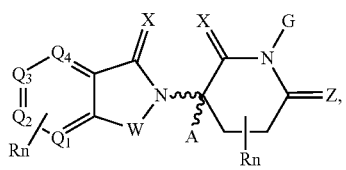
(a1)

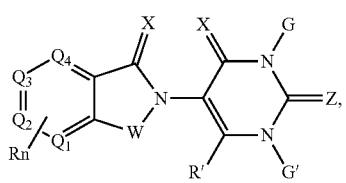
(b)

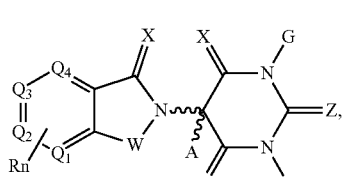
(c)

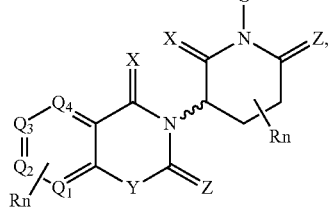
(d1)

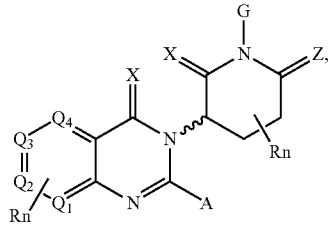
(e)

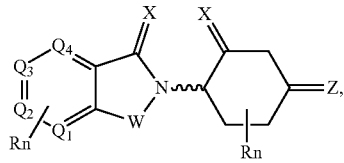
(f)

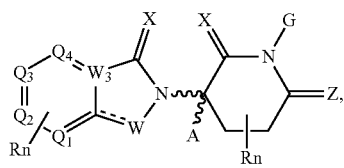
(a2)

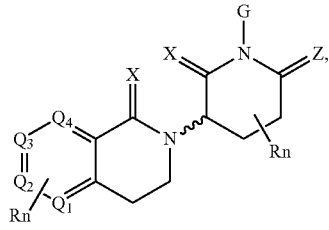
(d2)

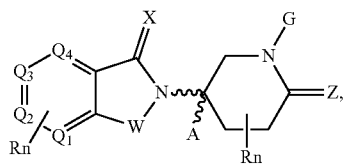
(a3)

wherein:
W of Formulas (a) through (e) is independently selected from the group $CH_2$, CHR, C=O, $SO_2$, NH, N, optionally substituted cyclopropyl group, optionally substituted cyclobutyl group, and N-alkyl;

$W_3$ is selected from C or N,

X of Formulas (a) through (e) is independently selected from the group O, S and $H_2$, Y of Formulas (a) through (e) is independently selected from the group CH2, —C=CR', NH, N-alkyl, N-aryl, N-hetaryl, N-cycloalkyl, N-heterocyclyl, O, and S;

Z of Formulas (a) through (e) is independently selected from the group O, and S or H2 except that both X and Z cannot be H2;

G and G' of Formulas (a) through (e) are independently selected from the group H, alkyl (linear, branched), OH, R'OCOOR, R'OCONRR", CH$_2$-heterocyclyl optionally substituted with R', and benzyl optionally substituted with R';

Q1-Q4 of Formulas (a) through (e) represent a carbon C substituted with a group independently selected from R', N or N-oxide;

A of Formulas (a) through (e) is independently selected from the group H, alkyl (linear, branched, optionally substituted), cycloalkyl, Cl and F, R of Formulas (a) through (e) comprises, but is not limited to: —CONR'R", —OR', —NR'R", —SR', —SO2R', —SO2NR'R", —CR'R"—, —CR'NR'R"—, (—CR'O)$_{n'}$ R", -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —CF3, —CN, —NR'SO2NR'R", —NR'CONR'R", —CONR'COR", —NR'C(=N—CN)NR'R", —C(=N—CN)NR'R", —NR'C(=N—CN)R", —NR'C(=C—NO2)NR'R", —SO2NR'COR", —NO2, —CO2R', —C(C=N—OR')R", —CR'=CR'R", —CCR', —S(C=O)(C=N—R')R", —SF5 and —OCF3

R' and R" of Formulas (a) through (e) are independently selected from a bond, H, alkyl, cycloalkyl, aryl, heteroaryl, heterocyclic, —C(=O)R, heterocyclyl, each of which is optionally substituted;

n' of Formulas (a) through (e) is an integer from 1-10 (e.g., 1-4);

⁓ represents a single bond or a double bond;

⁓⁓⁓ of Formulas (a) through (e) represents a bond that may be stereospecific ((R) or (S)) or non-stereospecific;

Rn comprises 1-4 independent functional groups, optionally substituted linear or branched alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted aryl (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted

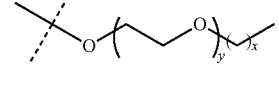

(e.g., optionally substituted with one or more halogen, alkyl, haloalky, fluoroalkyl, cycloalkyl (e.g., a C3-C6 cycloalkyl), or aryl (e.g., C5-C7 aryl)), or atoms; and each of x, y, and z are independently 0, 1, 2, 3, 4, 5, or 6.

In certain embodiments described herein, the CLM or ULM comprises a chemical structure selected from the group:

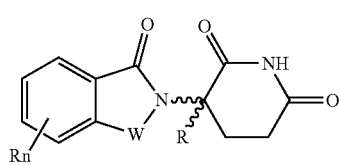

Formula (g)

wherein:

W of Formula (g) is independently selected from the group CH$_2$, C=O, NH, and N-alkyl;

R of Formula (g) is independently selected from a H, methyl, alkyl (e.g., a or C1-C6 alkyl (linear, branched, optionally substituted));

⁓⁓⁓ of Formula (g) represents a bond that may be stereospecific ((R) or (S)) or non-stereospecific; and Rn comprises 1-4 independent functional groups, optionally substituted linear or branched alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted aryl (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted

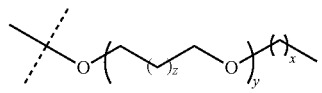

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted

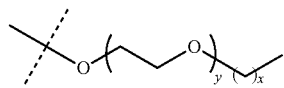

(e.g., optionally substituted with one or more halogen, alkyl, haloalky, fluoroalkyl, cycloalkyl (e.g., a C3-C6 cycloalkyl), or aryl (e.g., C5-C7 aryl)), or atoms.

In any of the embodiments described herein, the W, X, Y, Z, G, G', R, R', R", Q1-Q4, A, and Rn of Formulas (a) through (g) can independently be covalently coupled to a linker and/or a linker to which is attached one or more PTM, ULM, CLM or CLM' groups.

More specifically, non-limiting examples of CLMs include those shown below as well as those "hybrid" molecules that arise from the combination of 1 or more of the different features shown in the molecules below.

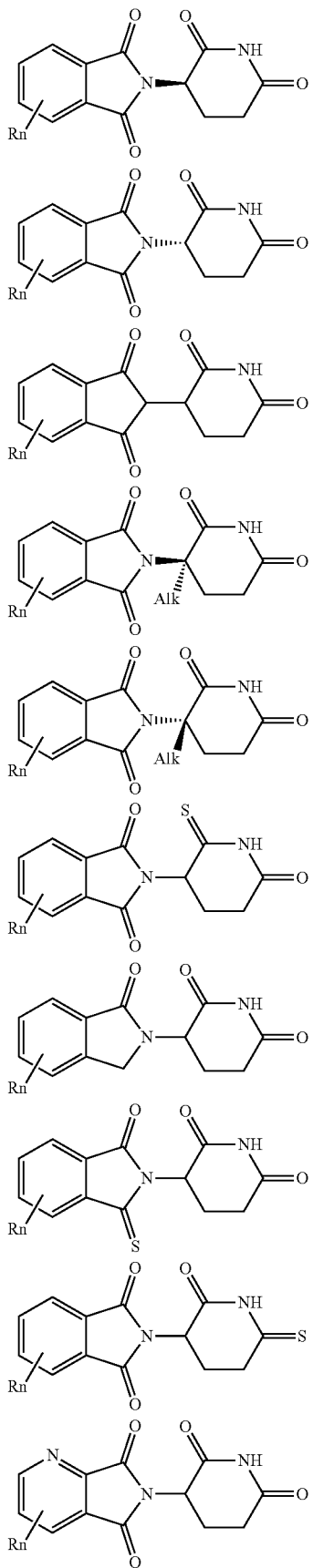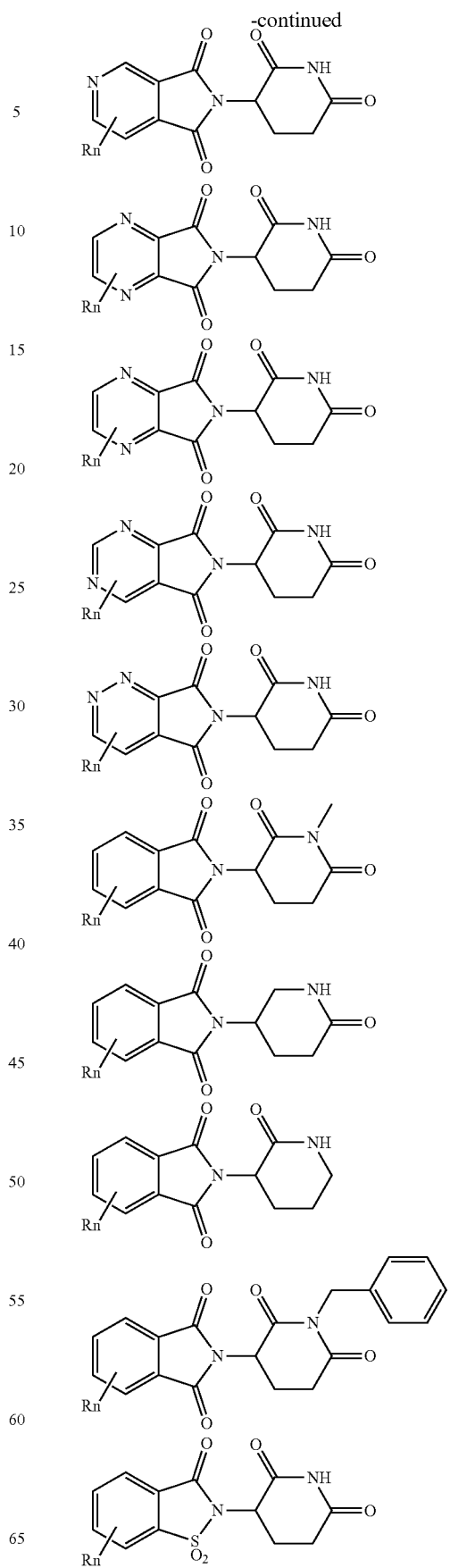

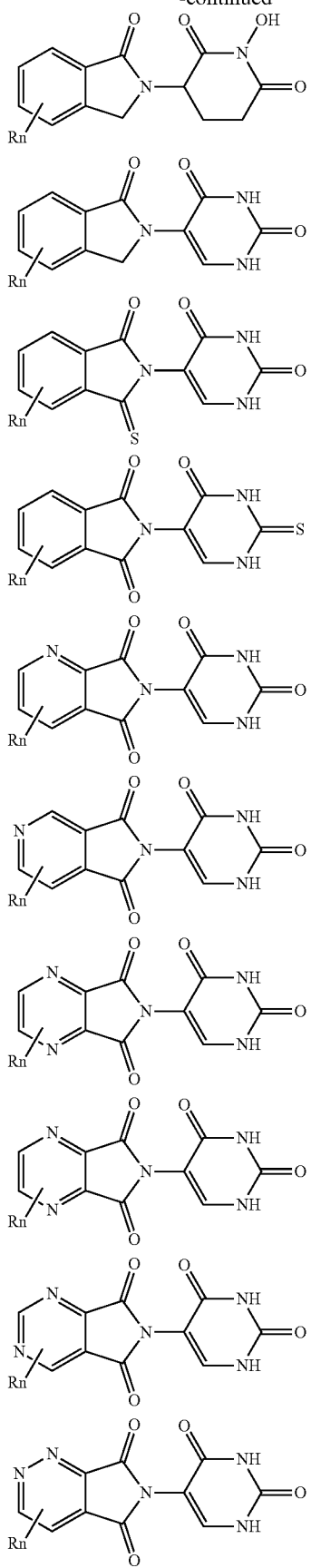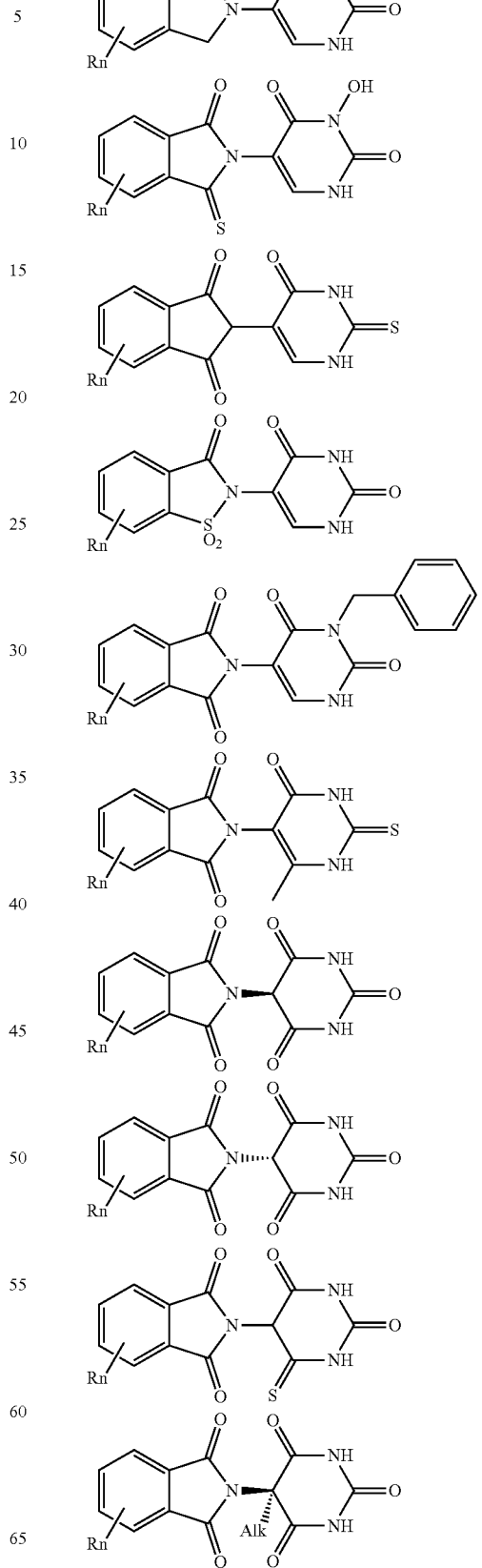

-continued
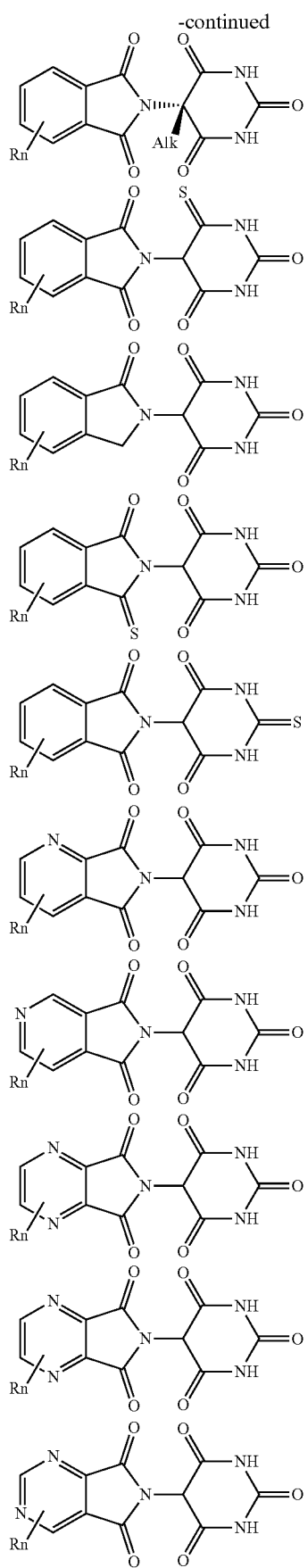
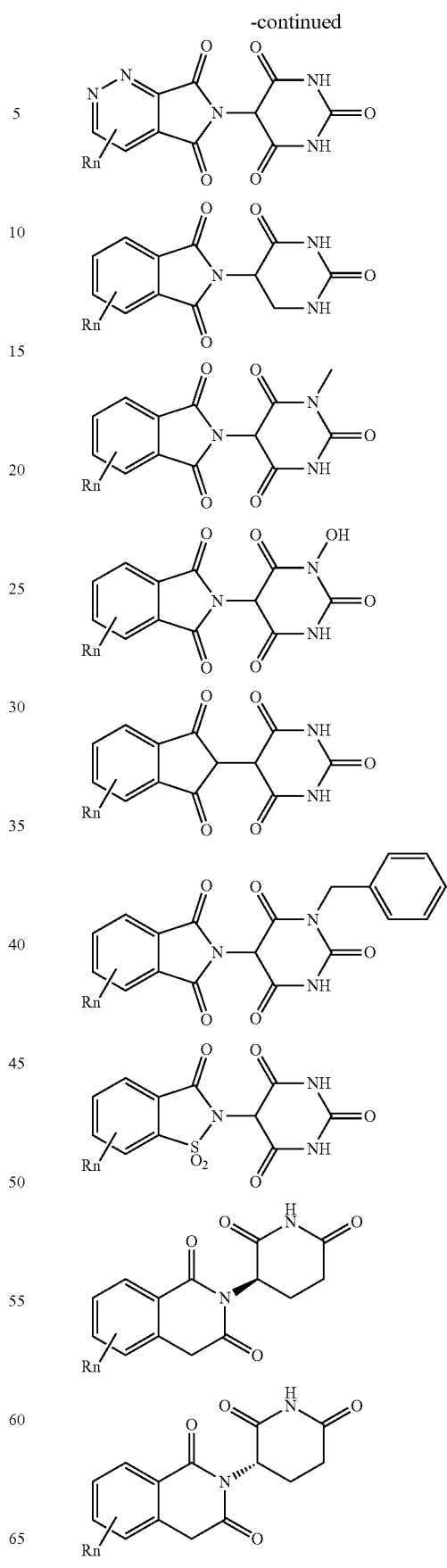

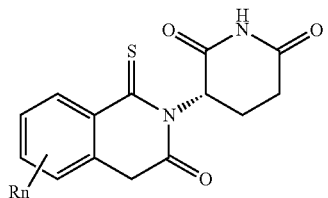
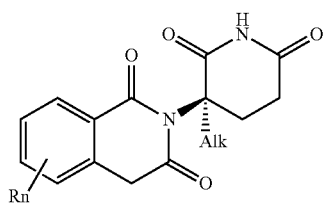
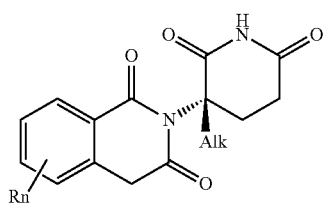
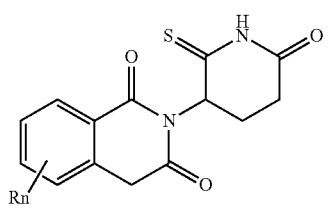
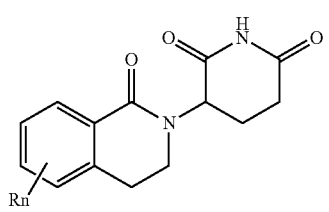
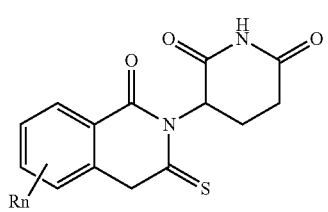
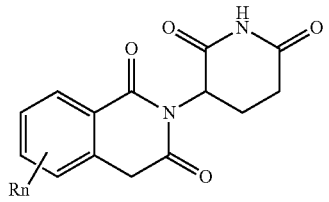
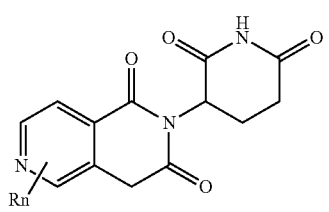
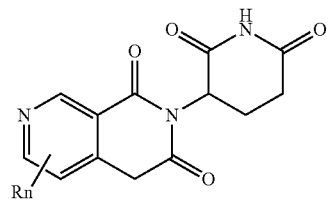
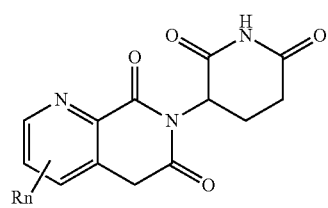
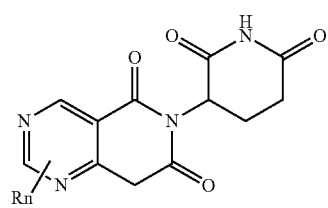
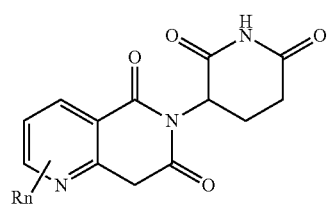
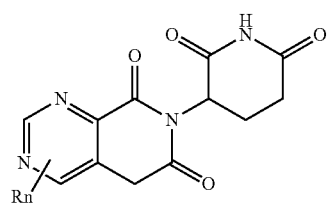
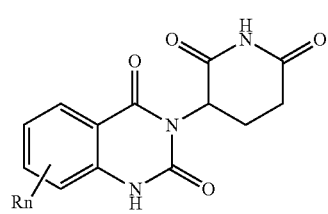
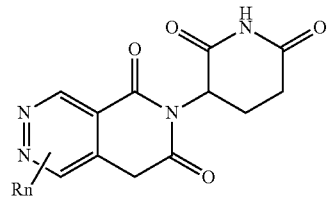
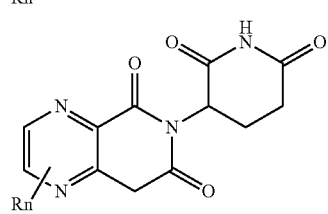

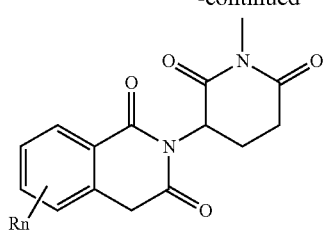
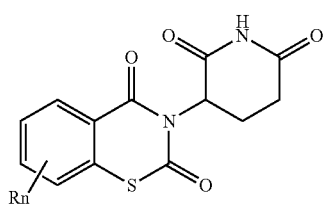
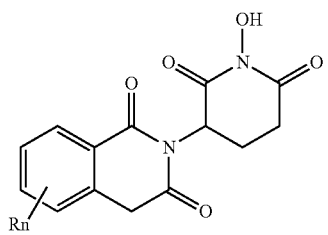
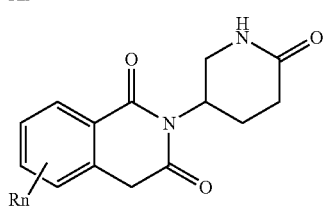
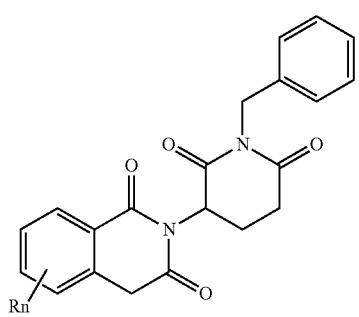
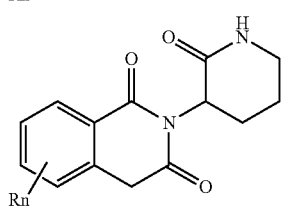
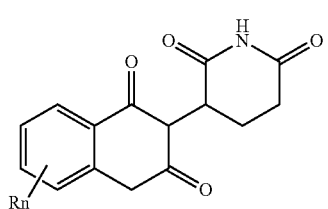
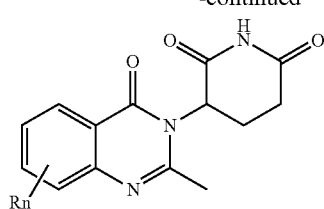
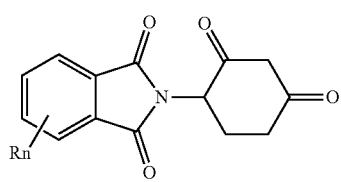
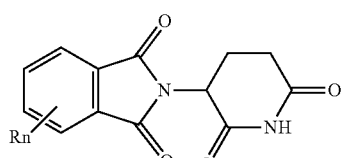
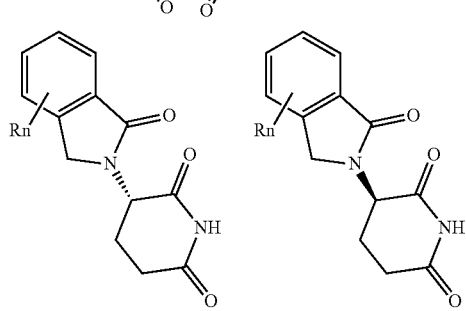
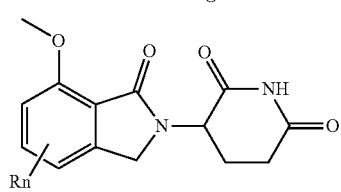
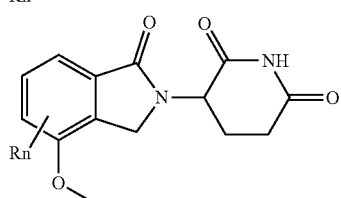
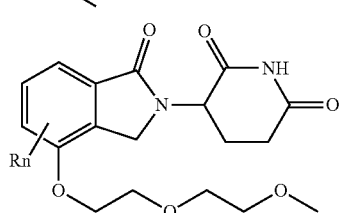
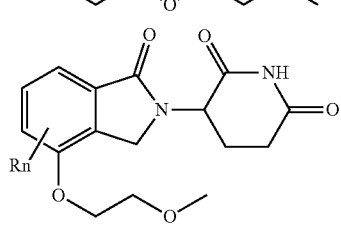

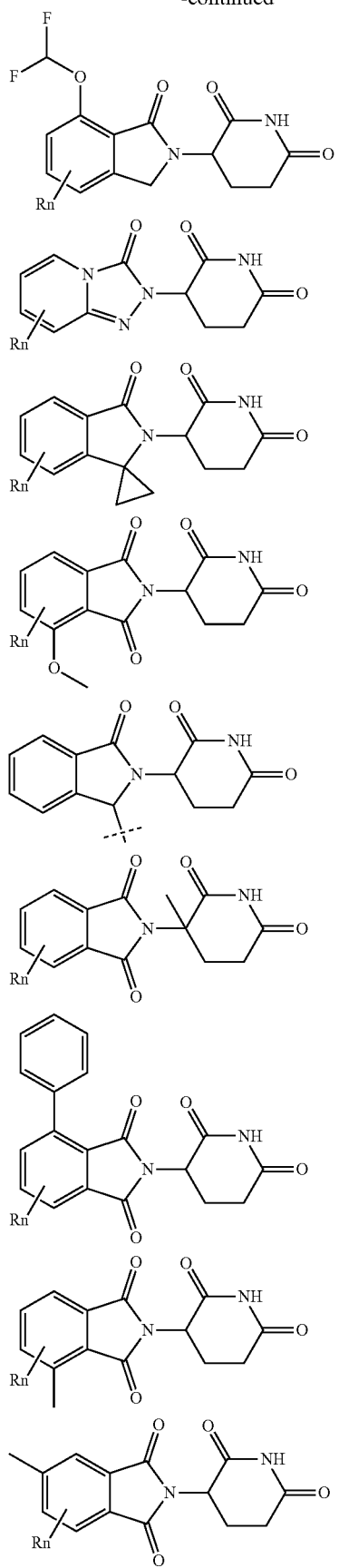
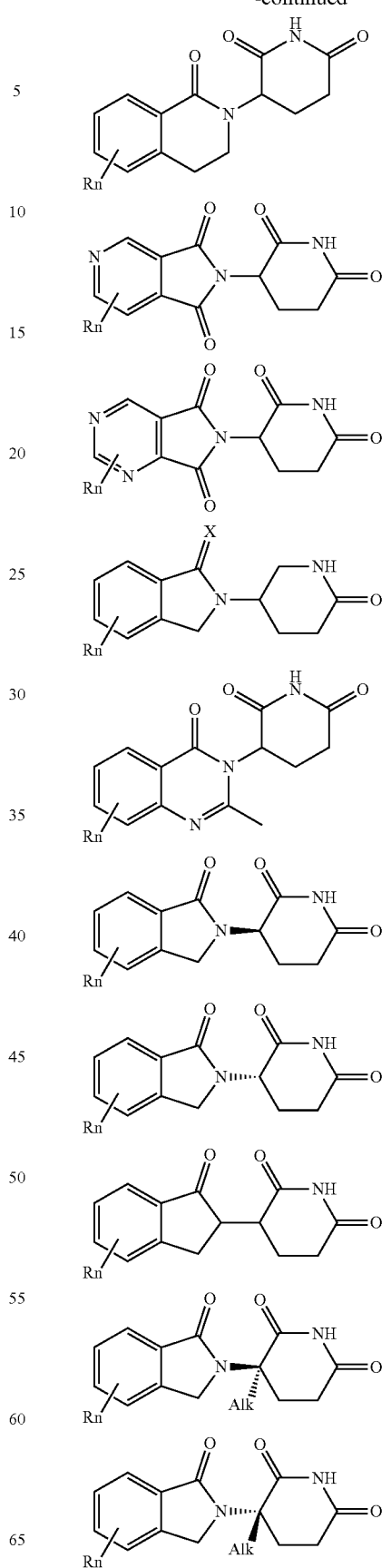

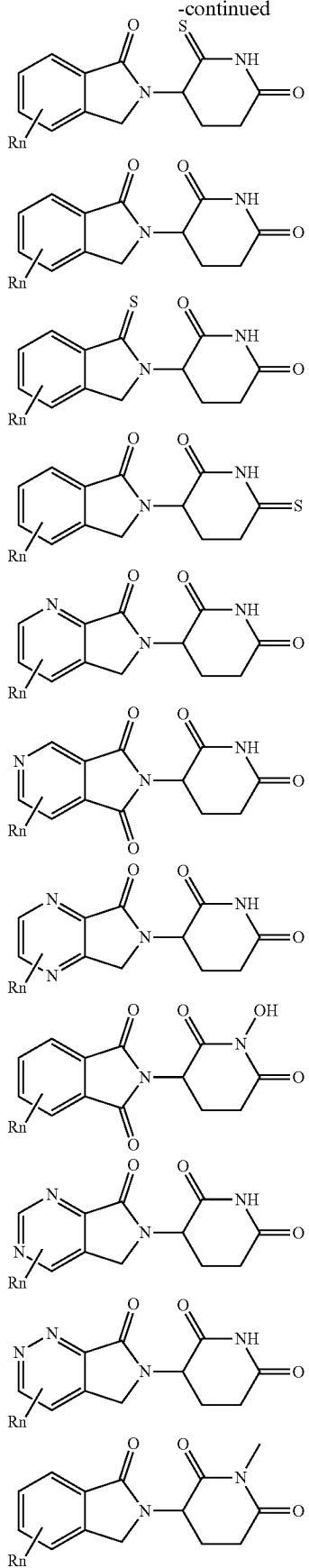
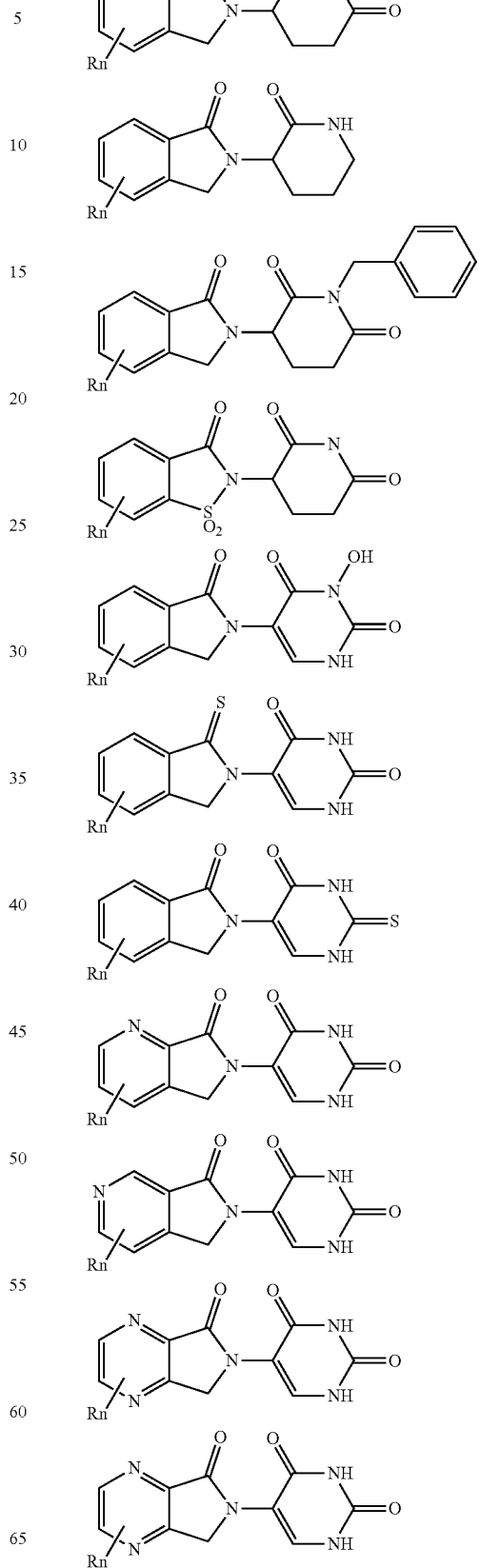

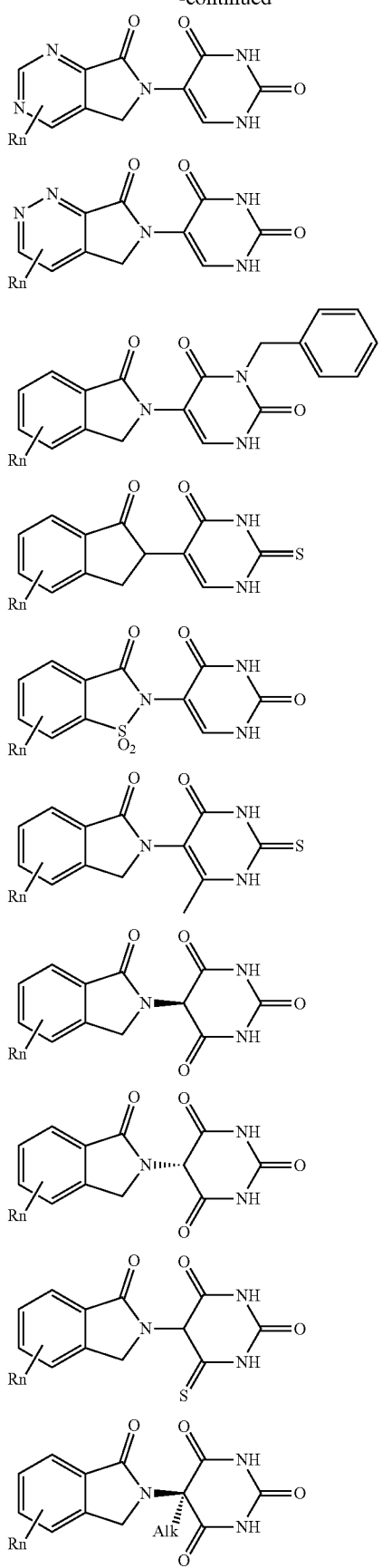
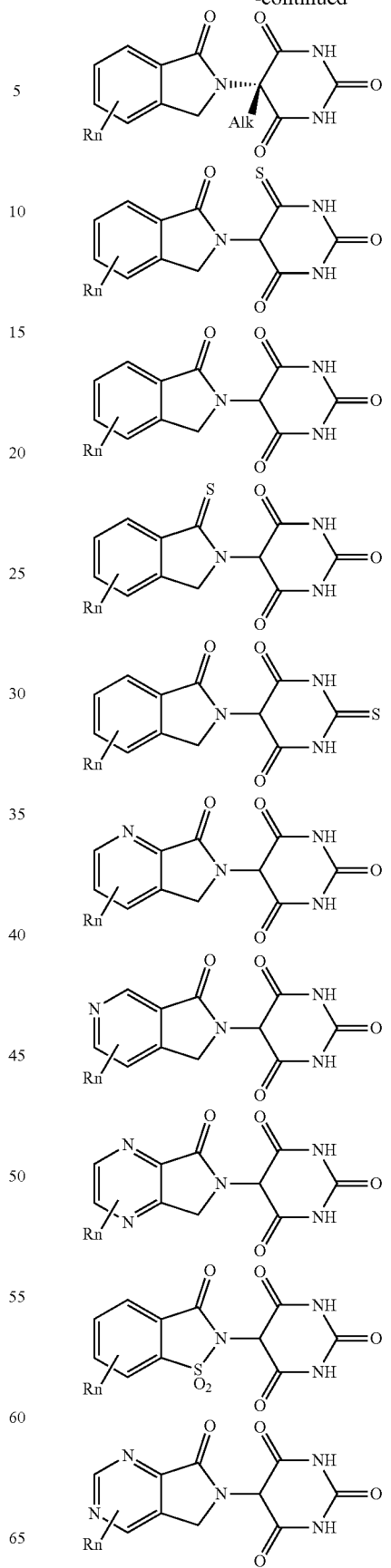

33
-continued
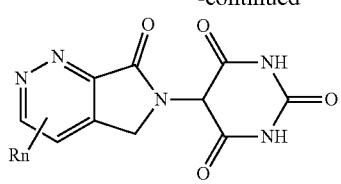
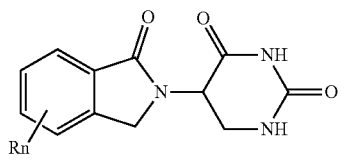
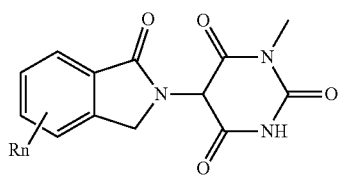
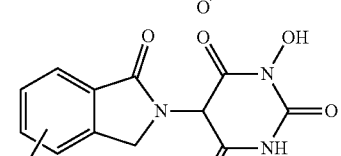
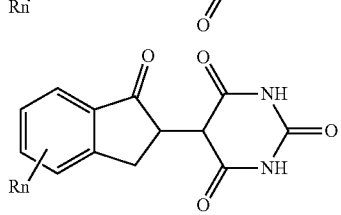
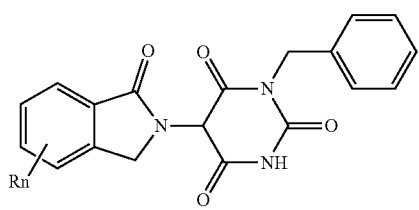
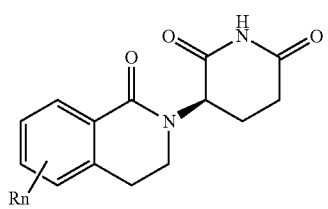
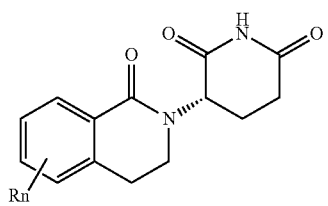
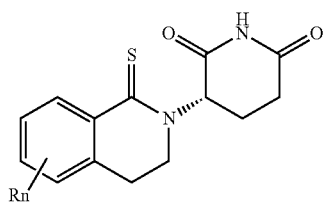
34
-continued
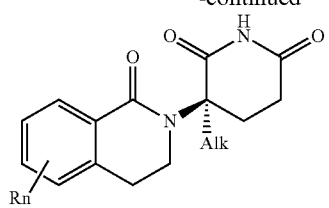
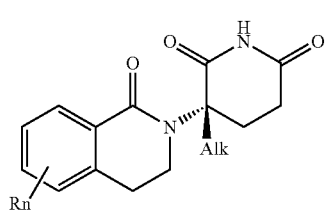
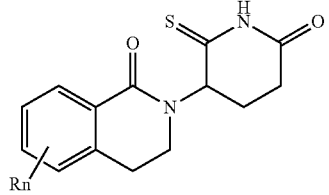
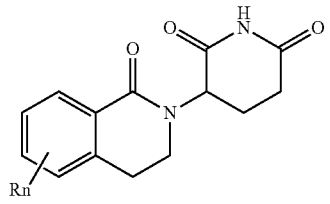
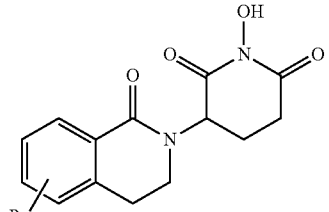
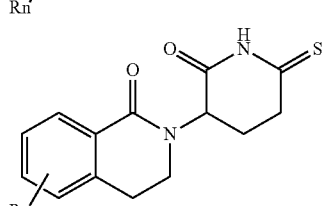
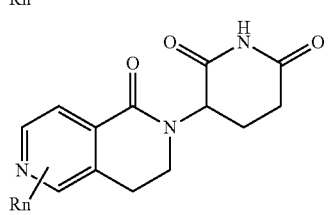
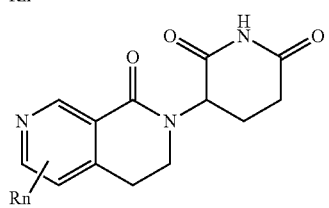

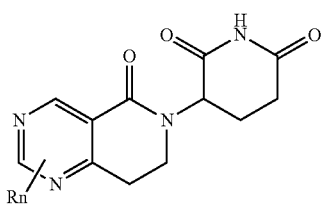
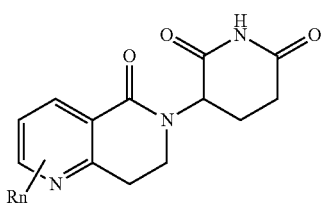
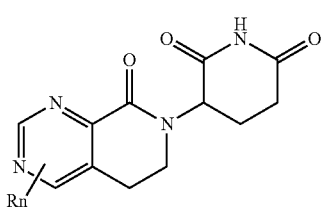
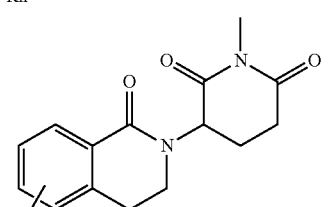
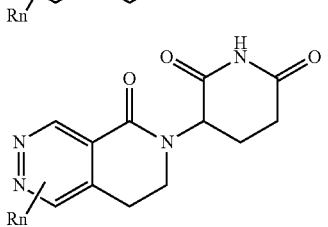
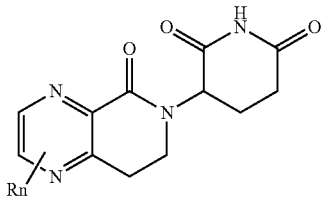
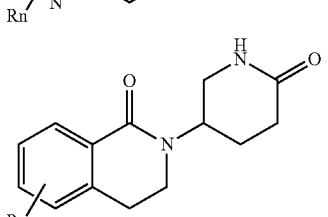

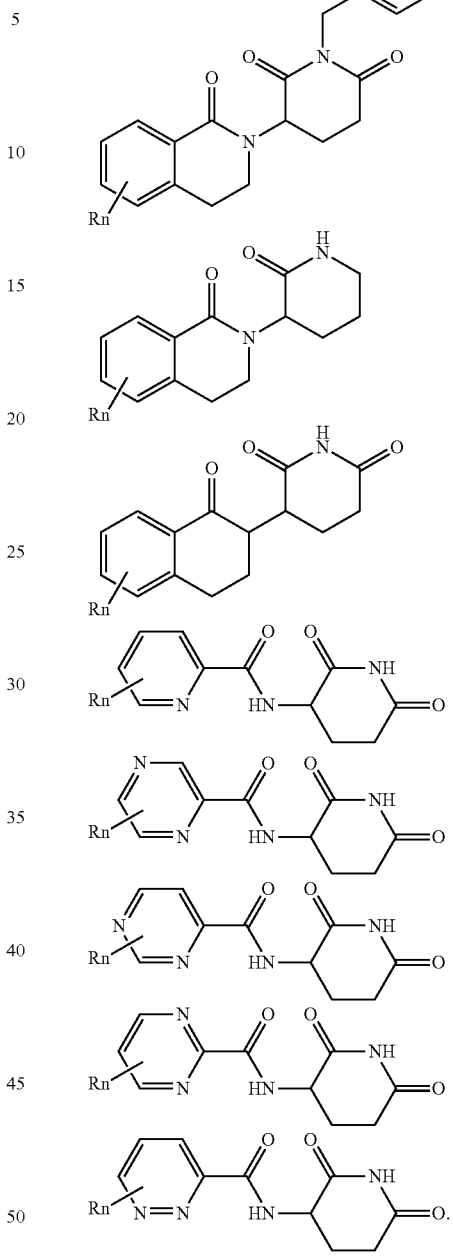

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I). In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkoxy" refers to an alkyl group singularly bonded to oxygen.

The term "Alkenyl" refers to linear, branch-chained or cyclic $C_2$-$C_{10}$ (preferably $C_2$-$C_6$) hydrocarbon radicals containing at least one C=C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C—N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —Si$R_{1sub}R_{2sub}R_{3sub}$ groups where each of $R_{1sub}$ and $R_{2sub}$ is as otherwise described herein and $R_{3sub}$ is H or a $C_1$-$C_6$ alkyl group, preferably $R_{1sub}$, $R_{2sub}$, $R_{3sub}$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteroaryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sidechain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure, moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—N$R_{1sub}R_{2sub}$ or —N($R_{1sub}$)—C(O)—O—$R_{1sub}$, nitro, cyano and amine (especially including a $C_1$-$C_6$ alkylene-N$R_{1sub}R_{2sub}$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —$(CH_2)_m$— (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)_n$NHC (O)—$R_{1sub}$, —$(CH_2)_nC(O)$—$NR_{1sub}R_{2sub}$, —$(OCH_2)_nOH$, —$(CH_2O)_nCOOH$, $C_1$-$C_6$ alkyl, —$(OCH_2)$, O—$(C_1$-$C_6$ alkyl), —$(CH_2O)_HC(O)$—$(C_1$-$C_6$ alkyl), —$(OCH_2)_nNHC(O)$—$R_{1sub}$, —$(CH_2O)_nC(O)$—$NR_{1sub}R_{2sub}$, —$S(O)_2$—$R_S$, —$S(O)$—$R_S$ ($R_S$ is $C_1$-$C_6$ alkyl or a —$(CH_2)_m$—$NR_{1sub}R_{2sub}$ group), $NO_2$, CN or halogen (F, Cl, Br, I, preferably F or Cl), depending on the context of the use of the substituent. $R_{1sub}$ and $R_{2sub}$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_{1sub}R_{2sub}$ group where $R_{1sub}$ and $R_{2sub}$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —$(CH_2)_nOH$, —$(CH_2)_n$—O—$(C_1$-$C_6)$alkyl, —$(CH_2)_n$—O—$(CH_2)_n$—$(C_1$-$C_6)$alkyl, —$(CH_2)_n$—C(O)($C_0$-$C_6$) alkyl, —$(CH_2)_n$—C(O)O($C_0$-$C_6$) alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably substituted with a linker group attached to a PTM group, including a ULM group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo—(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —(CH$_2$)$_m$—O—C$_1$-C$_6$ alkyl group or an optionally substituted —(CH$_2$)$_m$—C(O)—O—C$_1$-C$_6$ alkyl group), an optionally substituted pyridine (2-, 3-, or 4-pyridine) or a group according to the chemical structure:

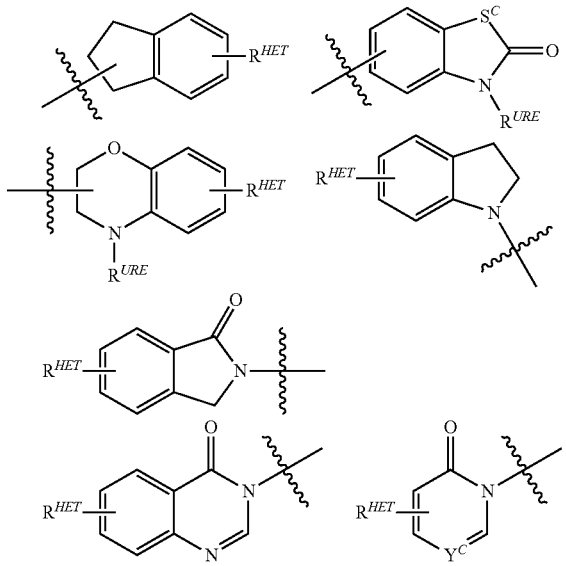

wherein
S$^c$ is CHR$^{SS}$, NR$^{URE}$, or O;
R$^{HET}$ is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);
R$^{SS}$ is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl)(preferably substituted with one or two hydroxyl groups or up to three halo groups);
R$^{URE}$ is H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
Y$^C$ is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl).

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO-heteroaryl, —SO2-alkyl, —SO2-substituted alkyl, —SO2-aryl, oxo (═O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "lower alkyl" refers to methyl, ethyl or propyl

The term "lower alkoxy" refers to methoxy, ethoxy or propoxy.

More specifically, non-limiting examples of CLMs include those shown below as well "hybrid" molecules or compounds that arise from combining 1 or more featrues of the following compounds:

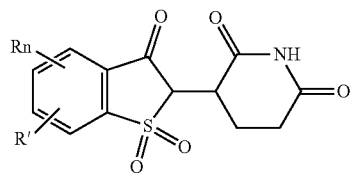
(v)

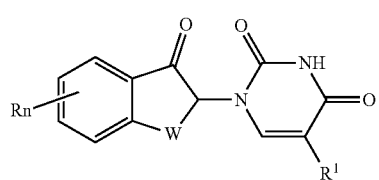
(w)

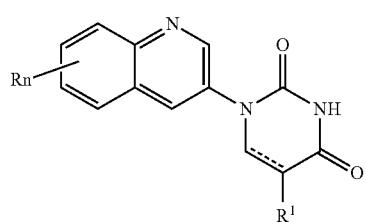
(x)

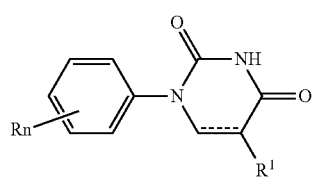
(y)

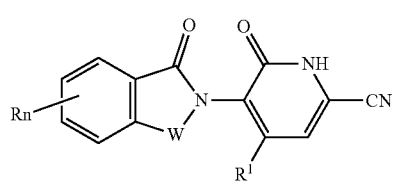
(z)

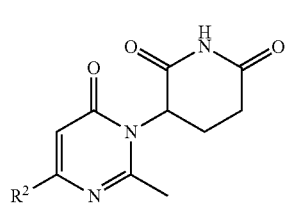
(aa)

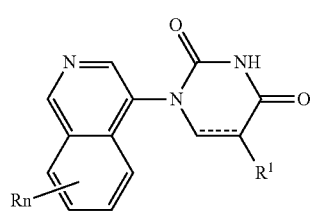
(ab)

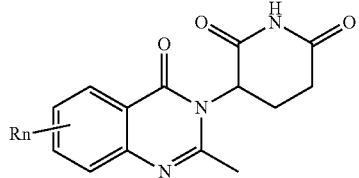
(ac)

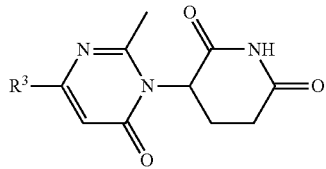
(ad)

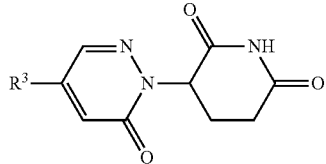
(ae)

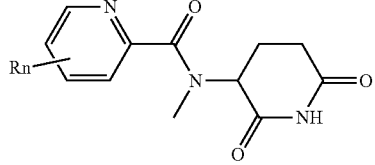
(af)

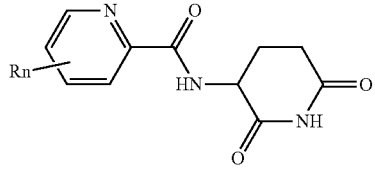
(ag)

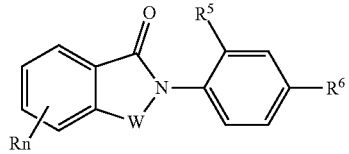

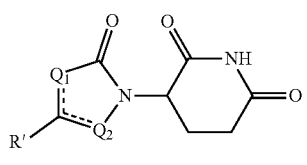

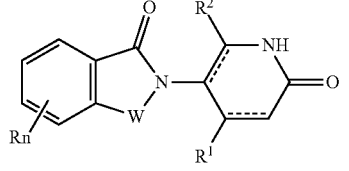

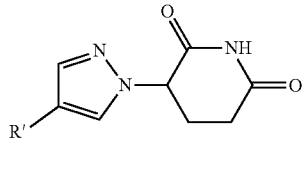

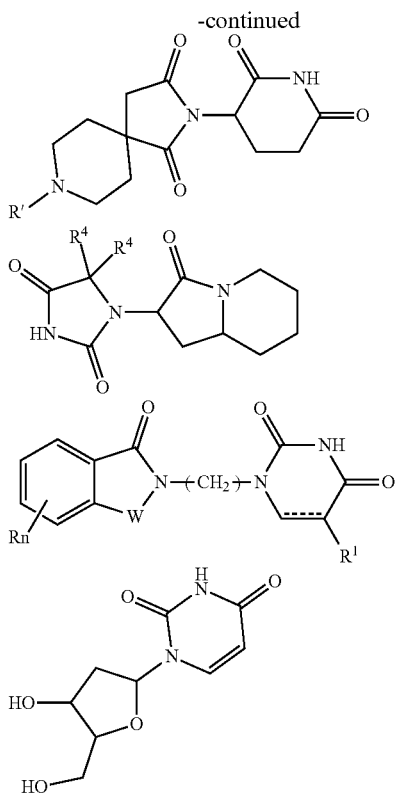

wherein:
W is independently selected from the group CH$_2$, CHR, C=O, SO$_2$, NH, and N-alkyl;
R$^1$ is selected from the group absent, H, CH, CN, C1-C3 alkyl,
R$^2$ is H or a C1-C3 alkyl;
R$^3$ is selected from H, alkyl, substituted alkyl, alkoxy, substituted alkoxy;
R$^4$ is methyl or ethyl;
R$^5$ is H or halo;
R$^6$ is H or halo;
R of the CLM is H;
R' is H or an attachment point for a PTM, a PTM', a chemical linker group (L), a ULM, a CLM, a CLM',
Q1 and Q2 are each independently C or N substituted with a group independently selected from H or C1-C3 alkyl;
═══ is a single or double bond; and
Rn comprises a functional group or an atom.

In any of the embodiments described herein, the W, R$^1$, R$^2$, Q$_1$, Q$_2$, Q$_3$, Q$_4$, and Rn can independently be covalently coupled to a linker and/or a linker to which is attached one or more PTM, ULM, ULM', CLM or CLM' groups.

In any of the embodiments described herein, the R$^1$, R$^2$, Q$_1$, Q$_2$, Q$_3$, Q$_4$, and Rn can independently be covalently coupled to a linker and/or a linker to which is attached one or more PTM, ULM, ULM', CLM or CLM' groups.

In any of the embodiments described herein, the Q$_1$, Q$_2$, Q$_3$, Q$_4$, and Rn can independently be covalently coupled to a linker and/or a linker to which is attached one or more PTM, ULM, ULM', CLM or CLM' groups.

In any aspect or embodiment described herein, R$_n$ is modified to be covalently joined to the linker group (L), a PTM, a ULM, a second CLM having the same chemical structure as the CLM, a CLM', a second linker, or any multiple or combination thereof.

Exemplary Linkers

In certain embodiments, the compounds as described herein include one or more CLMs chemically linked or coupled to one or more PTMs (e.g., PTM and/or PTM'), ULMs (e.g., ULM, ULM', and/or CLM') via a chemical linker (L). In certain embodiments, the linker group L is a group comprising one or more covalently connected structural units (e.g., -A$^L_1$ ... (A$^L$)$_q$- or -(A$^L$)$_q$-) wherein A$_1$ is a group coupled to PTM, and Aq is a group coupled to at least one of a ULM, a ULM', a CLM, a CLM', or a combination thereof. In certain embodiments, A$^L_1$ links a CLM or CLM' directly to another ULM, PTM, or combination thereof. In other embodiments, A$^L_1$ links a CLM or CLM' indirectly to another ULM, PTM, or combination thereof through A$_q$.

In any aspect or embodiment described herein, the linker group L is a bond or a chemical linker group represented by the formula -(A$^L$)$_q$-, wherein A is a chemical moiety and q is an integer from 1-100, and wherein L is covalently bound to the PTM and the ULM, and provides for sufficient binding of the PTM to the protein target and the ULM to an E3 ubiquitin ligase to result in target protein ubiquitination.

In certain embodiments, the linker group is -(A$^L$)$_q$-, wherein
-(A$^L$)$_q$-is a group which is connected to at least one of a ULM moiety, a PTM moiety, or a combination thereof;
q of the linker is an integer greater than or equal to 1;
each A$^L$ is independently selected from the group consisting of a bond, CR$^{L1}$R$^{L2}$, O, S, SO, SO$_2$, NR$^{L3}$, SO$_2$NR$^{L3}$, SONR$^{L3}$, CONR$^{L3}$, NR$^{L3}$CONR$^{L4}$, NR$^{L3}$SO$_2$NR$^{L4}$, CO, CR$^{L1}$=CR$^{L2}$, C≡C, SiR$^{L1}$R$^{L2}$, P(O)R$^{L1}$, P(O)OR$^{L1}$, NR$^{L3}$C(=NCN)NR$^{L4}$, NR$^{L3}$C(=NCN), NR$^{L3}$C(=CNO$_2$)NR$^{L4}$, C$_{3-11}$cycloalkyl optionally substituted with 0-6 R$^{L1}$ and/or R$^{L2}$ groups, C$_{5-13}$ spirocycloalkyl optionally substituted with 0-9 R$^{L1}$ and/or R$^{L2}$ groups, C$_{3-11}$ heterocyclyl optionally substituted with 0-6 R$^{L1}$ and/or R$^{L2}$ groups, C$_{5-13}$ spiroheterocycloalkyl optionally substituted with 0-8 R$^{L1}$ and/or R$^{L2}$ groups, aryl optionally substituted with 0-6 R$^{L1}$ and/or R$^{L2}$ groups, heteroaryl optionally substituted with 0-6 R$^{L1}$ and/or R$^{L2}$ groups, where R$^{L1}$ or R$^{L2}$, each independently are optionally linked to other groups to form cycloalkyl and/or heterocyclyl moiety, optionally substituted with 0-4 R$^{L5}$ groups; and
R$^{L1}$, R$^{L2}$, R$^{L3}$, R$^{L4}$ and R$^{L5}$ are, each independently, H, halo, C$_{1-8}$alkyl, OC$_{1-8}$alkyl, SC$_{1-8}$alkyl, NHC$_{1-8}$alkyl, N(C$_{1-8}$alkyl)$_2$, C$_{3-21}$cycloalkyl, aryl, heteroaryl, C$_{3-11}$heterocyclyl, OC$_{1-8}$cycloalkyl, SC$_{1-8}$cycloalkyl, NHC$_{1-8}$cycloalkyl, N(C$_{1-8}$cycloalkyl)$_2$, N(C$_{1-8}$cycloalkyl)(C$_{1-8}$alkyl), OH, NH$_2$, SH, SO$_2$C$_{1-8}$alkyl, P(O)(OC$_{1-8}$alkyl)(C$_{1-8}$alkyl), P(O)(OC$_{1-8}$alkyl)$_2$, CC—C$_{1-8}$alkyl, CCH, CH=CH(C$_{1-8}$alkyl), C(C$_{1-8}$alkyl)=CH(C$_{1-8}$alkyl), C(C$_{1-8}$alkyl)=C(C$_{1-8}$alkyl)$_2$, Si(OH)$_3$, Si(C$_{1-8}$alkyl)$_3$, Si(OH)(C$_{1-8}$alkyl)$_2$, COC$_{1-8}$alkyl, CO$_2$H, halogen, CN, CF$_3$, CHF$_2$, CH$_2$F, NO$_2$, SF$_5$, SO$_2$NHC$_{1-8}$alkyl, SO$_2$N(C$_{1-8}$alkyl)$_2$, SON(C$_{1-8}$alkyl, SON(C$_{1-8}$alkyl)$_2$, CONHC$_{1-8}$alkyl, CON(C$_{1-8}$alkyl)$_2$, N(C$_{1-8}$alkyl)CONH(C$_{1-8}$alkyl), N(C$_{1-8}$alkyl)CON(C$_{1-8}$alkyl)$_2$, NHCONH(C$_{1-8}$alkyl), NHCON(C$_{1-8}$alkyl)$_2$, NHCONH$_2$, N(C$_{1-8}$alkyl)SO$_2$NH(C$_{1-8}$alkyl), N(C$_{1-8}$alkyl) SO$_2$N(C$_{1-8}$alkyl)$_2$, NH SO$_2$NH(C$_{1-8}$alkyl), NH SO$_2$N(C$_{1-8}$alkyl)$_2$, NH SO$_2$NH$_2$.

In certain embodiments, q of the linker is an integer greater than or equal to 0. In certain embodiments, q is an integer greater than or equal to 1.

In certain embodiments, where q is greater than 2, A$^L_q$ is a group which is connected to a ULM or ULM' moiety (such as CLM or CLM'), and $A^L_1$ and $A^L_q$ are connected via structural units of the linker (L).

In certain embodiments, e.g., where q of the linker is 2, $A^L_q$ is a group which is connected to $A^L_1$ and to a ULM or a ULM' moiety (such as CLM or CLM').

In certain embodiments, e.g., where q of the linker is 1, the structure of the linker group L is -$A^L_1$-, and $A^L_1$ is a group which is connected to a ULM or ULM' moiety (such as CLM or CLM') and a PTM moiety.

In certain embodiments, the linker (L) comprises a group represented by a general structure selected from the group consisting of:
—NR(CH$_2$)$_n$-(lower alkyl)-, —NR(CH$_2$)$_n$-(lower alkoxyl)-, —NR(CH$_2$)$_n$-(lower alkoxyl)-OCH$_2$—, —NR(CH$_2$)$_n$-(lower alkoxyl)-(lower alkyl)-OCH$_2$—, —NR(CH$_2$)$_n$-(cycloalkyl)-(lower alkyl)-OCH$_2$—, —NR(CH$_2$)$_n$-(hetero cycloalkyl)-, —NR(CH$_2$CH$_2$O)$_n$-(lower alkyl)-O—CH$_2$—, —NR(CH$_2$CH$_2$O)$_n$-(hetero cycloalkyl)-O—CH$_2$—, —NR(CH$_2$CH$_2$O)$_n$-Aryl-O—CH$_2$—, —NR(CH$_2$CH$_2$O)$_n$-(hetero aryl)-O—CH$_2$—, —NR(CH$_2$CH$_2$O)$_n$-(cyclo alkyl)-O-(hetero aryl)-O—CH$_2$—, —NR(CH$_2$CH$_2$O)$_n$-(cyclo alkyl)-O-Aryl-O—CH$_2$—, —NR(CH$_2$CH$_2$O)$_O$-(lower alkyl)-NH-Aryl-O—CH$_2$—, —NR(CH$_2$CH$_2$O)$_n$-(lower alkyl)-O-Aryl-CH$_2$, —NR(CH$_2$CH$_2$O)$_n$-cycloalkyl-O-Aryl-, —NR(CH$_2$CH$_2$O)$_n$-cycloalkyl-O-(heteroaryl)l-, —NR(CH$_2$CH$_2$)$_n$-(cycloalkyl)-O-(heterocycle)-CH$_2$. —NR(CH$_2$CH$_2$)$_n$-(heterocycle)-(heterocycle)-CH$_2$, —N(R1R2)-(heterocycle)-CH$_2$; where
n of the linker can be 0 to 10;
R of the linker can be H, lower alkyl;
R1 and R2 of the linker can form a ring with the connecting N.

In certain embodiments, the $A^L$ group is represented by a general structure selected from the group consisting of:
—N(R)—(CH2)$_m$-O(CH2)$_n$-O(CH2)$_o$-O(CH2)$_p$-O(CH2)$_q$ -O(CH2)$_r$-OCH2-,
—O—(CH2)$_m$-O(CH2)$_n$-O(CH2)$_o$O(CH2)$_p$-O(CH2)$_q$-O(CH2)$_r$-OCH2-,
—O—(CH2)$_m$-O(CH2)$_n$-O(CH2)$_o$O(CH2)$_p$-O(CH2)$_q$-O(CH2)$_r$-O—;
—N(R)—(CH2)$_m$-O(CH2)$_n$-O(CH2)$_o$-O(CH2)$_p$-O(CH2)$_q$ -O(CH2)$_r$-O—;
—(CH2)$_m$-O(CH2)$_n$-O(CH2)$_o$-O(CH2)$_p$-O(CH2)$_q$-O(CH2)$_r$-O—;
—(CH2)$_m$-O(CH2)$_n$-O(CH2)$_o$-O(CH2)$_p$-O(CH2)$_q$-O(CH2)$_r$-OCH2-;

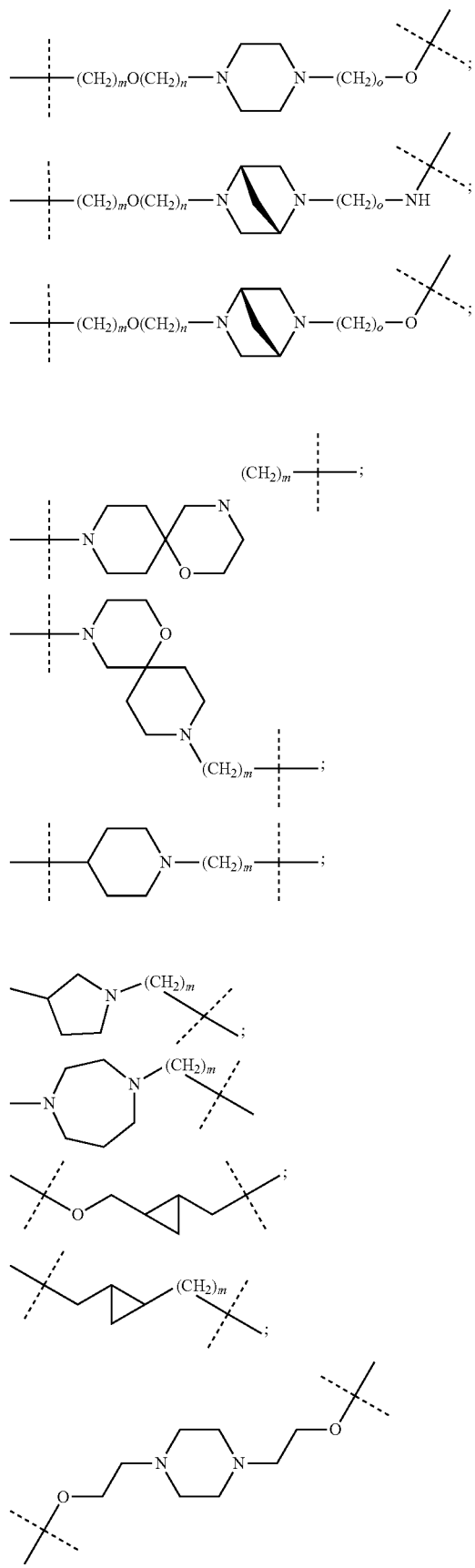

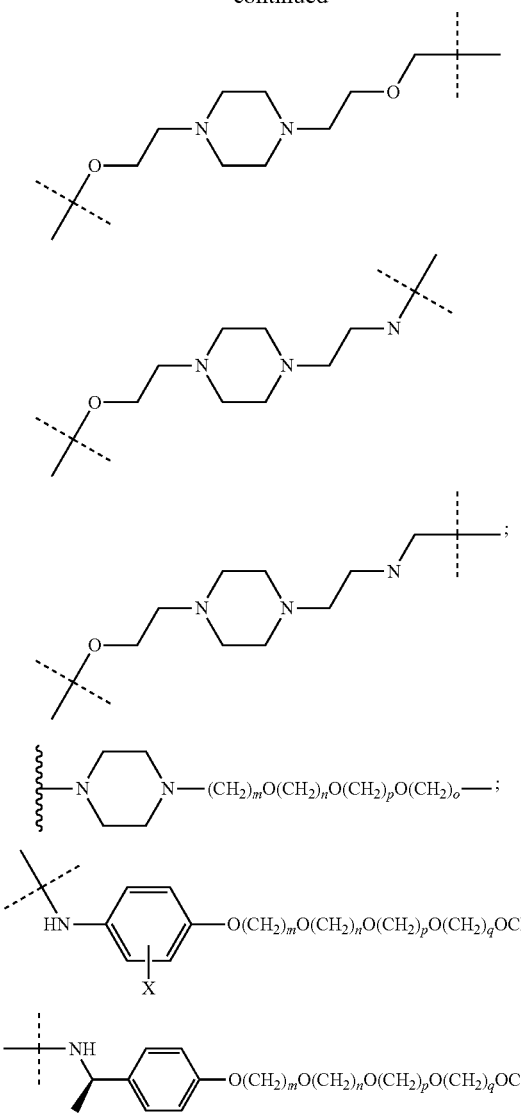
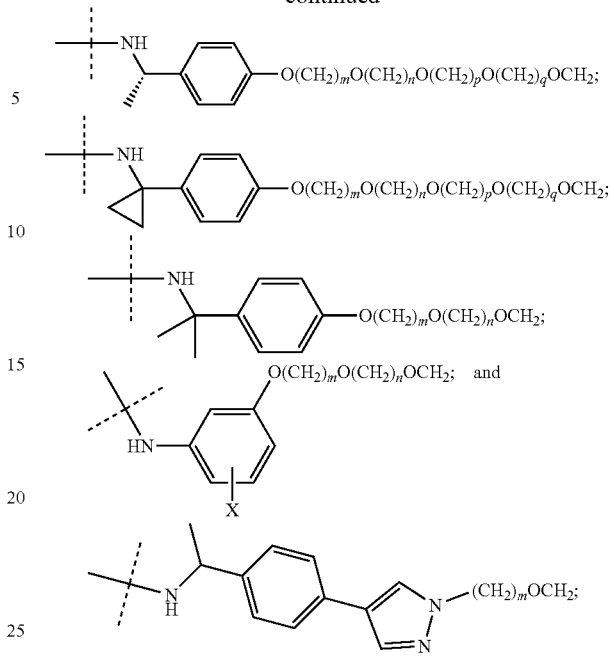
wherein
m, n, o, p, q, and r of the linker are independently 0, 1, 2, 3, 4, 5, 6; 7, 8, 9, 10, 11, 12, 13, 14, 15, 16, 17, 18, 19, or 20;
when the number is zero, there is no N—O or O—O bond
R of the linker is H, methyl and ethyl;
X of the linker is H and F
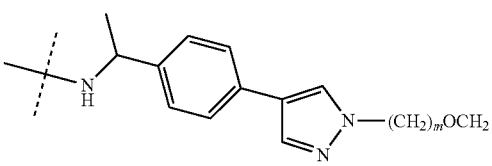
where m of the linker can be 2, 3, 4, 5;
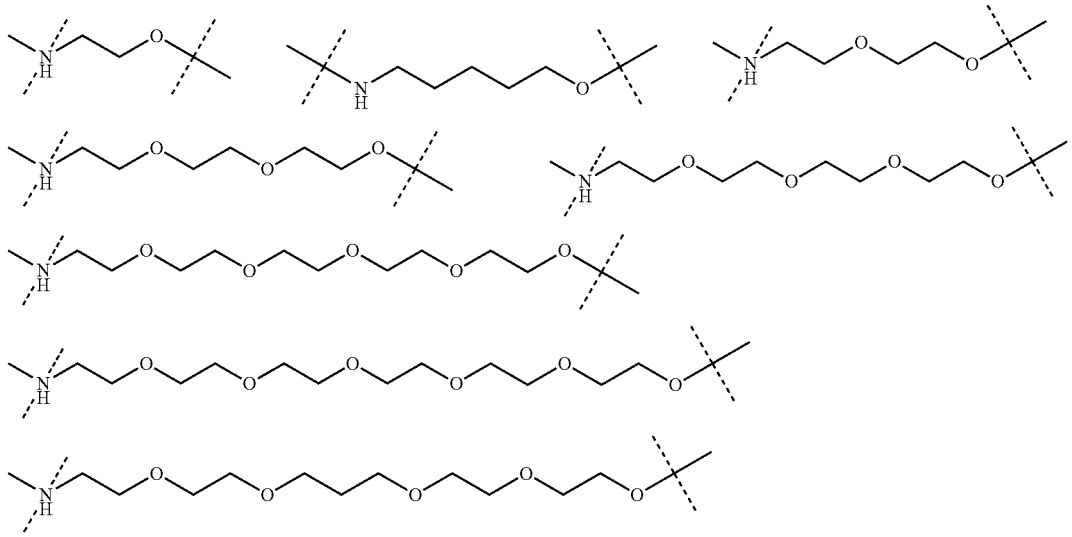

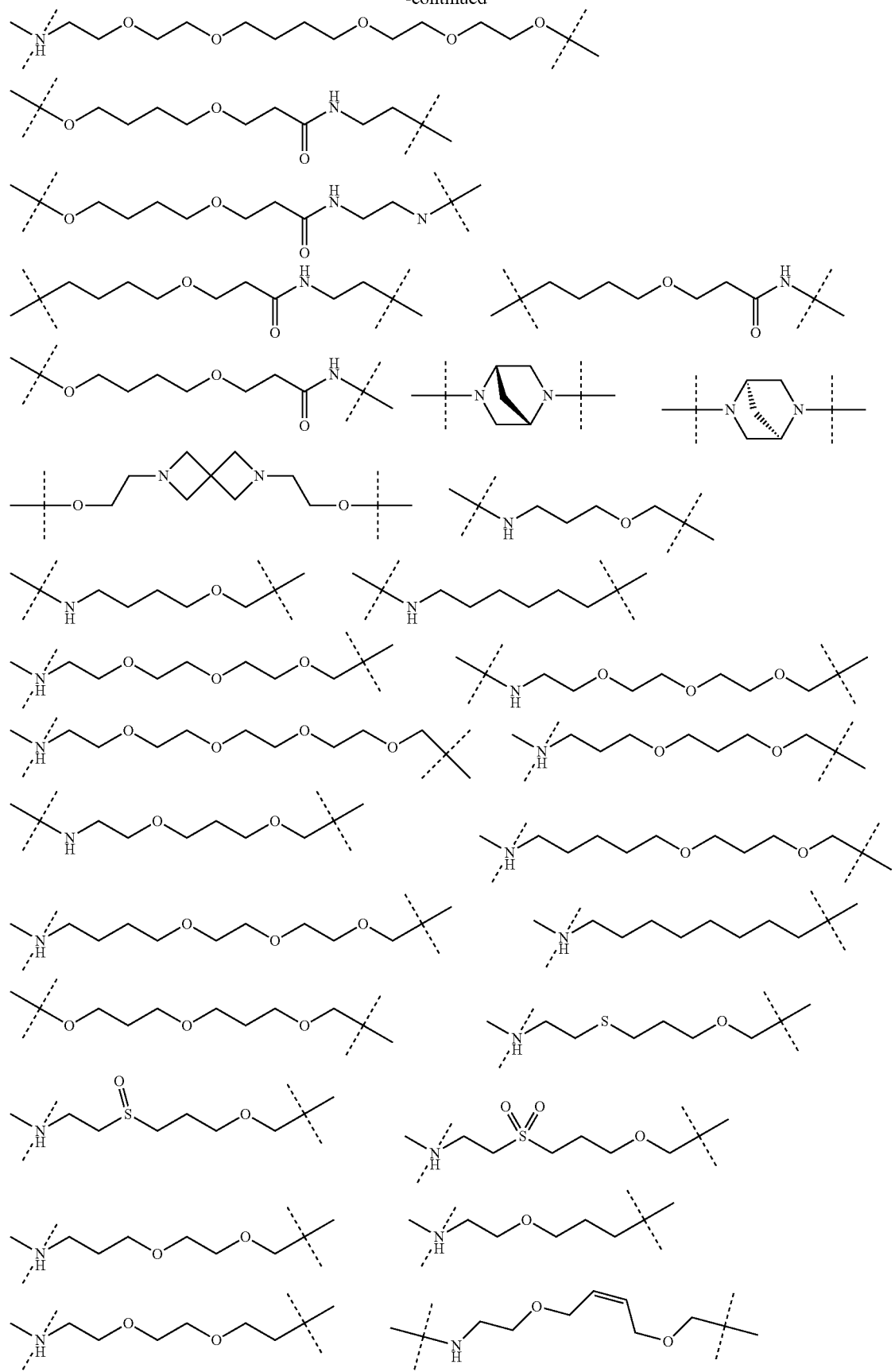

-continued
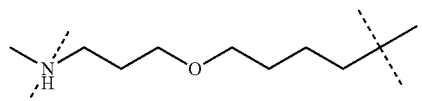
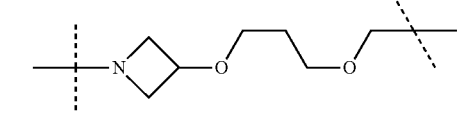
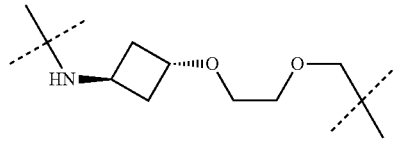
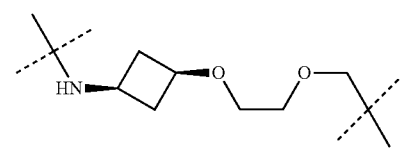
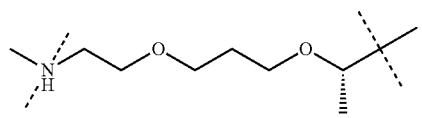
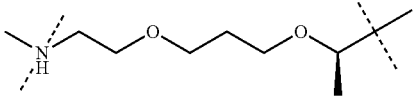
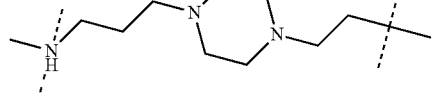
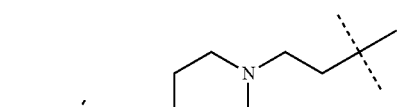
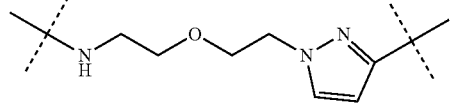
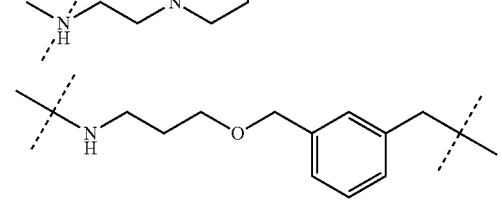
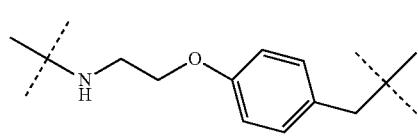
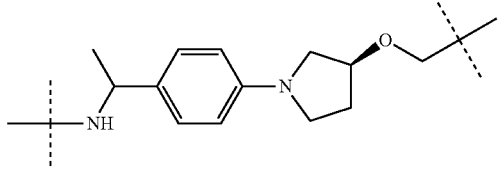
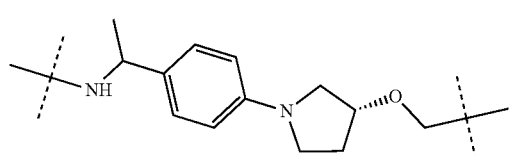
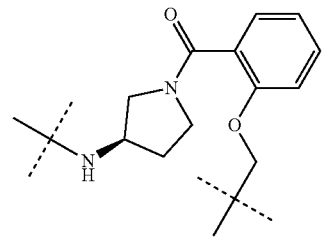
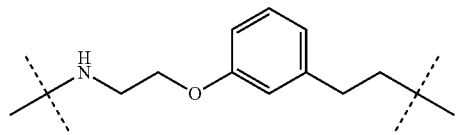
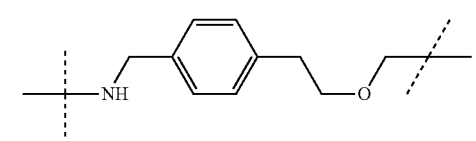
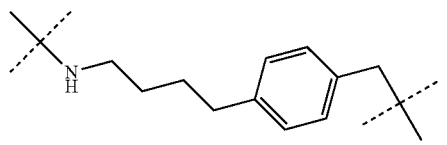
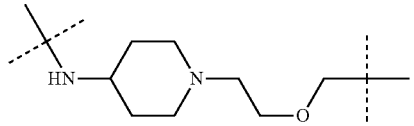
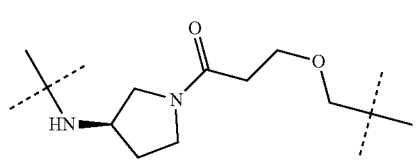
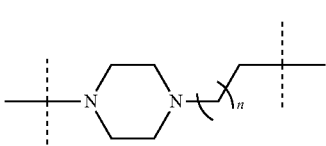

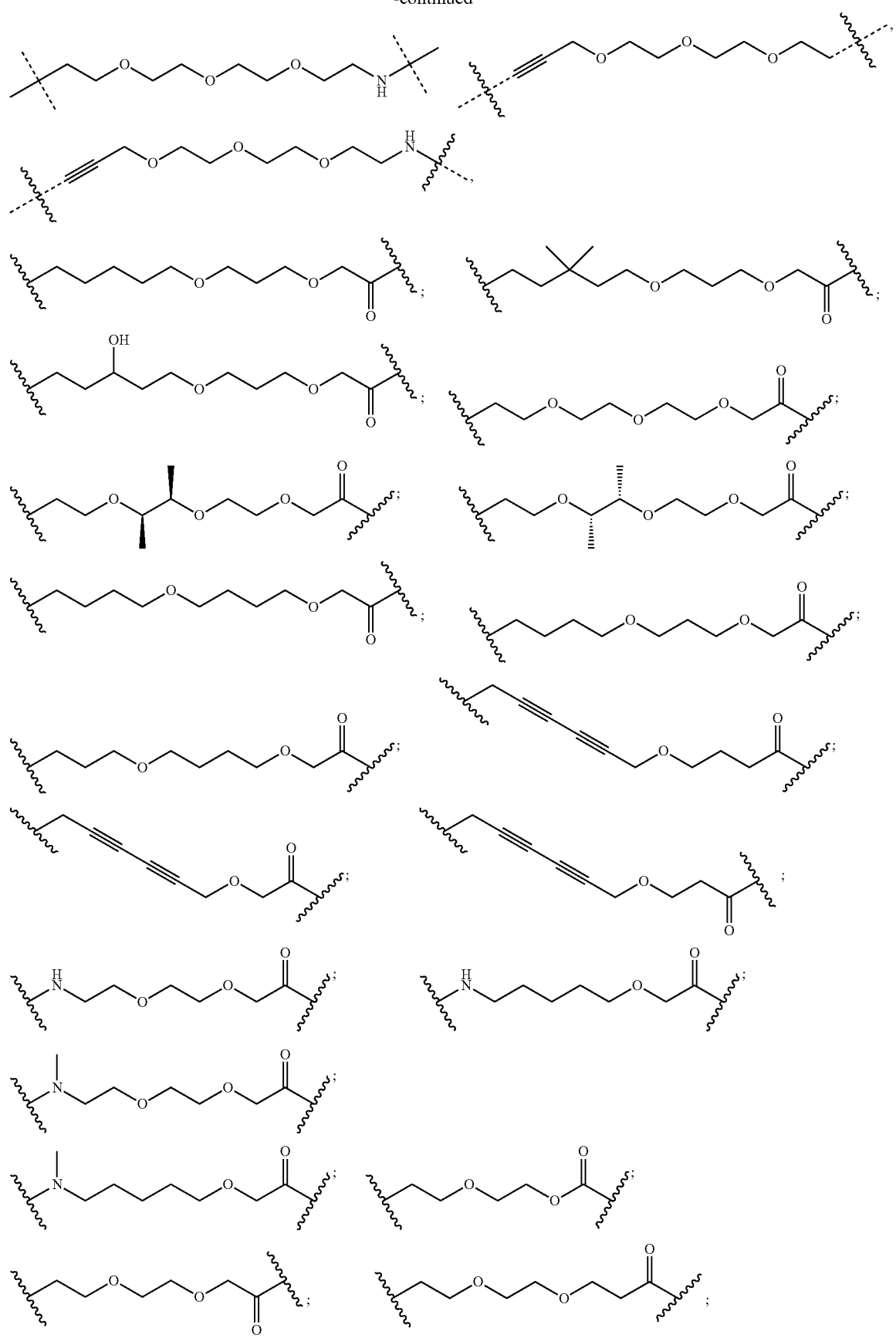

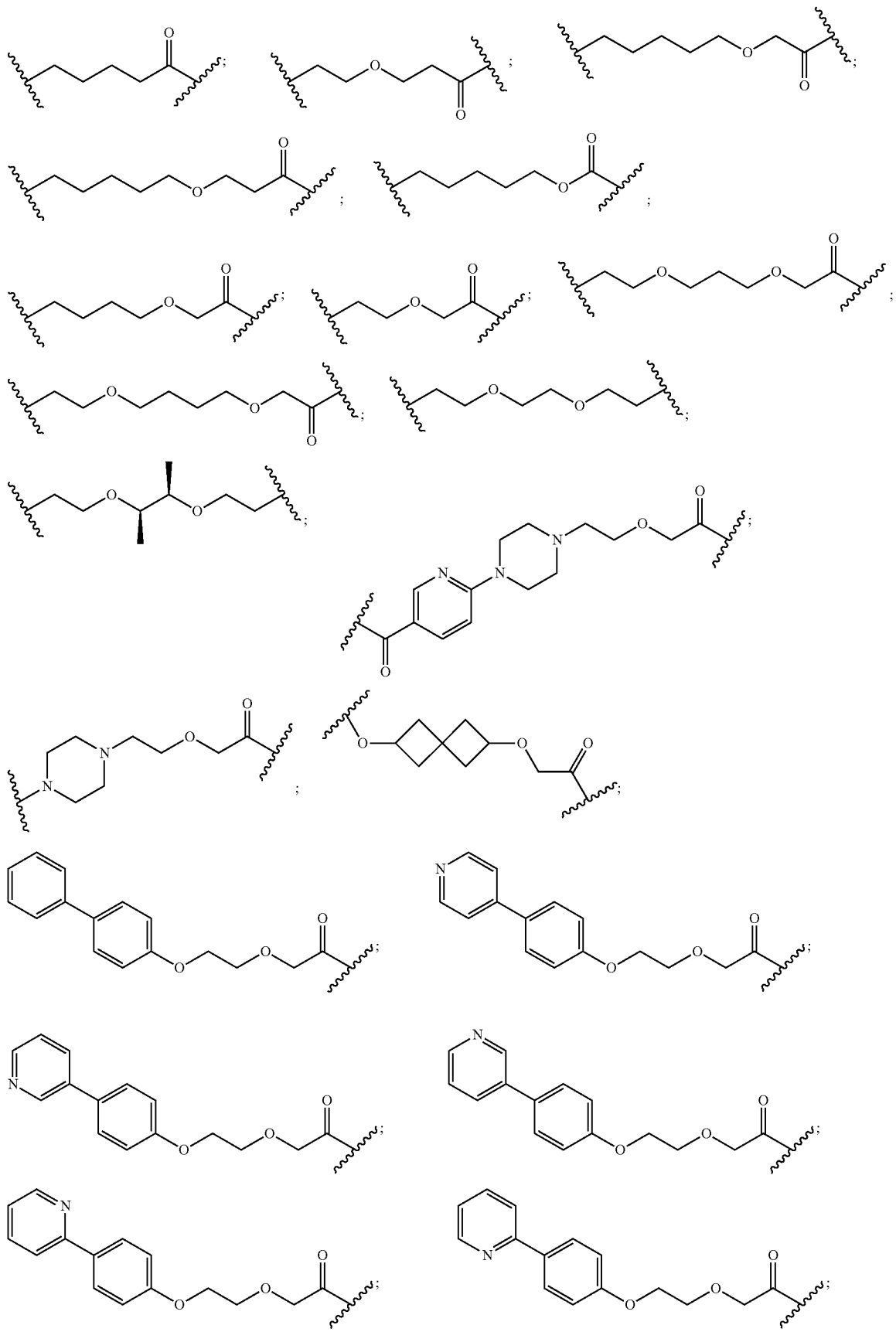

-continued
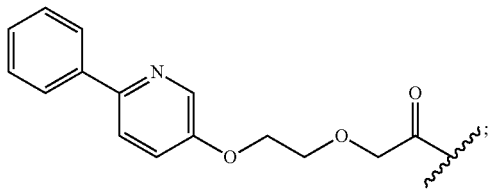
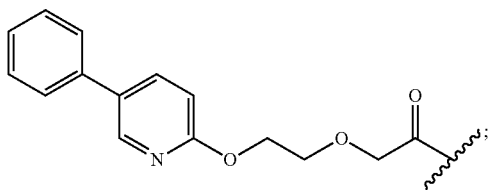
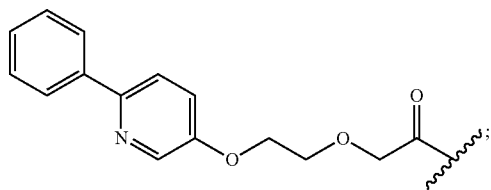
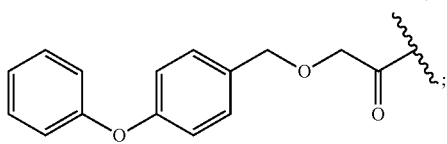
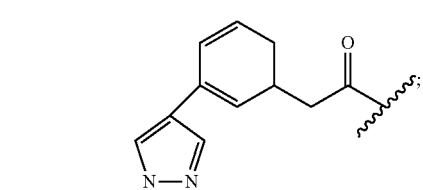
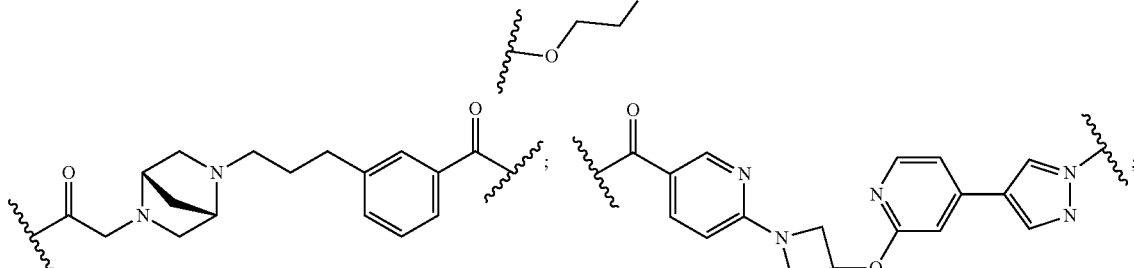
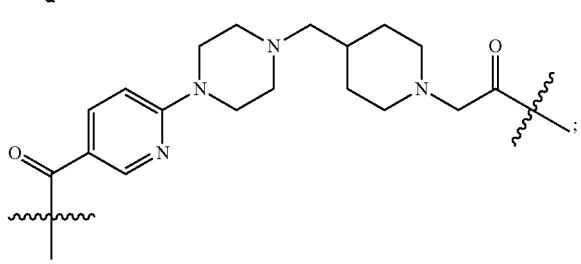
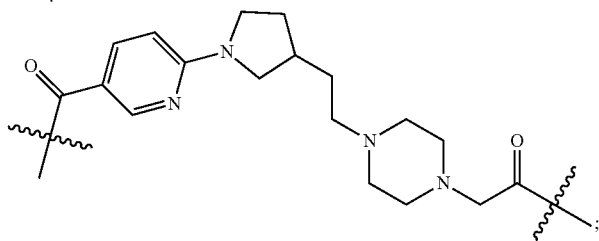
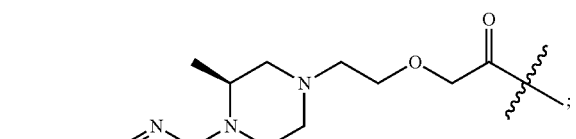
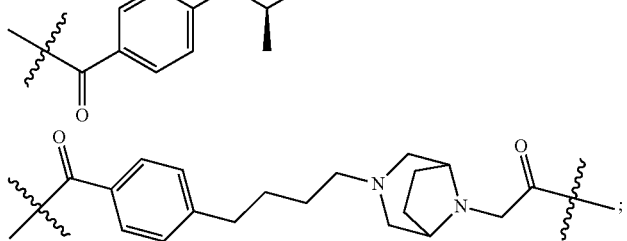

-continued
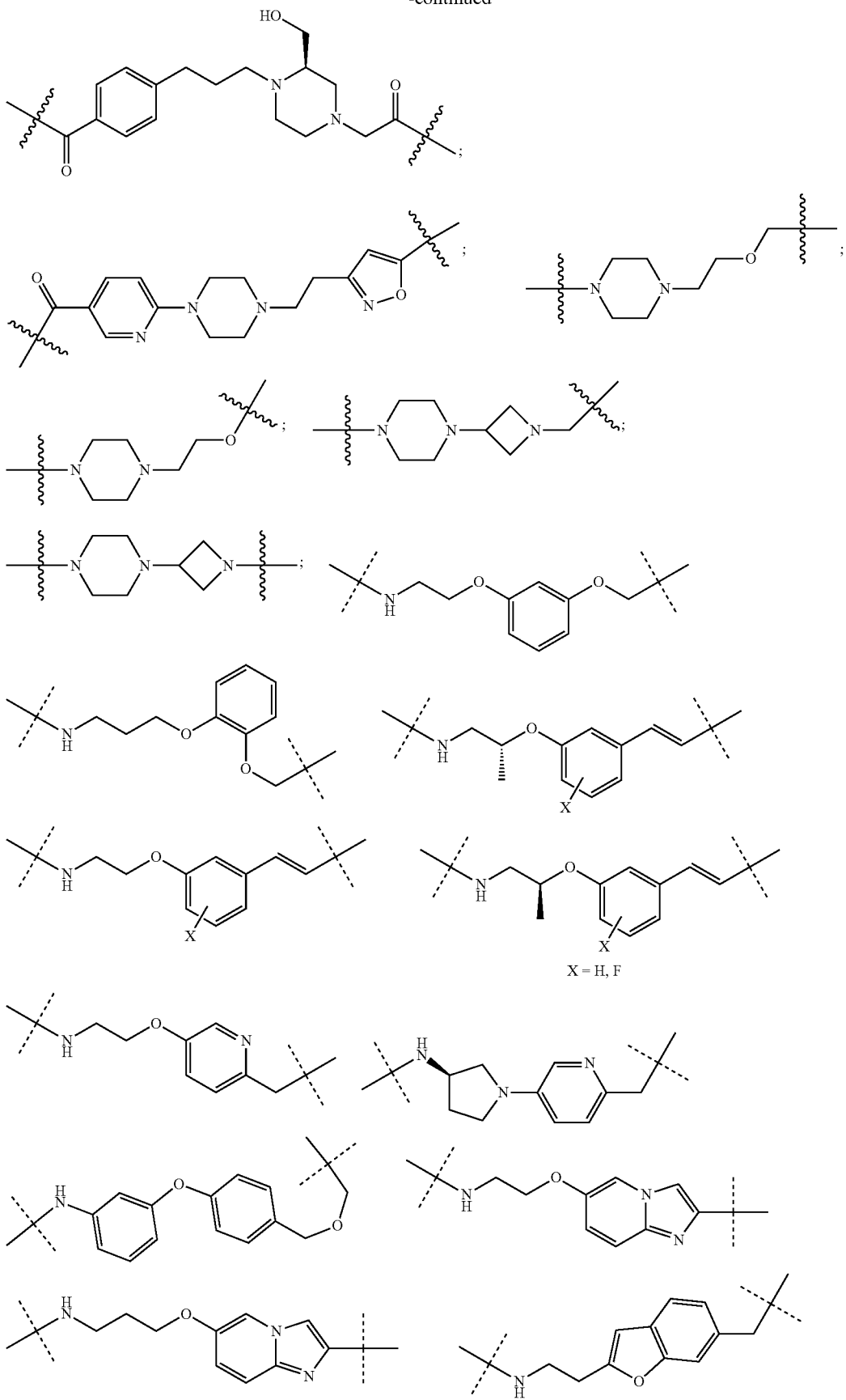

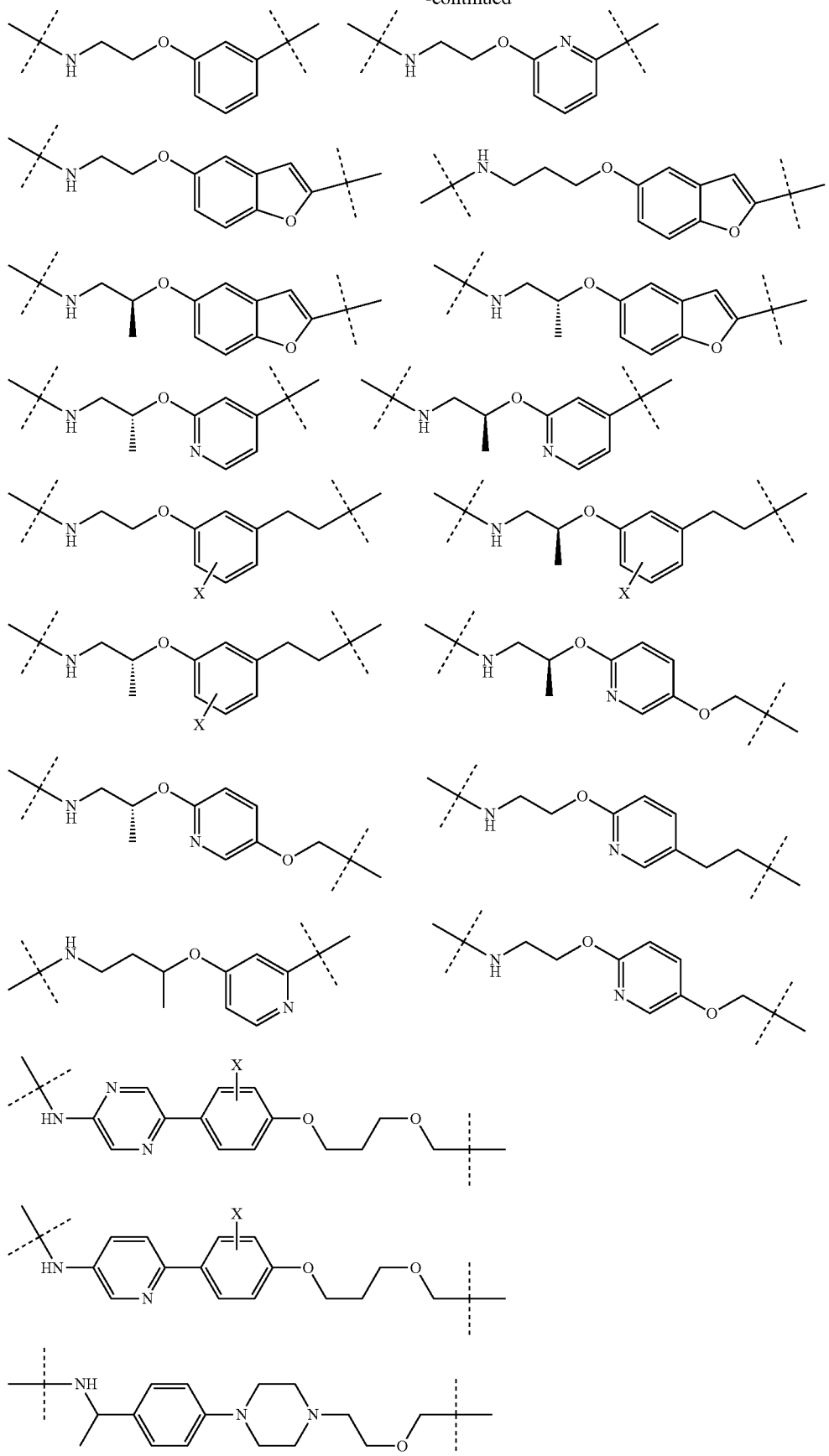

-continued
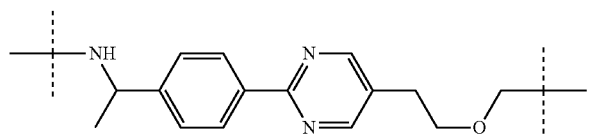
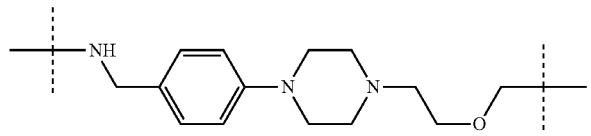
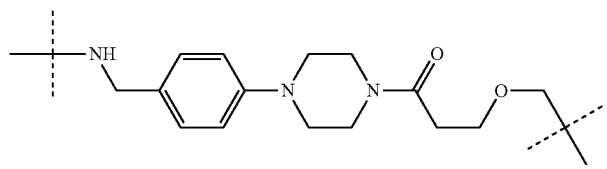
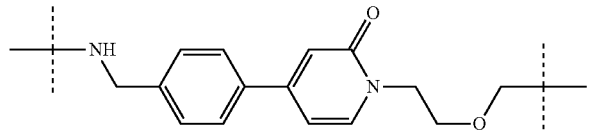
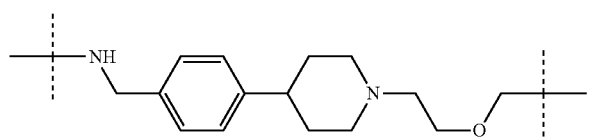
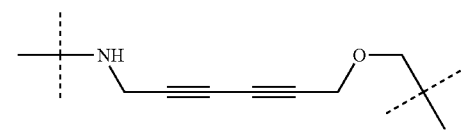
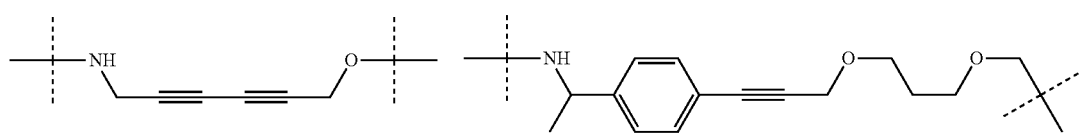
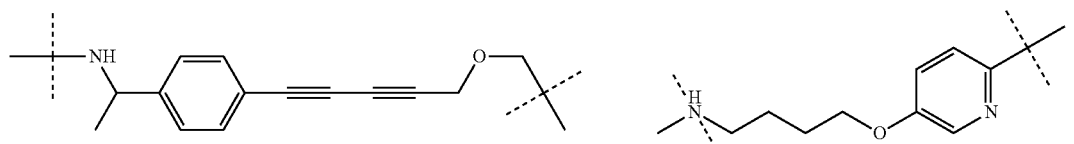
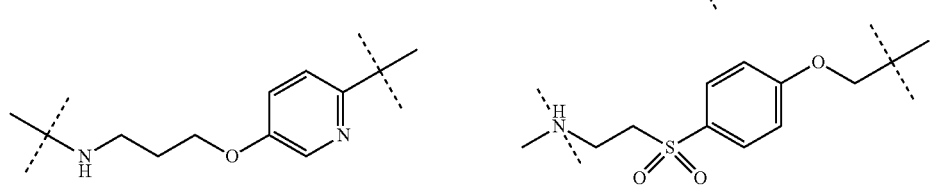
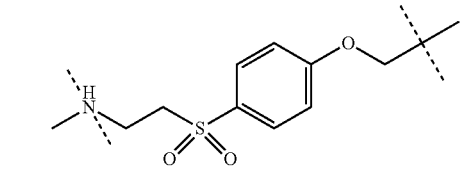
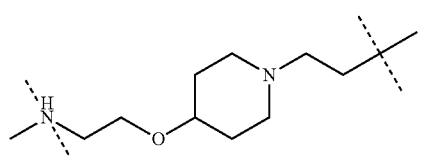
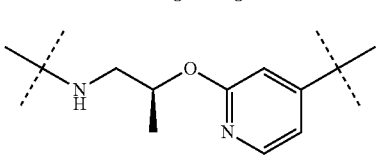
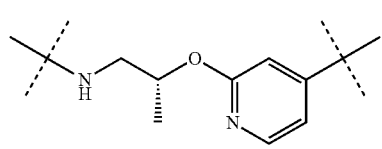
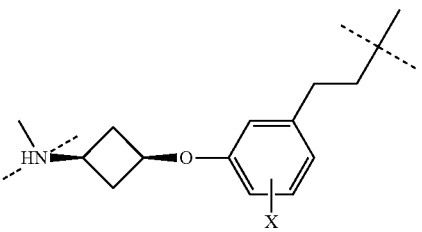

-continued
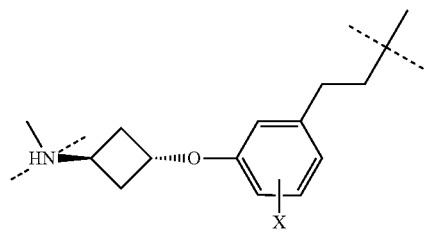
X = H, F
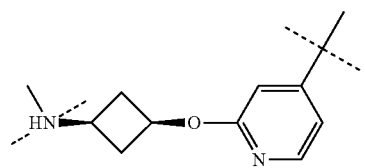
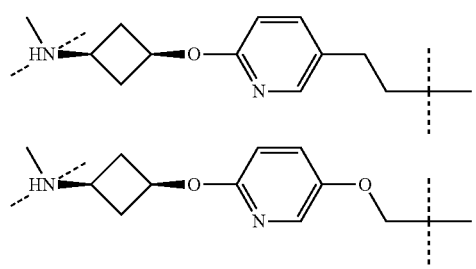
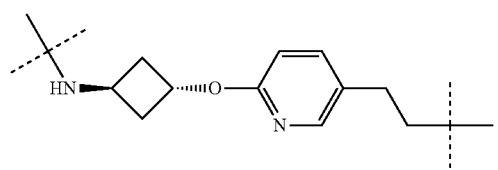
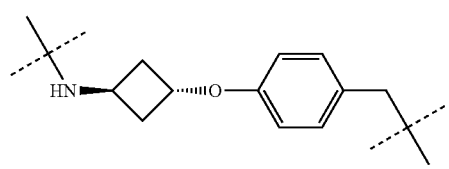
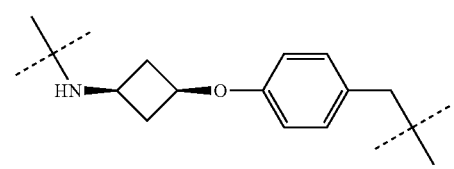
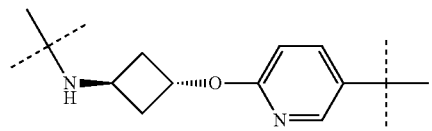
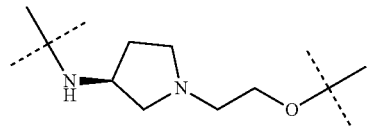
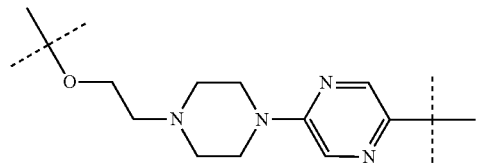
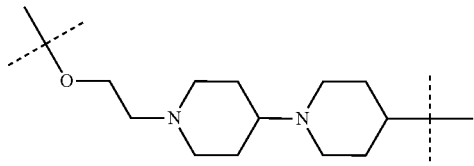
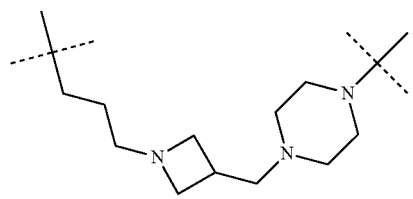
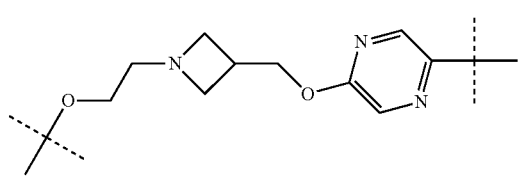
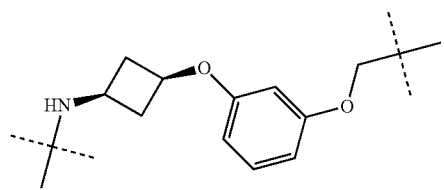
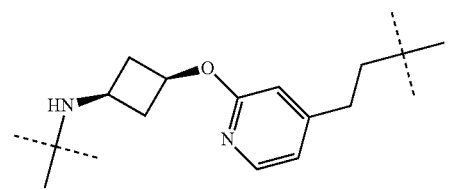
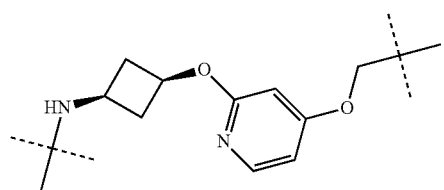
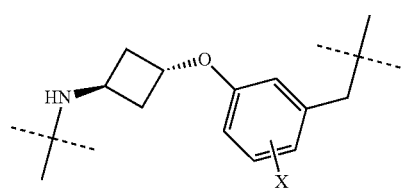

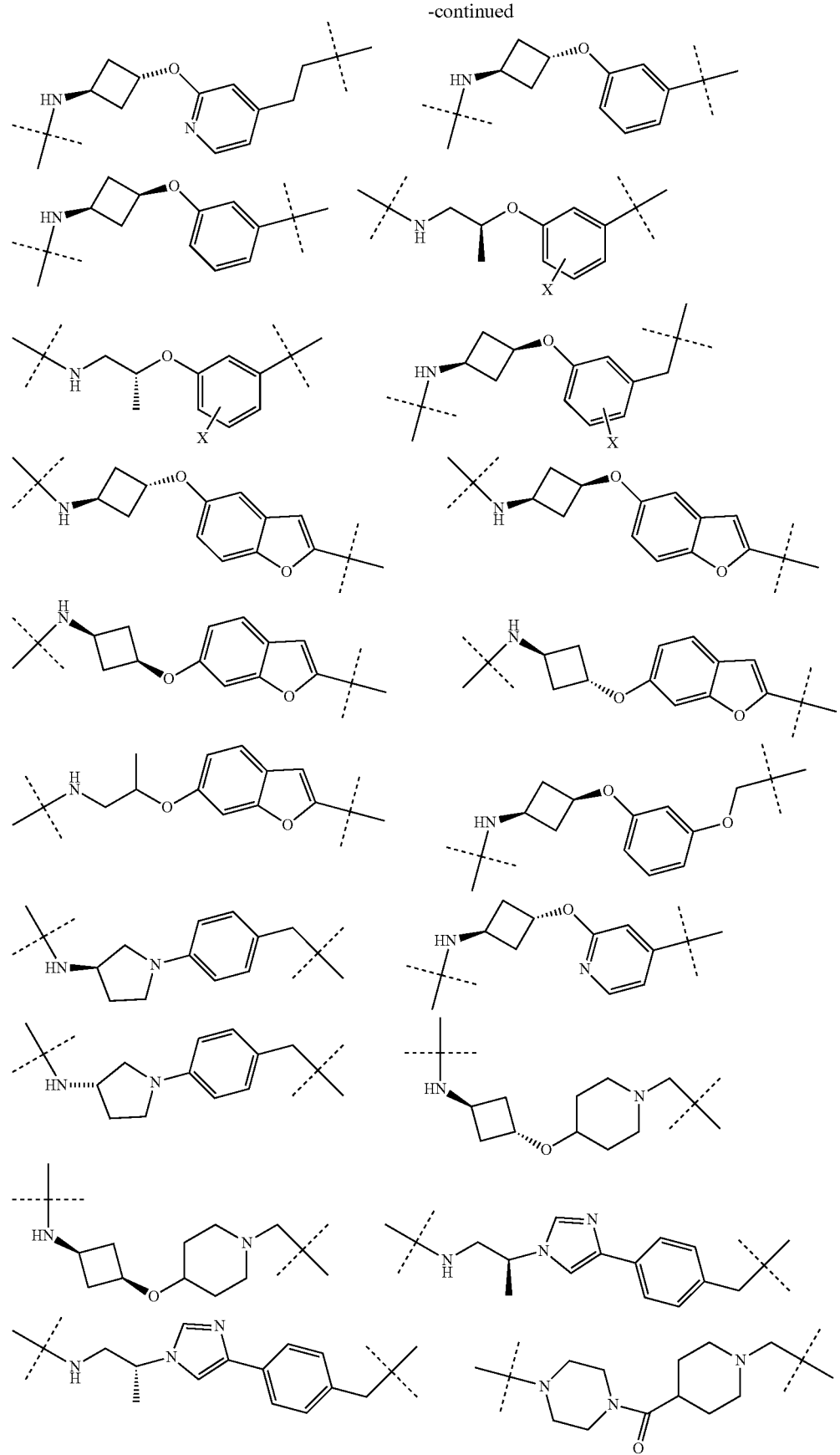

-continued
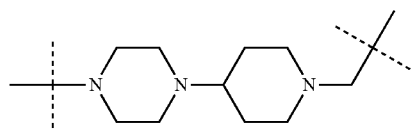 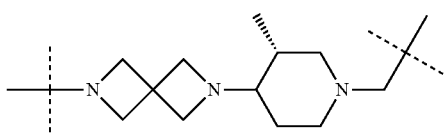
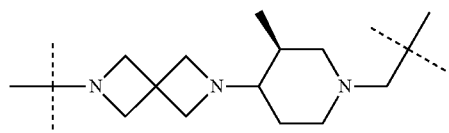 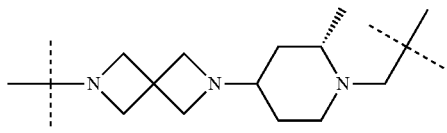
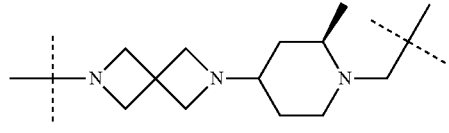 
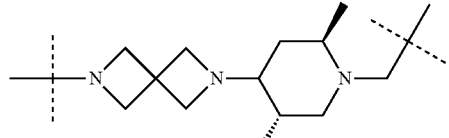 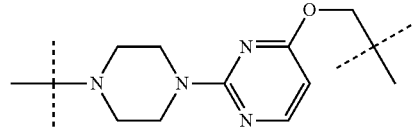
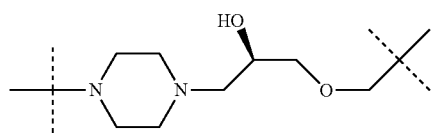 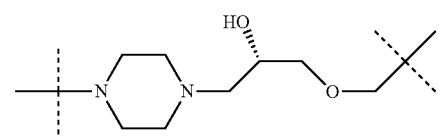
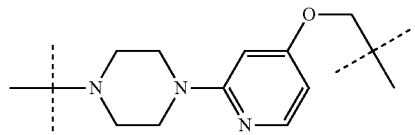 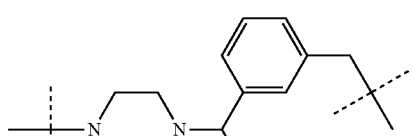
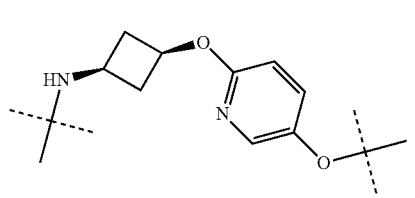 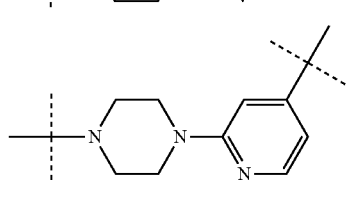
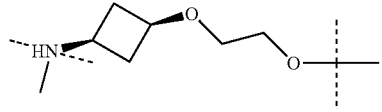 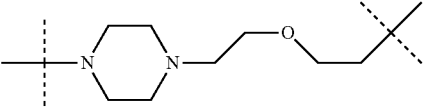
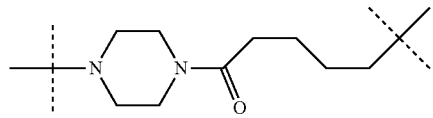 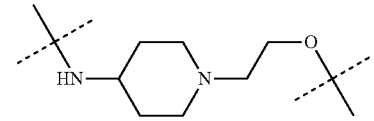
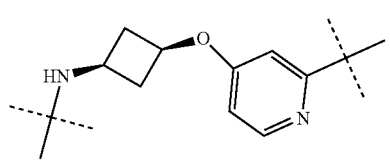 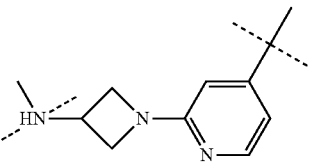
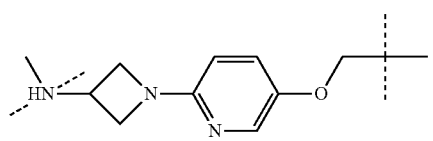 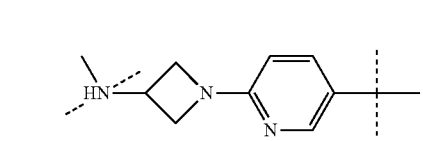

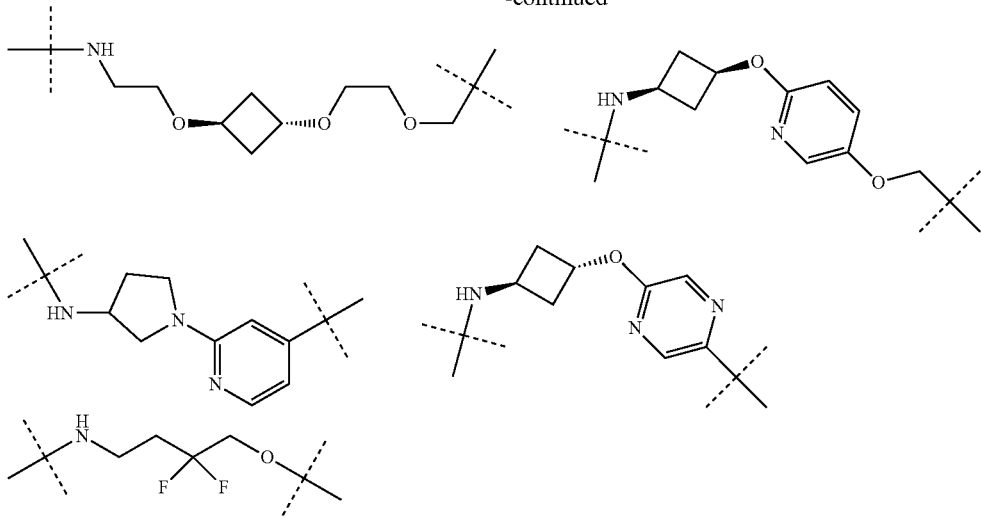
where each n and m of the linker can independently be 0, 1, 2, 3, 4, 5, 6.
In any aspect or embodiment described herein, the $A^L$ group is selected from the group consisting of:
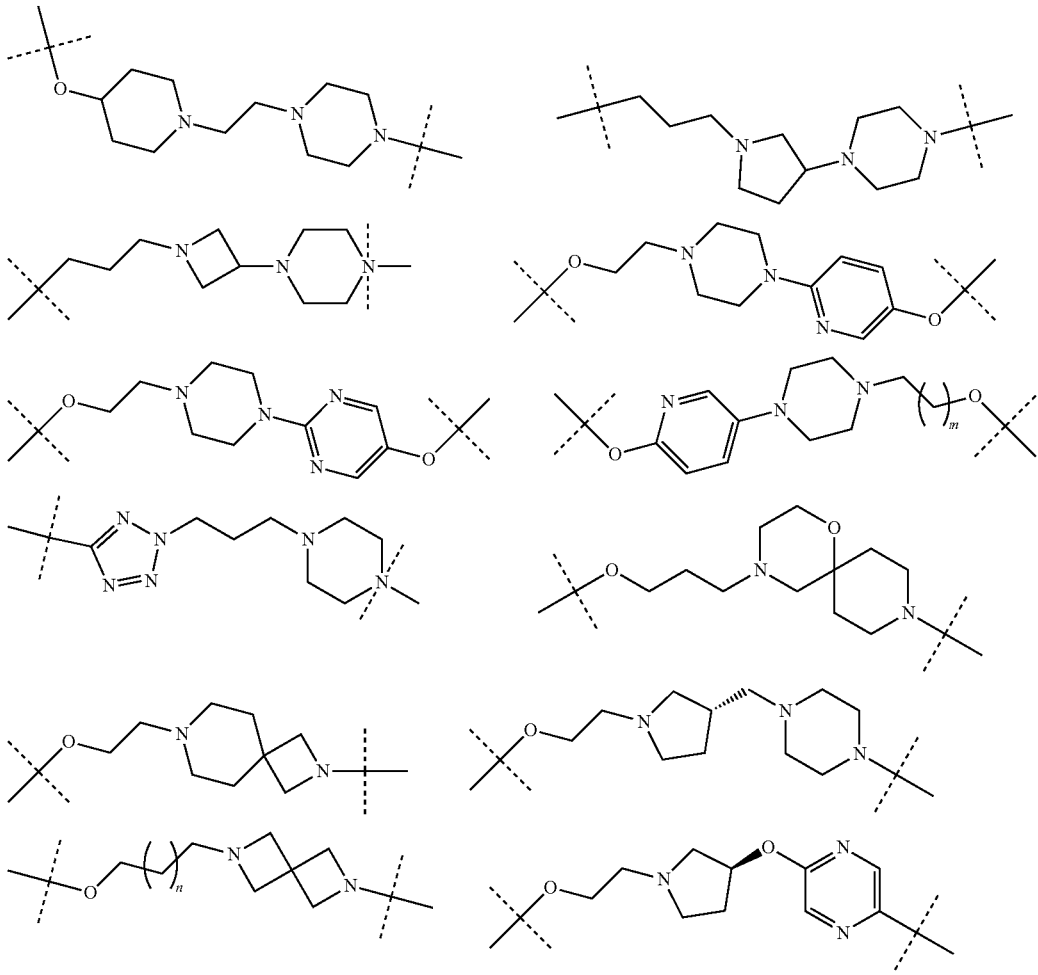

-continued
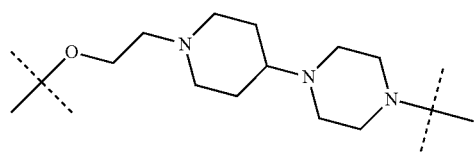
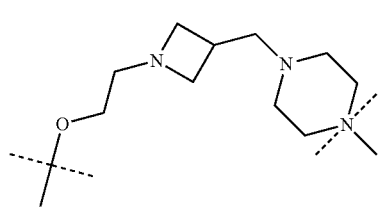
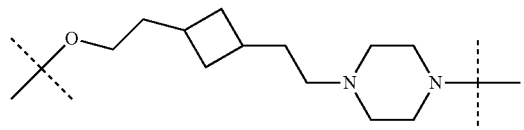
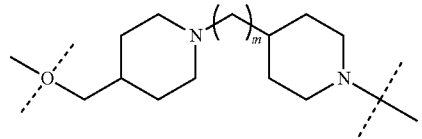
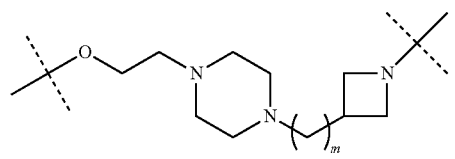
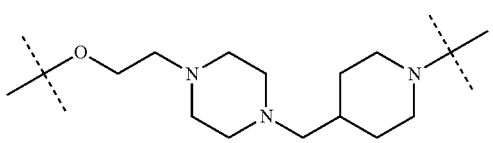
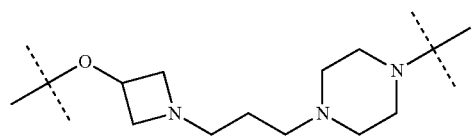
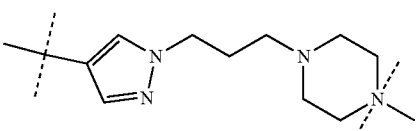
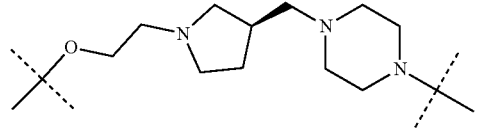
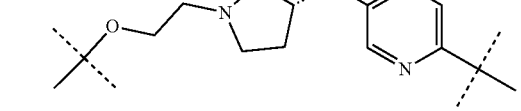
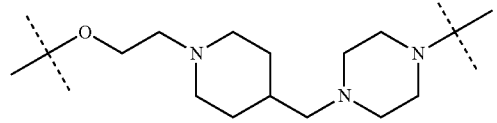
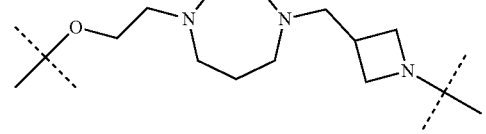
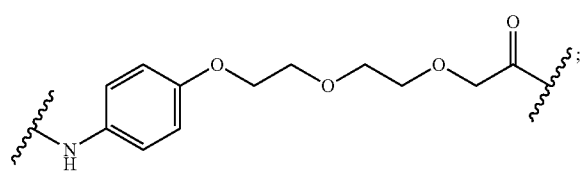
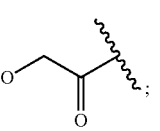
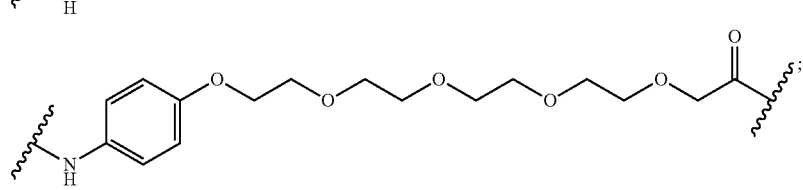
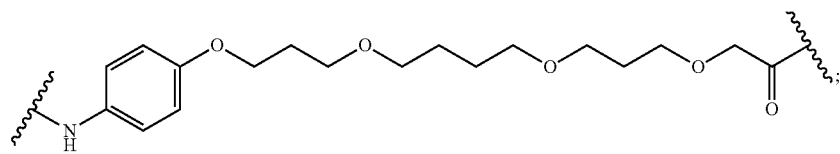

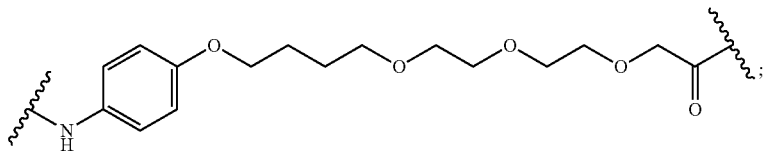
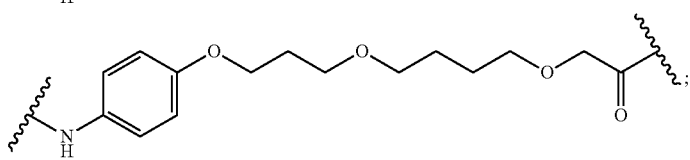
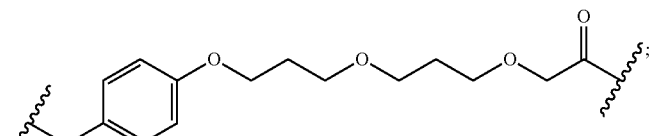
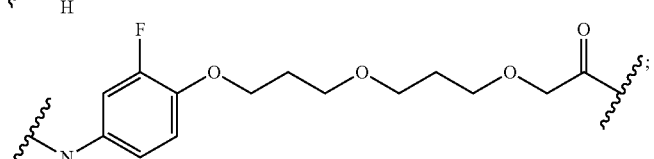
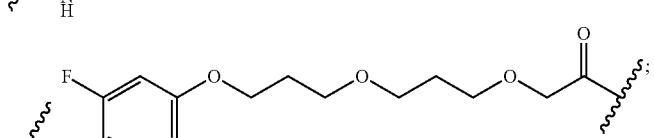
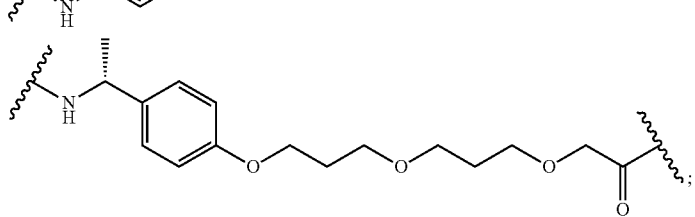
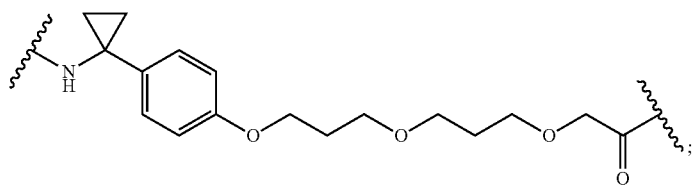
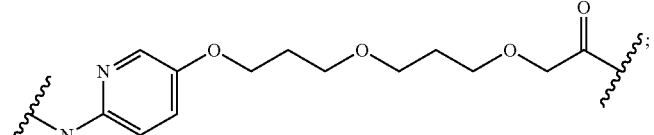
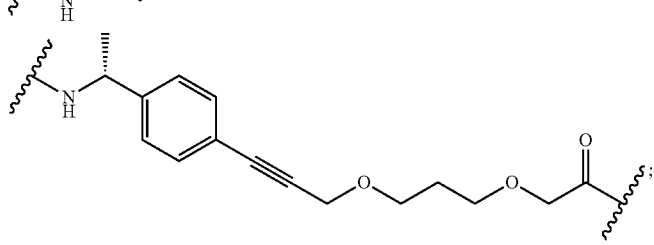

-continued
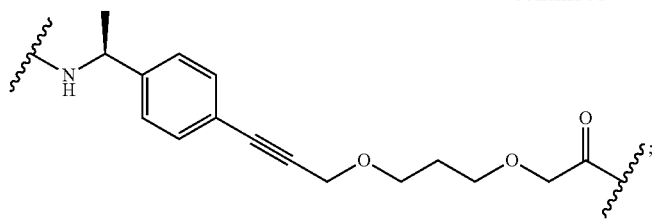
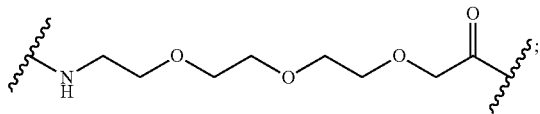
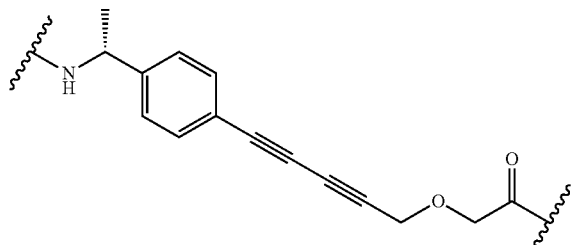
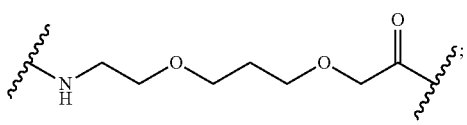
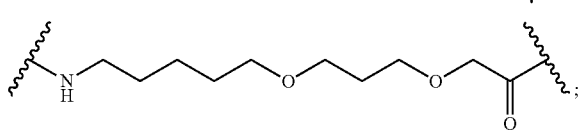
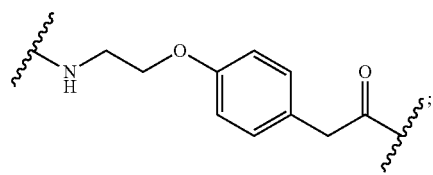
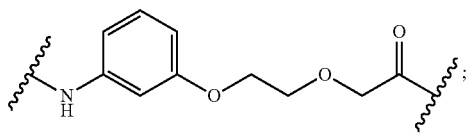
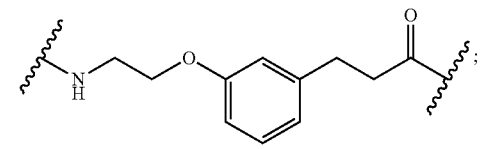
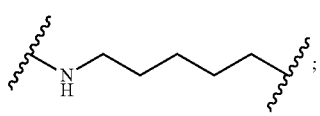
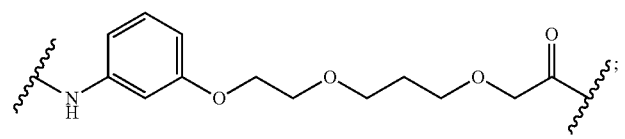
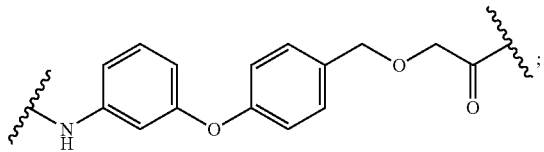
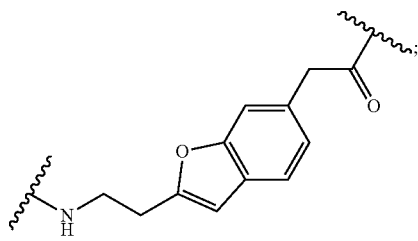
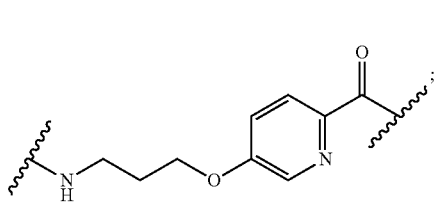
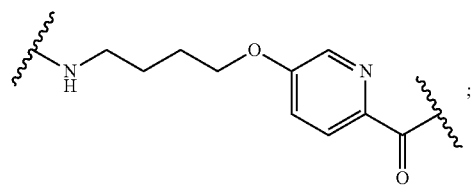

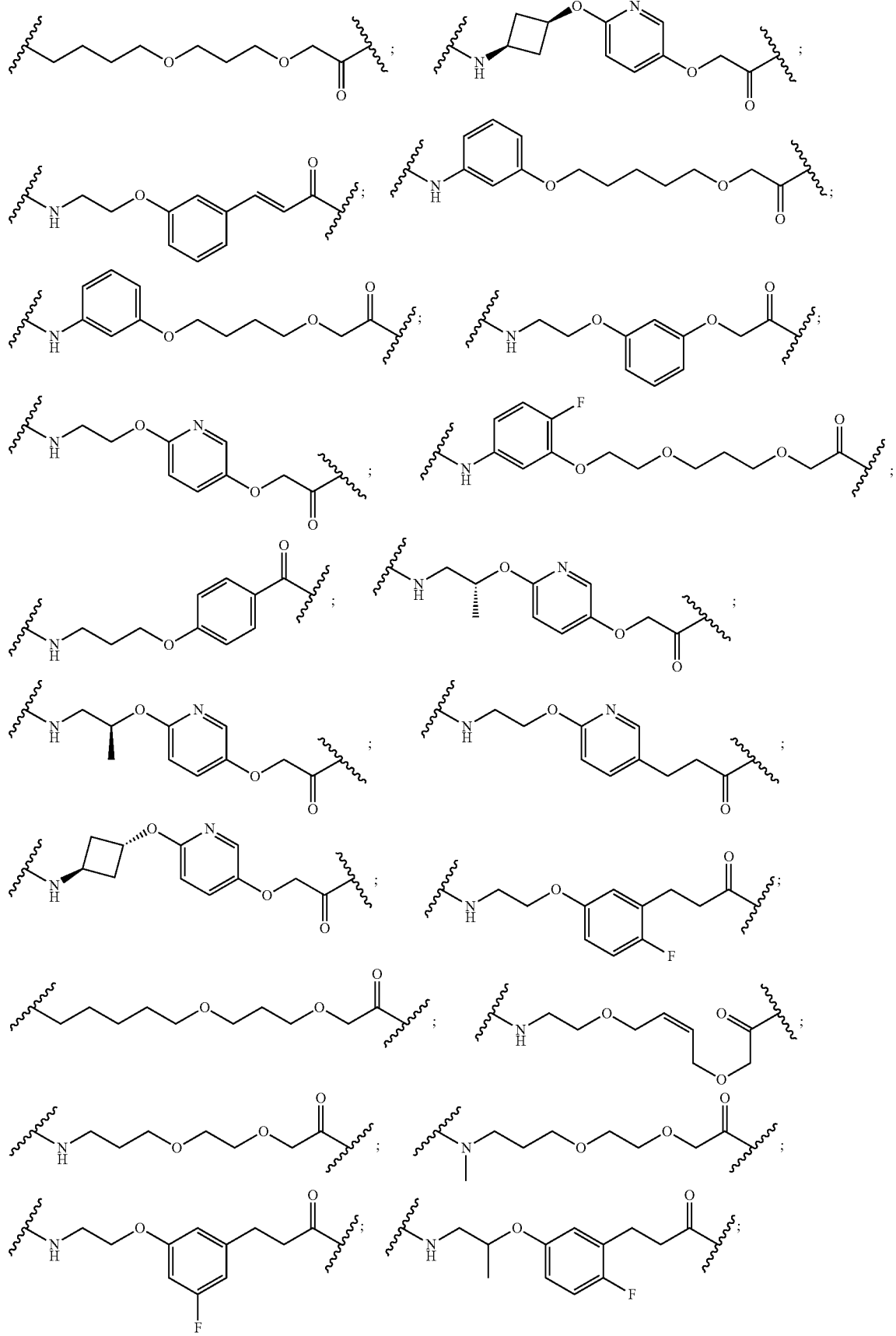

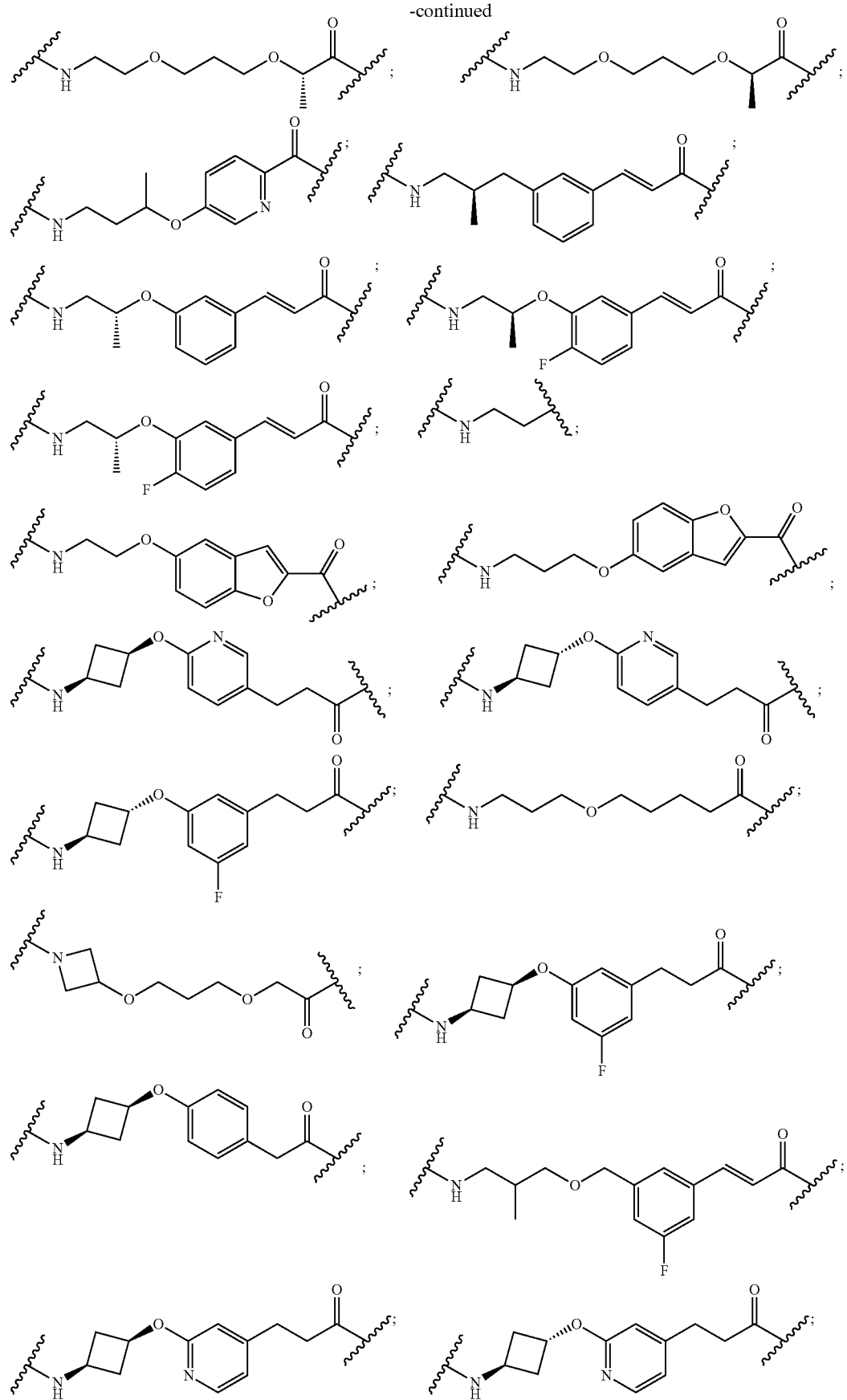

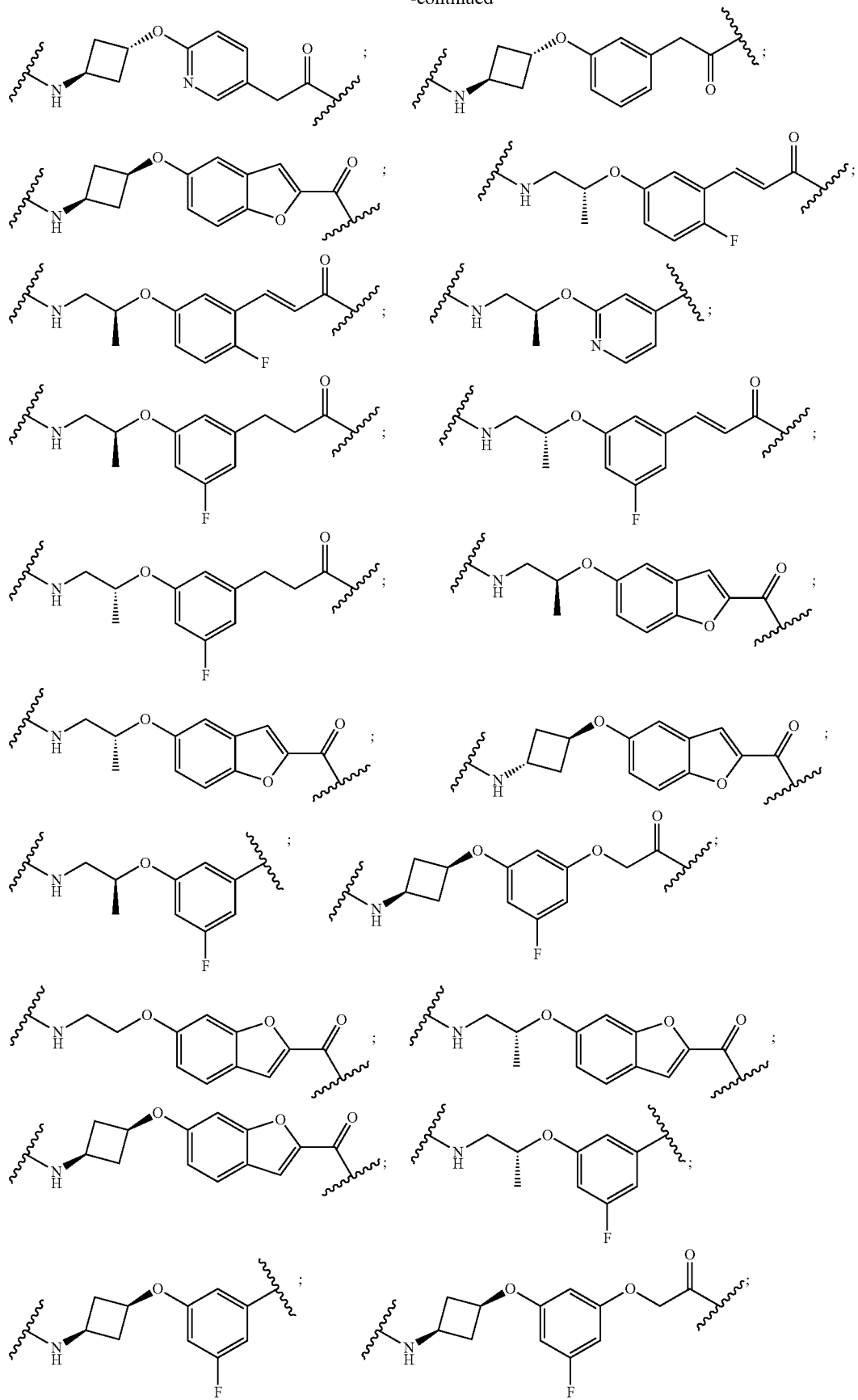

-continued
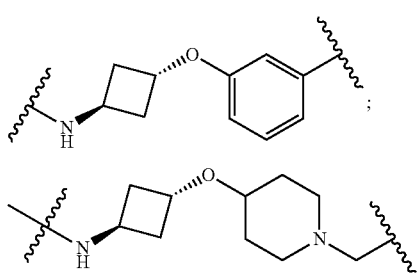
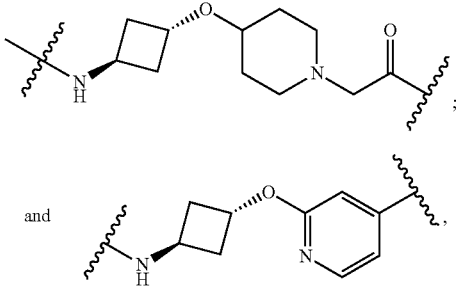
wherein each m and n is independently selected from 0, 1, 2, 3, 4, 5, or 6.
In any aspect or embodiment described herein, $A^L$ group is selected from the group consisting of:
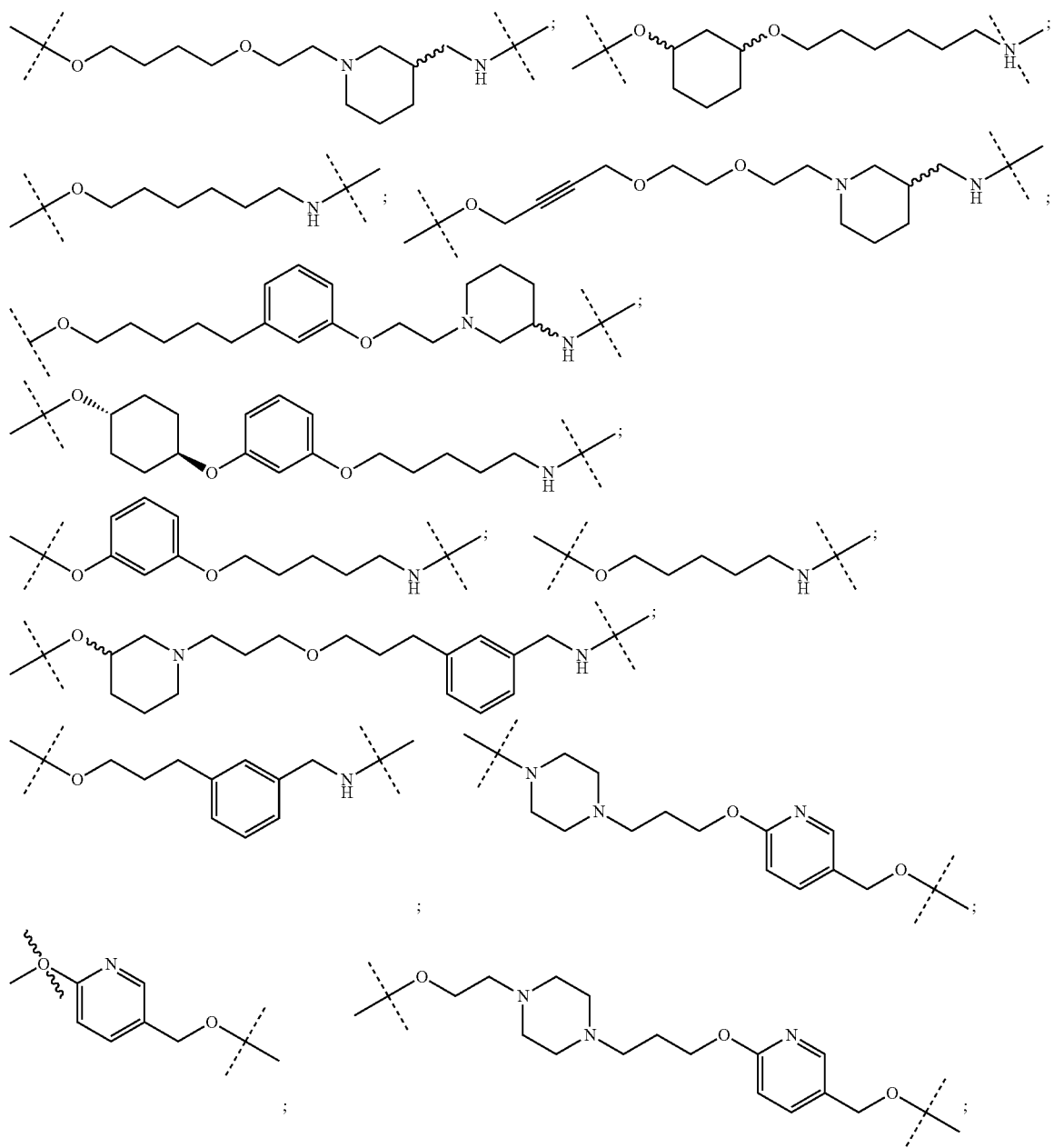

-continued
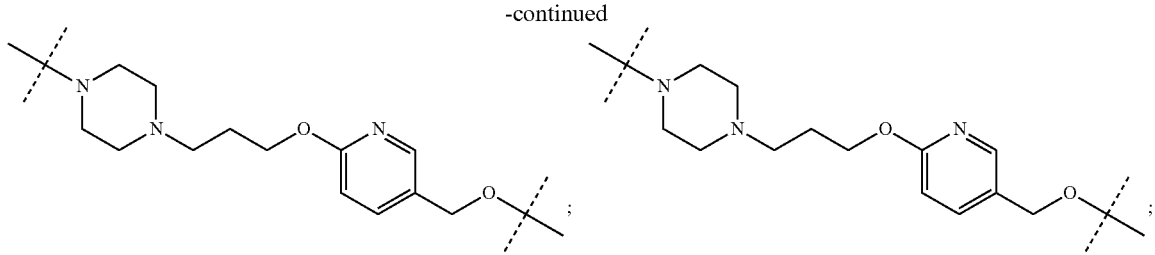
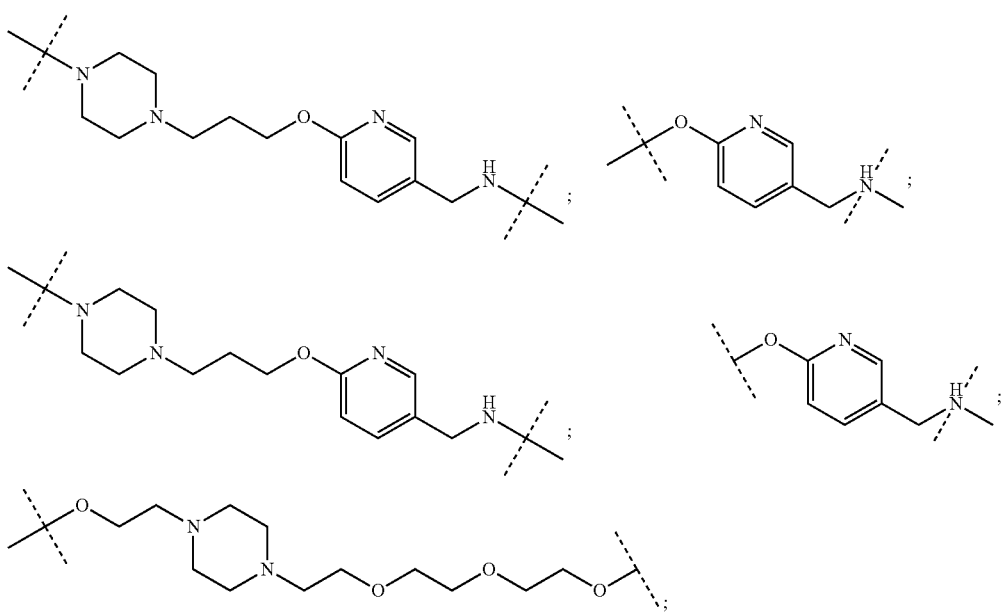
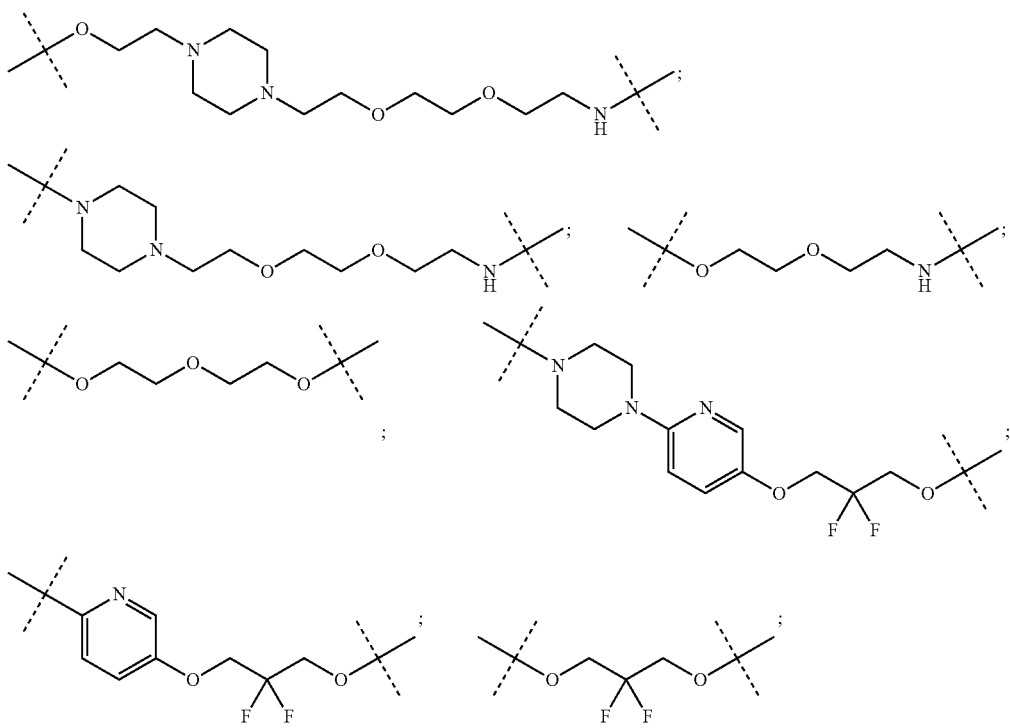

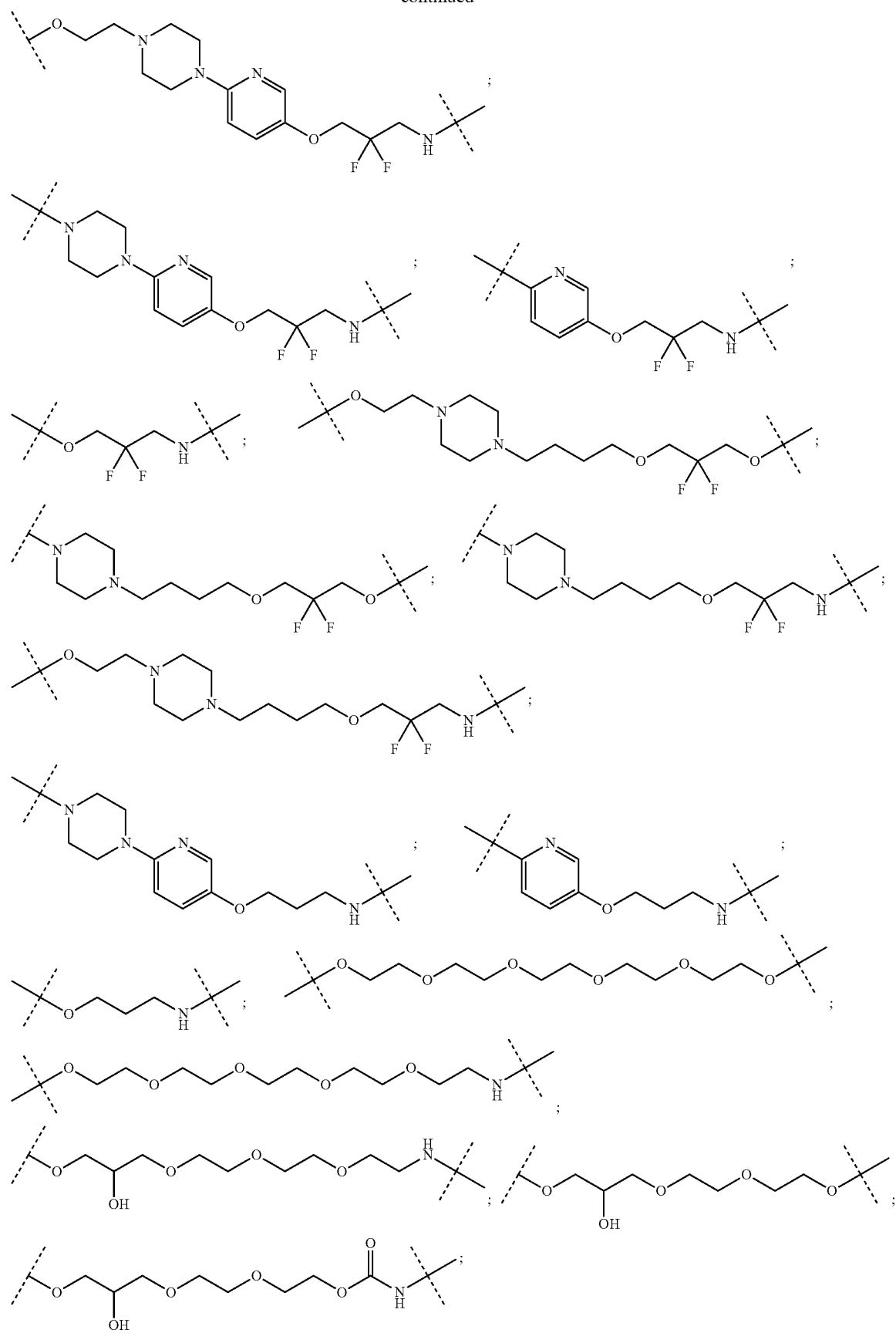

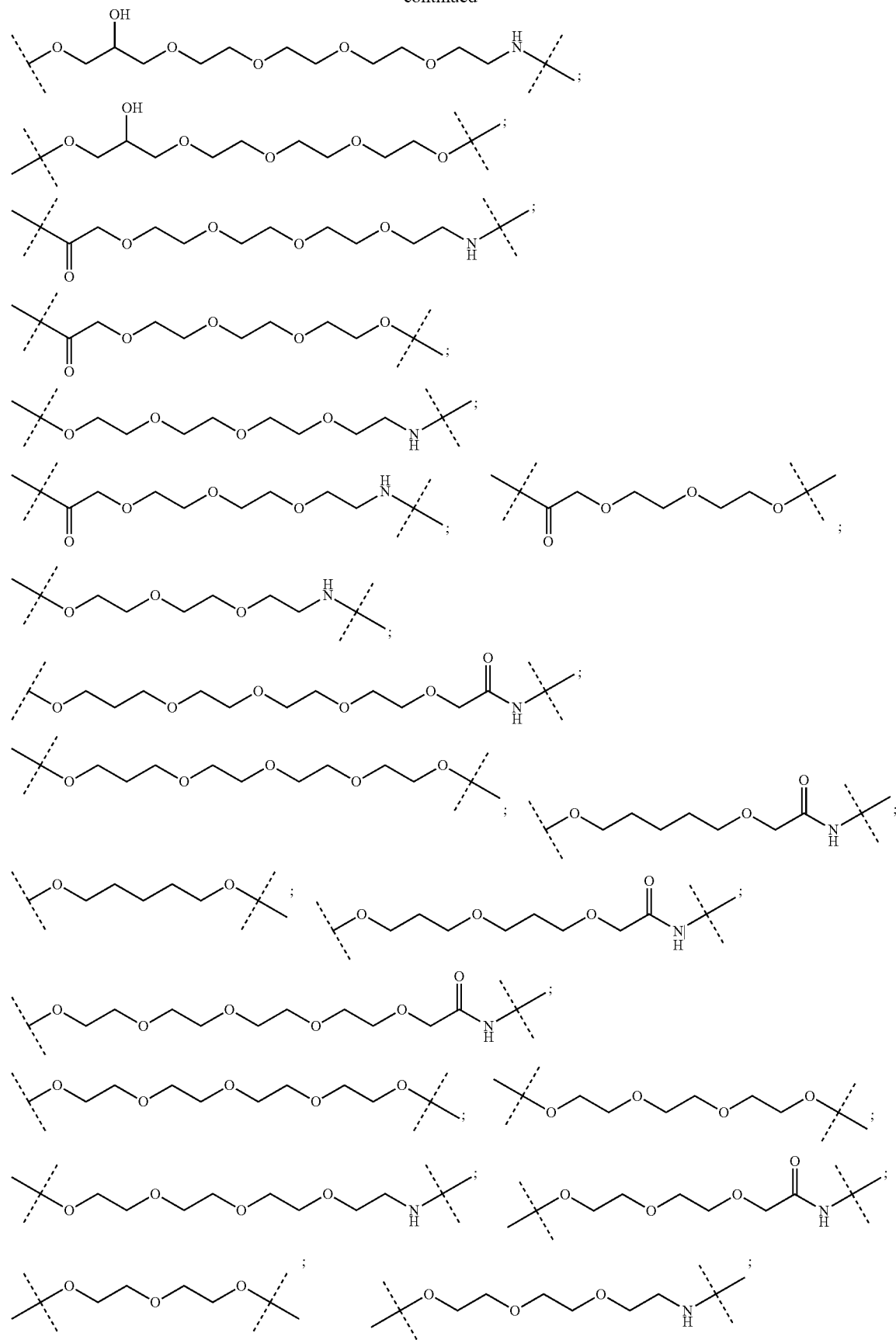

-continued
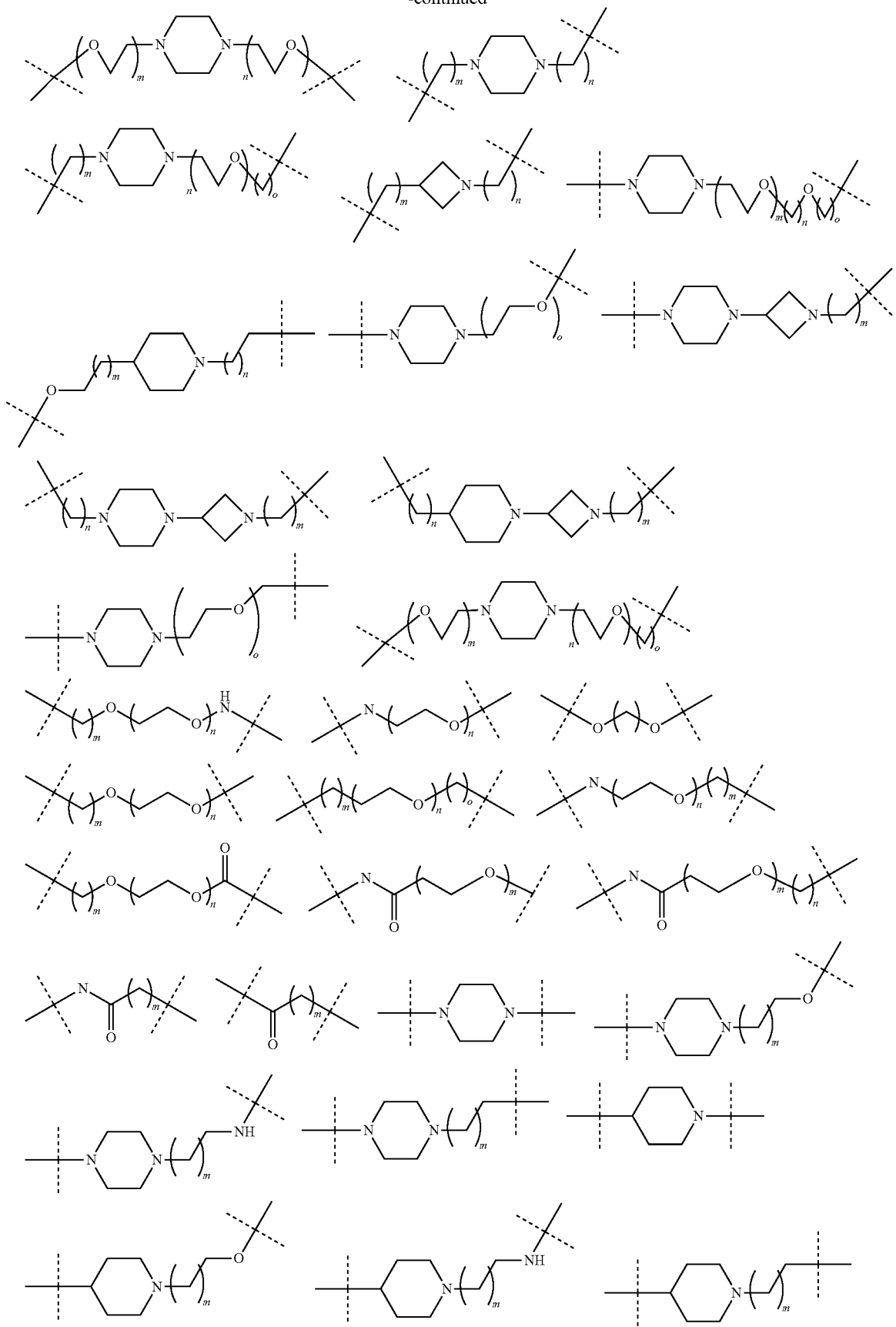

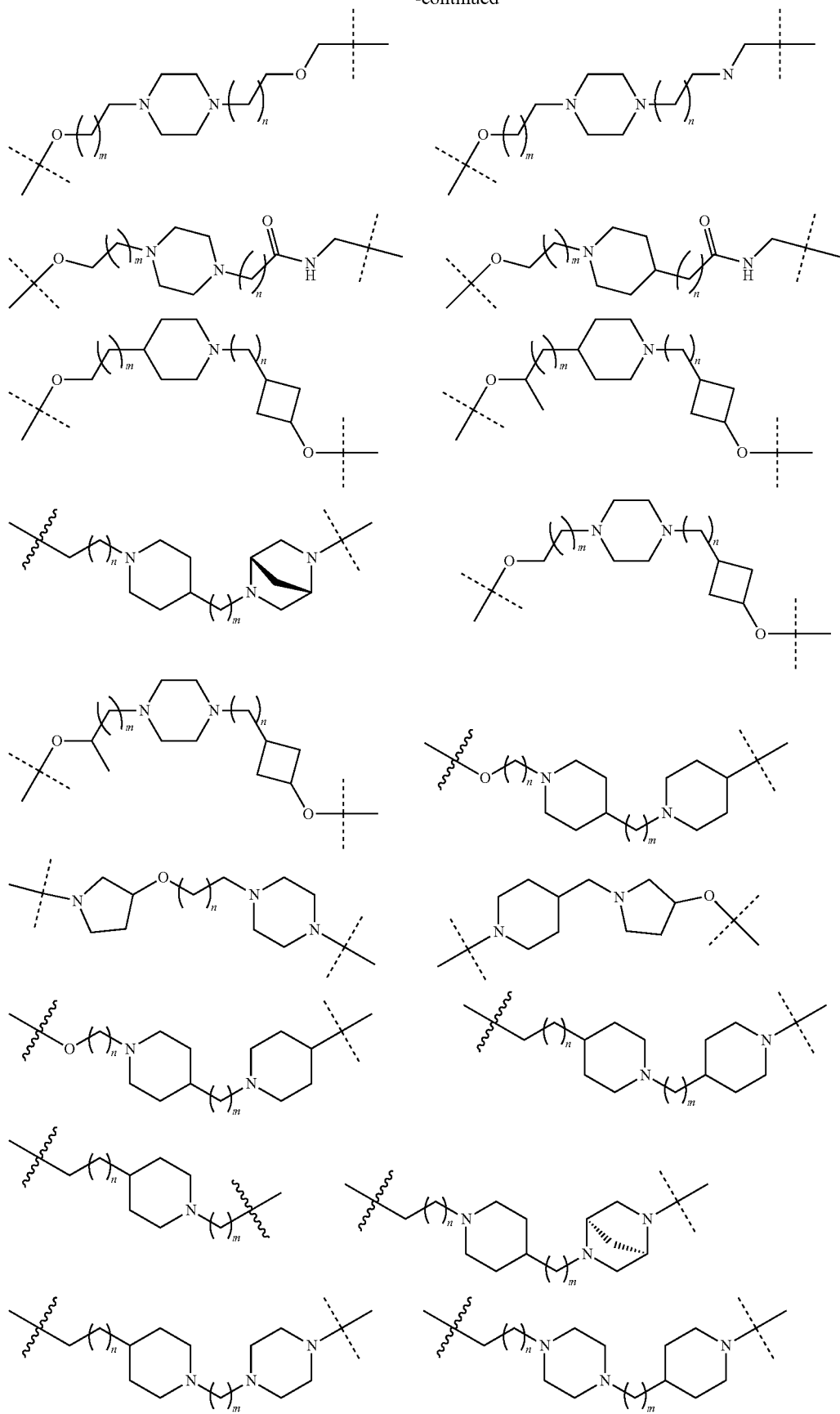

-continued
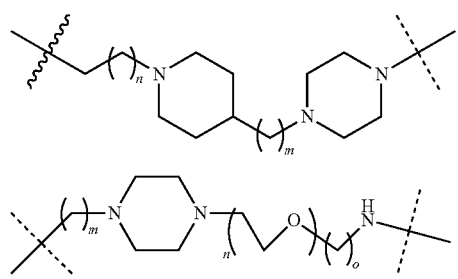
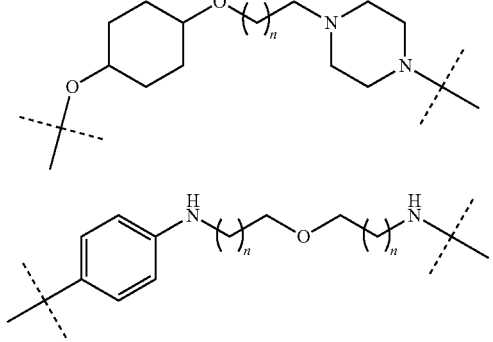
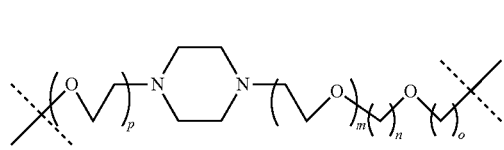
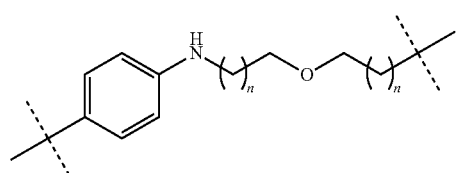
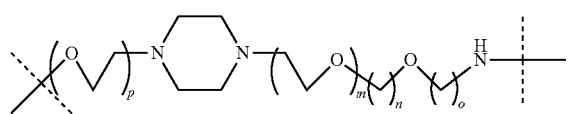
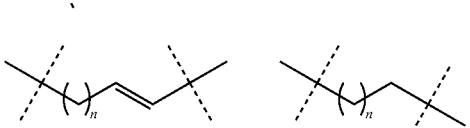
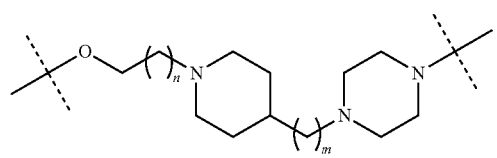
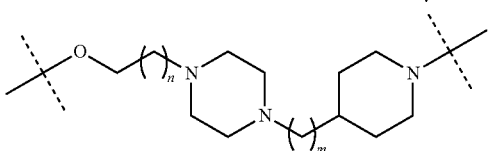
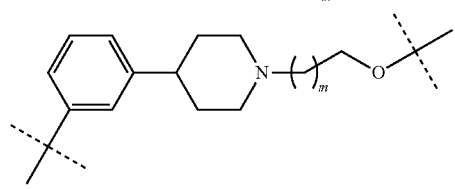
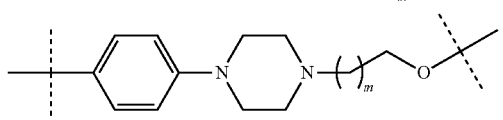
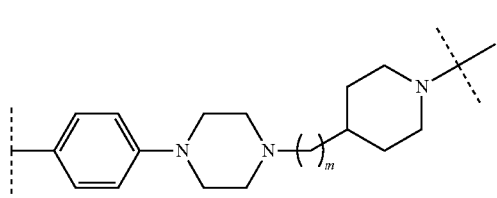
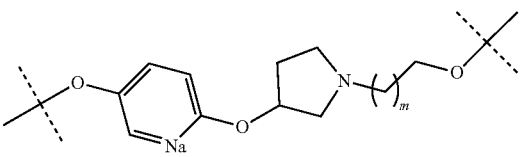
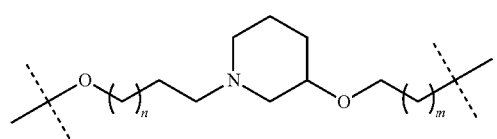
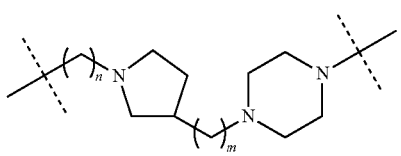
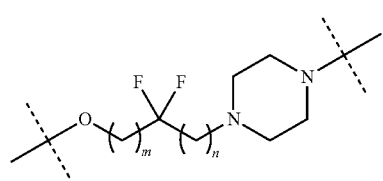
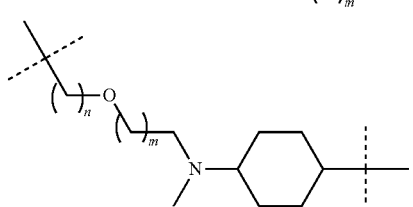
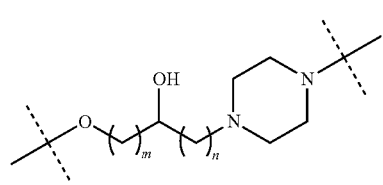
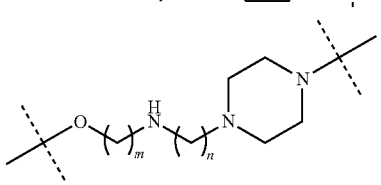

-continued
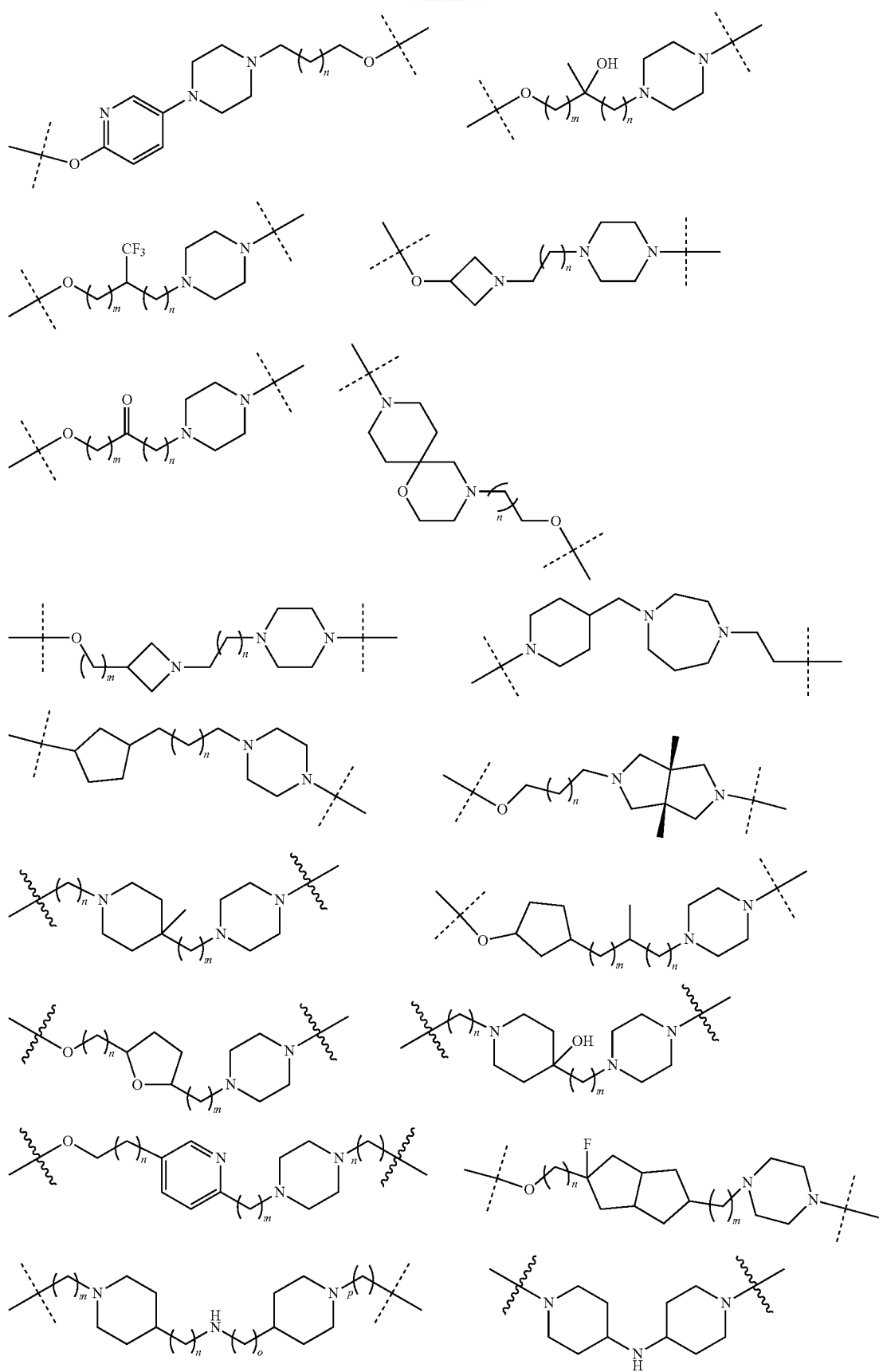

-continued
103
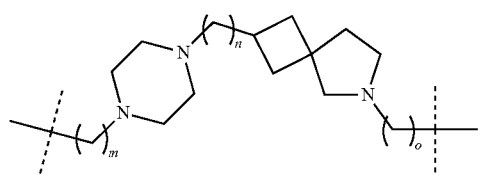
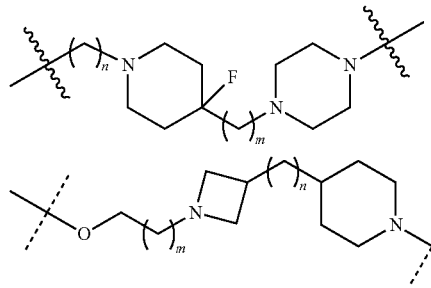
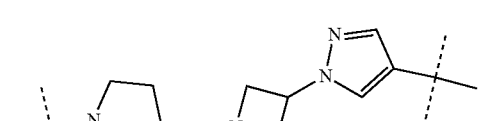
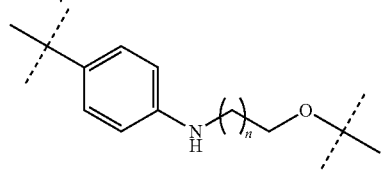
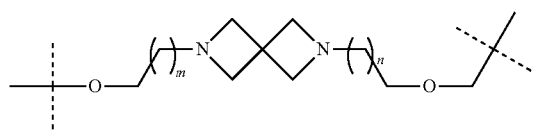
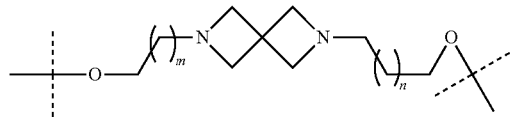
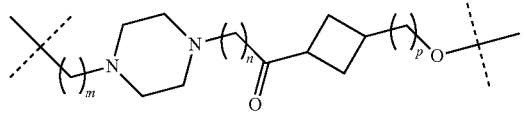
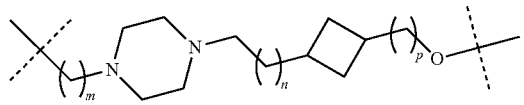
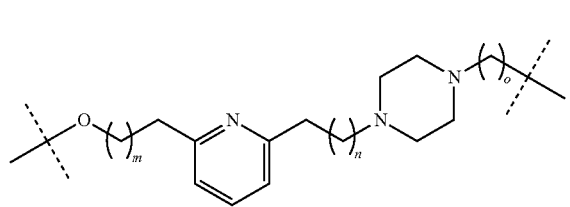
104
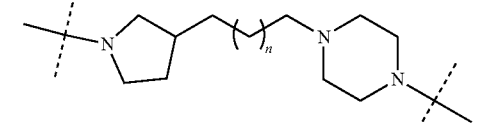
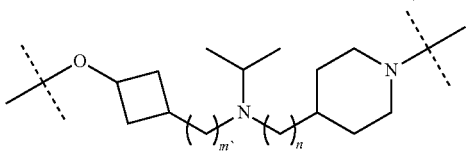
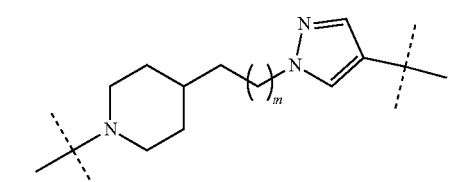
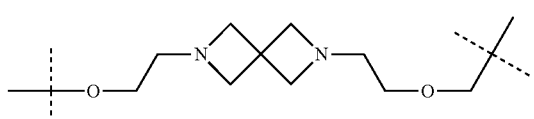
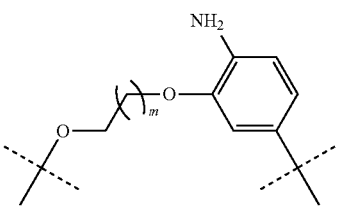
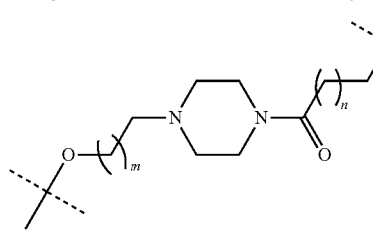
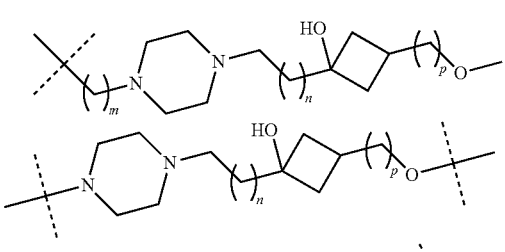
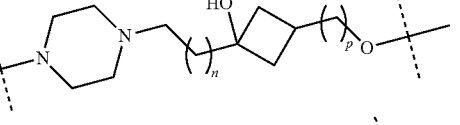
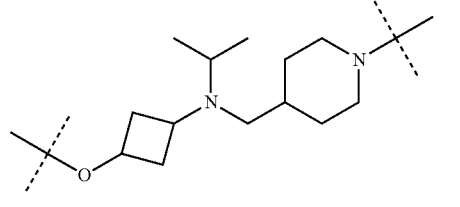

-continued
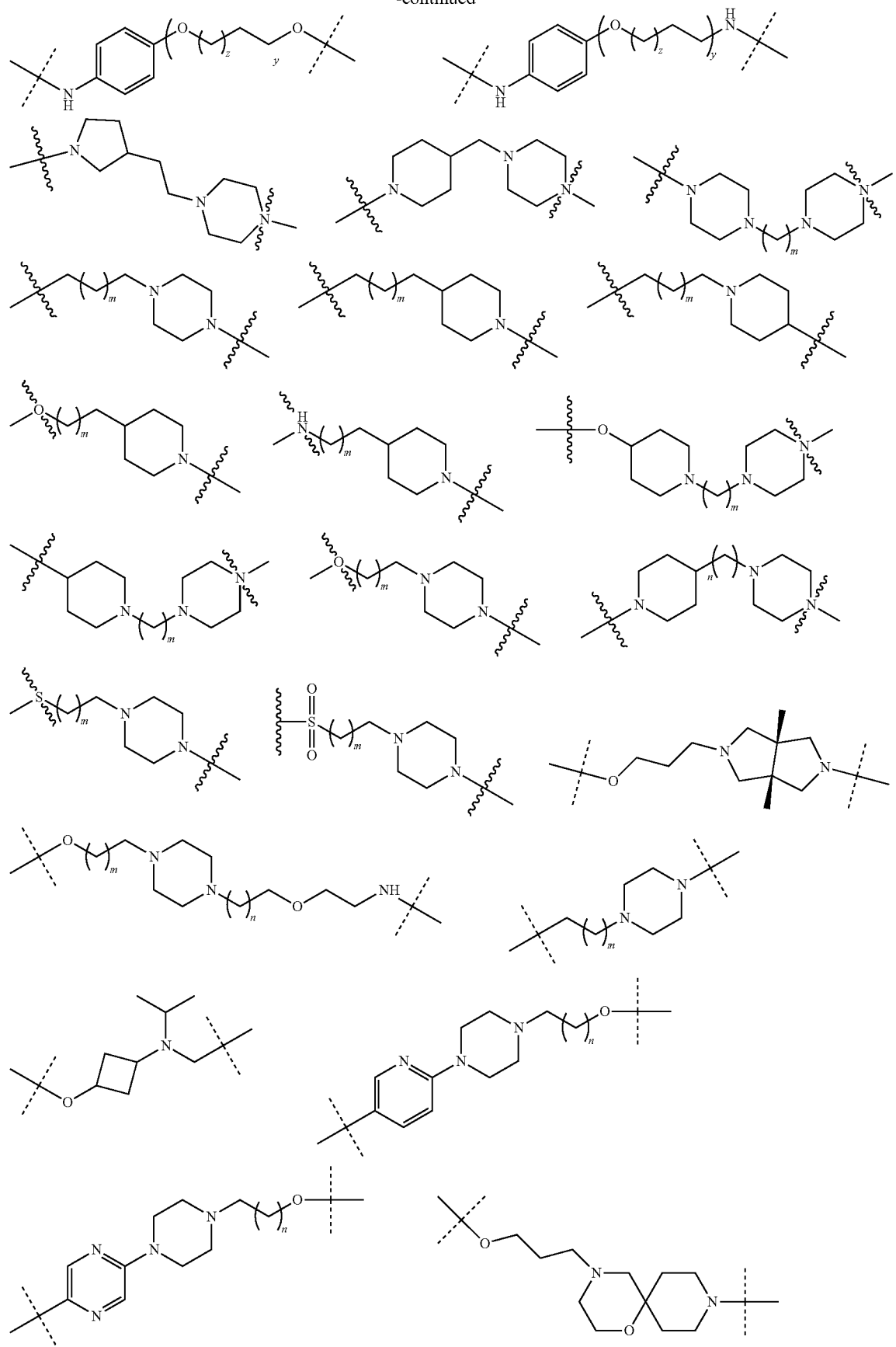

-continued
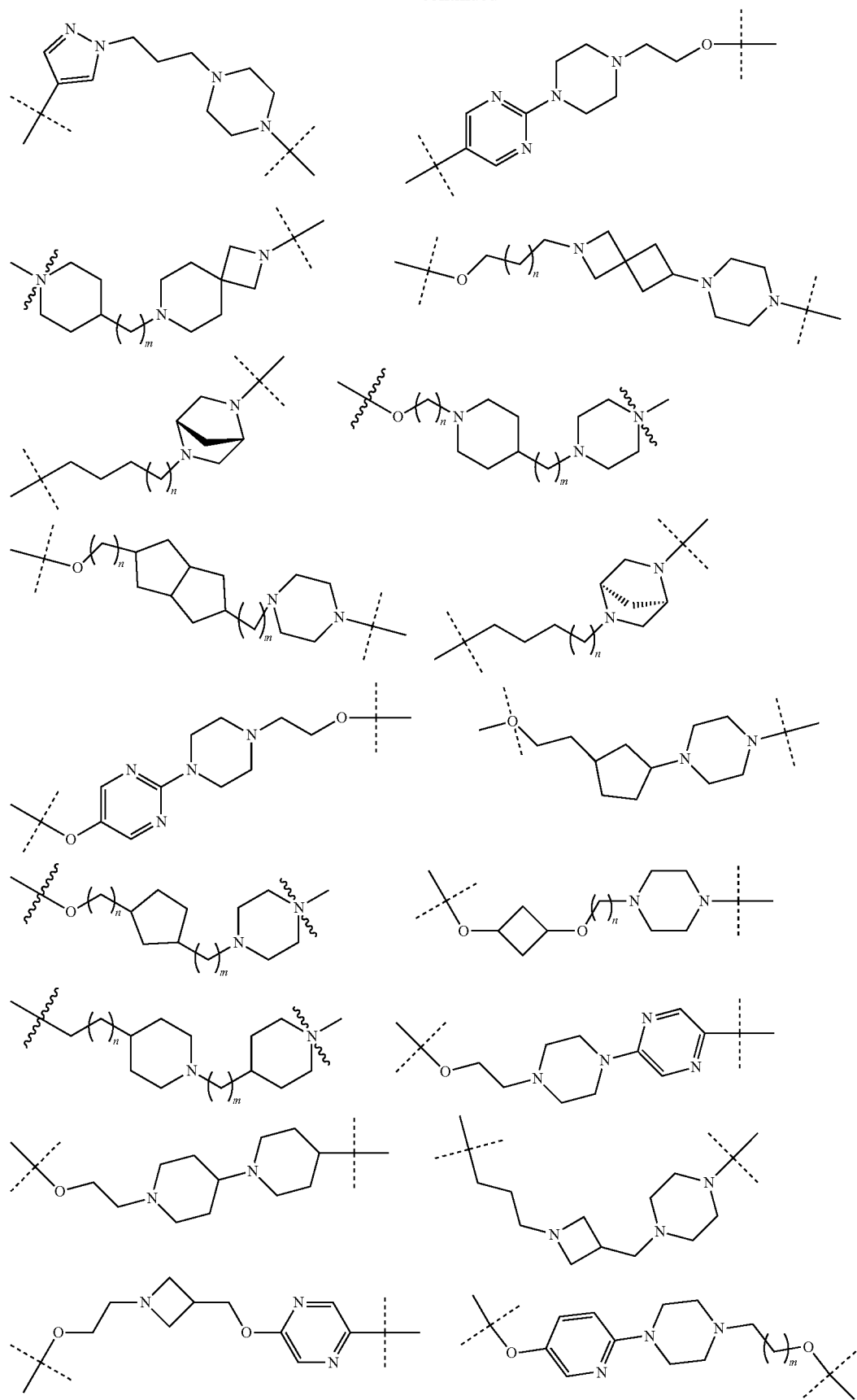

-continued
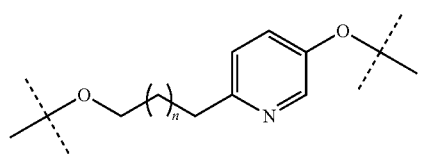
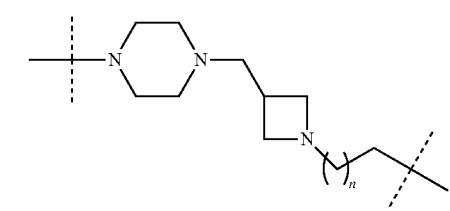
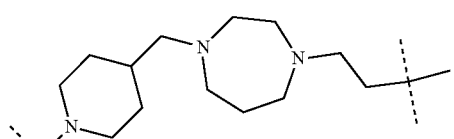
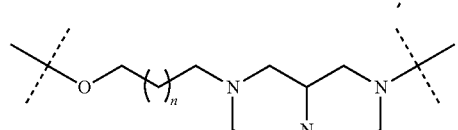
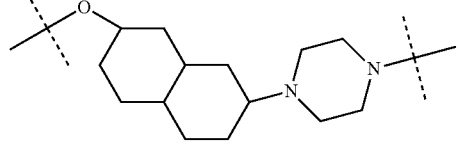
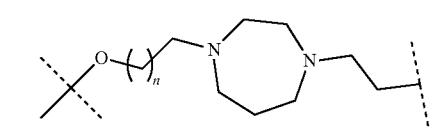
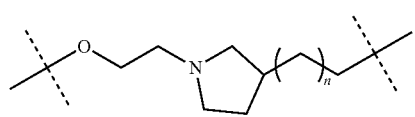
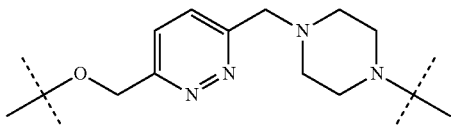
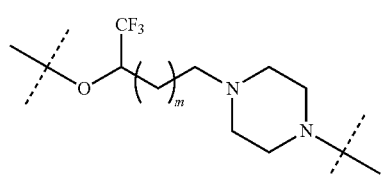
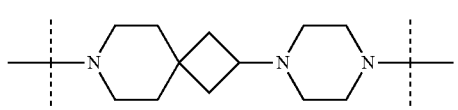
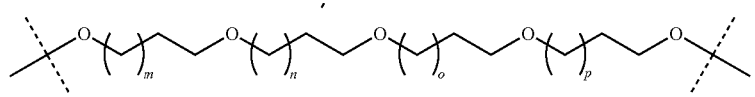
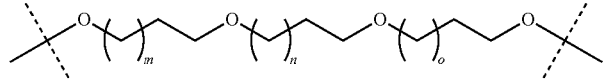
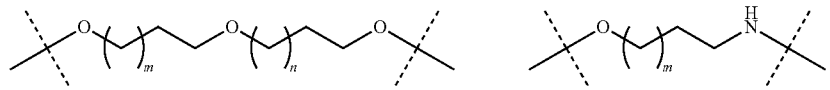
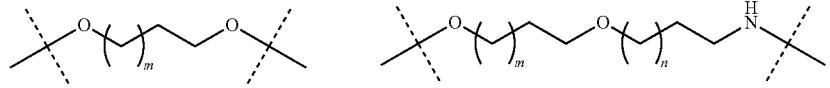
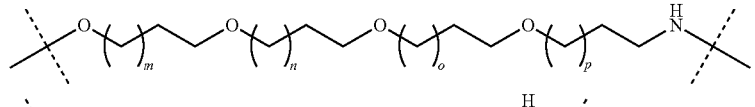
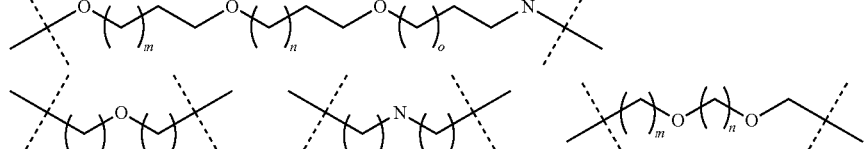
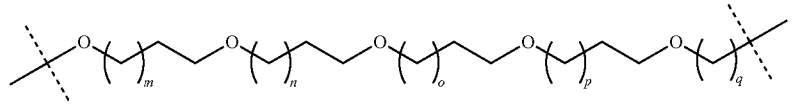
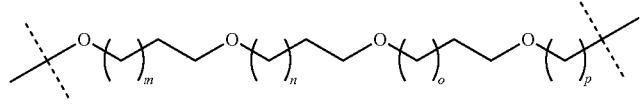

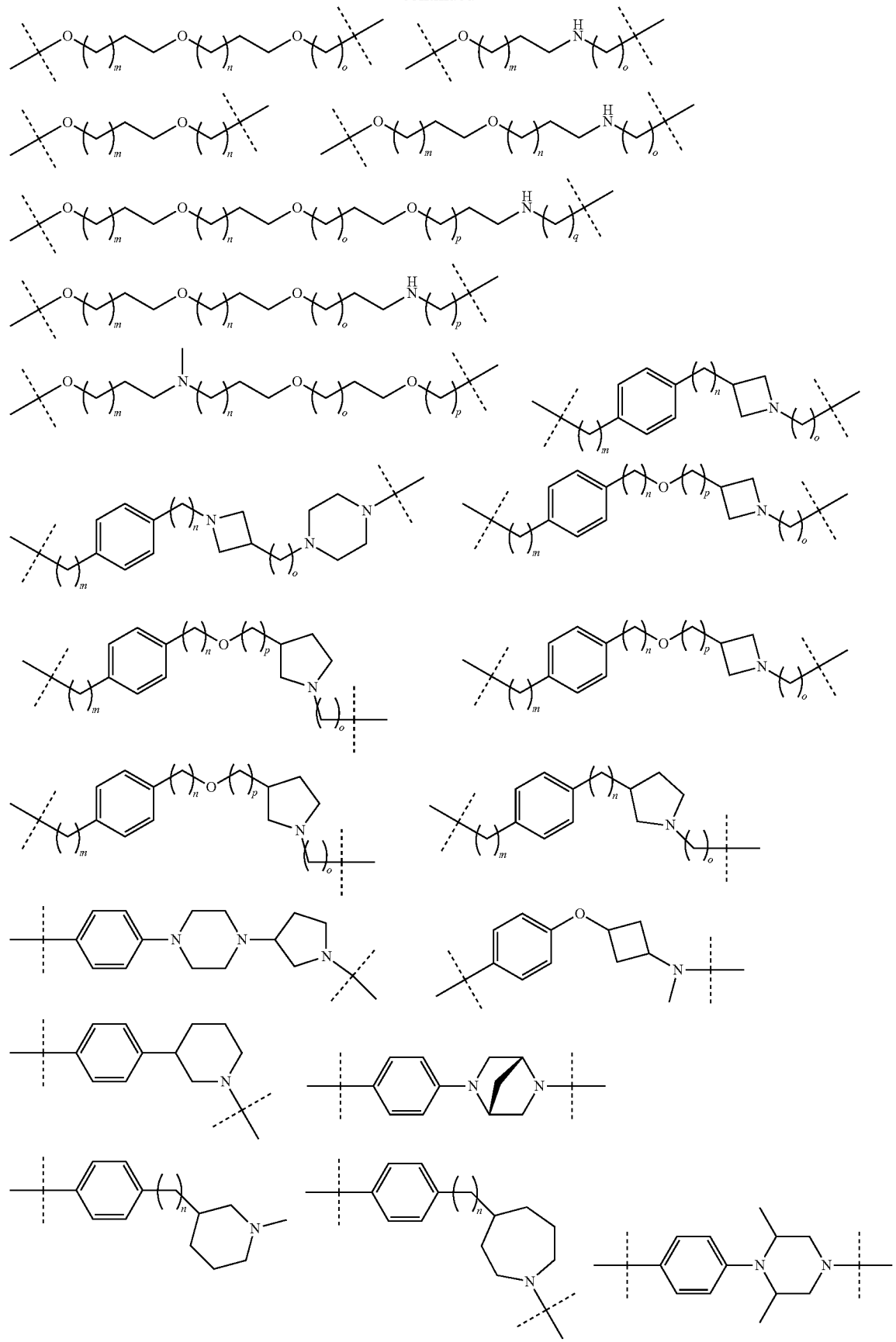

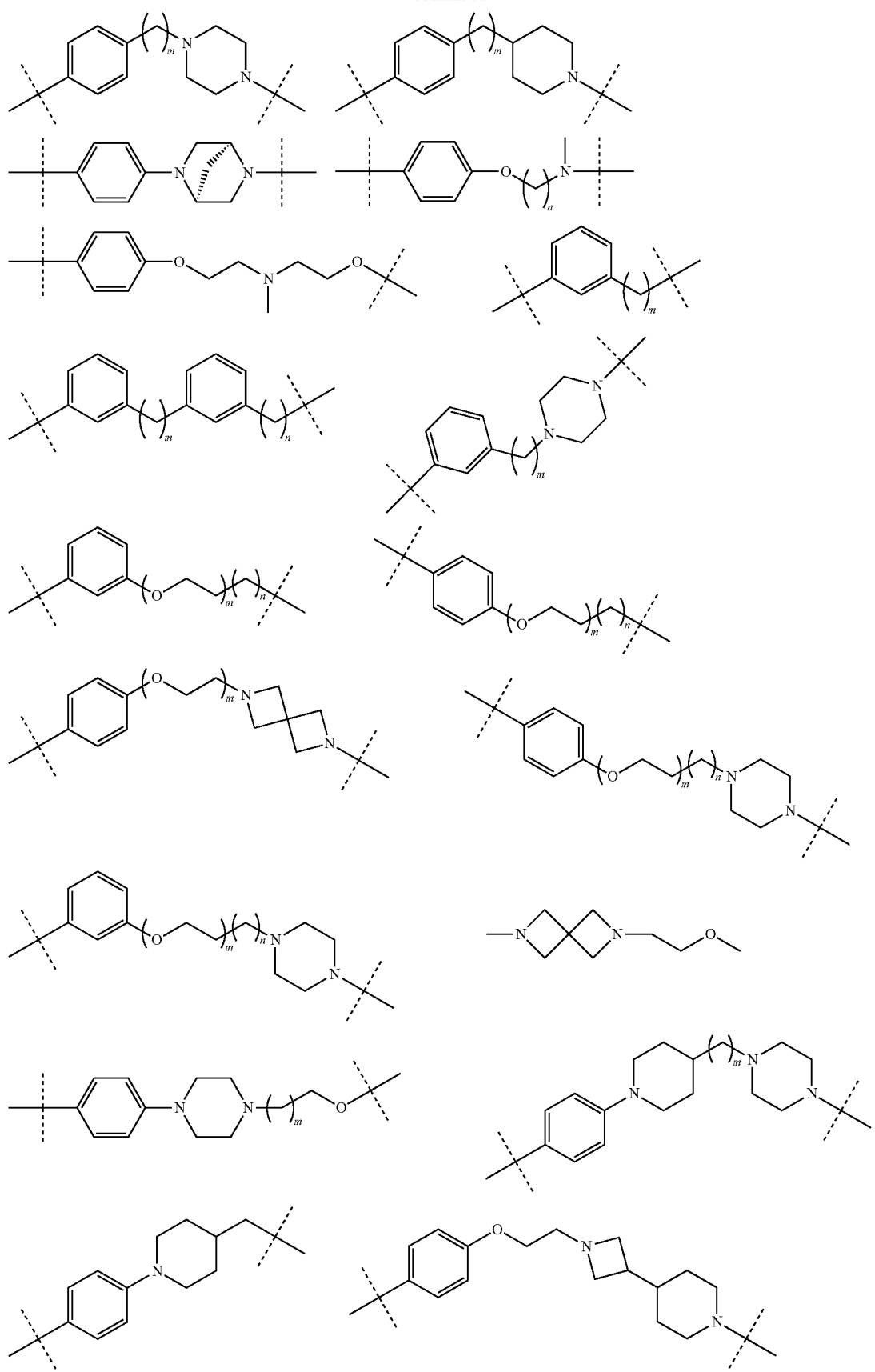

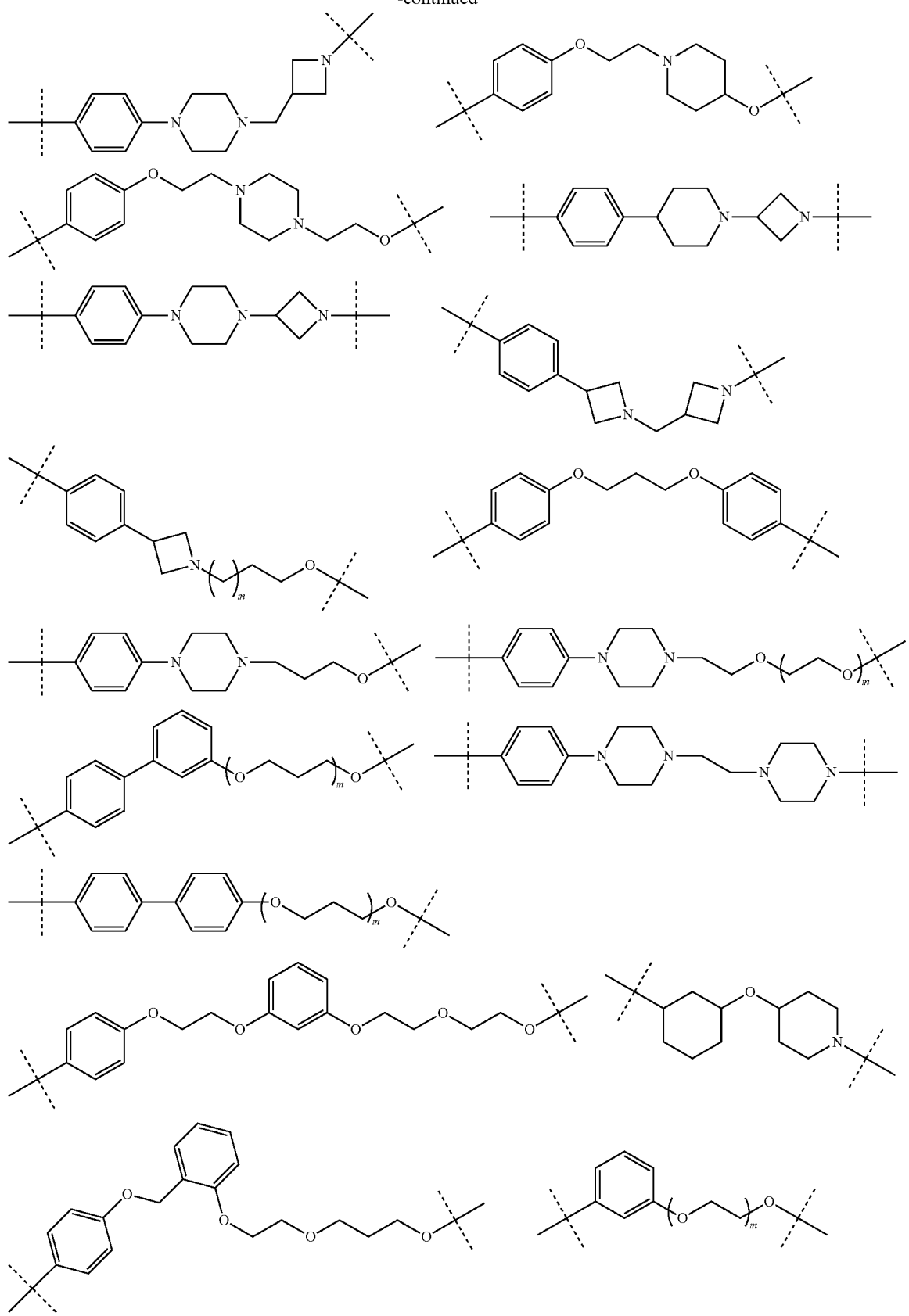

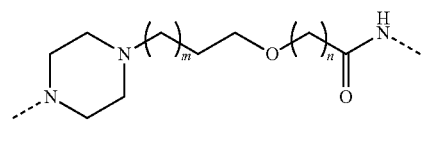 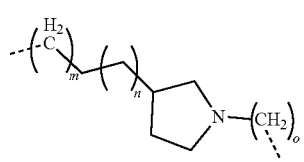 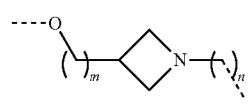
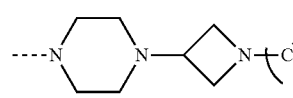 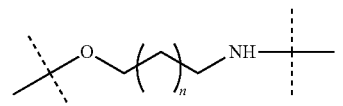 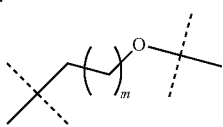
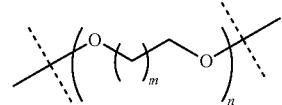 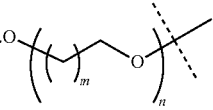 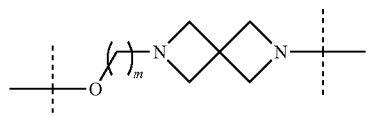
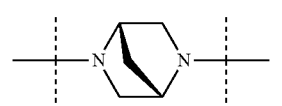 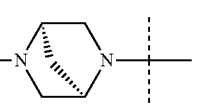 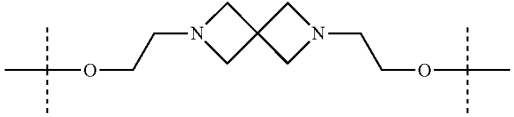
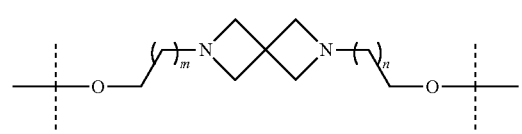 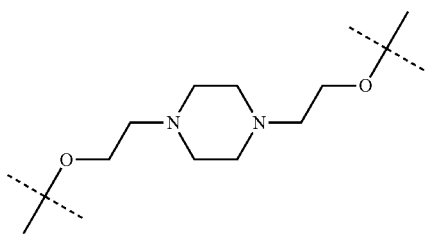
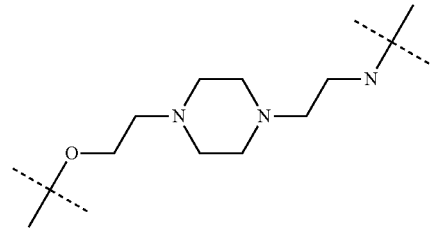 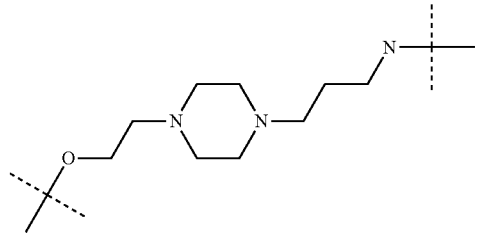
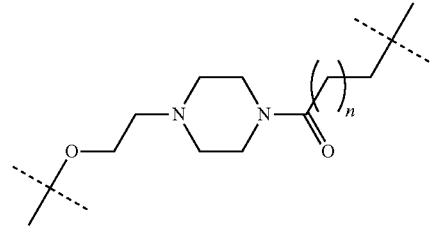 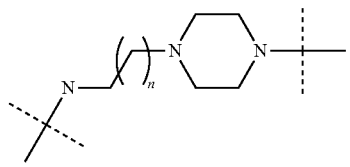
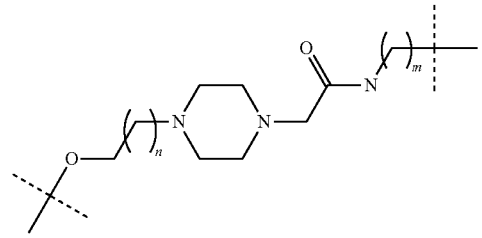 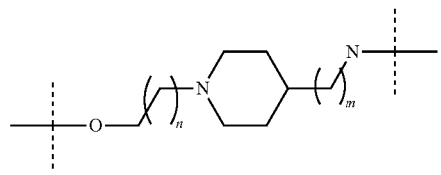
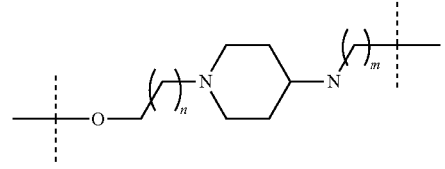 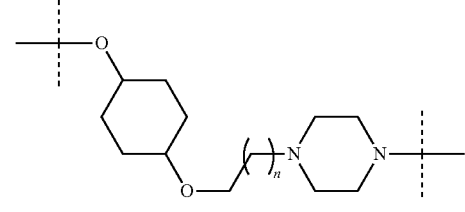

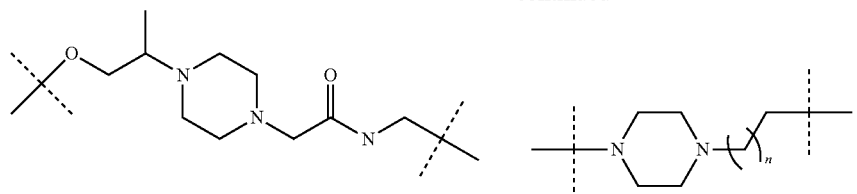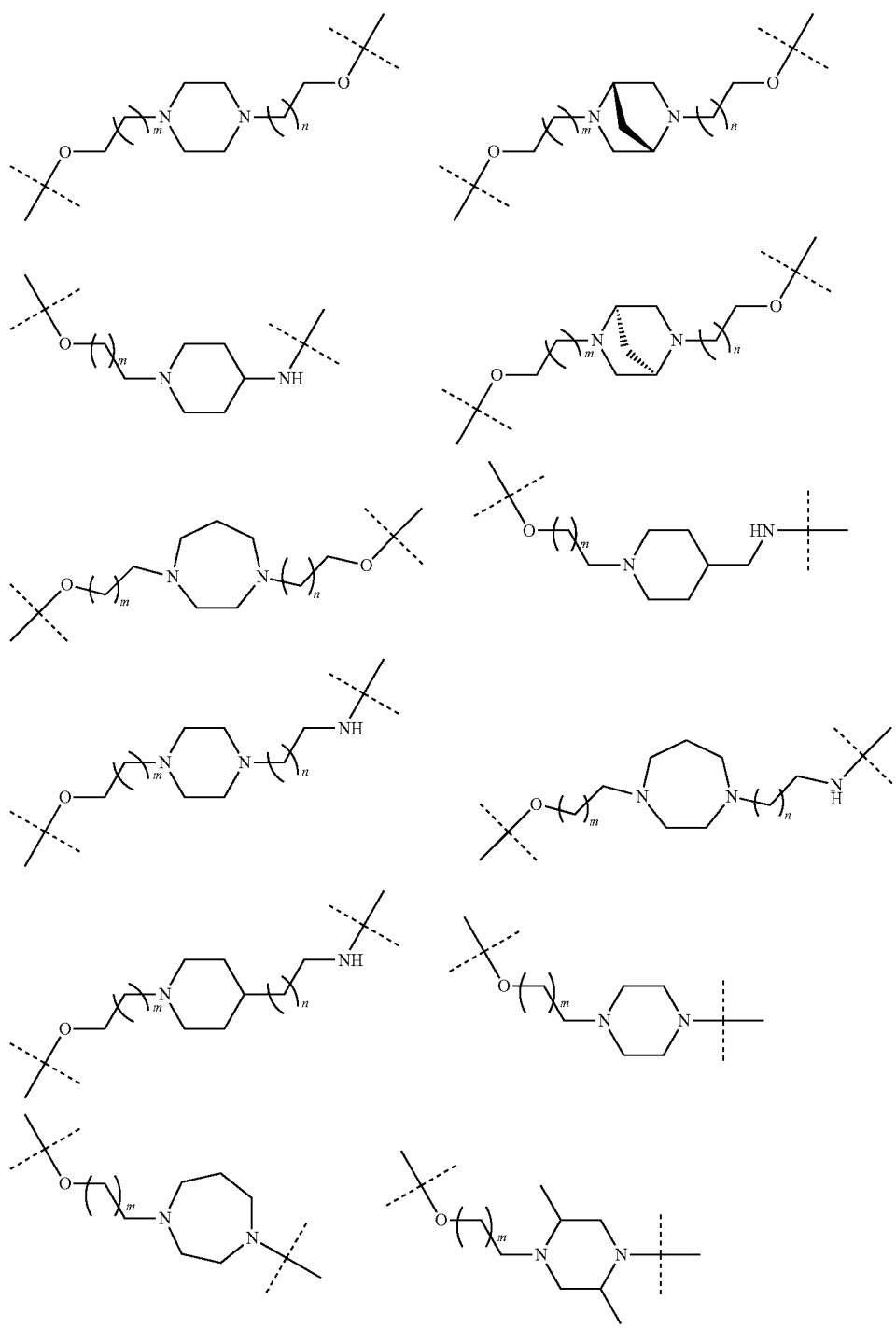

-continued
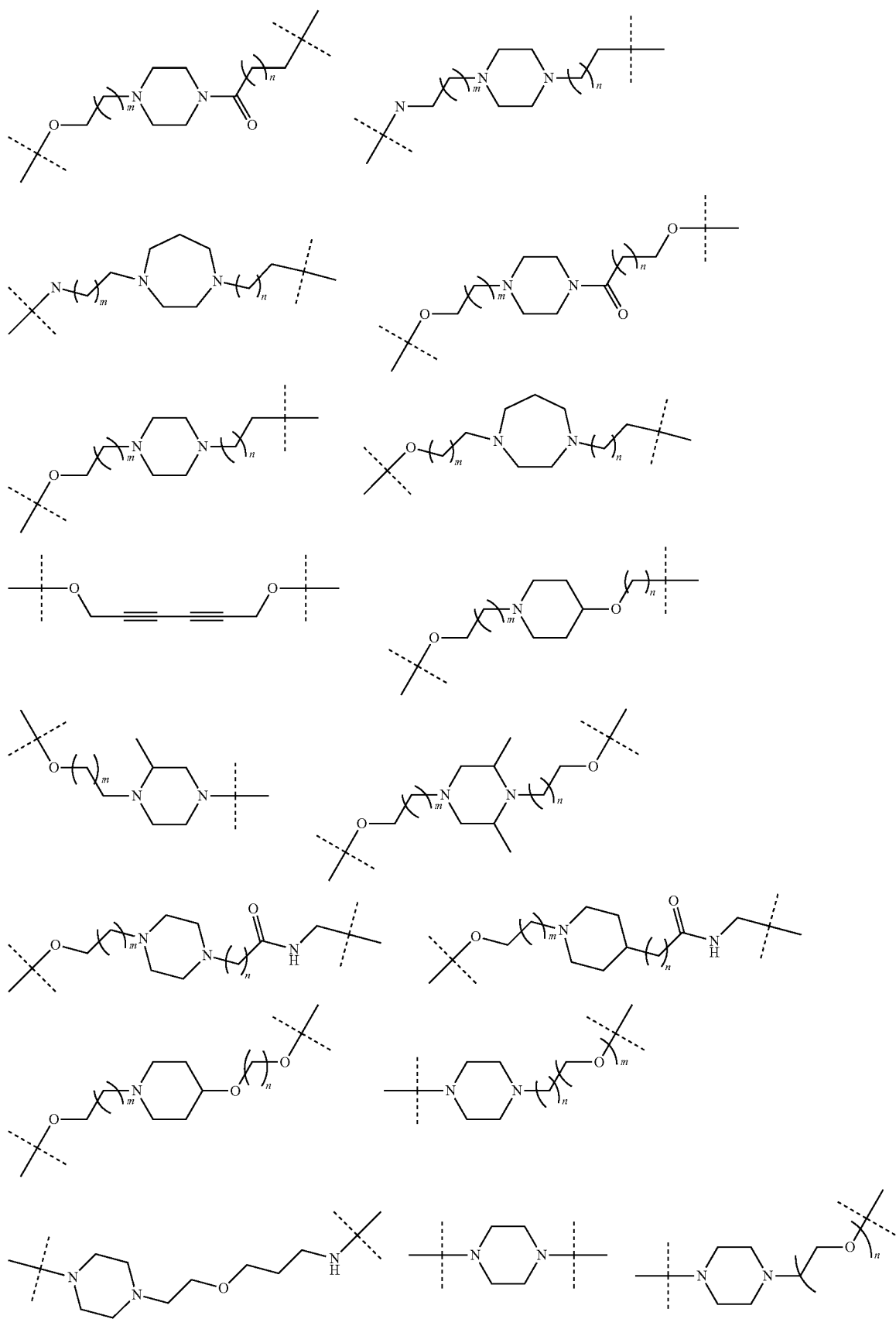

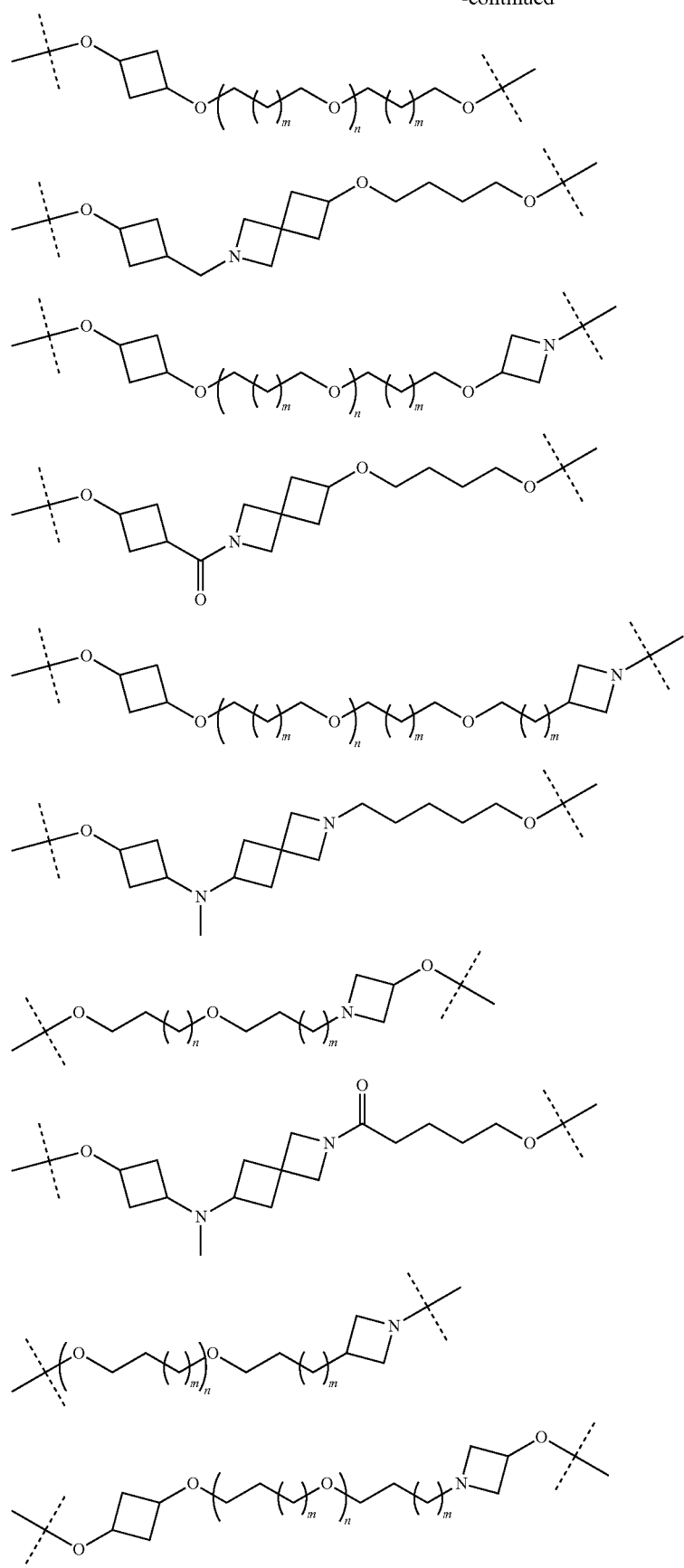

-continued
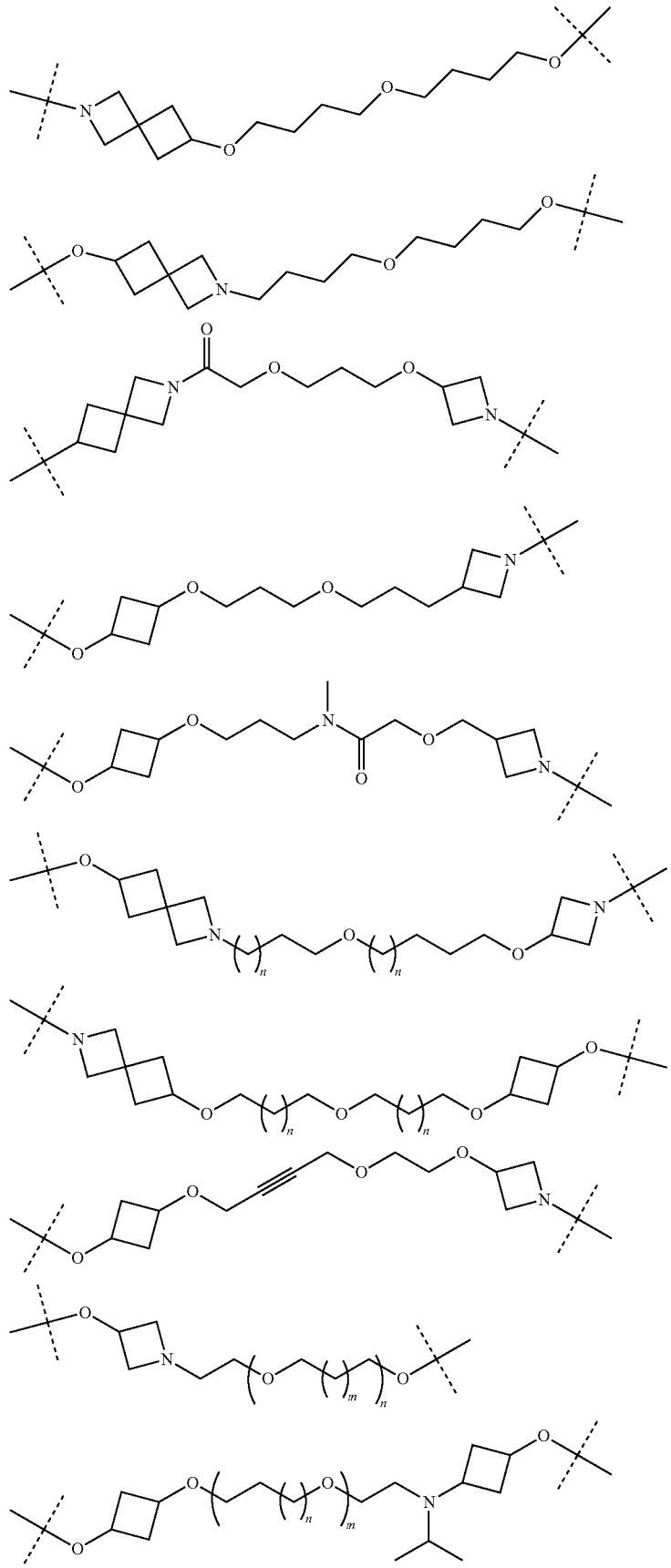

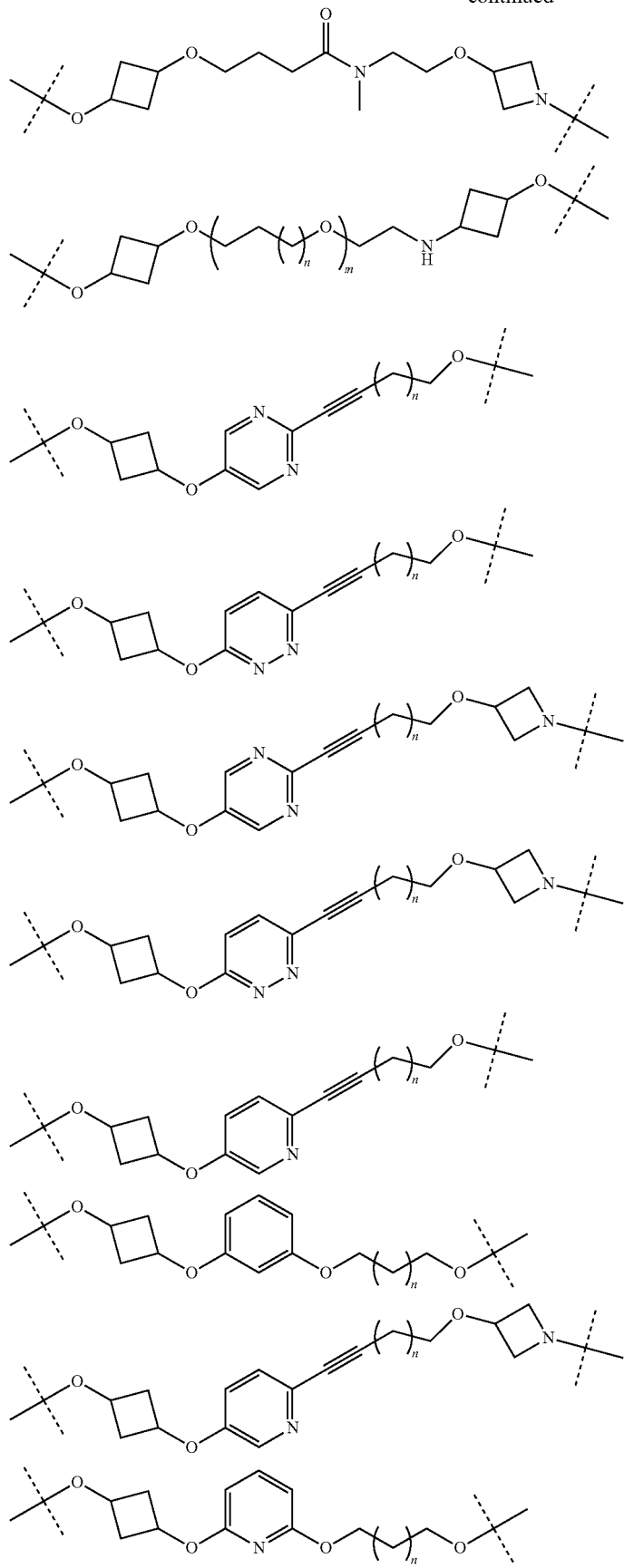

-continued
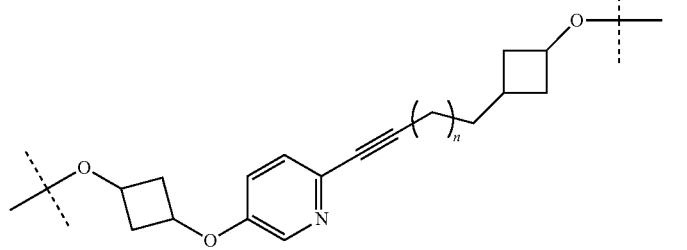
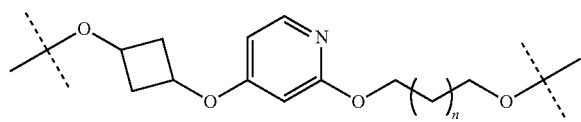
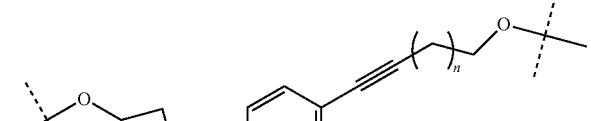
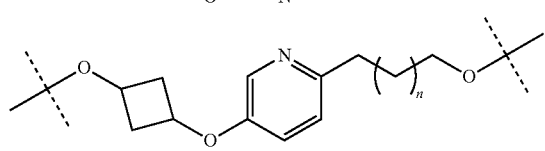
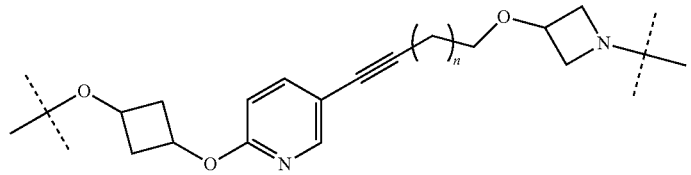
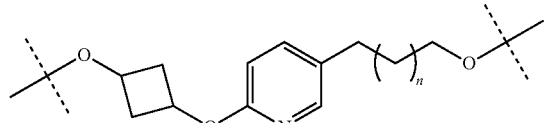
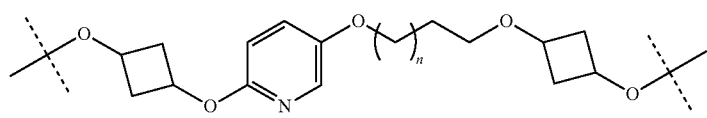
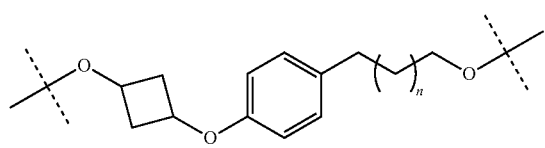
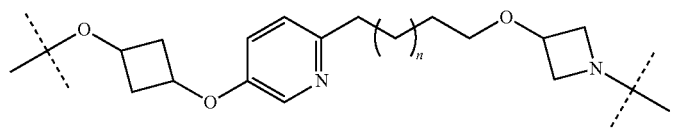
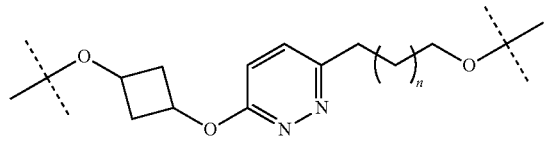

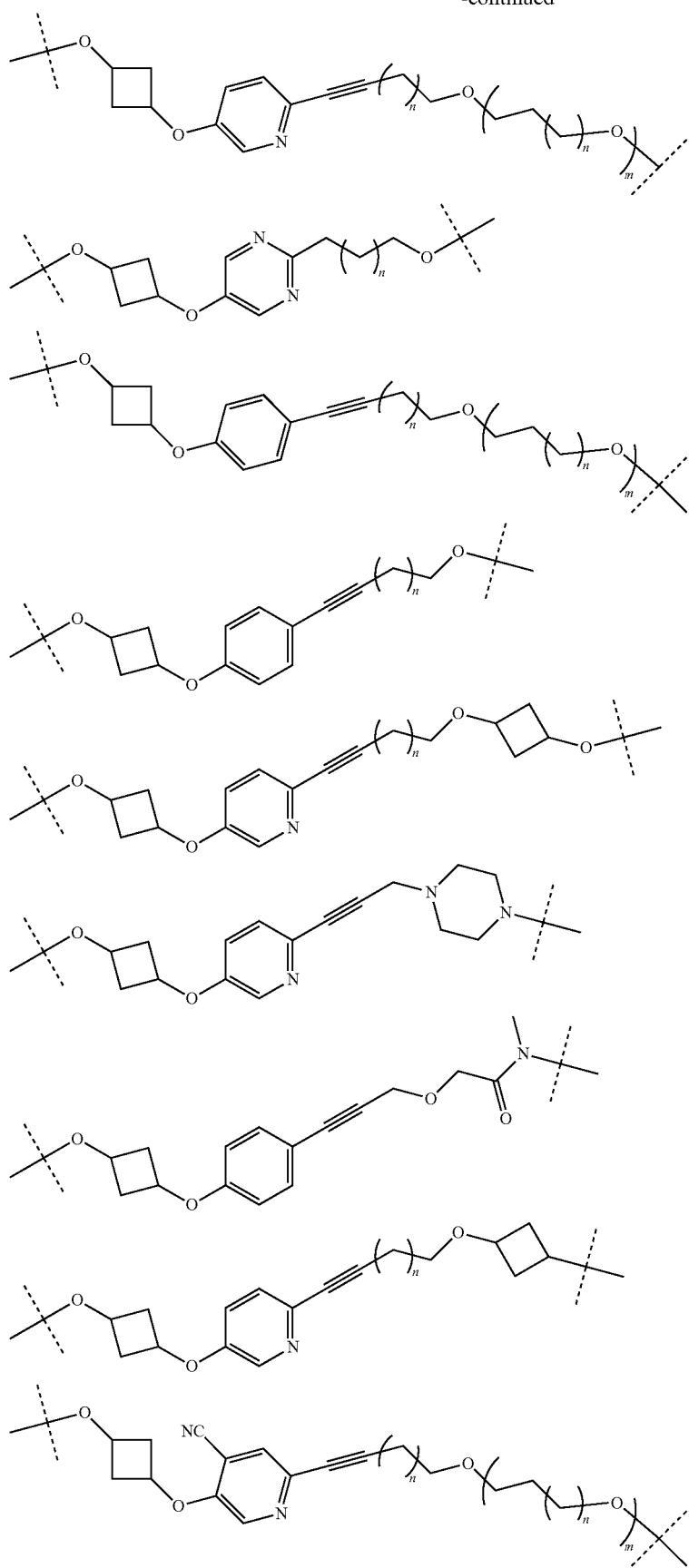

-continued
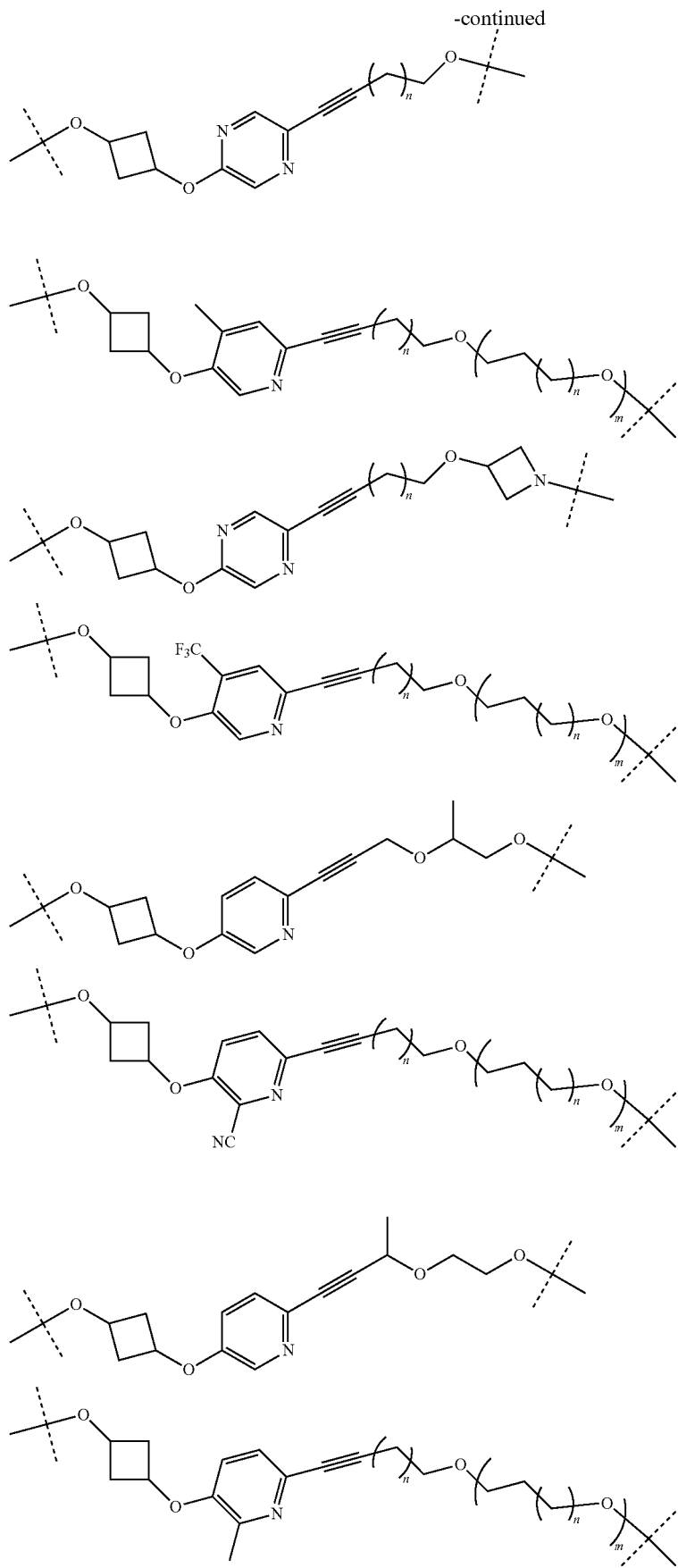

-continued
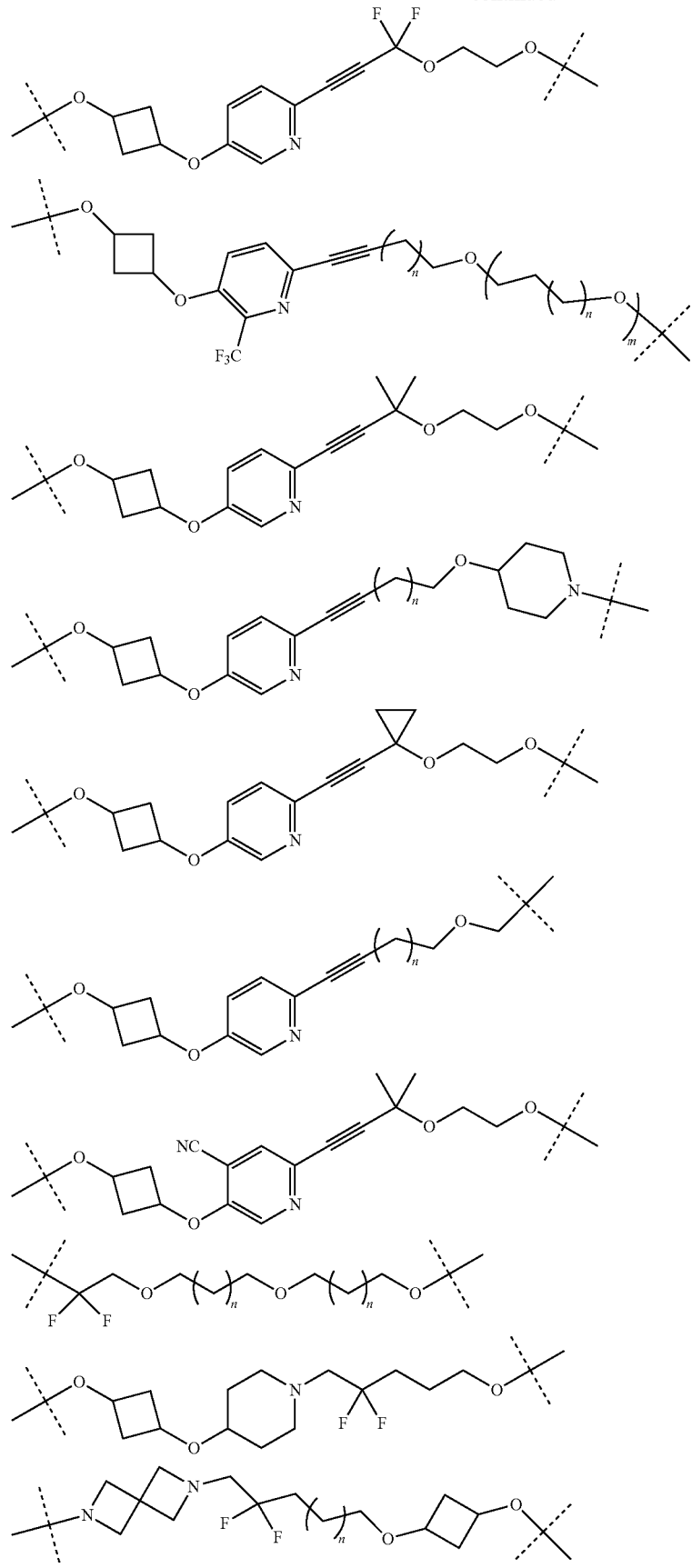

-continued
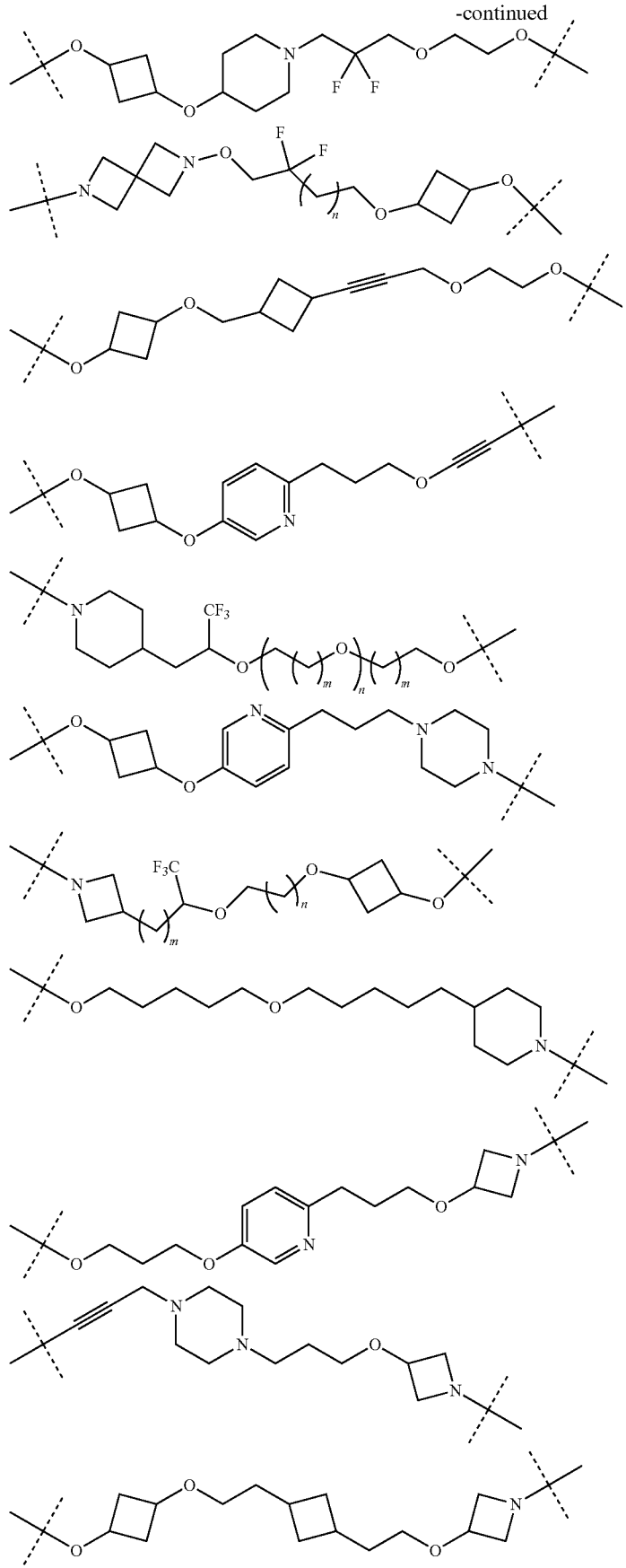

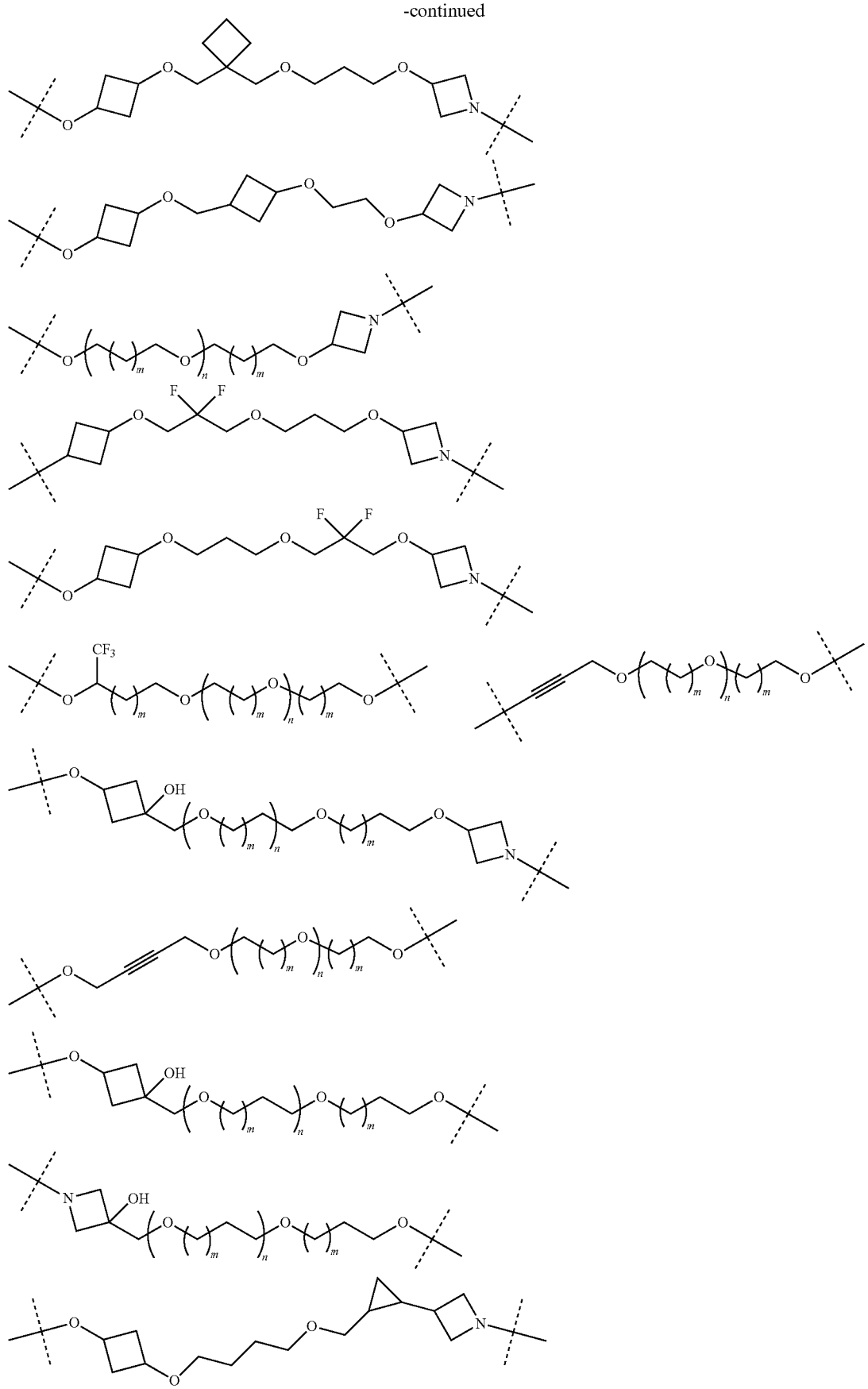

-continued
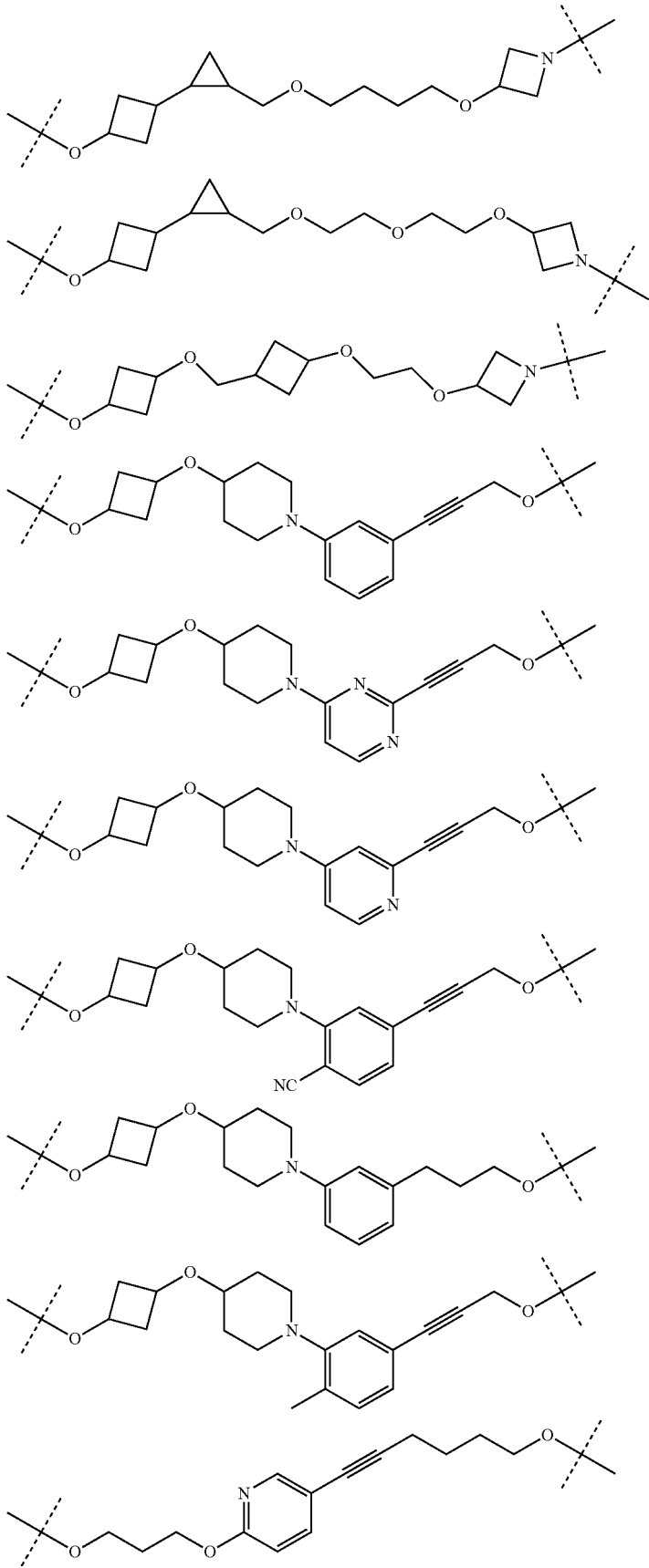

-continued
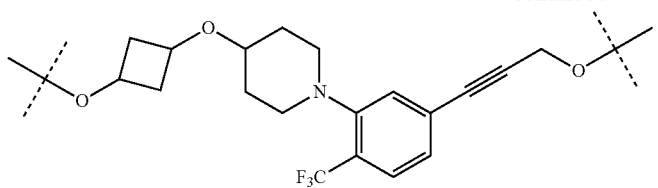
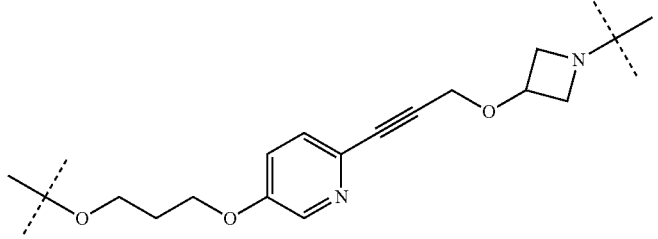
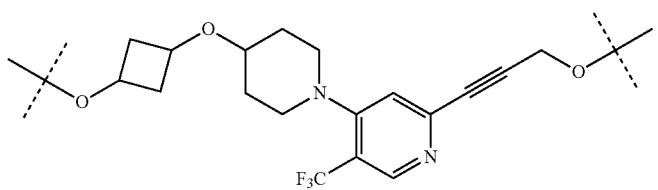
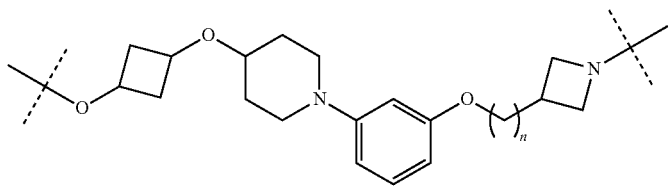
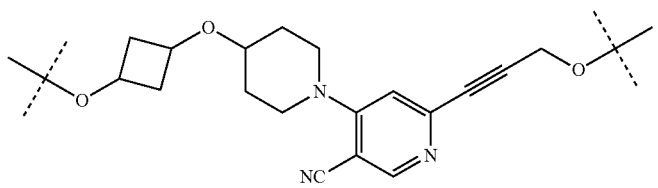
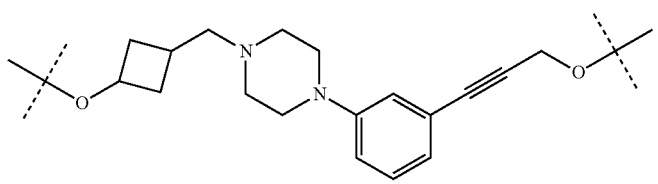
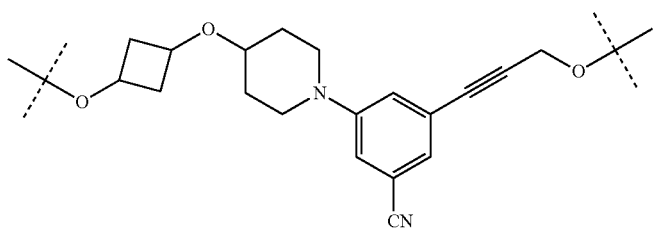
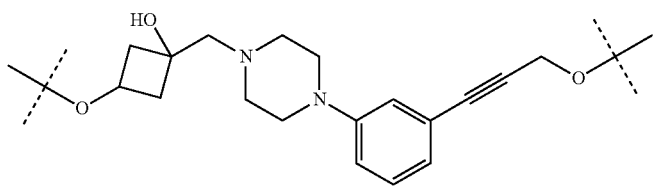

-continued
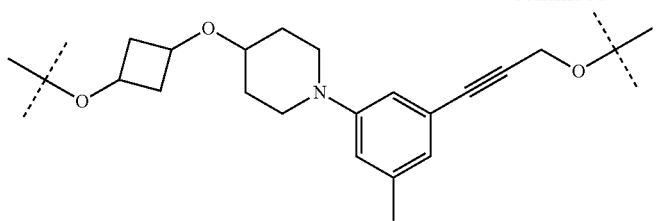
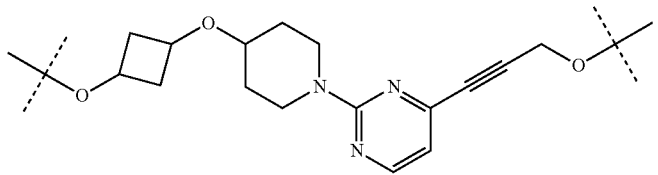
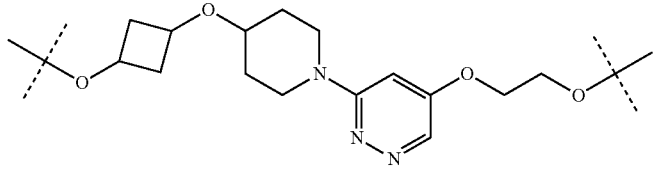
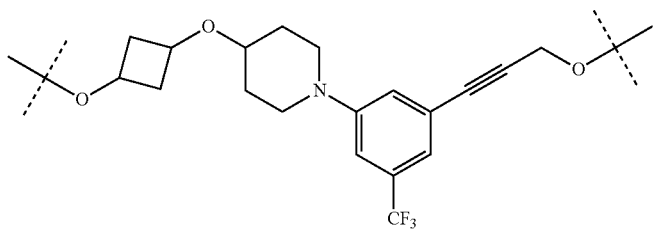
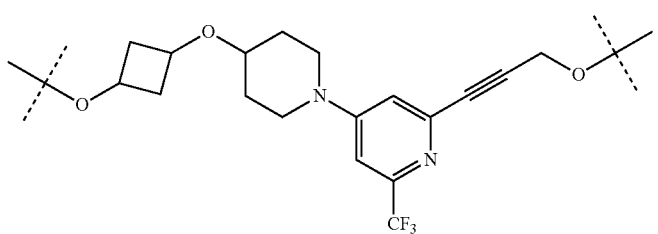
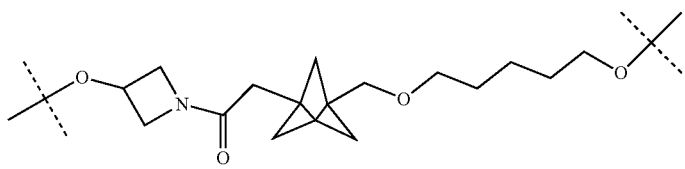
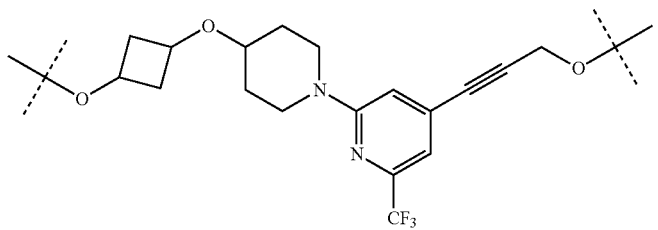
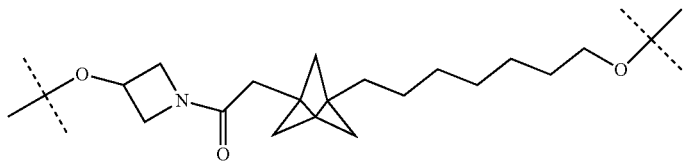

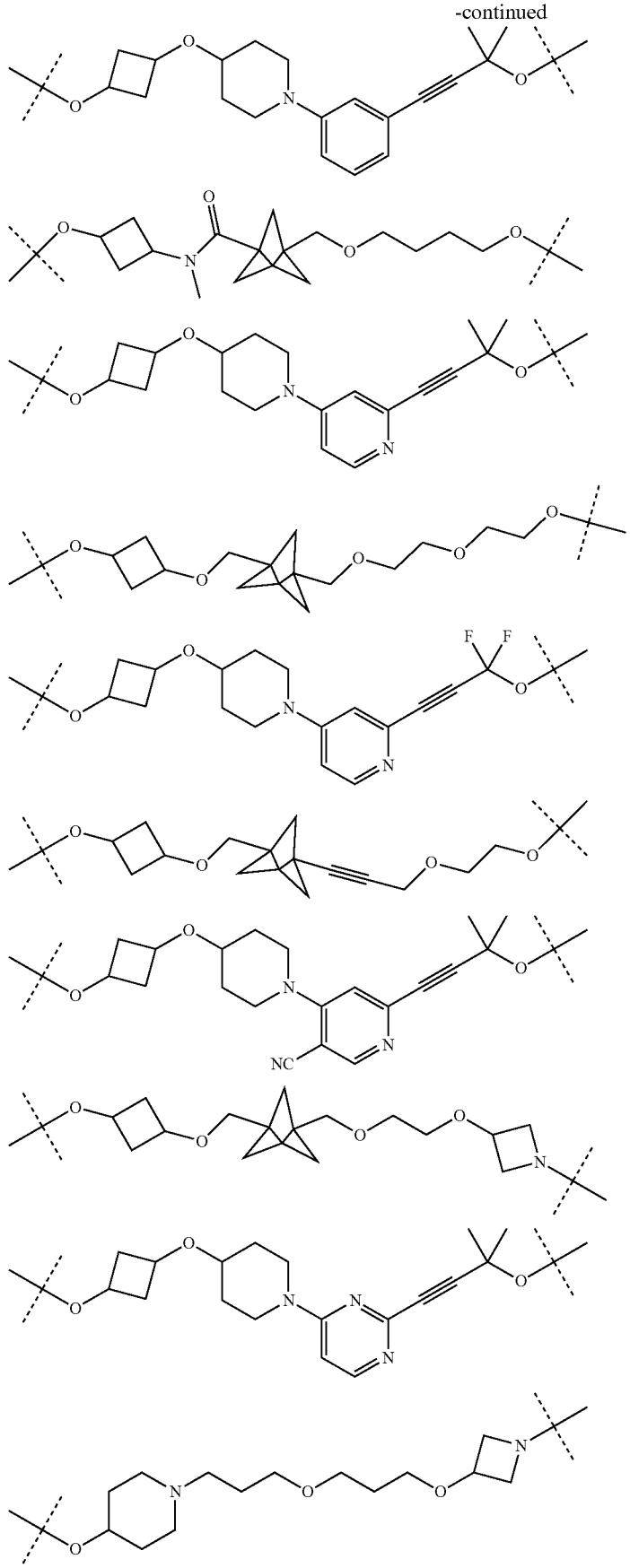

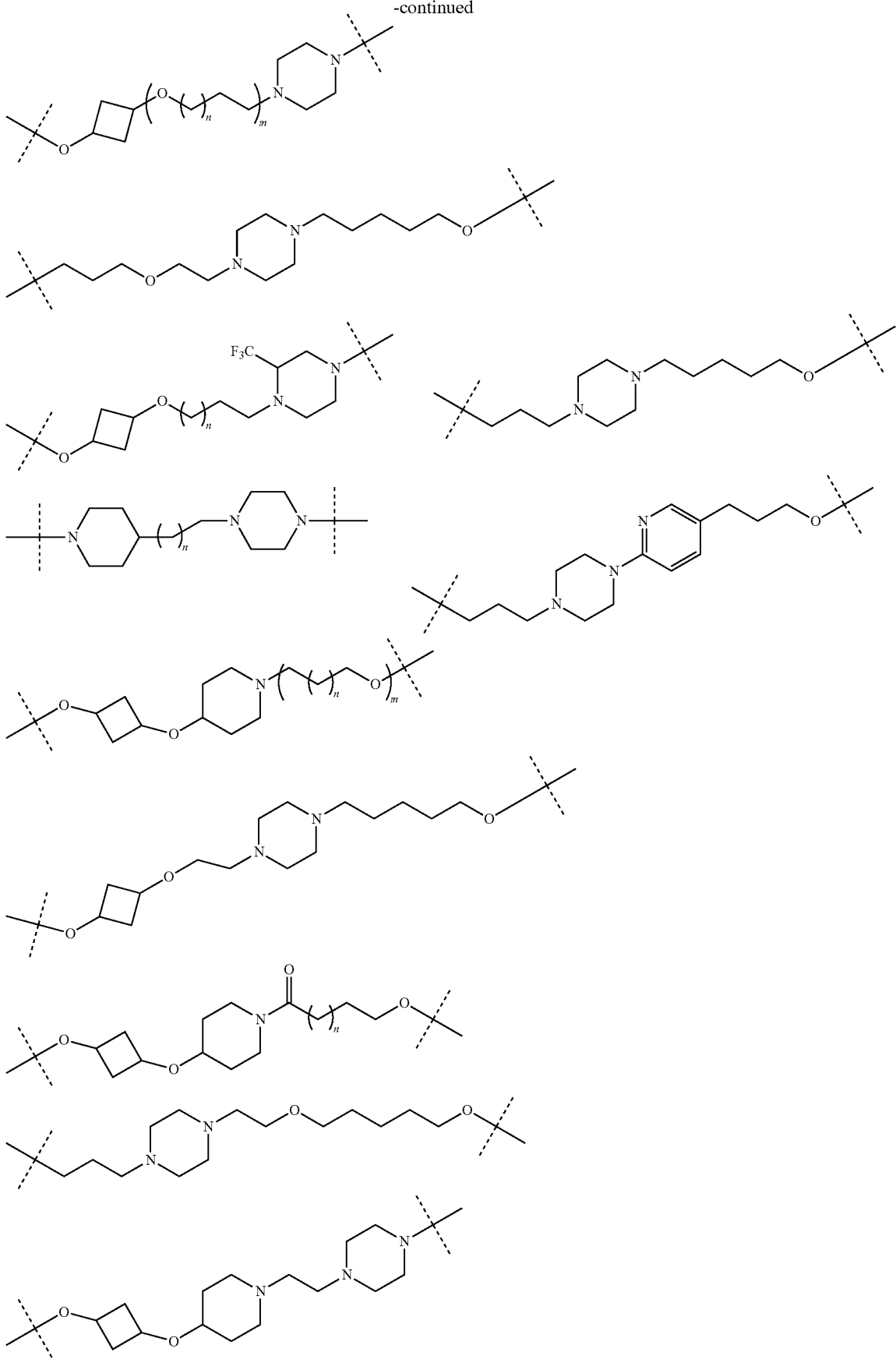

-continued
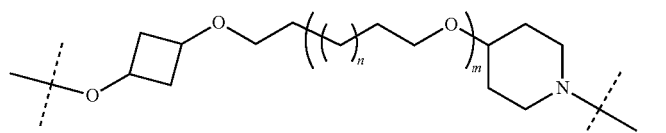
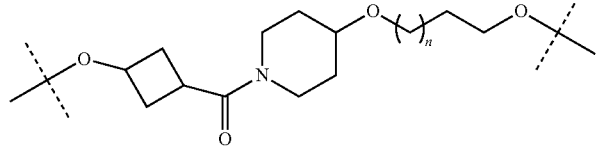
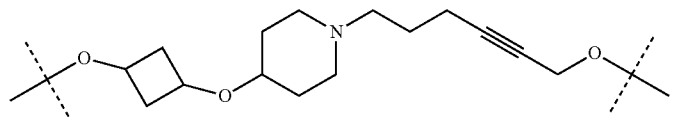
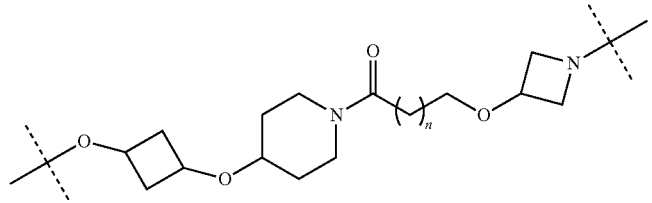
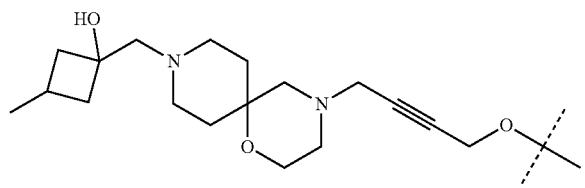
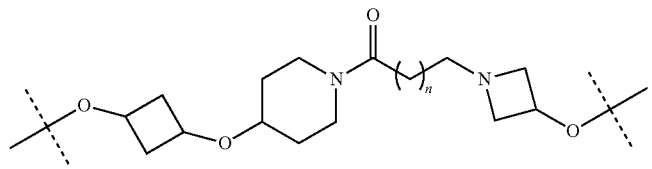
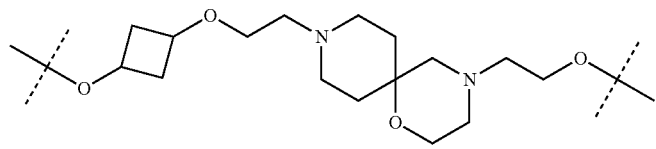
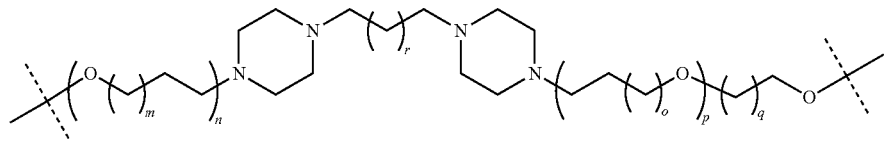
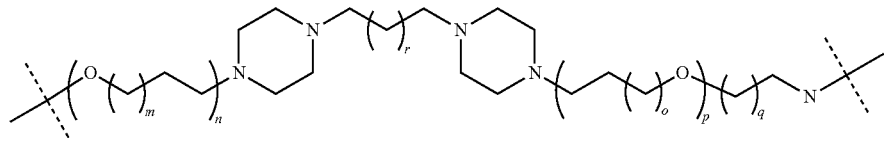
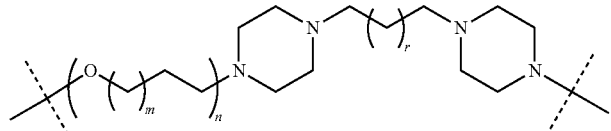
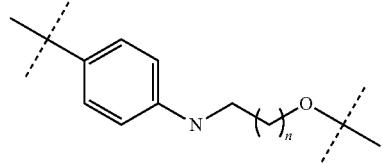

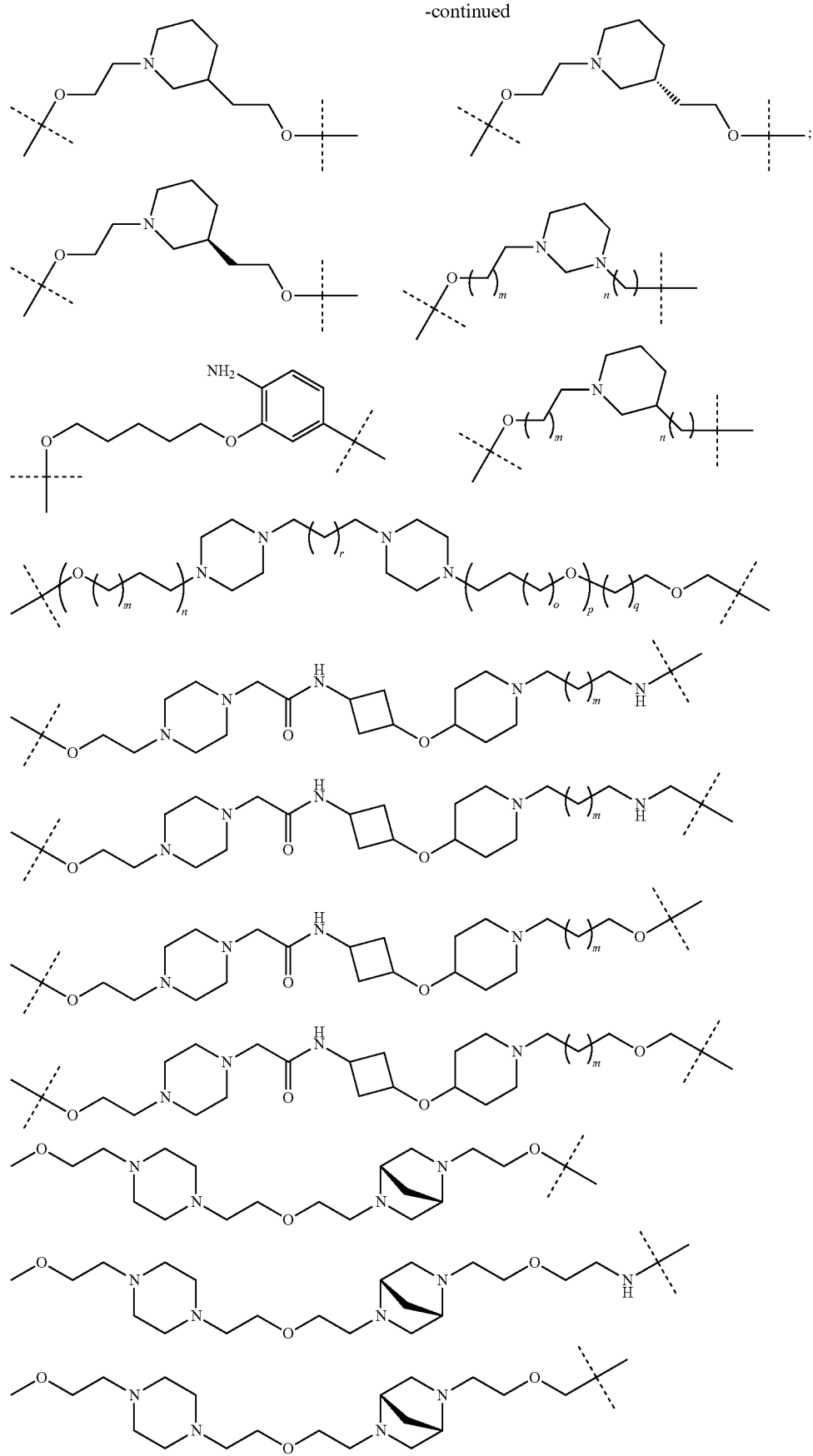

-continued
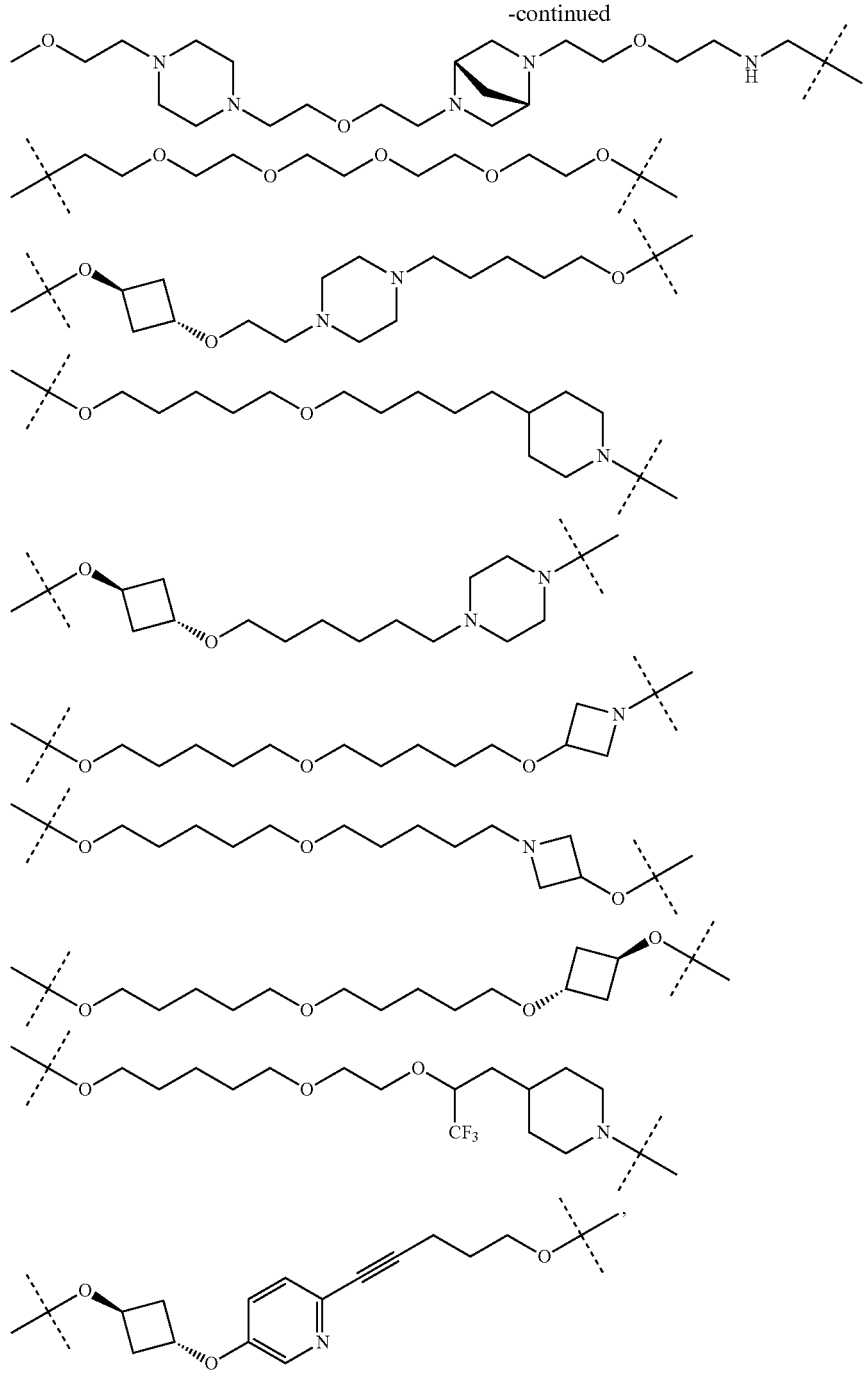
wherein each m, n, o, p, q, and r is independently 0, 1, 2, 3, 4, 5, 6, 7, 8, 9, 10, 11, 12, 13, 14, 15, 16, 17, 18, 19, or 20.
In any aspect or embodiment described herein, the $A^L$ group is selected from the group consisting of:
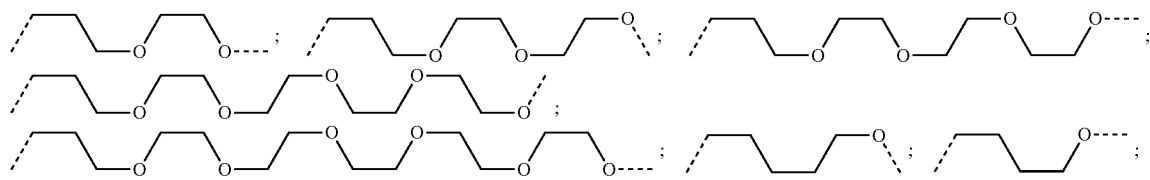

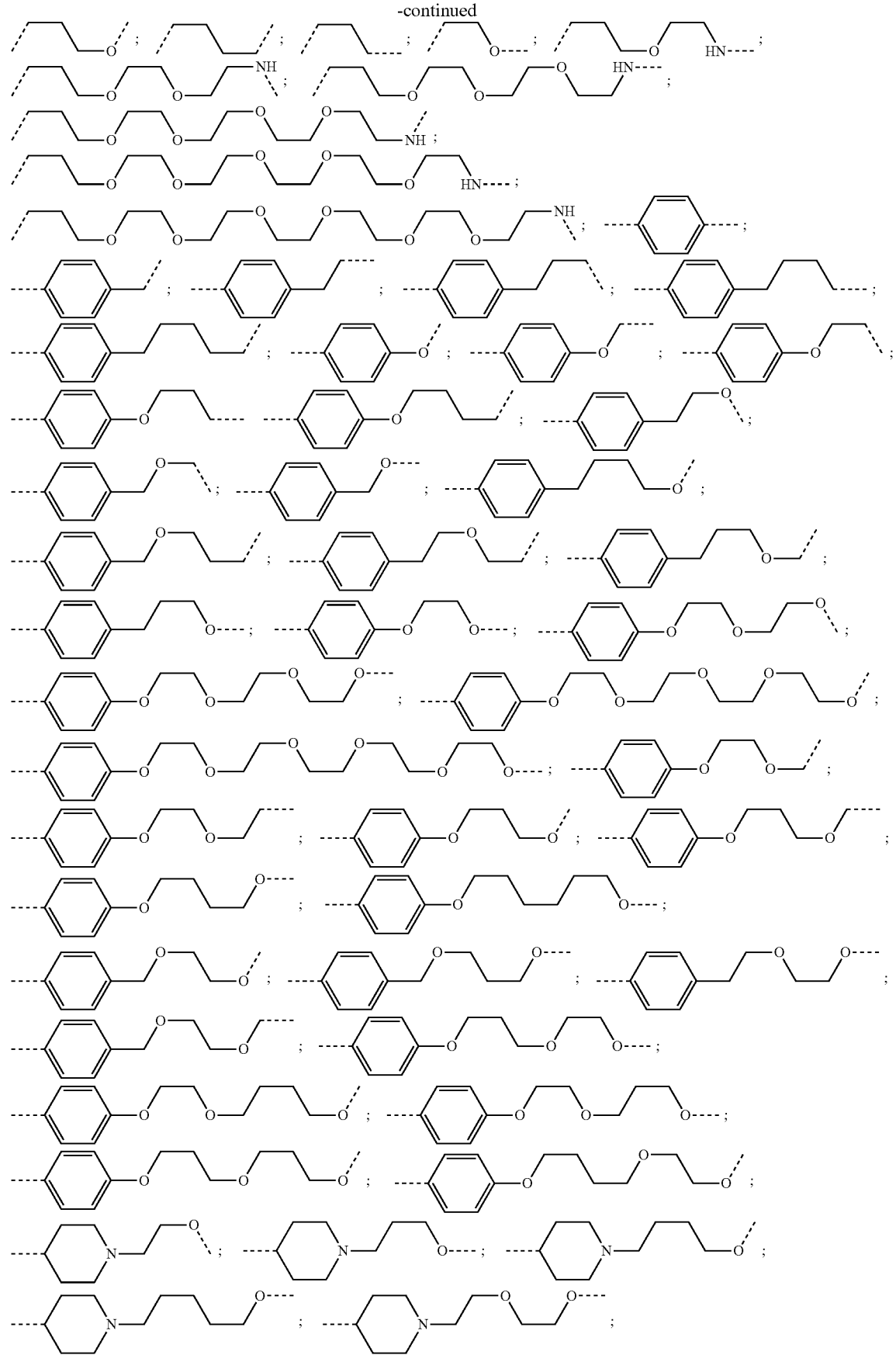

-continued
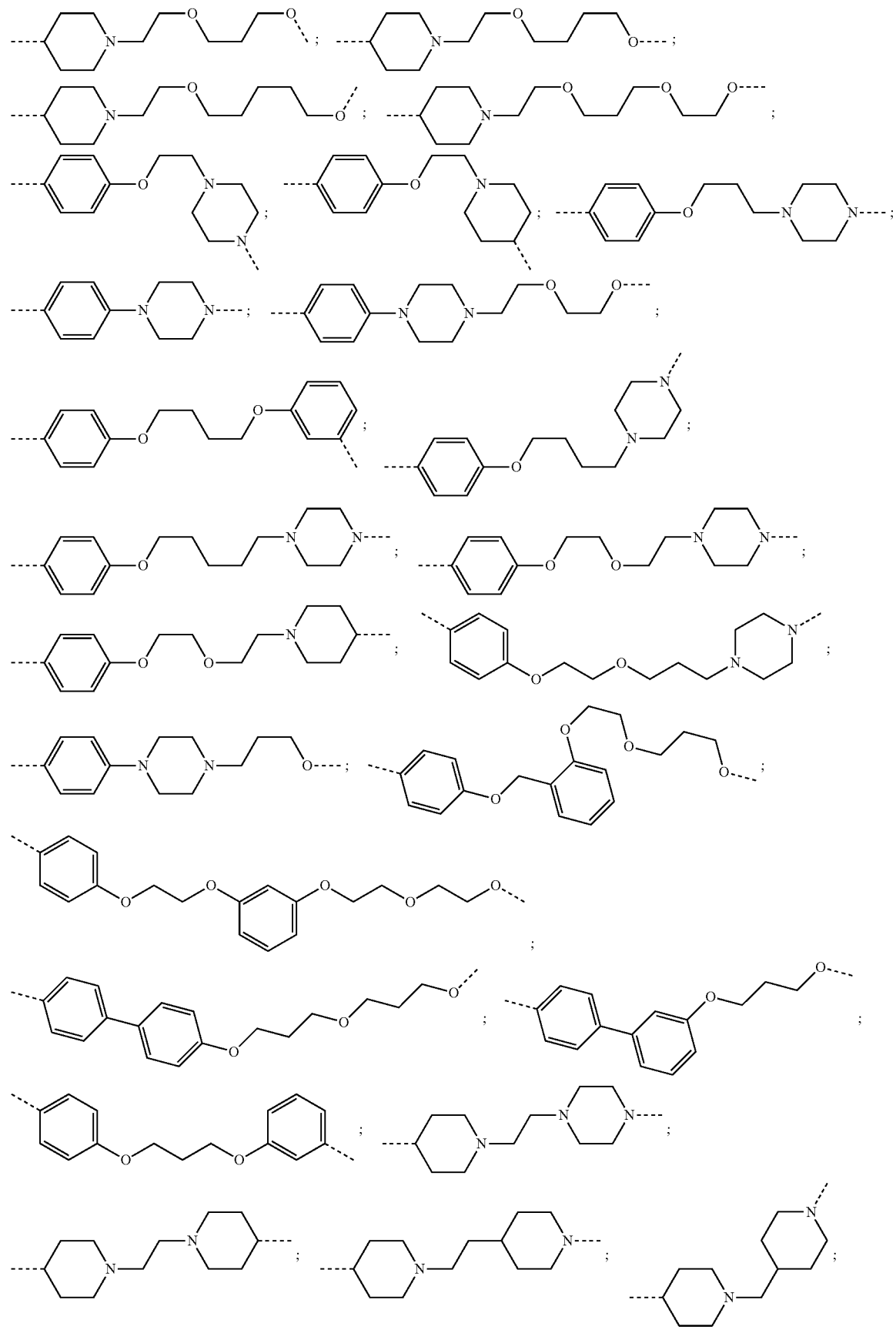

-continued
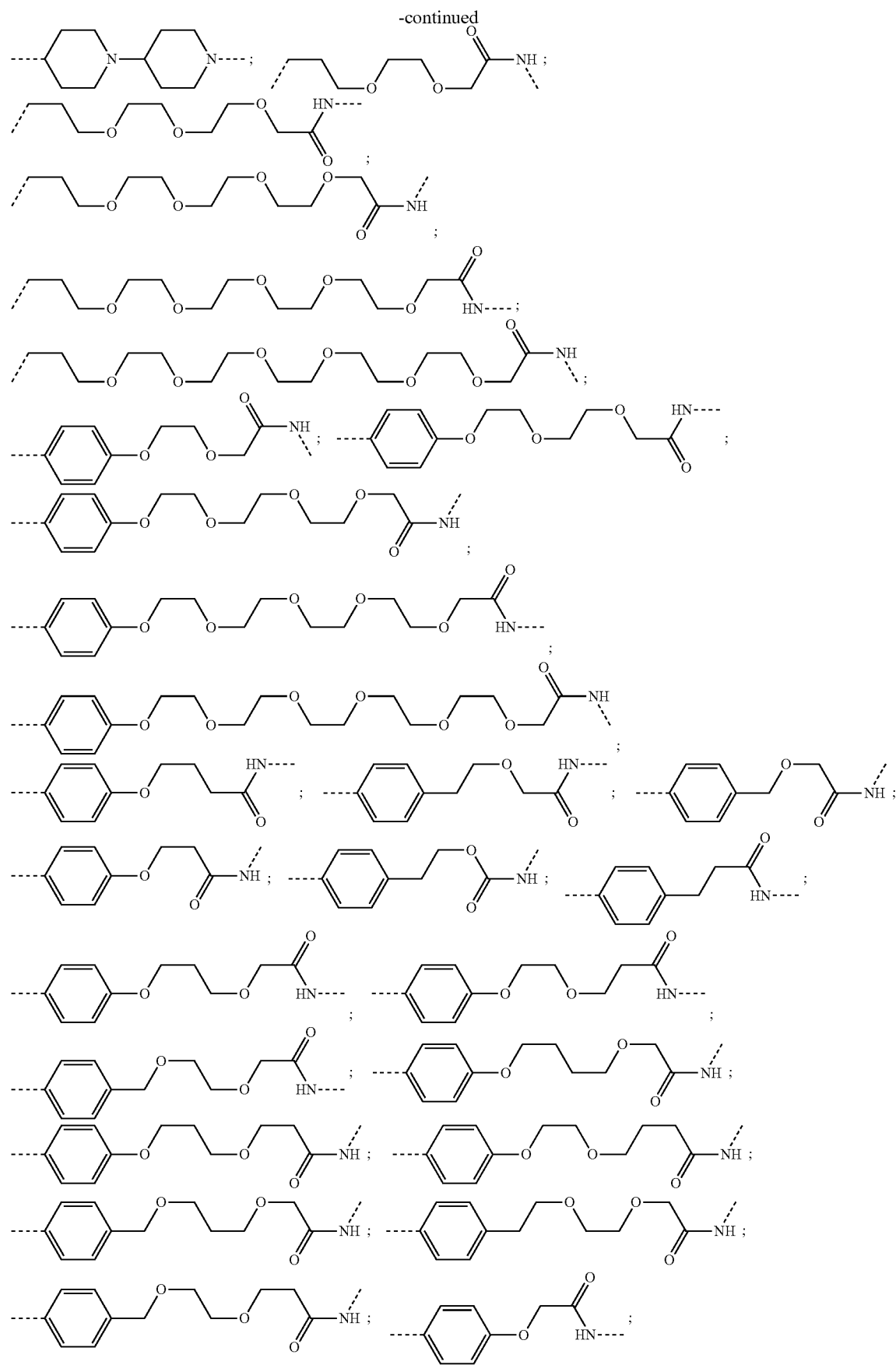

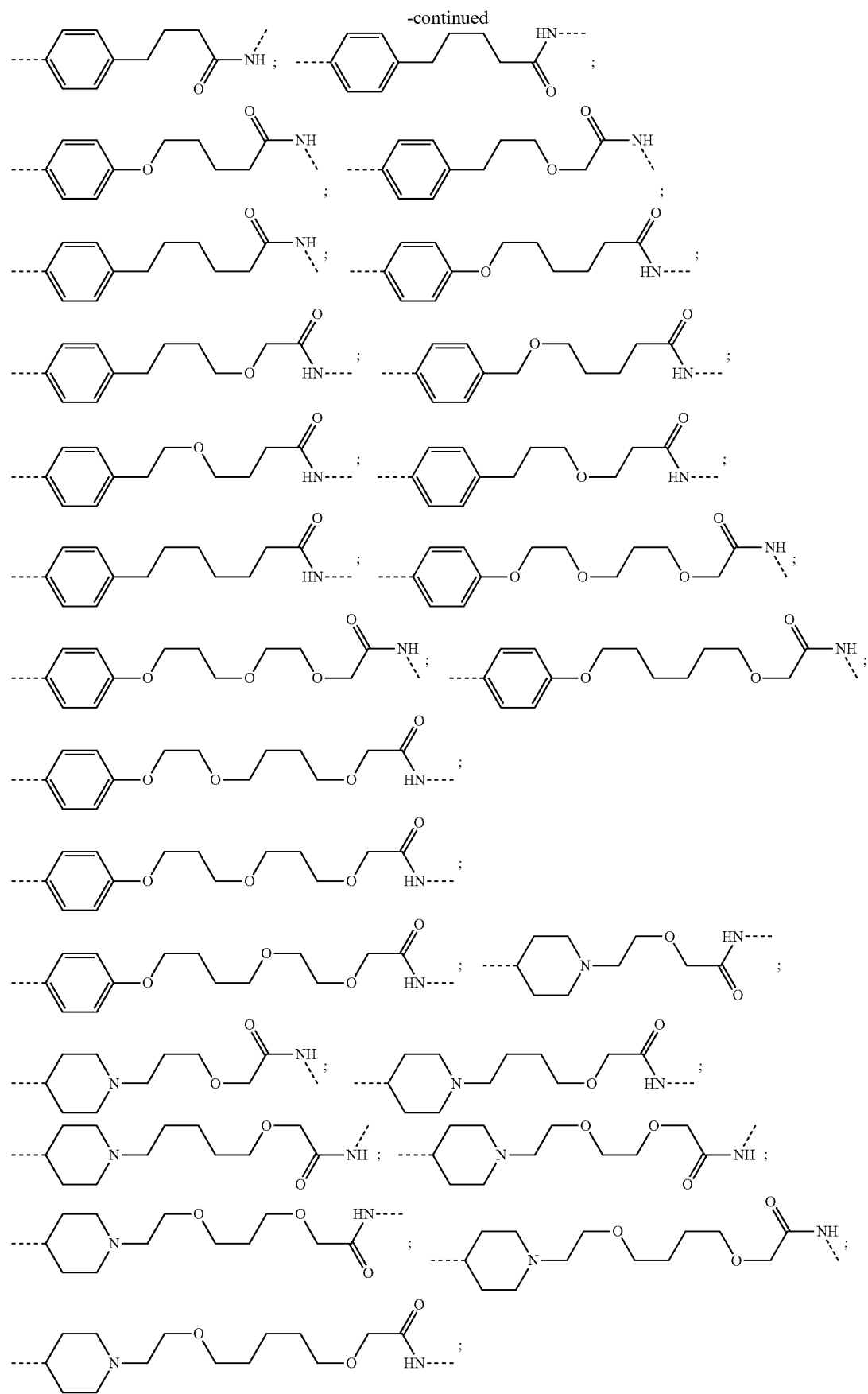

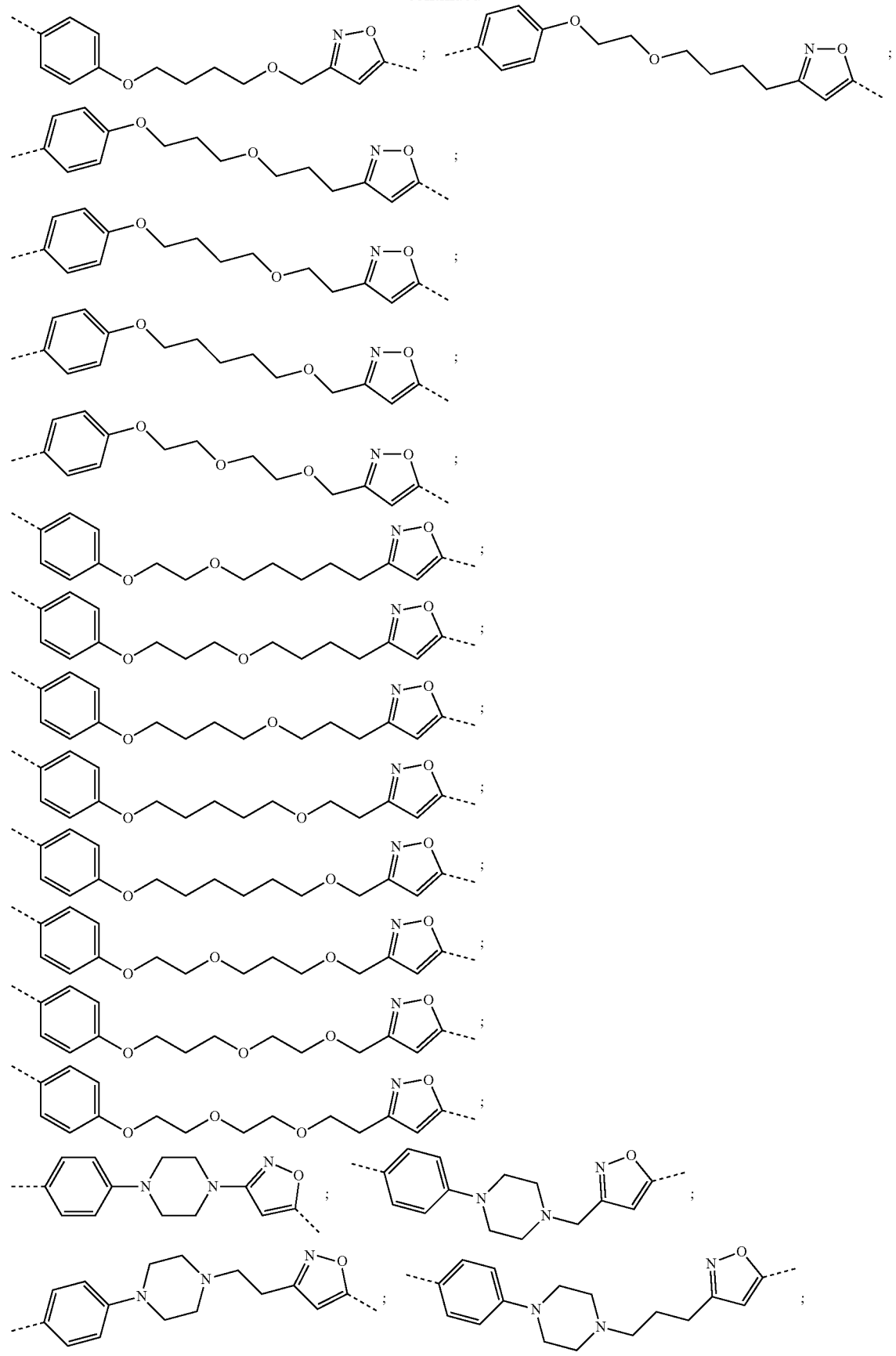

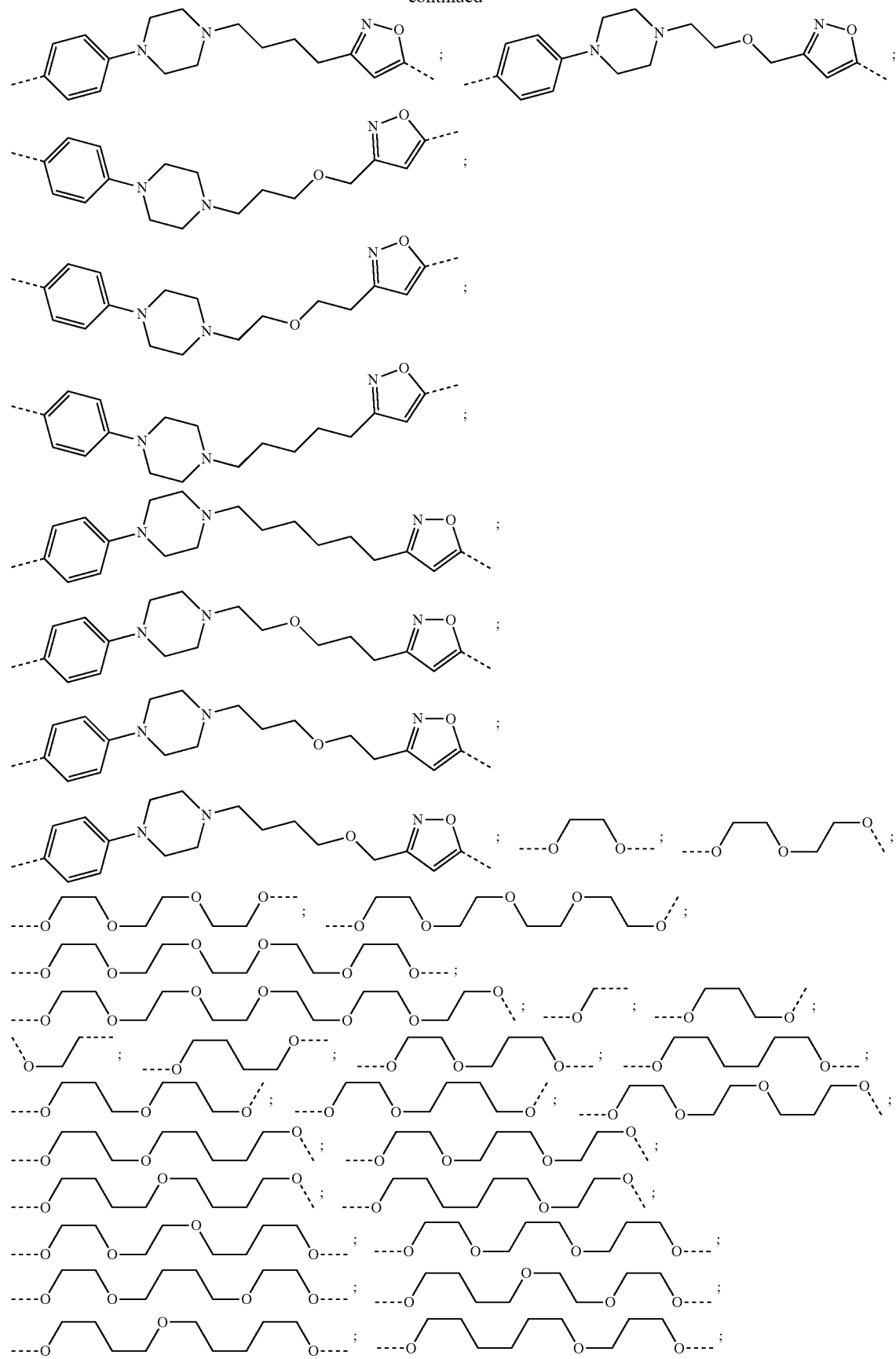

-continued
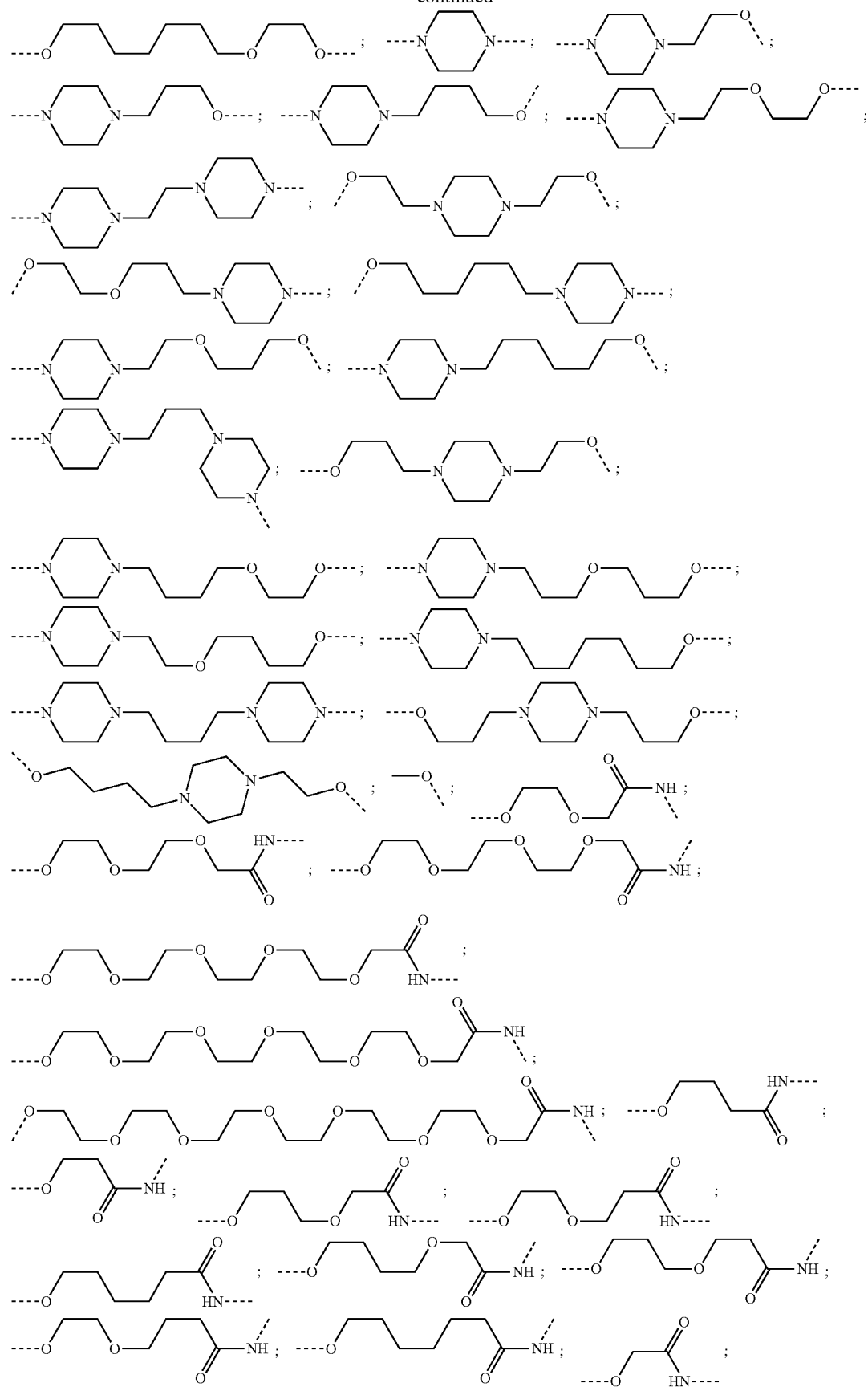

173
-continued
174
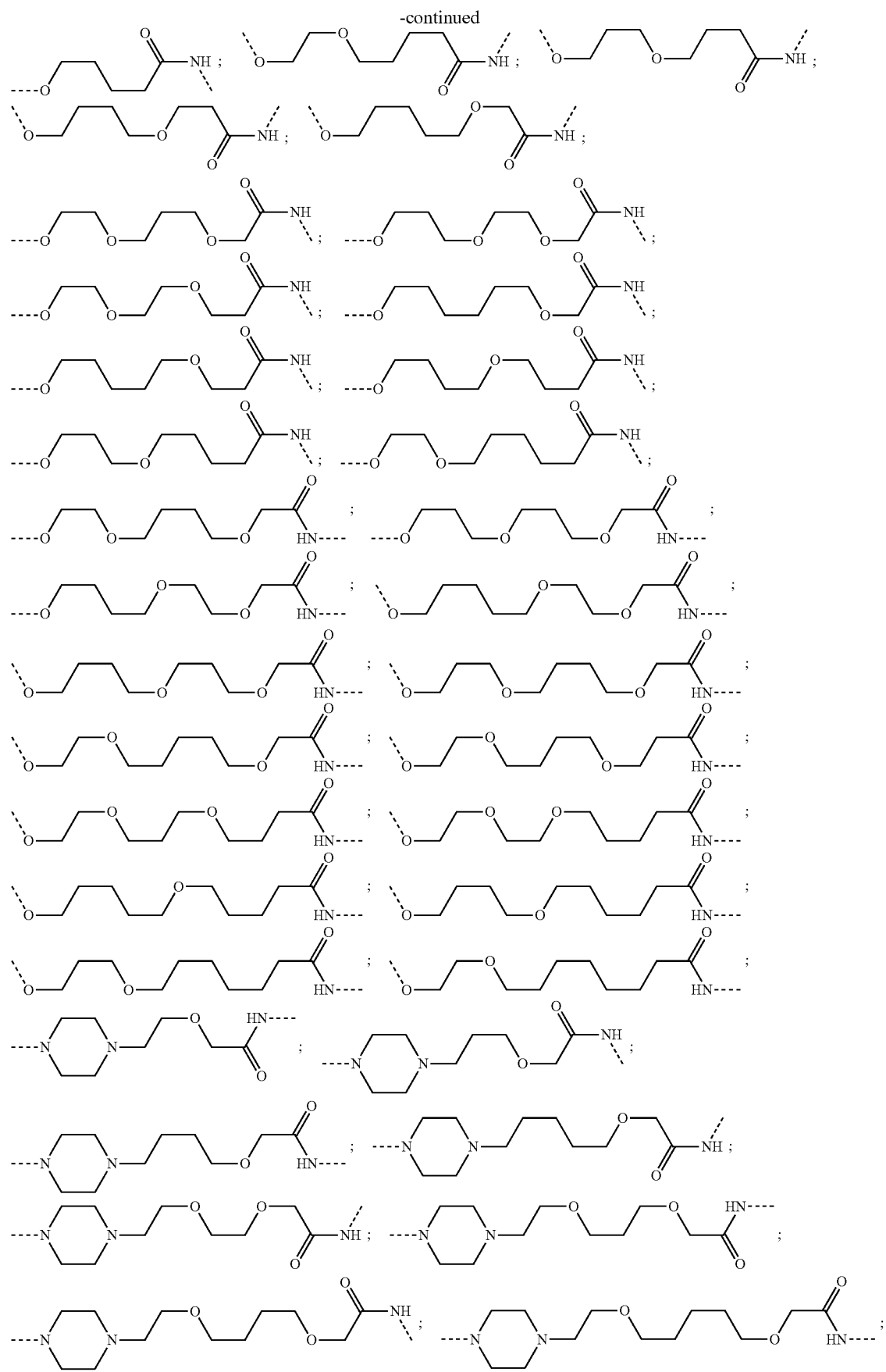

-continued
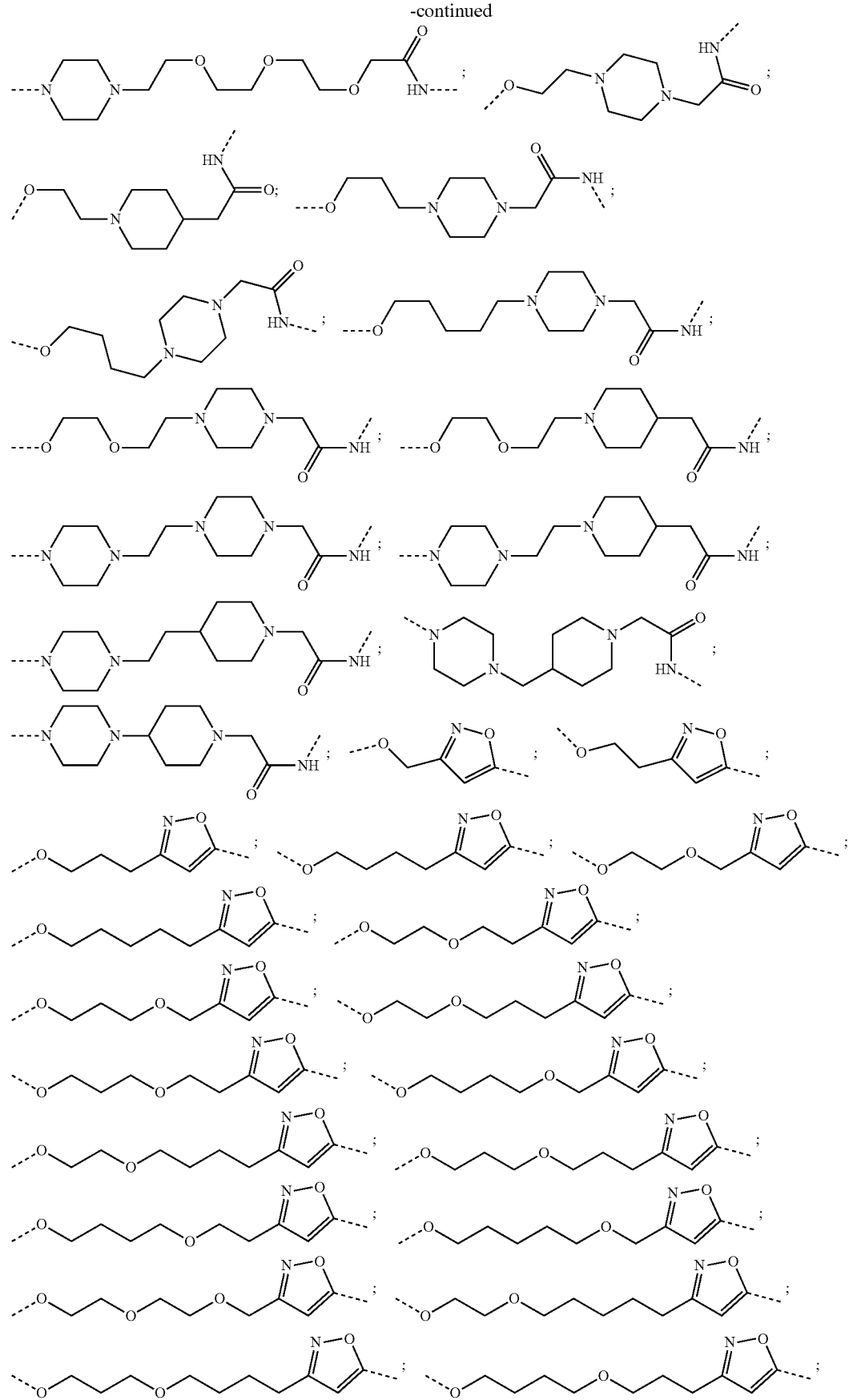

-continued

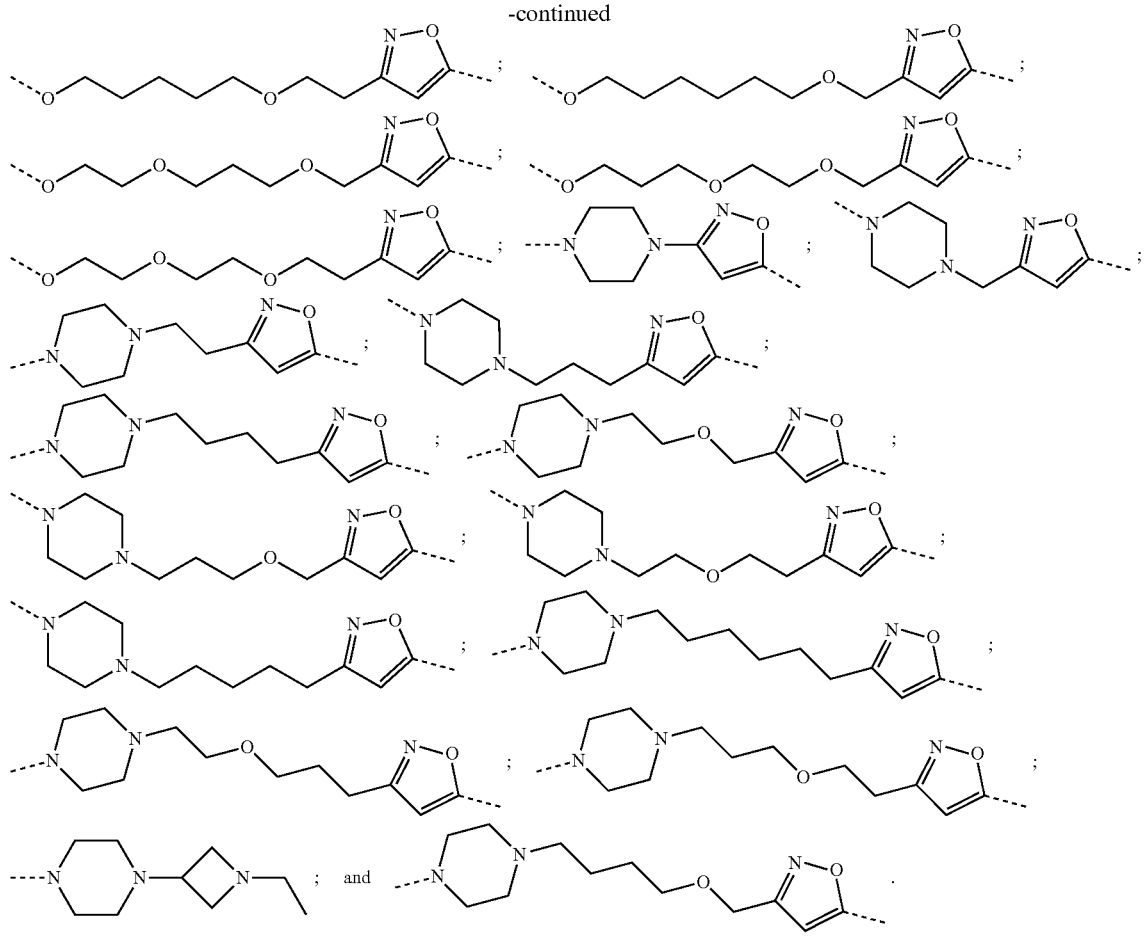

In additional embodiments, the linker (L) comprises a structure selected from, but not limited to the structure shown below, where a dashed line indicates the attachment point to the PTM or ULM moieties:

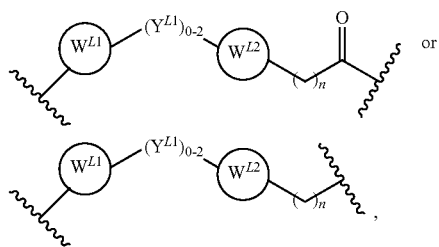

wherein:

$W^{L1}$ and $W^{L2}$ are each independently absent, a 4-8 membered ring with 0-4 heteroatoms, optionally substituted with $R^Q$, each $R^Q$ is independently a H, halo, OH, CN, $CF_3$, $C_1$-$C_6$ alkyl (linear, branched, optionally substituted), $C_1$-$C_6$ alkoxy (linear, branched, optionally substituted), or 2 $R^Q$ groups taken together with the atom they are attached to, form a 4-8 membered ring system containing 0-4 heteroatoms;

$Y^{L1}$ is each independently a bond, $C_1$-$C_6$ alkyl (linear, branched, optionally substituted) and optionally one or more C atoms are replaced with O; or $C_1$-$C_6$ alkoxy (linear, branched, optionally substituted);

n is 0-10; and a dashed line indicates the attachment point to the PTM or ULM moieties.

In additional embodiments, the linker (L) comprises a structure selected from, but not limited to the structure shown below, where a dashed line indicates the attachment point to the PTM or ULM moieties:

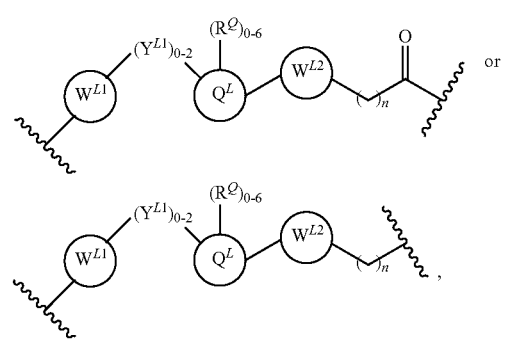

wherein:

$W^{L1}$ and $W^{L2}$ are each independently absent, aryl, heteroaryl, cyclic, heterocyclic. $C_{1-6}$ alkyl and optionally one or more C atoms are replaced with O, $C_{1-6}$ alkene and optionally one or more C atoms are replaced with O, $C_{1-6}$ alkyne and optionally one or more C atoms are replaced with O, bicyclic, biaryl, biheteroaryl, or biheterocyclic, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, $C_1$-$C_6$ alkyl (linear, branched, optionally substituted), $C_1$-$C_6$ alkoxy (linear, branched, optionally substituted), $OC_{1-3}$alkyl (optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C=O, C=S, SO, $SO_2$, $C_1$-$C_6$ alkyl (linear, branched, optionally substituted) and optionally one or more C atoms are replaced with O; $C_1$-$C_6$ alkoxy (linear, branched, optionally substituted);

$Q^L$ is a 3-6 membered alicyclic or aromatic ring with 0-4 heteroatoms, optionally bridged, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

n is 0-10; and a dashed line indicates the attachment point to the PTM or ULM moieties.

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In another embodiment, the present disclosure is directed to a compound which comprises a PTM group, which binds to a target protein or polypeptide, which is ubiquitinated by an ubiquitin ligase and is chemically linked directly to the ULM group (such as CLM) or through a linker moiety L, or PTM is alternatively a ULM' group (such as CLM') which is also a ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In certain embodiments, the linker group L is a group comprising one or more covalently connected structural units independently selected from the group consisting of:

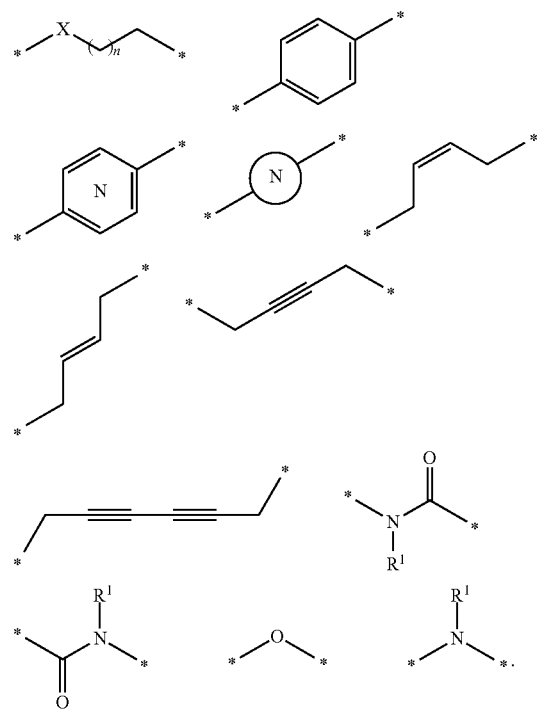

The X is selected from the group consisting of O, N, S, S(O) and $SO_2$; n is integer from 1 to 5; $R^{L1}$ is hydrogen or alkyl,

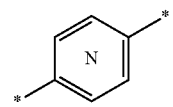

is a mono- or bicyclic aryl or heteroaryl optionally substituted with 1-3 substituents selected from alkyl, halogen, haloalkyl, hydroxy, alkoxy or cyano;

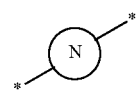

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the group consisting of alkyl, halogen, haloalkyl, hydroxy, alkoxy and cyano. In an embodiment, the linker group L comprises up to 10 covalently connected structural units, as described above.

Although the ULM group and PTM group may be covalently linked to the linker group through any group which is appropriate and stable to the chemistry of the linker, in preferred aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

In additional embodiments, q is an integer from 1 to 100, 1 to 90, 1 to 80, 1 to 70, 1 to 60, 1 to 50, 1 to 40, 1 to 30, 1 to 20, or 1 to 10.

In certain embodiments, the linker (L) is selected from the group consisting of:

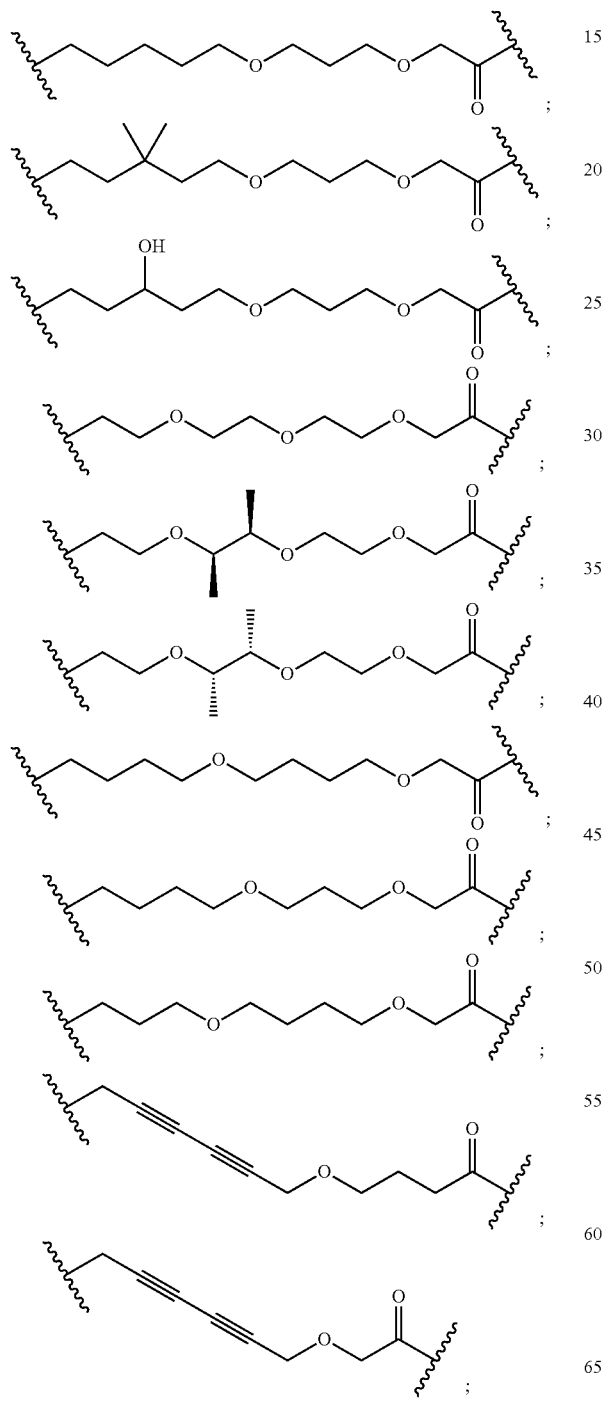

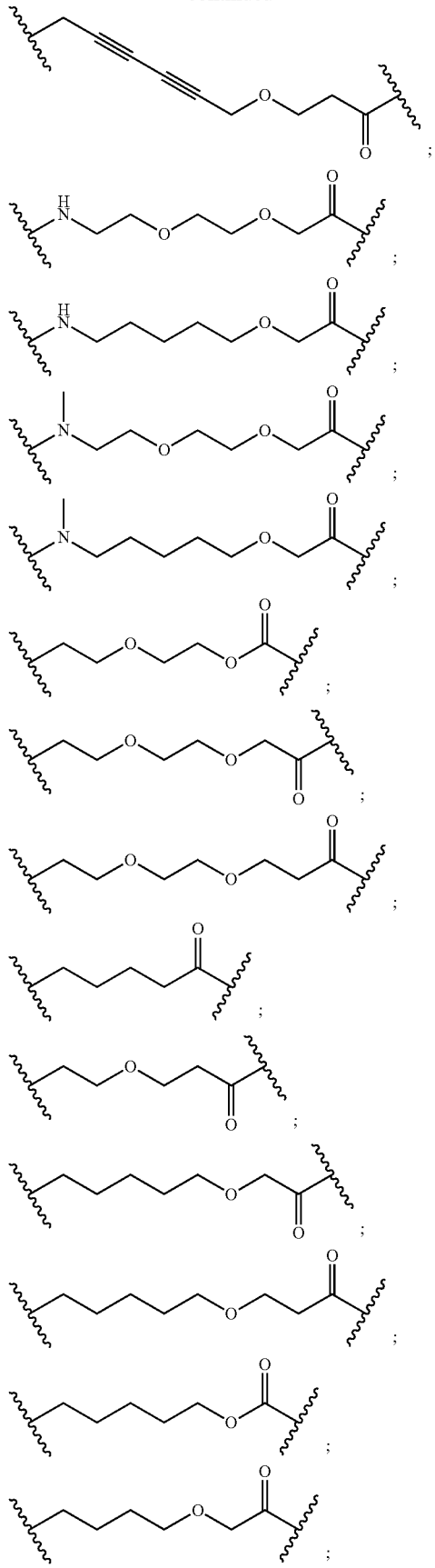

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

Although the CLM (or ULM) group and PTM group may be covalently linked to the linker group through any group which is appropriate and stable to the chemistry of the linker, in preferred aspects of the present disclosure, the linker is independently covalently bonded to the CLM group and the PTM group preferably through an amide, ester, thioester, keto group, carbamate (urethane), carbon or ether, each of which groups may be inserted anywhere on the CLM group and PTM group to provide maximum binding of the CLM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the CLM and/or PTM groups.

In certain embodiments, "L" can be linear chains with linear atoms from 4 to 24, the carbon atom in the linear chain can be substituted with oxygen, nitrogen, amide, fluorinated carbon, etc., such as the following:

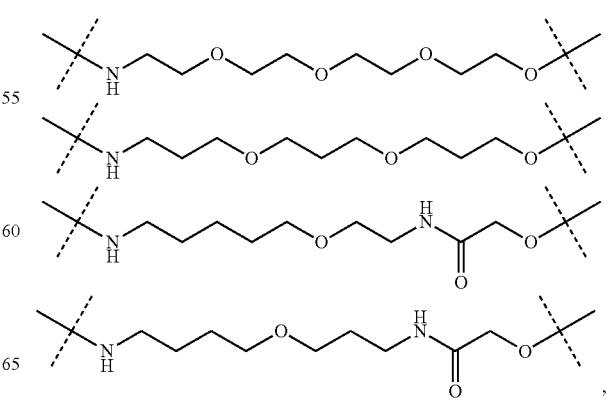

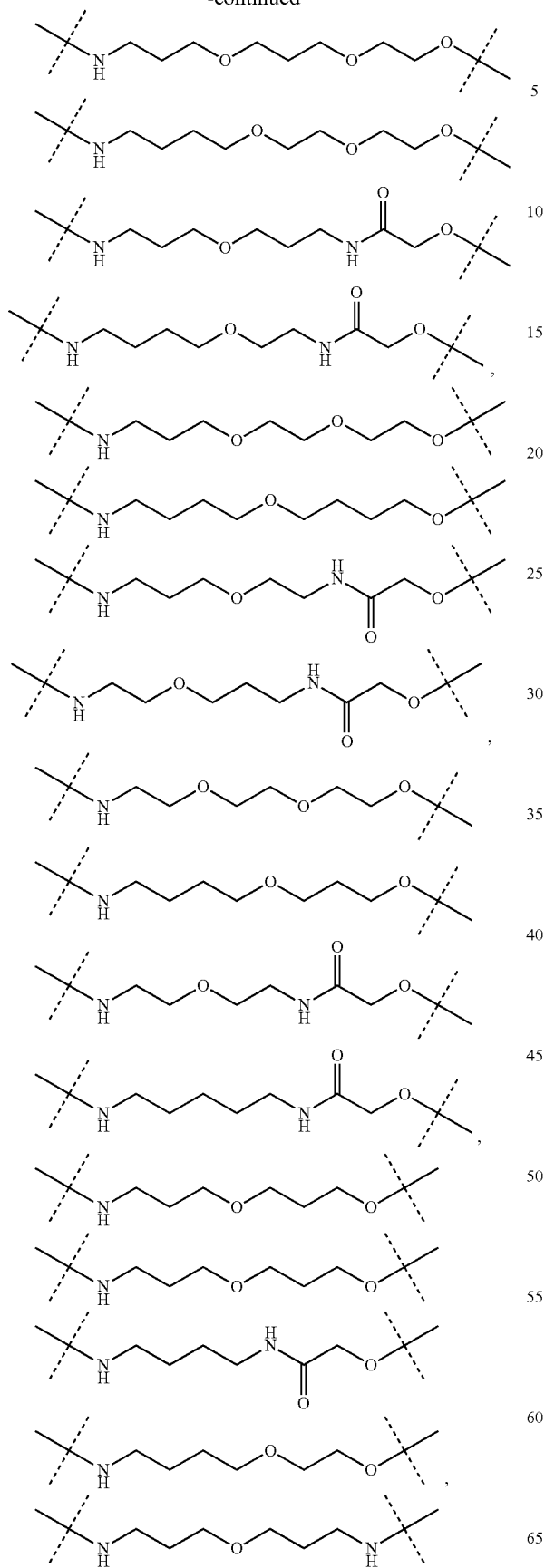
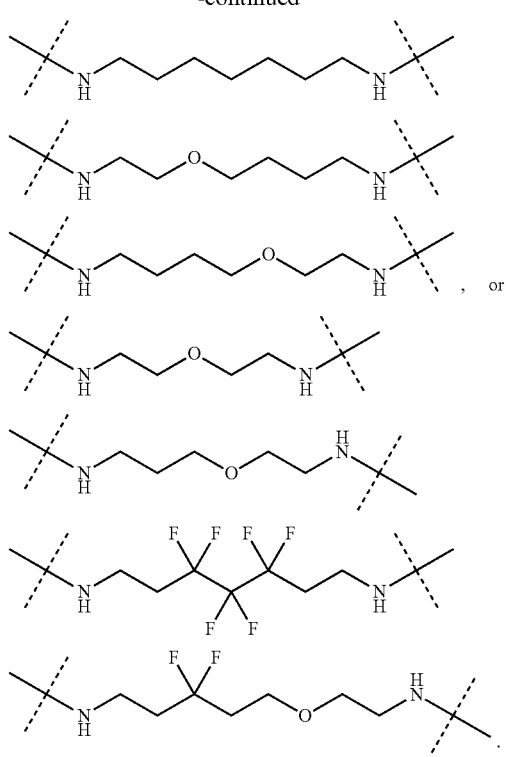
, or
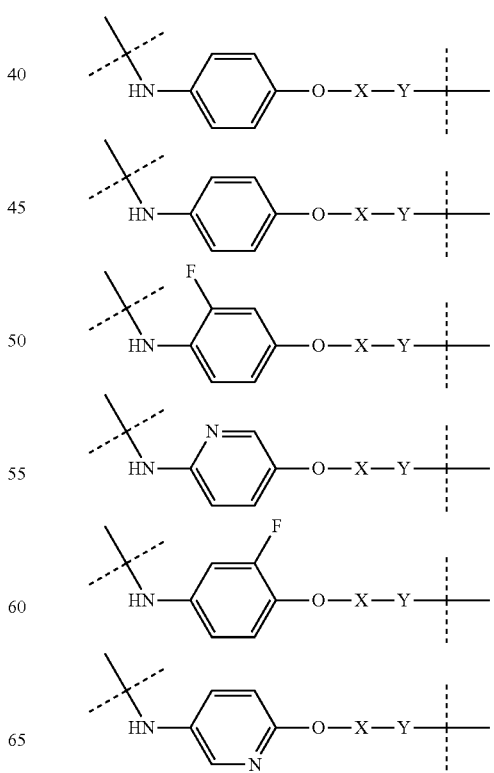
In certain embodiments, "L" can be nonlinear chains, and can be aliphatic or aromatic or heteroaromatic cyclic moieties, some examples of "L" include but not be limited to the following:

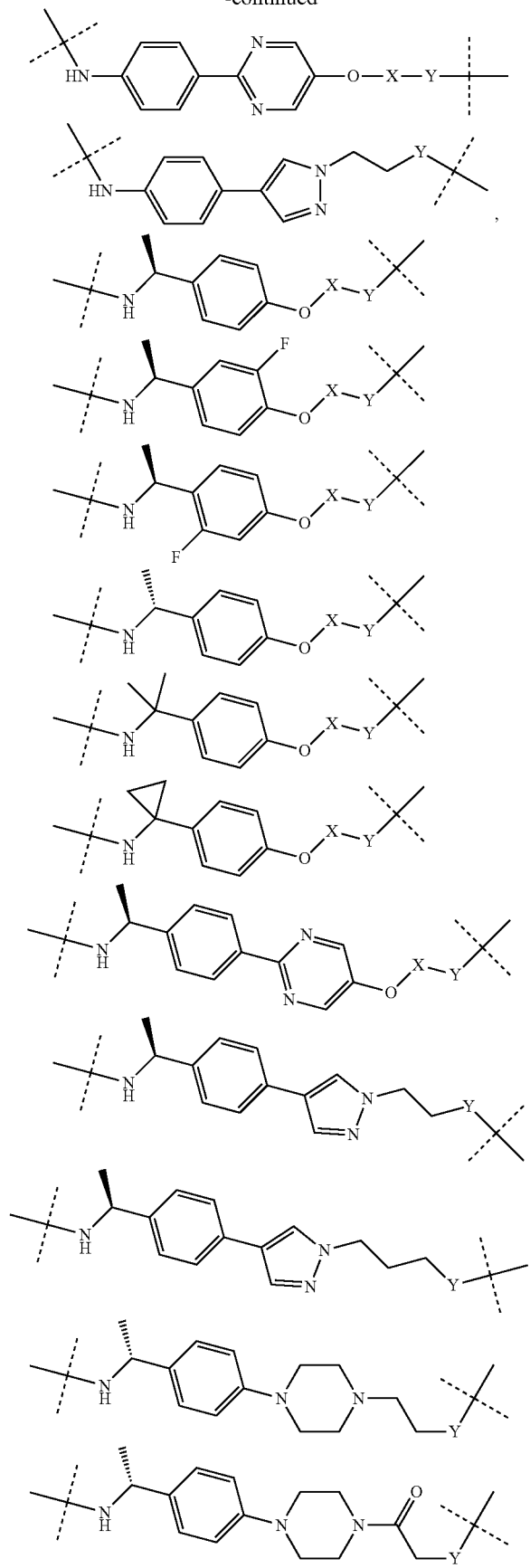
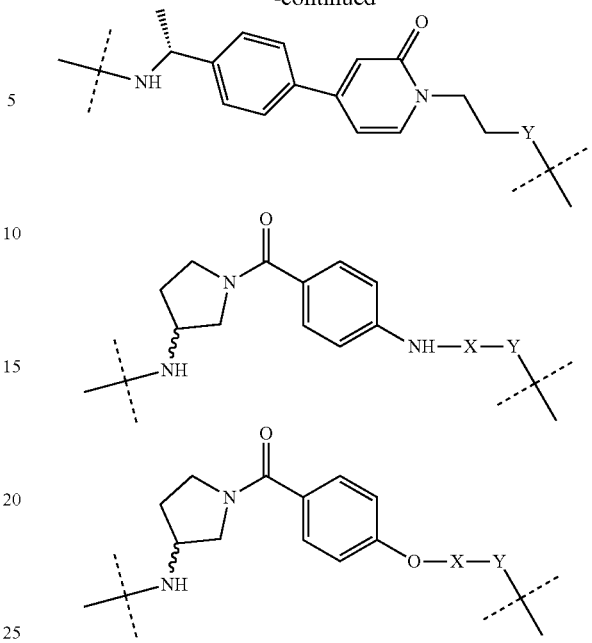

wherein:
'X' in above structures can be linear chain with atoms ranging from 2 to 14, and the mentioned chain can contain heteroatoms such as oxygen; and
"Y" in above structures can be O, N, S(O)$_n$ (n=0, 1, 2).

Exemplary PTMs

In preferred aspects of the present disclosure, the PTM group is a group, which binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present disclosure. Any protein in a eukaryotic system or a microbial system, including a virus, bacteria or fungus, as otherwise described herein, are targets for ubiquitination mediated by the compounds according to the present disclosure. Preferably, the target protein is a eukaryotic protein. In certain aspects, the protein binding moiety is a haloalkane (preferably a $C_1$-$C_{10}$ alkyl group which is substituted with at least one halo group, preferably a halo group at the distal end of the alkyl group, i.e., away from the linker or CLM group), which may covalently bind to a dehalogenase enzyme in a patient or subject or in a diagnostic assay.

PTM groups according to the present disclosure include, for example, include any moiety which binds to a protein specifically (binds to a target protein) and includes the following non-limiting examples of small molecule target protein moieties: Hsp90 inhibitors, kinase inhibitors, androgen receptor inhibitors, HDM2 & MDM2 inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. The compositions described below exemplify some of the members of these nine types of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a protein target moiety or PTM group and acted on or degraded by a ubiquitin ligase is a target protein according to the present disclosure. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes including humans as targets for drug therapy, other animals, including domesticated animals, microbials for the determination of targets for antibiotics and other antimicrobials and plants, and even viruses, among numerous others.

In still other embodiments, the PTM group is a haloalkyl group, wherein said alkyl group generally ranges in size from about 1 or 2 carbons to about 12 carbons in length, often about 2 to 10 carbons in length, often about 3 carbons to about 8 carbons in length, more often about 4 carbons to about 6 carbons in length. The haloalkyl groups are generally linear alkyl groups (although branched-chain alkyl groups may also be used) and are end-capped with at least one halogen group, preferably a single halogen group, often a single chloride group. Haloalkyl PT, groups for use in the present disclosure are preferably represented by the chemical structure $—(CH_2)_v$-Halo where v is any integer from 2 to about 12, often about 3 to about 8, more often about 4 to about 6. Halo may be any halogen, but is preferably Cl or Br, more often Cl.

In another embodiment, the present disclosure provides a library of compounds. The library comprises more than one compound wherein each composition has a formula of A-B, wherein A is a ubiquitin pathway protein binding moiety (preferably, an E3 ubiquitin ligase moiety as otherwise disclosed herein) and B is a protein binding member of a molecular library, wherein A is coupled (preferably, through a linker moiety) to B, and wherein the ubiquitin pathway protein binding moiety recognizes an ubiquitin pathway protein, in particular, an E3 ubiquitin ligase, such as cereblon. In a particular embodiment, the library contains a specific cereblon E3 ubiquitin ligase binding moiety bound to random target protein binding elements (e.g., a chemical compound library). As such, the target protein is not determined in advance and the method can be used to determine the activity of a putative protein binding element and its pharmacological value as a target upon degradation by ubiquitin ligase.

The present disclosure may be used to treat a number of disease states and/or conditions, including any disease state and/or condition in which proteins are dysregulated and where a patient would benefit from the degradation of proteins.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer (such as prostate cancer) and Kennedy's Disease. In certain additional embodiments, the disease is prostate cancer.

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer, by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to CLM or ULM groups through linker groups L.

Target proteins which may be bound to the protein target moiety and degraded by the ligase to which the ubiquitin ligase binding moiety is bound include any protein or peptide, including fragments thereof, analogues thereof, and/or homologues thereof. Target proteins include proteins and peptides having any biological function or activity including structural, regulatory, hormonal, enzymatic, genetic, immunological, contractile, storage, transportation, and signal transduction. In certain embodiments, the target proteins include structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eukaryotes and prokaryotes, including microbes, viruses, fungi and parasites, including humans, microbes, viruses, fungi and parasites, among numerous others, as targets for drug therapy, other animals, including domesticated animals, microbials for the determination of targets for antibiotics and other antimicrobials and plants, and even viruses, among numerous others.

More specifically, a number of drug targets for human therapeutics represent protein targets to which protein target moiety may be bound and incorporated into compounds according to the present disclosure. These include proteins which may be used to restore function in numerous polygenic diseases, including for example B7.1 and B7, TINFR1m, TNFR2, NADPH oxidase, BclIBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, RaslRaflMEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors (AR), adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvylshikimate-phosphate synthase.

Haloalkane dehalogenase enzymes are another target of specific compounds according to the present disclosure. Compounds according to the present disclosure which contain chloroalkane peptide binding moieties ($C_1$-$C_{12}$ often about $C_2$-$C_{10}$ alkyl halo groups) may be used to inhibit and/or degrade haloalkane dehalogenase enzymes which are used in fusion proteins or related dioagnostic proteins as described in PCT/US2012/063401 filed Dec. 6, 2011 and published as WO 2012/078559 on Jun. 14, 2012, the contents of which is incorporated by reference herein.

These various protein targets may be used in screens that identify compound moieties which bind to the protein and by incorporation of the moiety into compounds according to the present disclosure, the level of activity of the protein may be altered for therapeutic end result.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of these nine types of small molecule target protein.

Exemplary protein target moieties according to the present disclosure include, haloalkane halogenase inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR).

The compositions described below exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited hereinbelow are incorporated by reference herein in their entirety.

I. Heat Shock Protein 90 (HSP90) Inhibitors:

HSP90 inhibitors as used herein include, but are not limited to:

1. The HSP90 inhibitors identified in Vallee, et al., "Tricyclic Series of Heat Shock Protein 90 (HSP90) Inhibitors Part I: Discovery of Tricyclic Imidazo[4,5-C]Pyridines as Potent Inhibitors of the HSP90 Molecular Chaperone (2011)

J. Med. Chem. 54: 7206, including YKB (N-[4-(3H-imidazo[4,5-C]Pyridin-2-yl)-9H-Fluoren-9-yl]-succinamide):

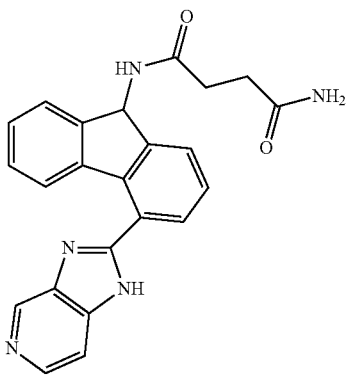 [SMILES: NC(=O)CCC(=O)NC1c2ccccc2-c2c(-c3nc4cnccc4[nH]3)cccc21]

derivatized where a linker group L or a -(L-CLM) group is attached, for example, via the terminal amide group;

2. The HSP90 inhibitor p54 (modified) (8-[(2,4-dimethylphenyl)sulfanyl]-3]pent-4-yn-1-yl-3H-purin-6-amine):

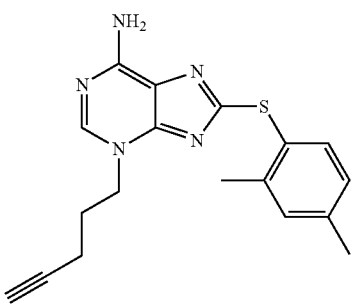 [SMILES: C#CCCCn1cnc(N)c2nc(Sc3ccc(C)cc3C)nc1-2]

derivatized where a linker group L or a -(L-CLM) group is attached, for example, via the terminal acetylene group;

3. The HSP90 inhibitors (modified) identified in Brough, et al., "4,5-Diarylisoxazole HSP90 Chaperone Inhibitors: Potential Therapeutic Agents for the Treatment of Cancer", *J. MED. CHEAM.* vol: 51, pag: 196 (2008), including the compound 2GJ (5-[2,4-dihydroxy-5-(1-methylethyl)phenyl]-n-ethyl-4-[4-(morpholin-4-ylmethyl)phenyl]isoxazole-3-carboxamide) having the structure:

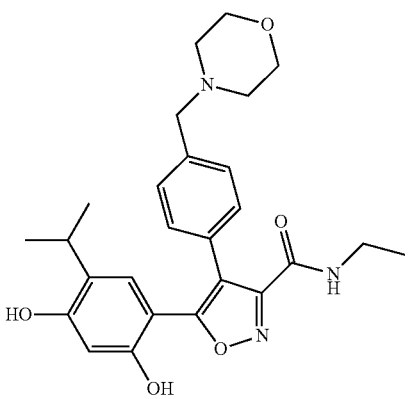 [SMILES: CCNC(=O)c1noc(-c2cc(C(C)C)c(O)cc2O)c1-c1ccc(CN2CCOCC2)cc1]

derivatized, where a linker group L or a -(L-CLM) group is attached, for example, via the amide group (at the amine or at the alkyl group on the amine);

4. The HSP90 inhibitors (modified) identified in Wright, el al., Structure-Activity Relationships in Purine-Based Inhibitor Binding to HSP90 Isoforms, *Chem Biol.* 2004 June; 11(6):775-85, including the HSP90 inhibitor PU3 having the structure:

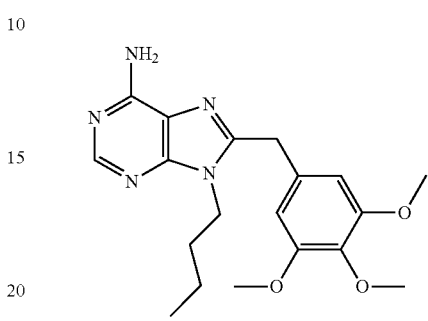

derivatized where a linker group L or -(L-CLM) is attached, for example, via the butyl group; and 5. The HSP90 inhibitor geldanamycin ((4E,6Z,8S,9S,10F,12S,13R,14S,16R)-13-hydroxy-8,14,19-trimethoxy-4,10,12,16-tetramethyl-3,20,22-trioxo-2-azabicyclo[16.3.1](derivatized) or any of its derivatives (e.g. 17-alkylamino-17-desmethoxygeldanamycin ("17-AAG") or 17-(2-dimethylaminoethyl)amino-17-desmethoxygeldanamycin ("17-DMAG")) (derivatized, where a linker group L or a -(L-CLM) group is attached, for example, via the amide group).

II. Kinase and Phosphatase Inhibitors:

Kinase inhibitors as used herein include, but are not limited to:

1. Erlotinib Derivative Tyrosine Kinase Inhibitor:

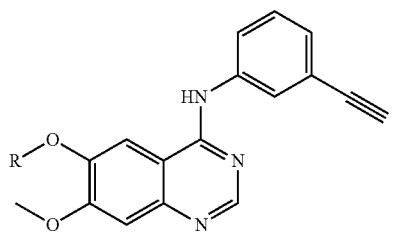

where R is a linker group L or a -(L-CLM) group attached, for example, via the ether group;

2. The kinase inhibitor sunitinib (derivatized):

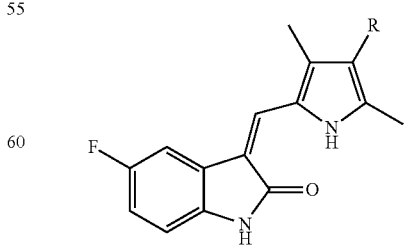

derivatized where R is a linker group L or a -(L-CLM) group attached, for example, to the pyrrole moiety;

3. Kinase Inhibitor sorafenib (derivatized):

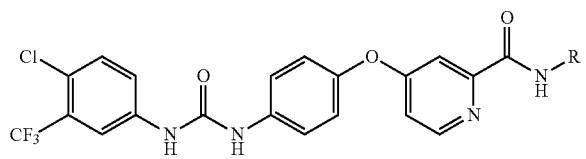

derivatized where R is a linker group L or a -(L-CLM) group attached, for example, to the amide moiety;

4. The kinase inhibitor desatinib (derivatized):

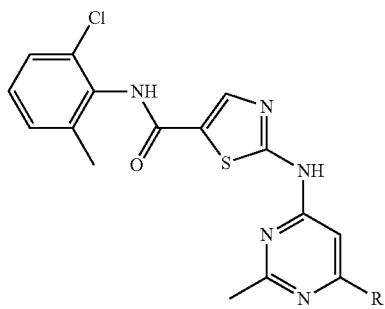

derivatized where R is a linker group L or a -(L-CLM) attached, for example, to the pyrimidine;

5. The kinase inhibitor lapatinib (derivatized):

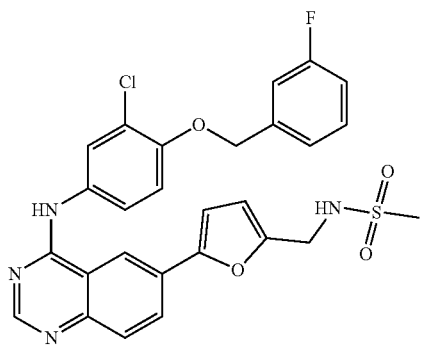 [SMILES: CS(=O)(=O)NCc1ccc(-c2ccc3ncnc(Nc4ccc(OCc5cccc(F)c5)c(Cl)c4)c3c2)o1]

derivatized where a linker group L or a -(L-CLM) group is attached, for example, via the terminal methyl of the sulfonyl methyl group;

6. The kinase inhibitor u09-cx-5279 (derivatized):

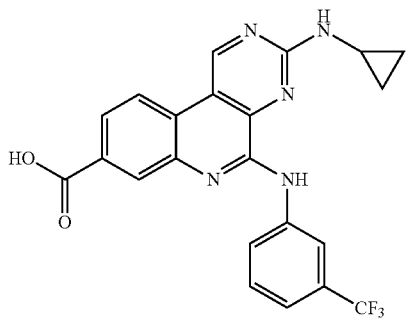 [SMILES: O=C(O)c1ccc2c(c1)nc(Nc1cccc(C(F)(F)F)c1)c1nc(NC3CC3)ncc12]

derivatized where a linker group L or a -(L-CLM) group is attached, for example, via the amine (aniline), carboxylic acid or amine alpha to cyclopropyl group, or cyclopropyl group;

7. The kinase inhibitors identified in Millan, el al., Design and Synthesis of Inhaled P38 Inhibitors for the Treatment of Chronic Obstructive Pulmonary Disease, *J. MED. CHEM.* vol: 54, pag: 7797 (2011), including the kinase inhibitors Y1W and Y1X (Derivatized) having the structures:

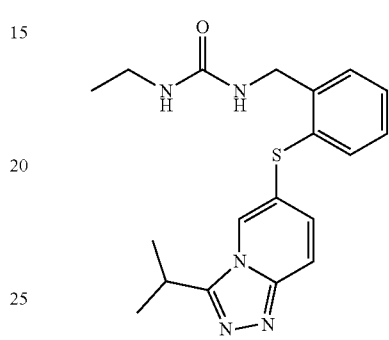

YIX(1-ethyl-3-(2-{[3-(1-methylethyl)[1,2,4]triazolo[4,3-a]pyridine-6-yl]sulfanyl}benzyl)urea, derivatized where a linker group L or a -(L-CLM) group is attached, for example, via the $^i$propyl group;

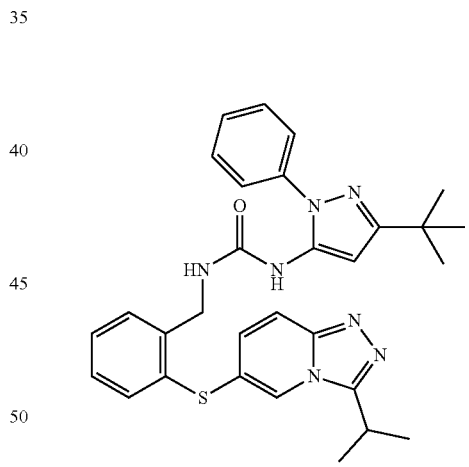

1-(3-ter-butyl-1-phenyl-1H-pyrazol-5-yl)-3-(2-{[3-(1-methylethyl)[1,2,4]triazolo[4,3-a]pyridin-6-yl]sulfanyl}benzyl)urea derivatized where a linker group L or a -(L-CLM) group is attached, for example, preferably via either the i-propyl group or the t-butyl group;

8. The kinase inhibitors identified in Schenkel, et al., Discovery of Potent and Highly Selective Thienopyridine Janus Kinase 2 Inhibitors *J. Med. Chem.*, 2011, 54 (24), pp 8440-8450, including the compounds 6TP and 0TP (Derivatized) having the structures:

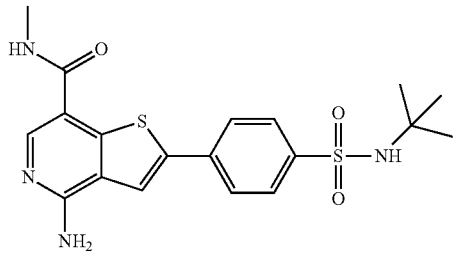

4-amino-2-[4-(tert-butylsulfamoyl)phenyl]-N-methylthieno[3,2-c]pyridine-7-carboxamide Thienopyridine 19 derivatized where a linker group L or a -(L-CLM) group is attached, for example, via the terminal methyl group bound to amide moiety,

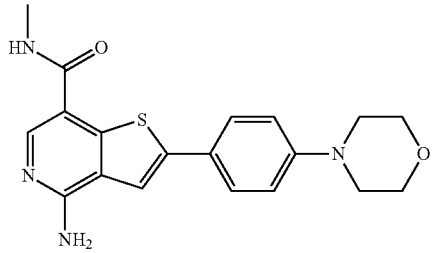 [SMILES: CNC(=O)c1cnc(N)c2cc(-c3ccc(N4CCOCC4)cc3)sc12]

4-amino-N-methyl-2-[4-(morpholin-4-yl)phenyl]thieno[3,2-c]pyridine-7-carboxamide Thienopyridine 8 derivatized where a linker group L or a -(L-CLM)group is attached, for example, via the terminal methyl group bound to the amide moiety;

9. The kinase inhibitors identified in Van Eis, et al., "2,6-Naphthyridines as potent and selective inhibitors of the novel protein kinase C isozymes", *Biorg. Med. Chem. Lett.* 2011 Dec. 15; 21(24):7367-72, including the kinase inhibitor 07U having the structure:

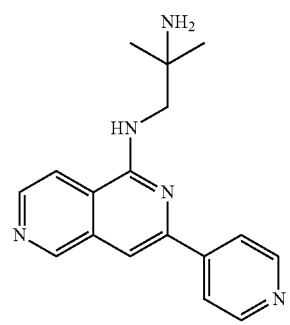

2-methyl-N~1~-[3-(pyridin-4-yl)-2,6-naphthyridin-1-yl]propane-1,2-diamine derivatized where a linker group L or a -(L-CLM)group is attached, for example, via the secondary amine or terminal amino group;

10. The kinase inhibitors identified in Lountos, et al., "Structural Characterization of Inhibitor Complexes with Checkpoint Kinase 2 (Chk2), a Drug Target for Cancer Therapy", *J. STRUCT. BIOL.* vol: 176, pag: 292 (2011), including the kinase inhibitor YCF having the structure:

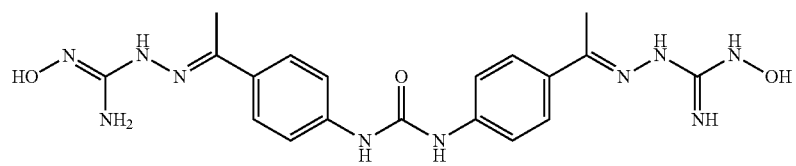 [SMILES: C/C(=N\NC(=N)NO)c1ccc(NC(=O)Nc2ccc(/C(C)=N/N/C(N)=N/O)cc2)cc1]

derivatized where a linker group L or a -(L-CLM) group is attached, for example, via either of the terminal hydroxyl groups;

11. The kinase inhibitors identified in Lountos, et al., "Structural Characterization of Inhibitor Complexes with Checkpoint Kinase 2 (Chk2), a Drug Target for Cancer Therapy", *J. STRUCT. BIOL. vol:* 176, pag: 292 (2011), including the kinase inhibitors XK9 and NXP (derivatized) having the structures:

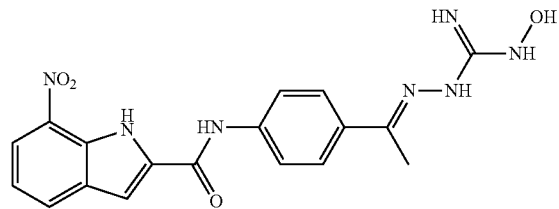 [SMILES: C/C(=N\NC(=N)NO)c1ccc(NC(=O)c2cc3cccc([N+](=O)[O-])c3[nH]2)cc1]

N-{4-[(1E)-N—(N-hydroxycarbamimidoyl)ethane-hydrazonoyl]phenyl}-7-nitro-1H-indole-2-carboxamide

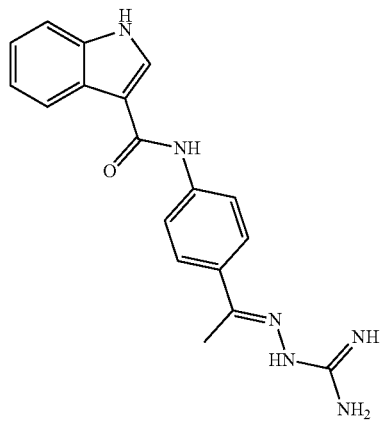

NXP

N-{4-[(1E)-N-CARBAMIMIDOYLETHANEHY-DRAZONOYL]PHENYL}-1H-INDOLE-3-CAR-BOXAMIDE derivatized where a linker group L or a -(L-CLM) group is attached, for example, via the terminal hydroxyl group (XK9) or the hydrazone group (NXP);

12. The kinase inhibitor afatinib (derivatized) (N-[4-[(3-chloro-4-fluorophenyl)amino]-7-[[(3S)-tetrahydro-3-furanyl]oxy]-6-quinazolinyl]-4(dimethylamino)-2-butenamide) (Derivatized where a linker group L or a -(L-CLM) group is attached, for example, via the aliphatic amine group);

13. The kinase inhibitor fostamatinib (derivatized) ([6-{(5-fluoro-2-[(3,4,5-trimethoxyphenyl)amino]pyrimidin-4-yl}amino)-2,2-dimethyl-3-oxo-2,3-dihydro-4H-pyrido[3,2-b]-1,4-oxazin-4-yl]methyl disodium phosphate hexahydrate) (Derivatized where a linker group L or a -(L-CLM) group is attached, for example, via a methoxy group);

14. The kinase inhibitor gefitinib (derivatized) (N-(3-chloro-4-fluoro-phenyl)-7-methoxy-6-(3-morpholin-4-yl-propoxy)quinazolin-4-amine):

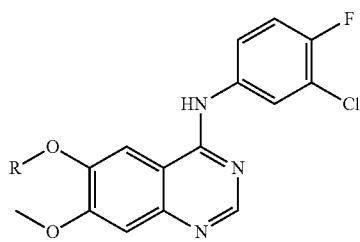

derivatized where a linker group L or a -(L-CLM) group is attached, for example, via a methoxy or ether group;

15. The kinase inhibitor lenvatinib (derivatized) (4-[3-chloro-4-(cyclopropylcarbamoylamino)phenoxy]-7-methoxy-quinoline-6-carboxamide) (derivatized where a linker group L or a -(L-CLM) group is attached, for example, via the cyclopropyl group);

16. The kinase inhibitor vandetanib (derivatized) (N-(4-bromo-2-fluorophenyl)-6-methoxy-7-[(1-methylpiperidin-4-yl)methoxy]quinazolin-4-amine) (derivatized where a linker group L or a -(L-CLM) group is attached, for example, via the methoxy or hydroxyl group);

17. The kinase inhibitor vemurafenib (derivatized) (propane-1-sulfonic acid {3-[5-(4-chlorophenyl)-1H-pyrrolo[2,3-b]pyridine-3-carbonyl]-2,4-difluoro-phenyl}-amide), derivatized where a linker group L or a -(L-CLM) group is attached, for example, via the sulfonyl propyl group;

18. The kinase inhibitor Gleevec (Derivatized):

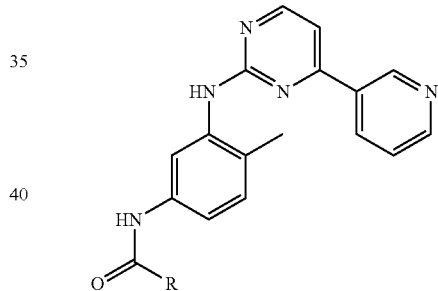

derivatized where R as a linker group L or a -(L-CLM) group is attached, for example, via the amide group or via the aniline amine group;

19. The kinase inhibitor pazopanib (derivatized) (VEGFR3 inhibitor):

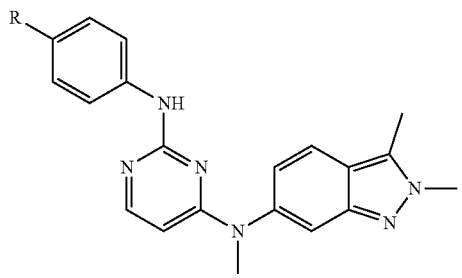

derivatized where R is a linker group L or a -(L-CLM) group attached, for example, to the phenyl moiety or via the aniline amine group:

20. The kinase inhibitor AT-9283 (Derivatized) Aurora Kinase Inhibitor

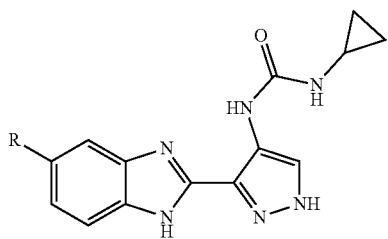

where R is a linker group L or a -(L-CLM) group attached, for example, to the phenyl moiety);

21. The kinase inhibitor TAE684 (Derivatized) ALK inhibitor

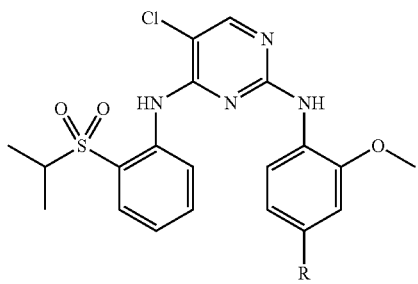

where R is a linker group L or a -(L-CLM) group attached, for example, to the phenyl moiety);

22. The kinase inhibitor nilotanib (derivatized) Abl inhibitor:

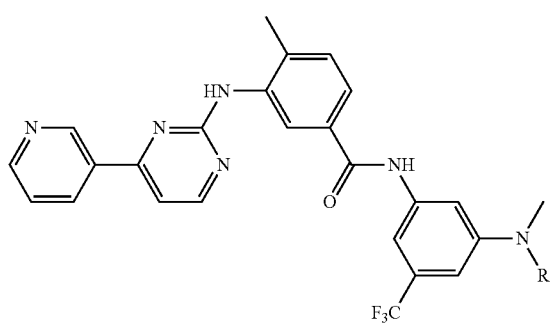

derivatized where R is a linker group L or a -(L-CLM) group attached, for example, to the phenyl moiety or the aniline amine group;

23. Kinase Inhibitor NVP-BSK805 (derivatized) JAK2 Inhibitor

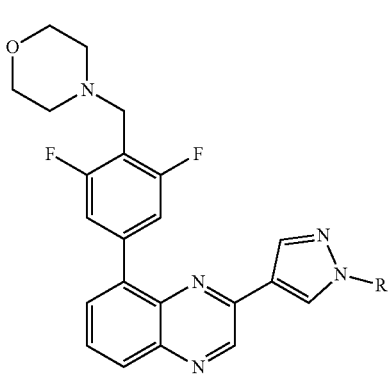

derivatized where R is a linker group L or a -(L-CLM) group attached, for example, to the phenyl moiety or the diazole group;

24. Kinase Inhibitor crizotinib Derivatized Alk Inhibitor

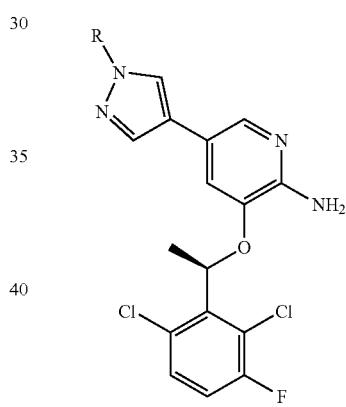

derivatized where R is a linker group L or a -(L-CLM) group attached, for example, to the phenyl moiety or the diazole group;

25. Kinase Inhibitor JNJ FMS (derivatized) Inhibitor

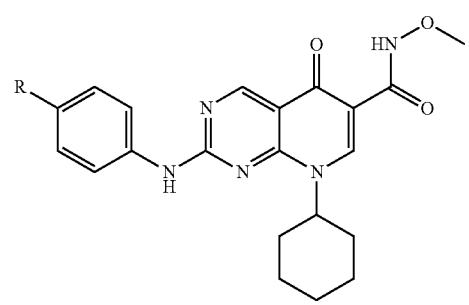

derivatized where R is a linker group L or a -(L-CLM) group attached, for example, to the phenyl moiety;

26. The kinase inhibitor foretinib (derivatized) Met Inhibitor

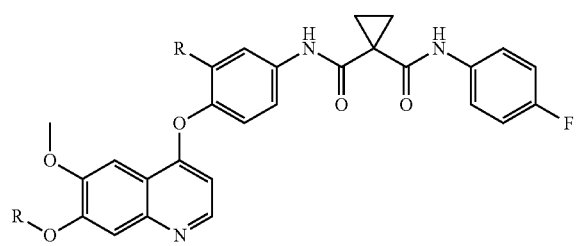

derivatized where R is a linker group L or a -(L-CLM)group attached, for example, to the phenyl moiety or a hydroxyl or ether group on the quinoline moiety;

27. The allosteric Protein Tyrosine Phosphatase Inhibitor PTP1B (derivatized):

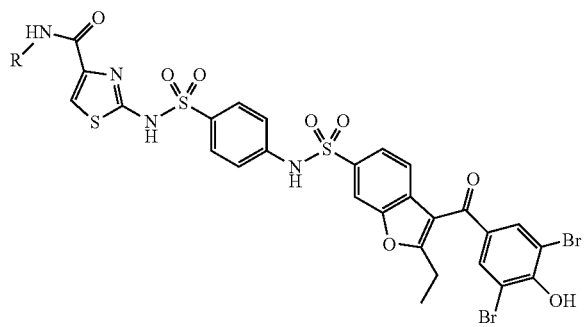

derivatized where a linker group L or a -(L-CLM) group is attached, for example, at R, as indicated;

28. The inhibitor of SHP-2 Domain of Tyrosine Phosphatase (derivatized):

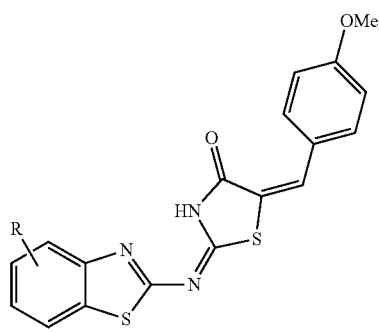

derivatized where a linker group L or a -(L-CLM) group is attached, for example, at R;

29. The inhibitor (derivatized) of BRaf (BRaf$^{V600E}$)/MEK:

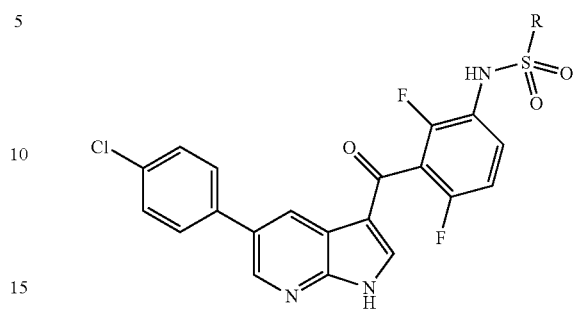

derivatized where a linker group L or a -(L-CLM) group is attached, for example, at R;

30. Inhibitor (derivatized) of Tyrosine Kinase ABL

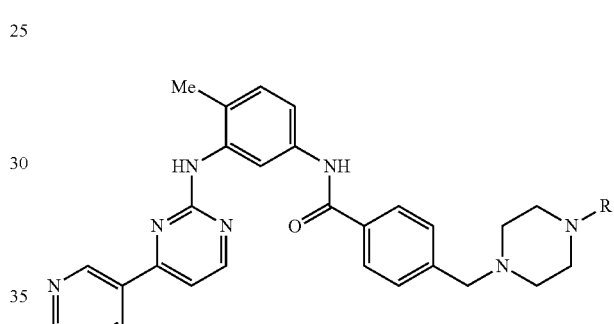

derivatized where a linker group L or a -(L-CLM) group is attached, for example, at R;

31. The kinase inhibitor OSI-027 (derivatized) mTORC1/2 inhibitor

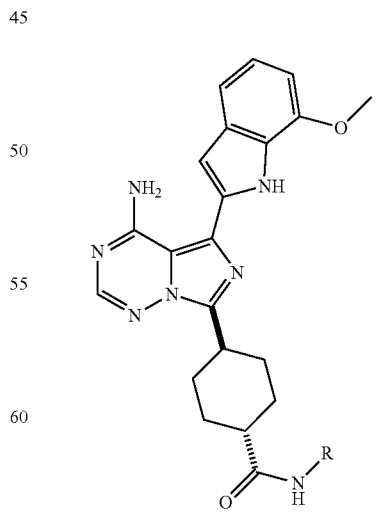

derivatized where a linker group L or a -(L-CLM) group is attached, for example, at R;

32. The kinase inhibitor OSI-930 (derivatized) c-Kit/KDR inhibitor

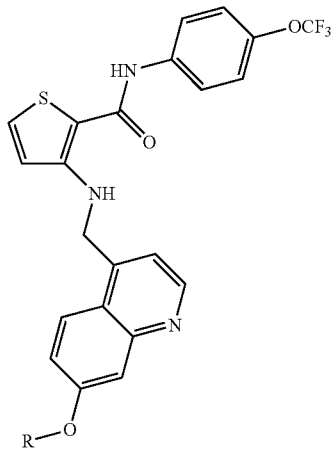

derivatized where a linker group L or a -(L-CLM) group is attached, for example, at R; and 33. The kinase inhibitor OSI-906 (derivatized) IGF1R/IR inhibitor

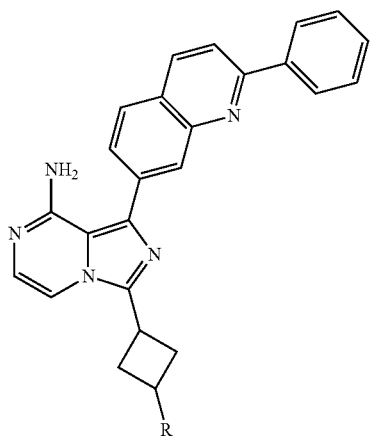

derivatized where a linker group L or a -(L-CLM) group is attached, for example, at R.

Wherein, in any of the embodiments described in sections I-XVII, "R" designates a site for attachment of a linker group L or a -(L-CLM)group on the piperazine moiety.

III. HDM2/MDM2 Inhibitors:

HDM2/MDM2 inhibitors as used herein include, but are not limited to:

1. The HDM2/MDM2 inhibitors identified in Vassilev, et al., In vivo activation of the p53 pathway by small-molecule antagonists of MDM2, *SCIENCE* vol: 303, pag: 844-848 (2004), and Schneekloth, el al., Targeted intracellular protein degradation induced by a small molecule. En route to chemical proteomics, *Bioorg. Med. Chem. Lett.* 18 (2008) 5904-5908, including (or additionally) the compounds nutlin-3, nutlin-2, and nutlin-1 (derivatized) as described below, as well as all derivatives and analogs thereof:

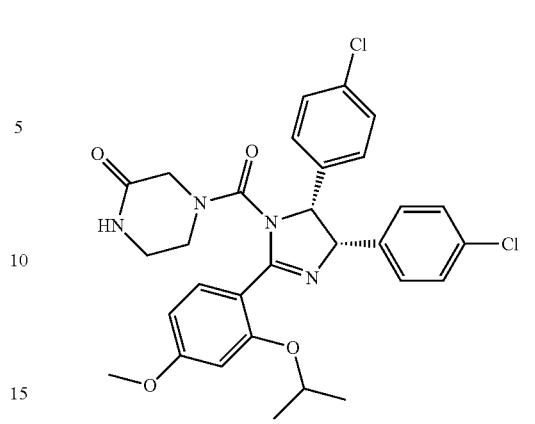

(derivatized where a linker group L or a -(L-CLM)group is attached, for example, at the methoxy group or as a hydroxyl group);

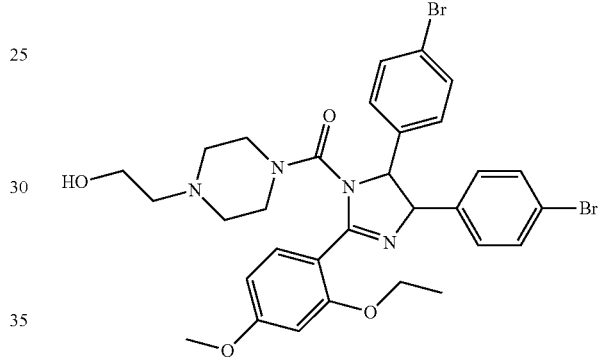

(derivatized where a linker group L or a -(L-CLM) group is attached, for example, at the methoxy group or hydroxyl group);

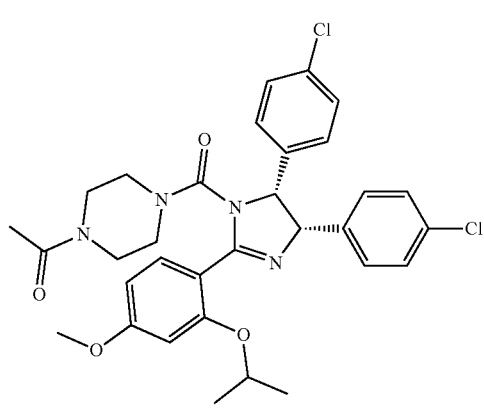 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a linker group L or a -(L-CLM) group is attached, for example, via the methoxy group or as a hydroxyl group); and 2. Trans-4-Iodo-4'-Boranyl-Chalcone

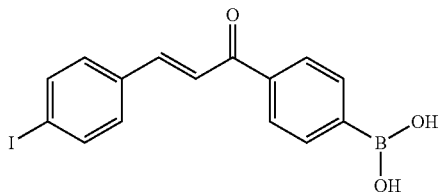 [SMILES: O=C(/C=C/c1ccc(I)cc1)c1ccc(B(O)O)cc1]

(derivatized where a linker group L or a a linker group L or a -(L-CLM) group is attached, for example, via a hydroxy group).

IV. Compounds Targeting Human BET Bromodomain-Containing Proteins:

In certain embodiments, "PTM" can be ligands binding to Bromo- and Extra-terminal (BET) proteins BRD2, BRD3 and BRD4. Compounds targeting Human BET Bromodomain-containing proteins include, but are not limited to the compounds associated with the targets as described below, where "R" or "linker" designates a site for linker group L or a -(L-CLM) group attachment, for example:

1. JQ1, Filippakopoulos et al. Selective inhibition of BET bromodomains. *Nature* (2010):

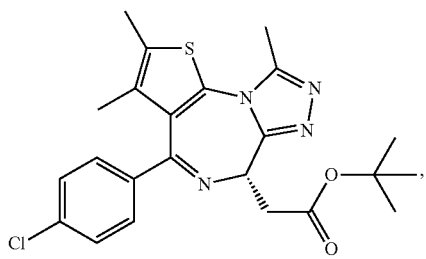

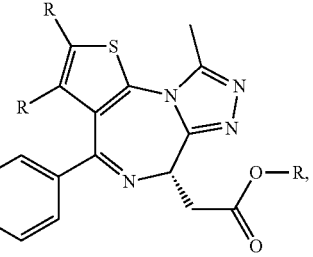

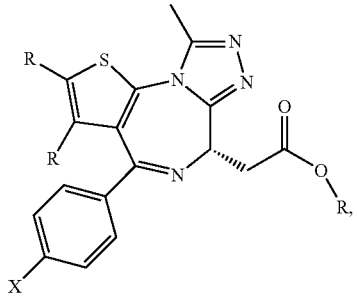

X = Cl, Br, F, H,
bond, or a chemical
moiety coupling the
CLM to the PTM
R = H, a lower alkyl,
a bond, or a chemcial
moiety coupling the
CLM to the PTM -continued

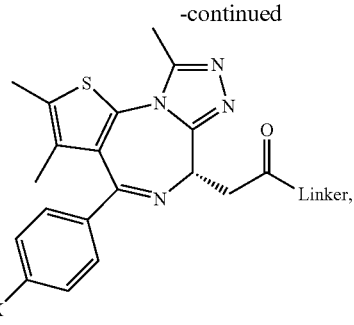

X = Cl, Br, F, H

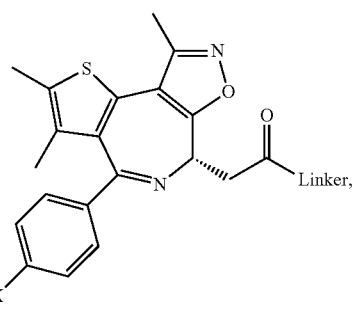

X = Cl, Br, F, H

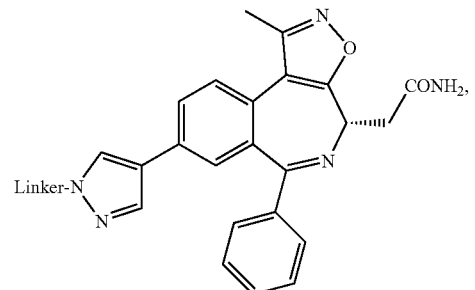

X = Cl, Br, F, H

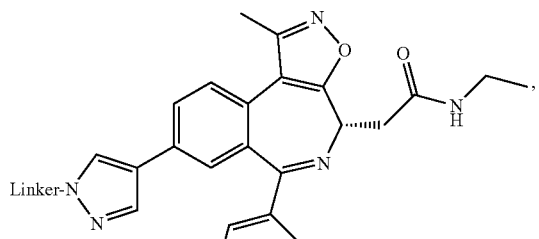

X = Cl, Br, F, H

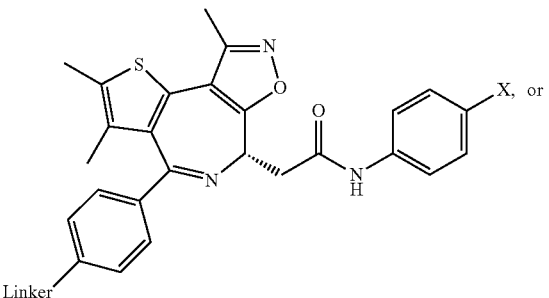

-continued

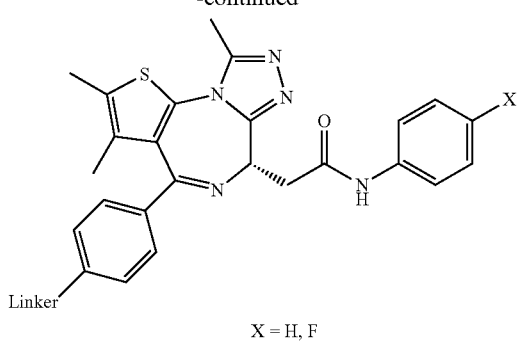

X = H, F

2. I-BET, Nicodeme et al. Supression of Inflammation by a Synthetic Histone Mimic. *Nature* (2010). Chung et al. Discovery and Characterization of Small Molecule Inhibitors of the BET Family Bromodomains. J. Med Chem. (2011):

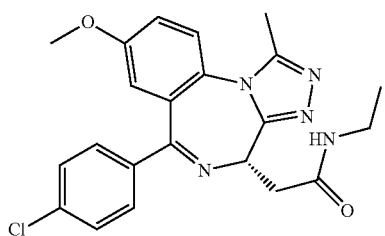

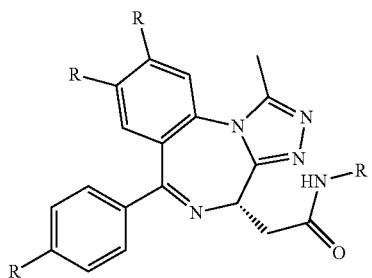

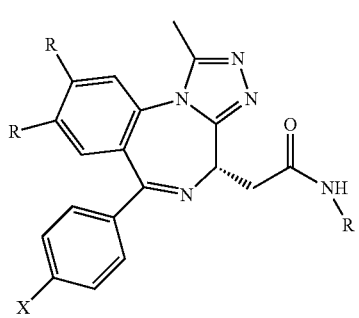

X = Cl, Br, F, H, bond, or a chemical moiety coupling the CLM to the PTM
R = H, a lower alkyl, a bond, or a chemcial moiety coupling the CLM to the PTM 3. Compounds described in Hewings et al. 3,5-Dimethylisoxazoles Act as Acetyl-lysine Bromodomain Ligands. J. Med. Chem. (2011) 54 6761-6770.

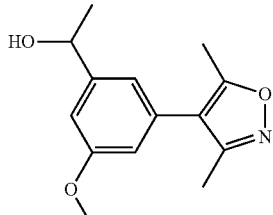

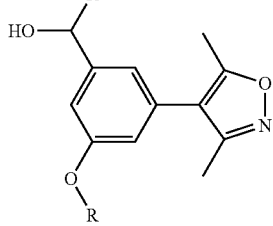

4. I-BET151, Dawson et al. Inhibition of BET Recruitment to Chromatin as an Effective Treatment for MLL-fusion Leukemia. Nature (2011):

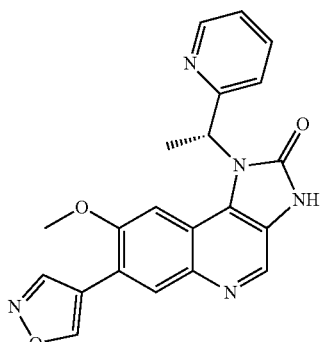

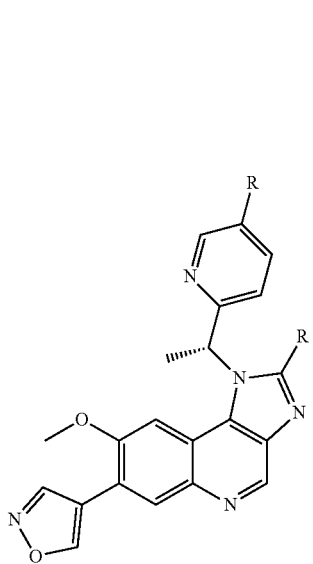

-continued
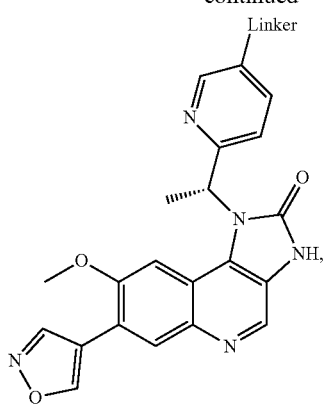
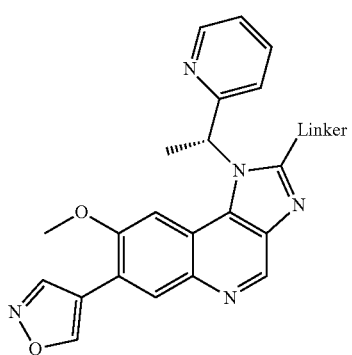
5. Carbazole type (US 2015/0256700)
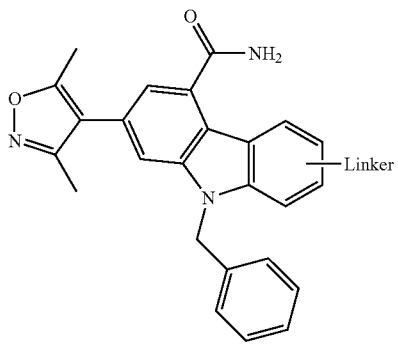
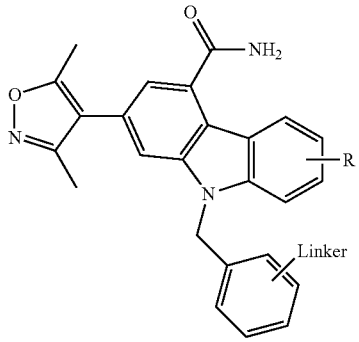
6. Pyrrolopyridone type (US 2015/0148342)
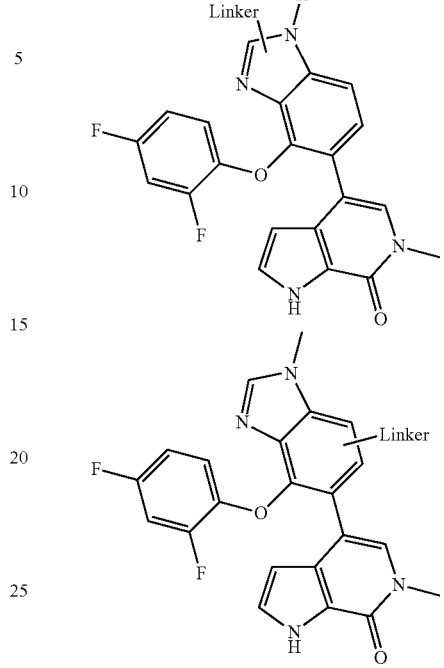
7. Tetrahydroquinoline type (WO 2015/074064)
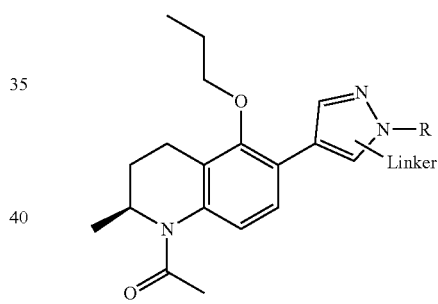
8. Triazolopyrazine type (WO 2015/067770)
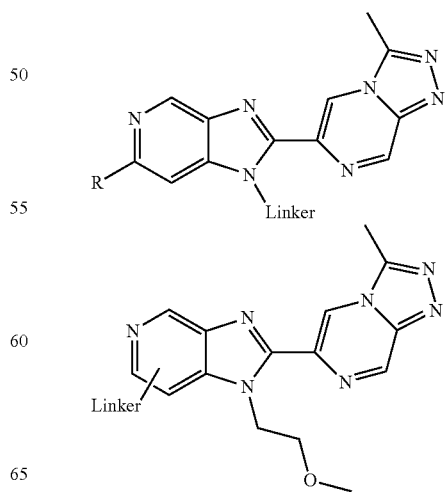

9. Pyridone type (WO 2015/022332)

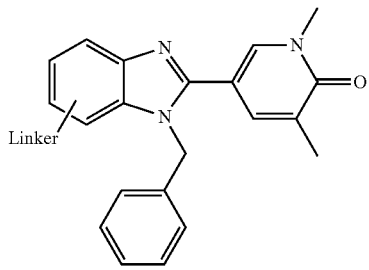

10. Quinazolinone type (WO 2015/015318)

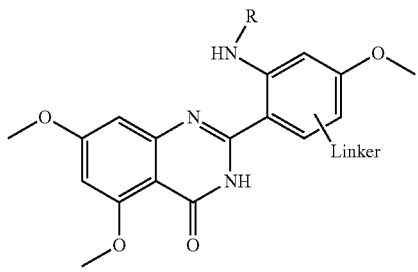

11. Dihydropyridopyrazinone type (WO 2015/011084)

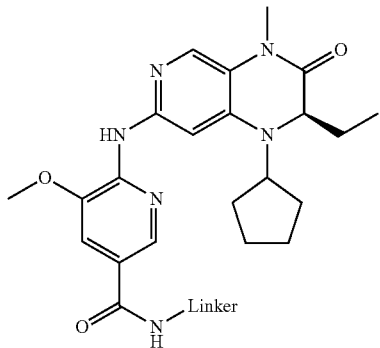

(Where R or L or linker, in each instance, designates a site for attachment, for example, of a linker group L or a -(L-CLM) group).

In any aspect or embodiment described herein, the claimed structure the PTM may be composed of tricyclic diazepine or tricyclic azepine as a BET/BRD4 targeting moiety (PTM-a), where the dashed lines indicate the linker connection trajectory and three sites are defined to which linkers may be attached:

PTM-a

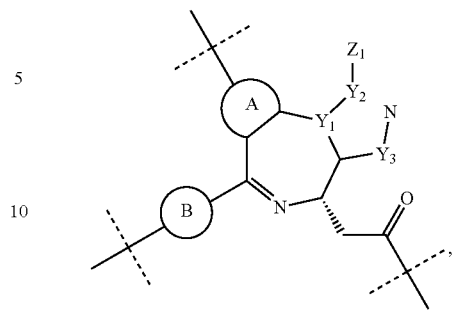

wherein:
A and B are independently an aromatic ring, a heteroaromatic ring, a 5-membered carbocyclic, a 6-membered carbocyclic, a 5-membered heterocyclic, a 6-membered heterocyclic, a thiophene, a pyrrole, a pyrazole, a pyridine, a pyrimidine, a pyrazine, optionally substituted by alkyl, aloxy, halogen, nitrile or another aromatic or heteroaromatic ring, where A is fused to the central azepine (Y1═C) or diazepine (Y1 ═N) moiety;

Y1, Y2, and Y3 and Y4 can be carbon, nitrogen or oxygen for to form a fused 5-membered aromatic ring as triazole or isoxazole; and Z1 is methyl, or lower alkyl group.

The fragment of PTM-a as BET/BRD4 targeting moiety is described in the literature (WO 2016/069578; WO2014/001356; WO2016/050821; WO 2015/195863: WO 2014/128111).

In any aspect or embodiment described herein comprising the structure CLM-L-PTM-a, PTM-a can be represented by the following general structures, where dashed line indicates a possible linker connection point. In structure PTM-aa through PTM-ai, the substitution pattern of X and Y can be mono- or bis-substitution.

PTM-aa

[Structure diagram]

X = Cl, F, Br, H, CN, methyl, acetylene, methoxy

PTM-ab

[Structure diagram]

X = Cl, F, Br, H, CN, methyl, acetylene, methoxy

PTM-ac

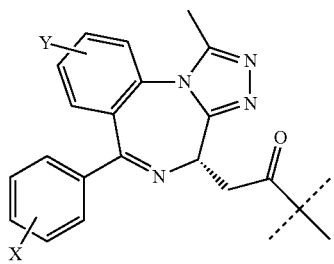

X = Cl, F, Br, H, CN, methyl, methoxy, acetylene
Y: mono- or di-substitution, Y = Me, OMe, N-methylpyrazole/imidazole PTM-ad

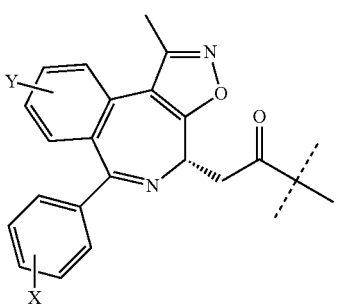

X = Cl, F, Br, H, CN, methyl, methoxy, acetylene
Y: mono- or di-substitution, Y = Me, OMe, N-methylpyrazole/imidazole PTM-ae

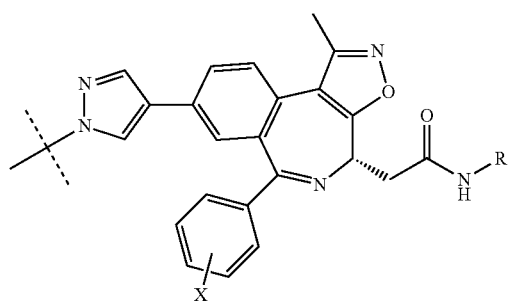

X = Cl, F, Br, H, CN, methyl, methoxy, acetylene
R = lower alkyl, aryl, substituted aryl PTM-af

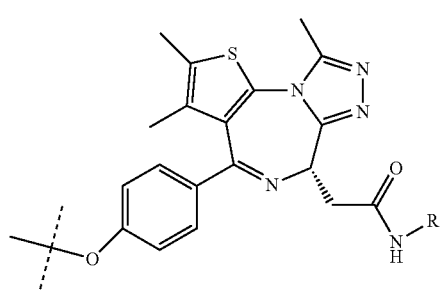

R = lower alkyl, aryl, substituted aryl

PTM-ag

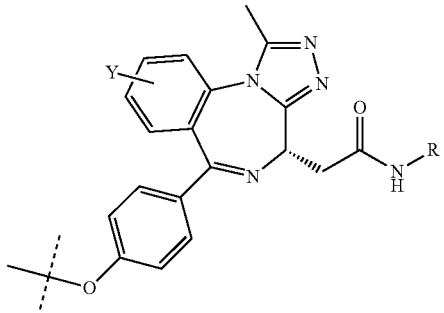

Y: mono- or di-substitution, Y = Me, OMe, N-methylpyrazole/imidazole
R = lower alkyl, aryl, substituted aryl PTM-ah

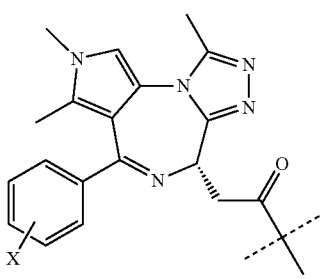

X = Cl, F, Br, H, CN, methyl, acetylene, methoxy

PTM-ai

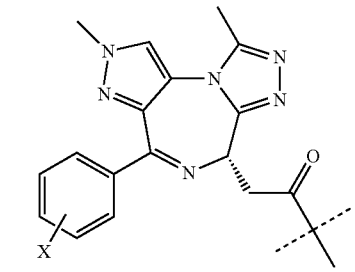

X = Cl, F, Br, H, CN, methyl, acetylene, methoxy

In any aspect or embodiment described herein, the structures of PTM-a as the BET/BRD4 targeting moiety includes, wherein the dashed line indicates the connection point between the BET/BRD4 targeting moiety and the linkers:

PTM-al

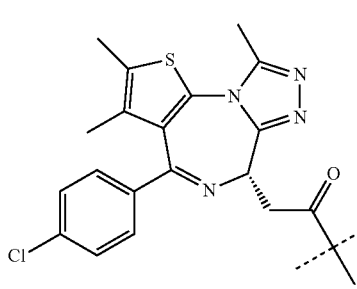

PTM-a2
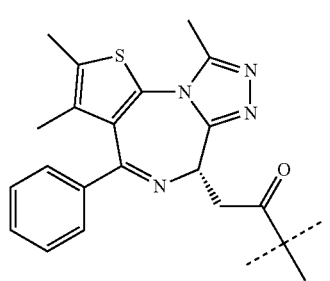
PTM-a3
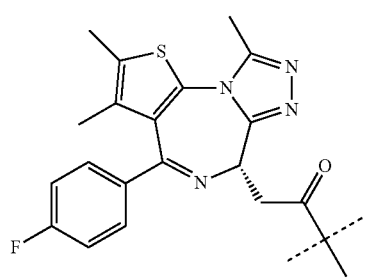
PTM-a4
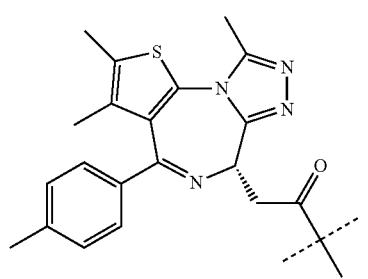
PTM-a5
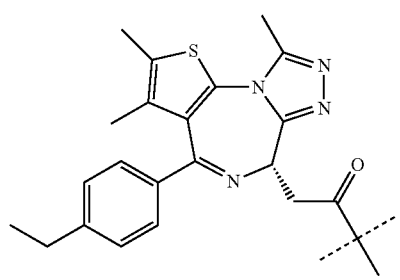
PTM-a6
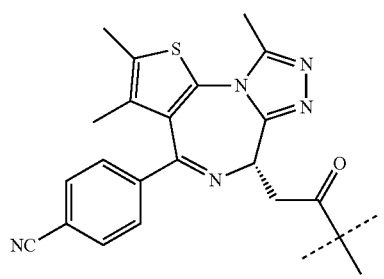
PTM-a7
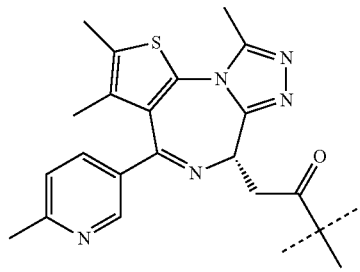
PTM-a8
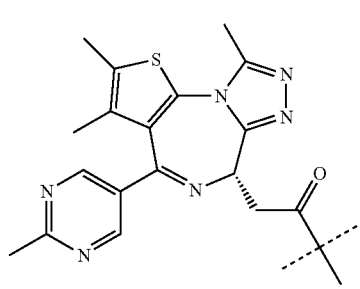
PTM-a9
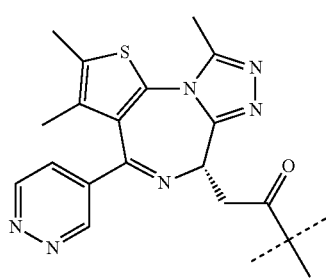
PTM-a10
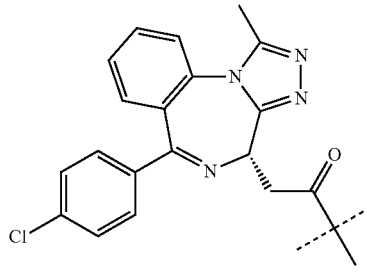
PTM-a11
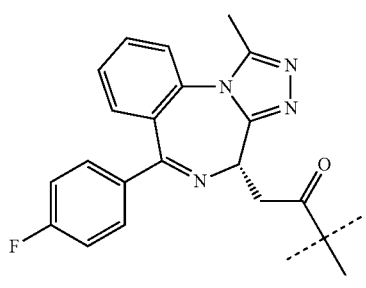

PTM-a12
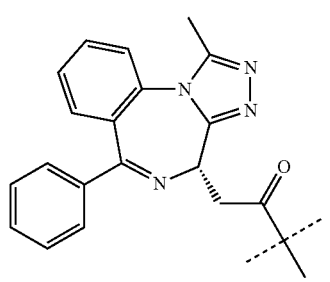
PTM-a13
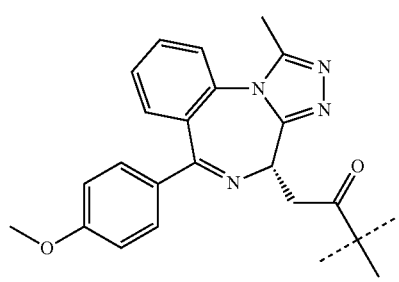
PTM-a14
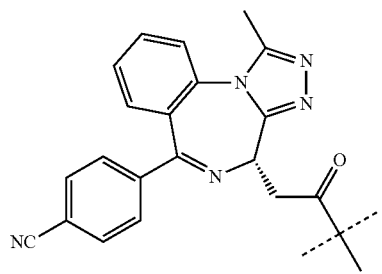
PTM-a15
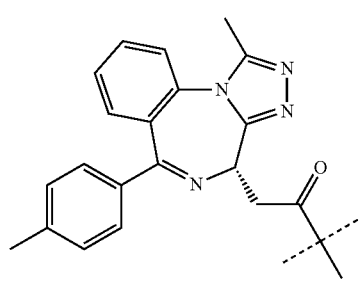
PTM-a16
PTM-a17
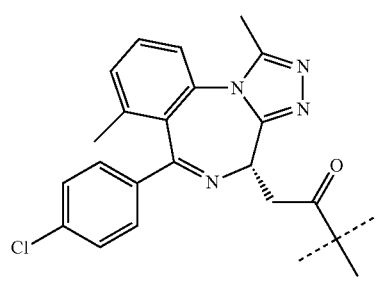
PTM-a18
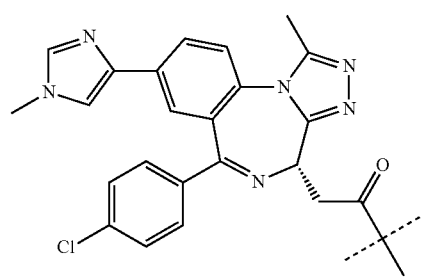
PTM-a19
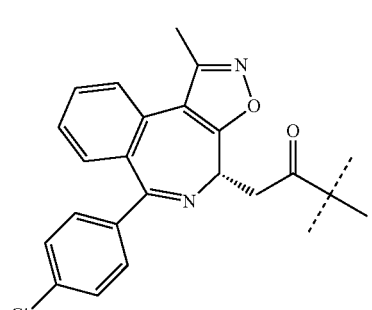
PTM-a20
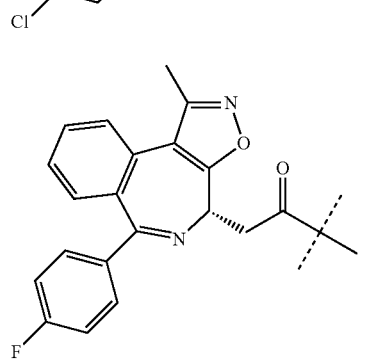
PTM-a21
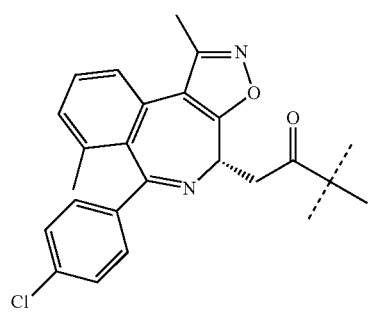

221
-continued
PTM-a22
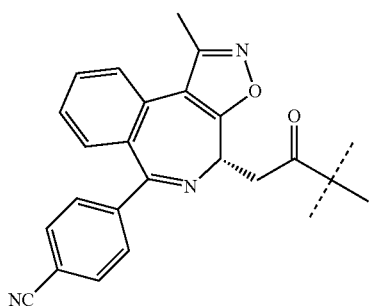
PTM-a23
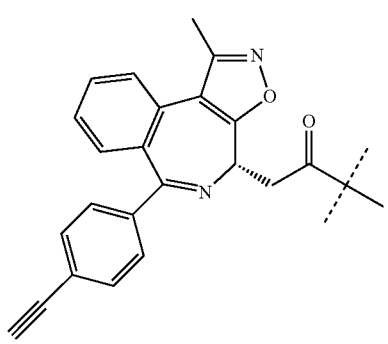
PTM-a24
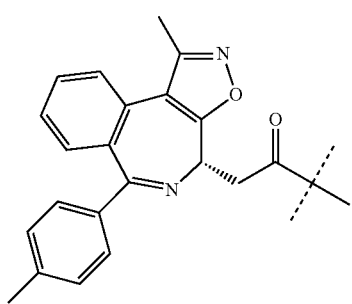
PTM-a25
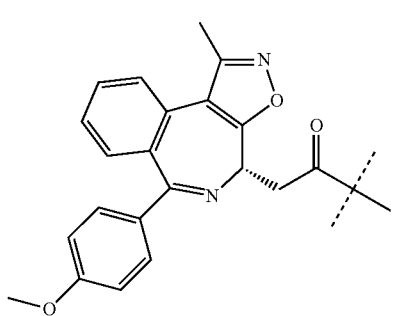
PTM-a26
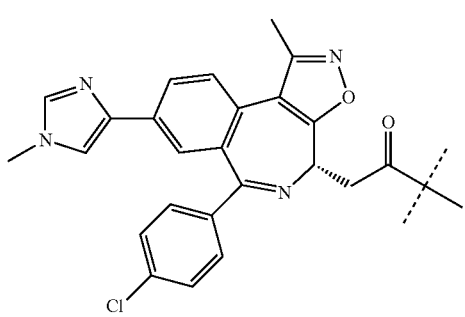
222
-continued
PTM-a27
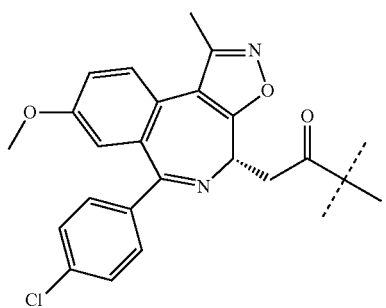
PTM-a28
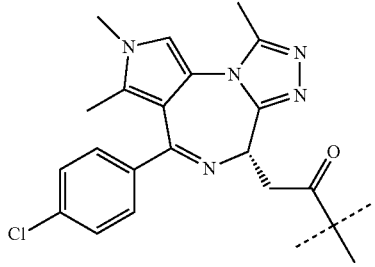
PTM-a29
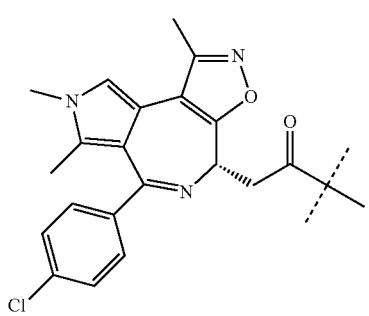
PTM-a30
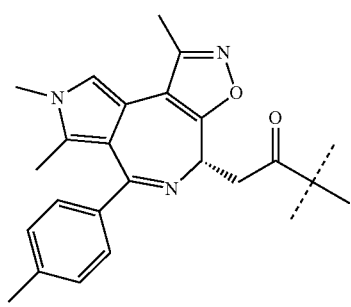
PTM-a31
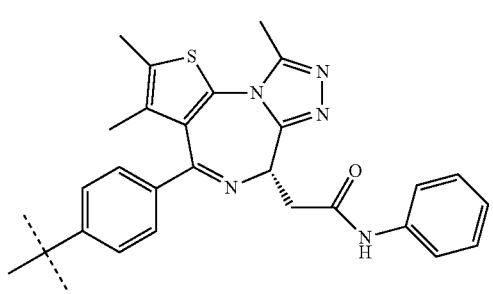

-continued

PTM-a32
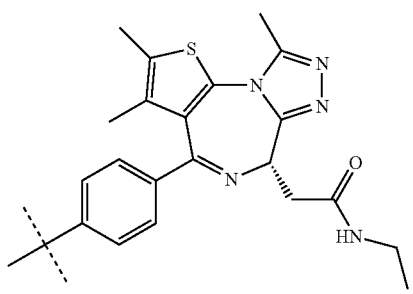

PTM-a33
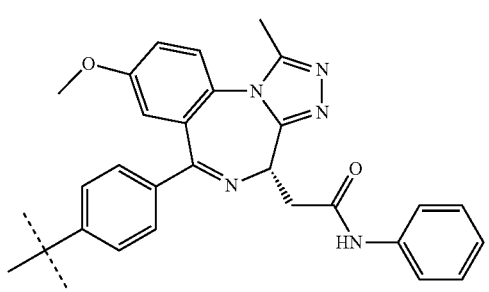

PTM-a34
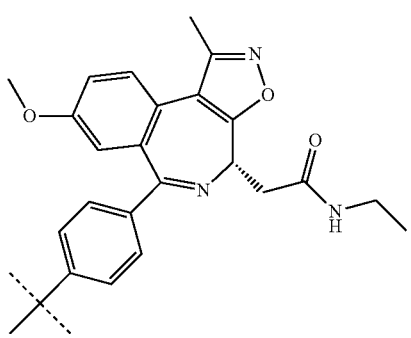

PTM-a35
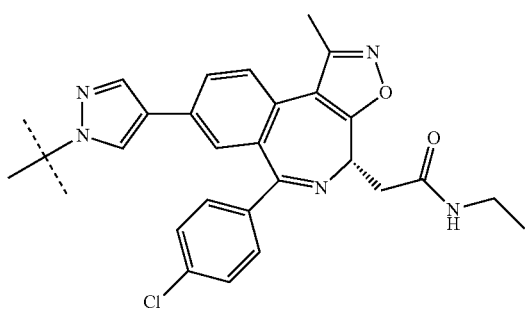

PTM-a36
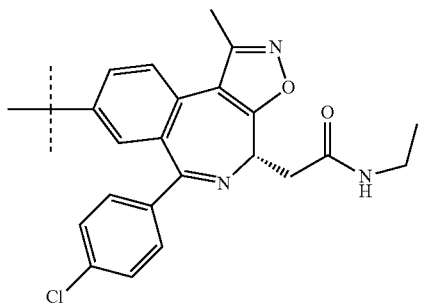

V. HDAC Inhibitors:

HDAC Inhibitors (derivatized) include, but are not limited to:

1. Finnin, M. S. et al. Structures of Histone Deacetylase Homologue Bound to the TSA and SAHA Inhibitors. Nature 40, 188-193 (1999).

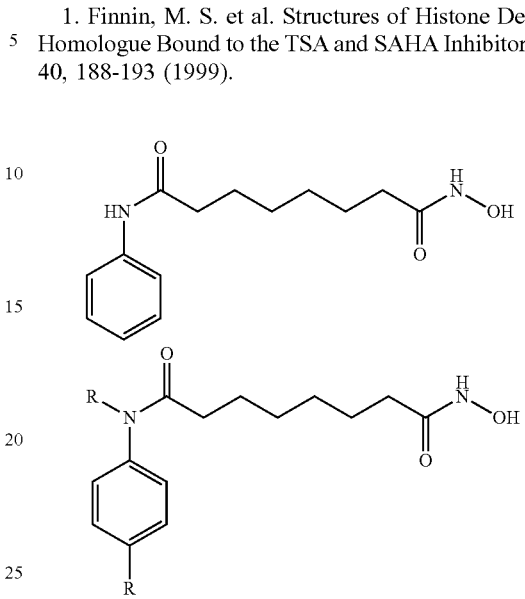

(Derivatized where "R" designates a site for attachment, for example, of a linker group L or a -(L-CLM) group); and 2. Compounds as defined by formula (I) of PCT WO0222577 ("DEACETYLASE INHIBITORS") (Derivatized where a linker group L or a -(L-CLM) group is attached, for example, via the hydroxyl group);

VI. Human Lysine Methyltransferase Inhibitors:

Human Lysine Methyltransferase inhibitors include, but are not limited to.

1. Chang et al. Structural Basis for G9a-Like protein Lysine Methyltransferase Inhibition by BIX-1294. Nat. Struct. Biol. (2009) 16(3) 312.

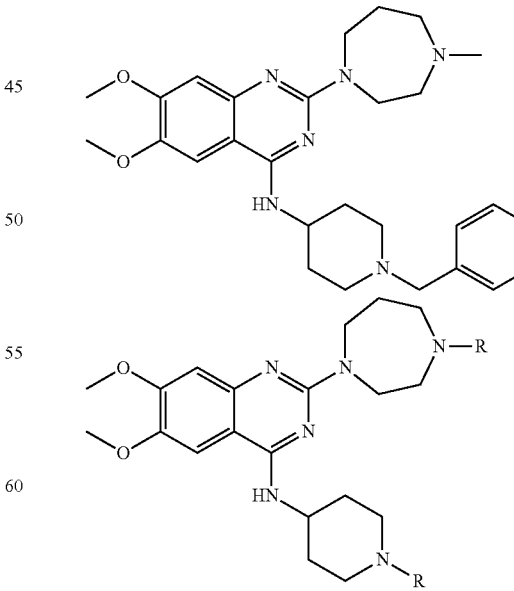

(Derivatized where "R" designates a site for attachment, for example, of a linker group L or a -(L-CLM) group);

2. Liu, F. et al Discovery of a 2,4-Diamino-7-aminoalkoxyquinazoline as a Potent and Selective Inhibitor of Histone Methyltransferase G9a. J. Med. Chem. (2009) 52(24) 7950.

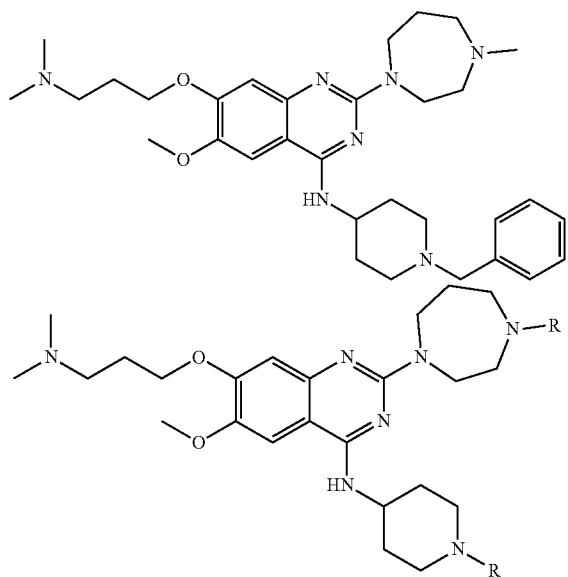

(Derivatized where "R" designates a potential site for attachment, for example, of a linker group L or a -(L-CLM) group);

3. Azacitidine (derivatized) (4-amino-1-β-D-ribofuranosyl-1,3,5-triazin-2(1H)-one) (Derivatized where a linker group L or a -(L-CLM) group is attached, for example, via the hydroxy or amino groups); and 4. Decitabine (derivatized) (4-amino-1-(2-deoxy-b-D-erythro-pentofuranosyl)-1, 3, 5-triazin-2(1H)-one) (Derivatized where a linker group L or a -(L-CLM) group is attached, for example, via either of the hydroxy groups or at the amino group).

VII. Angiogenesis Inhibitors:

Angiogenesis inhibitors include, but are not limited to:

1. GA-1 (derivatized) and derivatives and analogs thereof, having the structure(s) and binding to linkers as described in Sakamoto, et al., Development of Protacs to target cancer-promoting proteins for ubiquitination and degradation, *Mol Cell Proteomics* 2003 December; 2(12):1350-8;

2. Estradiol (derivatized), which may be bound to a linker group L or a -(L-CLM) group as is generally described in Rodriguez-Gonzalez, et al., Targeting steroid hormone receptors for ubiquitination and degradation in breast and prostate cancer, *Oncogene* (2008) 27, 7201-7211;

3. Estradiol, testosterone (derivatized) and related derivatives, including but not limited to DHT and derivatives and analogs thereof, having the structure(s) and binding to a linker group L or a -(L-CLM) group as generally described in Sakamoto, et al., Development of Protacs to target cancer-promoting proteins for ubiquitination and degradation, *Mol Cell Proteomics* 2003 December; 2(12):1350-8; and 4. Ovalicin, fumagillin (derivatized), and derivatives and analogs thereof, having the structure(s) and binding to a linker group L or a -(L-CLM) group as is generally described in Sakamoto, et al., Protacs: chimeric molecules that target proteins to the Skp1-Cullin-F box complex for ubiquitination and degradation *Proc Natl Acad Sci USA*. 2001 Jul. 17; 98(15):8554-9 and U.S. Pat. No. 7,208,157.

VIII. Immunosuppressive Compounds:

Immunosuppressive compounds include, but are not limited to:

1. AP21998 (derivatized), having the structure(s) and binding to a linker group L or a -(L-CLM) group as is generally described in Schneekloth, et al., Chemical Genetic Control of Protein Levels: Selective in Vivo Targeted Degradation, *J. AM CHEM. SOC.* 2004, 126, 3748-3754;

2. Glucocorticoids (e.g., hydrocortisone, prednisone, prednisolone, and methylprednisolone) (Derivatized where a linker group L or a -(L-CLM) group is to bound, e.g. to any of the hydroxyls) and beclometasone dipropionate (Derivatized where a linker group or a -(L-CLM) is bound, e.g. to a proprionate);

3. Methotrexate (Derivatized where a linker group or a -(L-CLM) group can be bound, e.g. to either of the terminal hydroxyls);

4. Ciclosporin (Derivatized where a linker group or a -(L-CLM) group can be bound, e.g. at any of the butyl groups);

5. Tacrolimus (FK-506) and rapamycin (Derivatized where a linker group L or a -(L-CLM) group can be bound, e.g. at one of the methoxy groups); and 6. Actinomycins (Derivatized where a linker group L or a -(L-CLM) group can be bound, e.g. at one of the isopropyl groups).

IX. Compounds Targeting the Aryl Hydrocarbon Receptor (AHR):

Compounds targeting the aryl hydrocarbon receptor (AHR) include, but are not limited to:

1. Apigenin (Derivatized in a way which binds to a linker group L or a -(L-CLM) group as is generally illustrated in Lee, et al., Targeted Degradation of the Aryl Hydrocarbon Receptor by the PROTAC Approach: A Useful Chemical Genetic Tool, ChemBioChem Volume 8, Issue 17, pages 2058-2062, Nov. 23, 2007); and 2. SR1 and LGC006 (derivatized such that a linker group L or a -(L-CLM) is bound), as described in Boitano, et al., Aryl Hydrocarbon Receptor Antagonists Promote the Expansion of Human Hematopoietic Stem Cells, *Science* 10 Sep. 2010. Vol. 329 no. 5997 pp. 1345-1348.

X. Compounds Targeting RAF Receptor (Kinase):

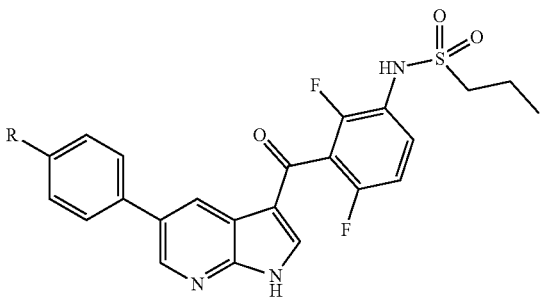

PLX4032

(Derivatized where "R" designates a site for linker group L or -(L-CLM) group attachment, for example).

Any protein, which can bind to a protein target moiety or PTM group and acted on or degraded by an ubiquitin ligase (e.g., RAF) is a target protein according to the present disclosure.

In any aspect or embodiment described herein, the PTM targets and/or binds RAF (i.e., a Raf or BRaf targeting moiety). For example, in any aspect or embodiment described herein, the PTM may comprise a chemical group selected from the group of chemical structures consisting of PTM-Ia or PTM-Ib:

PTM-Ia

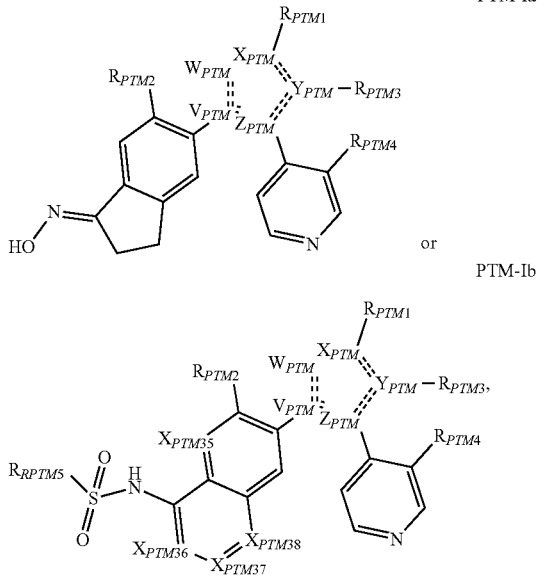

or

PTM-Ib wherein:
double dotted bonds are aromaric bonds;

$V_{PTM}$, $W_{PTM}$, $X_{PTM}$, $Y_{PTM}$, $Z_{PTM}$ is one of the following combinations: C, CH, N, N, C; C, N, N, CH, C; C, O, C, CH, C; C, S, C, CH, C; C, CH, C, O, C; C, CH, C, S, C; C, CH, N, CH, C; N, CH, C, CH, C; C, CH, C, CH, N; N, N, C, CH, C; N, CH, C, N, C; C, CH, C, N, N; C, N, C, CH, N; C, N, C, N, C; and C, N, N, N, C;

$X_{PTM35}$, $X_{PTM36}$, $X_{PTM37}$, and $X_{PTM38}$ are independently selected from CH and N;

$R_{PTM1}$ is covalently joined to a ULM, a chemical linker group (L), a CLM, an ILM, a VLM, MLM, a ULM', a CLM', a ILM', a VLM', a MLM', or combination thereof;

$R_{PMT2}$ is hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM3}$ is absent, hydrogen, aryl, methyl, ethyl, other alkyl, cyclic alkyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM4}$ is hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle; and $R_{PTM5}$ is selected from the group consisting of

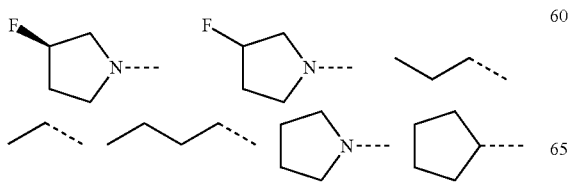

-continued

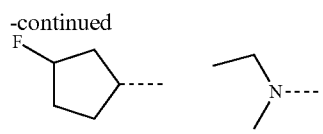

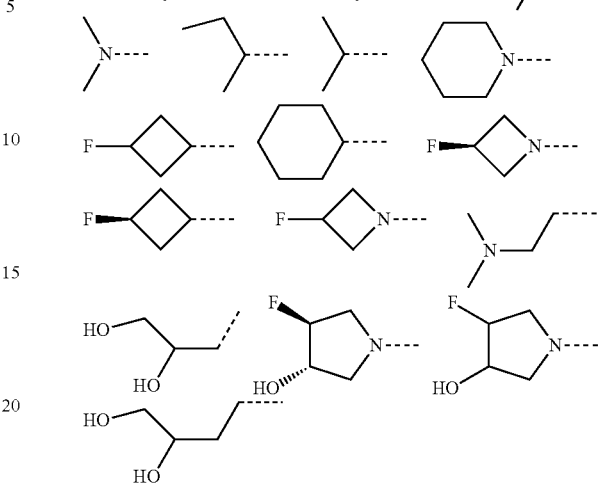

In any aspect or embodiment described herein, the PTM may comprise a chemical group selected from the group of chemical structures consisting of PTM-IIa or PTM-IIb:

PTM-IIa

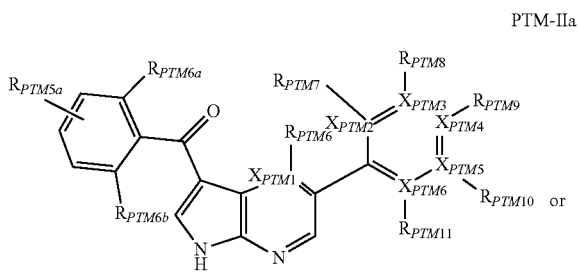

or

PTM-IIb

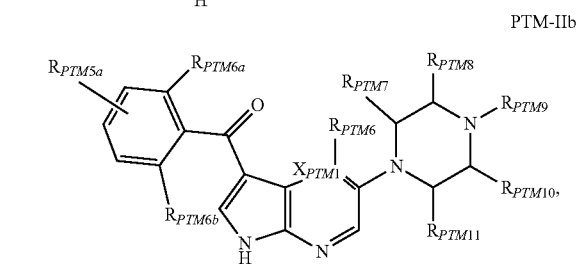

wherein
$X_{PTM1}$, $X_{PTM2}$, $X_{PTM3}$, $X_{PTM4}$, $X_{PTM5}$, and $X_{PTM6}$ are independently selected from CH or N;

$R_{PTM5a}$ is selected from the group consisting of: bond, optionally substituted amine, optionally substituted amide (e.g., optionally substituted with an alkyl, methyl, ethyl, propyl, or butyl group), H

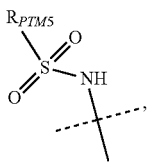

—NHC(O)R$_{PTM5}$;

R$_{PMT5}$ is selected from the group consisting of

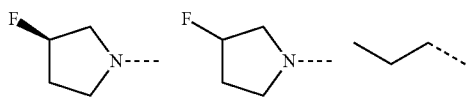

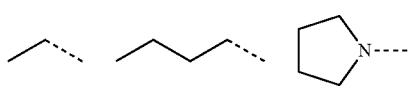

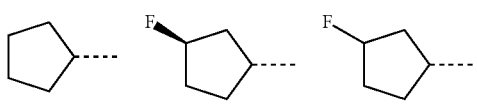

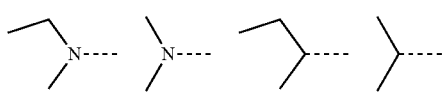

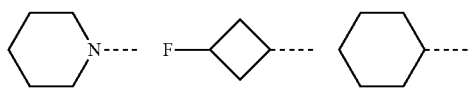

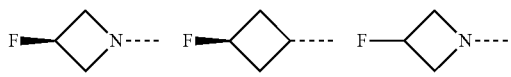

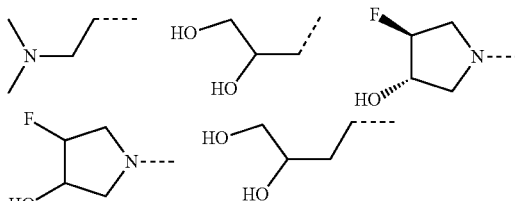

R$_{PTM6a}$ and R$_{PTM6b}$ are each independently selected from hydrogen, halogen, or optionally substituted C$_1$-C$_6$ alkyl (linear, branched, optionally substituted);

R$_{PTM6}$ is absent, hydrogen, halogen, aryl, methyl, ethyl, OCH$_3$, NHCH$_3$ or M1-CH$_2$—CH$_2$-M2, wherein M1 is CH$_2$, O and NH, and M2 is hydrogen, alkyl, cyclic alkyl, aryl or heterocycle;

R$_{PTM7}$ is absent, hydrogen, halogen, aryl, methyl, ethyl, OCH$_3$, NHCH$_3$ or M1-CH$_2$—CH$_2$-M2, wherein M1 is CH$_2$, O or NH, and M2 is hydrogen, alkyl, cyclic alkyl, aryl or heterocycle;

R$_{PTM8}$, R$_{PTM9}$ or R$_{PTM10}$ are independently selected from the group consisting of absent, hydrogen, halogen, aryl, heteroaryl, alkyl, cycloalkyl, heterocycle, methyl, ethyl, OCH$_3$, NHCH$_3$ or M1-CH$_2$—CH$_2$-M2, wherein M1 is CH$_2$, O and NH, and M2 is hydrogen, alkyl, cyclic alkyl, aryl or heterocycle;

R$_{PTM11}$ is absent, hydrogen, halogen, methyl, ethyl, OCH$_3$, NH CH$_3$ or M1-CH$_2$—CH$_2$-M2, wherein M1 is CH$_2$, O or NH, and M2 is hydrogen, alkyl, cyclic alkyl, aryl or heterocycle; and at least one of R$_{PTM8}$, R$_{PTM9}$ or R$_{PTM10}$ is modified to be covalently joined to a ULM, a chemical linker group (L), a CLM, an ILM, a VLM, MLM, a ULM', a CLM', a ILM', a VLM', a MLM', or combination thereof.

In certain embodiments, the PTM may comprise a chemical group selected from the group of chemical structures consisting of:

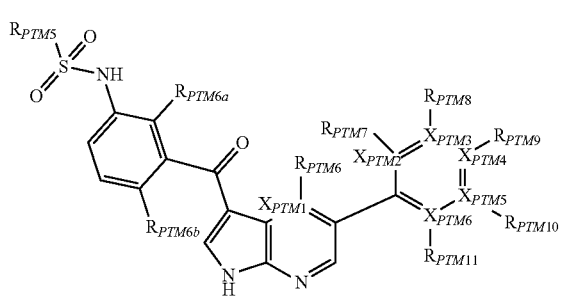

or

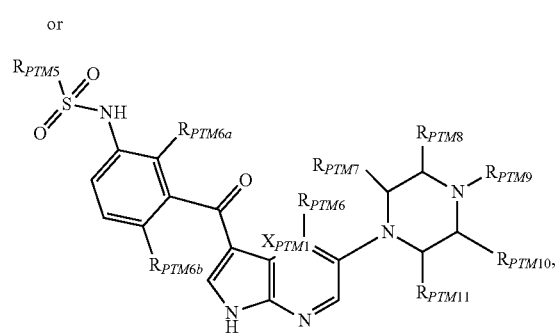

wherein R$_{PTM5}$, R$_{PTM6a}$, R$_{PTM6b}$, R$_{PTM6}$, R$_{PTM7}$, R$_{PTM8}$, R$_{PTM9}$, R$_{PTM10}$, R$_{PTM11}$ are as described herein.

In some embodiments, when R$_{PTM9}$ is the covalently joined position, R$_{PTM7}$ and R$_{PTM8}$ can be connected together via a covalent bond in a way to form a bicyclic group with the ring to which R$_{PTM7}$ and R$_{PTM8}$ are attached.

In other embodiments, when R$_{PTM8}$ is the covalently joined position, R$_{PTM9}$ and R$_{PTM10}$ can be connected together via a covalent bond in a way to form a bicyclic group with the ring to which R$_{PTM9}$ and R$_{PTM10}$ are attached.

In further embodiments, when R$_{PTM10}$ is the covalently joined position, R$_{PTM8}$ and R$_{PTM9}$ can be connected together via a covalent bond in a way to form a bicyclic group with the ring to which R$_{PTM8}$ and R$_{PTM9}$ are attached.

In any aspect or embodiment described herein, the PTM may comprise a chemical group selected from the group of chemical structures consisting of PTM-III:

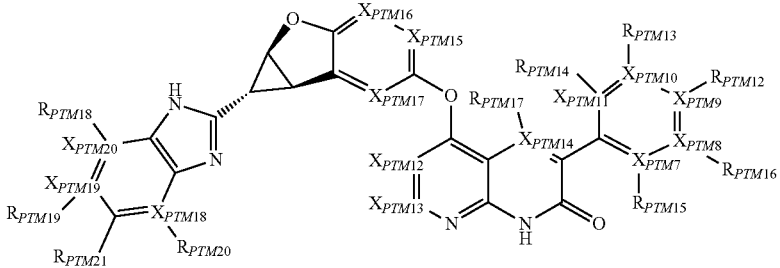

PTM-III wherein:

$X_{PTM7}$, $X_{PTM8}$, $X_{PTM9}$, $X_{PTM10}$, $X_{PTM11}$, $X_{PTM12}$, $X_{PTM13}$, $X_{PTM14}$, $X_{PTM15}$, $X_{PTM16}$, $X_{PTM17}$, $X_{PTM18}$, $X_{PTM19}$, $X_{PTM20}$ are independently CH or N, $R_{PTM12}$, $R_{PTM13}$, $R_{PTM14}$, $R_{PTM15}$, $R_{PTM16}$, $R_{PTM17}$, $R_{PTM18}$, $R_{PTM19}$ are independently selected from the group consisting of absent, hydrogen, halogen, aryl, heteroaryl, cycloalkyl, heterocycle, methyl, ethyl, other alkyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM20}$ is a small group containing less than four non-hydrogen atoms;

$R_{PTM21}$ is selected from the group consisting of trifluoromethyl, chloro, bromo, fluoro, methyl, ethyl, propyl, isopropyl, tert-butyl, butyl, iso-butyl, cyclopropyl, cyclobutyl, cyclopentyl, cyclohexyl, $OCH_3$, $NHCH_3$, dimethylamino or M1-$CH_2$—$CH_2$-M2, wherein M1 is $CH_2$, O or NH, and M2 is hydrogen, alkyl, cyclic alkyl, aryl or heterocycle; and at least one of $R_{PTM12}$, $R_{PTM13}$ and $R_{PTM16}$ is modified to be covalently joined to a ULM, a chemical linker group (L), a CLM, an ILM, a VLM, MLM, a ULM', a CLM', a ILM', a VLM', a MLM', or combination thereof.

In some embodiments, when $R_{PTM12}$ is the covalently joined position, $R_{PTM13}$ and $R_{PTM14}$ can be connected together via a covalent bond in a way to form a bicyclic group with the ring to which $R_{PTM13}$ and $R_{PTM14}$ are attached; and/or $R_{PTM15}$ and $R_{PTM16}$ can be connected together via a covalent bond in a way to form a bicyclic group with the ring to which $R_{PTM15}$ and $R_{PTM16}$ are attached.

In other embodiments, when $R_{PTM13}$ is the covalently joined position, $R_{PTM12}$ and $R_{PTM16}$ can be connected together via a covalent bond in a way to form a bicyclic group with the ring to which $R_{PTM12}$ and $R_{PTM16}$ are attached; and/or $R_{PTM15}$ and $R_{PTM16}$ can be connected together via a covalent bond in a way to form a bicyclic group with the ring to which $R_{PTM15}$ and $R_{PTM16}$ are attached.

In further embodiments, when $R_{PTM16}$ is the covalently joined position, $R_{PTM12}$ and $R_{PTM13}$ can be connected together via a covalent bond in a way to form a bicyclic group with the ring to which $R_{PTM12}$ and $R_{PTM13}$ are attached; and/or $R_{PTM13}$ and $R_{PTM14}$ can be connected together via a covalent bond in a way to form a bicyclic group with the ring to which $R_{PTM13}$ and $R_{PTM14}$ are attached.

In any aspect or embodiment described herein, the PTM may comprise a chemical group selected from the group of chemical structures consisting of PTM-IVa or PTM-IVb:

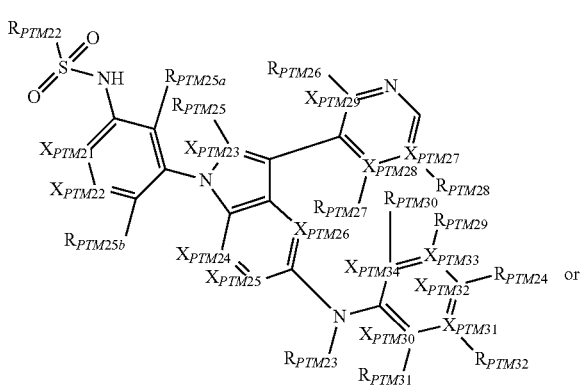

PTM-IVa

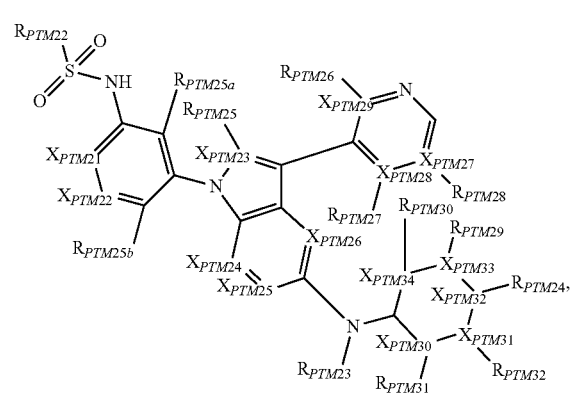

PTM-IVb wherein:

$X_{PTM21}$, $X_{PTM22}$, $X_{PTM23}$, $X_{PTM24}$, $X_{PTM25}$, $X_{PTM26}$, $X_{PTM27}$, $X_{PTM28}$, $X_{PTM29}$, $X_{PTM30}$, $X_{PTM31}$, $X_{PTM32}$, $X_{PTM33}$, $X_{PTM34}$ are independently CH or N;

$R_{PTM22}$ is selected from the group consisting of

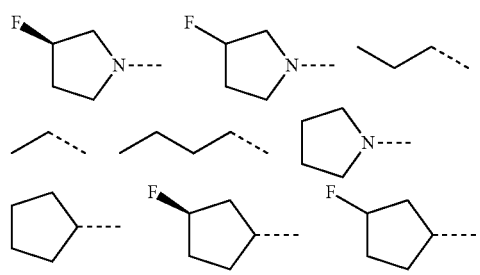

-continued

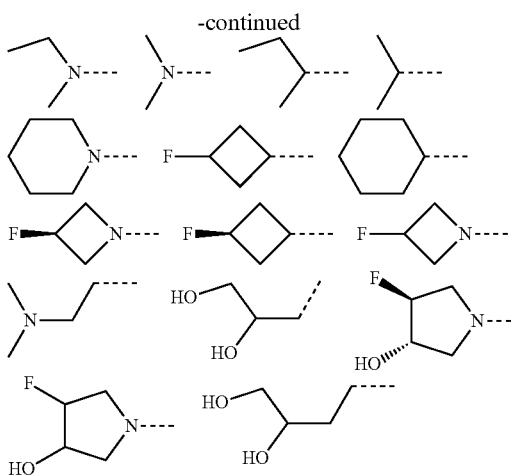

$R_{PTM25a}$ and $R_{PTM25b}$ are each independently selected from hydrogen, halogen, or $C_1$-$C_6$ alkyl (linear, branched, optionally substituted);

$R_{PTM23}$, $R_{PTM24}$, $R_{PTM28}$, $R_{PTM29}$, $R_{PTM30}$, $R_{PTM31}$, $R_{PTM32}$ are independently selected from the group consisting of absent, bond, hydrogen, halogen, aryl (optionally substituted), heteroaryl (optionally substituted), cycloalkyl (optionally substituted), heterocycle (optionally substituted), methyl, ethyl (optionally substituted), other alkyl (linear, branched, optionally substituted), $OCH_3$, $NHCH_3$ or M1-$CH_2$—$CH_2$-M2, wherein M1 is $CH_2$, O and NH, and M2 is hydrogen, alkyl (linear, branched, optionally substituted), cyclic alkyl (optionally substituted), aryl (optionally substituted) or heterocycle (optionally substituted); and $R_{PTM25}$ is absent, hydrogen, halogen, $C_1$-$C_6$ alkyl (linear, branched, optionally substituted), $OCH_3$, $NHCH_3$ or $SCH_3$;

$R_{PTM26}$ is absent, hydrogen, halogen, $C_1$-$C_6$ alkyl (linear, branched, optionally substituted), $OCH_3$, $NHCH_3$ or $SCH_3$;

$R_{PTM27}$ is selected from the group consisting of absent, hydrogen, halogen, $C_1$-$C_6$ alkyl (linear, branched, optionally substituted), $OCH_3$, $NHCH_3$ or $SCH_3$; and at least one of $R_{PTM24}$, $R_{PTM29}$, $R_{PTM32}$ is modified to be covalently joined to a ULM, a chemical linker group (L), a CLM, an ILM, a VLM, MLM, a ULM', a CLM', a ILM', a VLM', a MLM', or combination thereof.

In some embodiments, when $R_{PTM24}$ is the covalently joined position, $R_{PTM31}$ and $R_{PTM32}$ can be connected together via a covalent bond in a way to form a bicyclic group with the ring to which $R_{PTM31}$ and $R_{PTM32}$ are attached; or $R_{PTM29}$ and $R_{PTM30}$ can be connected together via a covalent bond in a way to form a bicyclic group with the ring to which $R_{PTM29}$ and $R_{PTM30}$ are attached.

In other embodiments, when $R_{PTM29}$ is the covalently joined position, $R_{PTM24}$ and $R_{PTM32}$ can be connected together via a covalent bond in a way to form a bicyclic group with the ring to which $R_{PTM24}$ and $R_{PTM29}$ are attached; and/or $R_{PTM31}$ and $R_{PTM32}$ can be connected together via a covalent bond in a way to form a bicyclic group with the ring to which $R_{PTM31}$ and $R_{PTM32}$ are attached.

In further embodiments, when $R_{PTM32}$ is the covalently joined position, $R_{PTM24}$ and $R_{PTM29}$ can be connected together via a covalent bond in a way to form a bicyclic group with the ring to which $R_{PTM24}$ and $R_{PTM29}$ are attached; and/or $R_{PTM29}$ and $R_{PTM30}$ can be connected together via a covalent bond in a way to form a bicyclic group with the ring to which $R_{PTM29}$ and $R_{PTM30}$ are attached.

In any aspect or embodiments described herein, the PTM is selected from the group consisting of chemical structures PTM-1, PTM-2, PTM-3, PTM-4, PTM-5, PTM-6, PTM-7, and PTM-8:

PTM-1

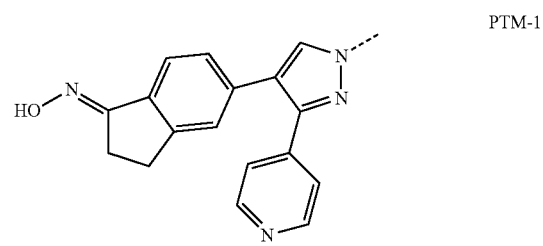

PTM-2

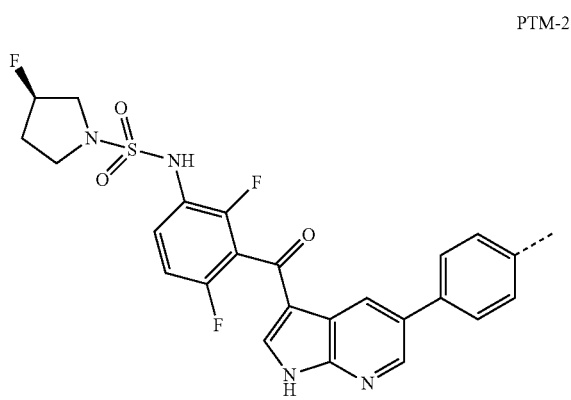

PTM-3

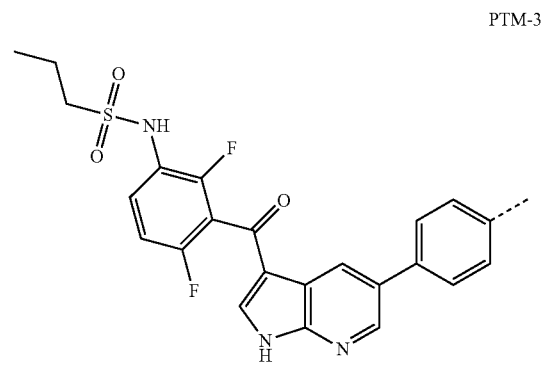

PTM-4

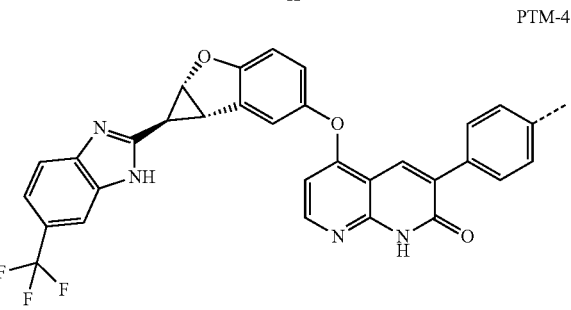

PTM-5
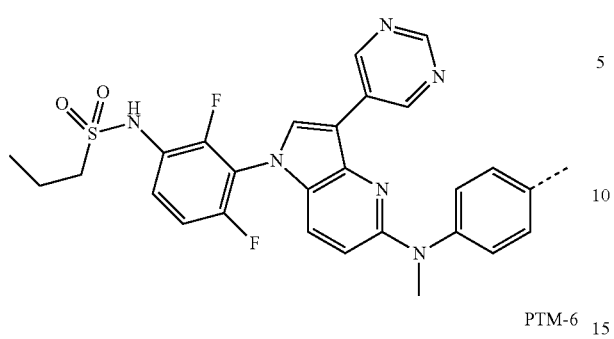
PTM-10
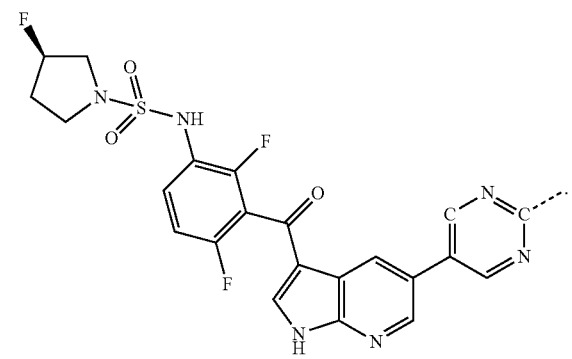
PTM-6
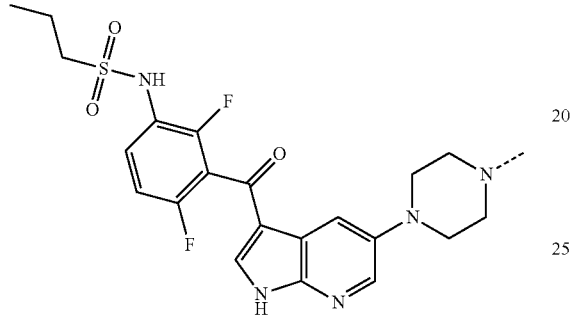
XI. Compounds Targeting FKBP:
PTM-7
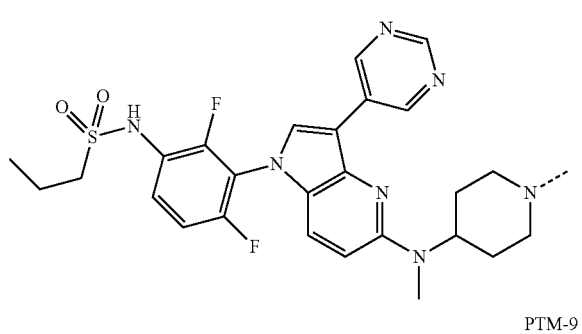
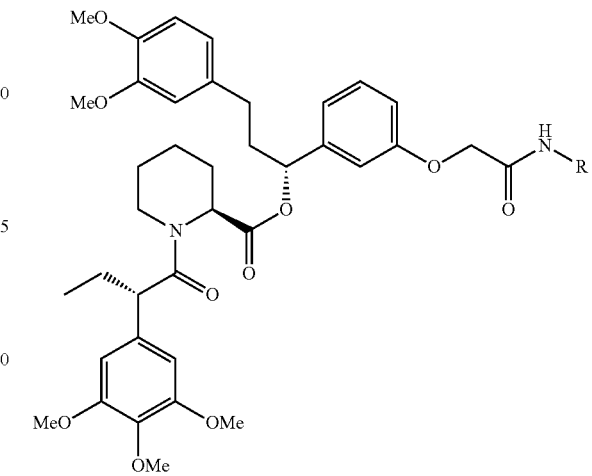
PTM-8
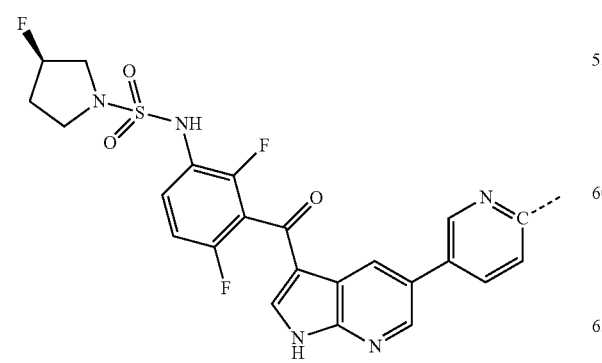
(Derivatized where "R" designates a site for a linker group L or a -(L-CLM) group attachment, for example).
XII. Compounds Targeting of Androgen Receptor (AR)
1. RU59063 Ligand (derivatized) of Androgen Receptor
PTM-9
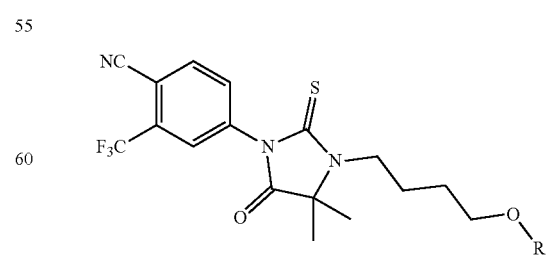
(Derivatized where "R" designates a site for a linker group L or a -(L-CLM) group attachment, for example).

2. SARM Ligand (derivatized) of Androgen Receptor

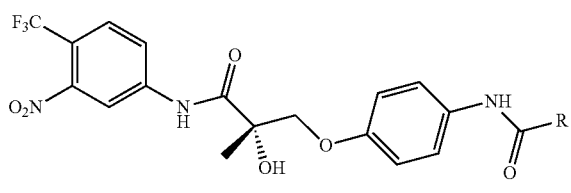

(Derivatized where "R" designates a site for a linker group L or a -(L-CLM) group attachment, for example).

3. Androgen Receptor Ligand DHT (derivatized)

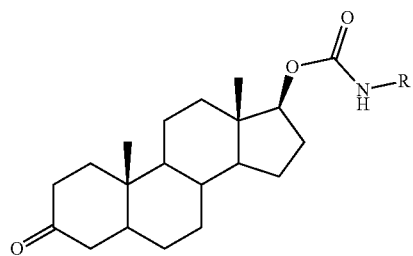

(Derivatized where "R" designates a site for a linker group L or -(L-CLM) group attachment, for example).

4. MDV3100 Ligand (derivatized)

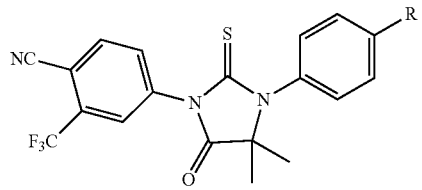

5. ARN-509 Ligand (derivatized)

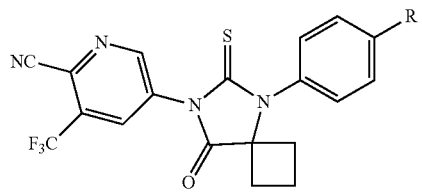

6. Hexahydrobenzisoxazoles

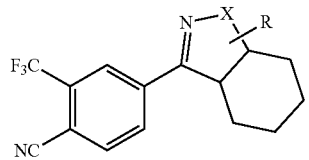

7. Tetramethylcyclobutanes

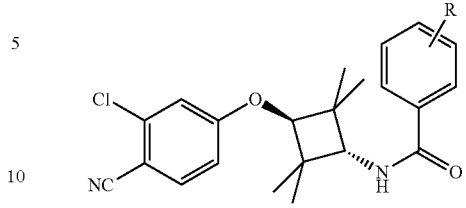

8. In any aspect or embodiment described herein, the PTM is a chemical moiety that binds to the androgen receptor (AR). Various androgen receptor binding compounds have been described in literature, including various androgen derivatives such as testosterone, dihydrotestosterone, and metribolone (also known as methyltrienolone or R1881), and non-steroidal compounds such as bicalutamide, enzalutamide, some of which are described above. Those of ordinary skill in the art would appreciate that these androgen receptor binding compounds could be potentially used as an androgen binding moiety (ABM) in a PROTAC compound. Such literature includes, but not limited to, G. F. Allan et. al, *Nuclear Receptor Signaling*, 2003, 1, e009; R. H. Bradbury et. al, *Bioorganic & Medicinal Chemistry Letters*, 2011 5442-5445; C. Guo et. al, *Bioorganic & Medicinal Chemistry Letters*, 2012 2572-2578; P. K. Poutiainen et. al, *J. Med. Chem.* 2012, 55, 6316-6327 A. Pepe et. al, *J. Med. Chem.* 2013, 56, 8280-8297; M. E. Jung et al, *J. Med. Chem.* 2010, 53, 2779-2796, which are incorporated by reference herein In any aspect or embodiment described herein, the ABM comprises a structure selected from, but not limited to the structures shown below, wherein a dashed line indicates the attachment point of a linker moiety or a ULM, such as a CLM:

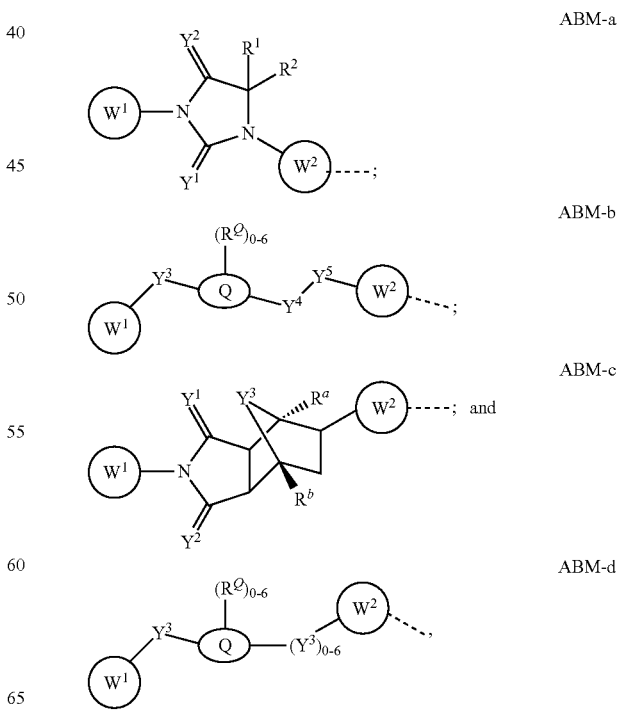

wherein:
- W¹ is aryl, heteroaryl, bicyclic, or biheterocyclic, each independently substituted by 1 or more H, halo, hydroxyl, nitro, CN, C≡CH, $C_{1-6}$ alkyl (linear, branched, optionally substituted; for example, optionally substituted by 1 or more halo, $C_{1-6}$ alkoxyl), $C_{1-6}$ alkoxyl (linear, branched, optionally substituted; for example, optionally substituted by 1 or more halo), $C_{2-6}$ alkenyl, $C_{2-6}$ alkynyl, or $CF_3$;
- $Y^1$, $Y^2$ are each independently $NR^{Y1}$, O, S;
- $Y^3$, $Y^4$, $Y^5$ are each independently a bond, O, $NR^{Y2}$, $CR^{Y1}R^{Y2}$, C=O, C=S, SO, $SO_2$, heteroaryl, or aryl;
- Q is a 3-6 membered ring with 0-4 heteroatoms, optionally substituted with 0-6 $R^Q$, each $R^Q$, is independently H, $C_{1-6}$ alkyl (linear, branched, optionally substituted; for example, optionally substituted by 1 or more halo, $C_{1-6}$ alkoxyl), halogen, $C_{1-6}$ alkoxy, or 2 $R^Q$ groups taken together with the atom they are attached to, form a 3-8 membered ring system containing 0-2 heteroatoms);
- $R^1$, $R^2$, $R^a$, $R^b$, $R^{Y1}$, $R^{Y2}$ are each independently H, $C_{1-6}$ alkyl (linear, branched, optionally substituted; for example, optionally substituted by 1 or more halo, $C_{1-6}$ alkoxyl), halogen, $C_{1-6}$ alkoxy, cyclic, heterocyclic, or $R^1$, $R^2$ together with the atom they are attached to, form a 3-8 membered ring system containing 0-2 heteroatoms);
- W² is a bond, $C_{1-6}$ alkyl, $C_{1-6}$ heteroalkyl, O, aryl, heteroaryl, alicyclic, heterocyclic, bicyclic, biheterocyclic, biaryl, or biheteroaryl, each optionally substituted by 1-10 $R^{W2}$;
- each $R^{W2}$ is independently H, halo, $C_{1-6}$ alkyl (linear, branched, optionally substituted; for example, optionally substituted by 1 or more F), $-OR^{W2A}$, $C_{3-6}$ cycloalkyl, $C_{4-6}$ cycloheteroalkyl, $C_{1-6}$ alicyclic (optionally substituted), heterocyclic (optionally substituted), aryl (optionally substituted), or heteroaryl (optionally substituted), bicyclic hereoaryl or aryl, $OC_{1-3}$ alkyl (optionally substituted), OH, $NH_2$, $NR^{Y1}R^{Y2}$, CN; and
- $R^{W2A}$ is H, $C_{1-6}$ alkyl (linear, branched), or $C_{1-6}$ heteroalkyl (linear, branched), each optionally substituted by a cycloalkyl, cycloheteroalkyl, aryl, heterocyclic, heteroaryl, halo, or $OC_{1-3}$alkyl.

In any aspect or embodiment described herein, the W² is covalently coupled to one or more ULM or CLM groups, or a linker to which is attached one or more ULM or CLM groups as described herein.

In any aspect or embodiment described herein, W¹ is

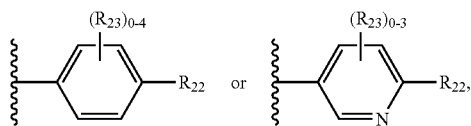

wherein each $R_{22}$ is independently halo, H, optionally substituted alkyl, haloalkyl, cyano, or nitro; and each $R_{23}$ is independently H, halo, $CF_3$, optionally substituted alkyl, alkoxy, haloalkyl, cyano, or nitro.

In any aspect or embodiment described herein, W¹ is selected from the group consisting of:

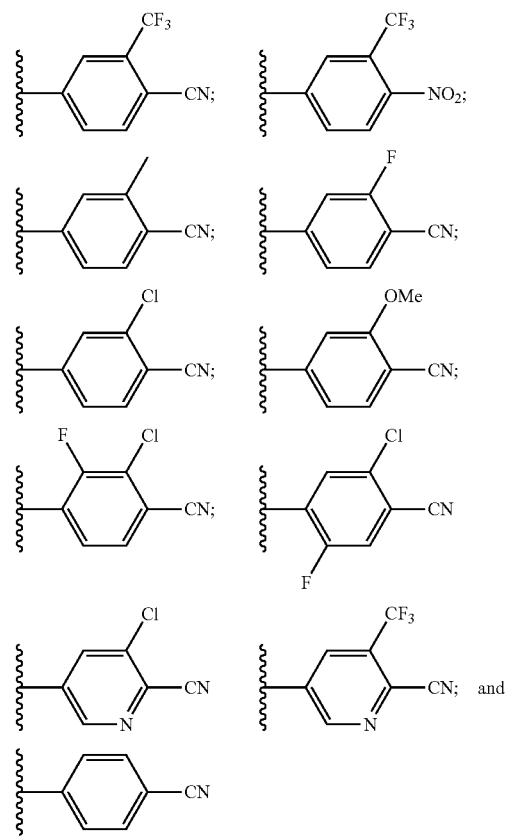

In any aspect or embodiment described herein, the ABM comprises a structure selected from the following structures shown below, where a ⸸ indicates that attachment point of a linker or a ULM:

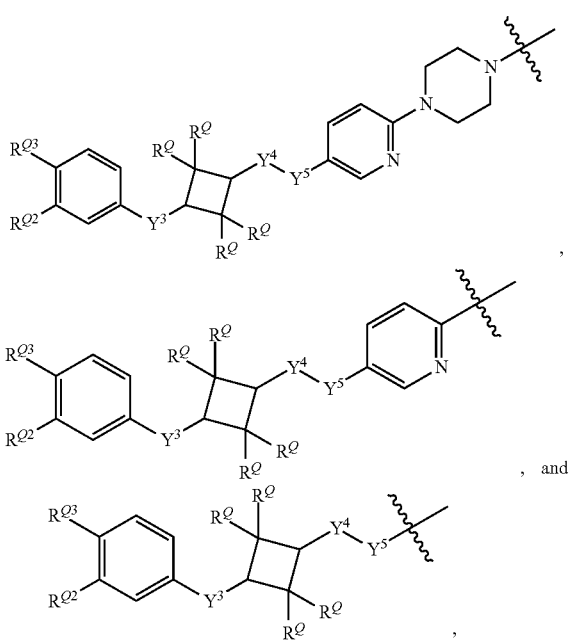

wherein:
 $R^{Q2}$ is a H, halogen, $CH_3$ or $CF_3$;
 $R^{Q3}$ is H, halo, hydroxyl, nitro, CN, C≡CH, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl, or $CF_3$;
 $Y^3$, $Y^4$, $Y^5$ are each independently a bond, O, $NR^{Y2}$, $CR^{Y1}R^{Y2}$, C=O, heteroaryl, or aryl;
 $R^{Y1}$, $R^{Y2}$ are each independently H, or $C_{1-6}$ alkyl (linear, branched, optionally substituted by 1 or more halo, $C_{1-6}$ alkoxyl, cyclic, or heterocyclic); and
 $R^Q$ each independently is H, $C_1$-$C_6$ alkyl (linear, branched, optionally substituted by 1 or more halo, or $C_{1-6}$ alkoxyl), or two $R^Q$ together with the atom they are attached to, form a 3-8 membered ring system containing 0-2 heteroatoms.

In any aspect or embodiment described herein, each $R^Q$ is independently H or $CH_3$. In another embodiment $R^{Q3}$ is CN.

In any aspect or embodiment described herein, the ABM comprises a structure selected from the following structures shown below, where a ⁂ indicates the attachment point of a linker or a ULM:

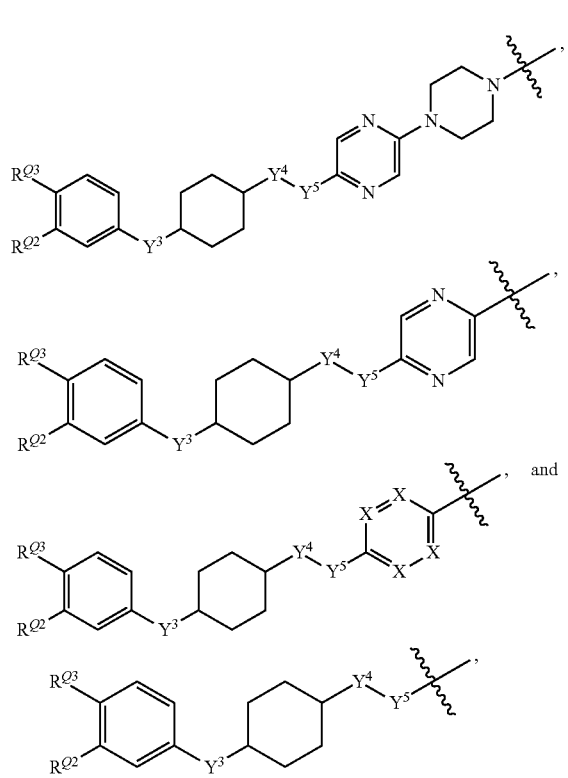

wherein:
 $R^{Q2}$ is a H, halogen, CN, $CH_3$ or $CF_3$; and
 $R^{Q3}$ is H, halo, hydroxyl, nitro, CN, C=CH, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl, or $CF_3$;
 $Y^3$, $Y^4$, $Y^5$ are each independently a bond, O, $NR^{Y2}$, $CR^{Y1}R^{Y2}$, C=O, heteroaryl, or aryl; and
 $R^{Y1}$, $R^{Y2}$ are each independently H or $C_{1-6}$ alkyl (linear, branched, optionally substituted by 1 or more halo, $C_{1-6}$ alkoxyl, cyclic, or heterocyclic); and
 X is N or C.

In any aspect or embodiment described herein, $R^{Q3}$ is a CN.

In any aspect or embodiment described herein, the ABM comprises a structure shown below, where a dashed line indicates the attachment point of a linker moiety or a ULM or a CLM:

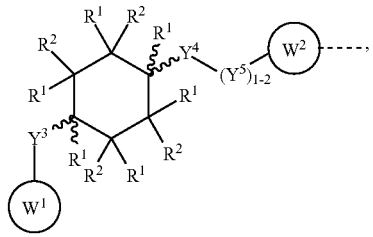

wherein:
 $W^1$ is

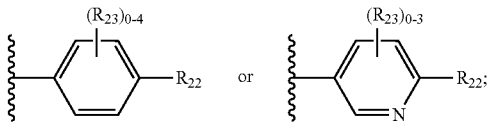

each $R_{22}$ is independently H or —CN;
 each $R_{23}$ is independently H, halo, $C_1$-$C_6$ alkyl (linear, branched, optionally substituted), $C_1$-$C_6$ alkoxy, or —$CF_3$;
 $Y^3$ is a bond or O;
 $Y^4$ is a bond or NH;
 $Y^5$ is a bond, C=O, $C_1$-$C_6$ heteroaryl, or $C_1$-$C_6$ aryl;
 $R^1$, $R^2$, are each independently H, or $C_1$-$C_6$ alkyl (linear or branched, optionally substituted; for example, optionally substituted by 1 or more halo, or $C_{1-6}$ alkoxyl);
 $W^2$ is a bond, $C_{1-6}$ aryl, $C_{1-6}$ heteroaryl, $C_{1-6}$ alicyclic, or $C_{1-6}$ heterocyclic, biheterocyclic, biaryl, or biheteroaryl, each optionally substituted by 1-10 $R^{W2}$; and
 each $R^{W2}$ is independently H, or halo; and
 ⁓⁓⁓ represents a bond that may be stereospecific ((R) or (S)) or non-stereospecific.

In any aspect or embodiment described herein, the $W^2$ is covalently coupled to one or more ULM or CLM groups, or a linker to which is attached one or more ULM or CLM groups as described herein.

In any aspect or embodiment described herein, $W^1$ is selected from the group consisting of:

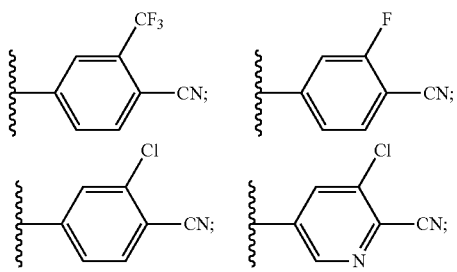

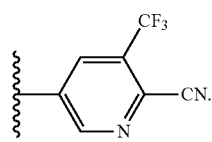

In any aspect or embodiment described herein, W² is selected from the group consisting of:

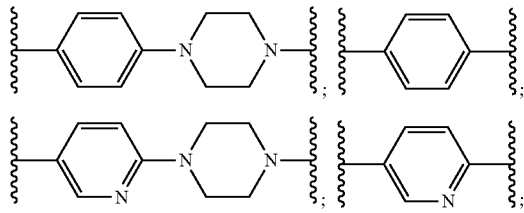

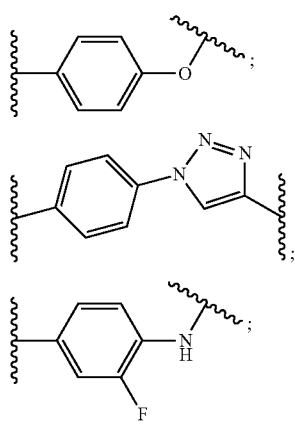

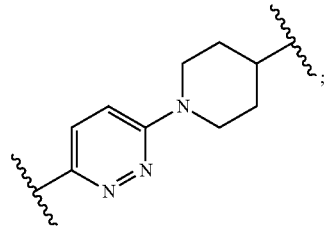

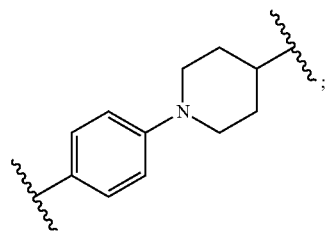

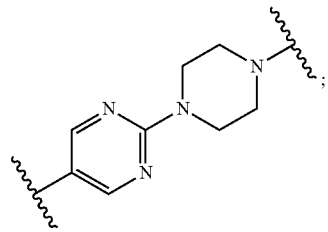

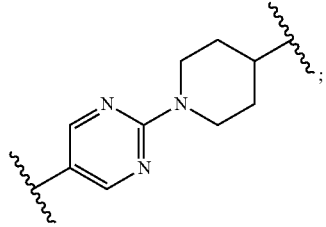

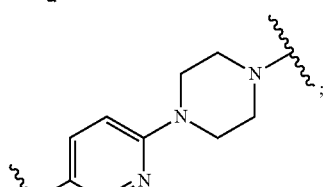

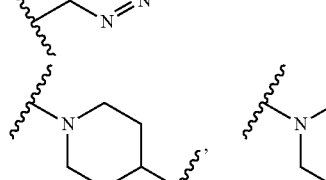

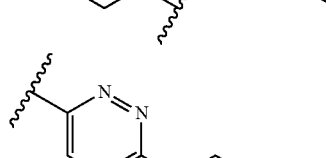

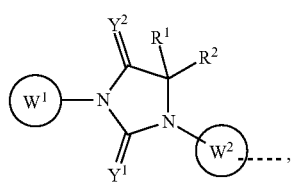

In any aspect or embodiment described herein, the ABM comprises a structure selected from, but not limited to the structures shown below, where a dashed line indicates the attachment point of a linker moiety or a ULM:

ABM-a

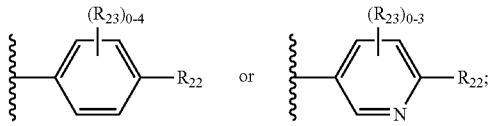

wherein.

W¹ is

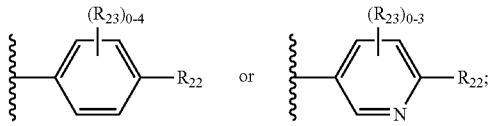

each $R_{22}$ is independently H or —CN;
each $R_{23}$ is independently H, halo, or —CF₃;
$Y^1$, $Y^2$ are each independently O or S;
$R^1$, $R^2$, are each independently H or a methyl group;
$W^2$ is a bond, $C_{1-6}$ aryl, or heteroaryl, each optionally substituted by 1, 2 or 3 $R^{W2}$; and each $R^{W2}$ is independently H, halo, $C_{1-6}$ alkyl (optionally substituted by 1 or more F), $OC_{1-3}$ alkyl (optionally substituted by 1 or more —F).

In any of the embodiments described herein, the $W^2$ is covalently coupled to one or more ULM or CLM groups, or a linker to which is attached one or more ULM or CLM groups as described herein.

In certain additional embodiments, $W^1$ is selected from the group consisting of:

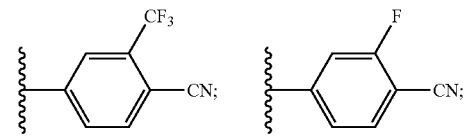

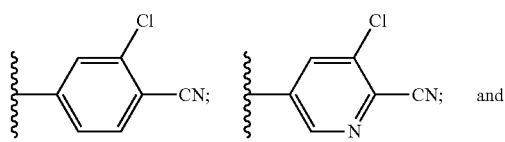

In any aspect or embodiment described herein, W2 is selected from the group consisting of:

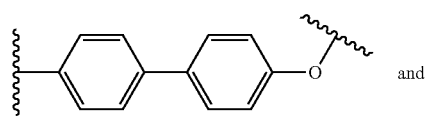
and
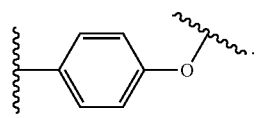

In any aspect or embodiment described herein, ABM is selected from the group consisting of:

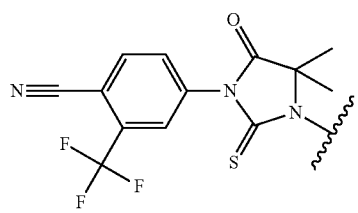

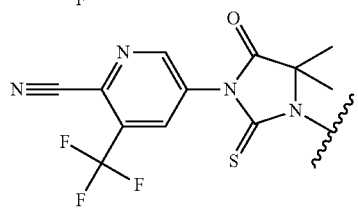

-continued

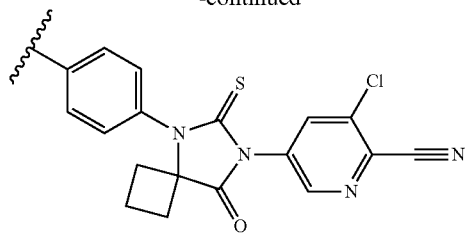

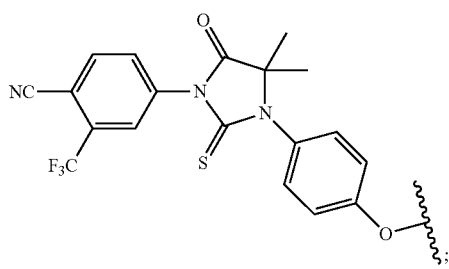

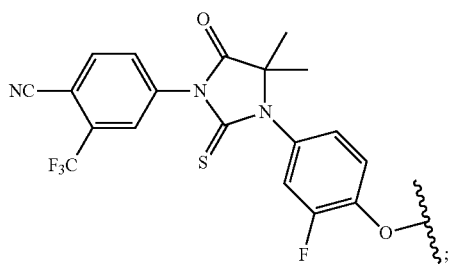

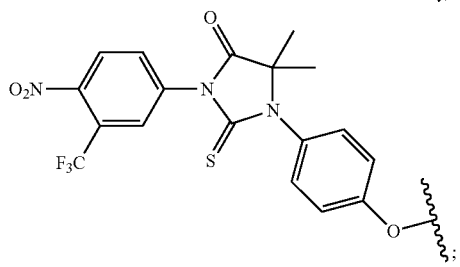

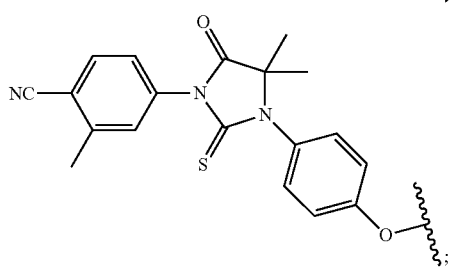

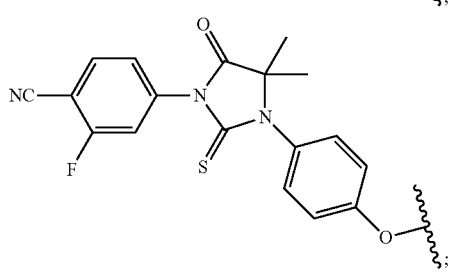

-continued
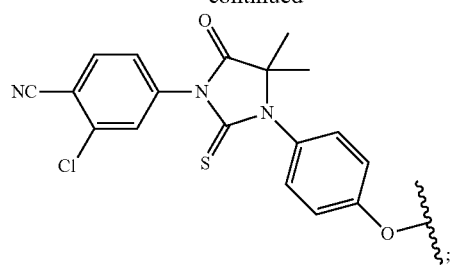
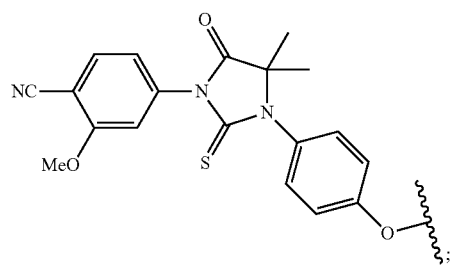
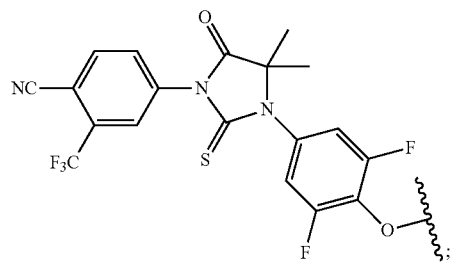
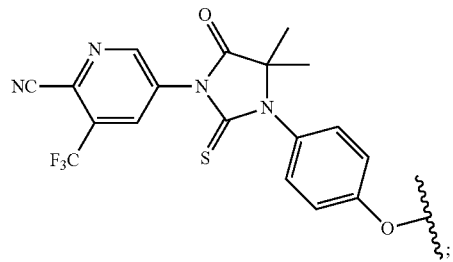
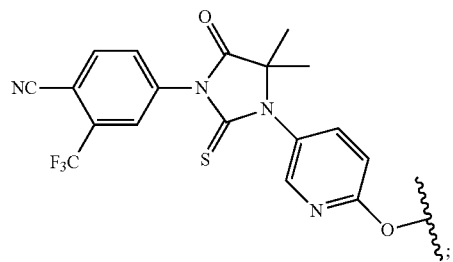
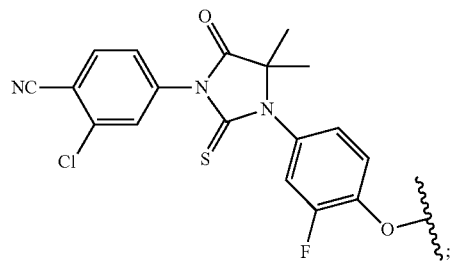
-continued
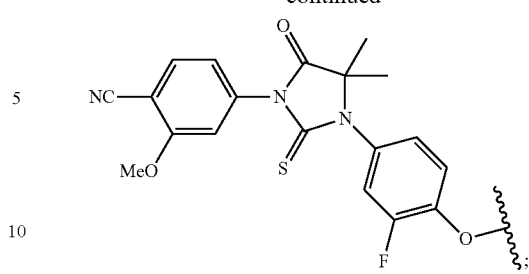
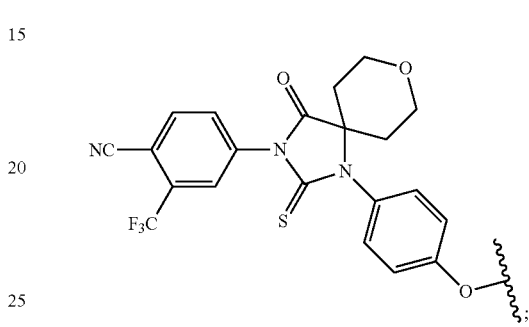
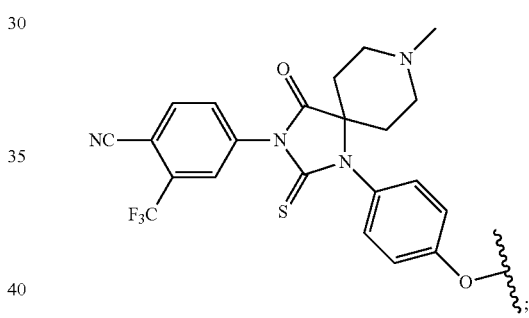
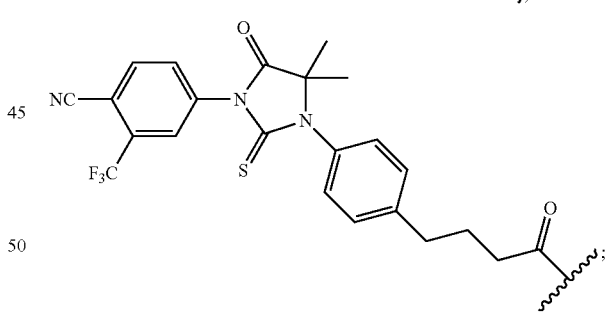
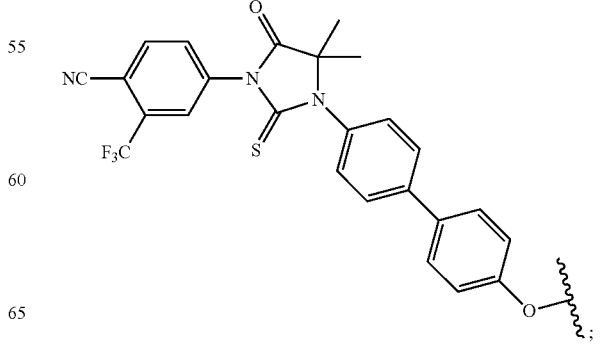

249
-continued
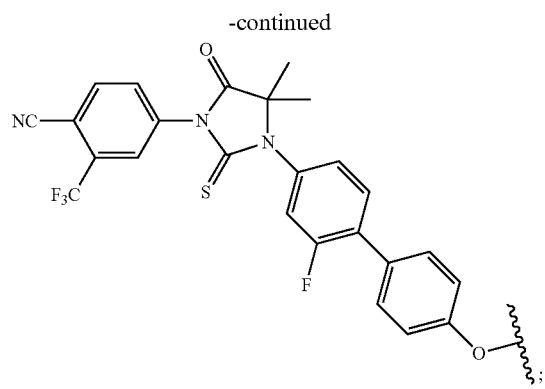
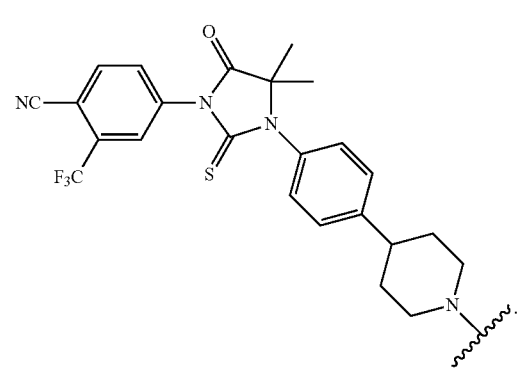
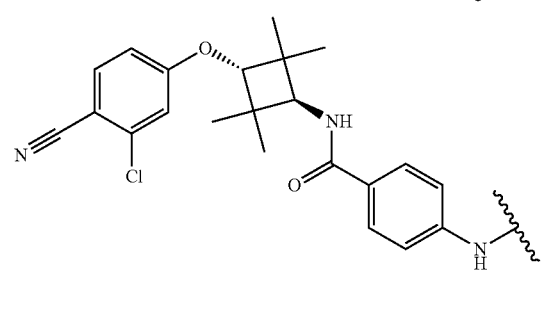
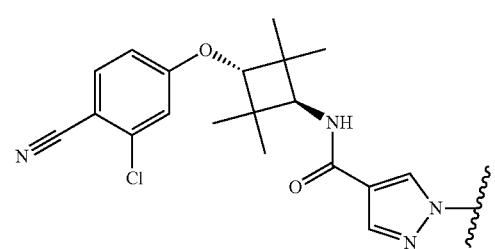
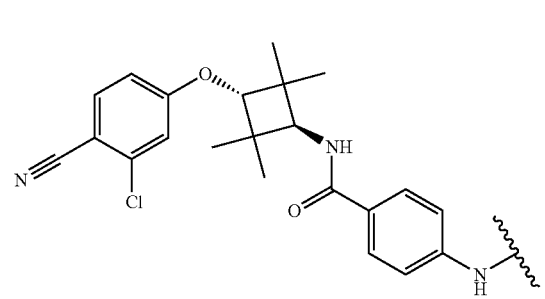
250
-continued
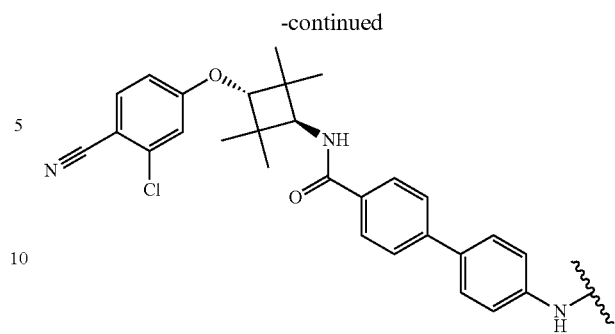
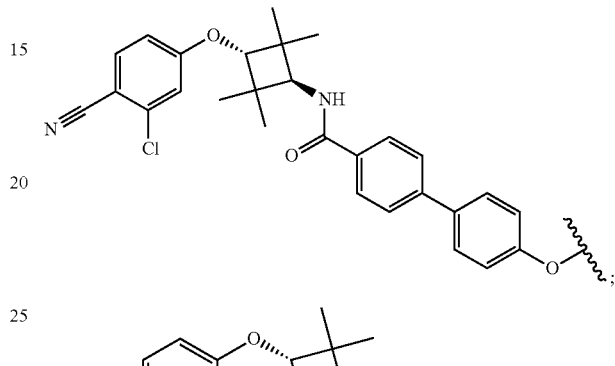
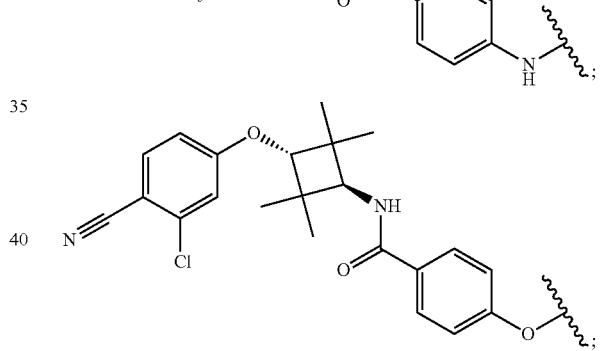
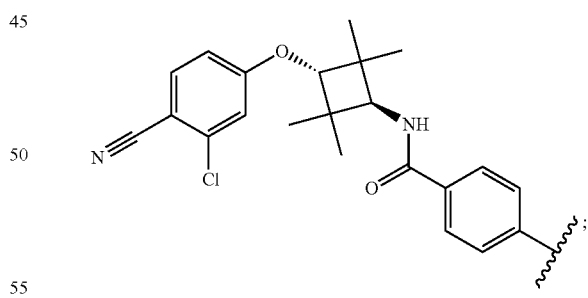
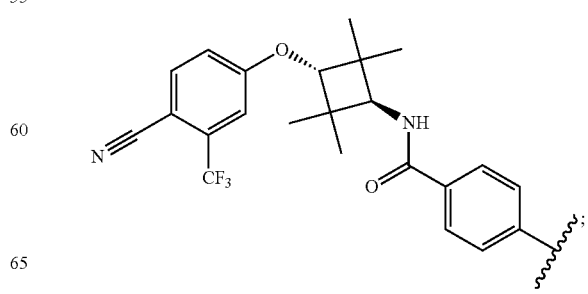

251
-continued
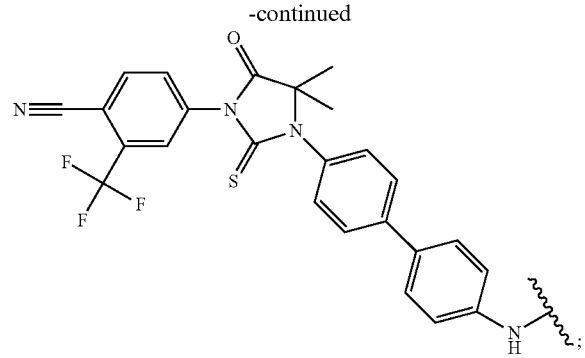
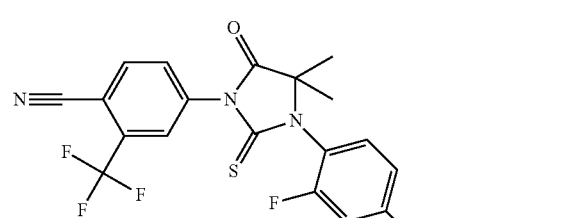
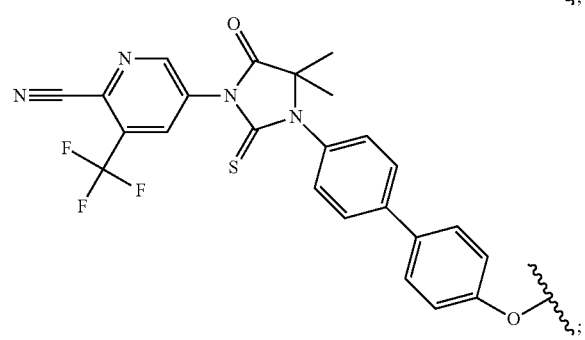
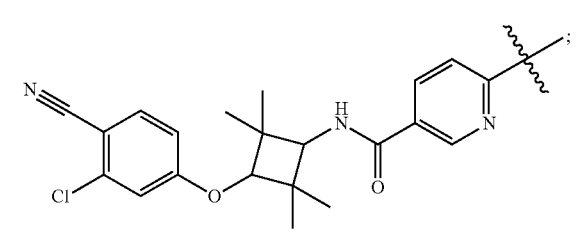
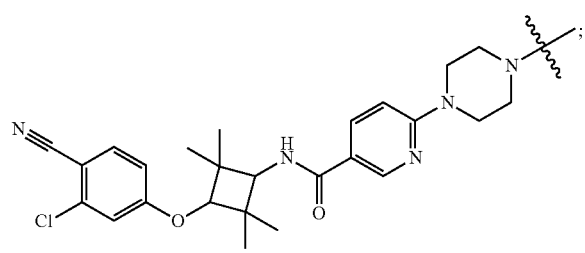
252
-continued
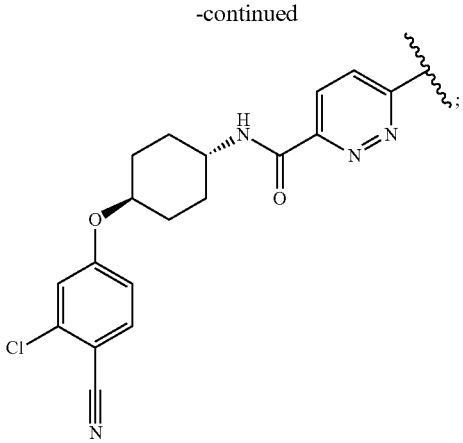
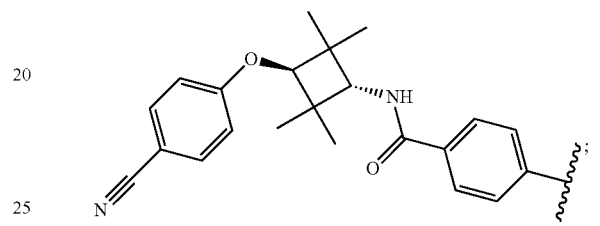
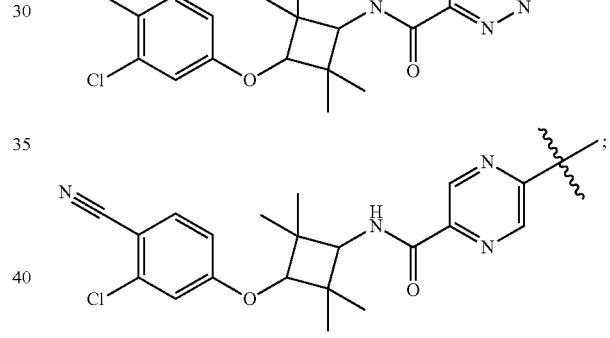
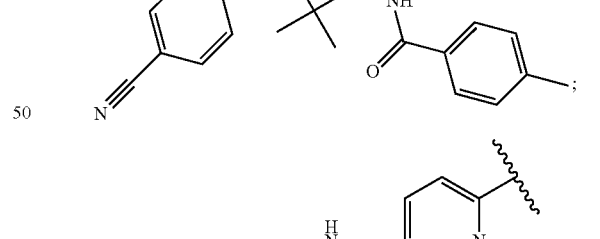
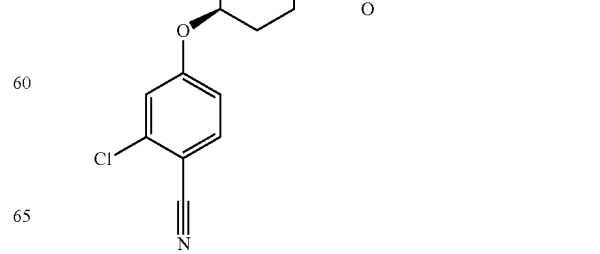

253
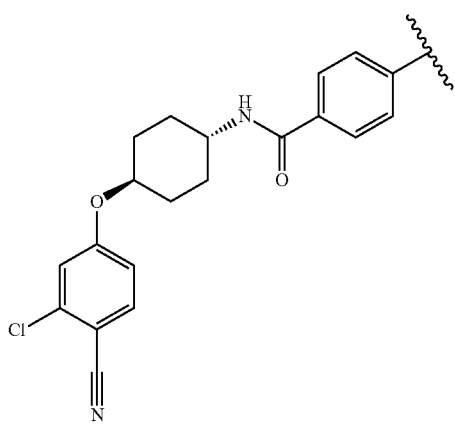
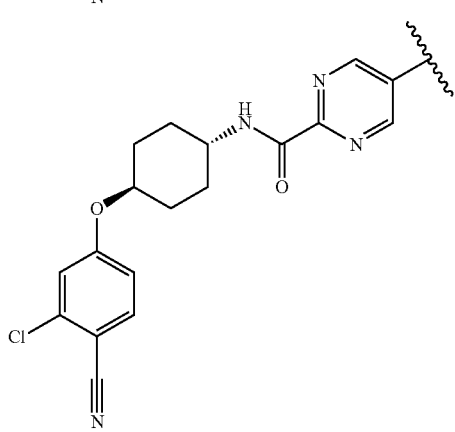
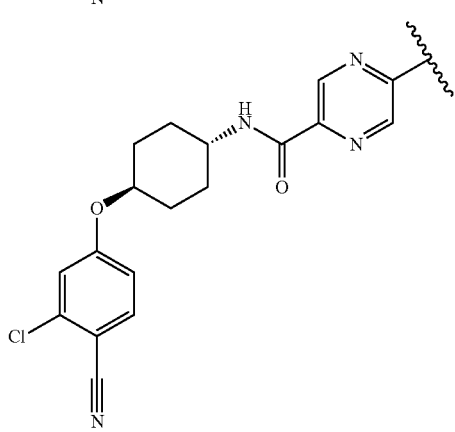
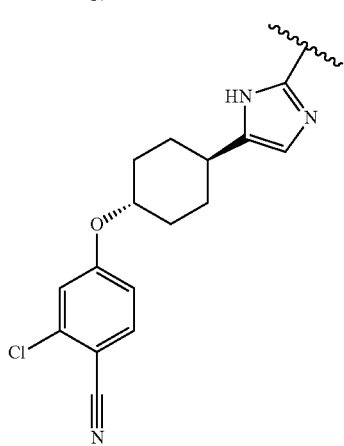
254
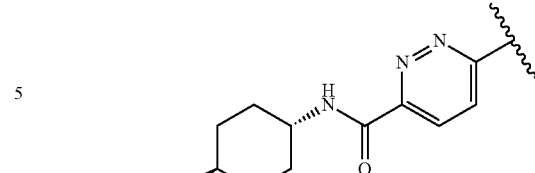
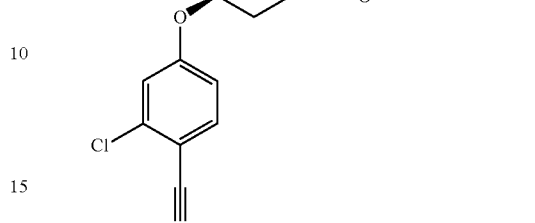
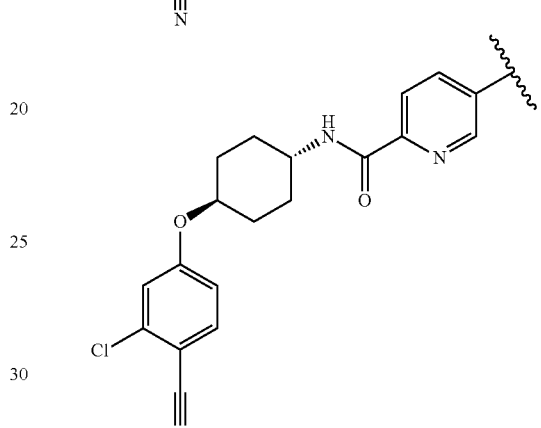
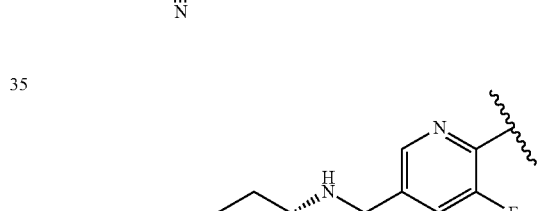
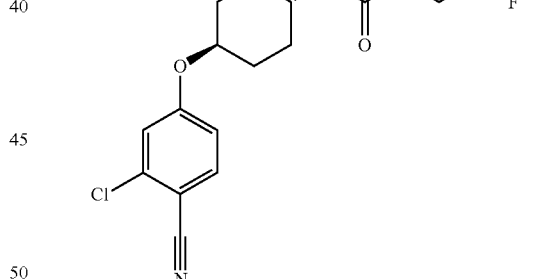
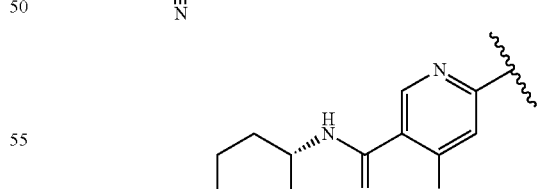
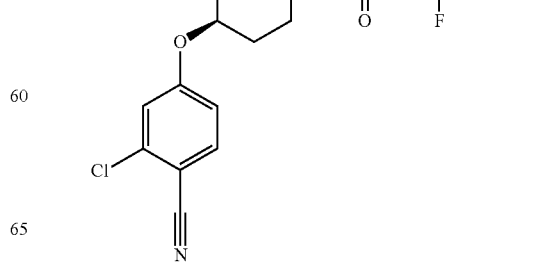

255
-continued
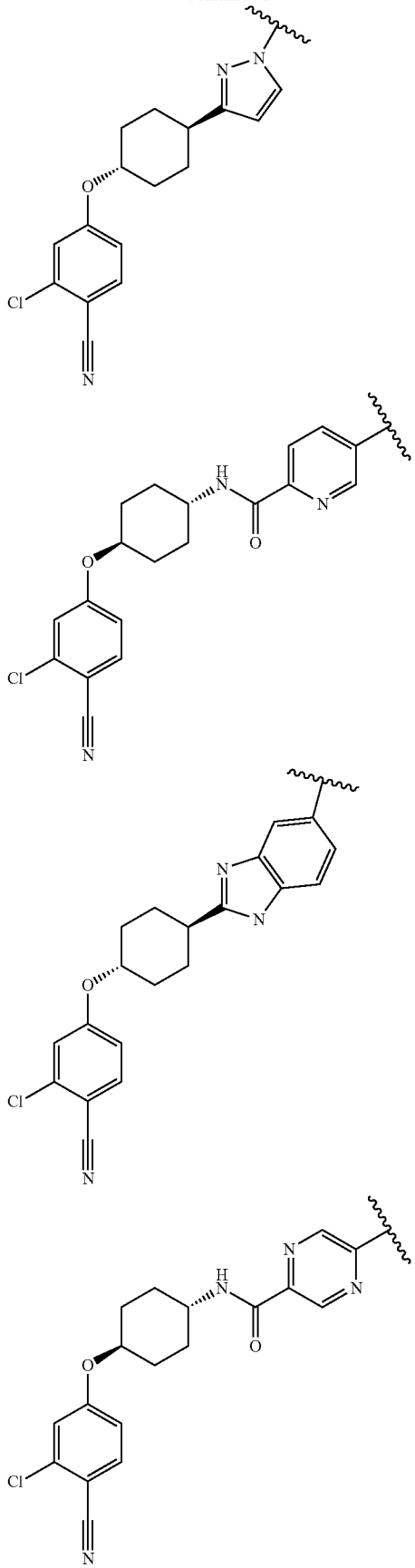
256
-continued
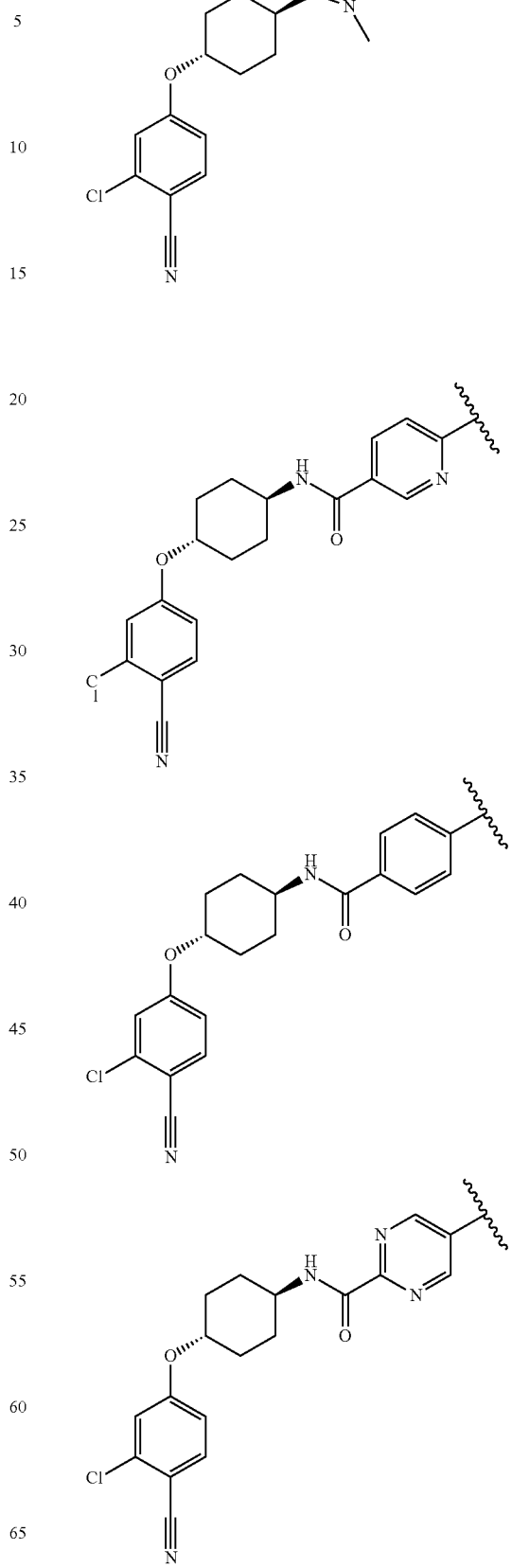

257
258
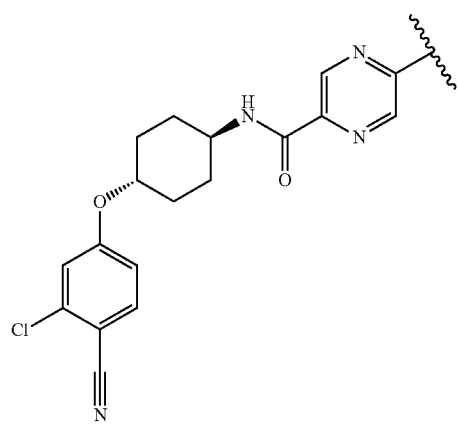
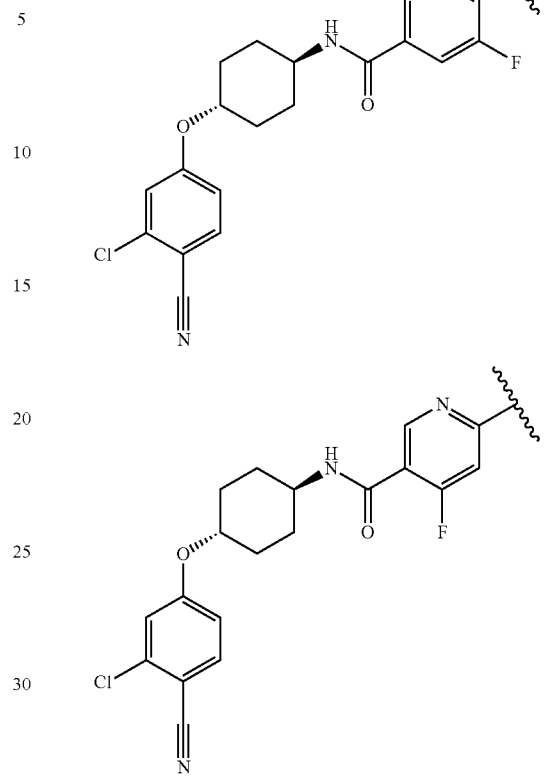
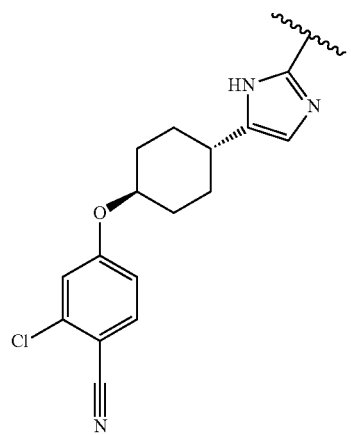
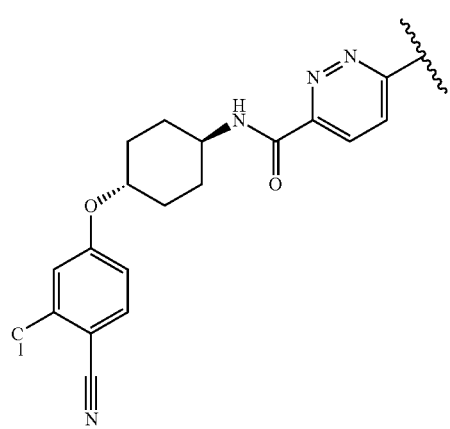
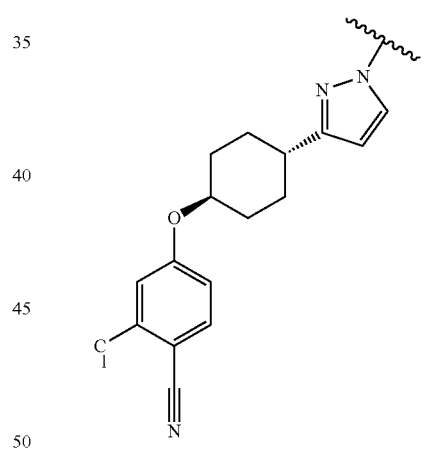
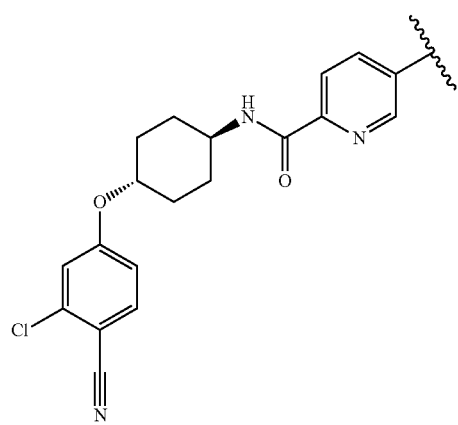
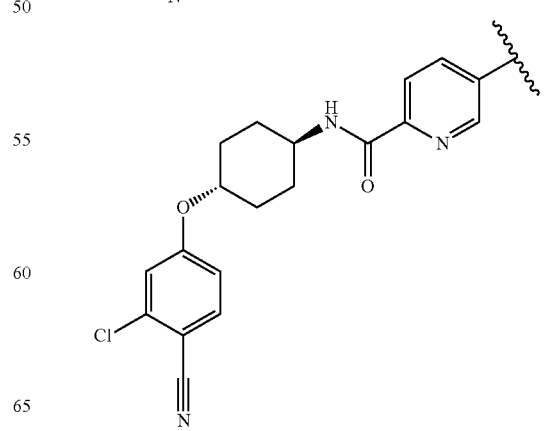

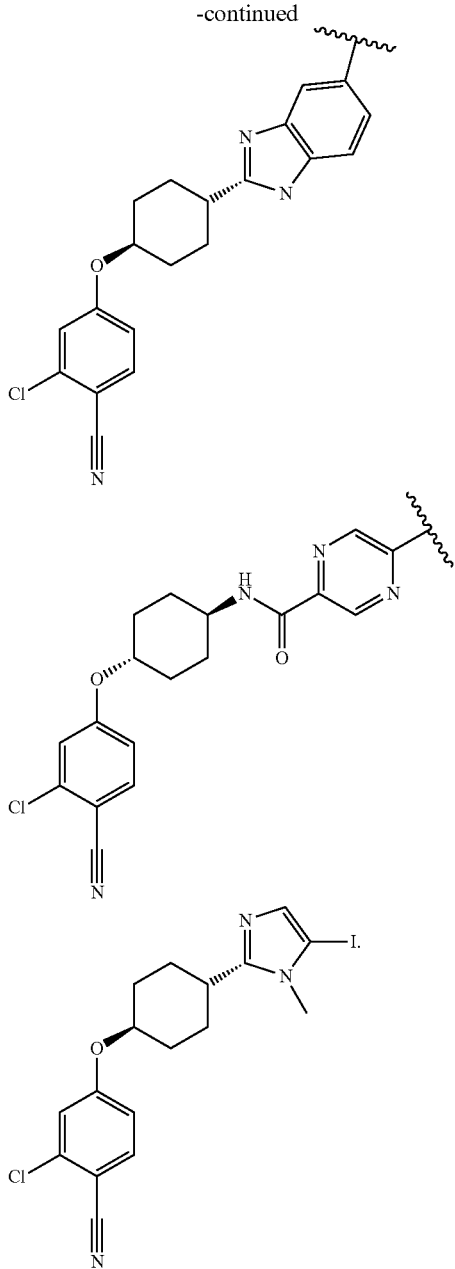

In any aspect or embodiment described herein, the ABM comprises the structure:

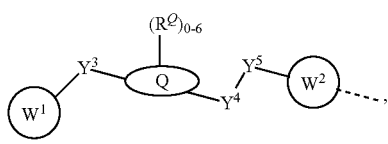
ABM-b wherein:
W¹ is aryl, or heteroaryl, each independently substituted by 1 or more H, halo, hydroxyl, nitro, CN, C≡CH, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl, or $CF_3$;

$Y^3$, $Y^4$, $Y^5$ are each independently a bond, O, $NR^{Y2}$, $CR^{Y1}R^{Y2}$, C=O, C=S, SO, $SO_2$, heteroaryl, or aryl;

Q is a 4 membered alicyclic ring with 0-2 heteroatoms, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{Y1}$, $R^{Y2}$ are each independently H, $C_{1-6}$ alkyl (linear, branched, optionally substituted by 1 or more halo, $C_{1-6}$ alkoxyl);

W² is a bond, $C_{1-6}$ alkyl, $C_{1-6}$ heteroalkyl, O, $C_{1-6}$ alicyclic, heterocyclic, aryl, biheterocyclic, biaryl, or biheteroaryl, or heteroaryl, each optionally substituted by 1, 2 or 3 $R^{W2}$; and each $R^{W2}$ is independently H, halo, $C_{1-6}$ alkyl (linear, branched, optionally substituted by 1 or more F), $C_{1-6}$ heteroalkyl (linear, branched, optionally substituted), —$OR^{W2A}OC_{1-3}$alkyl (optionally substituted by 1 or more —F), $C_{3-6}$ cycloalkyl, $C_{4-6}$ cycloheteroalkyl (optionally substituted), $C_{1-6}$ alkyl (optionally substituted), $C_{1-6}$ alicyclic (optionally substituted), heterocyclic (optionally substituted), aryl (optionally substituted), heteroaryl (optionally substituted), bicyclic heroaryl (optionally substituted), bicyclic aryl, OH, $NH_2$, $NR^{Y1}R^{Y2}$, or CN; and $R^{W2A}$ is H, $C_{1-6}$ alkyl (linear, branched), or $C_{1-6}$ heteroalkyl (linear, branched), each optionally substituted by a cycloalkyl, cycloheteroalkyl, aryl, heterocyclic, heteroaryl, halo, or $OC_{1-3}$alkyl.

In any aspect or embodiment described herein, the description provides an androgen receptor binding compound comprising a structure of:

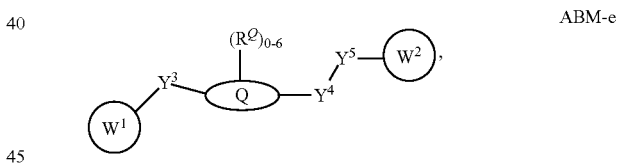
ABM-e wherein:
W¹ is aryl, heteroaryl, bicyclic, or biheterocyclic, each independently substituted by 1 or more H, halo, hydroxyl, nitro, CN, C≡CH, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl, or $CF_3$;

$Y^1$, $Y^2$ are each independently $NR^{Y1}$, O, or S;

$Y^3$, $Y^4$, $Y^5$ are each independently a bond, O, $NR^{Y2}$, $CR^{Y1}R^{Y2}$, C=O, C=S, SO, $SO_2$, heteroaryl, or aryl;

Q is a 3-6 membered alicyclic or aromatic ring with 0-4 heteroatoms, optionally substituted with 0-6 $R^Q$, each $R^Q$, is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^1$, $R^2$, $R^a$, $R^b$, $R^{Y1}$, $R^{Y2}$ are each independently H, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

$W^2$ is a bond, $C_{1-6}$ alkyl, $C_{1-6}$ heteroalkyl, O, $C_{1-6}$ alicyclic, heterocyclic, aryl, biheterocyclic, biaryl, or biheteroaryl, or heteroaryl, each optionally substituted by 1, 2 or 3 $R^{W2}$;

each $R^{W2}$ is independently H, halo, $C_{1-6}$ alkyl (linear, branched, optionally substituted by 1 or more F), $C_{1-6}$heteroalkyl (linear, branched, optionally substituted), —$OR^{W2A}$, $OC_{1-3}$alkyl (optionally substituted by 1 or more —F), $C_{3-6}$ cycloalkyl, $C_{4-6}$ cycloheteroalkyl, $C_{1-6}$ alkyl (optionally substituted), $C_{1-6}$ alicyclic (optionally substituted), heterocyclic (optionally substituted), aryl (optionally substituted), or heteroaryl (optionally substituted), bicyclic hereoaryl or aryl, OH, $NH_2$, $NR^{Y1}R^{Y2}$, CN; and $R^{W2A}$ is H, $C_{1-6}$ alkyl (linear, branched), or $C_{1-6}$ heteroalkyl (linear, branched), each optionally substituted by a cycloalkyl, cycloheteroalkyl, aryl, heterocyclic, heteroaryl, halo, or $OC_{1-3}$alkyl.

In any aspect or embodiment described herein, an androgen receptor binding moiety has a structure of:

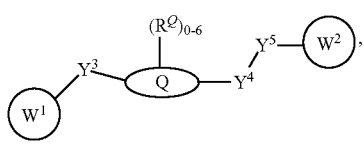

ABM-e wherein:
$W^1$ is

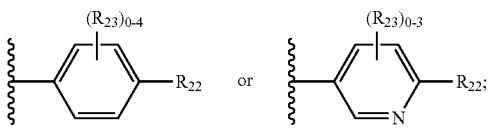

each $R_{22}$ is independently H or —CN;
each $R_{23}$ is independently H, halo, or —$CF_3$;
$Y^3$ is a bond or O;
Q is a 4 member ring, optionally substituted with 0-4 $R^Q$, each $R^Q$ is independently H or methyl;
Y4 is a bond or NH;
Y5 is a bond, a C=O, or a C=S; and
each $W^2$ is independently a bond, C1-6 aryl or heteroaryl, each optionally substituted by 1, 2 or 3 $R^{W2}$, each $R^{W2}$ is independently H, halo, a 6 member alicyclic ring with 1 or 2 heteroatoms or a 5 member aromatic ring with 1 or 2 or 3 heteroatoms.

In any aspect or embodiment described herein, $W^2$ is selected from the group consisting of:

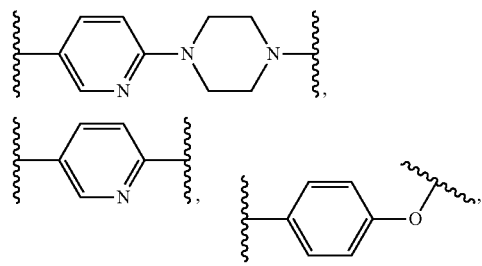

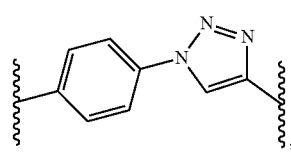

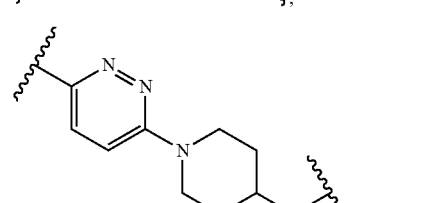

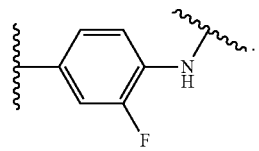

In any aspect or embodiment described herein, the $W^2$ is covalently coupled to one or more ULM or CLM groups, or a linker to which is attached one or more ULM or CLM groups as described herein.

In any aspect or embodiment described herein, $W^1$ is selected from the group consisting of:

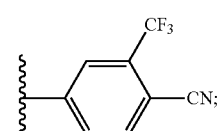 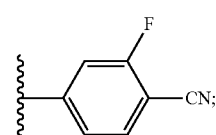

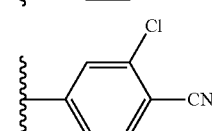 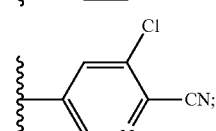

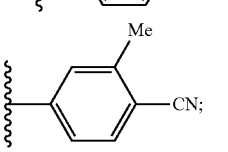 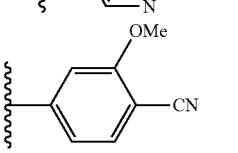

Me    OMe

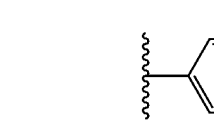 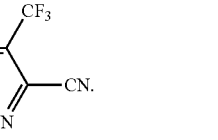 and

In any aspect or embodiment described herein, an androgen binding moiety has a structure of:

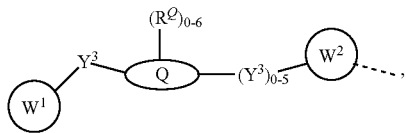

ABM-d wherein:
W¹ is aryl, independently substituted by 1 or more halo, CN;
Y³ are each independently a bond, $NR^{Y2}$, $CR^{Y1}R^{Y2}$, C=O;
Q is a 5 membered aromatic ring with 1 or 2 heteroatoms;
$R^{Y1}$, $R^{Y2}$ are each independently H, $C_{1-6}$ alkyl (linear, branched);
W² is a bond, aryl, or heteroaryl, each optionally substituted by 1, 2 or 3 $R^{W2}$; and
each $R^{W2}$ is independently H, halo, $C_{1-6}$ alkyl (optionally substituted by 1 or more F), $OC_{1-3}$alkyl (optionally substituted by 1 or more —F).

In any aspect or embodiment described herein, the W² is covalently coupled to one or more ULM or CLM groups, or a linker to which is attached one or more ULM or CLM groups as described herein.

In any aspect or embodiment described herein, W¹ is

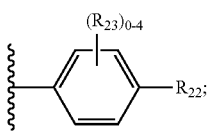

wherein each $R_{22}$ is independently halo or CN; and each $R_{23}$ is independently H or halo.

In any aspect or embodiment described herein, W¹ is selected from the group consisting of:

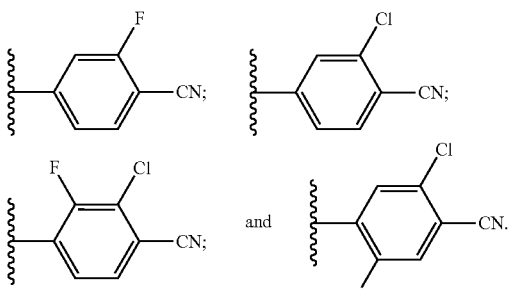

In any aspect or embodiment described herein, Q is

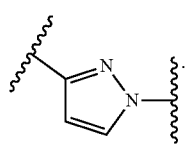 [SMILES: *c1ccn(*)n1]

In any aspect or embodiment described herein, W² is


In any aspect or embodiment described herein, $(Y^3)_{0.5}$ is

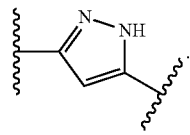 [SMILES: *c1cc(*)[nH]n1]

In any aspect or embodiment described herein, the ABM comprises a structure selected from, but not limited to the structures shown below, where a dashed line indicates the attachment point of a linker moiety or a ULM such as a CLM:

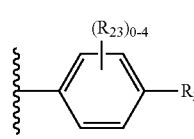

wherein:
W¹ is

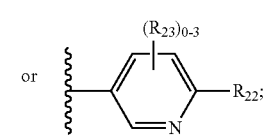

each $R_{22}$ is independently H or —CN;
each $R_{23}$ is independently H, halo, or —CF$_3$;
$Y^1$, $Y^2$ are each independently O or S;
$Y^3$, $Y_4$, $Y^5$ are each independently a bond, O, NR$^2$, CR$^{Y1}$R$^{12}$, C=O, C=S, SO, or SO$_2$;
$R^1$, $R^2$, are each independently H or a methyl group;
$W^2$ is a bond, C$_{1-6}$ aryl, or heteroaryl, each optionally substituted by 1, 2 or 3 R$^{W2}$; and
each R$^{W2}$ is independently H, halo, C$_{1-6}$ alkyl (optionally substituted by 1 or more F), C$_{3-6}$ cycloalkyl, C$_{4-6}$ cycloheteroalkyl, OC$_{1-3}$alkyl (optionally substituted by 1 or more —F).

In any aspect or embodiment described herein, the W$^2$ is covalently coupled to one or more ULM or CLM groups, or a linker to which is attached one or more ULM or CLM groups as described herein.

In any aspect or embodiment described herein, W$^1$ is selected from the group consisting of:

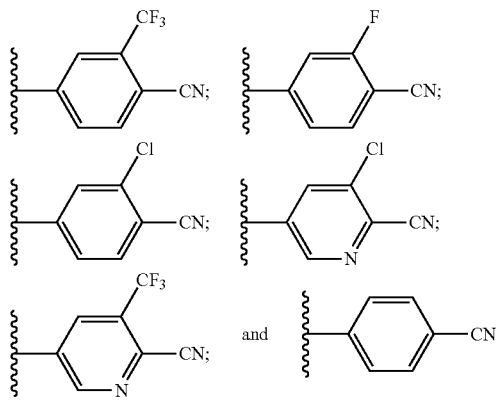

In any aspect or embodiment described herein, W2 is selected from the group consisting of:

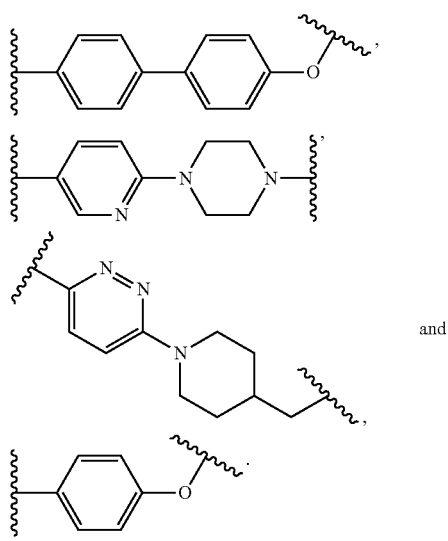

In any aspect or embodiment described herein, the ABM comprises a structure shown below, where a dashed line indicates the attachment point of a linker moiety or a ULM or a CLM:

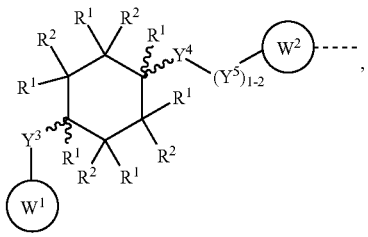

wherein:
$W_1$ is

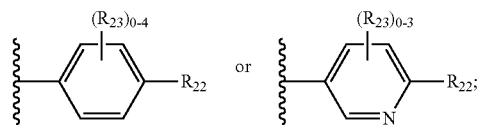

each $R_{22}$ is independently or —C;
each $R_{23}$ is independently H, halo, or —CF$_3$;
$Y^3$ is a bond or O;
$Y^4$ is a bond or NH;
$Y^5$ is a bond, C=O, C$_1$-C$_6$ heteroaryl, or C$_1$-C$_6$ aryl;
$R^1$, $R^2$, are each independently H, or C$_1$-C$_6$ alkyl (linear or branched, optionally substituted by 1 or more halo, or C$_{1-6}$ alkoxyl);
$W^2$ is a bond, C$_{1-6}$ aryl, C$_{1-6}$ heteroaryl, C$_{1-6}$ alicyclic, or C$_{1-6}$ heterocyclic, each optionally substituted by 1-10 R$^{W2}$; and
each R$^{W2}$ is independently H, or halo; and
∼∼∼ represents a bond that may be stereospecific ((R) or (S)) or non-stereospecific. ∼∼∼

In any of the embodiments described herein, the W$^2$ is covalently coupled to one or more ULM or CLM groups, or a linker to which is attached one or more ULM or CLM groups as described herein.

In certain additional embodiments, W$^1$ is selected from the group consisting of:

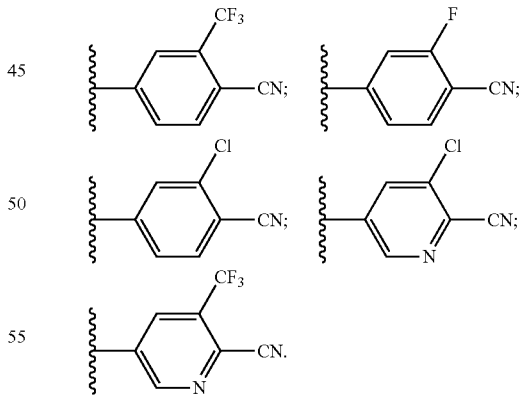

In certain additional embodiments, W$^2$ is selected from the group consisting of:

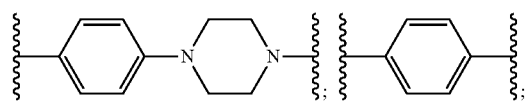

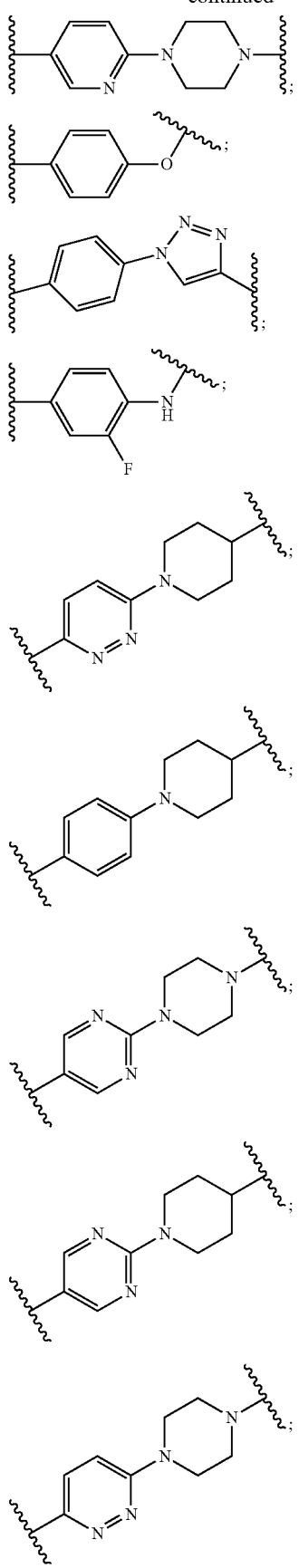

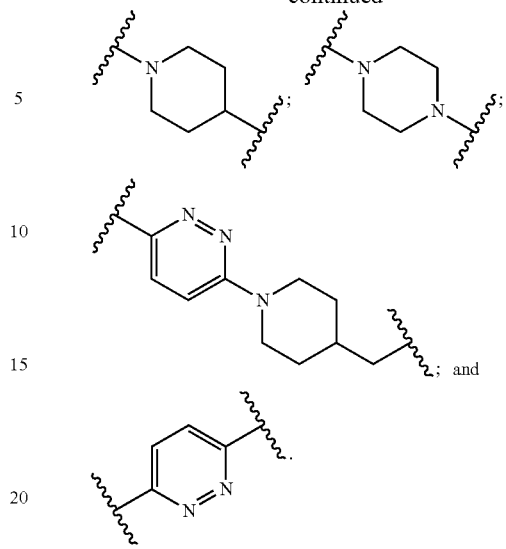

In certain embodiments, the androgen receptor binding compound of ABM is selected from the group consisting of:
trans-2-Chloro-4-[3-amino-2,2,4,4-tetramethylcyclobutoxy]benzonitrile;
cis-2-Chloro-4-[3-amino-2,2,4,4-tetramethylcyclobutoxy]benzonitrile;
trans 6-Amino-N-[3-(3-chloro-4-cyanophenoxy)-2,2,4,4-tetramethylcyclobutyl]pyridazine-3-carboxamide;
trans tert-Butyl N-[3-(3-chloro-4-cyanophenoxy)-2,2,4,4-tetramethylcyclobutyl]carbamate;
trans 4-Amino-N-[3-(3-chloro-4-cyanophenoxy)-2,2,4,4-tetramethylcyclobutyl]benzamide;
trans 5-Amino-N-[3-(3-chloro-4-cyanophenoxy)-2,2,4,4-tetramethylcyclobutyl]pyrazine-2-carboxamide;
trans 2-Amino-N-[3-(3-chloro-4-cyanophenoxy)-2,2,4,4-tetramethylcyclobutyl]pyrimidine-5-carboxamide;
4-Methoxy-N-[(1r,3r)-3-(3-chloro-4-cyanophenoxy)-2,2,4,4-tetramethylcyclobutyl]benzamide;
trans 1-(2-Hydroxyethyl)-N-[3-(3-chloro-4-cyanophenoxy)-2,2,4,4-tetramethylcyclobutyl]-1H-pyrazole-4-carboxamide;
trans 6-Amino-N-[3-(3-chloro-4-cyanophenoxy)-2,2,4,4-tetramethylcyclobutyl]pyridine-3-carboxamide;
trans 4-[(5-Hydroxypentyl)amino]-N-[3-(3-chloro-4-cyanophenoxy)-2,2,4,4-tetramethylcyclobutyl]benzamide; and
trans tert-Butyl 2-({5-[(4-{[3-(3-chloro-4-cyanophenoxy)-2,2,4,4-tetramethylcyclobutyl]carbamoyl}phenyl)aminopentyl}oxy)acetate; and
N-((1r,3r)-3-(4-cyanophenoxy)-2,2,4,4-tetramethylcyclobutyl)-4-methylbenzamide.

XII. Compounds Targeting Estrogen Receptor (ER) ICI-182780

1. Estrogen Receptor Ligand

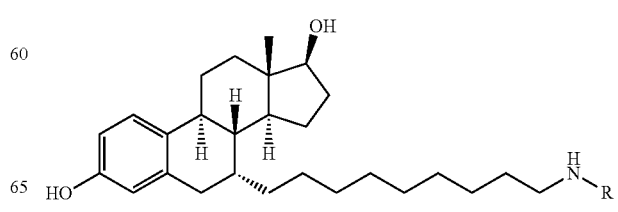

(Derivatized where "R" designates a site for linker group L or -(L-CLM) group attachment).

In any embodiment or aspect described herein, the PTM may be represented by the Formula PTM-I:

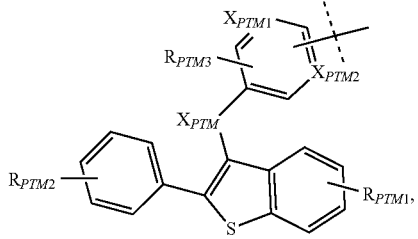

PTM-I wherein:
- $X_{PTM}$ is O or C=O;
- each of $X_{PTM1}$ and $X_{PTM2}$ is independently selected from N or CH;
- $R_{PTM1}$ is independently selected from OH, O(CO)$R_{PTM}$, O-lower alkyl, wherein $R_{PTM}$ is an alkyl or aryl group in the ester;
- at least one $R_{PTM2}$, each independently selected from H, OH, halogen, CN, CF$_3$, SO2-alkyl, O-lower alkyl;
- at least one $R_{PTM3}$, each independently selected from H, halogen; and
- the dashed line indicates the site of attachment of at least one linker, CLM, CLM', PTM, PTM', or a combination thereof.

In any embodiment or aspect described herein, the PTM may be represented by the Formula PTM-I:

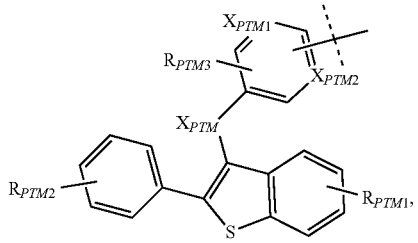

PTM-I wherein:
- $X_{PTM}$ is O or C=O;
- each of $X_{PTM1}$ and $X_{PTM2}$ is independently selected from N or CH;
- $R_{PTM1}$ is independently selected from OH, O(CO)$R_{PTM}$, O-lower alkyl, wherein $R_{PTM}$ is an alkyl or aryl group in the ester;
- each $R_{PTM2}$ is independently selected from H, OH, halogen, CN, CF$_3$, SO$_2$-alkyl, O-lower alkyl;
- each $R_{PTM3}$ is independently selected from H, halogen;
- the PTM-I comprises as least one $R_{PTM2}$, at least one $R_{PTM3}$, or a combination thereof on the respective rings; and
- the dashed line indicates the site of attachment of at least one linker, CLM, CLM', PTM, PTM', or a combination thereof.

In any embodiment or aspect described herein, PTM-I has at least one of: two $R_{PTM2}$, two $R_{PTM3}$, or a combination thereof.

In any embodiment or aspect described herein, the PTM may be represented by the Formula PTM-II:

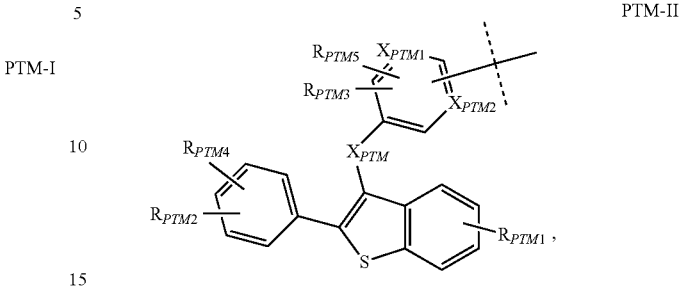

PTM-II wherein:
- $X_{PTM}$ is O or C=O;
- each of $X_{PTM1}$ and $X_{PTM2}$ is independently selected from N or CH;
- $R_{PTM1}$ is independently selected from OH, O(CO)$R_{PTM}$, O-lower alkyl, wherein $R_{PTM}$ is an alkyl or aryl group in the ester;
- $R_{PTM2}$ and $R_{PTM4}$ are independently selected from H, OH, halogen, CN, CF, SO$_2$-alkyl, O-lower alkyl;
- $R_{PTM3}$ and $R_{PTM5}$ are independently selected from H, halogen; and
- the dashed line indicates the site of attachment of at least one linker, CLM, CLM', PTM, PTM', or a combination thereof.

In aspect or embodiment described herein, O(CO)$R_{PTM}$ functions as a prodrug of the corresponding phenol in Formula PTM-I or PTM-II.

In any embodiment or aspect described herein, the O-lower alkyl of PTM-I or PTM-II an alkyl chain with carbon number 1 to 3.

In aspect or embodiment described herein, the present disclosure provides a compound or PTM of Formula ($I_{PTM}$):

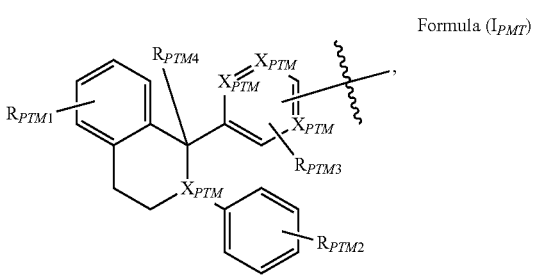

Formula ($I_{PMT}$)

wherein:
- each $X_{PTM}$ is independently CH, N;
- indicates the site of attachment of at least one linker, CLM, CLM', PTM, PTM', or a combination thereof;
- each $R_{PTM1}$ is independently OH, halogen, O(CO)$R_{PTM}$, where $R_{PTM}$ is alkyl or cycloalkyl group with 1 to 6 carbons or aryl groups, substitution can be mono-, di- or tri-substituted;
- each $R_{PTM2}$ is independently H, halogen, CN, CF$_3$, alkoxy, substitution can be mono- or di-substitution; and
- each $R_{PTM3}$ is independently H, halogen, substitution can be mono- or di-substitution.

In any aspect or embodiment described herein, the PTM is represented by the Formula (II$_{PTM}$):

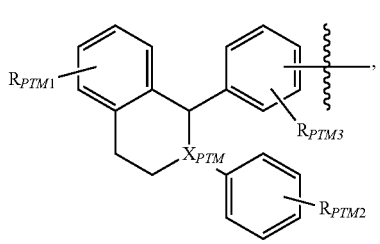

Formula (II$_{PMT}$)

wherein:

X$_{PTM}$ is CH, N;

⸸ indicates the site of attachment of at least one linker, CLM, CLM', PTM, PTM', ULM, an ILM, a VLM, MLM, a ULM', a ILM', a VLM', a MLM', or a combination thereof;

each R$_{PTM1}$ is independently OH, halogen (e.g., F);

each R$_{PTM2}$ is independently H, halogen (e.g., F), CF$_3$, substitution can be mono- or di-substitution; and each R$_{PTM3}$ is independently halogen (e.g. F), substitution can be mono- or di-substitution.

In certain embodiments, at least one of:

X$_{PTM}$ of Formula (II$_{PTM}$) is CH;

R$_{PTM1}$ of Formula (II$_{PTM}$) is OH;

R$_{PTM2}$ of Formula (II$_{PTM}$) is H;

each R$_{PTM3}$ of Formula (II$_{PTM}$) is independently H or F; or a combination thereof.

XIV. Compounds Targeting Thyroid Hormone Receptor (TR)
  1. Thyroid Hormone Receptor Ligand (Derivatized)

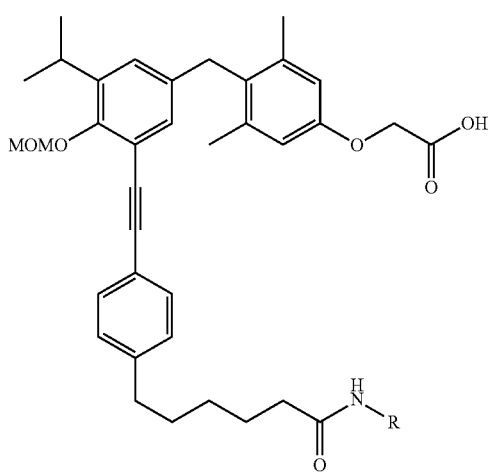

(Derivatized where "R" designates a site for linker group L or -(L-CLM) group attachment and MOMO indicates a methoxymethoxy group).

XV. Compounds Targeting HIV Protease
  1. Inhibitor of HIV Protease (derivatized)

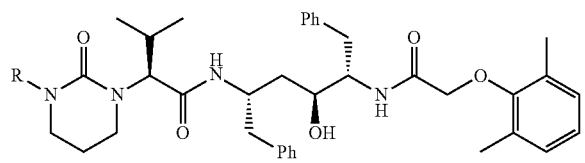

(Derivatized where "R" designates a site for linker group L or-(L-CLM) group attachment). See, *J. Med. Chem.* 2010, 53, 521-538.

2. Inhibitor of HIV Protease

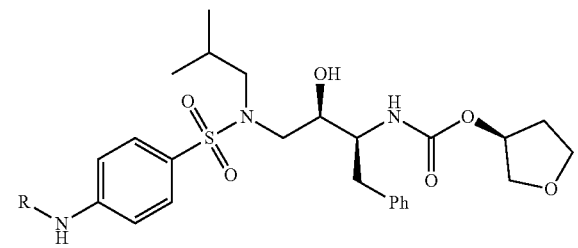

(Derivatized where "R" designates a potential site for linker group L or -(L-CLM) group attachment). See, *J. Med. Chem.* 2010, 53, 521-538.

XVI. Compounds Targeting HIV Integrase
  1. Inhibitor of HIV Integrase (derivatized)

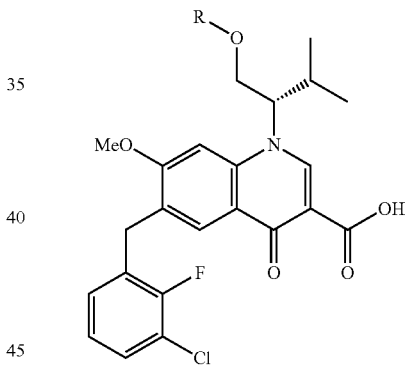

(Derivatized where "R" designates a site for linker group L or -(L-CLM) group attachment). See, *J. Med. Chem.* 2010, 53, 6466.

2. Inhibitor of HIV Integrase (derivatized)

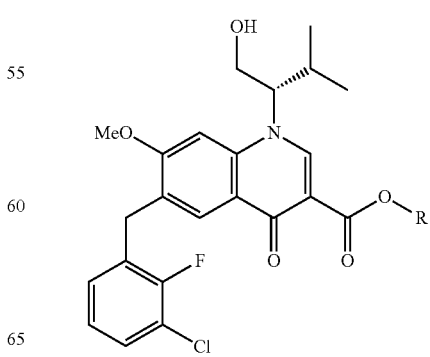

3. Inhibitor of HIV integrase Isetntress (derivatized)

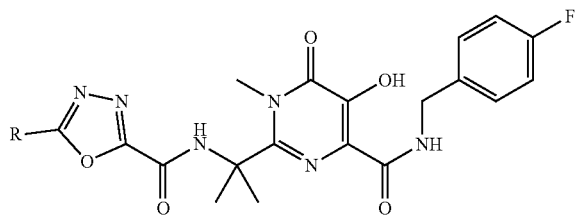

(Derivatized where "R" designates a site for linker group L or -(L-CLM) group attachment). See, *J. Med. Chem.* 2010, 53, 6466.

XVII. Compounds Targeting HCV Protease
  1. Inhibitors of HCV Protease (derivatized)

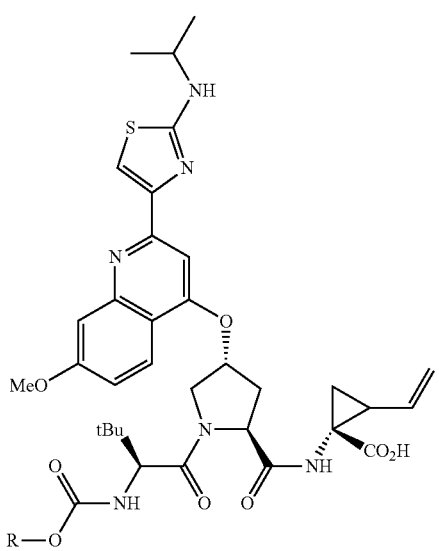

(Derivatized where "R" designates a site for linker group L or -(L-CLM) group attachment).

XVIII. Compounds Targeting Acyl-Protein Thioesterase-1 and -2 (APT1 and APT2)
  1. Inhibitor of APT1 and APT2 (derivatized)

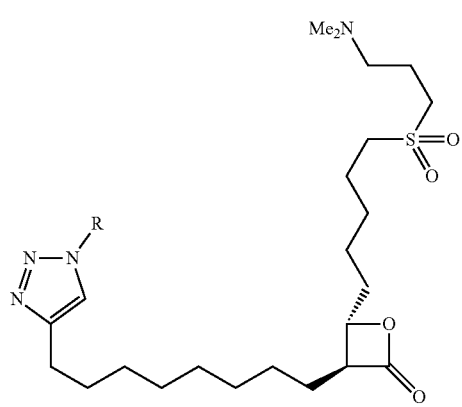

(Derivatized where "R" designates a site for linker group L or -(L-CLM) group attachment). See, *Angew. Chem. Int. Ed.* 2011, 50, 9838-9842, where L is a linker group as otherwise described herein and said CLM group is as otherwise described herein such that -(L-CLM) binds the CLM group to a PTMgroup as otherwise described herein.

VIV. Compound Targeting Tau Protein

In any aspect or embodiment described herein, the PTM may include a Tau protein binding moieties. For example, the PTM may be represented by Formula I, Formula II, Formula III, Formula IV, Formula V, Formula VI, Formula, VII, Formula, VIII, Formula IX, Formula X, or Formula XI:

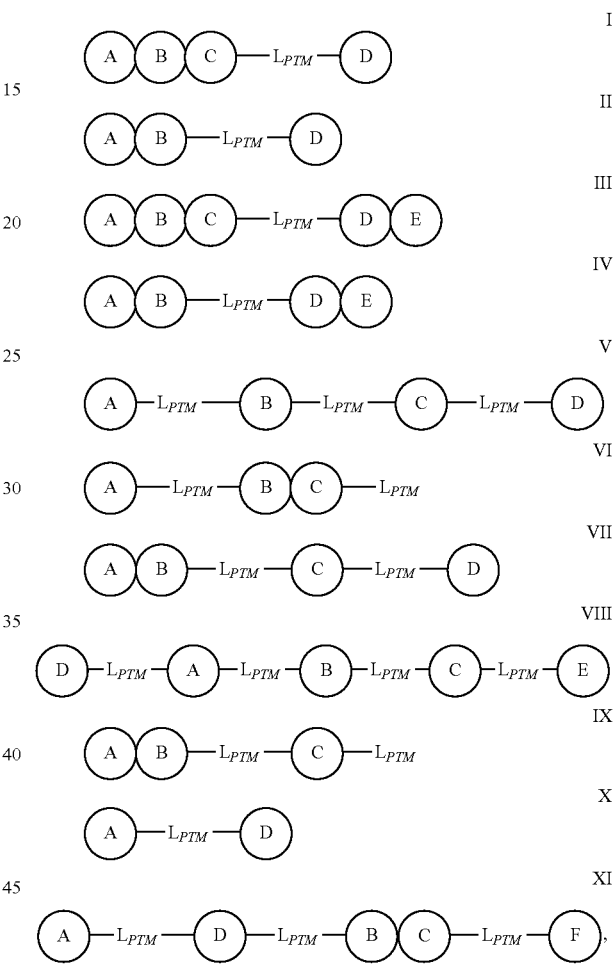

wherein:
  A, B, C, D, E, and F are independently selected from an optionally substituted 5- or 6-membered aryl or heteroaryl ring, an optionally substituted 4- to 7-membered cycloalkyl or a heterocycloalkyl, where contact between circles indicates ring fusion; and
  $L_{PTM}$ is selected from a bond, an alkyl, an alkenyl or an alkynyl, optionally interrupted by one or more rings (i.e., cycloalkyl, heterocycloalkyl, aryl or heteroaryl), or one or more functional groups selected from the groups —O—, —S—, —NR$^1_{PTM}$— (where R$^1_{PTM}$ is selected from H or alkyl), —N=N—, —S(O)—, —SO$_2$—, —C(O)—, —NHC(O)—, —C(O)NH—, —NHSO$_2$—, —NHC(O)NH—, —NHC(O)O—, or —OC(O)NH—, wherein the said functional group are optionally located at either end of the linker.

In any aspect or embodiment described herein, aryl and heteroaryl rings of A, B, C, D, E, and F of PTM are optionally substituted with 1-3 substituents each independently selected from alkyl, alkenyl, haloalkyl, halogen, hydroxyl, alkoxy, fluoroalkoxy, amino, alkylamino, dialkylamino, acylamino, trifluoromethyl, and cyano, wherein the said alkyl and alkenyl groups are further optionally substituted.

In any aspect or embodiment described herein, the rings of at least one of A, B, C, F, or a combination thereof is selected from optionally substituted 5- or 6-membered aryl or heteroaryl rings;

In any aspect or embodiment described herein, the PTM has the chemical structure of Formula I, wherein:
  A, B and C rings are independently 5- or 6-membered fused aryl or heteroaryl rings;
  $L_{PTM}$ is selected from a bond or an alkyl, and
  D is selected from a 6-membered aryl, heteroaryl or heterocycloalkyl,
  wherein A, B, C and D are optionally substituted with alkyl, haloalkyl, halogen, hydroxyl, alkoxy, amino, alkylamino, dialkylamino or cyano.

In any aspect or embodiment described herein, The PTM has the chemical structure of Formula I, wherein:
  A and C are a phenyl or a 6-membered heteroaryl ring;
  B is a 5-membered heteroaryl ring;
  $L_{PTM}$ is a bond; and
  D is a 6-membered heteroaryl or a 6-membered heterocycloalkyl ring;
  wherein each A, B, C and D is optionally independently substituted with alkyl, haloalkyl, halogen, hydroxyl, alkoxy, amino, dialkylamino or cyano, and wherein a nitrogen atom of any of the A, B, C and D rings is not directly connected to a heteroatom or to a carbon atom, to which another heteroatom is directly attached.

In any aspect or embodiment described herein, the PTM has the chemical structure of Formula III or IV, wherein A, B and C are 5- or 6-membered fused aryl or heteroaryl rings, $L_{PTM}$ is selected from a bond or an alkyl, and D and E are 5- or 6-membered fused aryl or heteroaryl rings, wherein A, B, C, D and E are optionally substituted with alkyl, haloalkyl, halogen, hydroxyl, alkoxy, amino, alkylamino, dialkylamino or cyano.

In any aspect or embodiment described herein, the PTM is represented by following chemical structure:

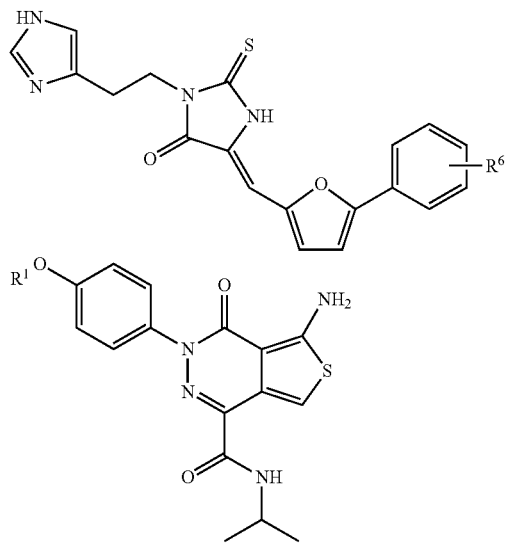

-continued

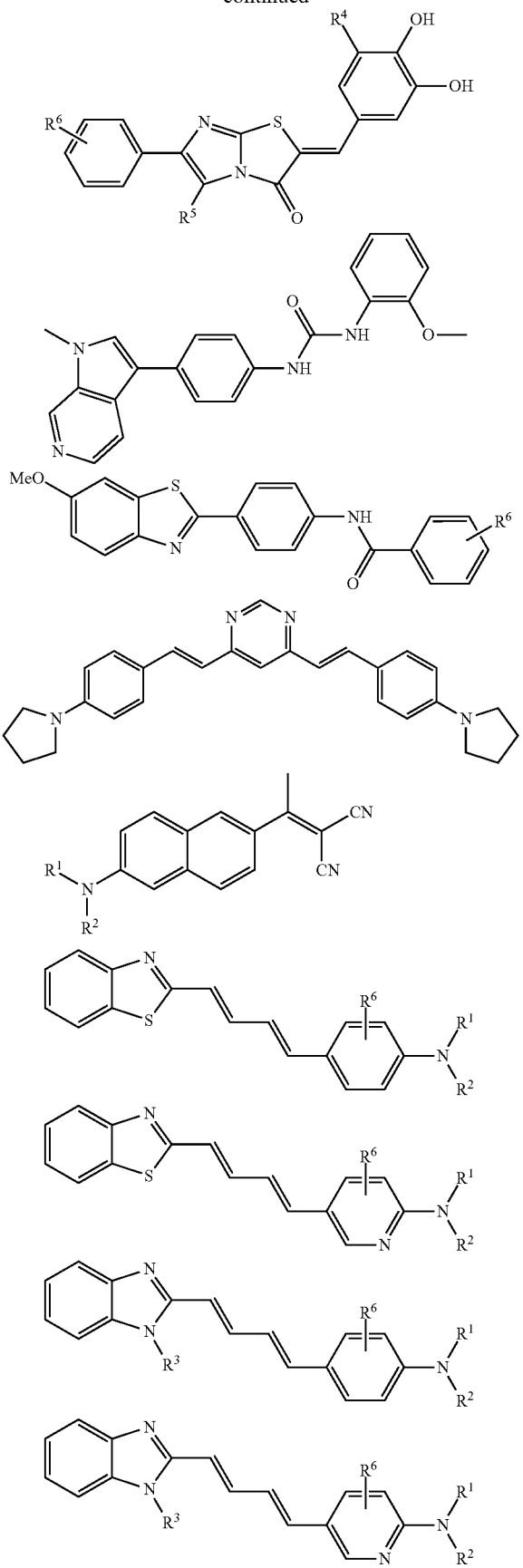

-continued

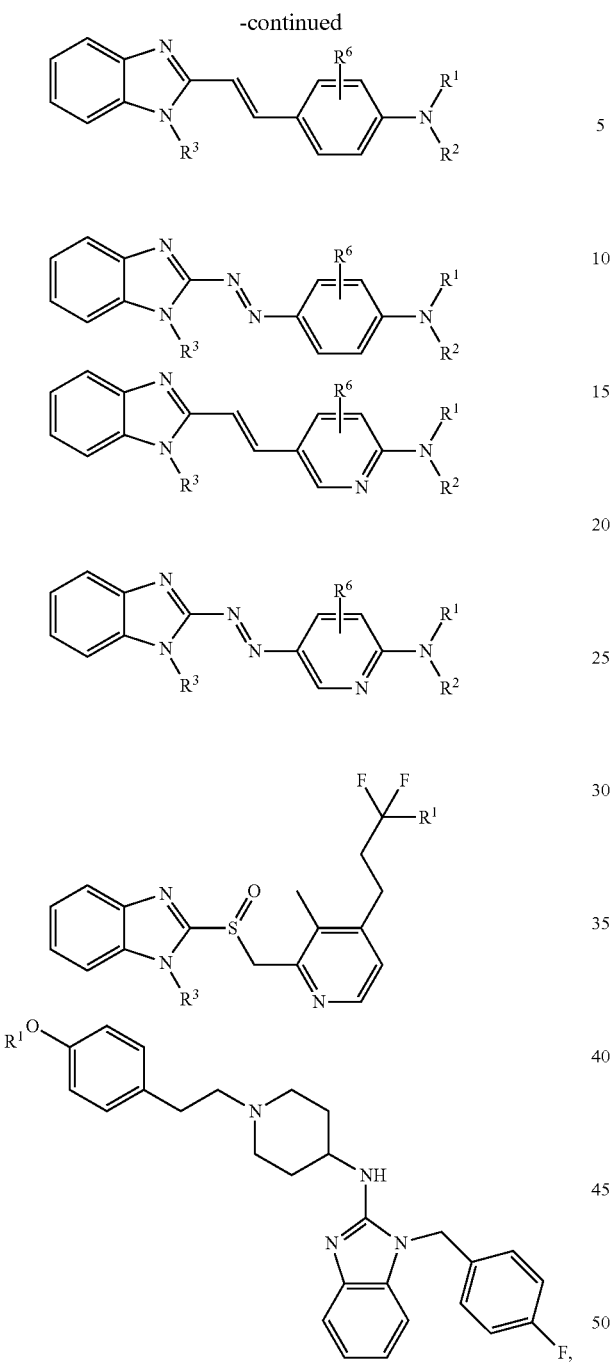

wherein:
$R^1$, $R^2$ and $R^3$ are independently selected from H, methyl, ethyl, 2-fluoroethyl and 2,2,2-trifluoroethyl;
$R^4$ and $R^5$ are independently selected from H, methyl, ethyl and halogen; and
$R^6$ is 1 to 2 substituents independently selected from H, methyl, ethyl and halogen,
wherein the PTM is coupled to a ULM via L.

In any of the aspects or embodiments described herein, the PTM is covalently coupled to one or more ULM (VLM or CLM) groups, or a linker to which is attached one or more ULM (VLM or CLM) groups as described herein.

In any aspect or embodiment described herein, PTM is represented by chemical structure:

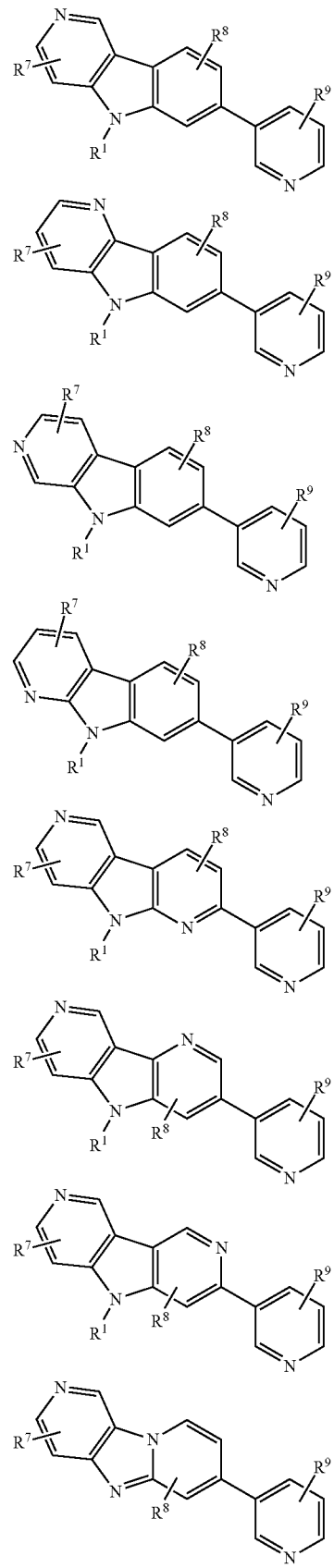

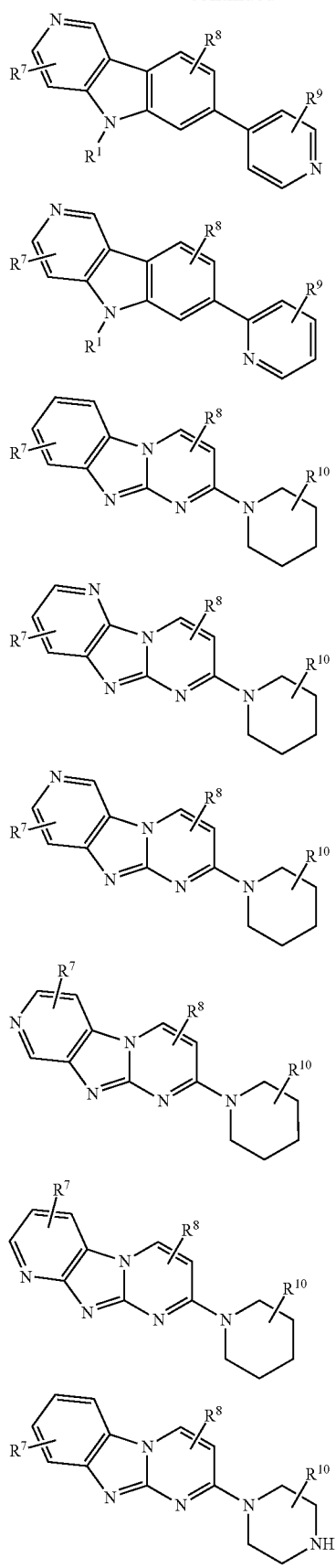
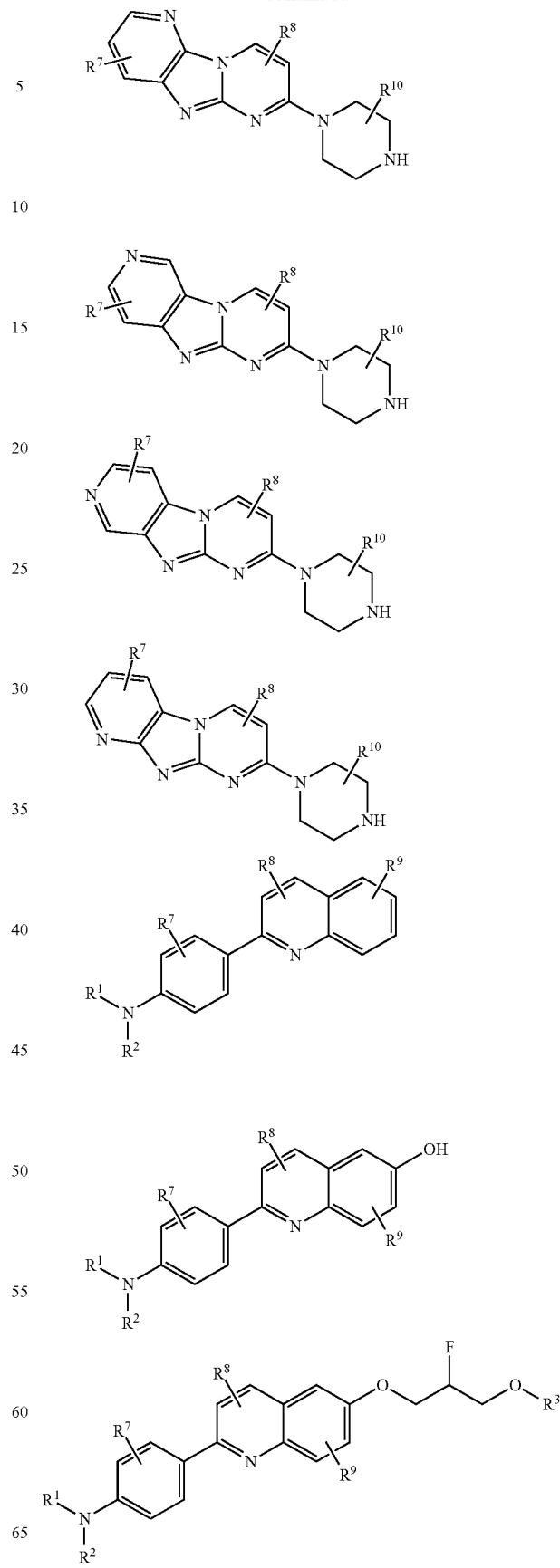

-continued

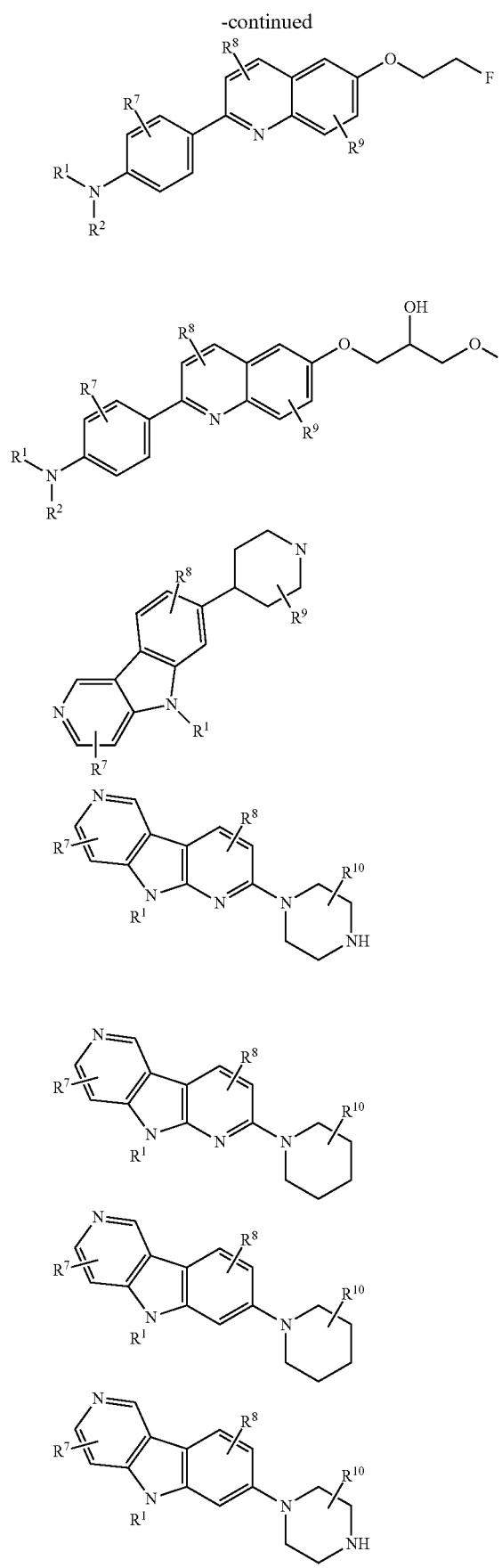

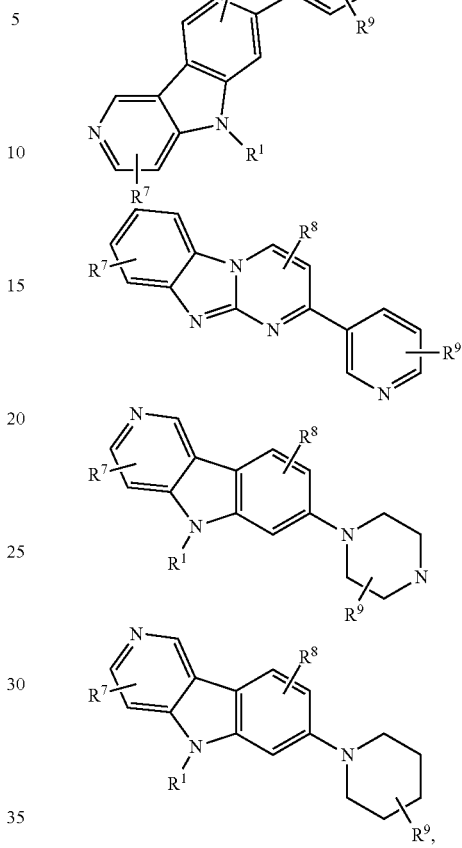

wherein:
R¹, R² and R³ are independently selected from H, optionally substituted alkyl, methyl, ethyl, 2-fluoroethyl and 2,2,2-trifluoroethyl; and
$R^7$, $R^8$, $R^9$ and $R^{10}$ are 1 to 8 substituents independently selected from H, optionally substituted alkyl, haloalkyl, halogen, hydroxyl, alkoxy, amino, dialkylamino, aceylamino, trifluoromethyl or cyano, and wherein the PTM is coupled to a ULM (VLM or CLM) via L.

In any aspect or embodiment described herein, PTM is represented by chemical structure:

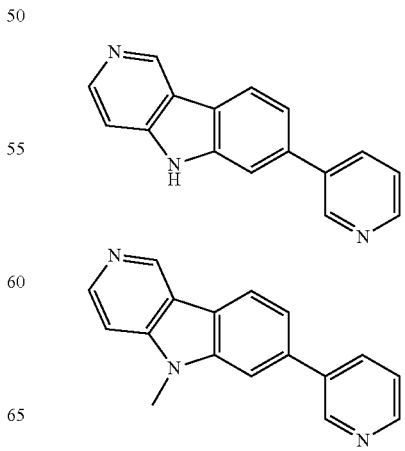

283
-continued
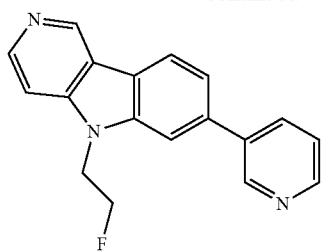
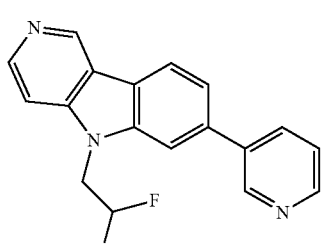
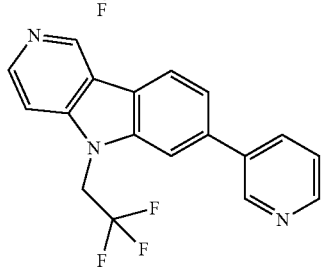
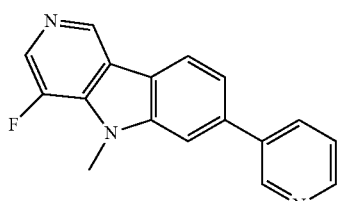
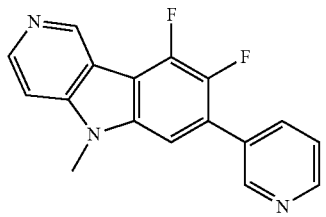
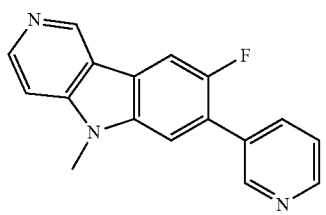
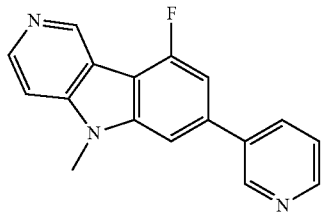
284
-continued
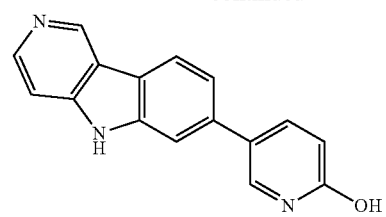
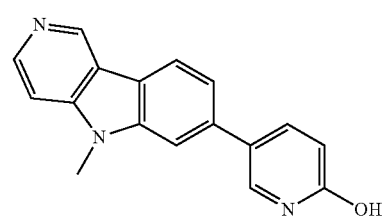
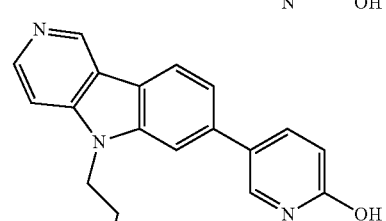
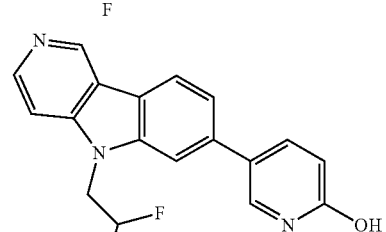
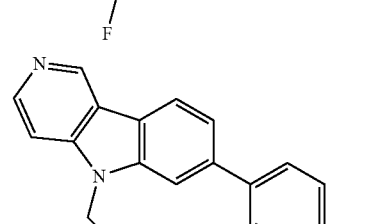
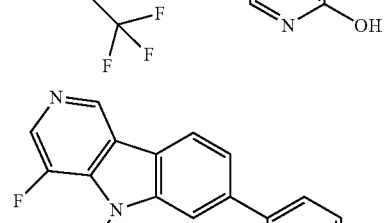
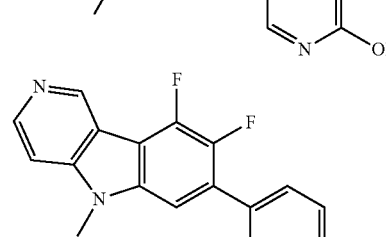

-continued
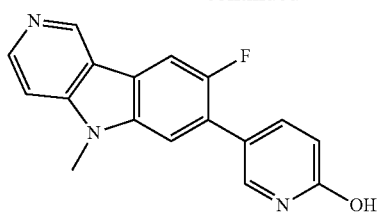
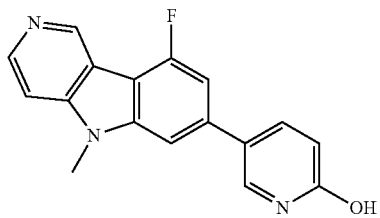
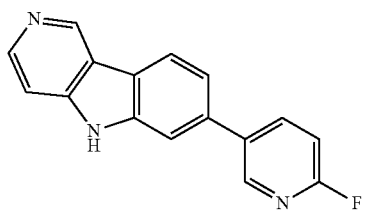
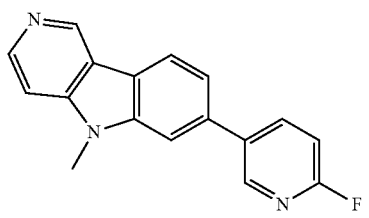
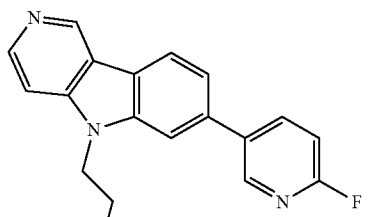
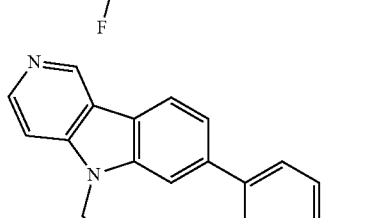
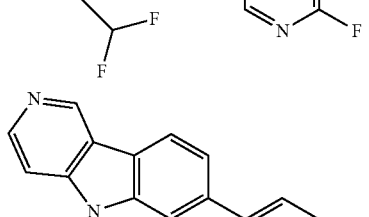
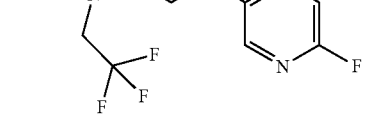
-continued
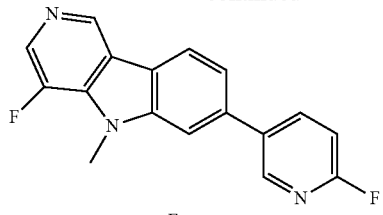
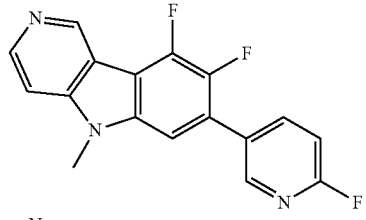
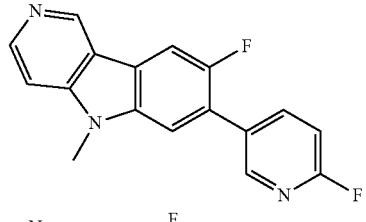
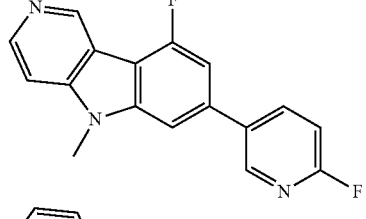
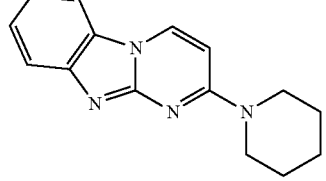
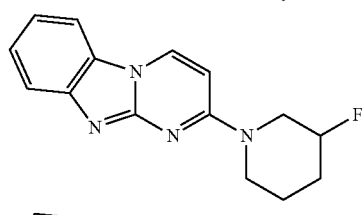
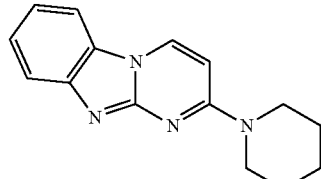
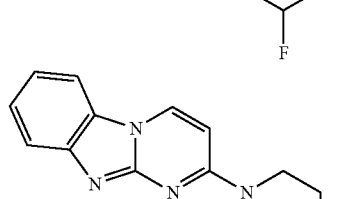

287
-continued
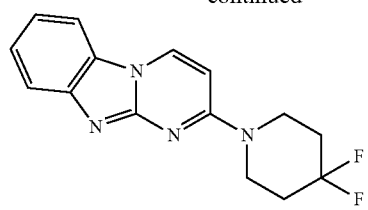
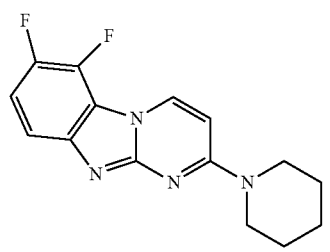
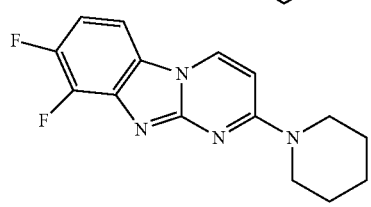
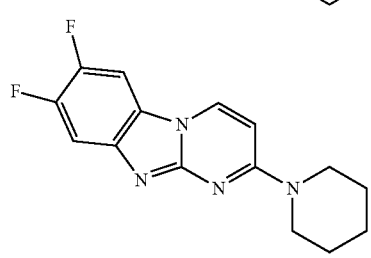
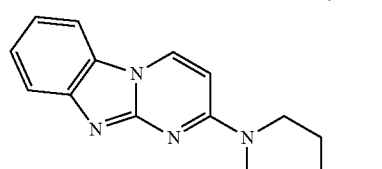
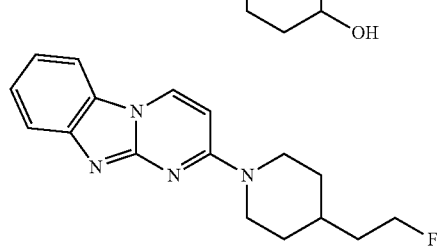
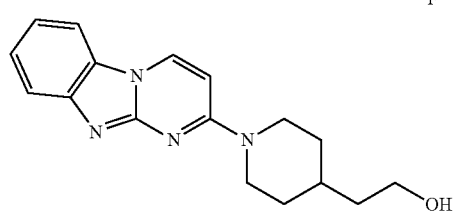
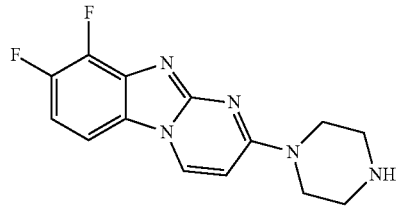
288
-continued
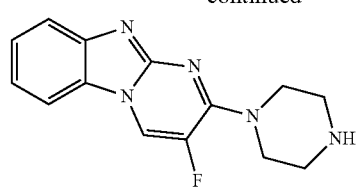
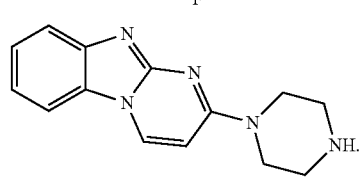
In any aspect or embodiment described herein, the linker attachment point to PTM is as indicated by the dotted line:
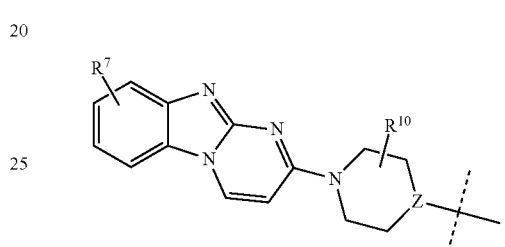
Z = N, CH
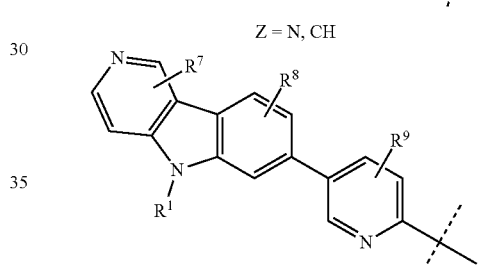
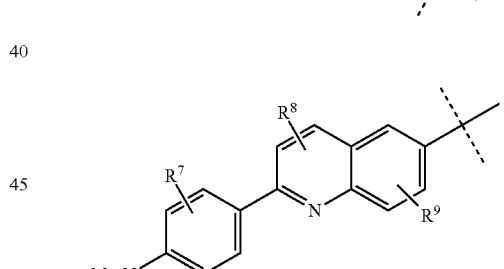
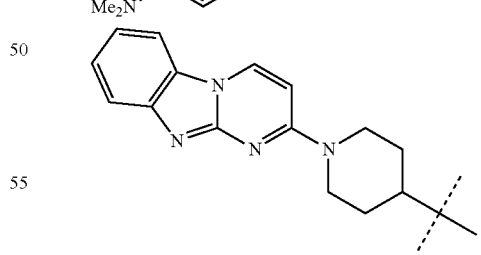
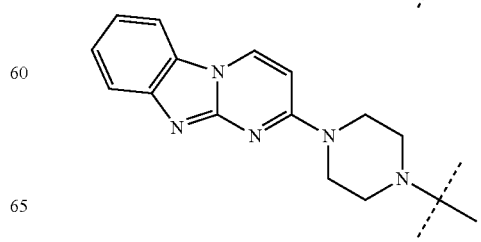

-continued

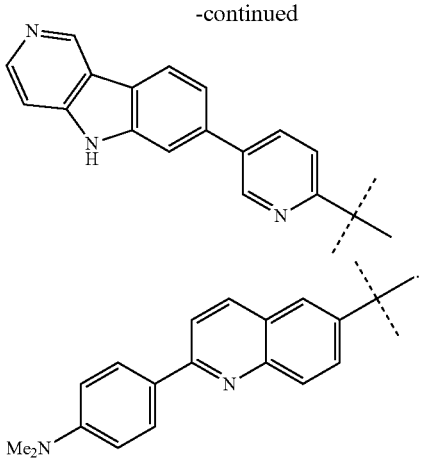

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosureion may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. In certain preferred aspects of the invention, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyl-dodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known erythopoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 PM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain preferred aspects of the invention, one or more compounds according to the present disclosure are coadministered with another bioactive agent, such as an erythropoietin stimulating agent or a would healing agent, including an antibiotic, as otherwise described herein.

Solutions or suspensions used for parenteral, intradermal, subcutaneous, or topical application can include the following components, a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present disclosure are set forth hereinabove.

The description provides therapeutic compositions as described herein for effectuating the degradation of proteins of interest for the treatment or amelioration of a disease, e.g., cancer. In certain additional embodiments, the disease is multiple myeloma. As such, in another aspect, the description provides a method of ubiquitinating/degrading a target protein in a cell. In certain embodiments, the method comprises administering a bifunctional compound as described herein comprising, e.g., a CLM and a PTM, preferably linked through a linker moiety, as otherwise described herein, wherein the CLM is coupled to the PTM and wherein the CLM recognizes a ubiquitin pathway protein (e.g., an ubiquitin ligase, preferably an E3 ubiquitin ligase such as, e.g., cereblon) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or emeliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in that patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states of conditions which may be treated using compounds according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

Further disease states or conditions which may be treated by compounds according to the present disclosure include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barre syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present disclosure include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alstrom syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia, familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Kennedy's syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alstrom syndrome), Vrolik disease, Waardenburg syndrome, Warburg Sjo Fledelius Syndrome, Weissenbacher-Zweymuller syndrome, Wolf-Hirschhorn syndrome, Wolff Periodic disease, Weissenbacher-Zweymuller syndrome and Xeroderma pigmentosum, among others.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent" or "additional anti-HIV agent" includes, for example, nucleoside reverse transcriptase inhibitors (NRTI), other non-nucloeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure include, for example, other NNRTI's (i.e., other than the NNRTI's according to the present disclosure) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea (PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/CLMs.

With PTMs and ULMs (e.g. CLMs) in hand one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

Abbreviations:
  ACN: acetonitrile
  AcOH, acetic acid
  ADDP: 1,1'-(azodicarbonyl)dipiperidine
  aq., aqueous
  BAST: N,N-bis(2-methoxyethyl)aminosulfur trifluoride
  BINAP, 2,2'-bis(diphenylphosphino)-1,1'-binaphthalene
  Boc, tert-butoxycarbonyl
  $Boc_2O$, di-tert-butyl decarbonate
  BOP, (benzotriazol-1-yloxy)tris(dimethylamino)phosphonium hexafluorophosphate
  BPO: benzoyl peroxide
  Cbz: Carbonylbezyloxy
  $CDCl_3$, deuteriochloroform
  CD3OD, deuteriomethanol
  $CH_3CN$, acetonitrile
  $CH_3OH$, methanol
  CsF, cesium fluoride
  $Cs_2CO_3$, cesium carbonate
  $Cu(OAc)_2$, copper (II) acetate
  $Cy_2NMe$, dicyclohexylmethylamine
  DAST: diethylaminosulfur trifluoride
  DBE: 1,2-dibromoethane
  DCM: dichloromethane
  DEAD: diethyl azodicarboxylate
  DIAD: diisopropyl azodicarboxylate
  DIBAL: disiobutylaluminium hydride
  DIEA or DIPEA: diisopropylethylamine
  DMA: N,N-dimethylacetamide
  DMAP, N,N-dimethylaminopyridine
  DMF: N,N-dimethylformamide
  DMP: Dess-Martin periodinane
  DMSO, dimethylsulfoxide
  $DMSO-d_6$, hexadeuterodimethyl sulfoxide
  EA: ethyl acetate
  EDCI: 1-ethyl-3-(3-dimethylaminopropyl)carbodiimide
  $Et_2NH$, diethylamine
  EtOAc or EA, ethyl acetate
  HCl, hydrochloric acid
  $H_2O$, water
  HBTU: N,N,N'N'-tetramethyl-O-(1H-benzotriazol-1-yl)uronium hexafluorophosphate
  HMDS: bis9trimethylsilyl)amine
  HMPA: hexamethylphosphoramide
  HPLC, high performance liquid chromatography
  IBX, 2-iodoxybenzoic acid
  KOAc, potassium acetate
  LCMS, liquid chromatography/mass spectrometry
  LDA: lithium diisopropylamide
  LiOH, lithium hydroxide
  MCPBA: meta-chloroperoxybenzoic acid
  MeOH, methanol
  MsCl: methanesulfonyl chloride
  M.W: microwave
  $N_2$, nitrogen
  NaH, sodium hydride
  $NaBH_3CN$, sodium cyanoborohydride
  $NaBH(OAc)_3$, sodium triacetoxyborohydride
  NaCl, sodium chloride
  $NaHCO_3$, sodium bicarbonate
  NaI, sodium iodide
  $Na_2SO_4$, sodium sulfate
  NBS: N-bromosuccinimide
  n-BuLi, n-butyllithium
  $NH_3$, ammonia
  $NH_4Cl$, ammonium chloride
  $NH_2OH$ HCl, hydroxylamine hydrochloride
  NMP, N-methylpyrrolidone
  NMR, nuclear magnetic resonance
  $O_2$, oxygen
  PCC: pyridinium chlorochromate Pd-118 or Pd(dtpf)Cl₂: 1,1'-bis(di-tert-butylphosphino)ferrocene dichloropalladium Pd(aMPhos)Cl₂, bis(di-tert-butyl(4-dimethylaminophenyl)phosphine)dichloropalladium(II)

Pd₂(dba)₃: Tris(dibenzylideneacetone)dipalladium

Pd(dppf)Cl₂: 1,1'-bis(diphenylphosphino)ferrocene dichloropalladium

Pd(dba)₂: bis(dibenzylideneacetone)palladium

Pd(OH)₂, palladium hydroxide

Pd(PPh₃)₄, tetrakis(triphenylphosphine)palladium(0)

PE, petroleum ether

Ph₃P, triphenylphosphine

PPTS: pyridium p-tolunesulfonate

PTSA: p-toluenesulfonic acid

Py, pyridine

PyBOP, (benzotriazol-1-yloxy)tripyrrolidinophosphonium hexafluorophosphate rt, room temperature RuPhos-Pd-G3: XPhos-Pd-G3: [(2-dicyclohexylphosphino-2',6'-diisopropoxy-1,1'-biphenyl)-2-(2'-amino-1,1'-biphenyl)] palladium(II) methanesulfonate RuPhos-Pd-G2: Chloro[(2-dicyclohexylphosphino-2',6'-diisopropoxy-1,1'-biphenyl)-2-(2'-amino-1,1'-biphenyl)] palladium(II)

SFC: supercritical fluid chromatography

TBAF, tetra-n-butylammonium fluoride

TBDPSCl, tert-butyldiphenylsilyl chloride

TBS, tert-butyldimethylsilyl tBuOK, potassium tert-butoxide

[tBu₃PH]BF₄, tri-tert-butyl phosphonium tetrafluoroborate t-BuXPhos-Pd-G3: [(2-di-tert-butylphosphino-2',4',6'-triisopropyl-1,1'-biphenyl)-2-(2'-amino-1,1'-biphenyl)] palladium(II) methanesulfonate TEA: trimethylamine TFA: trifluoroacetic acid TLC: thin layer chromatography TMP: 2,2,6,6-tetramethylpiperidine TEMPO: 2,2,6,6-tetramethylpiperidine-N-oxide TMSOTf, trimethylsilyl trifluoromethanesulfonate TosCl or TsCl: p-toluenesulfonyl chloride TsCl, p-toluenesufonyl chloride TsOH: p-toluenesulfonic acid XantPhos: 4,5-bis(diphenylphosphino)-9,9-dimethylxanthene XPhos: 2-dicyclohexylphosphino-2'4'6'-triisopropylbiphenyl XPhos-Pd-G3; [(2-dicyclohexylphosphino-2',4',6'-triisopropyl-1,1'-biphenyl)-2-(2'-amino-1,1'-biphenyl)] palladium(II) methanesulfonate 12354-85-7: bis(pentamethylcyclopentadienylrhodium dichloride)

A. Exemplary Synthetic Schemes for Exemplary Estrogen Receptor Binding Moiety Based Compounds Synthetic scheme A-1, A-2 through A-5, A-6, and A-7 described the routes used in the preparation of CRBN ligands, as well as CRBN ligands with partial linker moieties connected.

General Synthetic Scheme A-1 to Prepare Intermediate.

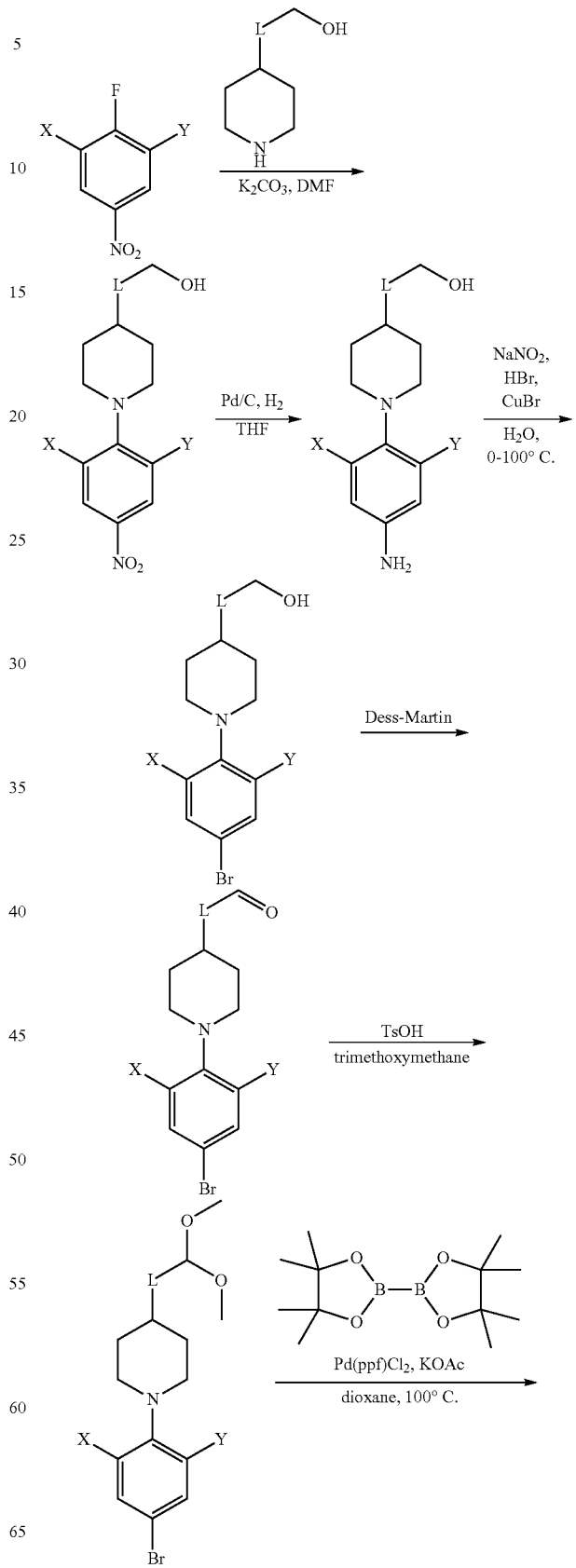

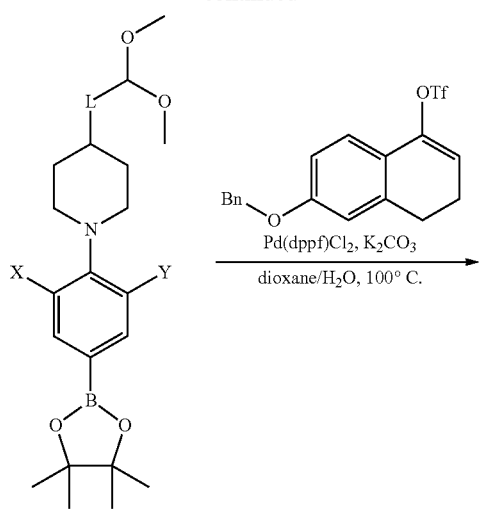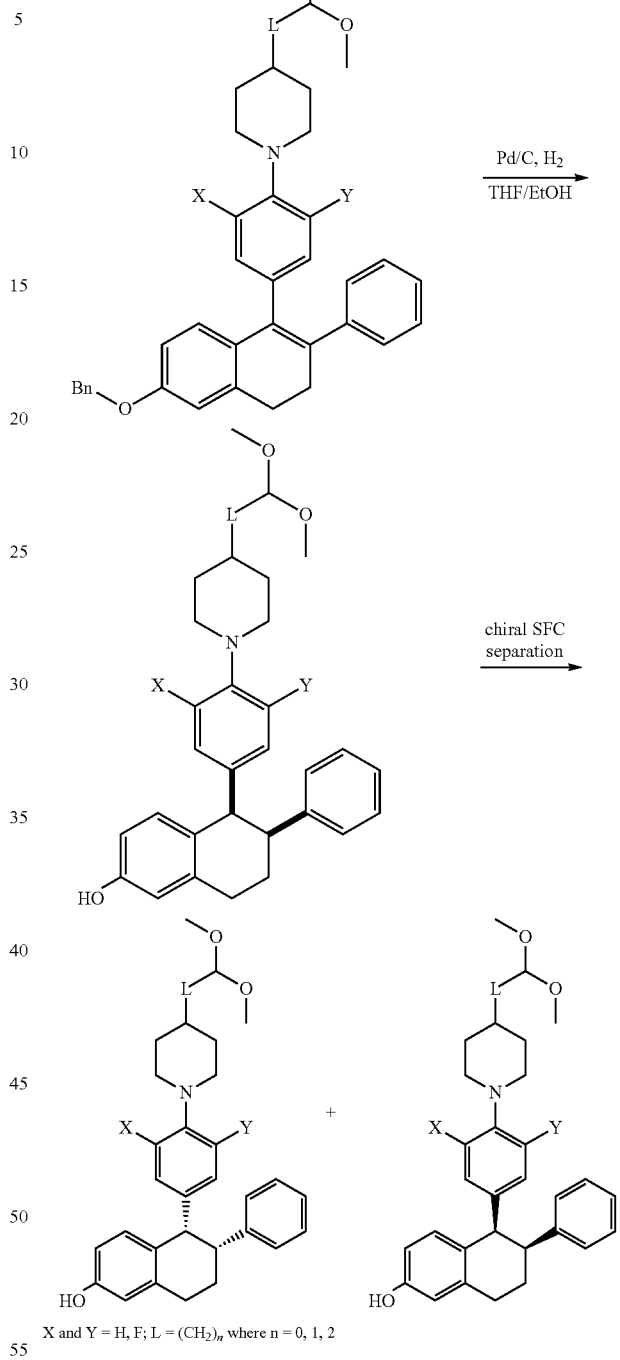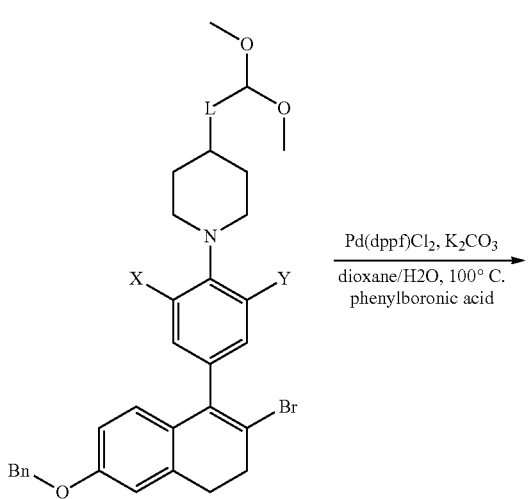
X and Y = H, F; L = $(CH_2)_n$ where n = 0, 1, 2
General Synthetic Scheme A-2 to Prepare Intermediate.
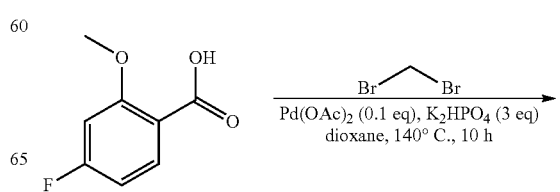

307 -continued
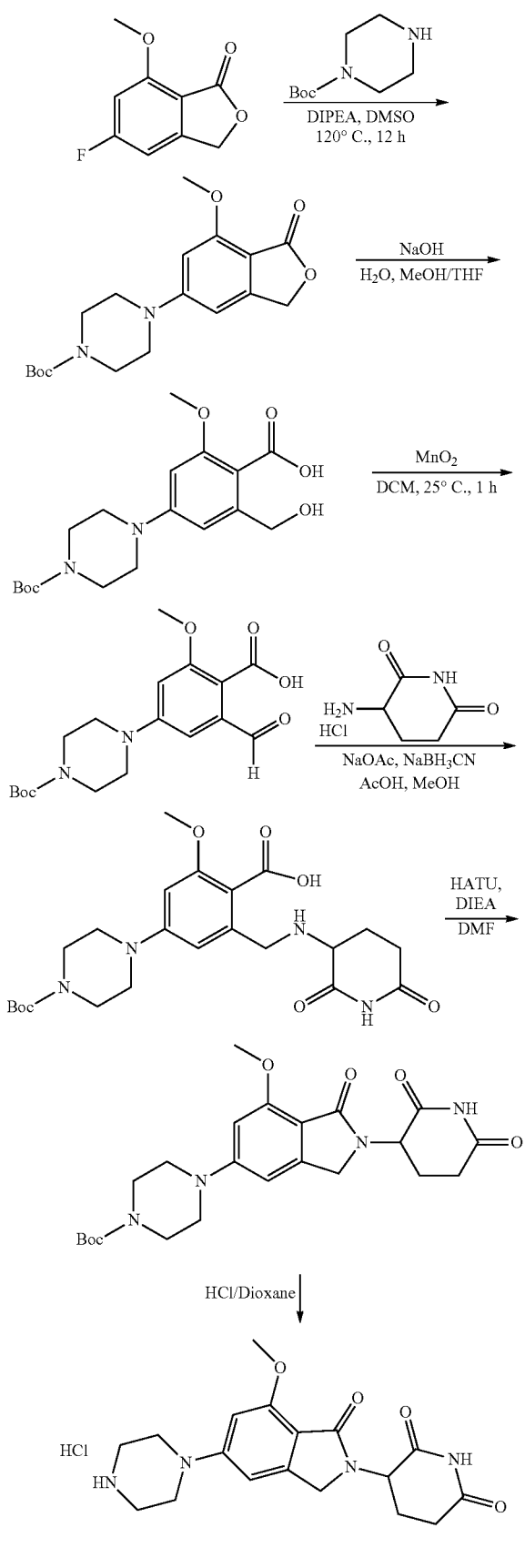
308
General Synthetic Scheme A-4 to Prepare Intermediate.
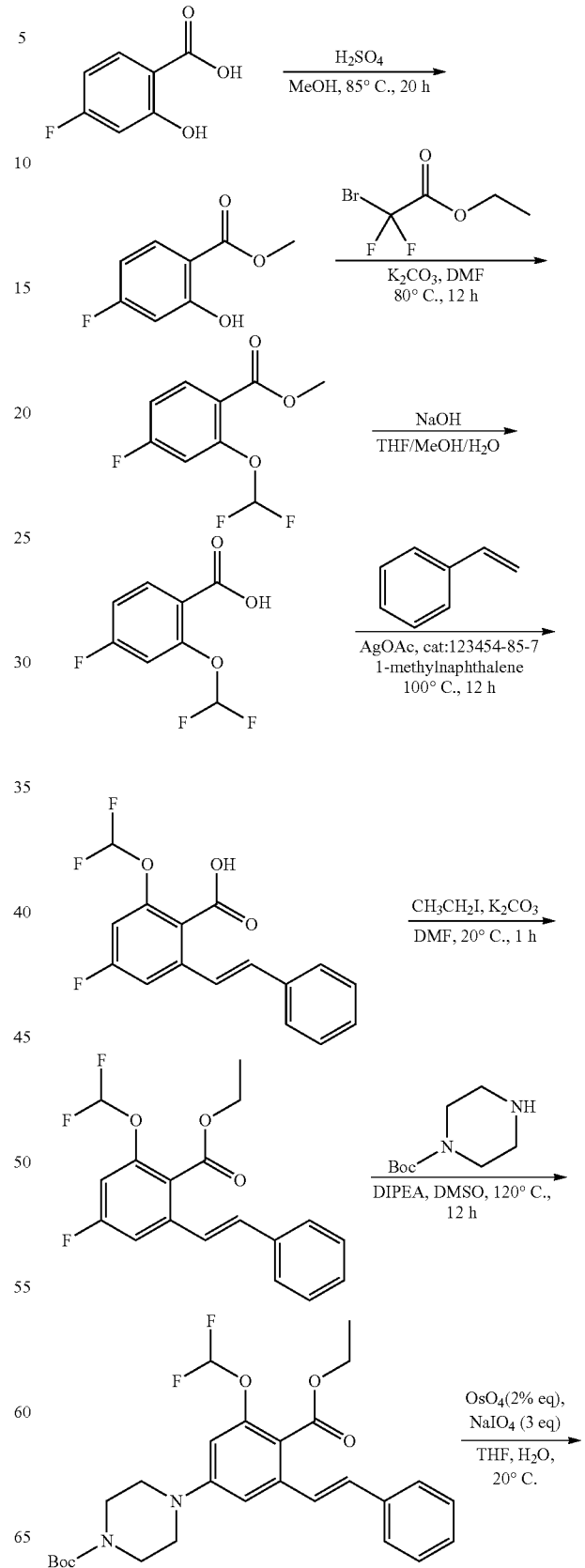

309
-continued
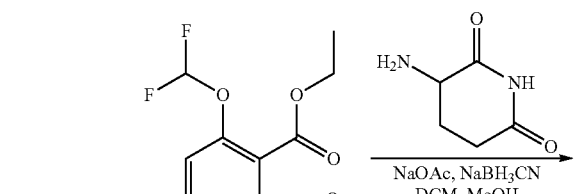
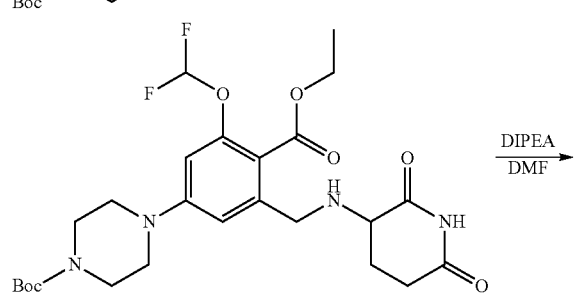
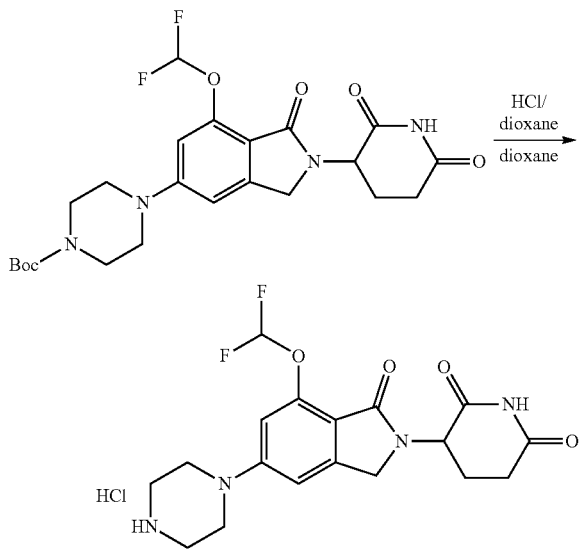
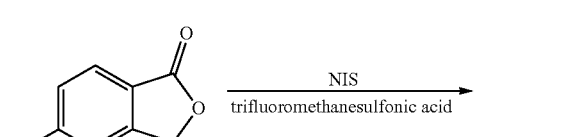
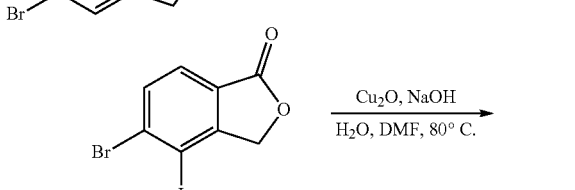
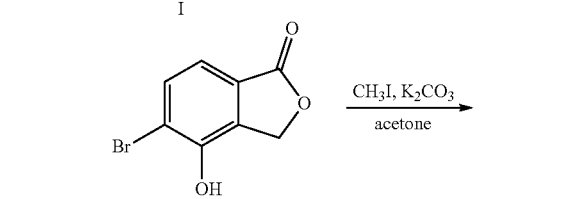
310
-continued
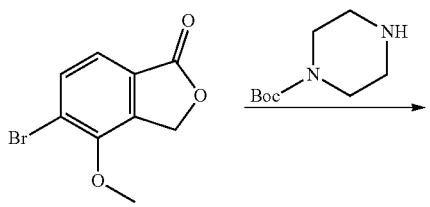
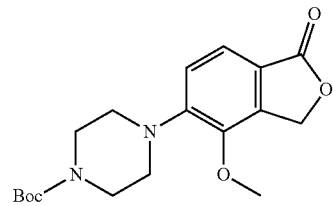
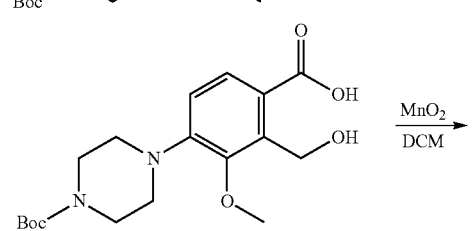
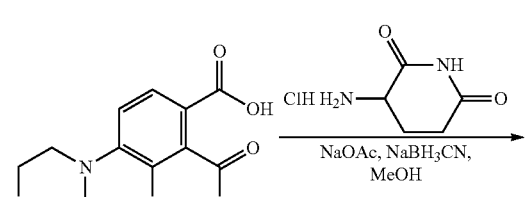
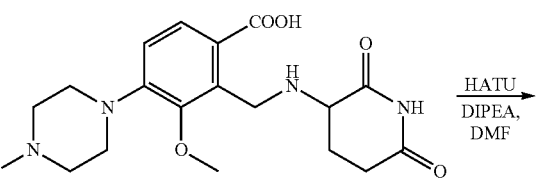
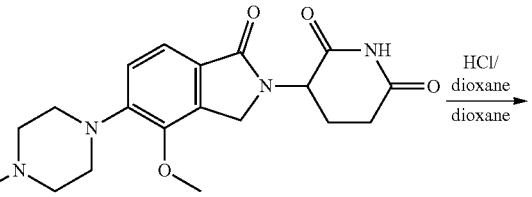
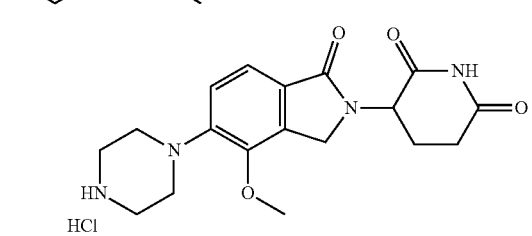

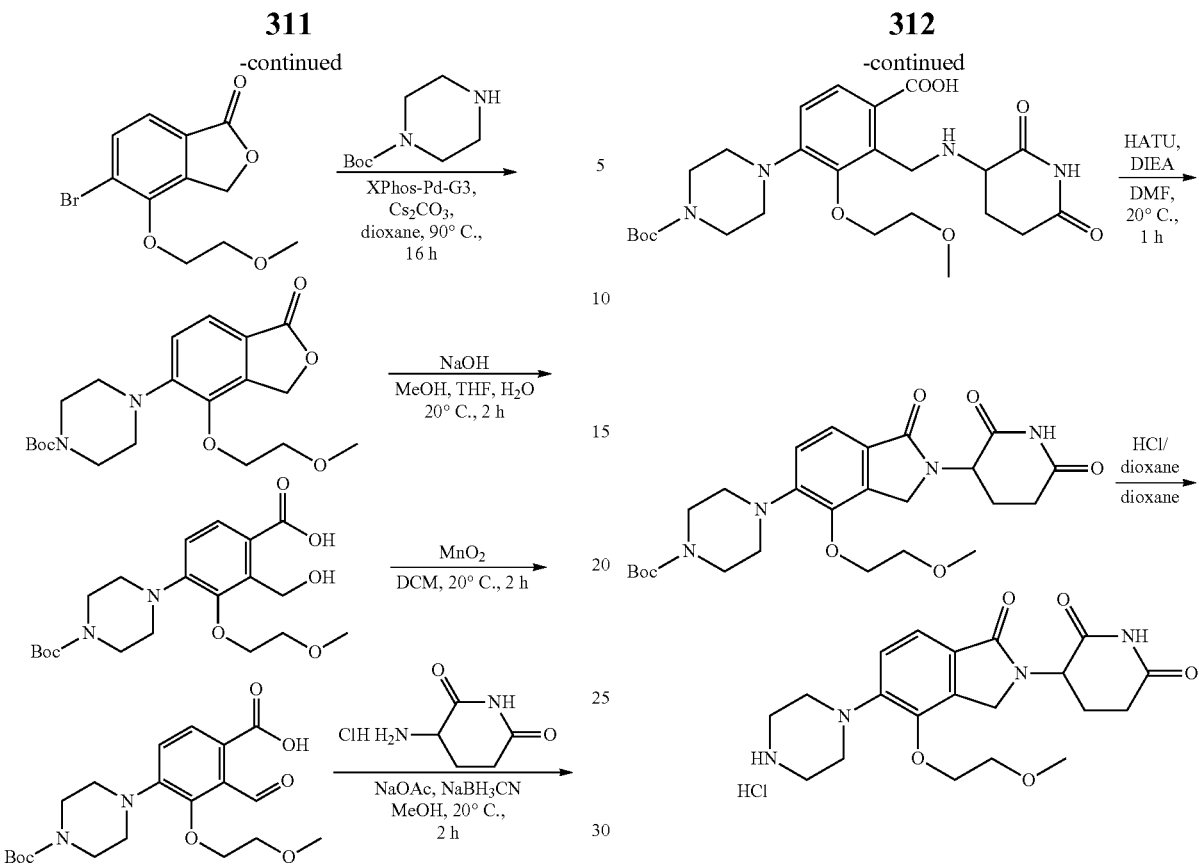
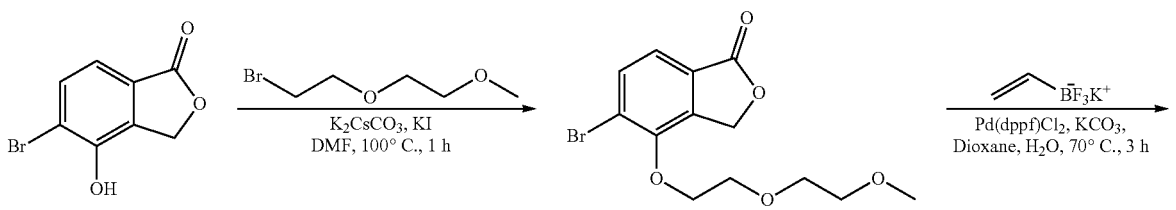
General Synthetic Scheme A-5 to Prepare Intermediate.
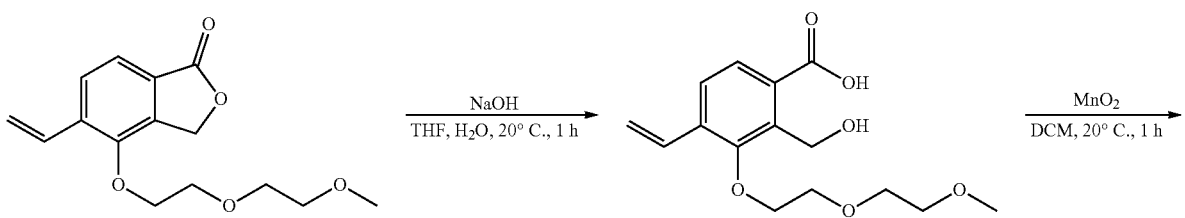
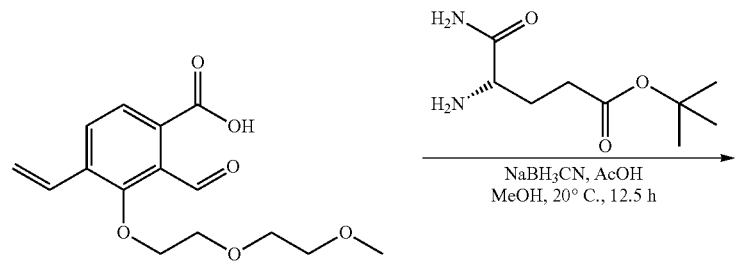

-continued
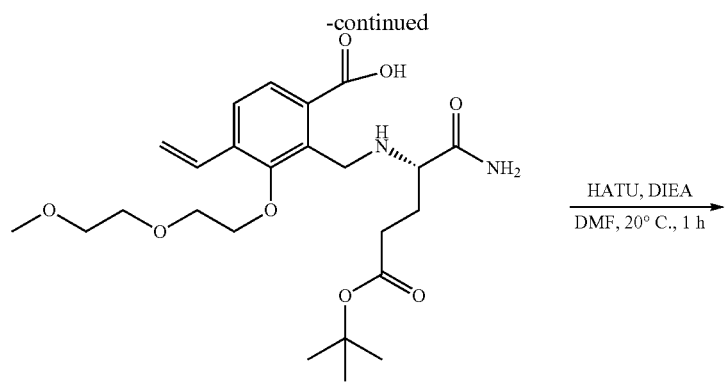
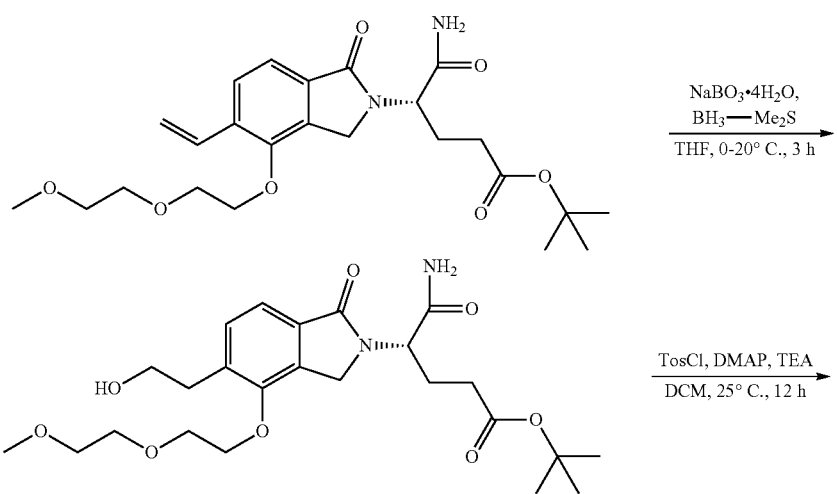
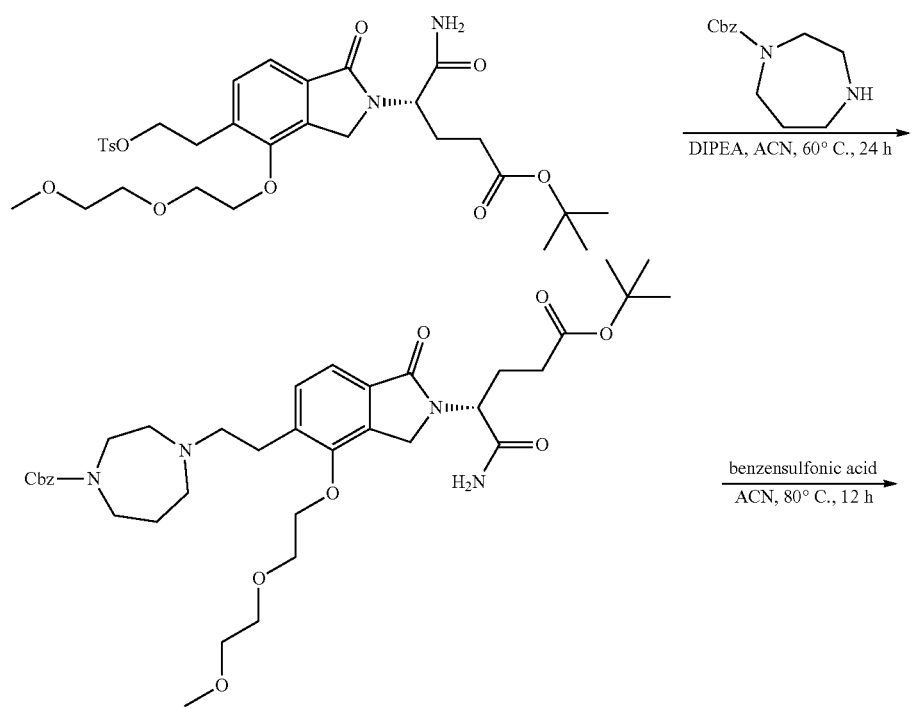

315
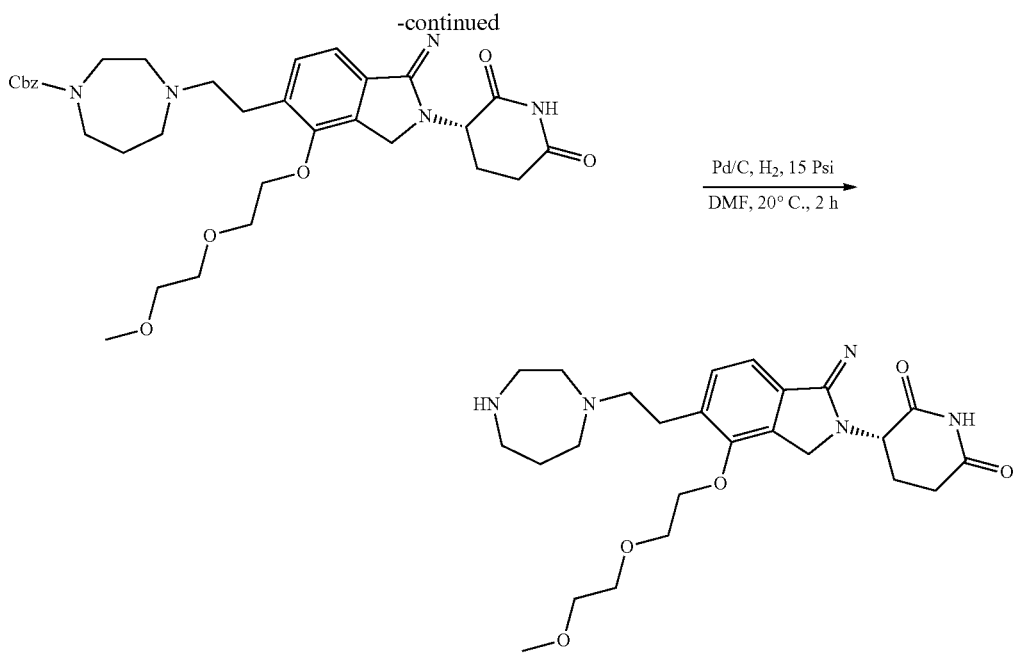
Pd/C, H₂, 15 Psi
DMF, 20° C., 2 h
General Synthetic Scheme A-6 to Prepare Intermediate.
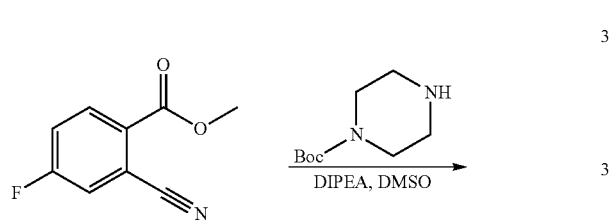
DIPEA, DMSO
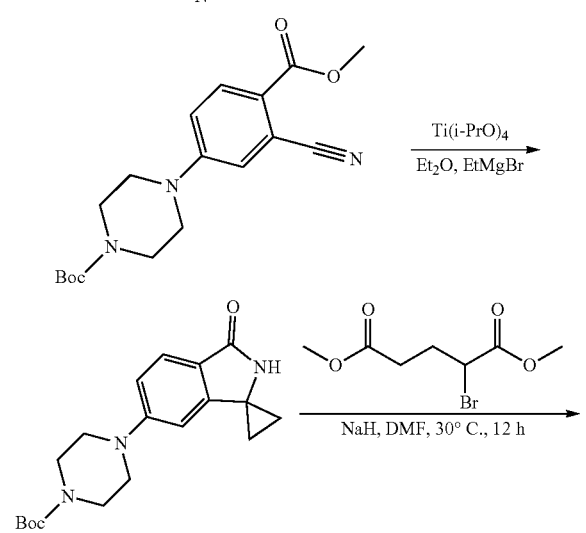
Ti(i-PrO)₄
Et₂O, EtMgBr
NaH, DMF, 30° C., 12 h
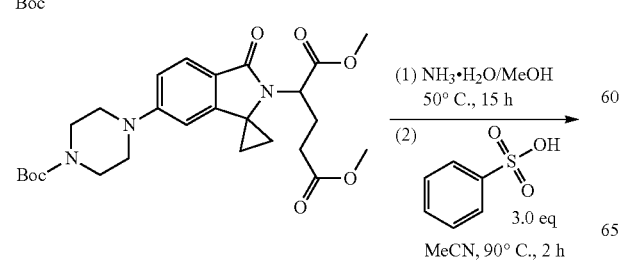
(1) NH₃·H₂O/MeOH
50° C., 15 h
(2) PhSO₃H 3.0 eq
MeCN, 90° C., 2 h
316
-continued
General Synthetic Scheme A-7 to Prepare Intermediate.
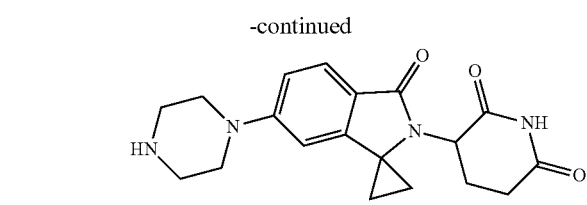
N₂H₄·H₂O
20° C., 12 hr
CDI
MeCN, 50° C., 12 h
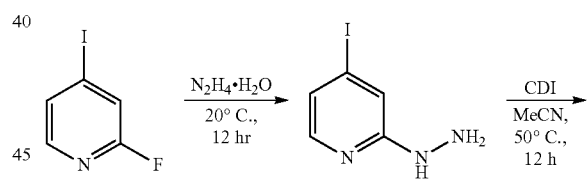
RuPhos-Pd-G2,
t-BuONa
t-Amyl-OH,
90° C., 16 h
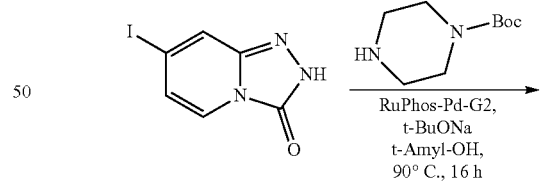
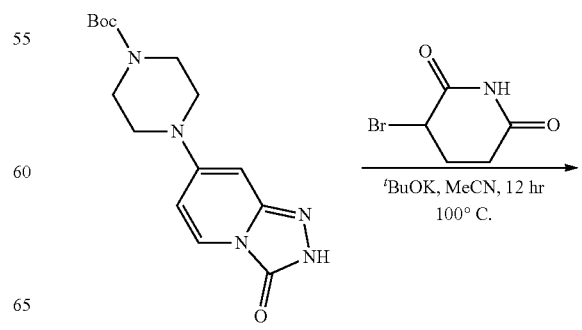
ᵗBuOK, MeCN, 12 hr
100° C.

317
-continued
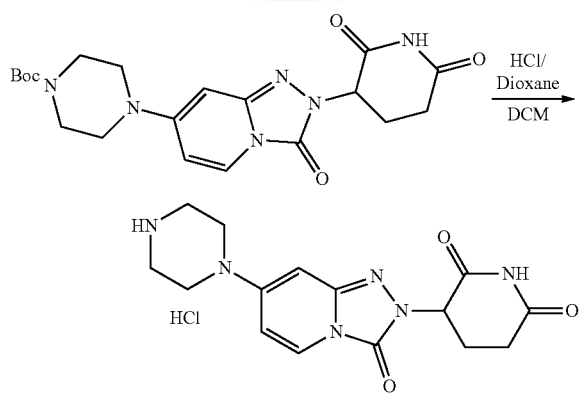
Synthetic schemes A-8, A-9, A-10, A-11, A-12, A-13, A-14, A-15, A-16, and A-17, described the routes used in the preparation of representative chimeric compounds claimed in this application.
General Synthetic Scheme A-8 to Prepare Claimed Compounds.
318
-continued
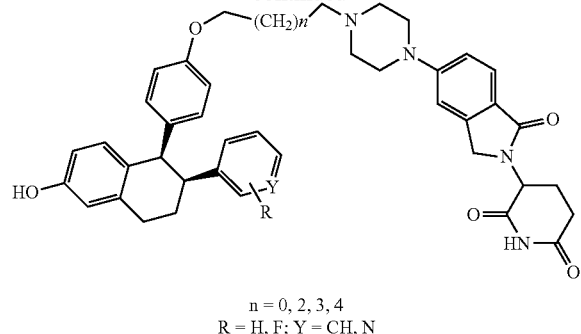
n = 0, 2, 3, 4
R = H, F; Y = CH, N
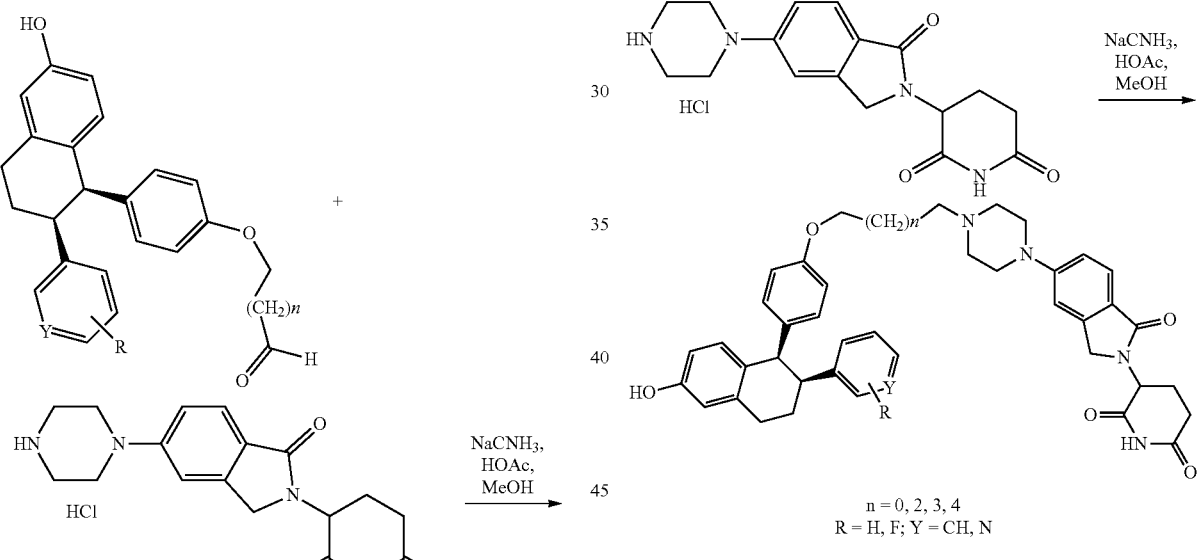
n = 0, 2, 3, 4
R = H, F; Y = CH, N
General Synthetic Scheme A-9 to Prepare Claimed Compounds.

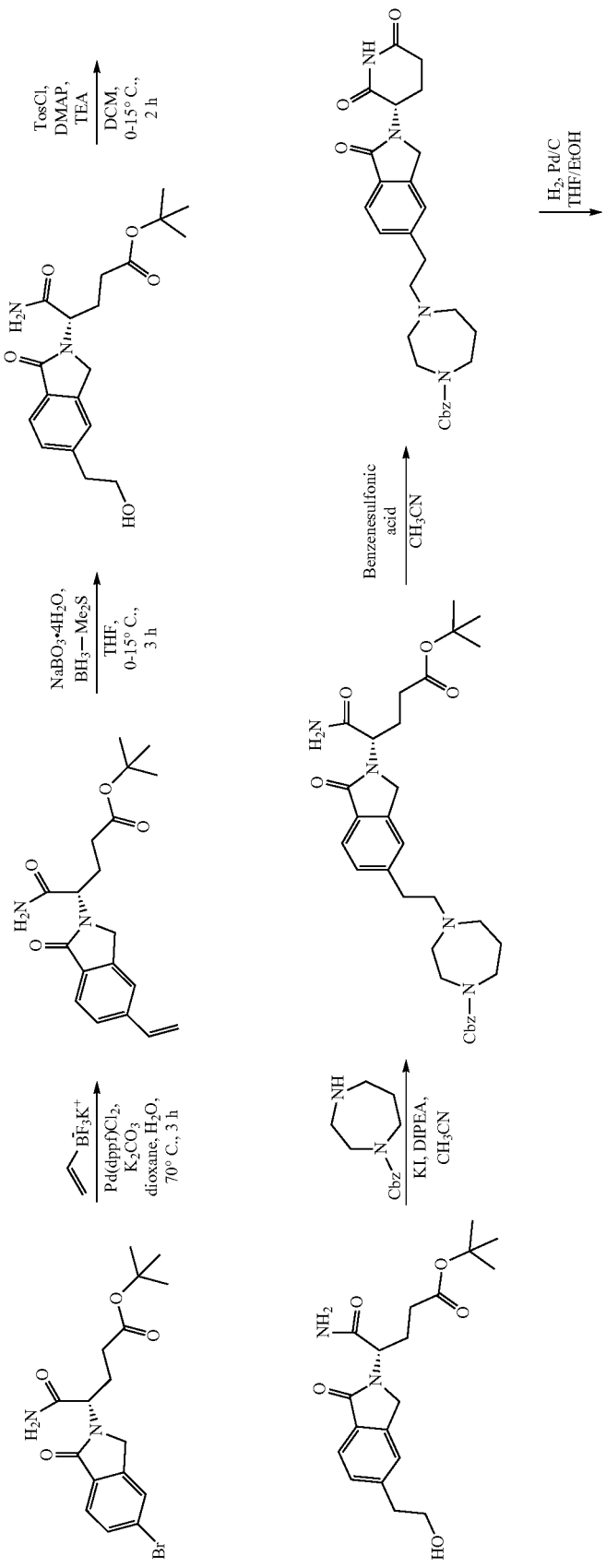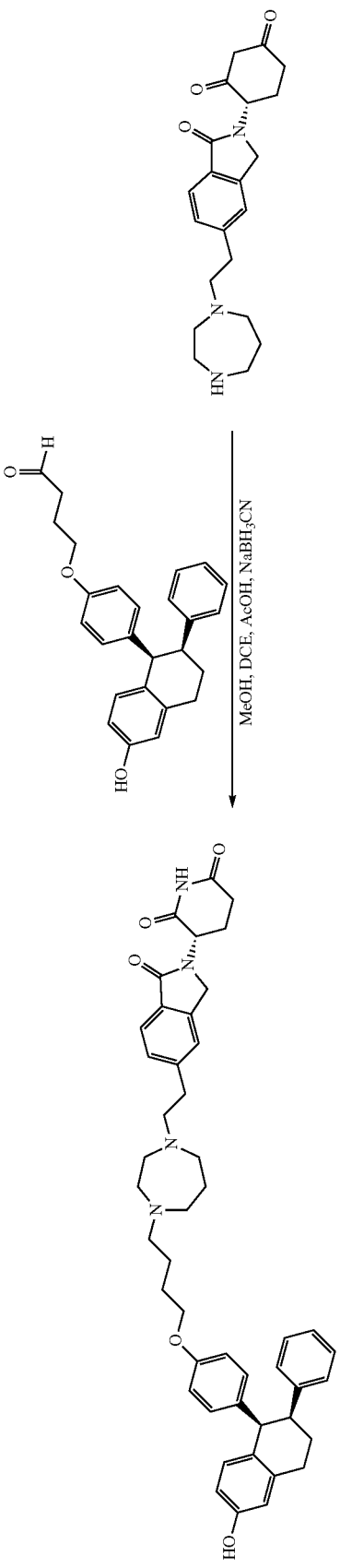

General Synthetic Scheme A-10 to Prepare Claimed Compounds.

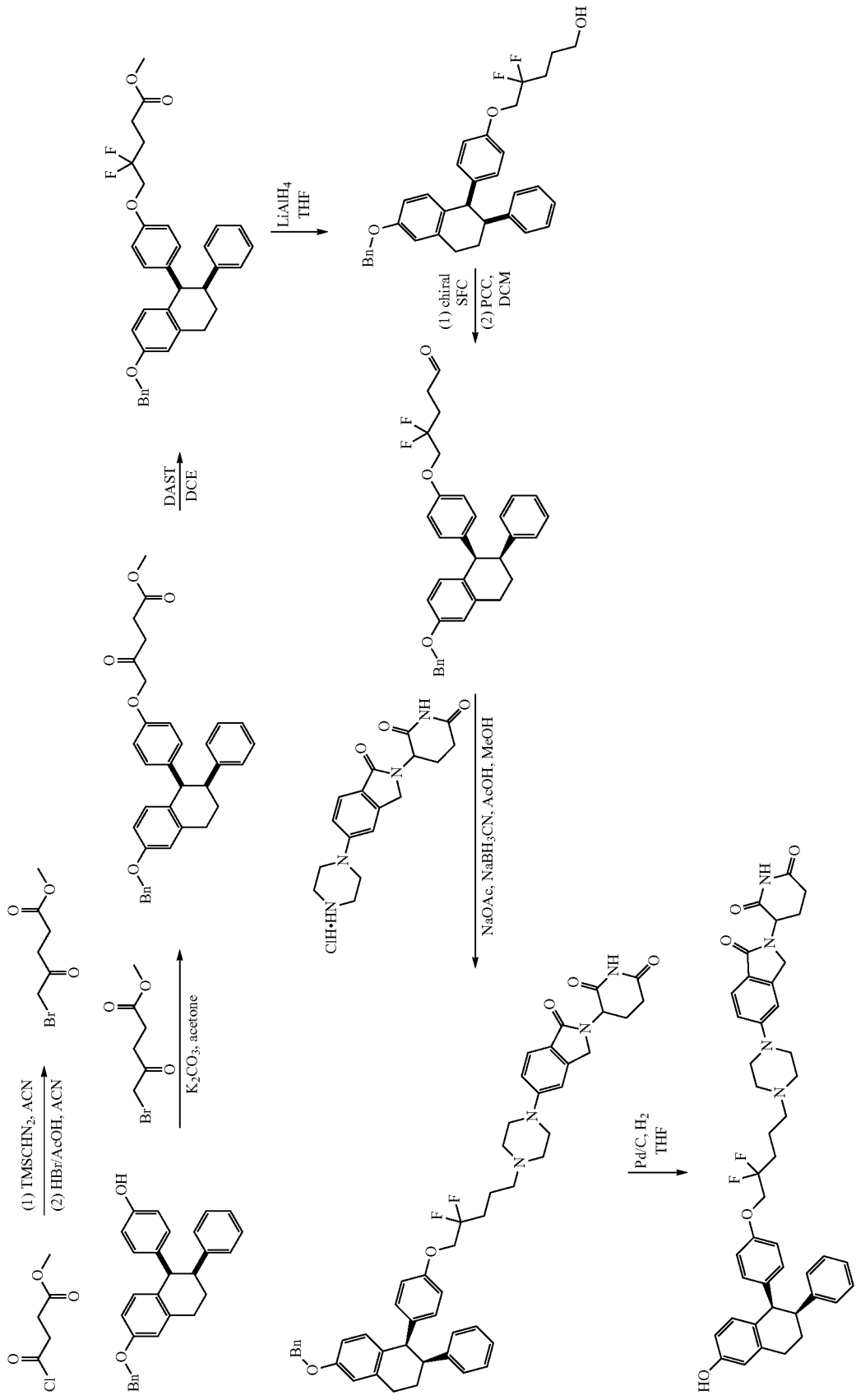

General Synthetic Scheme A-11 to Prepare Claimed Compounds.
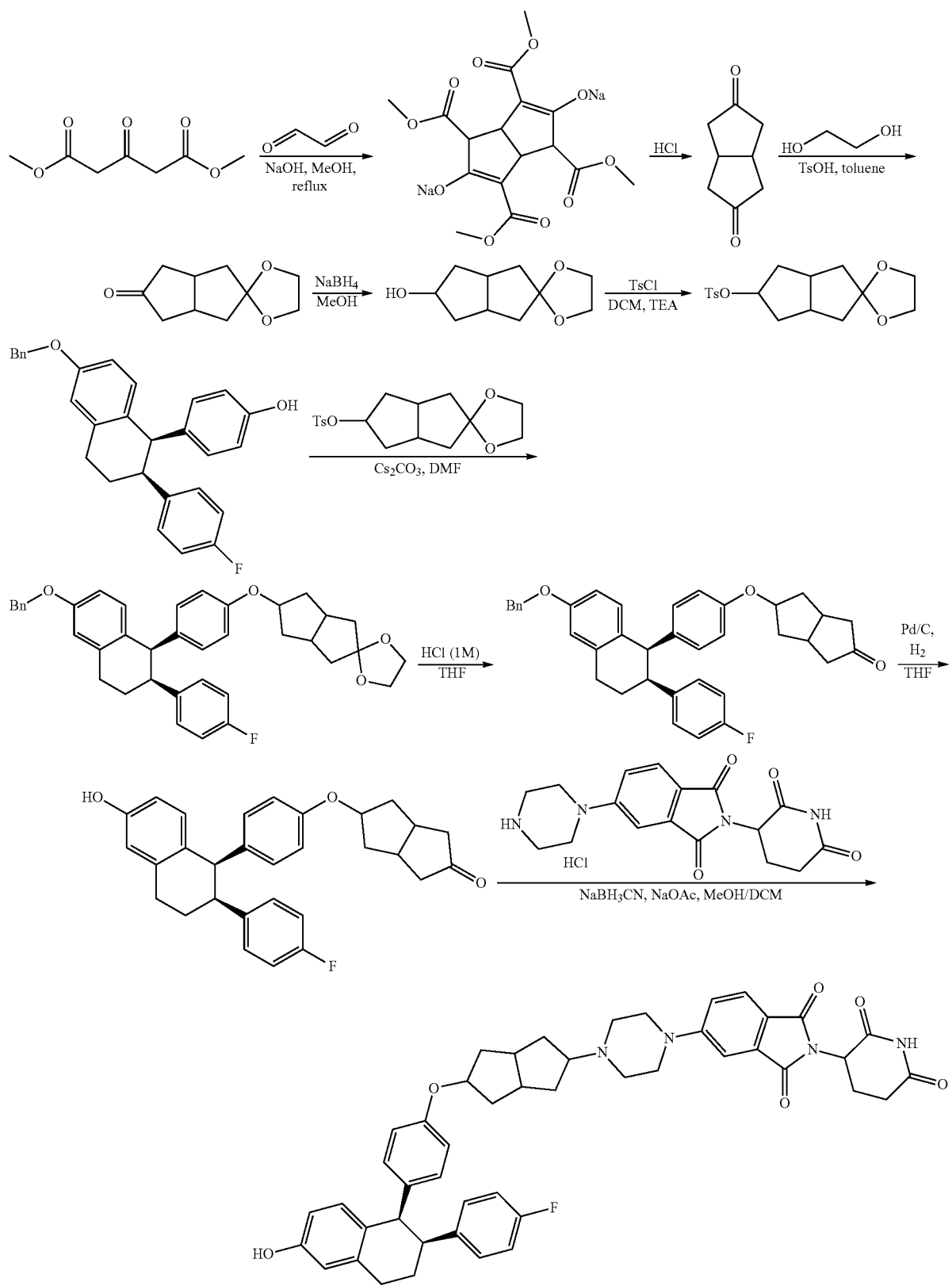

General Synthetic Scheme A-12 to Prepare Claimed Compounds.
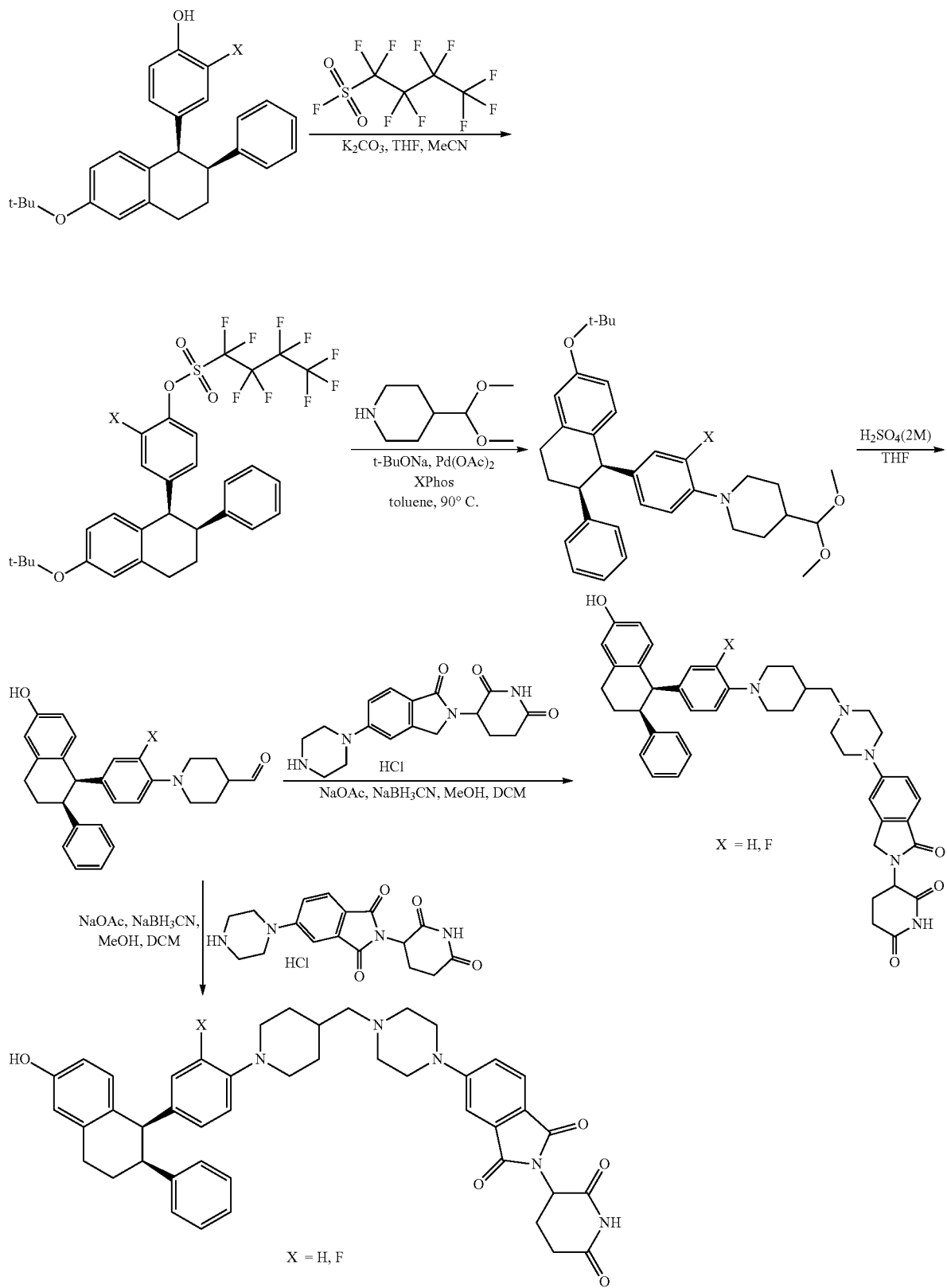

General Synthetic Scheme A-13 to Prepare Claimed Compounds.
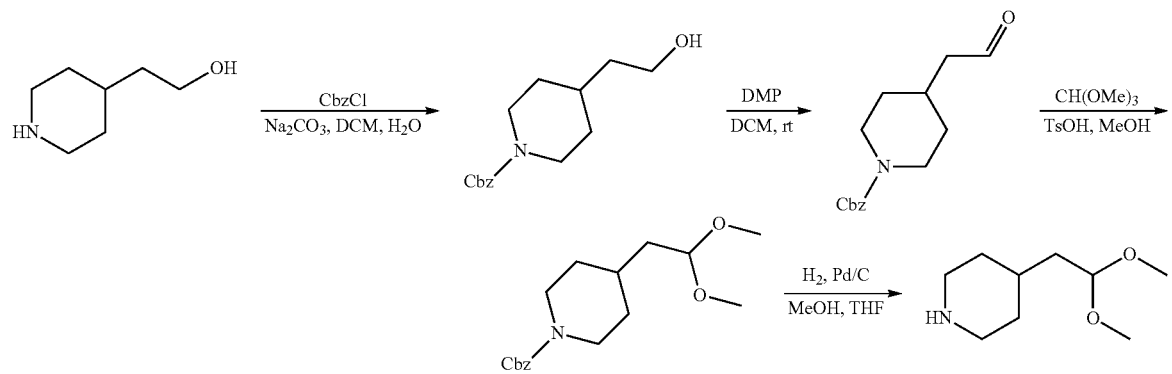
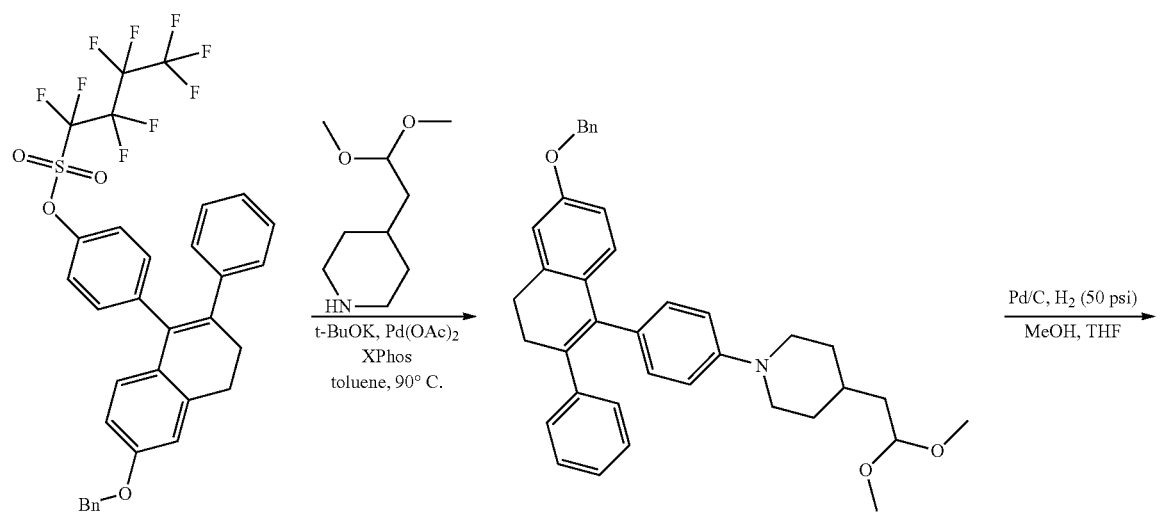
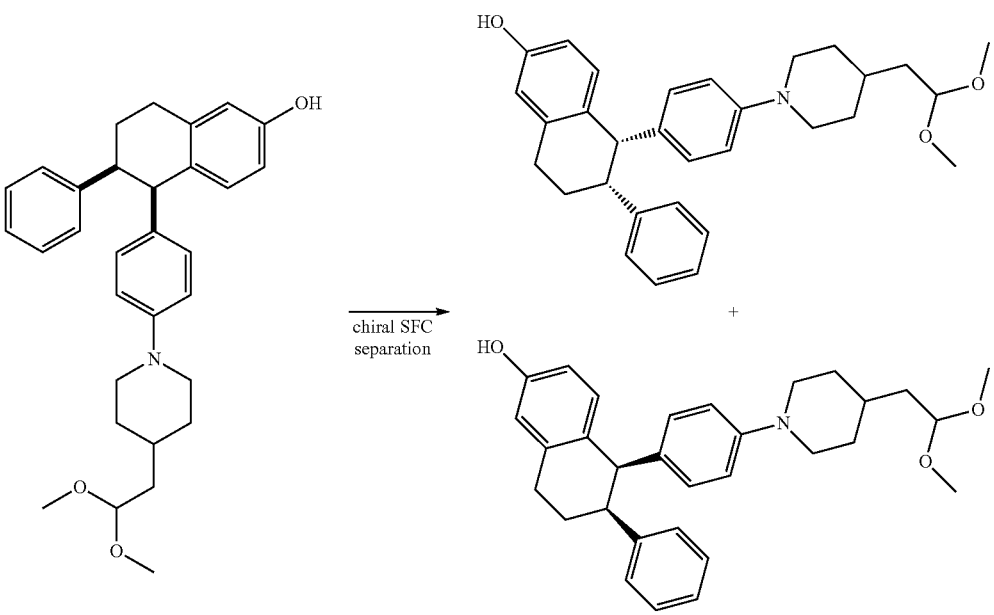

331
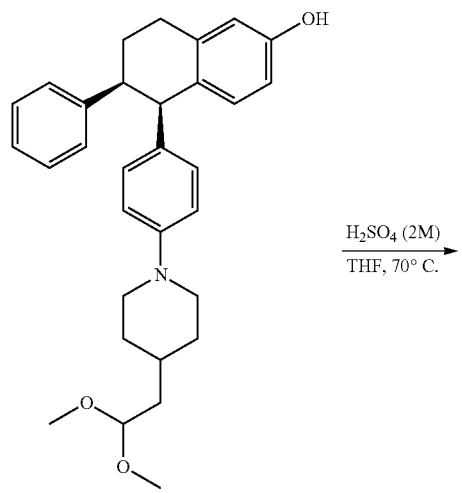
-continued
332
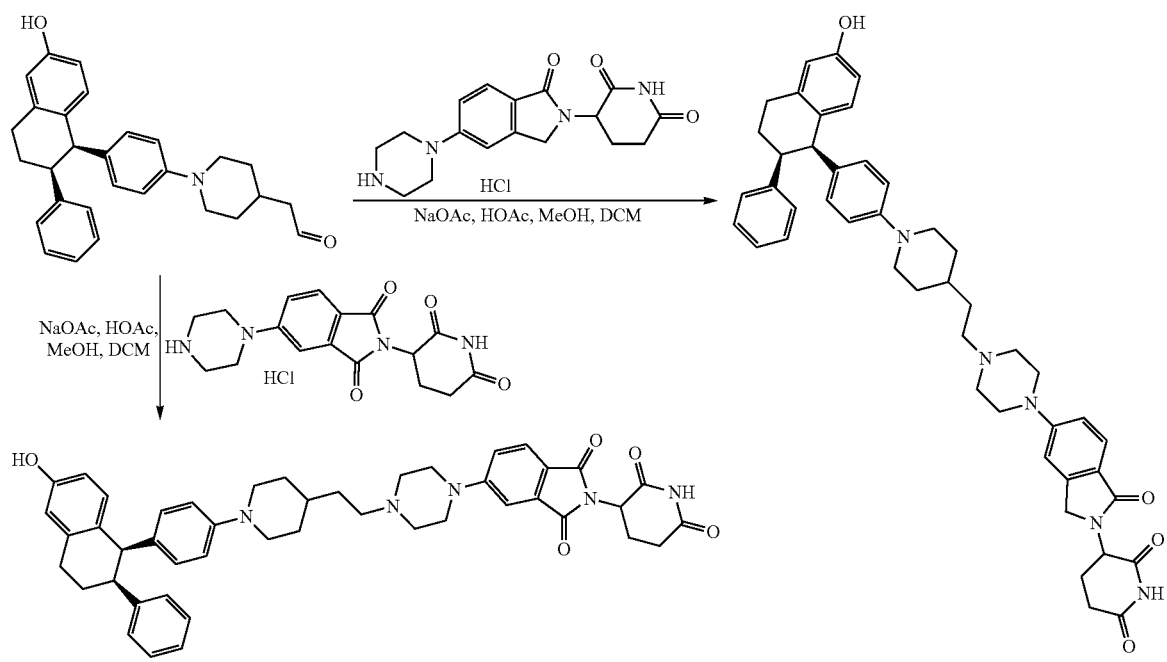
General Synthetic Scheme A-14 to Prepare Claimed Compounds.
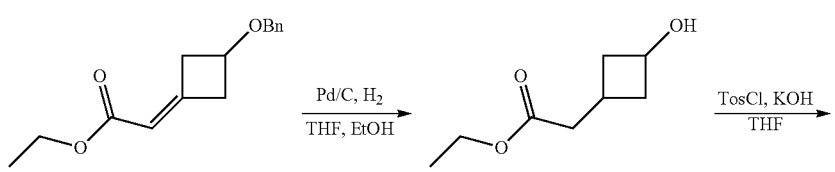

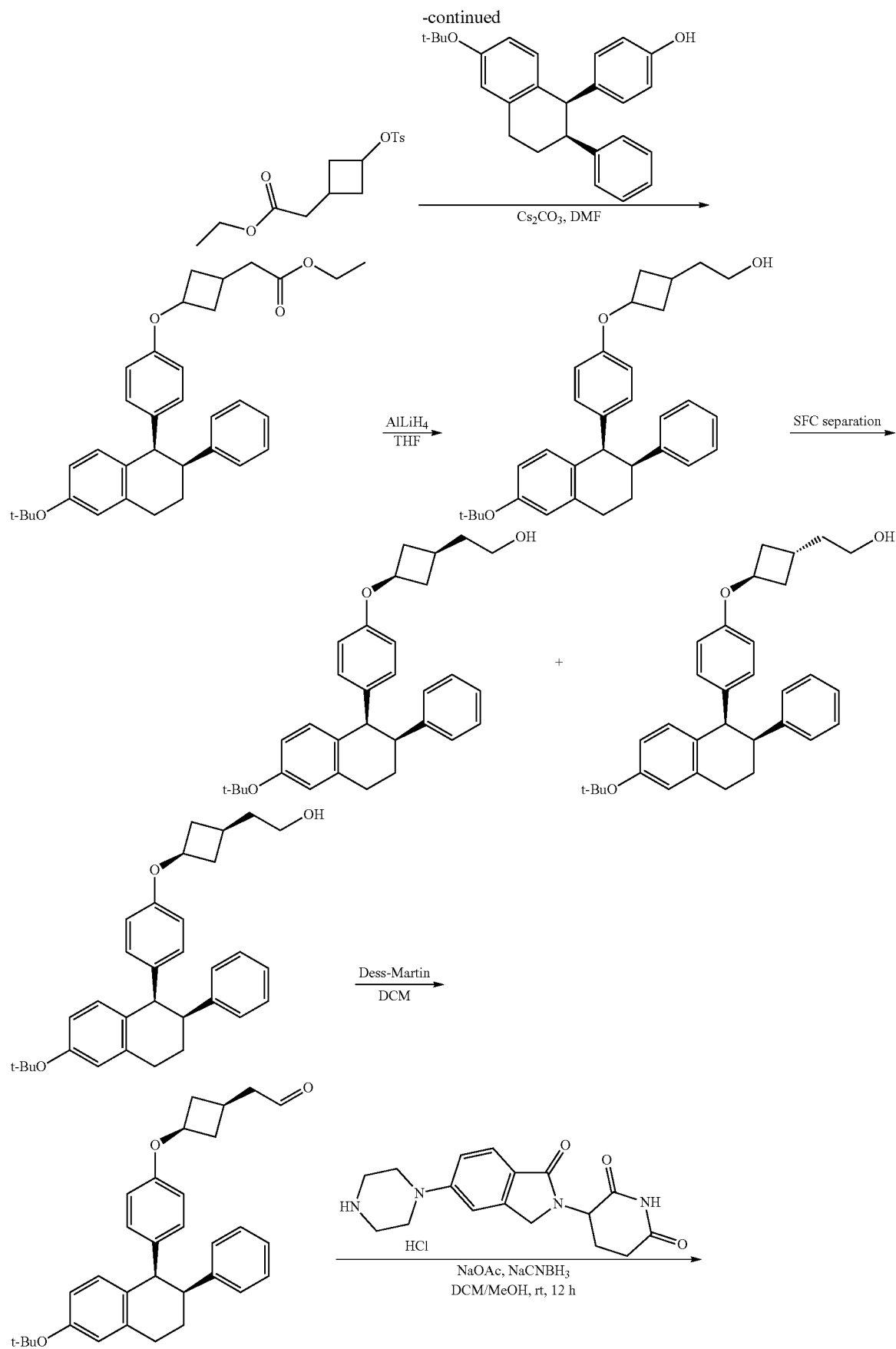

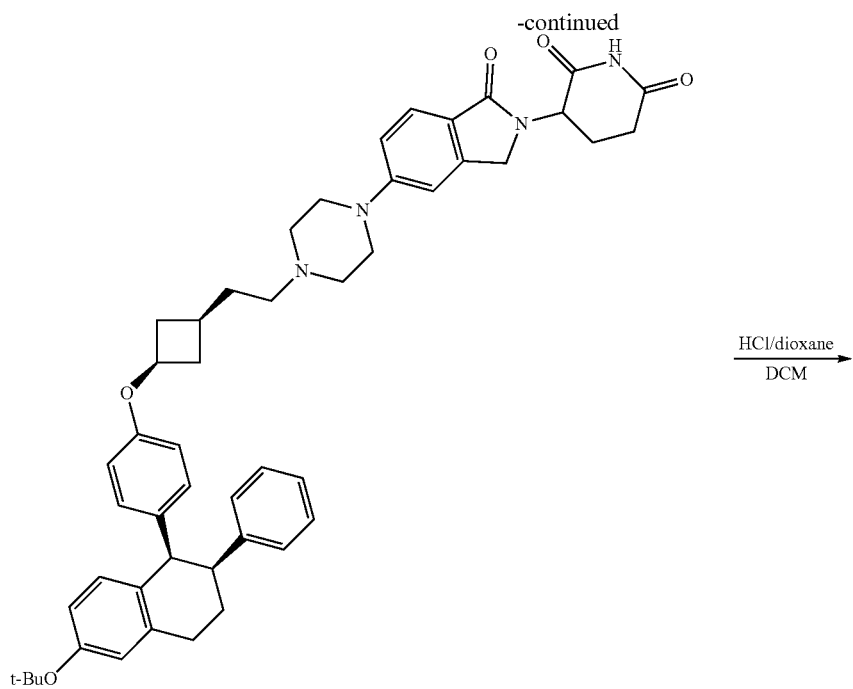
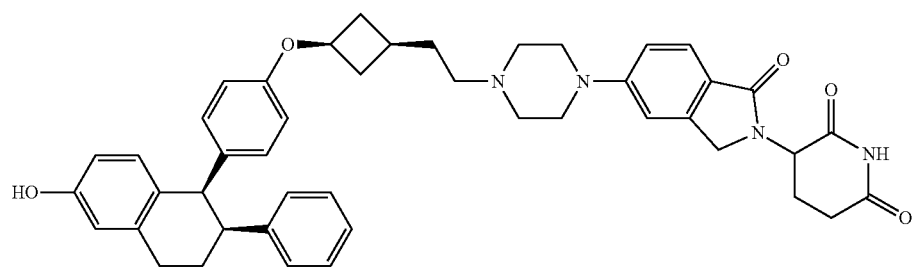
General Synthetic Scheme A-15 to Prepare Claimed Compounds.
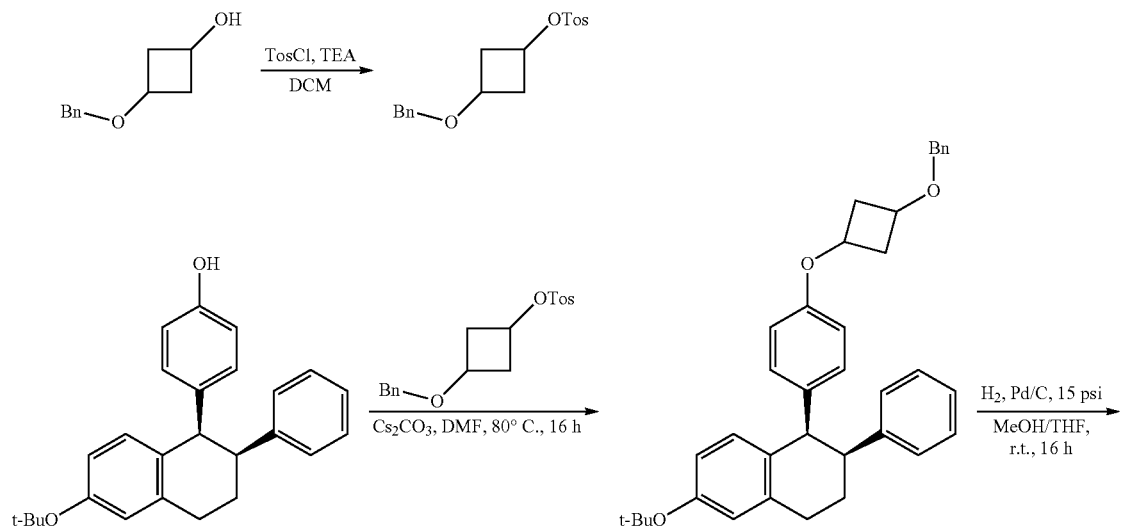

337 338
-continued
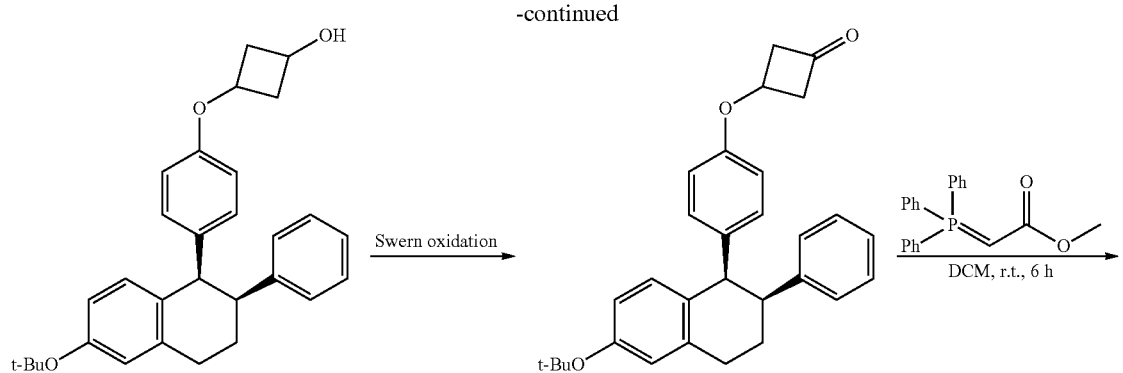
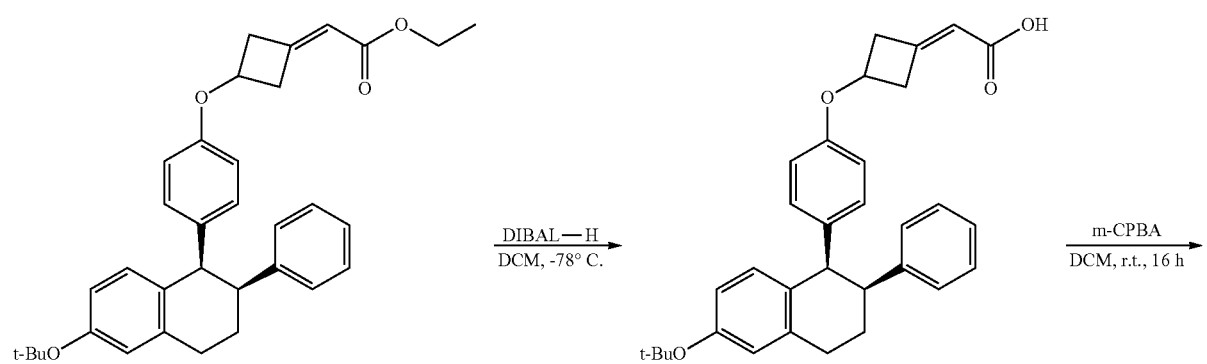
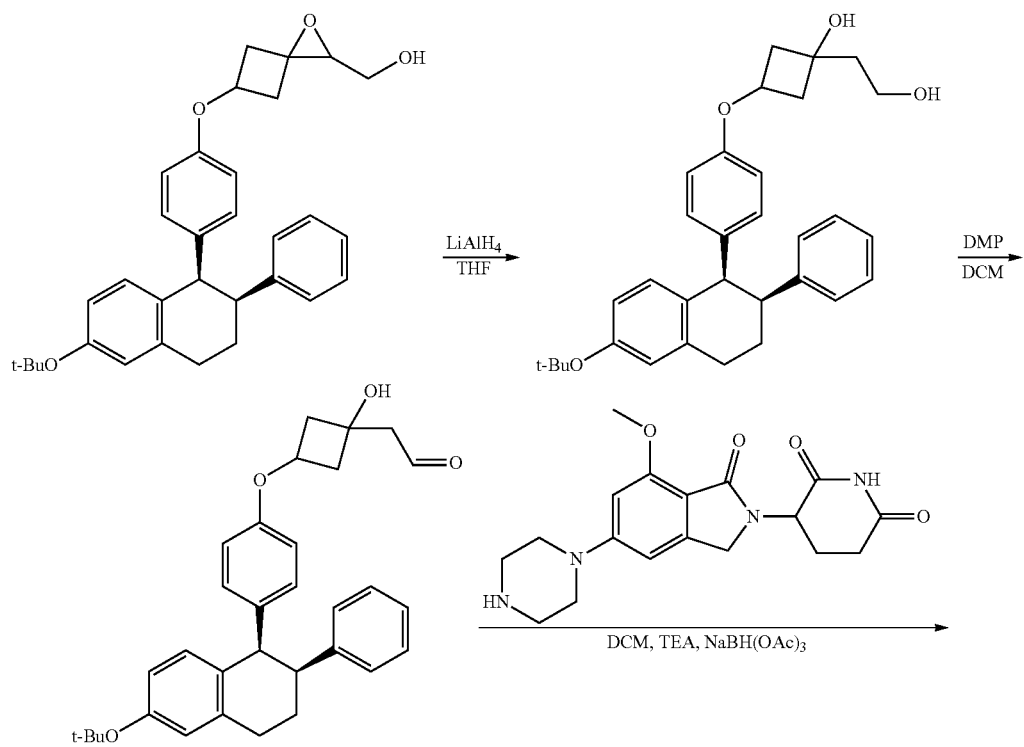

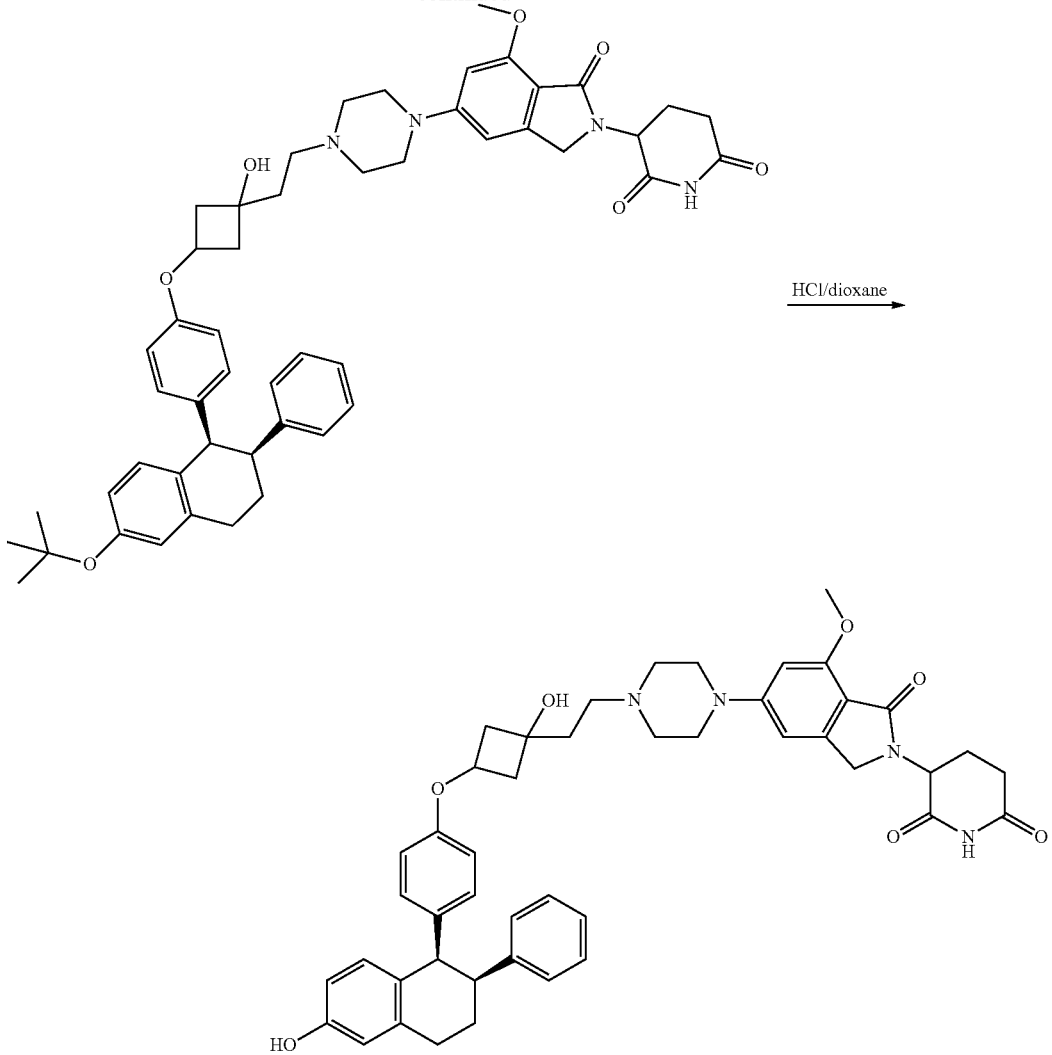
General Synthetic Scheme A-16 to Prepare Claimed Compounds.
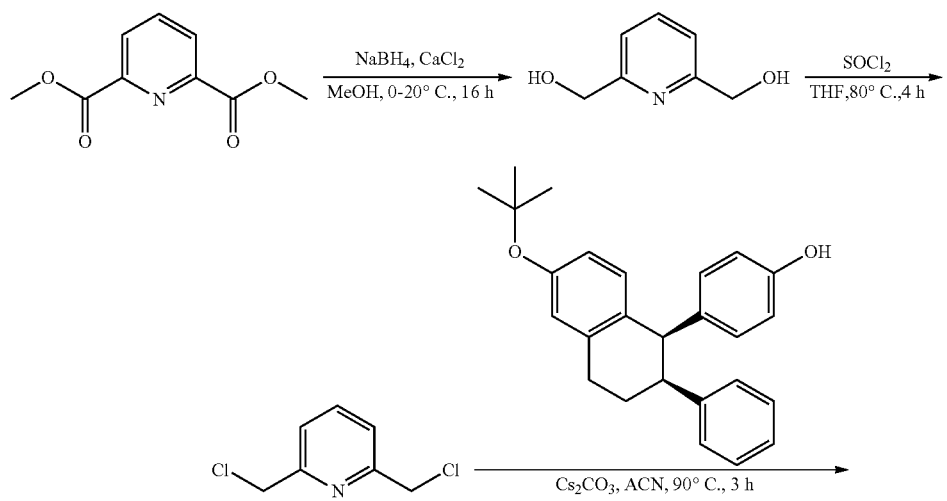

-continued
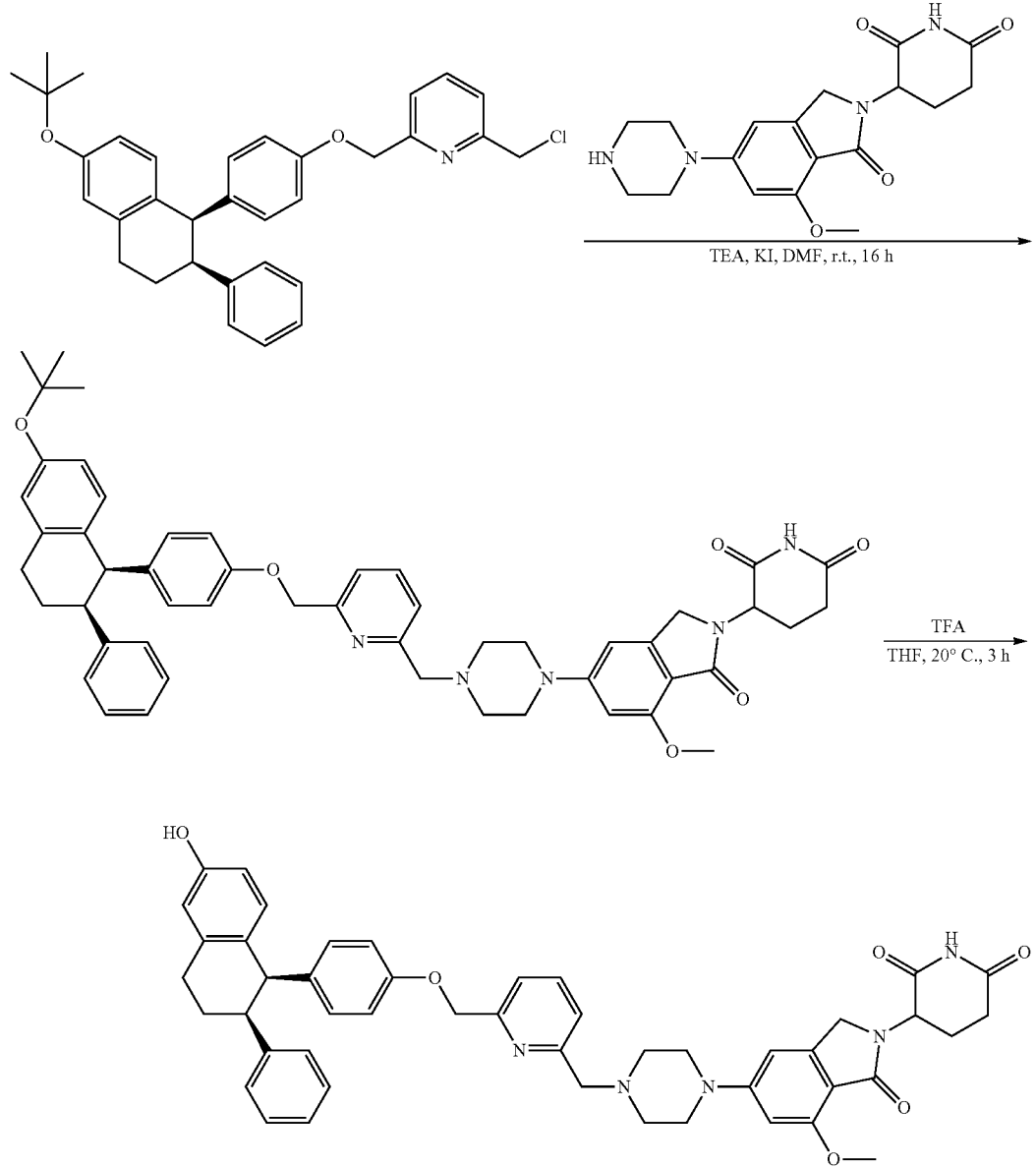
General Synthetic Scheme A-17 to Prepare Claimed Compounds.
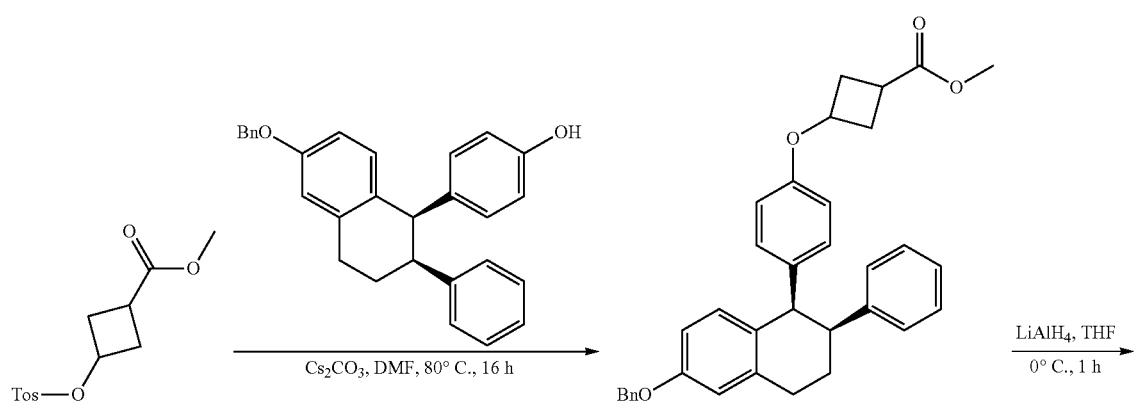

343
344
-continued
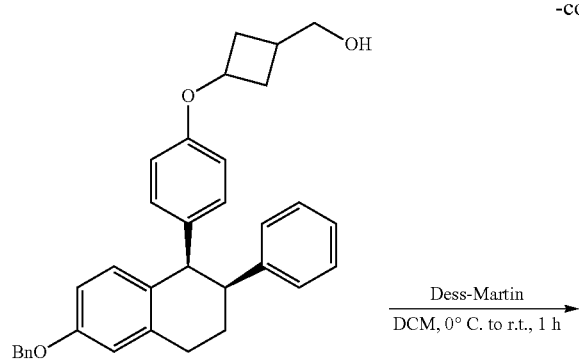
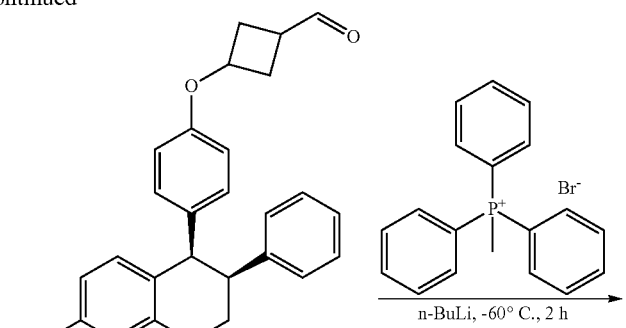
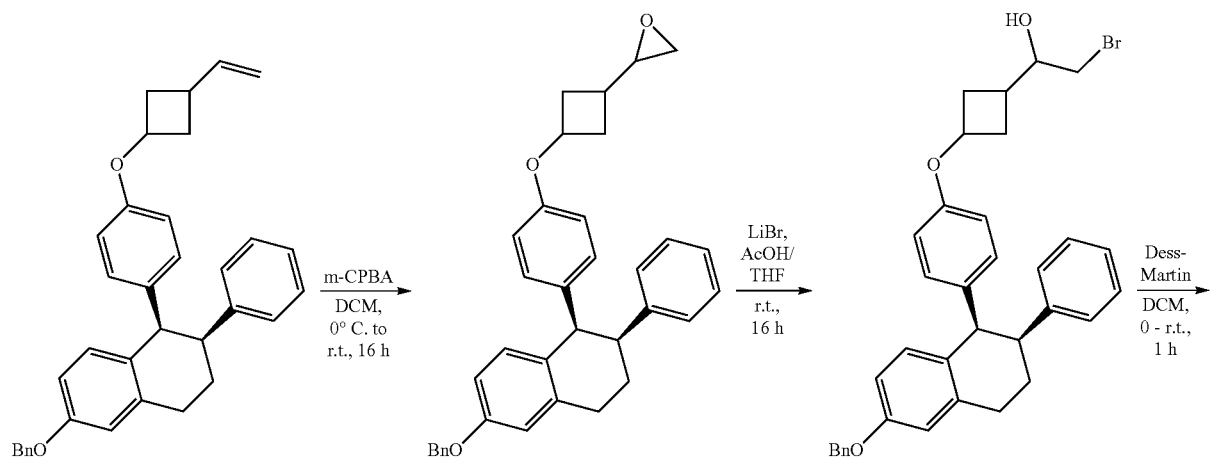
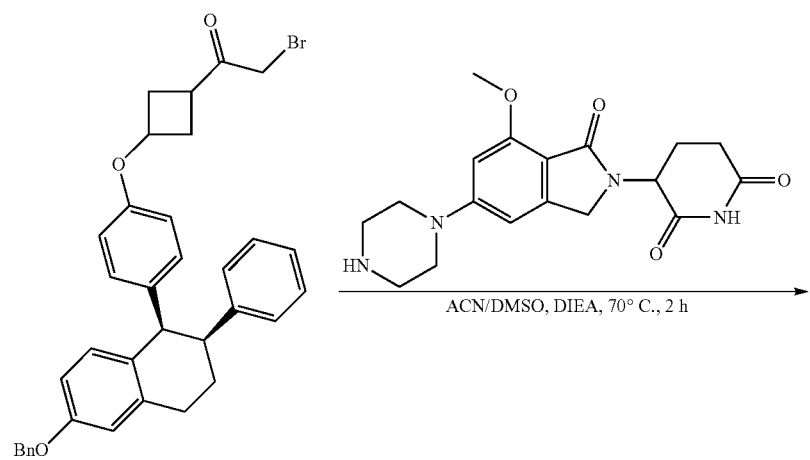

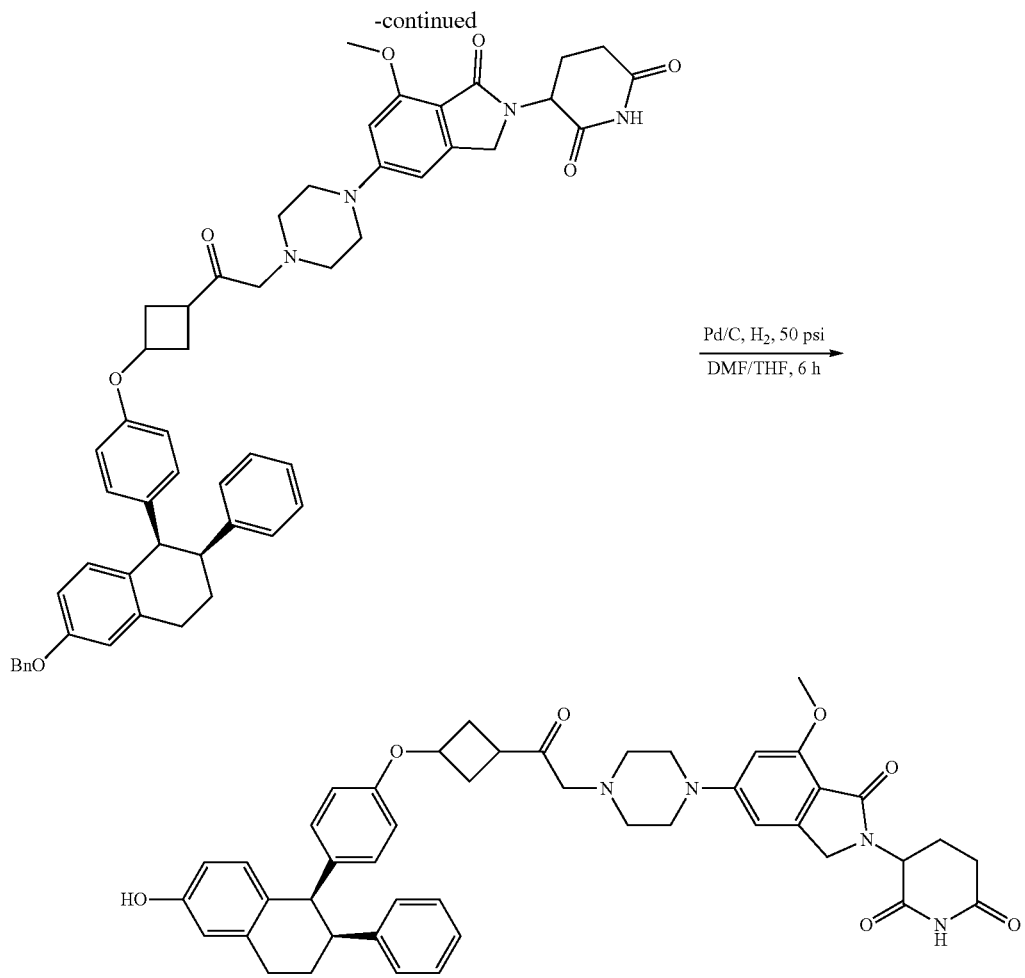

Exemplary Synthesis of Exemplary Compound 2: 3-{5-[4-(5-{4-[(1R,2S)-6-hydroxy-2-phenyl-1,2,3,4-tetrahydronaphthalen-1-yl]phenoxy}pentyl)piperazin-1-yl]-7-methoxy-1-oxo-2,3-dihydro-1H-isoindol-2-yl}piperidine-2,6-dione Step 1: Preparation of 5-bromopentanal

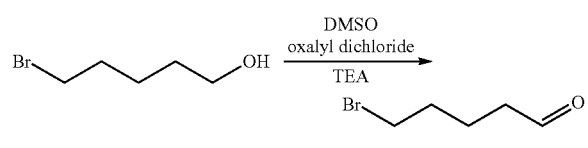

To a solution of oxalyl dichloride (9.12 g, 72 mmol, 6 mL, 4.00 eq) in dichloromethane (50 mL) was added a solution of dimethylsulfoxide (5.61 g, 72 mmol, 4.00 eq) in dichloromethane (10 mL) at −70° C. over 30 min, and then 5-bromopentan-1-ol (3.00 g, 18 mmol, 1.00 eq) was added at below −60° C. The resulting mixture was stirred at −70° C. for 1 hr. Thin-layer chromatography (petroleum ether: ethyl acetate=10:1) showed the reaction was complete. Triethylamine (14.54 g, 144 mmol, 20 mL, 8.00 eq) was added into the mixture and the reaction was stirred at −60° C. for 30 min. The mixture was poured into water (20 mL) and stirred for 1 min. The aqueous phase was extracted with dichloromethane (20 mL×3). The combined organic phase was washed with brine (20 mL×2), dried with anhydrous sodium sulfate, filtered and concentrated in vacuum. The residue was directly used for the next step without further purification. 5-bromopentanal (2.80 g, 17 mmol, 94% yield) was obtained as a colorless oil.

Step 2: Preparation of 5-bromo-1,1-dimethoxypentane

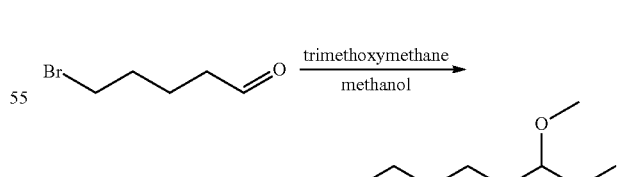

To a solution of 5-bromopentanal (2.80 g, 16.97 mmol, 1.00 eq) in methanol (50 mL) was added trimethoxymethane (9.00 g, 85 mmol, 9 mL, 5.00 eq) and 4-methylbenzenesulfonic acid hydrate (161 mg, 0.85 mmol, 0.05 eq) at 25° C. The resulting mixture was stirred at 25° C. for 16 hr. Thin-layer chromatography (petroleum ether:ethyl acetate=10:1) showed a major new spot. The mixture was poured into water (40 mL) and stirred for 1 min. The aqueous phase was extracted with ethyl acetate (30 mL×3). The combined organic phase was washed with brine (20 mL×2), dried with anhydrous sodium sulfate, filtered and concentrated in vacuum. The residue was purified by silica gel column chromatography (petroleum ether, ethyl acetate=15:1). 5-Bromo-1,1-dimethoxy-pentane (3.50 g, 16.58 mmol, 97% yield) was obtain as a colorless oil. $^1$H NMR (400 MHz, CDCl$_3$) δ 4.37 (t, J=5.6 Hz, 1H), 3.41 (s, 2H), 3.33 (s, 6H), 1.95-1.84 (m, 2H), 1.67-1.59 (m, 2H), 1.54-1.45 (m, 2H).

Step 3: Preparation of (1R,2S)-6-benzyloxy-1-[4-(5,5-dimethoxypentoxy)phenyl]-2-phenyl-tetralin

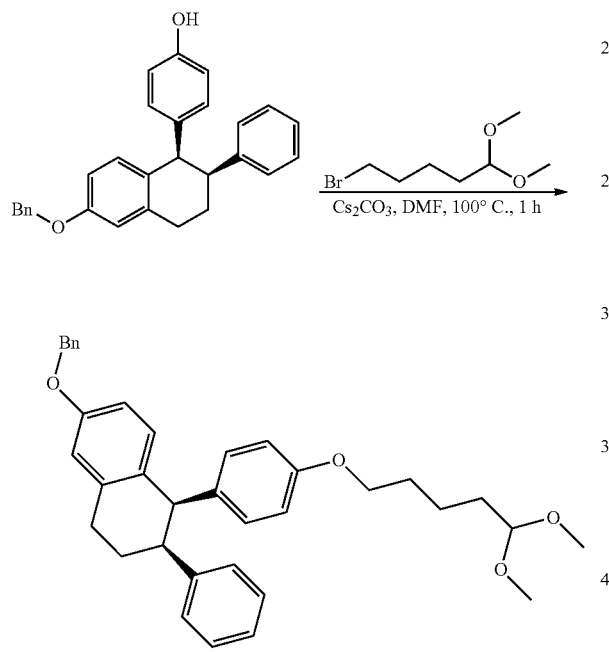

To a solution of 4-[(1R,2S)-6-benzyloxy-2-phenyl-tetralin-1-yl]phenol (500 mg, 1.23 mmol, 1.00 eq) in dimethylformamide (5 mL) was added cesium carbonate (1.2 g, 3.69 mmol, 3.00 eq) and 5-bromo-1,1-dimethoxy-pentane (390 mg, 1.84 mmol, 1.50 eq). The mixture was stirred at 100° C. for 1 hour. The reaction mixture was diluted with water (30 mL) and extracted with ethyl acetate (15 mL×2). The combined organic phase was washed with saturated brine (15 mL×2), dried with anhydrous sodium sulfate, filtered and concentrated in vacuum. The residue was purified by silica gel column chromatography (petroleum ether:ethyl acetate=50:1 to 10:1) to give (1R,2S)-6-benzyloxy-1-[4-(5,5-dimethoxypentoxy)phenyl]-2-phenyl-tetralin (500 mg, 0.93 mmol, 76% yield) as a white solid. LC/MS (ESI) m/z: 559.2 [M+23]$^+$, $^1$H NMR (400 MHz, CDCl$_3$) δ 7.49-7.45 (m, 2H), 7.44-7.38 (m, 2H), 7.37-7.31 (m, 1H), 7.21-7.13 (m, 3H), 6.90-6.85 (m, 2H), 6.82 (dd, J=2.0, 7.2 Hz, 2H), 6.76 (dd, J=2.4, 8.4 Hz, 1H), 6.53 (d, J=8.8 Hz, 2H), 6.32 (d, J=8.8 Hz, 2H), 5.07 (s, 2H), 4.38 (t, J=5.6 Hz, 1H), 4.25 (d, J=4.8 Hz, 1H), 3.84 (t, J=6.4 Hz, 2H), 3.41-3.28 (m, 7H), 3.17-2.99 (m, 2H), 2.28-2.13 (m, 1H), 1.87-1.71 (m, 3H), 1.69-1.60 (m, 2H), 1.54-1.42 (m, 2H).

Step 4: Preparation of (1R,2S)-1-[4-(5,5-dimethoxypentoxy)phenyl]-2-phenyl-tetralin-6-ol

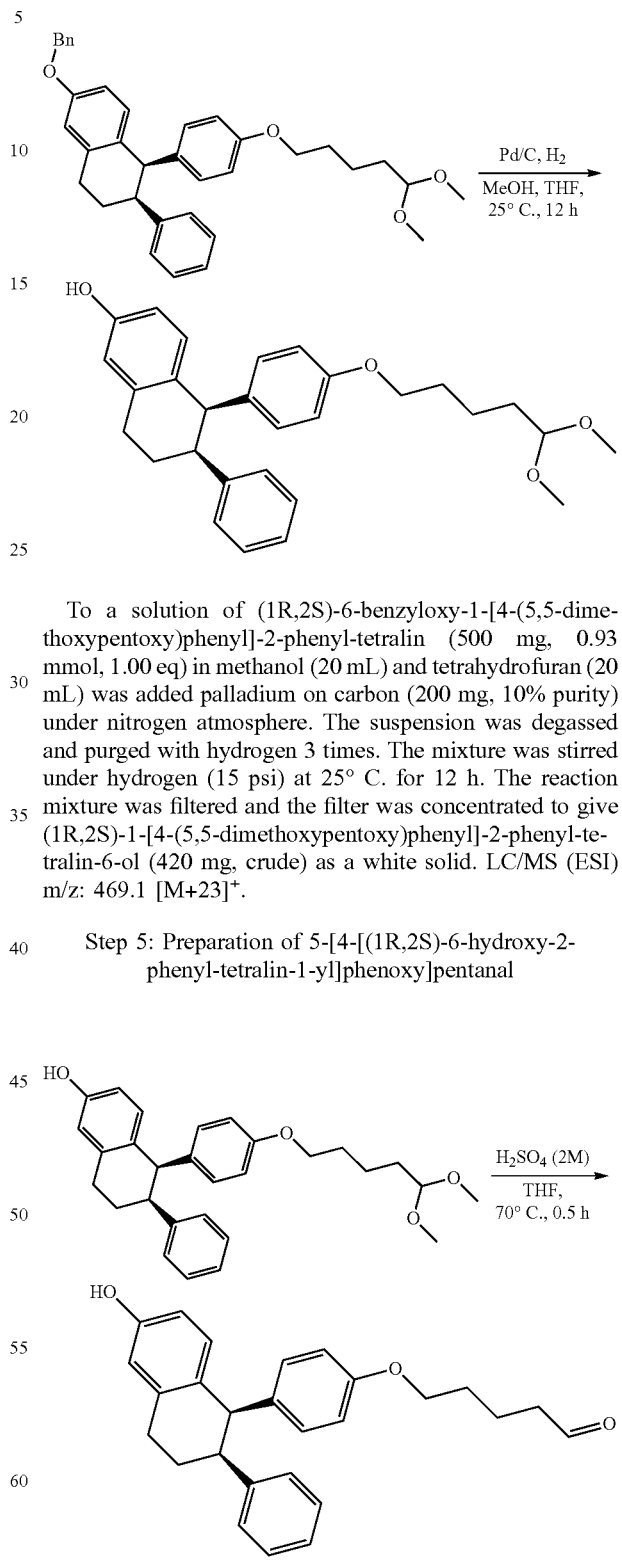

To a solution of (1R,2S)-6-benzyloxy-1-[4-(5,5-dimethoxypentoxy)phenyl]-2-phenyl-tetralin (500 mg, 0.93 mmol, 1.00 eq) in methanol (20 mL) and tetrahydrofuran (20 mL) was added palladium on carbon (200 mg, 10% purity) under nitrogen atmosphere. The suspension was degassed and purged with hydrogen 3 times. The mixture was stirred under hydrogen (15 psi) at 25° C. for 12 h. The reaction mixture was filtered and the filter was concentrated to give (1R,2S)-1-[4-(5,5-dimethoxypentoxy)phenyl]-2-phenyl-tetralin-6-ol (420 mg, crude) as a white solid. LC/MS (ESI) m/z: 469.1 [M+23]$^+$.

Step 5: Preparation of 5-[4-[(1R,2S)-6-hydroxy-2-phenyl-tetralin-1-yl]phenoxy]pentanal To a solution of (1R,2S)-1-[4-(5,5-dimethoxypentoxy)phenyl]-2-phenyl-tetralin-6-ol (420 mg, 0.94 mmol, 1.00 eq) in tetrahydrofuran (75 mL) was added sulfuric acid (2 M in water, 18 mL, 40.00 eq). The mixture was stirred at 70° C. for 0.5 h. Thin layer chromatography (petroleum ether:ethyl acetate=3:1) showed the reaction was completed and a new spot formed. The reaction mixture was diluted with water (40 mL) and extracted with ethyl acetate (20 mL×2). The combined organic phase was washed with saturated sodium bicarbonate (15 mL) and saturated brine (20 mL×2), dried with anhydrous sodium sulfate, filtered and concentrated in vacuum to give 5-[4-[(1R,2S)-6-hydroxy-2-phenyl-tetralin-1-yl]phenoxy] pentanal (370 mg, 0.92 mmol, 98% yield) as a white solid.

Step 6: Preparation of tert-butyl 4-(7-methoxy-1-oxo-1,3-dihydroisobenzofuran-5-yl)piperazine-1-carboxylate

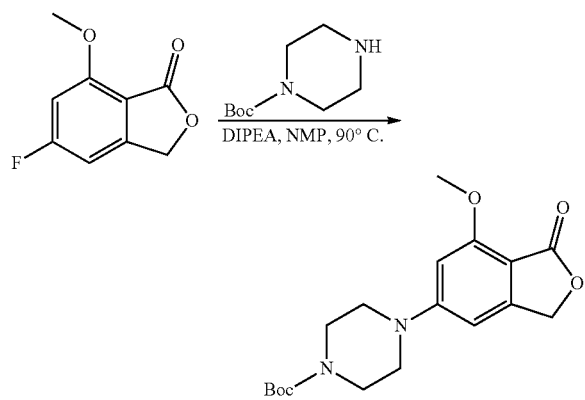

To a mixture of 5-fluoro-7-methoxy-3H-isobenzofuran-1-one (1 g, 5.49 mmol, 1 eq) and tert-butyl piperazine-1-carboxylate (2.05 g, 10.98 mmol, 2 eq) in 1-methylpyrrolidin-2-one (6 mL) was added N-ethyl-N-isopropylpropan-2-amine (2.84 g, 21.96 mmol, 3.83 mL, 4 eq) in one portion. The mixture was stirred at 100° C. for 12 hours. TLC (ethyl acetate/petroleum ether=1/1, $R_f$=0.1) indicated a new spot formed. The reaction mixture was diluted with water (20 mL) and extracted with ethyl acetate (40 mL×2). The combined organic layers were washed with water (15 mL), dried over sodium sulfate, filtered and concentrated under reduced pressure. The residue was purified by silica gel chromatography (petroleum ether/ethyl acetate=10/1 to 1:1). Tert-butyl 4-(7-methoxy-1-oxo-3H-isobenzofuran-5-yl)piperazine-1-carboxylate (1 g, 2.87 mmol, 52% yield) was obtained as a yellow solid. LC/MS (ESI) m/z: 349.3 [M+1]$^+$; $^1$H NMR (400 MHz, CDCl$_3$) δ 6.38 (s, 1H), 6.30 (s, 1H), 5.13 (s, 2H), 3.99 (s, 3H), 3.62-3.59 (m, 4H), 3.42-3.35 (m, 4H), 1.48 (s, 9H).

Step 7: Preparation of 4-(4-(tert-butoxycarbonyl) piperazin-1-yl)-2-(hydroxymethyl)-6-methoxybenzoic acid

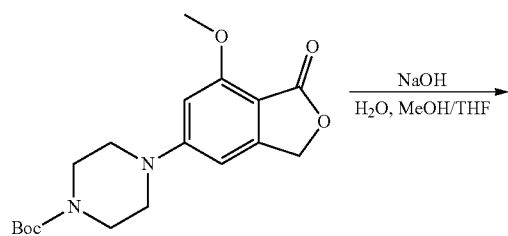

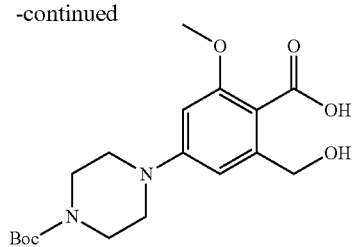

To a mixture of tert-butyl 4-(7-methoxy-1-oxo-3H-isobenzofuran-5-yl)piperazine-1-carboxylate (1 g, 2.87 mmol, 1 eq) in methyl alcohol (10 mL) and tetrahydrofuran (10 mL) was added the solution of sodium hydroxide (459 mg, 11.48 mmol, 4 eq) in water (2 mL). The mixture was stirred at 20° C. for 1 h. TLC (ethyl acetate/petroleum ether=1/1, $R_f$=0) indicated a new spot formed. The reaction mixture was concentrated under reduced pressure to remove solvent. The residue was diluted with water (20 mL) and extracted with ethyl acetate (30 mL×2). The aqueous phase was adjusted to pH value to 4-5 with hydrochloric acid (1.5 N), then filtered and the solid was collected. The solid was used for the next step without further purification. 4-(4-Tert-butoxycarbonylpiperazin-1-yl)-2-(hydroxymethyl)-6-methoxy-benzoic acid (700 mg, 1.68 mmol, 58% yield, 88% purity) was obtained as a white solid. LC/MS (ESI) m/z: 367.3 [M+1]$^+$.

Step 8: Preparation of 4-(4-(tert-butoxycarbonyl) piperazin-1-yl)-2-formyl-6-methoxybenzoic acid

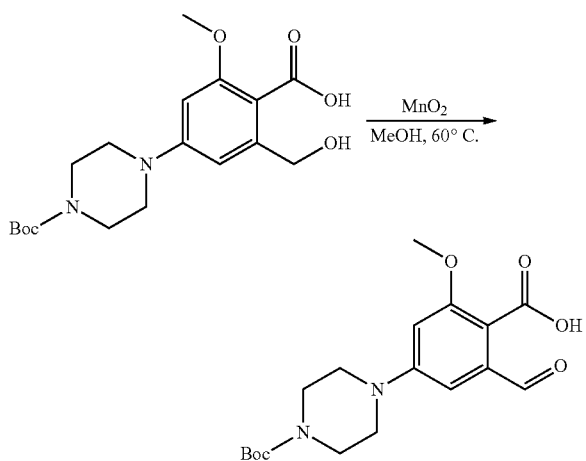

To a mixture of 4-(4-tert-butoxycarbonylpiperazin-1-yl)-2-(hydroxymethyl)-6-methoxy-benzoic acid (650 mg, 1.77 mmol, 1 eq) and in methyl alcohol (20 mL) was added manganese dioxide (1.54 g, 17.74 mmol, 10 eq) in one portion at 20° C. under nitrogen. The mixture was stirred at 50° C. for 12 hours. LC/MS showed the reaction was completed and desired product was formed. The reaction mixture was filtered and the solution was concentrated under vacuum. The reaction was used for the next step without further purification. 4-(4-Tert-butoxycarbonylpiperazin-1-yl)-2-formyl-6-methoxy-benzoic acid (600 mg, 1.65 mmol, 92% yield) was obtained as a yellow solid. LC/MS (ESI) m/z: 365.3 [M+1]$^+$.

Step 9: Preparation of 4-(4-(tert-butoxycarbonyl) piperazin-1-yl)-2-(((2,6-dioxopiperidin-3-yl)amino) methyl)-6-methoxybenzoic acid

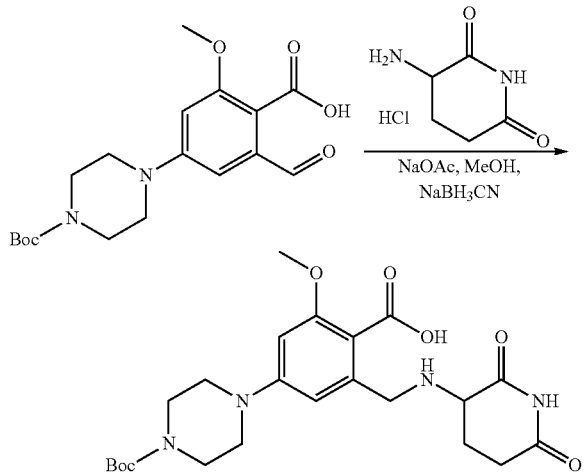

To a mixture of 4-(4-tert-butoxycarbonylpiperazin-1-yl)-2-formyl-6-methoxy-benzoic acid (600 mg, 1.65 mmol, 1 eq) and 3-aminopiperidine-2,6-dione (407 mg, 2.47 mmol, 1.5 eq, HCl) in methyl alcohol (10 mL) was added sodium acetate (203 mg, 2.47 mmol, 1.5 eq) and sodium cyanoborohydride (310 mg, 4.94 mmol, 3 eq) in one portion at 20° C. The mixture was stirred at 20° C. for 2 h. LC/MS showed the reaction was completed and desired product was formed. The reaction mixture was concentrated under vacuum. The residue was purified by reverse phase flash silica gel chromatography (120 g SepaFlash silica gel column, eluent of 0-60% acetonitrile in water with a flow rate of 30 mL/min). 4-(4-Tert-butoxycarbonylpiperazin-1-yl)-2-[[(2,6-dioxo-3-piperidyl)amino]methyl]-6-methoxy-benzoic acid (300 mg, 0.63 mmol, 38% yield) was obtained as a white solid. LC/MS (ESI) m/z: 477.4 [M+1]⁺.

Step 10: Preparation of tert-butyl 4-(2-(2,6-dioxopiperidin-3-yl)-7-methoxy-1-oxoisoindolin-5-yl)piperazine-1-carboxylate

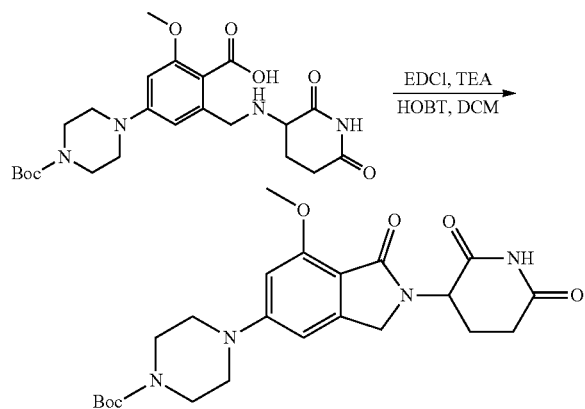

To a mixture of 4-(4-tert-butoxycarbonylpiperazin-1-yl)-2-[[(2,6-dioxo-3-piperidyl)amino]methyl]-6-methoxy-benzoic acid (300 mg, 0.63 mmol, 1 eq) in dichloromethane (10 mL) was added N-ethyl-N'-(3-dimethylaminopropyl)carbodiimide hydrochloride (181 mg, 0.94 mmol, 1.5 eq), N-hydroxybenzotrizole (128 mg, 0.94 mmol, 1.5 eq), and triethylamine (191 mg, 1.89 mmol, 3 eq). The mixture was stirred at 20° C. for 1 h. LC/MS showed the reaction was completed and desired product was formed. The reaction mixture was quenched by addition of water (15 mL), and then extracted with dichloromethane (40 mL×2). The combined organic layers were washed with brine (10 mL), dried over sodium sulfate, filtered and concentrated under reduced pressure. The residue was purified by preparative TLC (dichloromethane:methyl alcohol=10:1, R$_f$=0.60). Tert-butyl 4-[2-(2,6-dioxo-3-piperidyl)-7-methoxy-1-oxo-isoindolin-5-yl]piperazine-1-carboxylate (260 mg, 0.57 mmol, 90% yield) was obtained as a white solid. LC/MS (ESI) m/z: 459.4 [M+1]⁺.

Step 11: Preparation of 3-(7-methoxy-1-oxo-5-(piperazin-1-yl) isoindolin-2-yl) piperidine-2,6-dione

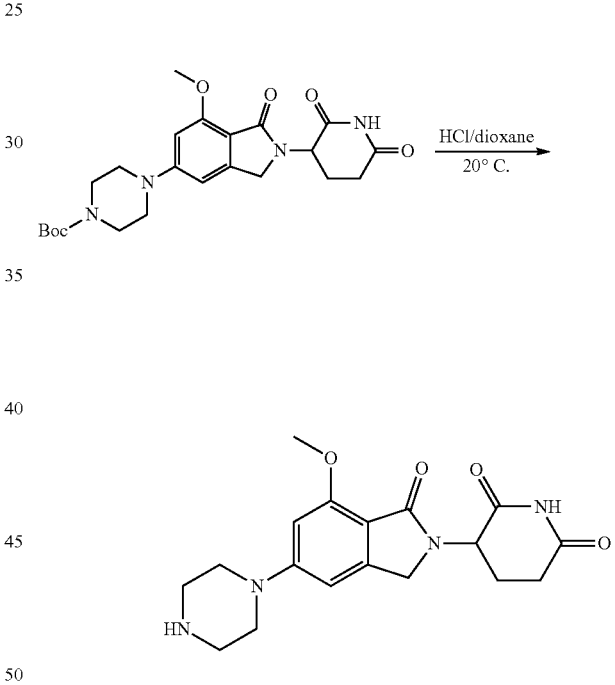

To a mixture of tert-butyl 4-[2-(2,6-dioxo-3-piperidyl)-7-methoxy-1-oxo-isoindolin-5-yl]piperazine-1-carboxylate (300 mg, 0.65 mmol, 1 eq) in dioxane (10 mL) was added hydrogen chloride/dioxane (4 M, 17 mL, 105.81 eq) in one portion. The mixture was stirred at 20° C. for 2 h. The reaction mixture was concentrated under reduced pressure to remove solvent. The residue was used for the next step without further purification. 3-(7-Methoxy-1-oxo-5-piperazin-1-yl-isoindolin-2-yl)piperidine-2,6-dione (216 mg, 0.55 mmol, 83% yield, HCl salt) was obtained as a white solid. LC/MS (ESI) m/z: 359.2 [M+1]⁺; ¹H-NMR (400 MHz, MeOD) δ: 6.72 (s, 1H), 6.60 (s, 1H), 5.08-5.04 (m, 1H), 4.36-4.35 (m, 2H), 3.92 (s, 3H), 3.66-3.65 (m, 5H), 3.38-3.35 (m, 4H), 2.89-2.78 (m, 1H), 2.77-2.67 (m, 1H), 2.45-2.42 (m, 1H), 2.14-2.14 (m, 1H).

Step 12: Preparation of 3-{5-[4-(5-{4-[(1R,2S)-6-hydroxy-2-phenyl-1,2,3,4-tetrahydronaphthalen-1-yl]phenoxy}pentyl)piperazin-1-yl]-7-methoxy-1-oxo-2,3-dihydro-1H-isoindol-2-yl}piperidine-2,6-dione (Exemplary Compound 2)

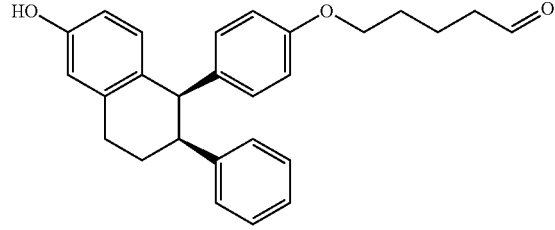
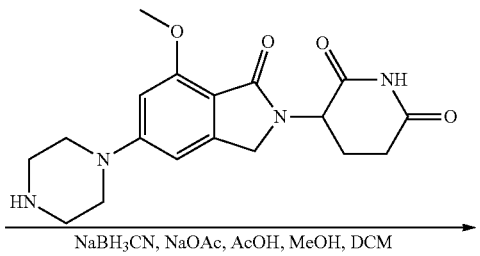
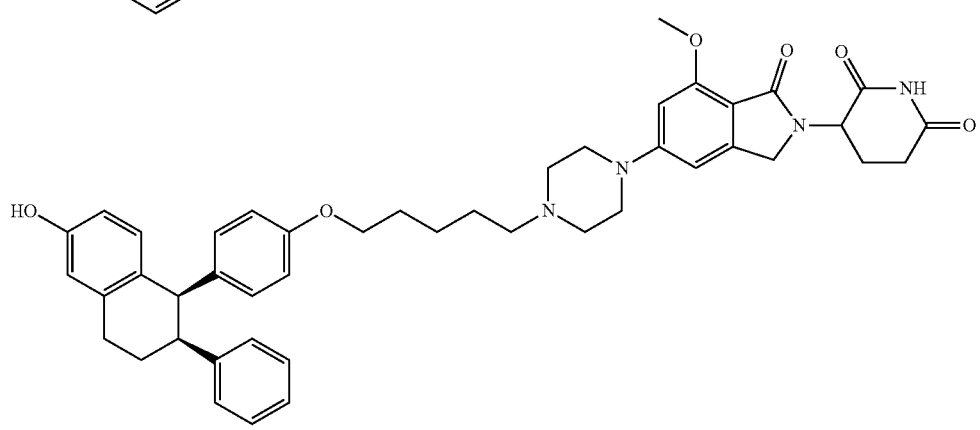

To a mixture of 3-(7-methoxy-1-oxo-5-piperazin-1-yl-isoindolin-2-yl)piperidine-2,6-dione hydrochloride (89 mg, 0.23 mmol) in methyl alcohol (5 mL) and dichloromethane (1 mL) was added sodium acetate (102 mg, 1.25 mmol, 5 eq) in one portion at 20° C. The mixture was stirred at 20° C. for 1 h, then 5-[4-[(1R,2S)-6-hydroxy-2-phenyl-tetralin-1-yl]phenoxy]pentanal (100 mg, 0.25 mmol, 1 eq) was added to the reaction mixture and stirred for 1 h. Sodium cyanoborohydride (31 mg, 0.50 mmol, 2 eq) and acetic acid (0.05 mL) was added to the reaction mixture. The resulting solution was stirred at 20° C. for 5 h. LC/MS showed the reaction was completed and desired product was formed. The reaction mixture was concentrated under reduced pressure to remove solvent. The residue was purified by preparative HPLC (column: Phenomenex Synergi C18 150×25×10 um; mobile phase: [water (0.05% HCl)-acetonitrile]; B %: 35%-55%, 7.8 min). 3-[5-[4-[5-[4-[(1R,2S)-6-Hydroxy-2-phenyl-tetralin-1-yl]phenoxy]pentyl]piperazin-1-yl]-7-methoxy-1-oxo-isoindolin-2-yl]piperidine-2,6-dione (109.9 mg, 0.14 mmol, 56% yield, 100% purity, HCl salt) was obtained as a white solid. LC/MS (ESI) m/z: 743.7 [M+1]⁺; ¹H-NMR (400 MHz, DMSO-d6) δ 10.93 (s, 1H), 10.56-10.43 (m, 1H), 9.18-9.13 (m, 1H), 7.16-7.13 (m, 3H), 6.84-6.83 (d, J=6.4 Hz, 2H), 6.69 (s, 1H), 6.62-6.61 (m, 2H), 6.55-6.52 (m, 3H), 6.28-6.26 (d, J=8.4 Hz, 2H), 4.99-4.97 (m, 1H), 4.29-4.25 (m, 1H), 4.23-4.18 (m, 1H), 4.17-4.15 (m, 1H), 4.06-4.00 (m, 2H), 3.85-3.83 (m, 5H), 3.56-3.53 (m, 1H), 3.34-3.33 (m, 4H), 3.10-3.02 (m, 4H), 3.00-2.85 (m, 2H), 2.60-2.58 (m, 3H), 2.16-2.08 (m, 1H), 1.91-1.88 (m, 1H), 1.76-1.69 (m, 5H), 1.43-1.41 (m, 2H).

Exemplary Synthesis of Exemplary Compound 3: 3-[5-[4-[5-[4-[(1R,2S)-6-hydroxy-2-phenyl-tetralin-1-yl] phenoxy]pentyl]piperazin-1-yl]-4-methoxy-1-oxo-isoindolin-2-yl]piperidine-2,6-dione Step 1: Preparation of 5-bromo-4-iodo-3H-isobenzofuran-1-one

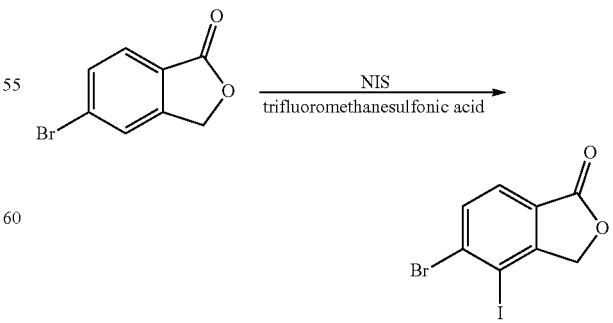

To a solution of 5-bromo-3H-isobenzofuran-1-one (50 g, 234.71 mmol, 1 eq) in trifluoromethanesulfonic acid (680 g, 4.53 mol, 400 mL, 19.30 eq) was added 1-iodopyrrolidine-2,5-dione (55.45 g, 246.45 mmol, 1.05 eq) at 0° C. in portions. The mixture was allowed to warm to 15° C. and held for 16 h. TLC (petroleum ether:ethyl acetate=5:1) showed no starting material remained and two new spots ($R_f$=0.4, 0.5) formed. The reaction mixture was poured into ice-water (1 L) and yellow solid precipitated. The mixture was filtered and the filter cake was washed with water. The filter cake was dissolved in ethyl acetate (500 mL) and the resulting orange solution was dried over sodium sulfate. The mixture was filtered and the filtrate was concentrated to afford a yellow solid. The residue was triturated with ethyl acetate (50 mL), filtered and washed with ethyl acetate (10 mL×2). 5-Bromo-4-iodo-3H-isobenzofuran-1-one (40 g, 118.02 mmol, 50% yield) was obtained as a yellow solid. $^1$H NMR (400 MHz, CDCl$_3$) δ 7.83 (d, J=8.0 Hz, 1H), 7.77 (d, J=8.0 Hz, 1H), 5.10 (s, 2H).

Step 2: Preparation of 5-bromo-4-hydroxy-3H-isobenzofuran-1-one

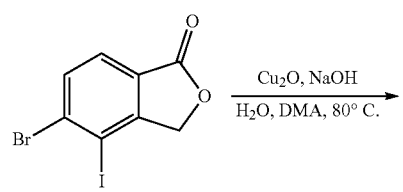

To a mixture of 5-bromo-4-iodo-3H-isobenzofuran-1-one (40 g, 118.02 mmol, 1 eq), sodium hydroxide (23.60 g, 590.10 mmol, 5 eq) in water (400 mL) and N,N-dimethylacetamide (200 mL) was added cuprous oxide (3.38 g, 23.60 mmol, 2.4 mL, 0.2 eq). The reaction mixture was heated to 80° C. and held for 16 h. TLC (petroleum ether:ethyl acetate=1:1, $R_f$=0.3) showed the reaction was completed. The reaction mixture was poured into 1N hydrochloride solution (400 mL) and extracted with ethyl acetate (400 mL×2). The combined organic layers were concentrated and dissolved in ethyl acetate (500 mL), washed with saturated aqueous sodium bicarbonate (150 mL), brine (150 mL) and then dried over sodium sulfate. The mixture was filtered and the filtrate was concentrated to afford a residue. The residue was triturated with ethyl acetate (20 mL), filtered and washed with ethyl acetate (10 mL) to give a solid. The filtrate was further concentrated and triturated with ethyl acetate. 5-Bromo-4-hydroxy-3H-isobenzofuran-1-one (14.5 g, 60.15 mmol, 50% yield, 95% purity) was obtained as a white solid. $^1$H NMR (400 MHz, DMSO) δ 10.90 (s, 1H), 7.72 (d, J=8.0 Hz, 1H), 7.23 (d, J=8.0 Hz, 1H), 5.35 (s, 2H).

Step 3: Preparation of 5-bromo-4-methoxy-3H-isobenzofuran-1-one

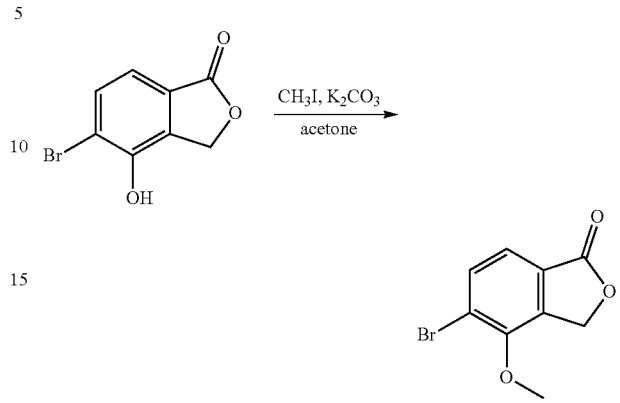

To a mixture of 5-bromo-4-hydroxy-3H-isobenzofuran-1-one (3 g, 13.10 mmol, 1 eq) in acetone (20 mL) was added iodomethane (17.5 g, 123.29 mmol, 7.7 mL, 9.41 eq) and potassium carbonate (5.43 g, 39.30 mmol, 3 eq). The mixture was stirred at 20° C. for 15 h. TLC (ethyl acetate: petroleum ether=1:3, $R_f$=0.37) indicated reaction was completed. The reaction mixture was quenched by addition of water (10 mL), and then extracted with ethyl acetate (20 mL×2). The combined organic layers were washed with saturated sodium bicarbonate (10 mL×2), dried over sodium sulfate, filtered and concentrated under reduced pressure. 5-Bromo-4-methoxy-3H-isobenzofuran-1-one (2.9 g, 11.93 mmol, 91% yield) was obtained as a yellow solid. $^1$H NMR (400 MHz, CDCl$_3$) δ 7.72 (d, J=8.0 Hz, 1H), 7.49 (d, J=8.0 Hz, 1H), 5.44 (s, 2H), 4.00 (s, 3H).

Step 4: Preparation of tert-butyl 4-(4-methoxy-1-oxo-3H-isobenzofuran-5-yl) piperazine-1-carboxylate

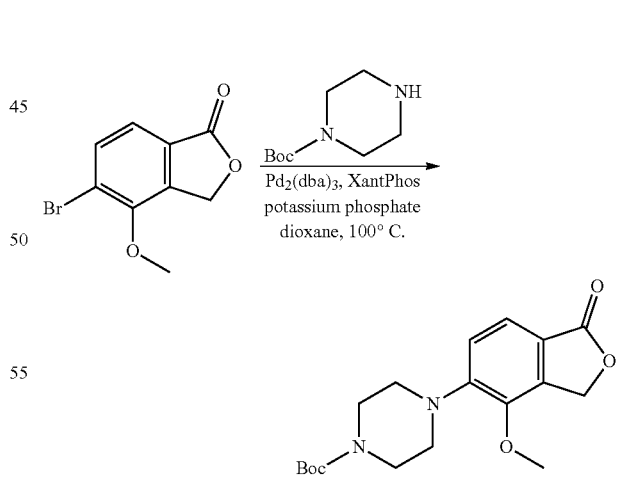

A vial was charged with 5-bromo-4-methoxy-3H-isobenzofuran-1-one (500 mg, 2.06 mmol, 1 eq), tert-butyl piperazine-1-carboxylate (383 mg, 2.06 mmol, 1 eq), tris(dibenzylideneacetone)dipalladium(0) (188 mg, 0.20 mmol, 0.1 eq), XantPhos (119 mg, 0.20 mmol, 0.1 eq), potassium phosphate (873 mg, 4.11 mmol, 2 eq) and dioxane (5 mL). The mixture was purged with nitrogen and heated to 100° C.

for 16 h. TLC (ethyl acetate:petroleum ether=1:3) showed reaction was complete. The mixture was diluted with ethyl acetate (30 mL) and washed with water (30 mL). The aqueous layer was extracted with ethyl acetate (15 mL×3). The organic layer was washed with brine (30 mL) and dried over sodium sulfate. The crude was purified by silica gel chromatography (ethyl acetate:petroleum ether=1:20 to 1:6). Tert-butyl 4-(4-methoxy-1-oxo-3H-isobenzofuran-5-yl)piperazine-1-carboxylate (700 mg, 2.01 mmol, 97% yield) was obtained as a yellow solid. LC/MS (ESI) m/z: 349.2 [M+1]$^+$.

Step 5: Preparation of 4-(4-tert-butoxycarbonylpiperazin-1-yl)-2-(hydroxylmethyl)-3-methoxy-benzoic acid

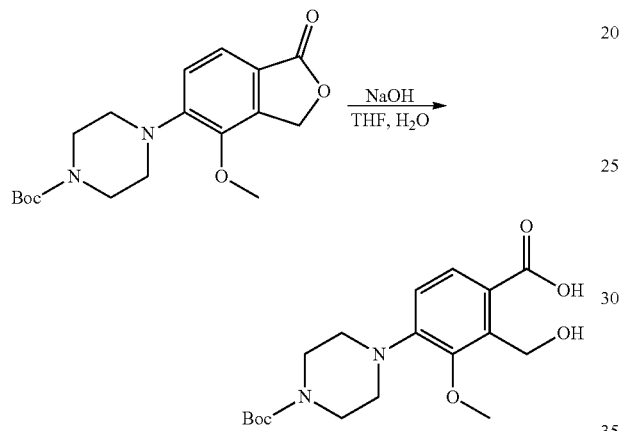

To a solution of tert-butyl 4-(4-methoxy-1-oxo-3H-isobenzofuran-5-yl)piperazine-1-carboxylate (700 mg, 2.01 mmol, 1 eq) in tetrahydrofuran (4 mL) and water (4 mL) was added sodium hydroxide (401 mg, 10.05 mmol, 5 eq). The mixture was stirred at 20° C. for 16 h. TLC (ethyl acetate:petroleum ether=1:2) showed reaction was complete. The mixture was adjusted to pH=4 with aqueous hydrochloric acid (1 M) and extracted with ethyl acetate (10 ml×3). The organic layer was washed with brine (20 mL) and dried over sodium sulfate. The crude material was not further purified. 4-(4-Tert-butoxycarbonylpiperazin-1-yl)-2-(hydroxymethyl)-3-methoxy-benzoic acid (700 mg, crude) was obtained as a yellow solid.

Step 6: Preparation of 4-(4-(tert-butoxycarbonyl)piperazin-1-yl)-2-formyl-3-methoxybenzoic acid

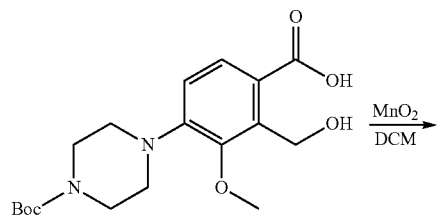

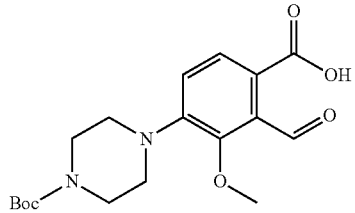

To a solution of 4-(4-tert-butoxycarbonylpiperazin-1-yl)-2-(hydroxymethyl)-3-methoxy-benzoic acid (700 mg, 1.91 mmol, 1 eq) in dichloromethane (10 mL) was added manganese dioxide (2.49 g, 28.66 mmol, 15 eq). The mixture was stirred at 20° C. for 1 h. TLC (dichloromethane:methanol=20:1) showed reaction was complete. The mixture was diluted with dichloromethane (10 mL) and filtered through a pad of Celite. The filtrate was concentrated in vacuum. The crude product was purified by silica gel column chromatography (dichloromethane:methanol=100:1 to 60:1). 4-(4-(Tert-butoxycarbonyl)piperazin-1-yl)-2-formyl-3-methoxybenzoic acid (300 mg, 0.82 mmol, 43% yield) was obtained as a pale yellow solid.

Step 7: Preparation of 4-(4-tert-butoxycarbonylpiperazin-1-yl)-2-[[(2,6-dioxo-3-piperidyl)amino]methyl]-3-methoxy-benzoic acid

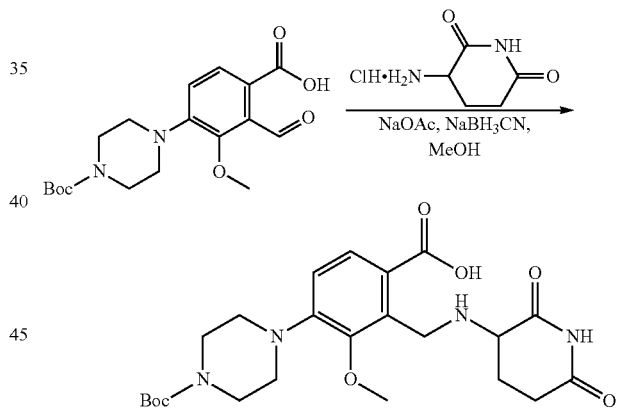

To a mixture of 3-aminopiperidine-2,6-dione (135 mg, 0.82 mmol, 1 eq, HCl salt) in methanol (2 mL) and dichloromethane (4 mL) was added sodium acetate (270 mg, 3.29 mmol, 4 eq). The mixture was stirred at 20° C. for 10 min, then 4-(4-tert-butoxycarbonylpiperazin-1-yl)-2-formyl-3-methoxy-benzoic acid (300 mg, 0.82 mmol, 1 eq) was added and the mixture was stirred for 10 min. Sodium cyanoborohydride (103 mg, 1.65 mmol, 2 eq) was added and the mixture was further stirred for 40 min. LCMS showed reaction was complete. The mixture was adjusted to pH=4-5 with aqueous hydrochloric acid solution (1 M) and extracted with ethyl acetate (10 mL×3). The organic layer was dried over sodium sulfate. The crude product was not further purified. 4-(4-Tert-butoxycarbonylpiperazin-1-yl)-2-[[(2,6-dioxo-3-piperidyl)amino]methyl]-3-methoxy-benzoic acid (400 mg, crude) was obtained as a white solid. LC/MS (ESI) mi: 477.1 [M+1]$^+$.

Step 8: Preparation of tert-butyl 4-[2-(2,6-dioxo-3-piperidyl)-4-methoxy-1-oxo-isoindolin-5-yl]piperazine-1-carboxylate

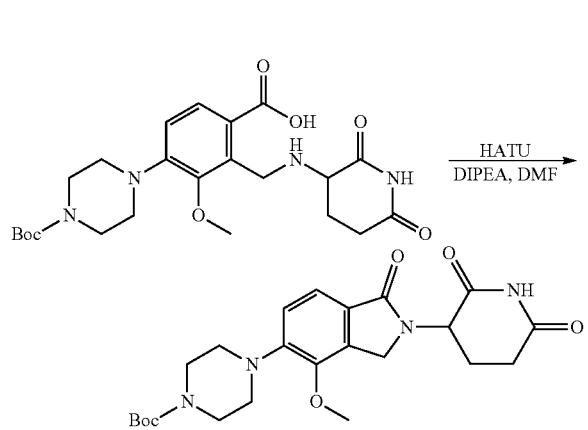

To a solution of 4-(4-tert-butoxycarbonylpiperazin-1-yl)-2-[[(2,6-dioxo-3-piperidyl)amino] methyl]-3-methoxy-benzoic acid (400 mg, 0.84 mmol, 1 eq) in dimethylformamide (5 mL) was added o-(7-azabenzotriazol-1-yl)-N,N,N',N'-tetramethyluronium hexafluorophosphate (383 mg, 1.01 mmol, 1.2 eq). The solution was stirred for 10 min, then N,N-diisopropylethylamine (325 mg, 2.52 mmol, 3 eq) was added. The solution was stirred at 20° C. for 20 min. LCMS showed reaction was complete. The solution was diluted with ethyl acetate (40 mL) and washed with water (30 mL×5) and brine (40 mL). The organic layer was dried over sodium sulfate. Tert-butyl 4-[2-(2,6-dioxo-3-piperidyl)-4-methoxy-1-oxo-isoindolin-5-yl]piperazine-1-carboxylate (400 mg, crude) was obtained as a pale yellow solid. LC/MS (ESI) m/z: 459.1 [M+1]$^+$.

Step 9: Preparation of 3-(4-methoxy-1-oxo-5-piperazin-1-yl-isoindolin-2-yl) piperidine-2,6-dione

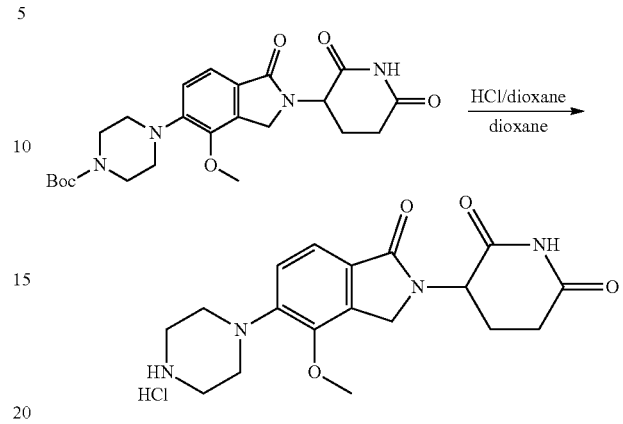

To a mixture of tert-butyl 4-[2-(2,6-dioxo-3-piperidyl)-4-methoxy-1-oxo-isoindolin-5-yl] piperazine-1-carboxylate (400 mg, 0.87 mmol, 1 eq) in dioxane (2 mL) was added hydrochloric acid in dioxane (4 M, 4 mL, 18.34 eq). The mixture was stirred at 20° C. for 10 min and solvent was removed under vacuum. 3-(4-Methoxy-1-oxo-5-piperazin-1-yl-isoindolin-2-yl)piperidine-2,6-dione (350 mg, crude, HCl salt) was obtained as a white solid. LC/MS (ESI) m/z: 359.1 [M+1]$^+$.

Step 10: Preparation of 3-[5-[4-[5-[4-[(1R,2S)-6-hydroxy-2-phenyl-tetralin-1-yl]phenoxy]pentyl]piperazin-1-yl]-4-methoxy-1-oxo-isoindolin-2-yl]piperidine-2,6-dione Exemplary Compound 3

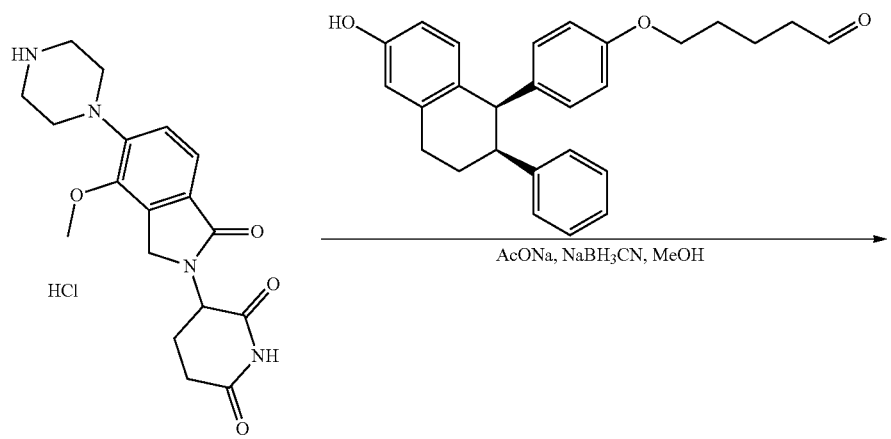

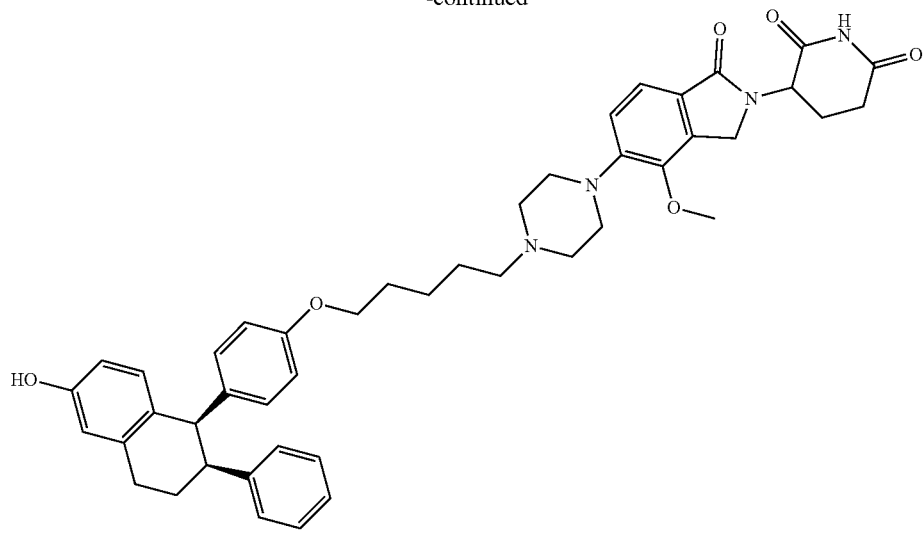

To a mixture of 3-(4-methoxy-1-oxo-5-piperazin-1-yl-isoindolin-2-yl)piperidine-2,6-dione (100 mg, 0.25 mmol, 1 eq, HCl salt) in dichloromethane (4 mL) and methanol (1 mL) was added sodium acetate (83 mg, 1.01 mmol, 4 eq). The mixture was stirred at 20° C. for 10 min. Then 5-[4-[(1R,2S)-6-hydroxy-2-phenyl-tetralin-1-yl]phenoxy]pentanal (101 mg, 0.25 mmol, 1.00 eq) was added and the mixture was stirred for 10 min. Sodium cyanoborohydride (31 mg, 0.51 mmol, 2 eq) was added to the mixture and stirring was kept for 40 min. LCMS and TLC (dichloromethane:methanol=10:1) showed reaction was complete. Solvent was removed under vacuum. The crude product was purified by prep-TLC (dichloromethane:methanol=10:1). 3-[5-[4-[5-[4-[(1R,2S)-6-Hydroxy-2-phenyl-tetralin-1-yl]phenoxy]pentyl]piperazin-1-yl]-4-methoxy-1-oxo-isoindolin-2-yl]piperidine-2,6-dione (55 mg, 0.07 mmol, 29% yield, 99% purity) was obtained as a white solid. LC/MS (ESI) m/z: 743.3 [M+1]$^+$; $^1$H-NMR (400 MHz, DMSO-d6) δ 10.96 (s, 1H), 9.12 (s, 1H), 7.39 (d, J=8.0 Hz, 1H), 7.25-6.98 (m, 4H), 6.83 (d, J=6.8 Hz, 2H), 6.72-6.43 (m, 5H), 6.26 (d, J=8.6 Hz, 2H), 5.06 (dd, J=5.0, 13.2 Hz, 1H), 4.56-4.11 (m, 3H), 3.94-3.70 (m, 5H), 3.30-3.25 (m, 1H), 3.21-2.77 (m, 8H), 2.64-2.55 (m, 5H), 2.46-2.26 (m, 2H), 2.16-1.94 (m, 2H), 1.80-1.22 (m, 7H).

B. Exemplary Synthetic Schemes for Exemplary Androgen Receptor Binding Moiety Based Compounds General Synthetic Scheme B-1

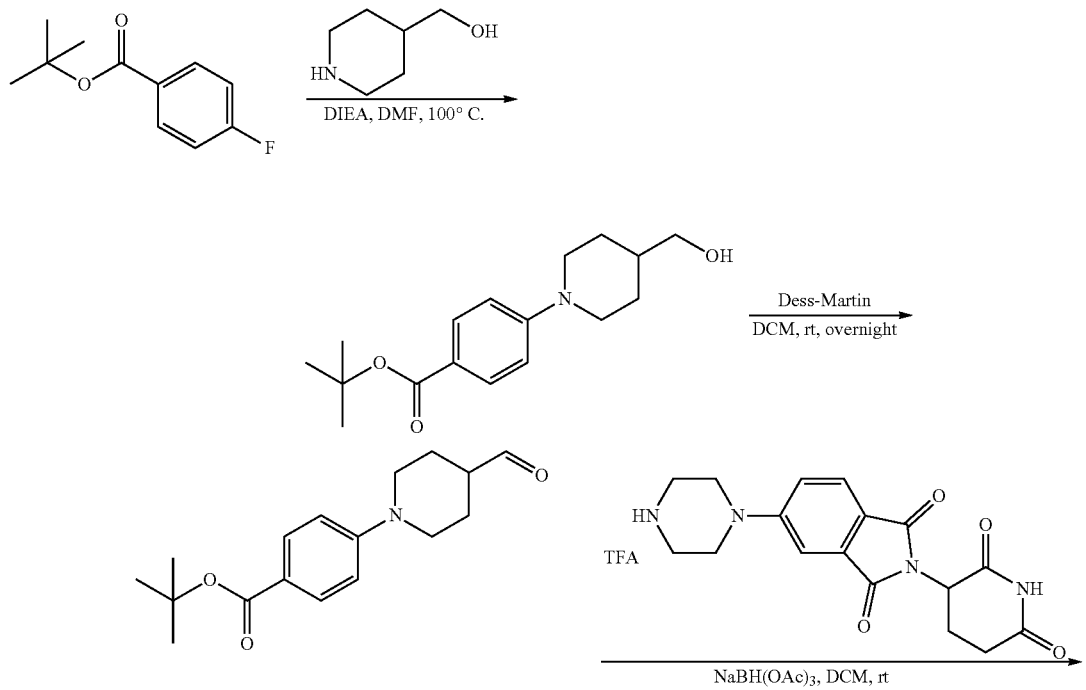

363 364
-continued
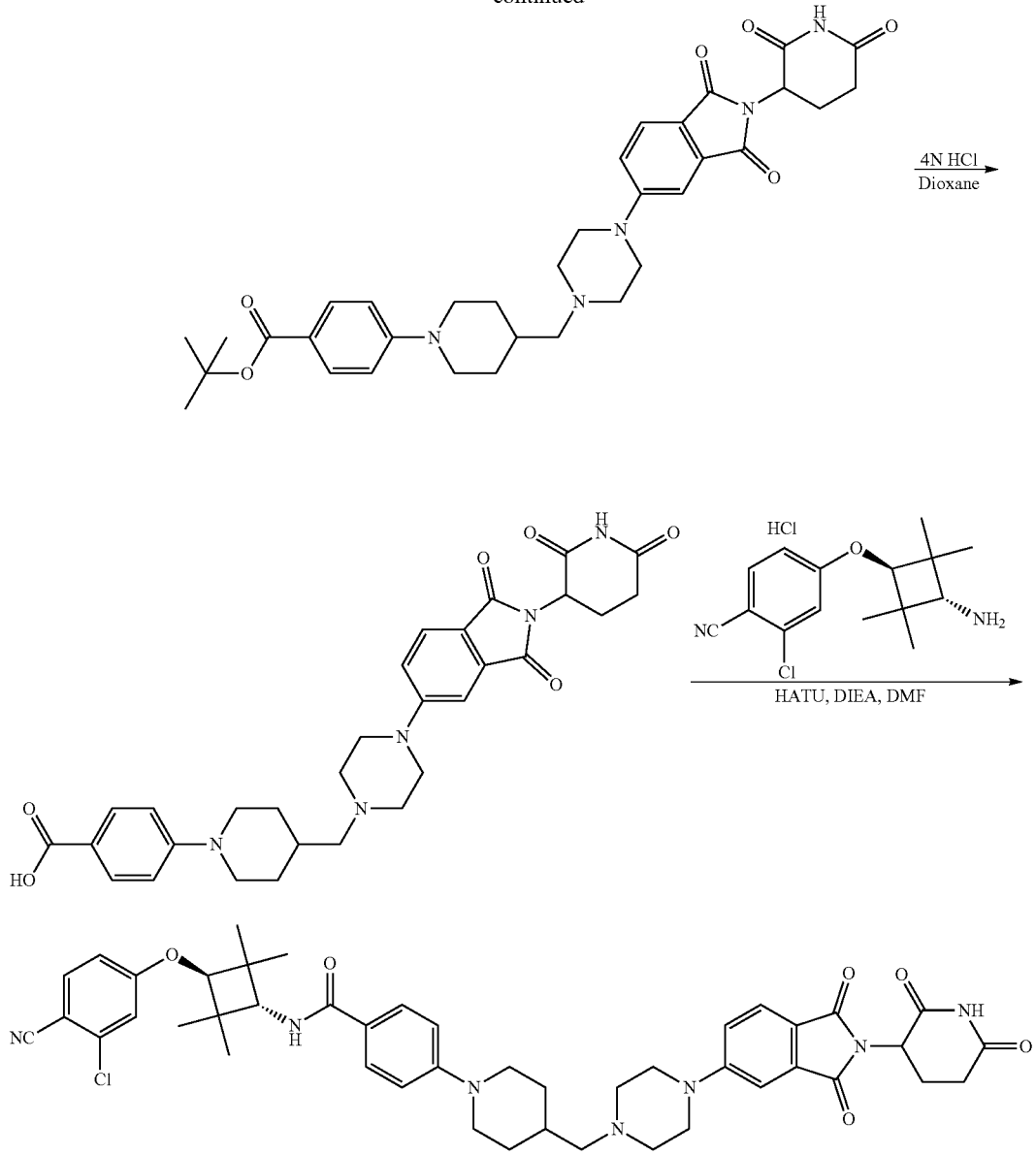
General Synthetic Scheme B-2
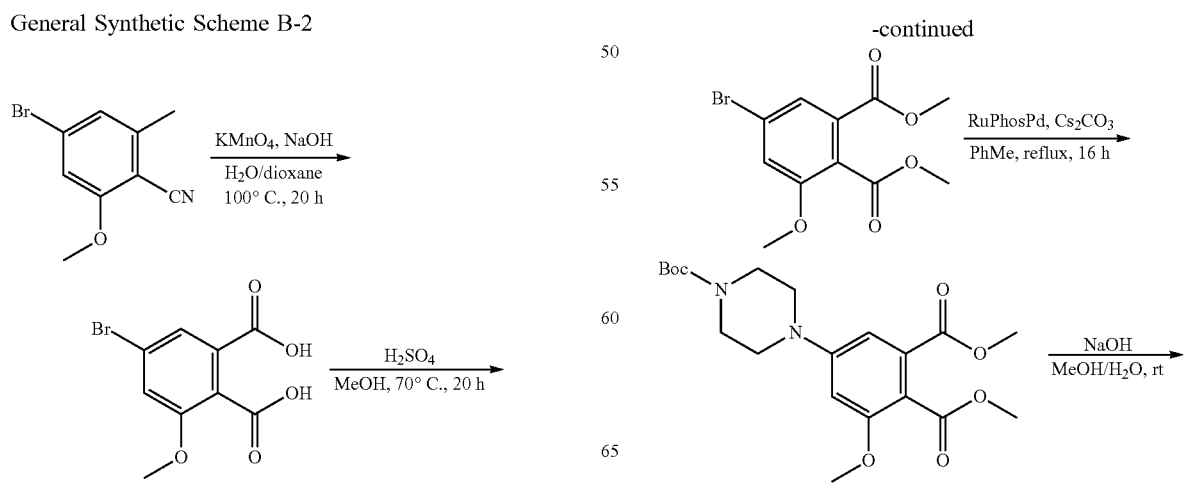

-continued
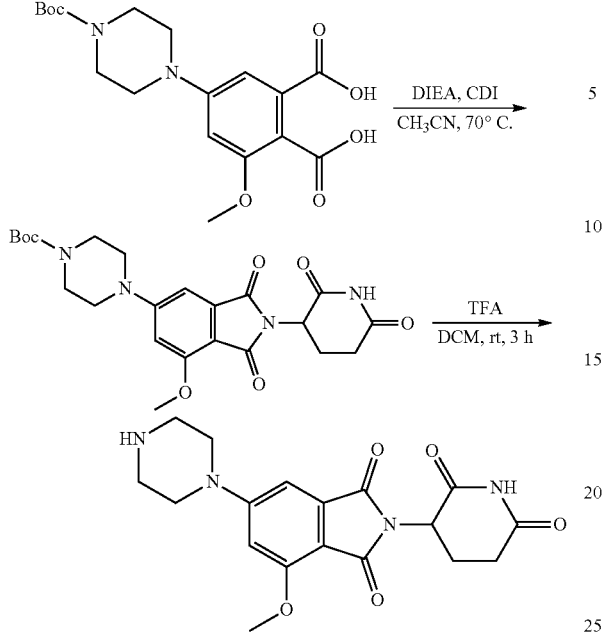
Exemplary Synthetic Scheme for Exemplary Compound 32:
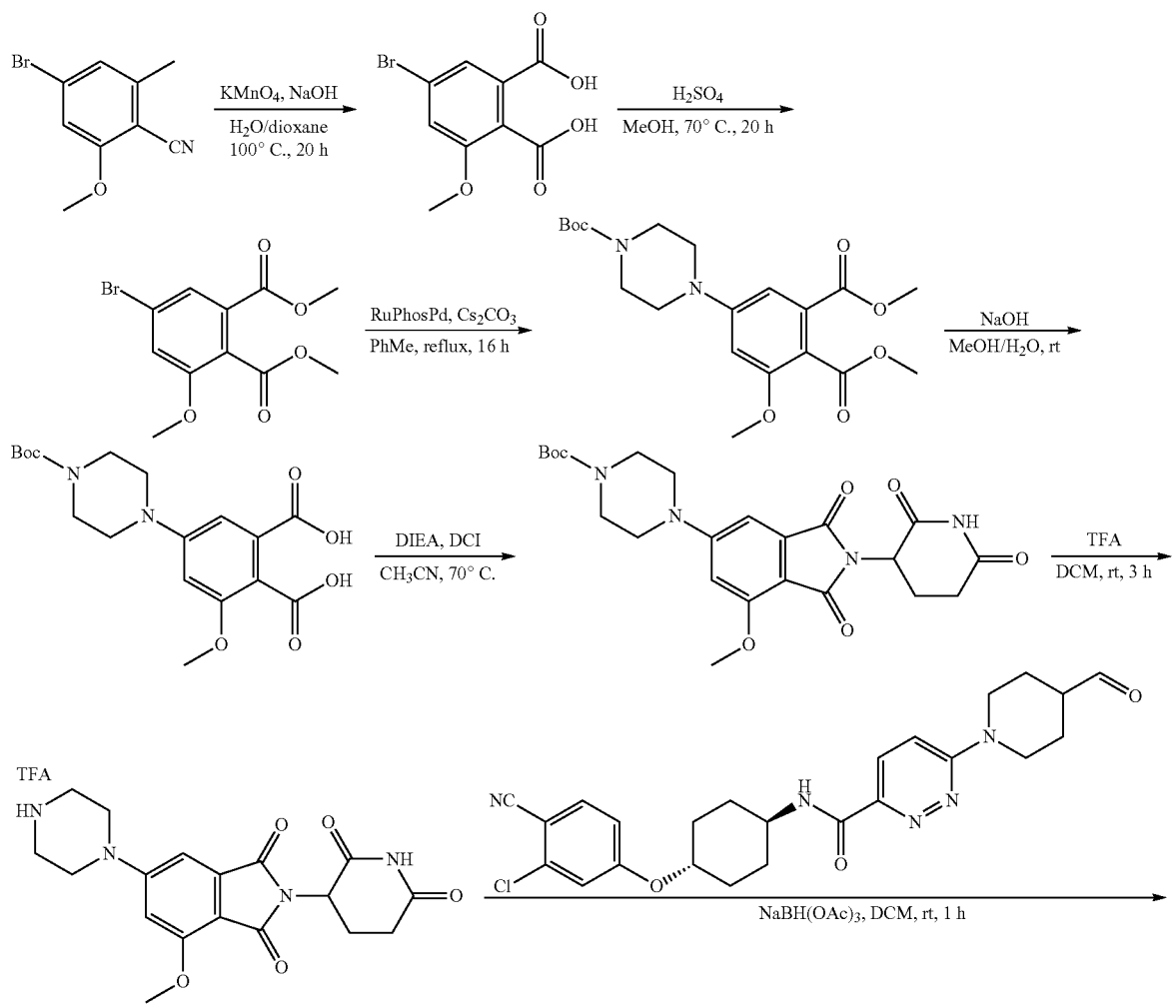

-continued

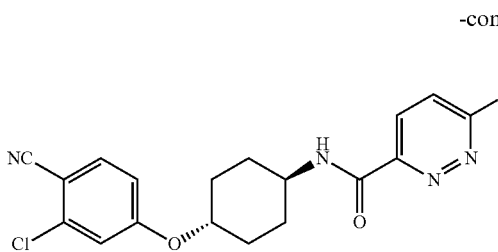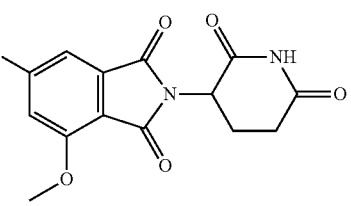

1. Synthesis of 5-bromo-3-methoxybenzene-1,2-dicarboxylic acid

Into a 100-mL round-bottom flask, was placed 4-bromo-2-methoxy-6-methylbenzonitrile (800 mg, 3.54 mmol, 1.00 equiv), water (10 mL), sodium hydroxide (708 mg, 17.70 mmol, 5.00 equiv), $KMnO_4$ (1.12 g, 7.09 mmol, 2.00 equiv). The resulting solution was stirred for 16 h at 100° C. in an oil bath. The solids were filtered out. The pH value of the solution was adjusted to 3 with hydrogen chloride (2 mol/L). The resulting solution was extracted with dichloromethane (15 mL×3) and the aqueous layers combined. The resulting solution was extracted with ethyl acetate/methanol=10:1 (15 mL×3) and the organic layers combined and dried in an oven under reduced pressure, concentrated under vacuum. This resulted in 330 mg (34%) of 5-bromo-3-methoxybenzene-1,2-dicarboxylic acid as a white solid.

2. Synthesis of 1,2-dimethyl 5-bromo-3-methoxybenzene-1,2-dicarboxylate

Into a 100-mL round-bottom flask, was placed 5-bromo-3-methoxybenzene-1,2-dicarboxylic acid (330 mg, 1.20 mmol, 1.00 equiv), methanol (20 mL), sulfuric acid (5 mL). The resulting solution was stirred for 16 h at 70° C. in an oil bath. The resulting solution was diluted with water (40 mL). The pH value of the solution was adjusted to 8 with sodium carbonate. The resulting solution was extracted with ethyl acetate (30 mL×3) and the organic layers combined and dried over anhydrous sodium sulfate and concentrated under vacuum. The residue was applied onto a silica gel column with ethyl acetate/petroleum ether (1:10). This resulted in 340 mg (93%) of 1,2-dimethyl 5-bromo-3-methoxybenzene-1,2-dicarboxylate as a white solid.

LC-MS (ES+): m/z 302.85 [MH+], $t_R$=0.906 min (2.0 minute run).

3. Synthesis of 1,2-dimethyl-5-[4-[(tert-butoxy)carbonyl]piperazin-1-yl]-3-methoxybenzene-1,2-dicarboxylate Into a 100-mL round-bottom flask, was placed 1,2-dimethyl 5-bromo-3-methoxybenzene-1,2-dicarboxylate (300 mg, 0.99 mmol, 1.00 equiv), tert-butyl piperazine-1-carboxylate (277 mg, 1.49 mmol, 1.50 equiv), RuphosPd (39 mg, 0.05 mmol, 0.05 equiv), $Cs_2CO_3$ (978 mg, 3.00 mmol, 3.00 equiv), toluene (15 mL). The resulting solution was stirred for 12 h at 100° C. in an oil bath. The resulting solution was diluted with water (30 mL). The resulting solution was extracted with ethyl acetate (30 mL×3) and the organic layers combined and dried over anhydrous sodium sulfate and concentrated under vacuum. The residue was applied onto a silica gel column with dichloromethane/ethyl acetate (10:1). This resulted in 340 mg (84%) of 1,2-dimethyl 5-[4-[(tert-butoxy)carbonyl]piperazin-1-yl]-3-methoxybenzene-1,2-dicarboxylate as light yellow oil.

LC-MS (ES+): m/z 409.05 [MH+], $t_R$=0.963 min (2.0 minute run).

4. Synthesis of 5-[4-[(tert-butoxy)carbonyl]piperazin-1-yl]-3-methoxybenzene-1,2-dicarboxylic acid Into a 100-mL round-bottom flask, was placed 1,2-dimethyl 5-[4-[(tert-butoxy)carbonyl]piperazin-1-yl]-3-methoxybenzene-1,2-dicarboxylate (340 mg, 0.83 mmol, 1.00 equiv), methanol/$H_2O$/THF (8 mL), sodiumol (100 mg, 2.50 mmol, 3.00 equiv). The resulting solution was stirred for 12 h at 25° C. The resulting solution was diluted with water (30 mL). The pH value of the solution was adjusted to 8 with hydrogen chloride (2 mol/L), citric acid monohydrate was employed to adjust the pH to 3. The resulting solution was extracted with ethyl acetate (30 mL×3) and the organic layers combined and dried over anhydrous sodium sulfate and concentrated under vacuum. This resulted in 300 mg (95%) of 5-[4-[(tert-butoxy)carbonyl]piperazin-1-yl]-3-methoxybenzene-1,2-dicarboxylic acid as colorless oil.

LC-MS (ES+): m/z 306.95 [MH+], $t_R$=0.853 min (2.0 minute run).

5. Synthesis of tert-butyl-4-[2-(2,6-dioxopiperidin-3-yl)-7-methoxy-1,3-dioxo-2,3-dihydro-1H-isoindol-5-yl]piperazine-1-carboxylate Into a 100-mL round-bottom flask, was placed tert-butyl 4-(7-methoxy-1,3-dioxo-1,3-dihydro-2-benzofuran-5-yl)piperazine-1-carboxylate (260 mg, 0.72 mmol, 1.00 equiv), 3-aminopiperidine-2,6-dione hydrochloride (153.6 mg, 0.93 mmol, 1.30 equiv), pyridine (10 mL). The resulting solution was stirred for 4 h at 120° C. in an oil bath. The resulting solution was diluted with water (30 mL). The resulting solution was extracted with ethyl acetate (30 mL×3) and the organic layers combined and dried over anhydrous sodium sulfate and concentrated under vacuum. The residue was applied onto a silica gel column with dichloromethane/methanol (100:1). This resulted in 280 mg (83%) of tert-butyl 4-[2-(2,6-dioxopiperidin-3-yl)-7-methoxy-1,3-dioxo-2,3-dihydro-1H-isoindol-5-yl]piperazine-1-carboxylate as a yellow solid.

LC-MS (ES+): m/z 417.05 [MH+], $t_R$=0.852 min (2.0 minute run).

6. Synthesis of 2-(2,6-dioxopiperidin-3-yl)-4-methoxy-6-(piperazin-1-yl) isoindoline-1,3-dione Into a 50-mL round-bottom flask, was placed tert-butyl 4-[2-(2,6-dioxopiperidin-3-yl)-7-methoxy-1,3-dioxo-2,3-dihydro-1H-isoindol-5-yl]piperazine-1-carboxylate (270 mg, 0.57 mmol, 1 equiv), dichloromethane (6 mL, 0.07 mmol, 0.124 equiv), TFA (2 mL, 0.02 mmol, 0.031 equiv). The resulting solution was stirred for 2 hr at 25° C. The resulting mixture was concentrated to give 2-(2,6-dioxopiperidin-3-yl)-4-methoxy-6-(piperazin-1-yl) isoindoline-1,3-dione as a brown oil.

LC-MS (ES+): m/z 373.05 [MH+], $t_R$=0.155 min (2.0 minute run).

7. Synthesis of 6-[4-([4-[2-(2,6-dioxopiperidin-3-yl)-7-methoxy-1,3-dioxo-2,3-dihydro-1H-isoindol-5-yl]piperazin-1-yl]methyl)piperidin-1-yl]-N-[(1r,4r)-4-(3-chloro-4-cyanophenoxy)cyclohexyl]pyridazine-3-carboxamide Into a 100-mL round-bottom flask, was placed 2,2,2-trifluoroacetaldehyde; 2-(2,6-dioxopiperidin-3-yl)-4-methoxy-6-(piperazin-1-yl)-2,3-dihydro-1H-isoindole-1,3-dione (130 mg, 0.28 mmol, 1.078 equiv), dichloromethane (10 mL, 0.12 mmol), 6-(4-formylpiperidin-1-yl)-N-[(1r,4r)-4-(3-chloro-4-cyanophenoxy)cyclohexyl]pyridazine-3-carboxamide (120 mg, 0.26 mmol, 1 equiv), NaBH(OAc)$_3$ (163.4 mg, 0.77 mmol, 3.006 equiv). The resulting solution was stirred for 2 hr at 25° C. The resulting solution was diluted with dichloromethane (30 mL). The resulting mixture was washed with H$_2$O (30 mL×3). The mixture was dried over anhydrous sodium sulfate and concentrated under vacuum. The resulting mixture was concentrated under vacuum. The residue was applied onto a silica gel column with dichloromethane/ethyl acetate (3:1). The crude product was purified by Prep-HPLC with the following conditions: Column, XBridge Prep C18 OBD Column, 5 um, 19*150 mm; mobile phase, Water (10 mmol/L NH$_4$HCO$_3$) and acetonitrile (43% Phase B up to 65% in 8 min); Detector, uv. This resulted in 70 mg (33.11%) of 6-[4-([4-[2-(2,6-dioxopiperidin-3-yl)-7-methoxy-1,3-dioxo-2,3-dihydro-1H-isoindol-5-yl]piperazin-1-yl]methyl)piperidin-1-yl]-N-[(1r,4r)-4-(3-chloro-4-cyanophenoxy)cyclohexyl]pyridazine-3-carboxamide as a yellow solid.

1H NMR (400 MHz, DMSO-d6) δ 11.04 (s, 1H), 8.57 (d, J=8.4 Hz, 1H), 7.87-7.79 (m, 2H), 7.39-7.32 (m, 2H), 7.15-7.12 (m, 1H), 6.96 (s, 1H), 6.68 (s, 1H), 5.04-4.98 (m, 1H), 4.50-4.47 (m, 3H), 4.93-3.85 (m, 4H), 3.35-3.33 (m, 5H), 3.07-2.81 (m, 3H), 2.51 (s, 3H), 2.27-22.1 (m, 2H), 2.09-2.01 (m, 2H), 2.00-1.49 (m, 11H), 1.23-1.11 (m, 3H); LC-MS (ES+): m/z 824.25/826.25 [MH+], $t_R$=182 min (3.0 minute run).

Chemical Formula: C$_{42}$H$_{43}$ClN$_9$O$_7$ [823.32/825.32]
Total H count from HNMR data: 46.

Exemplary Synthesis of Exemplary Compound 34

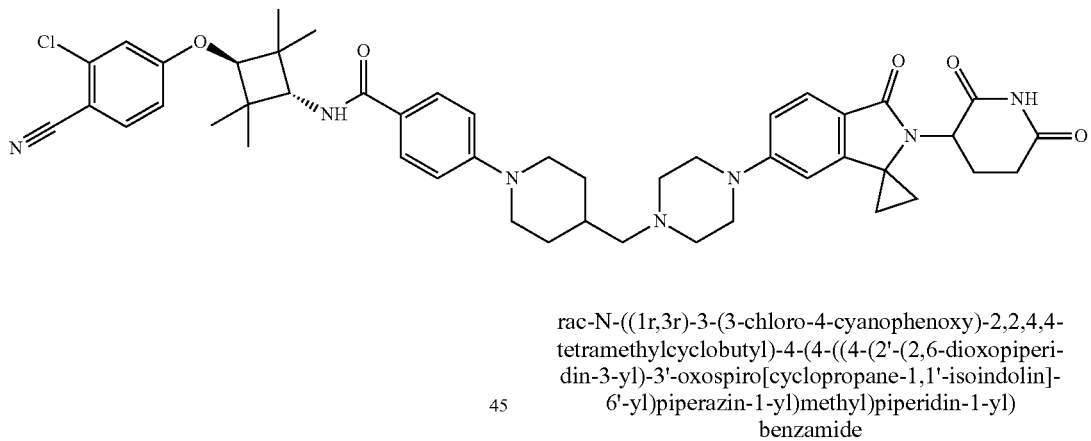

rac-N-((1r,3r)-3-(3-chloro-4-cyanophenoxy)-2,2,4,4-tetramethylcyclobutyl)-4-(4-((4-(2'-(2,6-dioxopiperidin-3-yl)-3'-oxospiro[cyclopropane-1,1'-isoindolin]-6'-yl)piperazin-1-yl)methyl)piperidin-1-yl)benzamide Synthetic Scheme

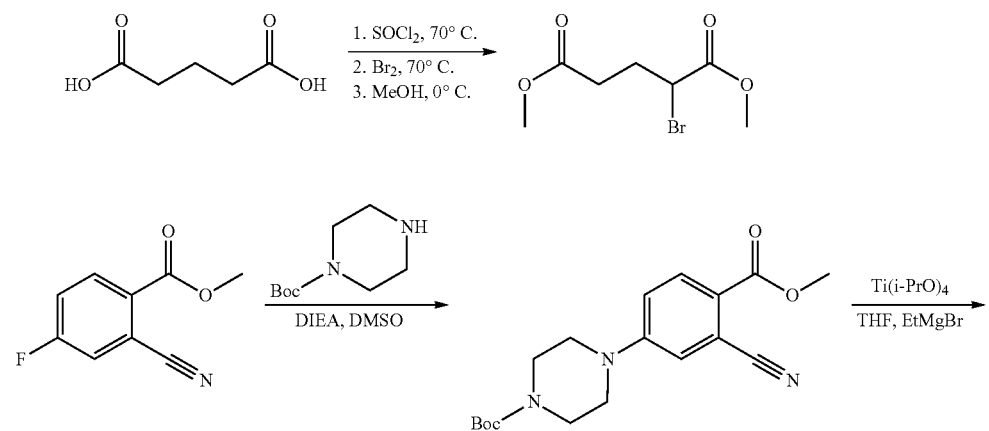

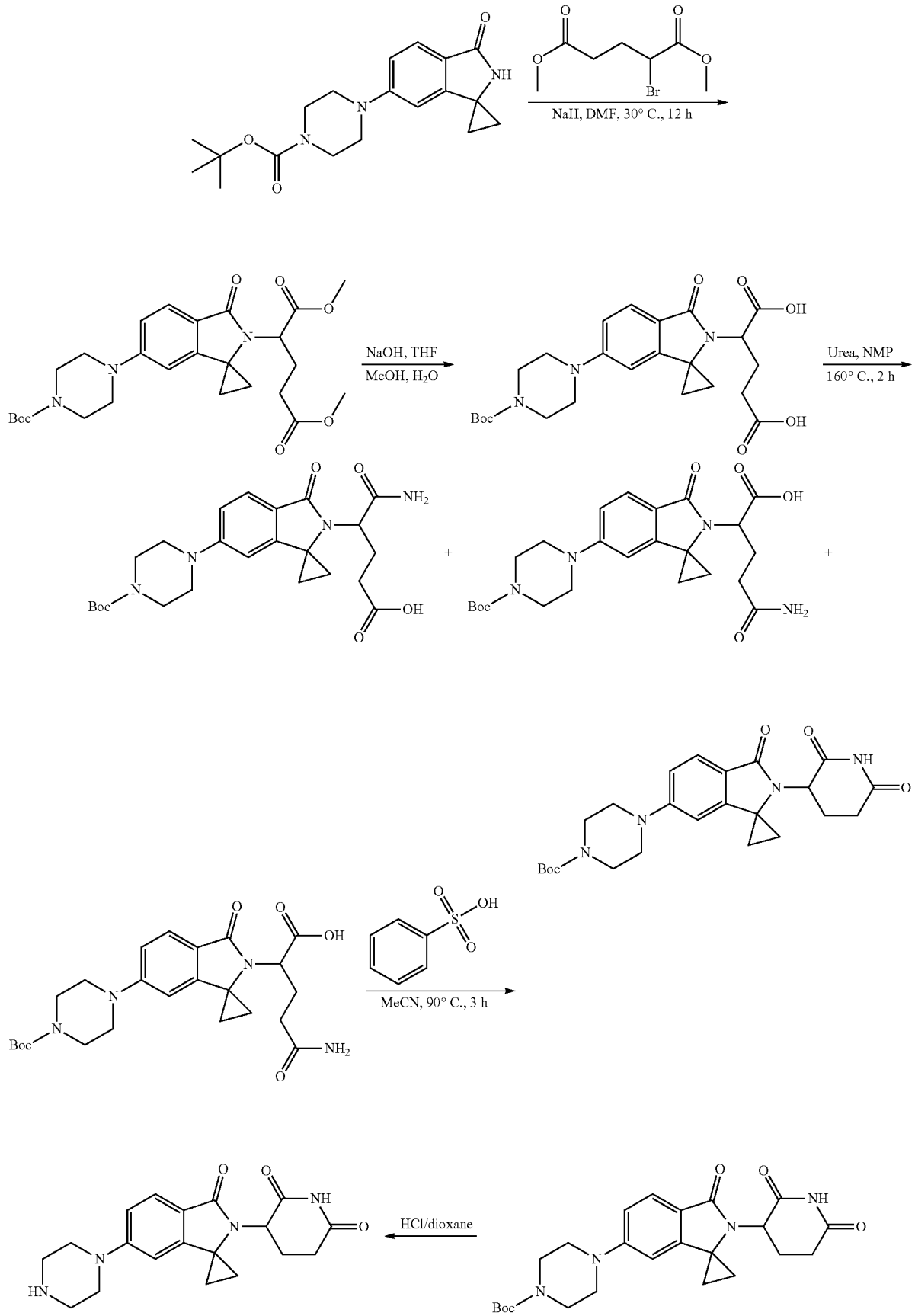

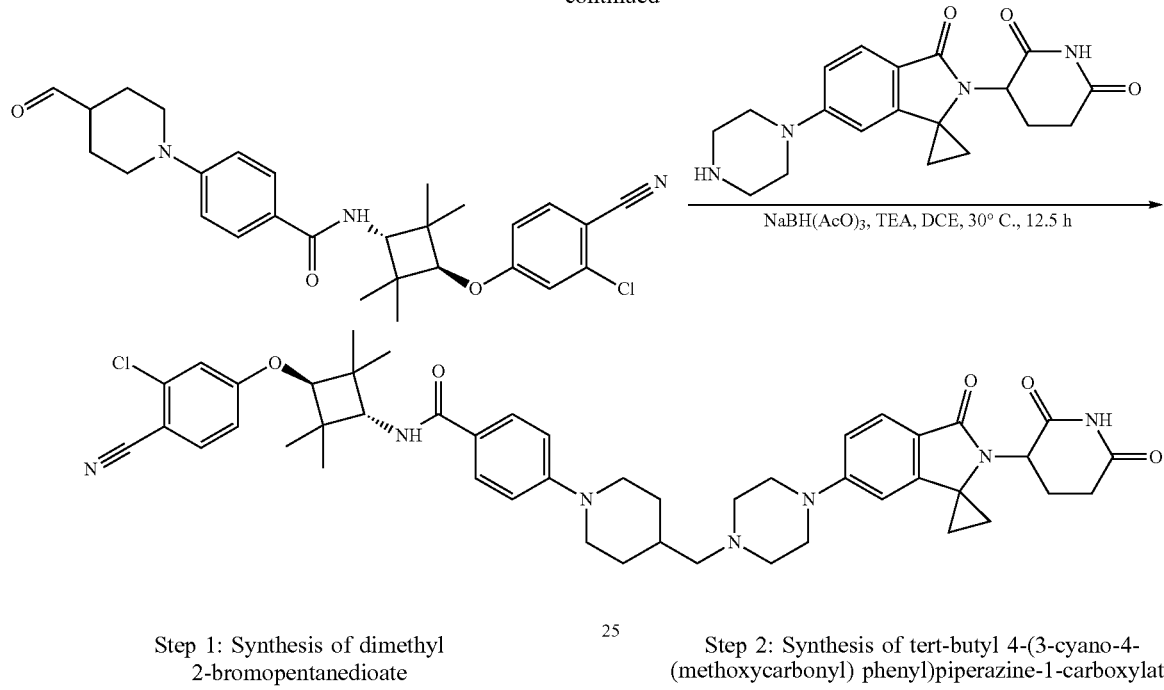

Step 1: Synthesis of dimethyl 2-bromopentanedioate

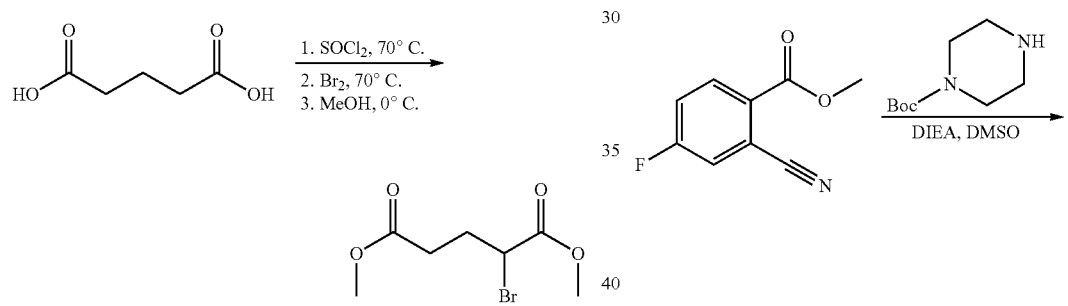

To a solution of glutaric acid (30 g, 227.07 mmol, 1 eq) in chloroform (90 mL) was added thionyl chloride (59 g, 499.56 mmol, 36 mL, 2.2 eq). The mixture was stirred at 70° C. for 1 h. Liquid bromine (36.29 g, 227.07 mmol, 1 eq) was added into the mixture dropwise. The mixture was stirred at 70° C. for 12 h. The mixture was cooled to 0° C. and methanol (58 g, 1.82 mol, 73 mL, 8 eq) was added into the mixture drop wise at 0° C. LCMS detected the desired product. The mixture was extracted with ethyl acetate (150 mL×3) and washed with saturated aqueous sodium bicarbonate (200 mL). The organic layer was dried over anhydrous sodium sulfate and concentrated. The residue was purified with Flash C18 column chromatography (acetonitrile:water=1:0 to 1:1). Dimethyl 2-bromopentanedioate (4 g+20 g (crude), 16.73 mmol, 7% yield) was obtained as a yellow oil.

LCMS: MS (ESI) m/z: 241.0 [M+1]$^+$.

Chemical Formula: $C_7H_{11}BrO_4$, Molecular Weight: 239.06

$^1$H NMR: (400 MHz, DCCl$_3$) δ: 4.39-4.36 (m, 1H), 3.78 (s, 3H), 3.72 (s, 3H), 2.56-2.49 (m, 2H), 2.44-2.34 (m, 1H), 2.33-2.23 (m, 1H).

Total H count from HNMR data: 11.

Step 2: Synthesis of tert-butyl 4-(3-cyano-4-(methoxycarbonyl) phenyl)piperazine-1-carboxylate To a solution of methyl 2-cyano-4-fluoro-benzoate (10 g, 55.82 mmol, 1 eq), tert-butyl piperazine-1-carboxylate (12.48 g, 66.98 mmol, 1.2 eq) in dimethylsulfoxide (100 mL) was added diisopropylethylamine (28.86 g, 223.28 mmol, 4 eq). The reaction mixture was stirred at 120° C. for 12 h. Thin layer chromatography (petroleum ether:Ethyl acetate=3:1) showed methyl 2-cyano-4-fluoro-benzoate was consumed, and desired product was detected. The mixture was poured into water (50 mL), and filtered. The filtrate was dried under vacuum. The residue was purified with silica gel column chromatography (petroleum ether:ethyl acetate=10:1 to 3:1). Tert-butyl 4-(3-cyano-4-methoxycarbonyl-phenyl)piperazine-1-carboxylate (18 g, 52.11 mmol, 93% yield) was obtained as a yellow solid.

Chemical Formula: $C_{18}H_{23}N_3O_4$, Molecular Weight: 345.39

Step 3: Synthesis of tert-butyl 4-(1'-oxospiro[cyclopropane-1,3'-isoindoline]-5'-yl)piperazine-1-carboxylate

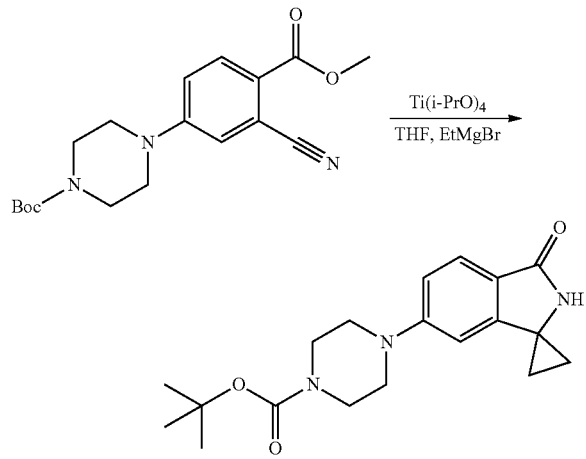

To a solution of tert-butyl 4-(3-cyano-4-methoxycarbonyl-phenyl)piperazine-1-carboxylate (18 g, 52.11 mmol, 1 eq) in tetrahydrofuran (200 mL) was added tetraisopropyl titanate (17.77 g, 62.54 mmol, 1.2 eq) and a solution of ethyl magnesium bromide in tetrahydrofuran (2 M, 52.11 mL, 2 eq) at 0° C. The mixture was stirred at 25° C. for 1 h. Thin layer chromatography (petroleum ether:ethyl acetate=1:1) showed tert-butyl 4-(3-cyano-4-methoxycarbonyl-phenyl)piperazine-1-carboxylate was consumed, and desired product was detected. The mixture was added into saturated aqueous ammonuim chloride (150 mL). The mixture was extracted with ethyl acetate (100 mL×3). The organic layer was dried over sodium sulfate and concentrated. The residue was triturated with ethyl acetate (30 mL) and filtered. Tert-butyl 4-(1'-oxospiro[cyclopropane-1,3'-isoindoline]-5'-yl)piperazine-1-carboxylate (6 g, 17.47 mmol, 33% yield) was obtained as a yellow solid.

Chemical Formula: $C_{19}H_{25}O_3N_3$, Molecular Weight: 343.42

$^1$H NMR: (400 MHz, CDCl$_3$) δ: 7.75-7.73 (d, J=8.8 Hz, 1H), 6.97-6.95 (d, J=8.8 Hz, 1H), 6.94-6.85 (m, 1H), 6.41 (s, 1H), 3.61-3.58 (t, J=4.8 Hz, 4H), 3.28-3.25 (t, J=4.8 Hz, 4H), 1.56 (s, 2H), 1.49 (s, 9H), 1.38-1.36 (m, 2H).

Total H count from HNMR data: 25.

Step 4: Synthesis of dimethyl 2-[6'-(4-tert-butoxycarbonylpiperazin-1-yl)-3'-oxo-spiro[cyclopropane-1,1'-isoindoline]-2'-yl]pentanedioate

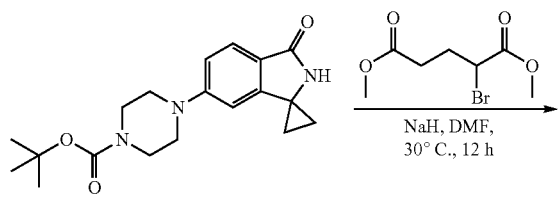

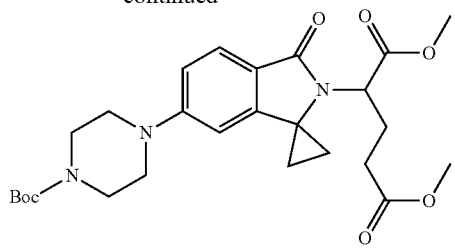

20 batches in parallel:
To a solution of tert-butyl 4-(1'-oxospiro[cyclopropane-1,3'-isoindoline]-5'-yl)piperazine-1-carboxylate (100 mg, 0.29 mmol, 1 eq) and dimethyl 2-bromopentanedioate (104 mg, 0.44 mmol, 1.5 eq) in dimethylformamide (2 mL) was added sodium hydride (35 mg, 0.88 mmol, 60% in mineral oil, 3 eq). The mixture was stirred at 30° C. for 12 h. Thin layer cromatography (petroleum ether:ethyl acetate=1:1) showed 30% of the tert-butyl 4-(1'-oxospiro[cyclopropane-1,3'-isoindoline]-5'-yl)piperazine-1-carboxylate was consumed. The 20 reaction mixtures were poured into 50 mL of brine, and extracted with ethyl acetate (30 mL×2), the combined organic layers were dried over anhydrous sodium sulfate, filtered and concentrated in vacuum. The residue was purified by silica gel column chromatography (petroleum ether/ethyl acetate=3/1 to 1/1). Dimethyl 2-[6'-(4-tert-butoxycarbonylpiperazin-1-yl)-3'-oxo-spiro[cyclopropane-1,1'-isoindoline]-2'-yl]pentanedioate (200 mg, 0.40 mmol, 10% yield corrected for recovered starting material) was obtained as a yellow oil. Also isolated was tert-butyl 4-(1'-oxospiro[cyclopropane-1,3'-isoindoline]-5'-yl)piperazine-1-carboxylate (675 mg).

Chemical Formula: $C_{26}H_{35}N_3O_7$, Molecular Weight: 501.57

Step 5: Synthesis of 2-[6'-(4-tert-butoxycarbonylpiperazin-1-yl)-3'-oxo-spiro[cyclopropane-1,1'-isoindoline]-2'-yl]pentanedioic acid

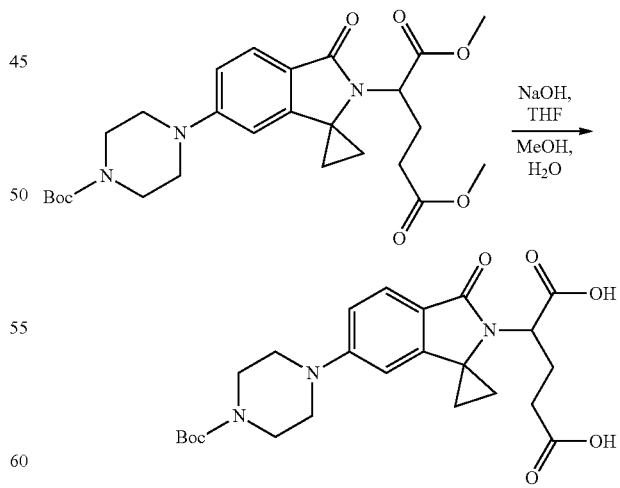

To a solution of dimethyl 2-[6'-(4-tert-butoxycarbonylpiperazin-1-yl)-3'-oxo-spiro [cyclopropane-1,1'-isoindoline]-2'-yl]pentanedioate (800 mg, 1.59 mmol, 1 eq) in tetrahydrofuran (5 mL) and methanol (5 mL) was added a solution of sodium hydroxide (255 mg, 6.38 mmol, 4 eq) in water (3 mL). The mixture was stirred at 25° C. for 2 hr. LCMS showed the reaction was completed and desired MS was detected. The mixture together with the other batch was poured into 20 mL water, and adjusted the pH to 3.0 with 2.0 N hydrochloride acid, then extracted with ethyl acetate (30 mL×3). The combined organic layers were dried over anhydrous sodium sulfate, then concentrated in vacuum. 2-[6'-(4-tert-butoxycarbonylpiperazin-1-yl)-3'-oxo-spiro[cyclopropane-1,1'-isoindoline]-2'-yl]pentanedioic acid (740 mg, 1.56 mmol, 97% yield) as an off-white solid was obtained, which was directly used for the next step without further purification.

LCMS: MS (ESI) m/z: 474.3[M+1]$^+$.

Chemical Formula: $C_{24}H_{31}N_3O_7$, Molecular Weight: 473.52

Step 6: Synthesis of 5-amino-4-[6'-(4-tert-butoxycarbonylpiperazin-1-yl)-3'-oxo-spiro[cyclopropane-1,1'-isoindoline]-2'-yl]-5-oxo-pentanoic acid; 5-amino-2-[6'-(4-tert-butoxycarbonylpiperazin-1-yl)-3'-oxo-spiro[cyclopropane-1,1'-isoindoline]-2'-yl]-5-oxo-pentanoic acid and tert-butyl 4-12'-(2,6-dioxo-3-piperidyl)-1'-oxo-spiro[cyclopropane-1,3'-isoindoline-5'-yl]piperazine-1-carboxylate

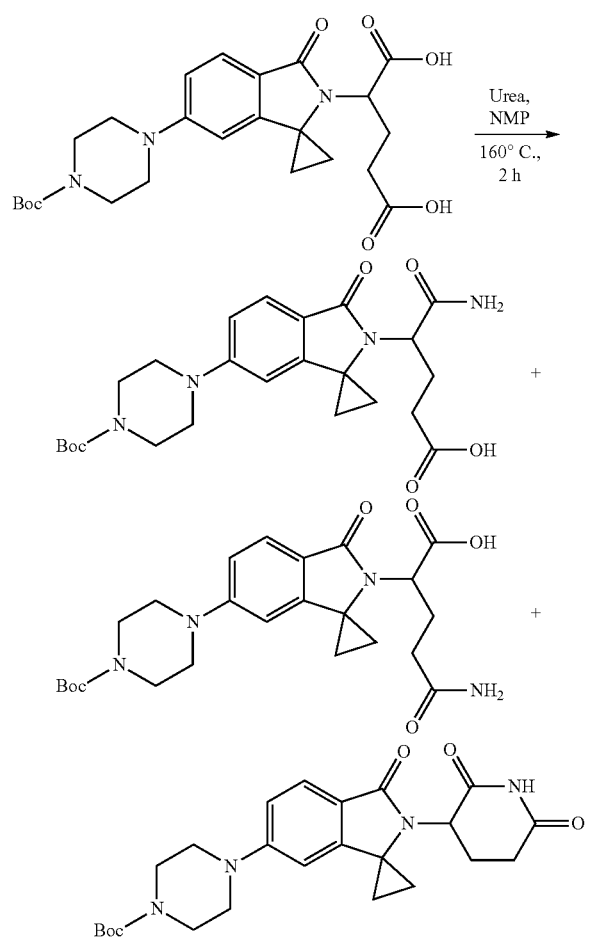

A mixture of 2-[6'-(4-tert-butoxycarbonylpiperazin-1-yl)-3'-oxo-spiro[cyclopropane-1,1'-isoindoline]-2'-yl]pentanedioic acid (400 mg, 0.85 mmol, 1 eq) and urea (253 mg, 4.22 mmol, 5 eq) in 1-methyl-2-pyrrolidinone (4 mL) was heated to 160° C. and stirred at 160° C. for 2 hours. LCMS showed two peaks with desired MS signals. The mixture together with the other batch was filtered. The filtrate was further purified by Semi-preparative reverse phase HPLC (column: Boston Green ODS 150*30 5 um; mobile phase: [water (0.225% formic acid)-acetonitrile]; B %: 35%-45%, 10 min). 2 isomeric mono-amides 5-amino-4-[6'-(4-tert-butoxycarbonylpiperazin-1-yl)-3'-oxo-spiro[cyclopropane-1,1'-isoindoline]-2'-yl]-5-oxo-pentanoic acid and 5-amino-2-[6'-(4-tert-butoxycarbonylpiperazin-1-yl)-3'-oxo-spiro[cyclopropane-1,1'-isoindoline]-2'-yl]-5-oxo-pentanoic acid were obtained (170 mg, 0.36 mmol, 42% yield and 90 mg, 0.19 mmol, 22% yield respectively. It was not conclusively established which of the 2 isomeres corresponds to which structure.) Also isolated was tert-butyl 4-[2'-(2,6-dioxo-3-piperidyl)-1'-oxo-spiro[cyclopropane-1,3'-isoindoline]-5'-yl]piperazine-1-carboxylate (90 mg, 0.20 mmol, 23% yield) as an off-white solid.

LCMS: mono-amide product 1: MS (ESI) m/z: 473.1[M+1]$^+$, Mono-amide product 2: MS (ESI) m/z: 473.1[M+1]$^+$, Imide product 3: MS (ESI) m/z: 455.1 [M+1]$^+$.

Chemical Formula mono-amide product 1: $C_{24}H_{32}N_4O_6$, Molecular Weight: 472.53.

Chemical Formula mono-amide product 2: $C_{24}H_{32}N_4O_6$, Molecular Weight: 472.53.

Chemical Formula Imide product: $C_{24}H_{30}N_4O_5$, Molecular Weight: 454.52.

Step 7a: Synthesis of 3-(3'-oxo-6'-piperazin-1-yl-spiro[cyclopropane-1,1'-isoindoline]-2'-yl)piperidine-2,6-dione from the Mono-Amide Product 1 of Step 6

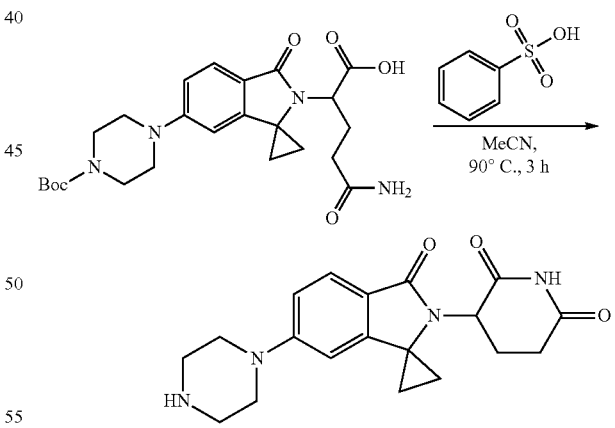

To a mixture of 5-amino-2-[6'-(4-tert-butoxycarbonylpiperazin-1-yl)-3'-oxo-spiro [cyclopropane-1,1'-isoindoline]-2'-yl]-5-oxo-pentanoic acid (190 mg, 0.40 mmol, 1 eq, the first eluting mono-amide product from above) in acetonitrile (15 mL) was added benzenesulfonic acid (114 mg, 0.72 mmol, 1.80 eq) in one portion at 25° C. under nitrogen atmosphere. The mixture was stirred at 90° C. for 3 hours. LCMS showed the product was the main peak. The mixture was concentrated in vacuum. The residue was purified by Semi-preparative reverse phase HPLC (column: Boston Green ODS 150*30 5 um; mobile phase: [water (0.225% formic acid)-acetonitrile]; B %: 1%-27%, 10 min). The product 3-(3'-oxo-6'-piperazin-1-yl-spiro[cyclopropane-1,1'-isoindoline]-2'-yl)piperidine-2,6-dione (55 mg, 0.14 mmol, 34% yield, benzene sulfonate) was obtained as a brown solid.

LCMS: EW4875-628-P1B, MS (ESI) m/z: 355.1[M+1]+.

Chemical Formula: $C_{19}H_{22}N_4O_3$, Molecular Weight: 354.40.

Step 7b: Synthesis of 3-(3'-oxo-6'-piperazin-1-yl-spiro[cyclopropane-1,1'-isoindoline]-2'-yl)piperidine-2,6-dione from the Imide Product of Step 6

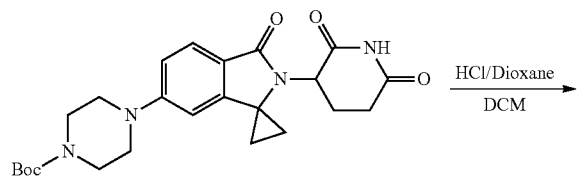

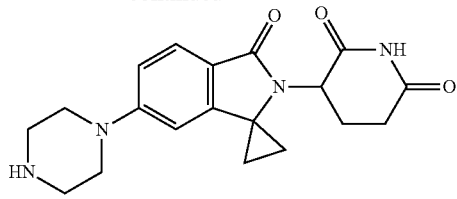

To a mixture of tert-butyl 4-[2'-(2,6-dioxo-3-piperidyl)-1'-oxo-spiro[cyclopropane-1,3'-isoindoline]-5'-yl]piperazine-1-carboxylate (90 mg, 0.20 mmol, 1 eq) in dichloromethane (5 mL) was added hydrochloric acid (4 M in dioxane, 2.5 mL, 50 eq) in one portion at 25° C. The mixture was stirred at 25° C. for 1 hour. LCMS showed the product was the main peak. The mixture was concentrated in vacuum. The crude solid The product 3-(3'-oxo-6'-piperazin-1-yl-spiro[cyclopropane-1,1'-isoindoline]-2'-yl)piperidine-2,6-dione (70 mg, 0.18 mmol, 90% yield, hydrochloride) was obtained as a brown solid, which was directly used into the next step without further purification.

LCMS: MS (ESI) m/z: 355.1[M+1]+.

Chemical Formula: $C_{19}H_{22}N_4O_3$, Molecular Weight: 354.40

Step 8: Synthesis of N-[3-(3-chloro-4-cyano-phenoxy)-2,2,4,4-tetramethyl-cyclobutyl]-4-[4-[[4-[2'-(2,6-dioxo-3-piperidyl)-1'-oxo-spiro[cyclopropane-1,3'-isoindoline]-5'-yl]piperazin-1-yl]methyl]-1-piperidyl]benzamide

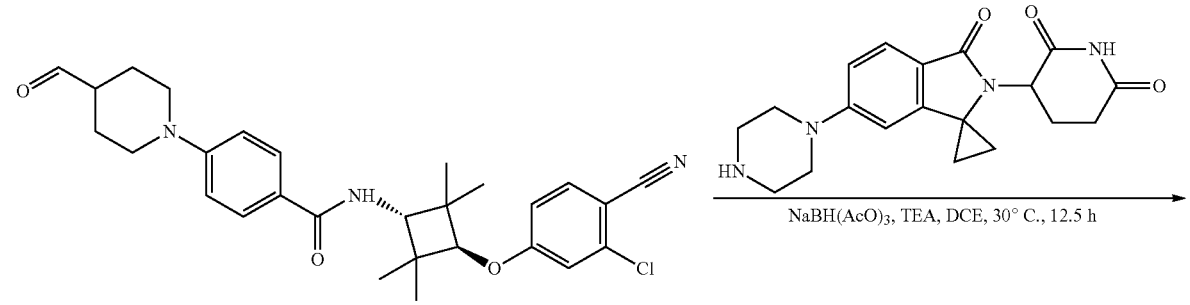

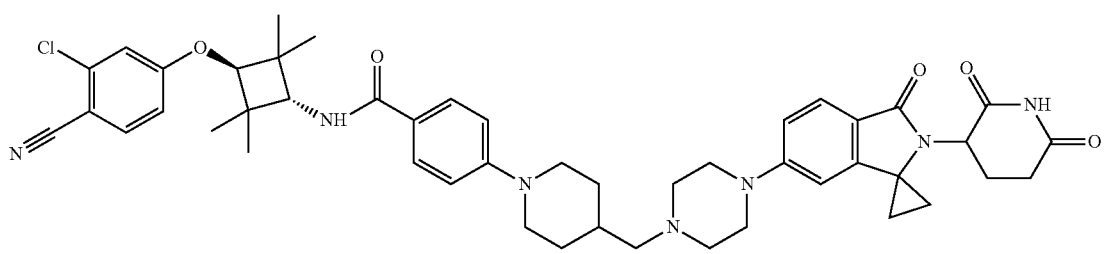

To a solution of N-[3-(3-chloro-4-cyano-phenoxy)-2,2,4,4-tetramethyl-cyclobutyl]-4-(4-formyl-1-piperidyl)benzamide (63 mg, 0.12 mmol, 1 eq) in 1,2-dichloroethane (3 mL) was added triethylamine (38 mg, 0.38 mmol, 3 eq) and 3-(3'-oxo-6'-piperazin-1-yl-spiro[cyclopropane-1,1'-isoindoline]-2'-yl)piperidine-2,6-dione (50 mg, 0.12 mmol, 1 eq, hydrochloride). The mixture was stirred at 30° C. for 30 min. Sodium triacetoxyborohydride (54 mg, 0.25 mmol, 2 eq) was added, then the mixture was stirred at 30° C. for 12 hours. LCMS showed the reaction was completed and desired MS can be detected. The reaction mixture was concentrated under reduced pressure to remove solution. The residue was purified by Semi-preparative reverse phase HPLC (column: Phenomenex Synergi C18 150*25*10 um; mobile phase: [water (0.225% FA)-ACN]; B %: 40%-70%, 10 min) to give N-[3-(3-chloro-4-cyano-phenoxy)-2,2,4,4-tetramethyl-cyclobutyl]-4-[4-[[4-[2'-(2,6-dioxo-3-piperidyl)-1'-oxo-spiro[cyclopropane-1,3'-isoindoline]-5'-yl]piperazin-1-yl]methyl]-1-piperidyl]benzamide (17.8 mg, 0.02 mmol, 16% yield, 98% purity) as a white solid.

LCMS: MS (ESI) m/z: 932.3 [M+1]$^+$.

$^1$H NMR: (400 MHz, DMSO-d$_6$) δ: 10.88 (s, 1H), 8.22 (s, 1H), 7.91 (d, J=8.8 Hz, 1H), 7.74 (d, J=8.8 Hz, 2H), 7.53-7.45 (m, 2H), 7.21 (d, J=2.4 Hz, 1H), 6.99 (dd, J=9.2, 17.6 Hz, 4H), 6.73 (s, 1H), 4.33 (s, 1H), 4.06 (d, J=9.2 Hz, 1H), 3.86 (d, J=12.4 Hz, 3H), 3.32-3.29 (m, 9H), 2.80 (t, J=12.0 Hz, 3H), 2.59-2.54 (m, 4H), 2.22 (d, J=6.8 Hz, 2H), 1.81 (d, J=10.3 Hz, 4H), 1.55-1.47 (m, 2H), 1.45-1.31 (m, 2H), 1.25-1.17 (s, 8H), 1.13 (s, 6H).

Chemical Formula: C$_{47}$H$_{54}$ClN$_7$O$_5$, Molecular Weight: 832.43.

Total H count from HNMR data: 54.

C. Exemplary Synthetic Schemes for Exemplary Androgen Receptor Binding Moiety Based Compounds that are Imide Isosteres General Synthetic Scheme C-1

Synthesis of Building Block N-((1r,3r)-3-(3-chloro-4-cyanophenoxy)-2,2,4,4-tetramethylcyclobutyl)-6-(piperazin-1-yl)nicotinamide

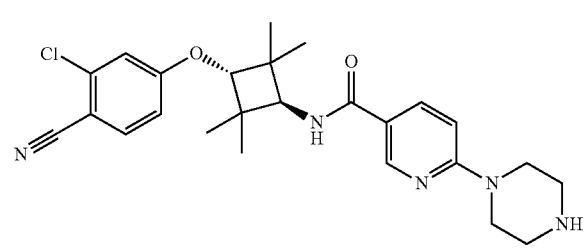 [SMILES: CC1(C)[C@H](NC(=O)c2ccc(N3CCNCC3)nc2)C(C)(C)[C@H]1Oc1ccc(C#N)c(Cl)c1]

Synthetic Scheme

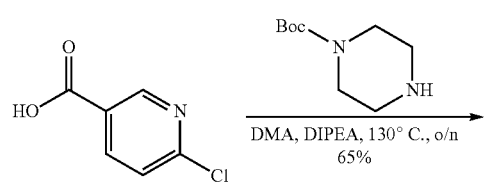

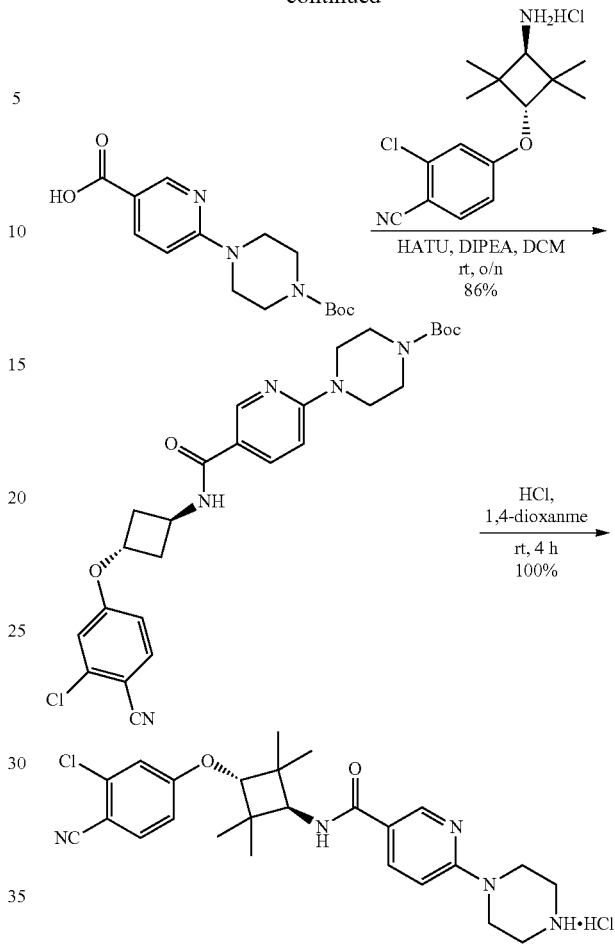

Step 1: Synthesis of 6-(4-(tert-butoxycarbonyl)piperazin-1-yl)nicotinic acid

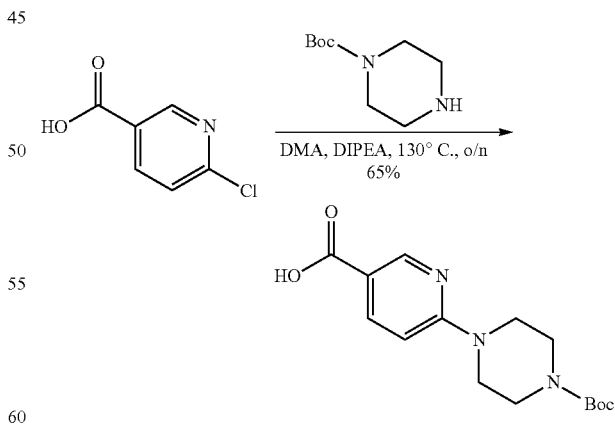

6-Chloronicotinic acid (1.6 g, 10.0 mmol) was dissolved in N,N-dimethylacetamide (15 mL), and tert-butyl piperazine-1-carboxylate (1.9 g, 10.0 mmol) and ethyldiisopropylamine (2.6 g, 20 mmol) were added thereto, followed by stirring at 130° C. overnight. The reaction mixture was concentrated under reduced pressure, and to the obtained residue was added a 1 M aqueous NaOH solution (10 mL), followed by washing with CHCl₃ (50 mL). The pH of the aqueous layer was adjusted to around 6 to 7 by the addition of 1 M hydrochloric acid, followed by extraction with CHCl₃ (50 mL×3). The organic layer was dried over anhydrous sodium sulfate and the solvent was concentrated under reduced pressure. The obtained residue was purified by silica gel column chromatography (CH$_2$Cl$_2$/MeOH=10/1) to give 6-(4-(tert-butoxycarbonyl)piperazin-1-yl)nicotinic acid (2.0 g, 65% yield) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity is 83.17%, Rt=1.312 min; MS Calcd.: 307.15; MS Found: 308.2 [M+H]⁺.

Chemical Formula: C$_{15}$H$_{21}$N$_3$O$_4$, Molecular Weight: 307.34.

Step 2: Synthesis of tert-butyl 4-(5-((1r,3r)-3-(3-chloro-4-cyanophenoxy)-2,2,4,4-tetramethylcyclobutylcarbamoyl)pyridin-2-yl)piperazine-1-carboxylate

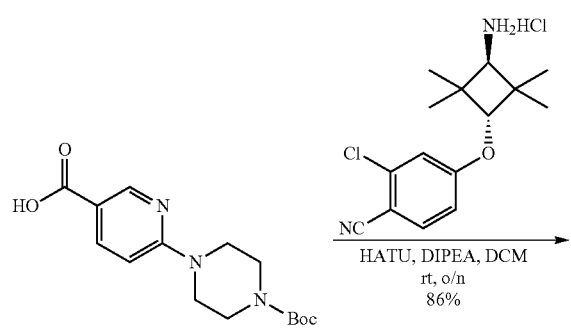

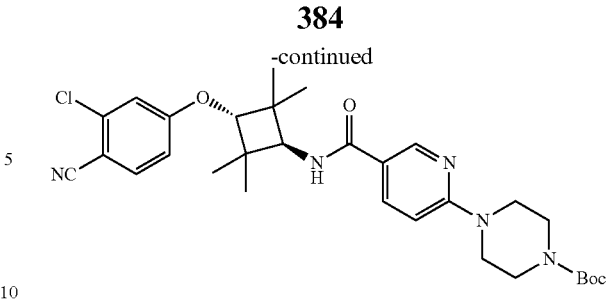

A mixture of 6-(4-(tert-butoxycarbonyl)piperazin-1-yl)nicotinic acid (614 mg, 2.0 mmol), 4-((1r,3r)-3-amino-2,2,4,4-tetramethylcyclobutoxy)-2-chlorobenzonitrile hydrochloride (630 mg, 2.0 mmol), 2-(7-Aza-1H-benzotriazole-1-yl)-1,1,3,3-tetramethyluronium hexafluorophosphate (1.1 g, 3.0 mmol) and ethyldiisopropylamine (516 mg, 4.0 mmol) in dichloromethane (20 mL) was stirred at room temperature overnight. Water (50 mL) was added and extracted with dichloromethane (50 mL×3). Combined organic layers were washed by brine (50 mL×2), dried over anhydrous sodium sulfate. The solvent was concentrated to give the residue, which was purified by column chromatography on silica gel (petroleum ether/ethyl acetate=1/1) to give tert-butyl 4-(5-((1r,3r)-3-(3-chloro-4-cyanophenoxy)-2,2,4,4-tetramethylcyclobutylcarbamoyl)pyridin-2-yl)piperazine-1-carboxylate (977 mg, 86% yield) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity is 88.26%, Rt=2.161 min; MS Calcd.: 567.26; MS Found: 568.3 [M+H]⁺.

¹H NMR (400 MHz, DMSO-d$_6$) δ1.12 (6H, s), 1.22 (6H, s), 1.43 (9H, s), 3.42-3.44 (4H, m), 3.60-3.63 (4H, m), 4.02-4.07 (1H, m), 4.31 (1H, s), 6.88 (1H, d, J=8.8 Hz), 7.00 (1H, dd, J=8.4, 2.4 Hz), 7.21 (1H, d, J=2.4 Hz), 7.65 (11H, d, J=9.2 Hz), 7.91 (1H, d, J=8.8 Hz), 7.99 (1H, dd, J=8.8, 2.4 Hz), 8.64 (1H, d, J=2.4 Hz).

Chemical Formula: C$_{30}$H$_{38}$ClN$_5$O$_4$, Molecular Weight: 568.11.

Total H count from HNMR data: 38.

Step 3: Synthesis of N-((1r,3r)-3-(3-chloro-4-cyanophenoxy)-2,2,4,4-tetramethylcyclobutyl)-6-(piperazin-1-yl)nicotinamide hydrochloride

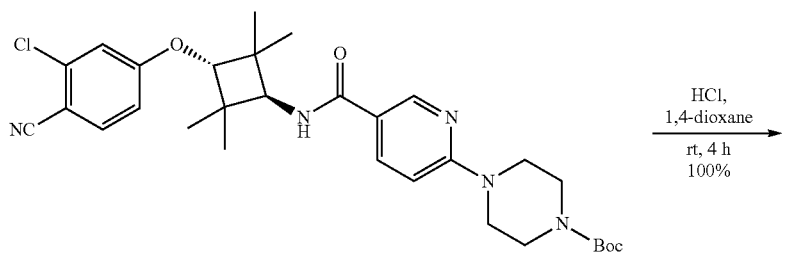

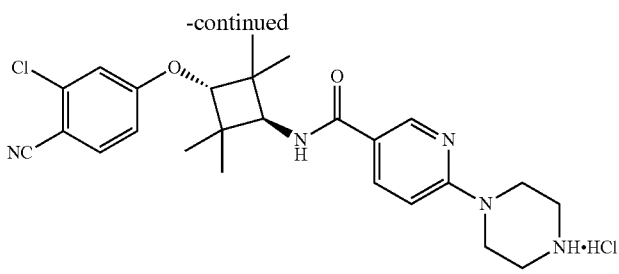

A mixture of tert-butyl 4-(5-(((1r,3r)-3-(3-chloro-4-cyanophenoxy)-2,2,4,4-tetramethylcyclobutyl carbamoyl)pyridin-2-yl)piperazine-1-carboxylate (405 mg, 0.7 mmol) in HCl/1,4-dioxane (10 mL) was stirred at room temperature for 4 h. The solvent was removed in vacuum to give N-((1r,3r)-3-(3-chloro-4-cyanophenoxy)-2,2,4,4-tetramethylcyclobutyl)-6-(piperazin-1-yl)nicotinamide hydrochloride (353 mg, 100% yield) as a white solid.

LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Rt=1.791 min; MS Calcd.: 467.21; MS Found: 468.3 $[M+H]^+$.

Chemical Formula: $C_{25}H_{31}Cl_2N_5O_2$, Molecular Weight: 504.45

General Synthetic Scheme C-2

Synthesis of Building Block tert-butyl 4-(4-formylpiperidin-1-yl)benzoate

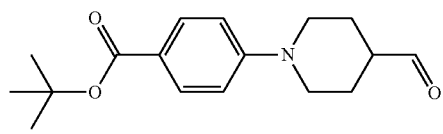

Synthetic Scheme

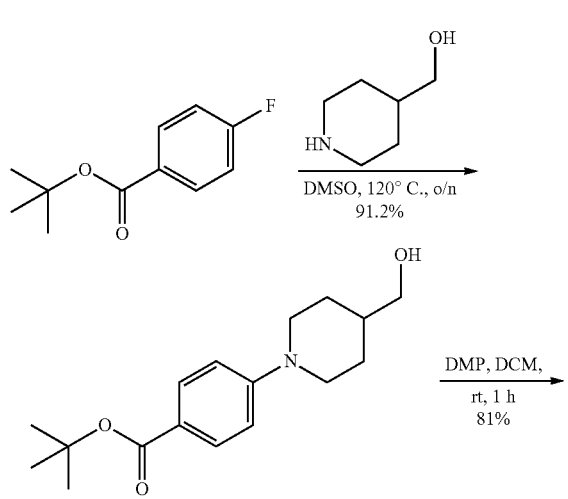

-continued

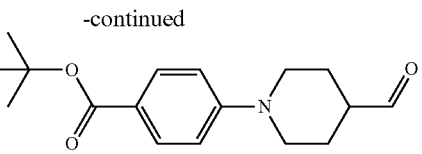

Step 1: Synthesis of tert-butyl 4-(4-(hydroxymethyl)piperidin-1-yl)benzoate

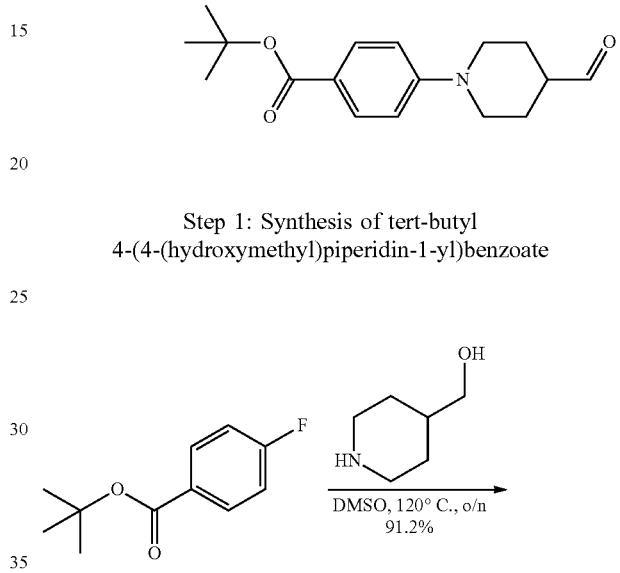

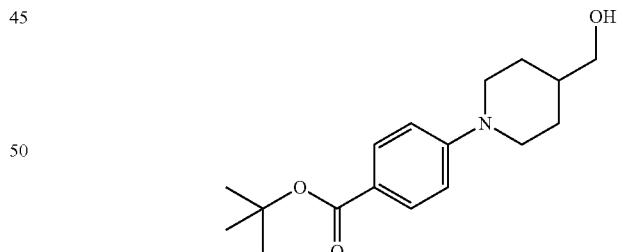

To a solution of tert-butyl 4-fluorobenzoate (23 g, 0.12 mmol) in DMSO (100 mL) was added piperidin-4-ylmethanol (40.5 g, 0.35 mmol). The mixture was heated to 120° C. overnight under nitrogen. After cooling to room temperature, water (50 mL) was added to the reaction mixture, and extracted with ethyl acetate (20 mL×3). The organic layer was washed with brine (15 mL×3). The combined organic phases were dried over anhydrous sodium sulfate and concentrated in vacuo, and purified by CC (PE/EA=10:1) to give compound tert-butyl 4-(4-(hydroxymethyl)piperidin-1-yl)benzoate (31 g, 91.2%) as a white solid.

LCMS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 90% [(total 10 mM AcONH$_4$) water/CH$_3$CN=900/100 (v/v)] and 10% [(total 10 mM AcONH$_4$) water/CH$_3$CN=100/900 (v/v)] to 10% [(total 10 mM AcONH$_4$) water/CH$_3$CN=900/100 (v/v)] and 90% [(total 10 mM AcONH$_4$) water/CH$_3$CN=100/900 (v/v)] in 1.6 min, then under this condition for 2.4 min, finally changed to 90% [(total 10 mM AcONH$_4$) water/CH$_3$CN=900/100 (v/v)] and 10% [(total 10 mM AcONH$_4$) water/CH$_3$CN=100/900 (v/v)] in 0.1 min and under this condition for 0.7 min). Purity is 99.57%, Rt=2.035 min.; MS Calcd.: 291.2; MS Found: 292.2 [M+H]$^+$.

HPLC (Agilent HPLC 1200, Column: Waters X-Bridge C18 (150 mm×4.6 mm×3.5 μm): Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100/6 [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity is 93.27%, Rt=9.542 min.

$^1$H NMR (400 MHz, CDCl$_3$) δ 1.29-1.40 (2H, m), 1.49 (1H, d, J=5.4 Hz), 1.57 (9H, s), 1.70-1.75 (1H, m), 1.82 (2H, d, J=12.8 Hz), 2.80-2.87 (2H, m), 3.53 (2H, t, J=5.8 Hz), 3.87-3.90 (2H, m), 6.85 (2H, d, J=9.2 Hz), 7.84 (2H, d, J=9.2 Hz).

Chemical Formula: C$_{17}$H$_{25}$NO$_3$, Molecular Weight: 291.39.

Total H count from HNMR data: 25.

Step 2: Synthesis of tert-butyl 4-(4-formylpiperidin-1-yl)benzoate

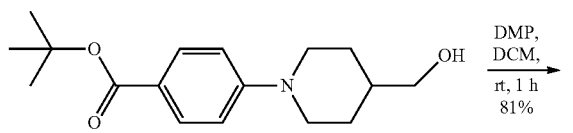

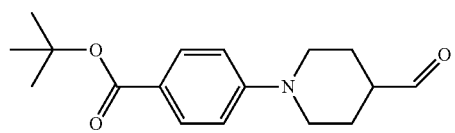

To a solution of tert-butyl 4-(4-(hydroxymethyl)piperidin-1-yl)benzoate (300 mg, 1.03 mmol) in dichloromethane (20 mL) was added Dess-Martin periodinane (1.31 g, 3.09 mmol) slowly at 0° C. The reaction mixture was stirred at room temperature for 1 h. Then filtered, and concentrated in vacuo to give compound tert-butyl 4-(4-formylpiperidin-1-yl)benzoate (240 mg, 81%) as a pale yellow solid.

Exemplary Synthesis of Exemplary Compound 46

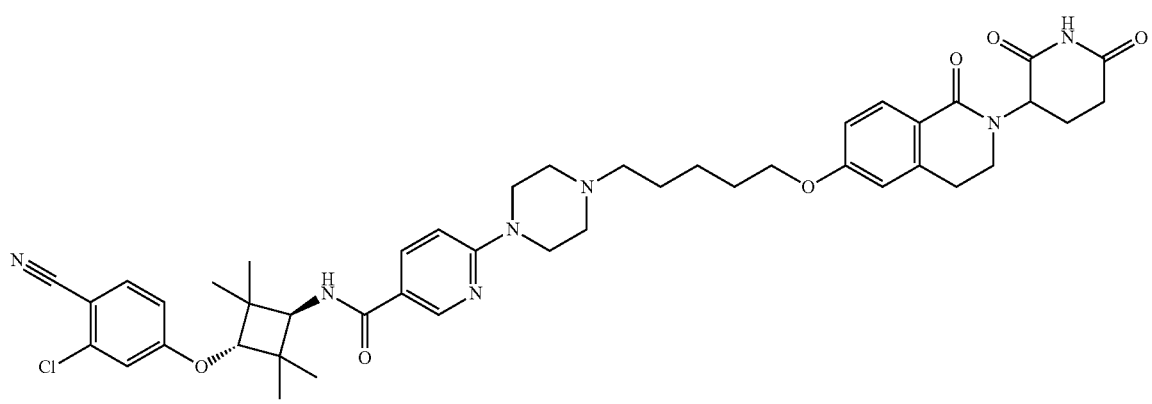 [SMILES: CC1(C)[C@H](NC(=O)c2ccc(N3CCN(CCCCCOc4ccc5c(c4)CCN(C4CCC(=O)NC4=O)C5=O)CC3)nc2)C(C)(C)[C@H]1Oc1ccc(C#N)c(Cl)c1]

N-((1r,3r)-3-(3-chloro-4-cyanophenoxy)-2,2,4,4-tetramethylcyclobutyl)-6-(4-(5-((2-(2,6-dioxopiperidin-3-yl)-1-oxo-1,2,3,4-tetrahydroisoquinolin-6-yl)oxy)pentyl)piperazin-1-yl)nicotinamide
Synthetic Scheme
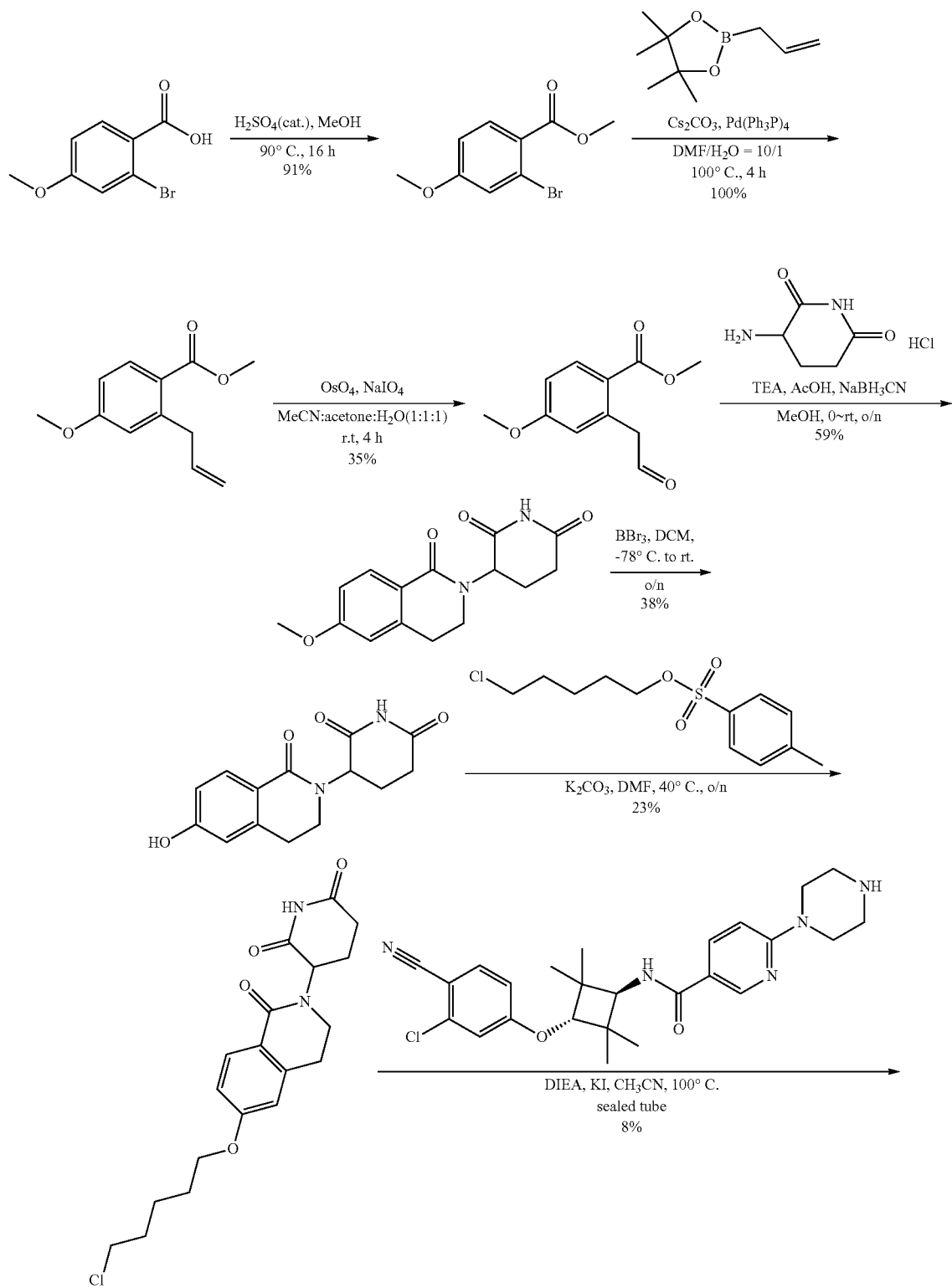

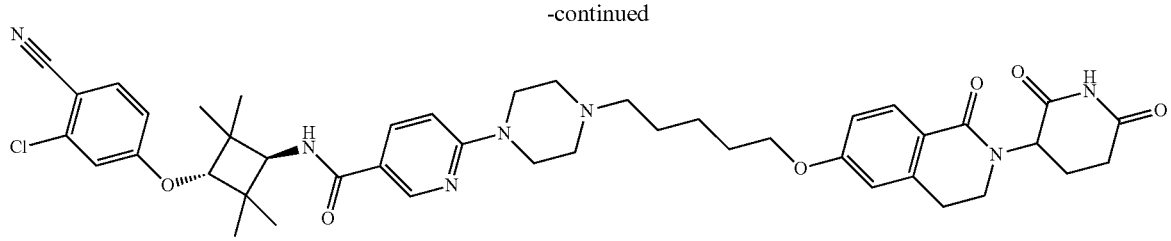

Step 1: Synthesis of methyl 2-bromo-4-methoxybenzoate

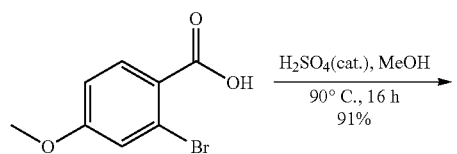

Step 2: Synthesis of methyl 2-allyl-4-methoxybenzoate

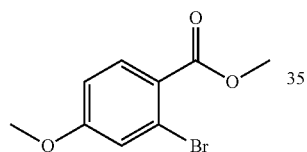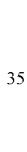

To a solution of 2-bromo-4-methoxybenzoic acid (5.0 g, 21.7 mmol) in methanol (50 mL) was added 98% sulfuric acid (0.5 ml). The reaction mixture was heated to 90° C. for 16 h under nitrogen gas, and concentraction under reduced pressure. After cooling to room temperature, sodium bicarbonate (2.0 M) was added to adjust PH=8. Thus was extracted with ethyl acetate (50 mL×3). The organic layer was washed with brine (30 mL). The combined organic phases were dried over anhydrous sodium sulfate, filtered, and concentrated in vacuo to give 2-bromo-4-methoxybenzoate (4.8 g, 91%) as yellow oil.

Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 90% [(total 10 mM AcONH$_4$) water/CH$_3$CN=900/100 (v/v)] and 10% [(total 10 mM AcONH$_4$) water/CH$_3$CN=100/900 (v/v)] to 10% [(total 10 mM AcONH$_4$) water/CH$_3$CN=900/100 (v/v)] and 90% [(total 10 mM AcONH$_4$) water/CH$_3$CN=100/900 (v/v)] in 1.6 min, then under this condition for 2.4 min, finally changed to 90% [(total 10 mM AcONH$_4$) water/CH$_3$CN=900/100 (v/v)] and 10% [(total 10 mM AcONH$_4$) water/CH$_3$CN=100/900 (v/v)] in 0.1 min and under this condition for 0.7 min. Purity is 98.94%, Rt=2.609 min; MS Calcd.: 243.97; MS Found: 245.0 [M+H]$^+$.

To a solution of methyl 2-bromo-4-methoxybenzoate (3.0 g, 12.3 mmol), cesium carbonate (12.0 g, 36.9 mmol), 2-allyl-4,4,5,5-tetramethyl-1,3,2-dioxaborolane (2.98 g, 18.5 mmol) in N,N-dimethylformamide/water (30.0 mL/3.0 mL) was added tetrakis(triphenylphosphine)palladium (1.42 g, 1.23 mmol) under nitrogen atmosphere. The reaction mixture was heated to 100° C. and stirred for 4 h. The resulting reaction was concentrated under reduced pressure, and then water (10 mL) was added. The mixture was extracted with ethyl acetate (50 mL×3). The combined organic phase was washed with brine (20 mL), dried over anhydrous sodium sulfate, filtered, and concentrated. The residue was purified by silica gel chromatography column (petroether/ethyl acetate=4:1) to give the methyl 2-allyl-4-methoxybenzoate (2.6 g, 100%) as yellow oil.

Agilent LCMS 1200-6110, Column: Waters X-Bridge C18 (50 mm×4.6 mm×3.5 μm); Column Temperature: 40° C.; Flow Rate: 1.5 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.5 min, then under this condition for 0.5 min, finally changed to 95% [water+0.05% TFA] and 5% [CH$_3$CN+0.05% TFA] in 0.1 min and under this condition for 0.5 min. Purity is 96.85%, Rt=1.293 min; MS Calcd.: 206.09; MS Found: 207.3 [M+H]$^+$.

Step 3: Synthesis of methyl 4-methoxy-2-(2-oxoethyl)benzoate

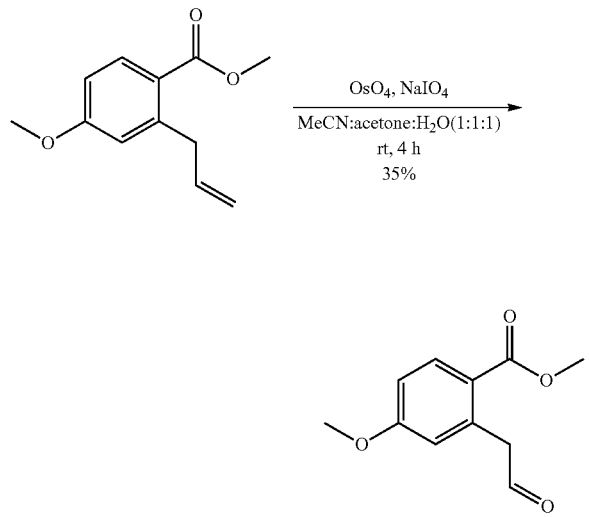

To a solution of methyl 2-allyl-4-methoxybenzoate (1.20 g, 5.83 mmol) and osmium tetraoxide (5 mg) in acetonitrile, acetone, and water (v:v:v=10 mL: 10 mL: 10 mL) was added sodium periodate (4.99 g, 23.3 mmol) at 0° C. The mixture was stirred at room temperature for 4 h. The mixture was filtered through a pad of celite and extracted with ethyl acetate (20×3 mL). The organic layer was separated, washed with water and brine, dried over anhydrous sodium sulfate, filtered, and concentrated. The residue was purified by prep-TLC (petroether/ethyl acetate=4:1) to give compound methyl 4-methoxy-2-(2-oxoethyl)benzoate (420 mg, 35%) as yellow oil.

LC-MS (Agilent LCMS 1200-6110, Column: Waters X-Bridge C18 (50 mm×4.6 mm×3.5 μm); Column Temperature: 40° C.; Flow Rate: 1.5 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.5 min, then under this condition for 0.5 min, finally changed to 95% [water+0.05% TFA] and 5% [CH$_3$CN+0.05% TFA] in 0.1 min and under this condition for 0.5 min.). Purity is 96.26%, Rt=1.007 min; MS Calcd.: 208.1; MS Found: 209.3 [M+H]$^+$.

Step 4: Synthesis of 3-(6-methoxy-1-oxo-3,4-dihydroisoquinolin-2(1H)-yl)piperidine-2,6-dione

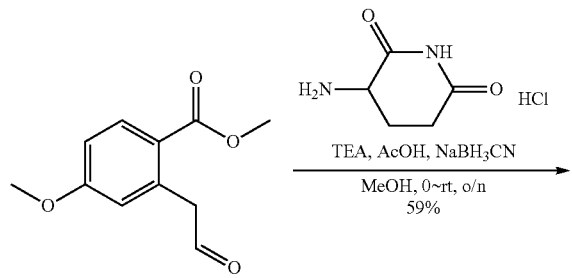

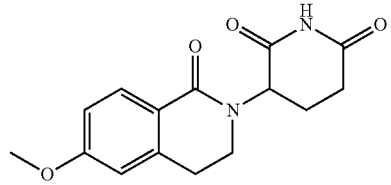

To a solution of methyl 4-methoxy-2-(2-oxoethyl)benzoate (420 mg, 2.02 mmol) in methanol (6 mL) was added a solution of 3-aminopiperidine-2,6-dione hydrochloride (397 mg, 2.42 mmol) and triethylamine (245 mg, 2.24 mmol) in methanol (2 mL). The reaction mixture was stirred at room temperature for 1 h, then sodium cyanoborohydride (254 mg, 4.04 mmol) was added at 0° C. The reaction was stirred at room temperature overnight, water (10 mL) was added, and extracted with ethyl acetate (20 mL×3), washed with water and brine, dried over anhydrous sodium sulfate, filtered, and concentrated. The residue was purified by prep-TLC (dichloromethane/methanol=20:1) to give 3-(6-methoxy-1-oxo-3,4-dihydroisoquinolin-2(1H)-yl)piperidine-2,6-dione (340 mg, 59%) as a pale yellow solid.

LC-MS (Agilent LCMS 1200-6120, Column: Waters X-Bridge C18 (30 mm×3 mm×2.5 μm); Column Temperature: 40° C.; Flow Rate: 1.5 mL/min; Mobile Phase: from 95% [water+10 mM NH$_4$HCO$_3$] and 5% [CH$_3$CN+10 mM NH$_4$HCO$_3$] to 5% [water+10 mM NH$_4$HCO$_3$] and 95% [CH$_3$CN+10 mM NH$_4$HCO$_3$] in 1.5 min, then under this condition for 0.5 min, finally changed to 95% [water+10 mM NH$_4$HCO$_3$] and 5% [CH$_3$CN+10 mM NH$_4$HCO$_3$] in 0.1 min and under this condition for 0.5 min.). Purity is 80.84%, Rt=0.924 min; MS Calcd.: 288.1; MS Found: 289.1 [M+H]$^+$.

Step 5: Synthesis of 3-(6-hydroxy-1-oxo-3,4-dihydroisoquinolin-2(1H)-yl)piperidine-2,6-dione

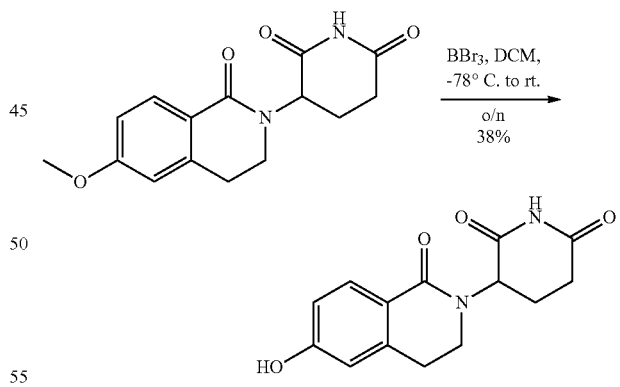

To a solution of 3-(6-methoxy-1-oxo-3,4-dihydroisoquinolin-2(1H)-yl)piperidine-2,6-dione (220 mg, 0.76 mmol) in dichloromethane (10 mL) was added boron tribromide (0.5 mL) in dichloromethane (2 mL) dropwise at −78° C. and stirred overnight at room temperature. The reaction mixture was added to water (10 mL) and sodium bicarbonate (20 mL), then extracted with dichloromethane/methanol (30 mL×5). The organic layer was washed with brine (10 mL). The combined organic phases were dried over anhydrous sodium sulfate, filtered, and concentrated in vacuo. The residue was purified by prep-TLC (dichloromethane/methanol=10:1) to give compound 3-(6-hydroxy-1-oxo-3,4-dihydroisoquinolin-2(1H)-yl)piperidine-2,6-dione (80 mg, 38%) as a yellow solid.

LC-MS (Agilent LCMS 1200-6120, Column: Waters X-Bridge C18 (30 mm×3 mm×2.5 μm); Column Temperature: 40° C.; Flow Rate: 1.5 mL/min; Mobile Phase: from 95% [water+10 mM $NH_4HCO_3$] and 5% [$CH_3CN$+10 mM $NH_4HCO_3$] to 5% [water+10 mM $NH_4HCO_3$] and 95% [$CH_3CN$+10 mM $NH_4HCO_3$] in 1.5 min, then under this condition for 0.5 min, finally changed to 95% [water+10 mM $NH_4HCO_3$] and 5% [$CH_3CN$+10 mM $NH_4HCO_3$] in 0.1 min and under this condition for 0.5 min.). Purity is 96.22%, Rt=0.736 min; MS Calcd.: 274.1; MS Found: 275.1 $[M+H]^+$.

Step 6: Synthesis of 3-(6-(5-chloropentyloxy)-1-oxo-3,4-dihydroisoquinolin-2(1H)-yl)piperidine-2,6-dione

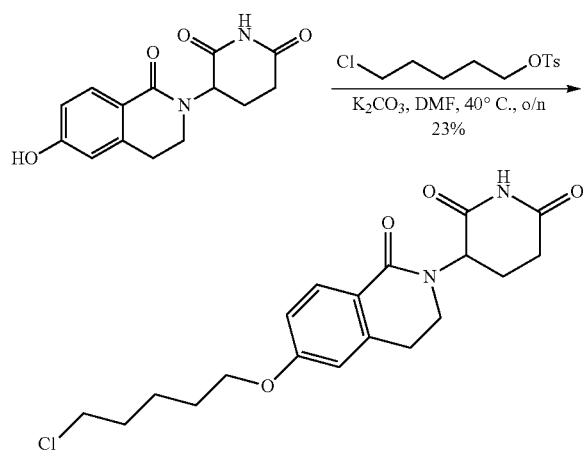

To a solution of 3-(6-hydroxy-1-oxo-3,4-dihydroisoquinolin-2(1H)-yl)piperidine-dione (80 mg, 0.292 mmol) in N,N-dimethylformamide (5.0 mL) was added 5-chloropentyl 4-methylbenzenesulfonate (64.5 mg, 0.234 mmol) and potassium carbonate (121 mg, 0.876 mmol). The mixture was heated to 40° C. overnight. After cooling to rt., the reaction mixture was added to water (10 mL), and extracted with ethyl acetate (20 mL×3). The organic layer was washed with brine (10 mL×3). The combined organic phases were dried over anhydrous sodium sulfate, filtered, and concentrated in vacuo. The residue was purified by prep-TLC (dichloromethane/methanol=10:1) to give 3-(6-(5-chloropentyloxy)-1-oxo-3,4-dihydroisoquinolin-2(1H)-yl)piperidine-2,6-dione (25 mg, 23%) as a yellow solid.

LC-MS (Agilent LCMS 1200-6120, Column: Waters X-Bridge C18 (30 mm×3 mm×2.5 μm); Column Temperature: 40° C.; Flow Rate: 1.5 mL/min; Mobile Phase: from 95% [water+10 mM $NH_4HCO_3$] and 5% [$CH_3CN$+10 mM $NH_4HCO_3$] to 5% [water+10 mM $NH_4HCO_3$] and 95% [$CH_3CN$+10 mM $NH_4HCO_3$] in 1.5 min, then under this condition for 0.5 min, finally changed to 95% [water+10 mM $NH_4HCO_3$] and 5% [$CH_3CN$+10 mM $NH_4HCO_3$] in 0.1 min and under this condition for 0.5 min.). Purity is 93.68%, Rt=1.263 min; MS Calcd.: 378.1; MS Found: 379.1 $[M+H]^+$.

Step 7: Synthesis of N-((1r,3r)-3-(3-chloro-4-cyanophenoxy)-2,2,4,4-tetramethylcyclobutyl)-6-(4-(5-(2-(2,6-dioxopiperidin-3-yl)-1-oxo-1,2,3,4-tetrahydroisoquinolin-6-yloxy)pentyl)piperazin-1-yl)nicotinamide

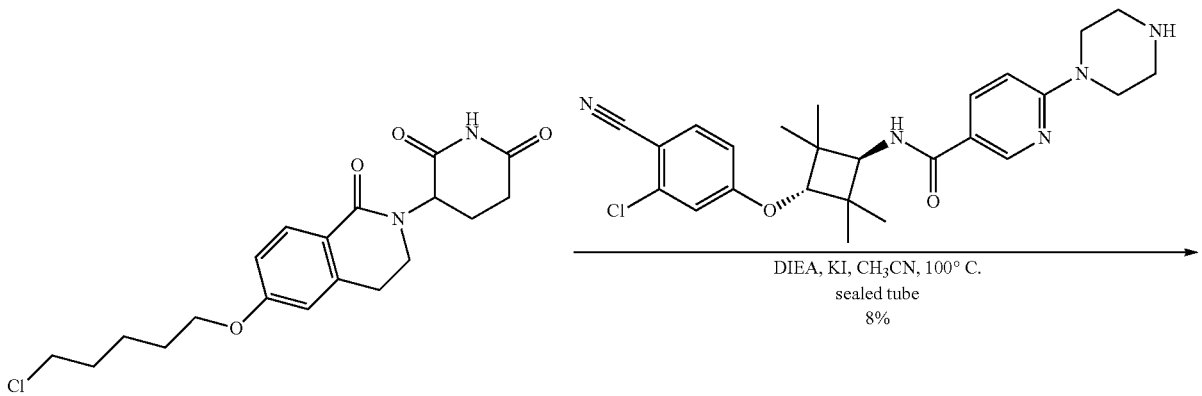

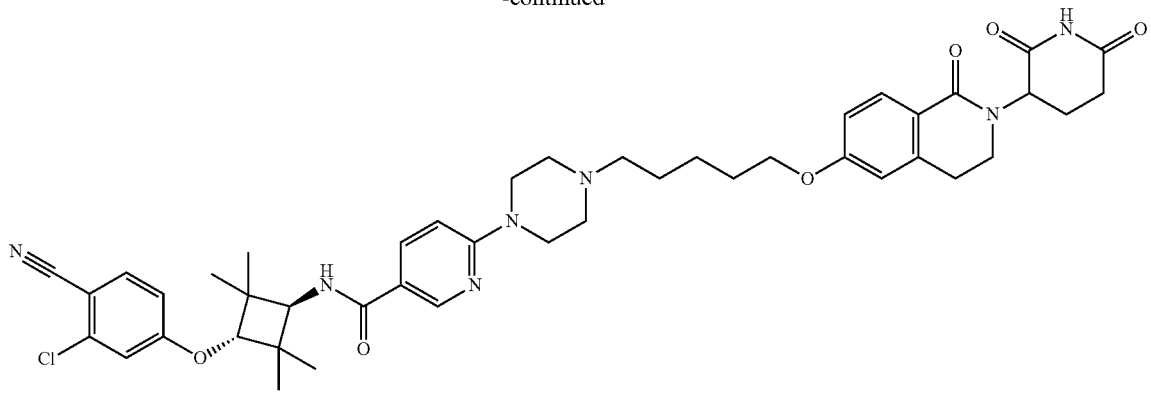

A solution of 3-(6-(5-chloropentyloxy)-1-oxo-3,4-dihydroisoquinolin-2(1H)-yl)piperidine-2,6-dione (25 mg, 0.066 mmol) was dissolved in acetonitrile (2 mL), N-((1r,3r)-3-(3-chloro-4-cyanophenoxy)-2,2,4,4-tetramethylcyclobutyl)-6-(piperazin-1-yl)nicotinamide (31 mg, 0.066 mmol), ethyldiisopropylamine (17 mg, 0.132 mmol), potassium iodide (2 mg) was added to the solution. The mixture was heated to 100° C. for 16 h under sealed tube. After cooling to rt., the reaction mixture was added to water (10 mL), and extracted with ethyl acetate (10 mL×3). The organic layer was washed with brine (10 mL×3). The combined organic phases were dried over anhydrous sodium sulfate, filtered, and concentrated in vacuo, then purified by prep-HPLC to give compound N-((1r,3r)-3-(3-chloro-4-cyanophenoxy)-2,2,4,4-tetramethylcyclobutyl)-6-(4-(5-(2-(2,6-dioxopiperidin-3-yl)-1-oxo-1,2,3,4-tetrahydroisoquinolin-6-yloxy)pentyl)piperazin-1-yl)nicotinamide (4.1 mg, 8%) as a white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min.). Purity is 87.84%, Rt=2.923 min; MS Calcd.: 809.4; MS Found: 810.3 [M+H]$^+$.

HPLC (Agilent HPLC 1200, Column: Waters X-Bridge C18 (150 mm×4.6 mm×3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity is 84.56%, Rt=10.161 min.

$^1$H NMR (400 MHz, DMSO-$d_6$) δ 1.12 (6H, s), 1.21 (6H, s), 1.43-1.54 (4H, m), 1.74-1.78 (2H, m), 1.88-1.91 (1H, m), 2.30-2.44 (8H, m), 2.90-2.97 (3H, m), 3.42-3.59 (7H, m), 4.03-4.07 (3H, m), 4.30 (1H, s), 6.86-6.91 (3H, m), 6.99-7.02 (1H, m), 7.22 (OH, d, J=2.4 Hz), 7.64 (1H, d, J=8.8 Hz), 7.79 (1H, d, J=8.8 Hz), 7.90-7.97 (2H, m), 8.62 (1H, d, J=2.0 Hz), 10.90 (1H, s).

Chemical Formula: $C_{44}H_{52}ClN_7O_6$, Molecular Weight: 810.38.

Total H count from HNMR data: 52.

Exemplary Synthesis of Exemplary Compound 47

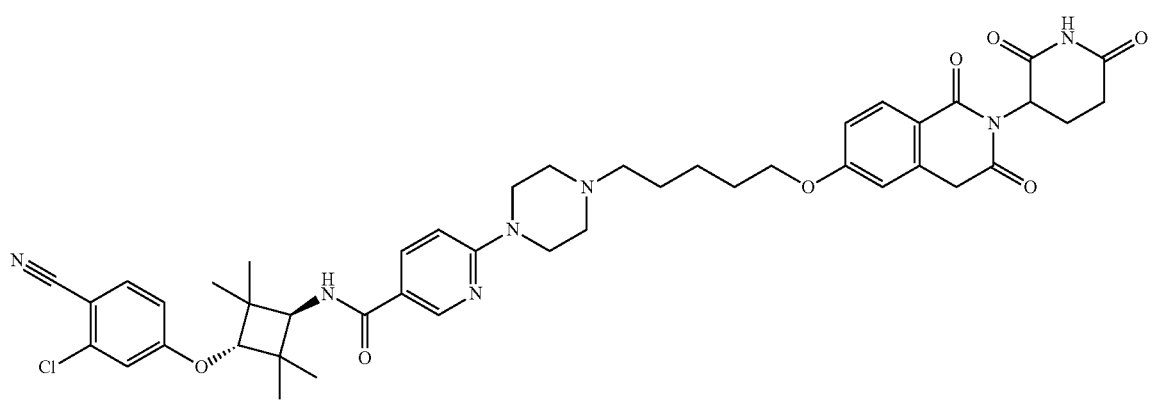 [SMILES: CC1(C)[C@H](NC(=O)c2ccc(N3CCN(CCCCCOc4ccc5c(c4)CC(=O)N(C4CCC(=O)NC4=O)C5=O)CC3)nc2)C(C)(C)[C@H]1Oc1ccc(C#N)c(Cl)c1]

N-((1r,3r)-3-(3-chloro-4-cyanophenoxy)-2,2,4,4-tetramethylcyclobutyl)-6-(4-(5-((2-(2,6-dioxopiperidin-3-yl)-1,3-dioxo-1,2,3,4-tetrahydroisoquinolin-6-yl)oxy)pentyl)piperazin-1-yl)nicotinamide
Synthetic Scheme 5
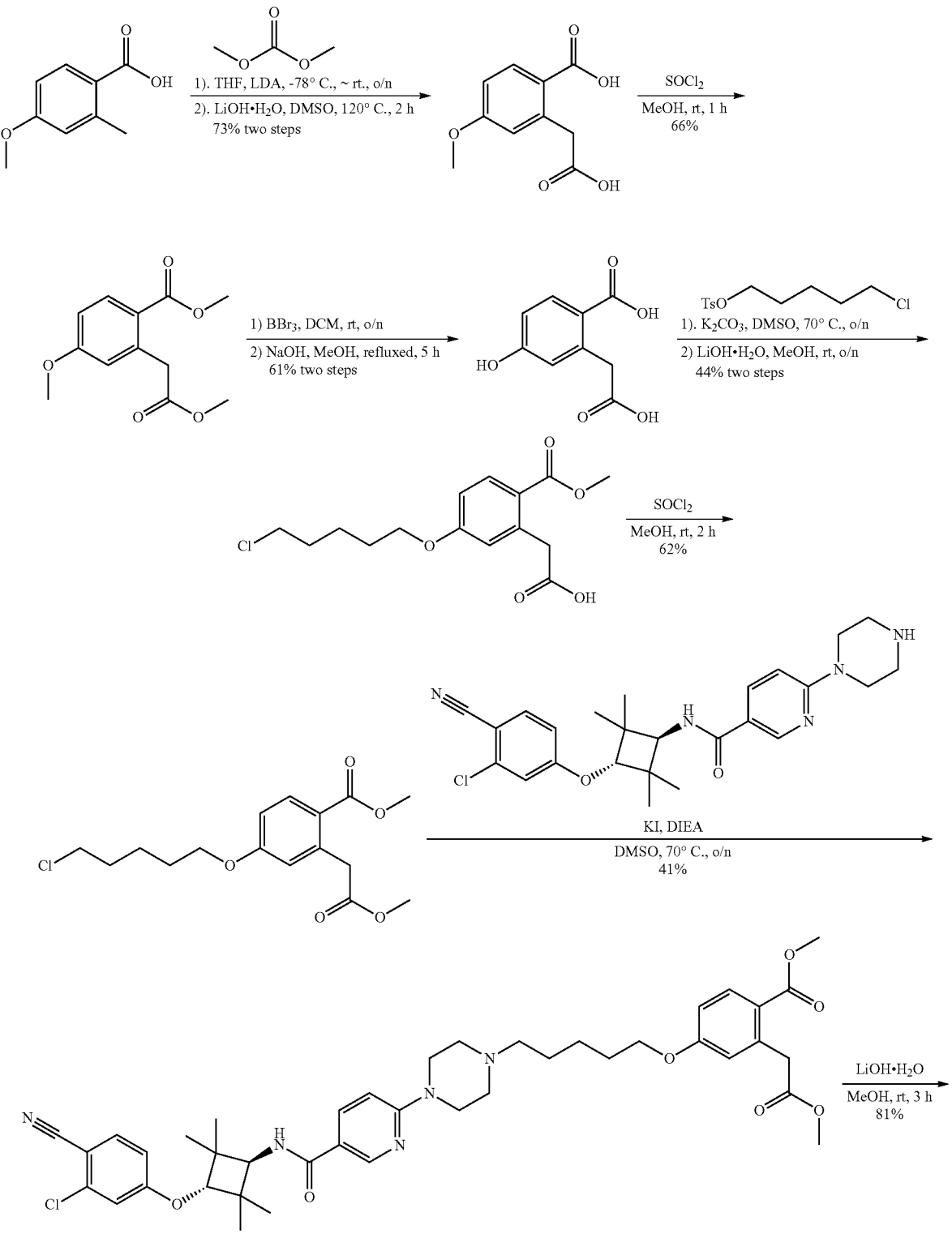

-continued
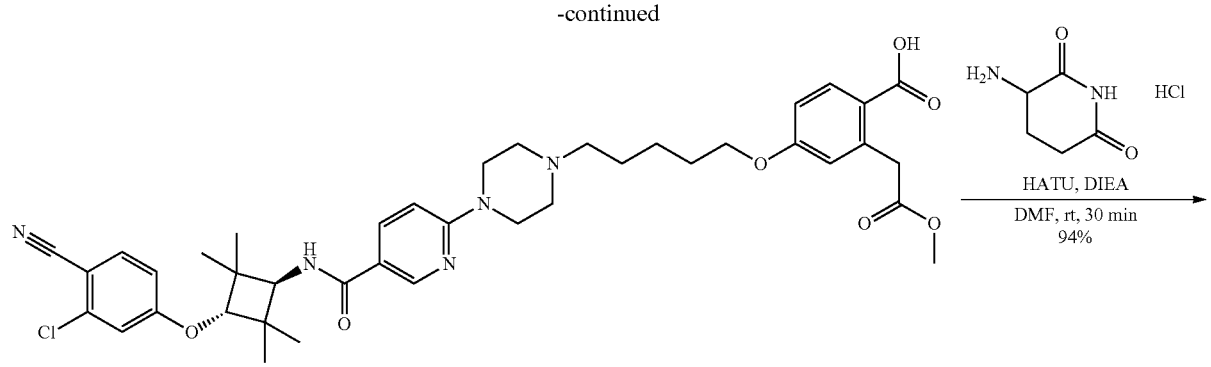
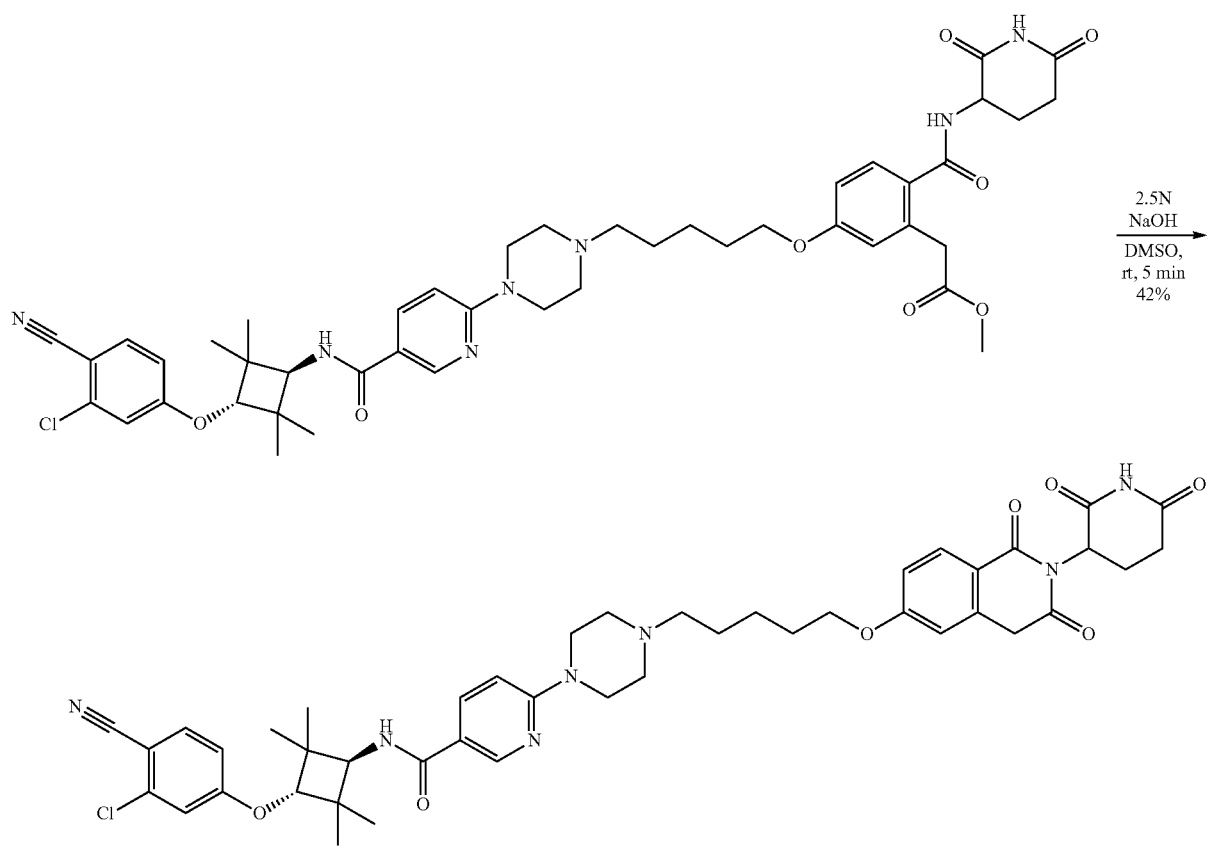
Step 1: Synthesis of
2-(carboxymethyl)-4-methoxybenzoic acid
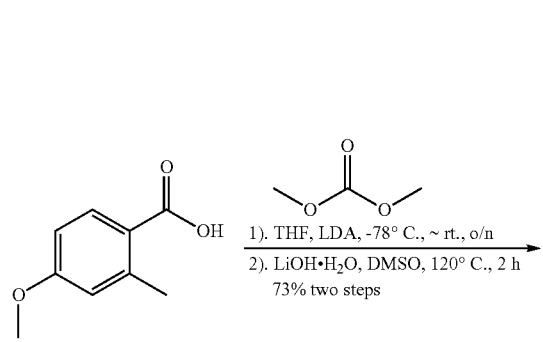
-continued
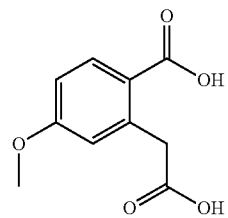
To a solution of 4-methoxy-2-methylbenzoic acid (5.0 g, 30.1 mmol) in dry tetrahydrofuran (50 mL) was added lithium diisopropylamide in tetrahydrofuran (1.0 mol/L) (66.3 mL, 66.3 mmol) at −78° C. under nitrogen gas. The mixture was left to stir for 1 hour at that temperature and then dimethyl carbonate (2.98 g, 33.1 mmol) was added. The reaction mixture was left to stir overnight. Water (200 mL) and ethyl acetate (100 mL) was added. The aqueous layer was separated, extracted with ethyl acetate (50 mL×2) and neutralized with hydrochloric acid (1 N) until pH<4. The mixture was extracted with ethyl acetate (100 mL×2). The combined organic layers were washed with saturated brine (50.0 mL×2), dried over anhydrous sodium sulfate, filtered, and concentrated in vacuo. The residue was dissolved in dimethyl sulfoxide (40 mL) and lithium hydroxide hydrate (5.06 g, 120.4 mmol) was added. The mixture was stirred at 120° C. for 2 hour, cooled down to room temperature and poured into ice-water (200 mL). Hydrochloric acid (1 N) was added until pH<4. The mixture was extracted with ethyl acetate (100 mL×2). The combined organic layers were washed with saturated brine (50.0 mL×2), dried over anhydrous sodium sulfate, filtered, and concentrated in vacuo to give 2-(carboxymethyl)-4-methoxybenzoic acid (4.6 g, 73% two steps) as a yellow solid.

LC-MS (Agilent LCMS 1200-6120, Column: Waters X-Bridge C18 (30 mm*4.6 mm*3.5 μm); Column Temperature: 40° C.; Flow Rate: 1.5 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 0.5 min, then under this condition for 1.5 min, finally changed to 95% [water+0.1% TFA] and 5% [CH$_3$CN+0.1% TFA] in 0.1 min and under this condition for 0.5 min). Purity is 94.6%, Rt=0.774 min; MS Calcd.: 210.1; MS Found: 233.1 [M+23]$^+$.

Step 2: Synthesis of methyl 4-methoxy-2-(2-methoxy-2-oxoethyl)benzoate

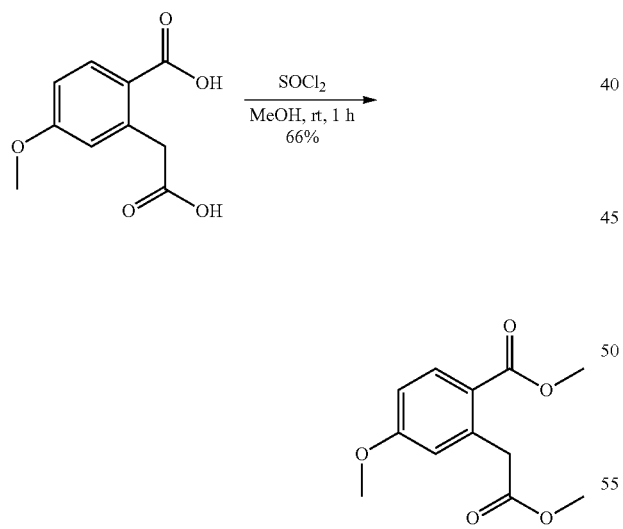

To a solution of (2-(carboxymethyl)-4-methoxybenzoic acid (1.2 g, 5.7 mmol) in methanol (10.0 mL) was added thionyl chloride (1.7 g, 14.3 mmol) dropwise. The mixture was refluxed for 2 hour. The mixture was cooled down to room temperature and then the solvent was removed in vacuo to give crude product which was purified by column chromatography on silica gel (ethyl acetate/petroleum ether=1:1) to give 4-methoxy-2-(2-methoxy-2-oxoethyl) benzoate (900 mg, 66%) as a white solid.

Step 3: Synthesis of 2-(carboxymethyl)-4-hydroxybenzoic acid

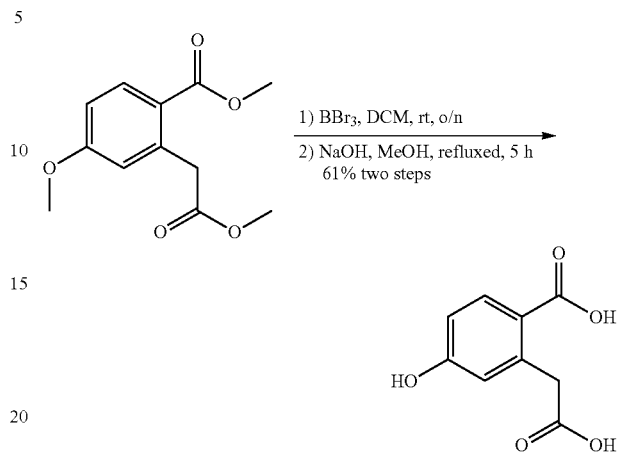

To a solution of 4-methoxy-2-(2-methoxy-2-oxoethyl) benzoate (0.9 g, 3.78 mmol) in dichloromethane (30 mL) was added boron tribromide (4.7 g, 18.9 mmol) dropwise under ice-water bath. The resulting mixture was allowed to warm to room temperature and stirred overnight. Water (100 mL) was added. The organic layer was separated, washed with brine (50 mL×2), dried over anhydrous sodium sulfate, filtered, and concentrated in vacuo to give a mixture. The mixture was dissolved in methanol (30 mL) and sodium hydroxide (0.76 g, 18.9 mmol) in water (4.0 mL) was added. The mixture was refluxed for 5 hour. The solvent was removed. The residue was dissolved in water (30 mL). Hydrochloric acid (1 N) was added until pH<4. The mixture was extracted with ethyl acetate (50 mL×2). The combined organic layers were washed with saturated brine (20.0 mL×2), dried over anhydrous sodium sulfate, filtered, and concentrated in vacuo to give 2-(carboxymethyl)-4-hydroxybenzoic acid (0.45 g, 61% two steps) as a yellow solid.

LC-MS (Agilent LCMS 1200-6120, Column: Waters X-Bridge C18 (30 mm*4.6 mm*3.5 μm); Column Temperature: 40° C.; Flow Rate: 1.5 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 0.5 min, then under this condition for 1.5 min, finally changed to 95% [water+0.1% TFA] and 5% [CH$_3$CN+0.1% TFA] in 0.1 min and under this condition for 0.5 min). Purity is 95.2%, Rt=0.570 min; MS Calcd.: 196.0; MS Found: 197.2 [M+H]$^+$.

Step 4: Synthesis of 2-(5-(5-chloropentyloxy)-2-(methoxycarbonyl)phenyl)acetic acid

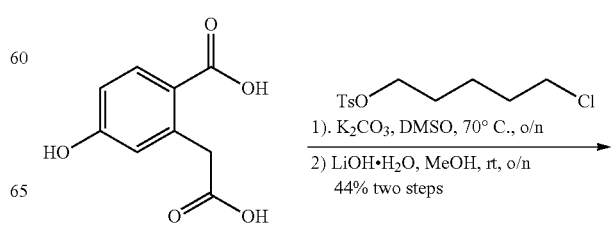

405
-continued

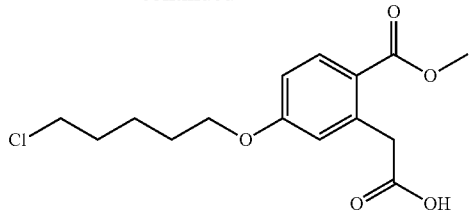

The mixture of 2-(carboxymethyl)-4-hydroxybenzoic acid (120 mg, 0.61 mmol), potassium carbonate (253 mg, 1.83 mmol) and 5-chloropentyl 4-methylbenzenesulfonate (506 mg, 1.83 mmol) in dimethyl sulfoxide (5 mL) was stirred at 70° C. overnight. The resulting mixture was allowed to cooled down to room temperature and stirred overnight. Water (20 mL) and ethyl acetate (20 mL) was added. The organic layer was separated, washed with brine (50 mL×2), dried over anhydrous sodium sulfate, filtered, and concentrated in vacuo to give a mixture. The mixture was dissolved in methanol (30 mL) and lithium hydroxide hydrate (128 mg, 3.05 mmol) was added. The mixture was stirred at room temperature overnight. The solvent was removed. The residue was dissolved in water (30 mL). Hydrochloric acid (1 N) was added until pH<4. The mixture was extracted with ethyl acetate (20 mL×2). The combined organic layers were washed with saturated brine (10 mL×2), dried over anhydrous sodium sulfate, filtered, and concentrated in vacuo to give 2-(5-(5-chloropentyloxy)-2-(methoxycarbonyl)phenyl)acetic acid (85 mg, 44% two steps) as yellow oil.

LC-MS (Agilent LCMS 1200-6120, Column: Waters X-Bridge C18 (30 mm*4.6 mm*3.5 µm); Column Temperature: 40° C.; Flow Rate: 2.0 mL/min; Mobile Phase: from 90°/[water+10 mM NH$_4$HCO$_3$] and 10% [CH$_3$CN] to 5% [water+10 mM NH$_4$HCO$_3$] and 95% [CH$_3$CN] in 0.5 min, then under this condition for 1.5 min, finally changed to 90% [water+10 mM NH$_4$HCO$_3$] and 10% [CH$_3$CN] in 0.1 min and under this condition for 0.5 min.). Purity is 69.9%, Rt=0.829 min; MS Calcd.: 314.1; MS Found: 315.1 [M+H]$^+$.

Step 5: Synthesis of methyl 4-(5-chloropentyloxy)-2-(2-methoxy-2-oxoethyl)benzoate

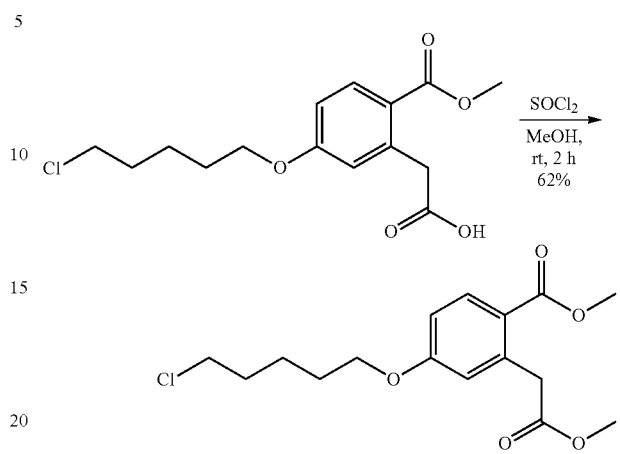

To a solution of 2-(5-(5-chloropentyloxy)-2-(methoxycarbonyl)phenyl)acetic acid (85 mg, 0.27 mmol) in methanol (2 mL) was added thionyl chloride (48.3 mg, 0.41 mmol) dropwise. The mixture was refluxed for 2 hour. The mixture was cooled down to room temperature and then the solvent was removed in vacuo to give crude product which was purified by prep-TLC (ethyl acetate/petroleum ether=1:1) to give methyl 4-(5-chloropentyloxy)-2-(2-methoxy-2-oxoethyl)benzoate (55 mg, 62%) as yellow oil.

LC-MS (Agilent LCMS 1200-6120, Column: Waters X-Bridge C18 (30 mm*4.6 mm*3.5 µm); Column Temperature: 40° C.; Flow Rate: 2.0 mL/min; Mobile Phase: from 90% [water+10 mM NH$_4$HCO$_3$] and 10% [CH$_3$CN] to 5% [water+10 mM NH$_4$HCO$_3$] and 95% [CH$_3$CN] in 0.5 min, then under this condition for 1.5 min, finally changed to 90% [water+10 mM NH$_4$HCO$_3$] and 10% [CH$_3$CN] in 0.1 min and under this condition for 0.5 min.). Purity is 72.9%, Rt=1.208 min; MS Calcd.: 328.1; MS Found: 329.2 [M+H]$^+$.

Step 6: Synthesis of methyl 4-(5-(4-(5-((1r,3r)-3-(3-chloro-4-cyanophenoxy)-2,2,4,4-tetramethylcyclobutylcarbamoyl)pyridin-2-yl)piperazin-1-yl)pentyloxy)-2-(2-methoxy-2-oxoethyl)benzoate

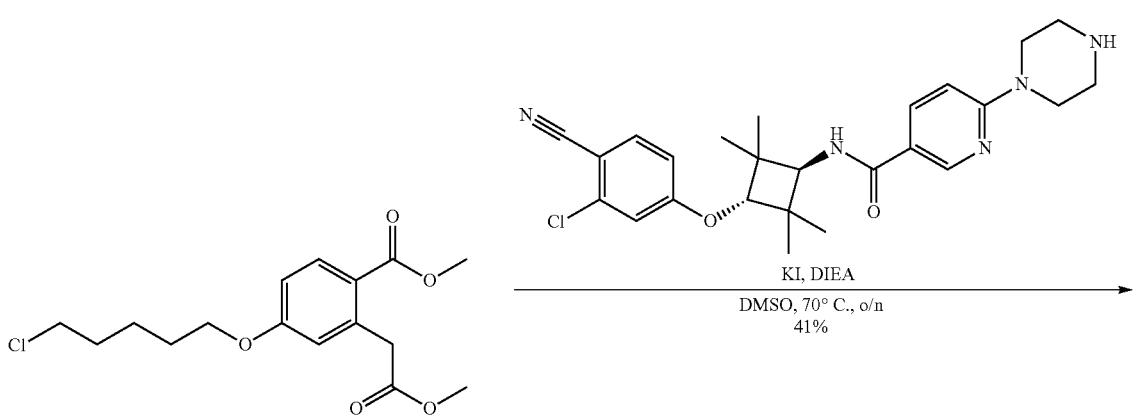

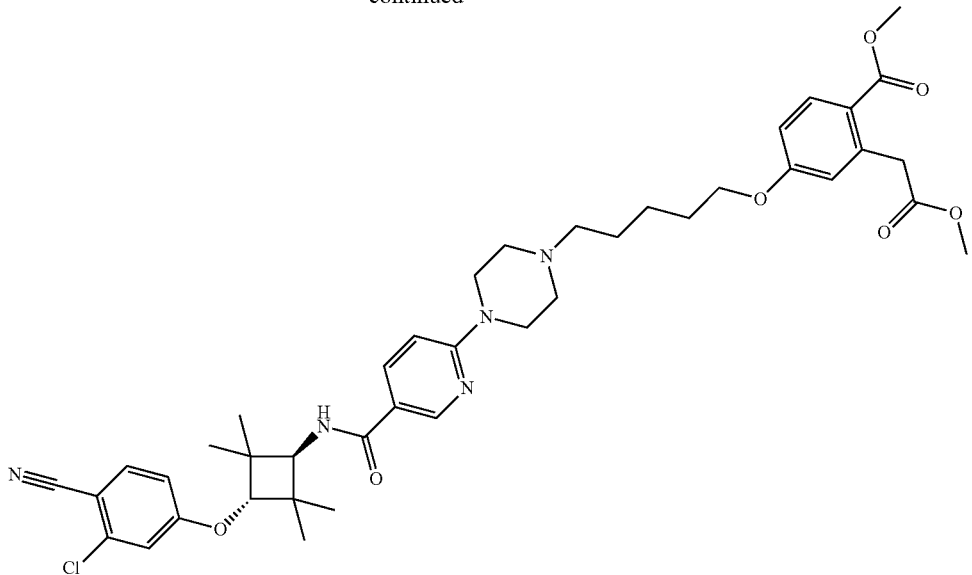

The mixture of methyl 4-(5-chloropentyloxy)-2-(2-methoxy-2-oxoethyl)benzoate (55 mg, 0.17 mmol), ethyldiisopropylamine (65.8 mg, 0.51 mmol), potassium iodide (28.2 mg, 0.17 mmol) and N-((1r,3r)-3-(3-chloro-4-cyanophenoxy)-2,2,4,4-tetramethylcyclobutyl)-6-(piperazin-1-yl)nicotinamide (78.5 mg, 0.17 mmol) in dimethyl sulfoxide (2 mL) was stirred at 70° C. overnight. The resulting mixture was allowed to cooled down to room temperature and stirred overnight. Water (20 mL) and ethyl acetate (20 mL) was added. The organic layer was separated, washed with brine (50 mL×2), dried over anhydrous sodium sulfate, filtered, and concentrated in vacuo to give the crude product which was purified by column and flash chromatography (ethyl acetate/petroleum ether=1:1) to give methyl 4-(5-(4-(5-((1r,3r)-3-(3-chloro-4-cyanophenoxy)-2,2,4,4-tetramethylcyclobutylcarbamoyl)pyridin-2-yl)piperazin-1-yl)pentyloxy)-2-(2-methoxy-2-oxoethyl)benzoate (53 mg, 41%) as a white solid.

Step 7: Synthesis of 4-(5-(4-(5-((1r,3r)-3-(3-chloro-4-cyanophenoxy)-2,2,4,4-tetramethylcyclobutylcarbamoyl)pyridin-2-yl)piperazin-1-yl)pentyloxy)-2-(2-methoxy-2-oxoethyl)benzoic acid

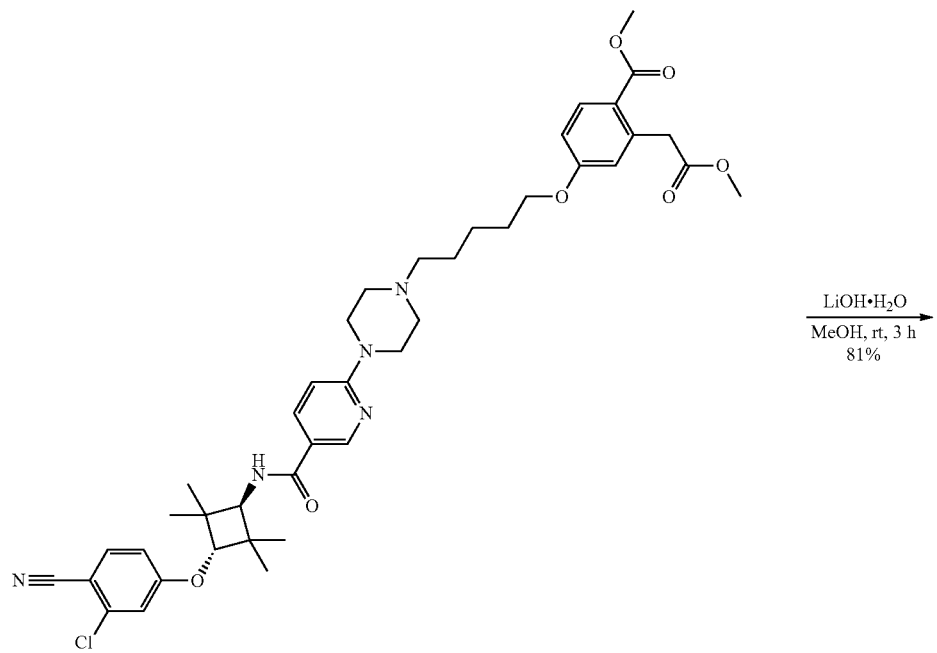

LiOH·H$_2$O
MeOH, rt, 3 h
81%

-continued

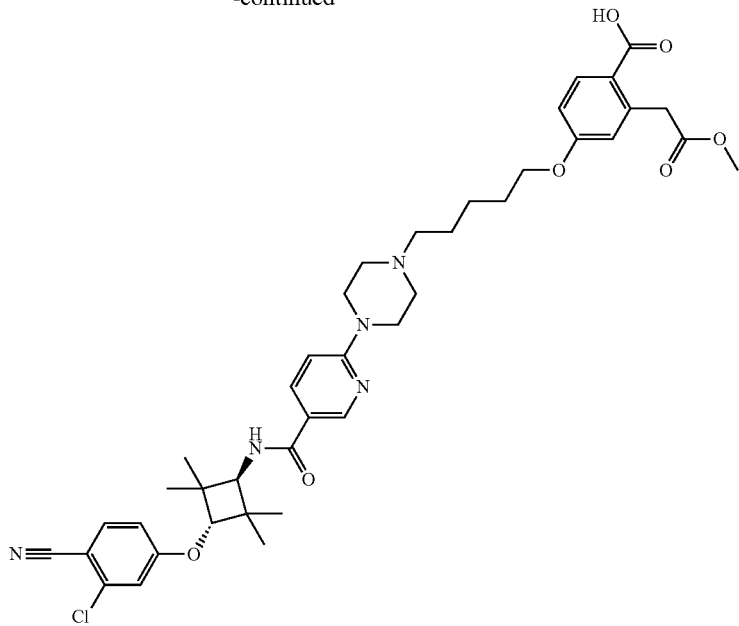

The mixture of methyl 4-(5-(4-(5-((1r,3r)-3-(3-chloro-4-cyanophenoxy)-2,2,4,4-tetramethylcyclobutylcarbamoyl)pyridin-2-yl)piperazin-1-yl)pentyloxy)-2-(2-methoxy-2-oxoethyl)benzoate (53 mg, 0.07 mmol) was dissolved in methanol (2 mL) and lithium hydroxide hydrate (14.7 mg, 0.35 mmol) was added. The mixture was stirred at room temperature for 3 hour. The solvent was removed. The residue was dissolved in water (15 mL). Hydrochloric acid (1 N) was added until pH<4. The mixture was extracted with ethyl acetate (15 mL×2). The combined organic layers were washed with saturated brine (10 mL×2), dried over anhydrous sodium sulfate, filtered, and concentrated in vacuo to give 4-(5-(4-(5-((1r,3r)-3-(3-chloro-4-cyanophenoxy)-2,2,4,4-tetramethylcyclobutylcarbamoyl)pyridin-2-yl)piperazin-1-yl)pentyloxy)-2-(2-methoxy-2-oxoethyl)benzoic acid (42 mg, 81%) as a white solid.

LC-MS (Agilent LCMS 1200-6120, Column: Waters X-Bridge C18 (30 mm*4.6 mm*3.5 µm); Column Temperature: 40° C.; Flow Rate: 2.0 mL/min; Mobile Phase: from 90% [water+10 mM $NH_4HCO_3$] and 10% [$CH_3CN$] to 5% [water+10 mM $NH_4HCO_3$] and 95% [$CH_3CN$] in 0.5 min, then under this condition for 1.5 min, finally changed to 90% [water+10 mM $NH_4HCO_3$] and 10% [$CH_3CN$] in 0.1 min and under this condition for 0.5 min.). Purity is 75.4%, Rt=1.041 min; MS Calcd.: 745.3; MS Found: 746.2 [M+H]$^+$.

Step 8: Synthesis of methyl 2-(5-(5-(4-(5-((1r,3r)-3-(3-chloro-4-cyanophenoxy)-2,2,4,4-tetramethylcyclobutylcarbamoyl)pyridin-2-yl)piperazin-1-yl)pentyloxy)-2-(2,6-dioxopiperidin-3-ylcarbamoyl)phenyl)acetate

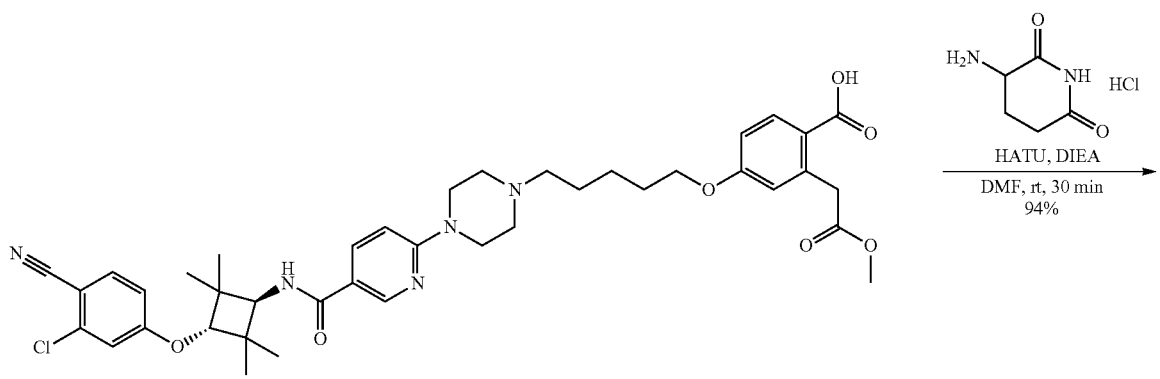

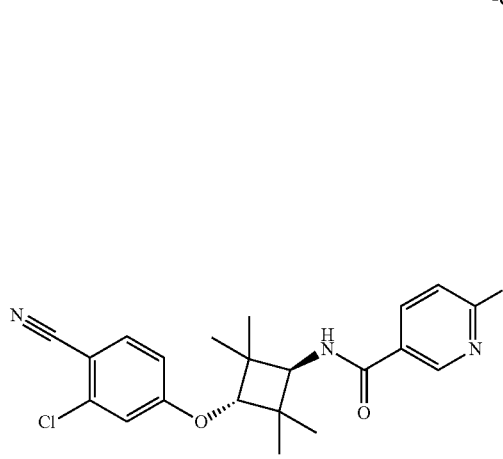
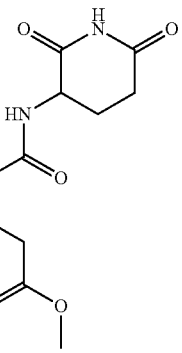

A solution of 4-(5-(4-(5-((1r,3r)-3-(3-chloro-4-cyanophenoxy)-2,2,4,4-tetramethylcyclobutylcarbamoyl)pyridin-2-yl)piperazin-1-yl)pentyloxy)-2-(2-methoxy-2-oxoethyl)benzoic acid (42 mg, 0.056 mmol), HATU (25.5 mg, 0.067 mmol) and ethyldiisopropylamine (29.7 mg, 0.23 mmol) in N,N-dimethylformamide (2 mL) was stirred for 30 min, and then 3-aminopiperidine-2,6-dione hydrochloride (9.2 mg, 0.056 mmol) was added. The mixture was stirred at room temperature overnight and water (10 mL) was added. The mixture was extracted by ethyl acetate (20 mL×3). The combined organic layers were washed with brine (10 mL×3), dried over anhydrous sodium sulfate, filtered, and concentrated in vacuo. The residue was purified by prep-TLC (dichloromethane/methanol=10:1) to give methyl 2-(5-(5-(4-(5-((1r,3r)-3-(3-chloro-4-cyanophenoxy)-2,2,4,4-tetramethylcyclobutylcarbamoyl)pyridin-2-yl)piperazin-1-yl)pentyloxy)-2-(2,6-dioxopiperidin-3-ylcarbamoyl)phenyl)acetate (45 mg, 94%) as a white solid.

LC-MS (Agilent LCMS 1200-6120, Column: Waters X-Bridge C18 (30 mm*4.6 mm*3.5 μm); Column Temperature: 40° C.; Flow Rate: 2.0 mL/min; Mobile Phase: from 90°/[water+10 mM NH$_4$HCO$_3$] and 10% [CH$_3$CN] to 5% [water+10 mM NH$_4$HCO$_3$] and 95% [CH$_3$CN] in 0.5 min, then under this condition for 1.5 min, finally changed to 90% [water+10 mM NH$_4$HCO$_3$] and 10% [CH$_3$CN] in 0.1 min and under this condition for 0.5 min.). Purity is 77.7%, Rt=1.213 min; MS Calcd.: 855.4; MS Found: 856.3 [M+H]$^+$.

Step 9: Synthesis of N-((1r,3r)-3-(3-chloro-4-cyanophenoxy)-2,2,4,4-tetramethylcyclobutyl)-6-(4-(5-(2-(2,6-dioxopiperidin-3-yl)-1,3-dioxo-1,2,3,4-tetrahydroisoquinolin-6-yloxy)pentyl)piperazin-1-yl)nicotinamide

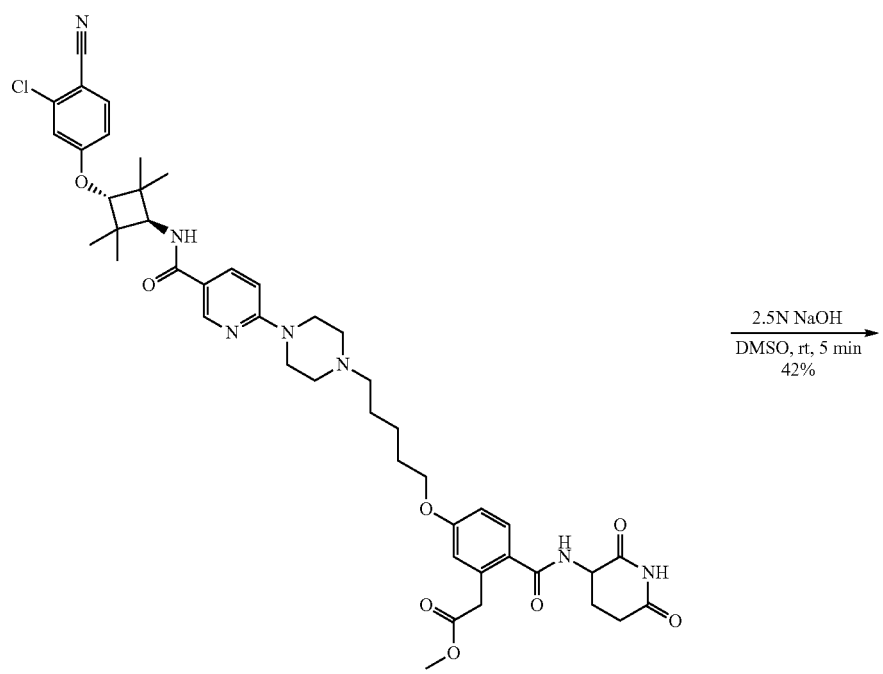

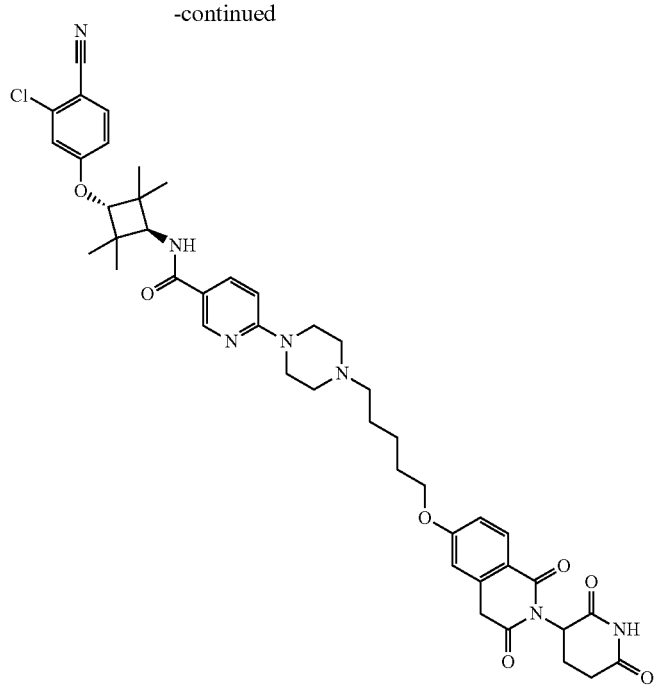

A solution of methyl 2-(5-(5-(4-(5-((1r,3r)-3-(3-chloro-4-cyanophenoxy)-2,2,4,4-tetramethylcyclobutylcarbamoyl)pyridin-2-yl)piperazin-1-yl)pentyloxy)-2-(2,6-dioxopiperidin-3-ylcarbamoyl)phenyl)acetate (45 mg, 0.053 mmol) in dimethyl sulfoxide (2 mL) was added sodium hydroxide in water (2.5 moL/L, 2 drops). The mixture was stirred at room temperature for 5 min. Water (20 mL) and ethyl acetate (20 mL) was added. The organic layer was separated, washed with brine (10 mL×2), dried over anhydrous sodium sulfate, filtered, and concentrated in vacuo to give the crude product which was purified by prep-HPLC to give N-((1r,3r)-3-(3-chloro-4-cyanophenoxy)-2,2,4,4-tetramethylcyclobutyl)-6-(4-(5-(2-(2,6-dioxopiperidin-3-yl)-1,3-dioxo-1,2,3,4-tetrahydroisoquinolin-6-yloxy)pentyl)piperazin-1-yl)nicotinamide (18.5 mg, 42%) as a white solid.

LC-MS (Agilent LCMS 1200-6120, Column: Waters X-Bridge C18 (50 mm*4.6 mm*3.5 μm); Column Temperature: 40° C.; Flow Rate: 2.0 m/min; Mobile Phase: from 90% [(total 10 mM AcONH$_4$) water/CH$_3$CN=900/100 (v/v)] and 10% [(total 10 mM AcONH$_4$) water/CH$_3$CN=100/900 (v/v)] to 10% [(total 10 mM AcONH$_4$) water/CH$_3$CN=900/100 (v/v)] and 90% [(total 10 mM AcONH$_4$) water/CH$_3$CN=100/900 (v/v)] in 1.6 min, then under this condition for 2.4 min, finally changed to 90% [(total 10 mM AcONH$_4$) water/CH$_3$CN=900/100 (v/v)] and 10% [(total 10 mM AcONH$_4$) water/CH$_3$CN=100/900 (v/v)] in 0.1 min and under this condition for 0.7 min). Purity is 100.0%, Rt=2.988 min; MS Calcd.: 823.4; MS Found: 824.3 [M+H]$^+$.

HPLC (Agilent HPLC 1200; Column: L-column2 ODS (150 mm*4.6 mm*5.0 m); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min). Purity is 95.2%, Rt=8.168 min.

$^1$H NMR (400 MHz, DMSO-d$^6$) δ 1.12 (6H, s), 1.21 (6H, s), 1.37-1.58 (4H, m), 1.73-1.81 (2H, m), 1.86-1.91 (1H, m), 2.30-2.37 (2H, m), 2.40-2.46 (2H, m), 2.82-2.91 (1H, m), 3.30-3.35 (4H, m), 3.55-3.65 (4H, m), 4.03-4.30 (6H, m), 5.54-5.63 (OH, m), 6.87 (1H, d, J=9.6 Hz), 6.96-7.07 (3H, m), 7.21 (1H, d, J=2.4 Hz), 7.63 (1H, d, J=9.6 Hz), 7.90-8.04 (3H, m), 8.62 (1H, d, J=2.4 Hz), 10.93 (1H, s).

Chemical Formula: C$_{44}$H$_{50}$ClN$_7$O$_7$, Molecular Weight: 824.36.

Total H count from HNMR data: 50.

Exemplary Synthesis of Exemplary Compound 48

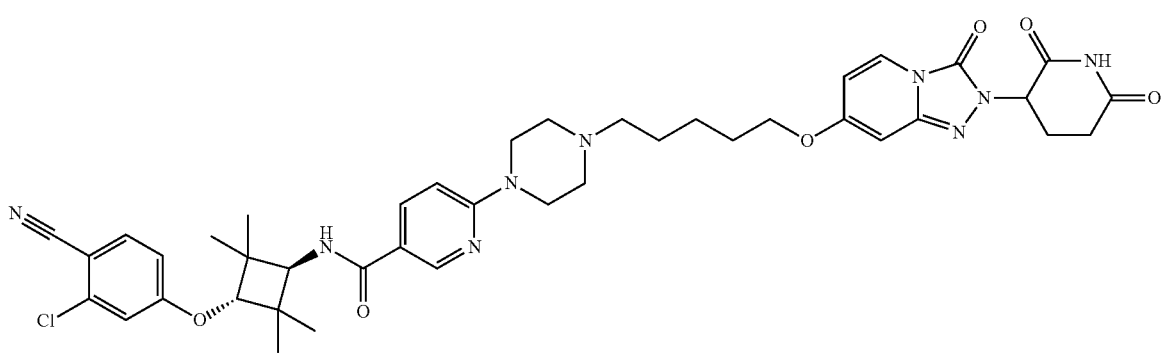 [SMILES: CC1(C)[C@H](NC(=O)c2ccc(N3CCN(CCCCCOc4ccn5c(=O)n(C6CCC(=O)NC6=O)nc5c4)CC3)nc2)C(C)(C)[C@H]1Oc1ccc(C#N)c(Cl)c1]

N-((1r,3r)-3-(3-chloro-4-cyanophenoxy)-2,2,4,4-tetramethylcyclobutyl)-6-(4-(5-((2-(2,6-dioxopiperidin-3-yl)-3-oxo-2,3-dihydro-[1,2,4]triazolo[4,3-a]pyridin-7-yl)oxy)pentyl)piperazin-1-yl)nicotinamide
Synthetic Scheme
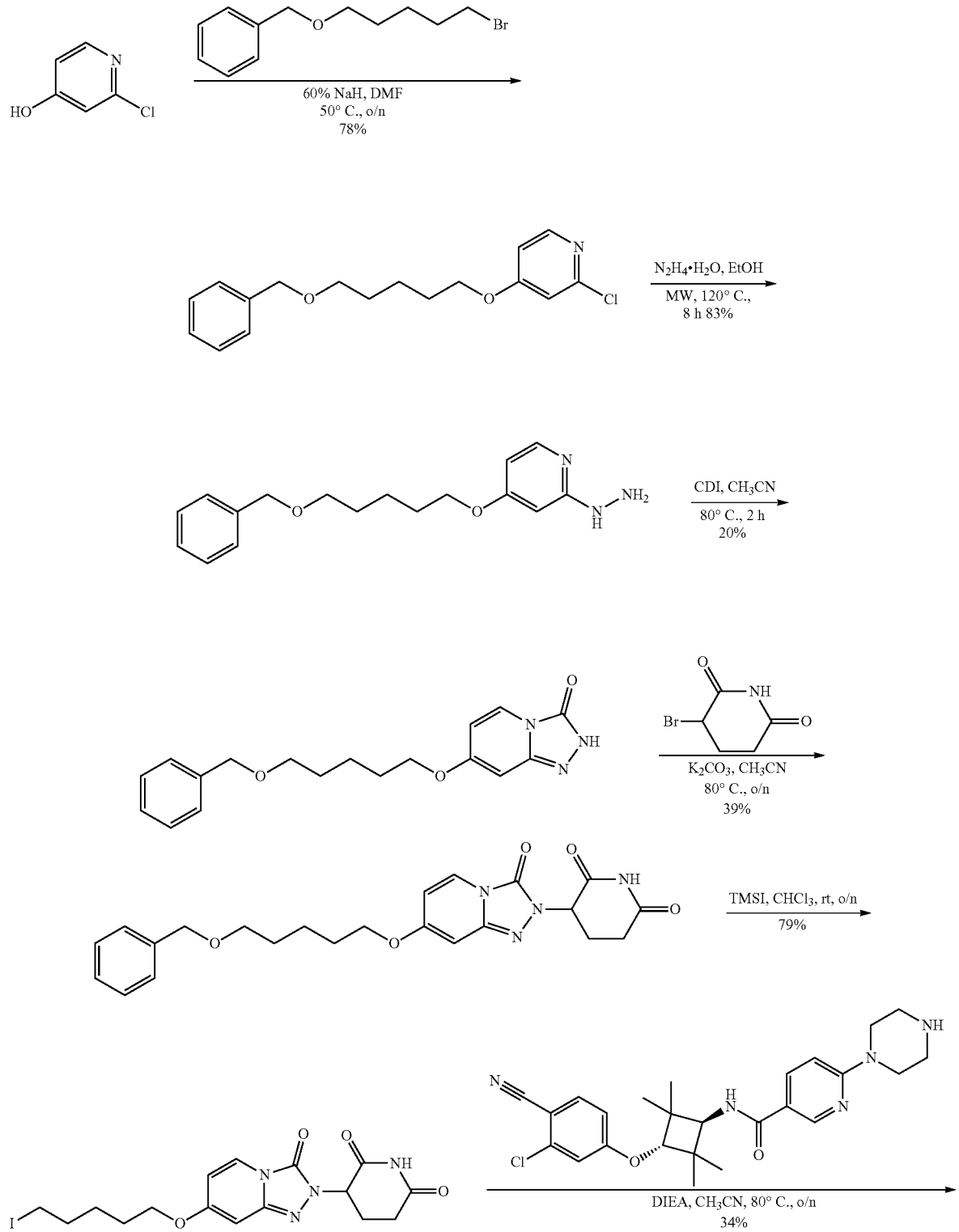

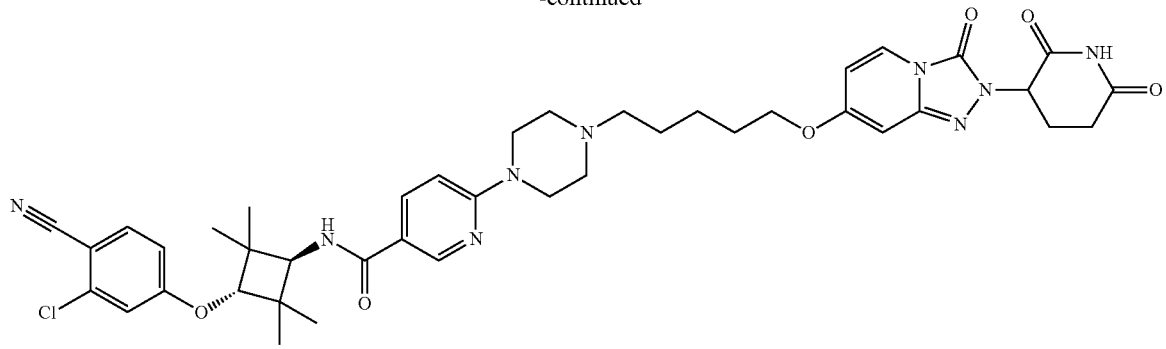

Step 1: Synthesis of 4-(5-(benzyloxy)pentyloxy)-2-chloropyridine

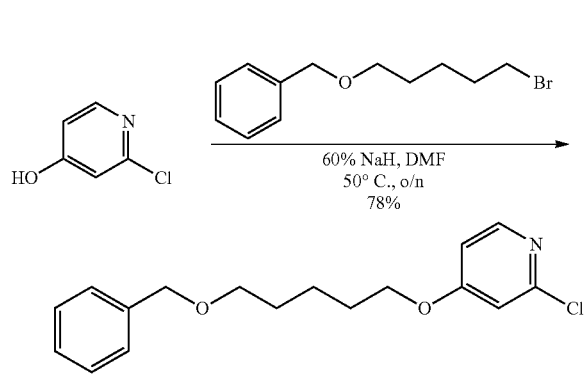

To a solution of 2-chloropyridin-4-ol (1.3 g, 10.0 mmol) in DMF (15 mL) was added sodium hydride (60% dispersed in mineral oil, 482 mg, 12.0 mmol) at 0° C., and the mixture was stirred at room temperature for 30 min. Then ((5-bromopentyloxy)methyl)benzene (3.1 g, 12.0 mmol) was added to the reaction and the resulted mixture was stirred at 50° C. overnight. When the reaction was completed (monitored by TLC), water (30 mL) was added. The resultant mixture was extracted by ethyl acetate (10 mL×3) and the combined organic layers were washed by brine (20 mL×3), dried over anhydrous sodium sulfate, filtered and concentrated. The residue was purified by column chromatography on silica (petroleum/ethyl acetate=1/4) to give 4-(5-(benzyloxy)pentyloxy)-2-chloropyridine (2.4 g, 78% yield) as a brown solid.

$^1$H NMR (400 MHz, CDCl$_3$) δ 1.47-1.53 (2H, m), 1.59-1.64 (2H, m), 1.71-1.76 (2H, m), 3.42 (2H, t, J=6.4 Hz), 3.91 (2H, t, J=6.4 Hz), 4.44 (2H, s), 7.07-7.15 (2H, m), 7.23-7.28 (5H, m), 7.96 (1H, d, J=3.2 Hz).

Step 2: Synthesis of 4-(5-(benzyloxy)pentyloxy)-2-hydrazinylpyridine

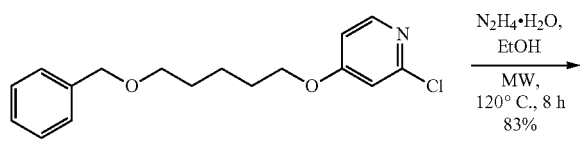

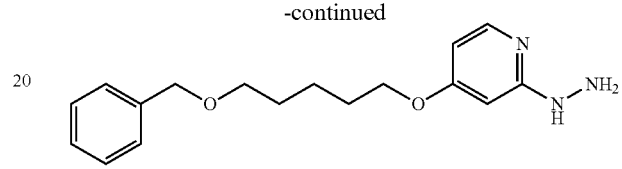

To a microwave glass vial was added 4-(5-(benzyloxy)pentyloxy)-2-chloropyridine (2.0 g, 6.5 mmol), hydrazine monohydrate (10 mL) and EtOH (10 mL), and the mixture was stirred under microwave conditions at 120° C. for 8 h. When it was cooled to room temperature, water (20 mL) was added to the reaction. The resultant mixture was extracted by ethyl acetate (10 mL×3) and the combined organic layers were washed by brine (15 mL×3), dried over anhydrous sodium sulfate, filtered, and concentrated in vacuo. The residue (1.6 g, 83% yield) was directly used to the next step without further purification as brown oil.

Step 3: Synthesis of 7-(5-(benzyloxy)pentyloxy)-[1,2,4]triazolo[4,3-a]pyridin-3(2H)-one

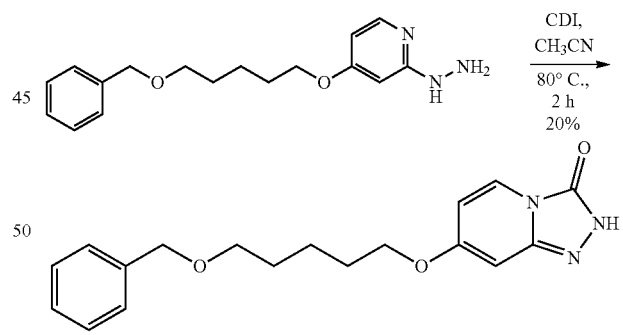

To a solution of 5-ethoxy-2-hydrazinylpyridine (1.6 g, 5.4 mmol) in acetonitrile (25 mL) was added CDI (1.3 g, 8.2 mmol), and the mixture was stirred at 80° C. for 2 h. When it was cooled to room temperature, water (20 mL) was added to the reaction. The resultant mixture was extracted by ethyl acetate (10 mL×3) and the combined organic layers were washed by brine (15 mL×3), dried over anhydrous sodium sulfate, filtered, and concentrated in vacuo. The residue was purified by column chromatography on silica (DCM/MeOH=20/1) to give 7-(5-(benzyloxy)pentyloxy)-[1,2,4]triazolo[4,3-a]pyridin-3(2H)-one (360 mg, 20% yield) as a white solid.

LC-MS (Agilent LCMS 1200-6120, Column: Waters X-Bridge C18 (50 mm×4.6 mm×3.5 µm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min.) Purity is 96.77%, Rt=1.716 min. MS Calcd.: 327.16; MS Found: 328.2 $[M+H]^+$.

Step 4: Synthesis of 3-(7-(5-(benzyloxy)pentyloxy)-3-oxo-[1,2,4]triazolo[4,3-a]pyridin-2(3H)-yl)piperidine-2,6-dione

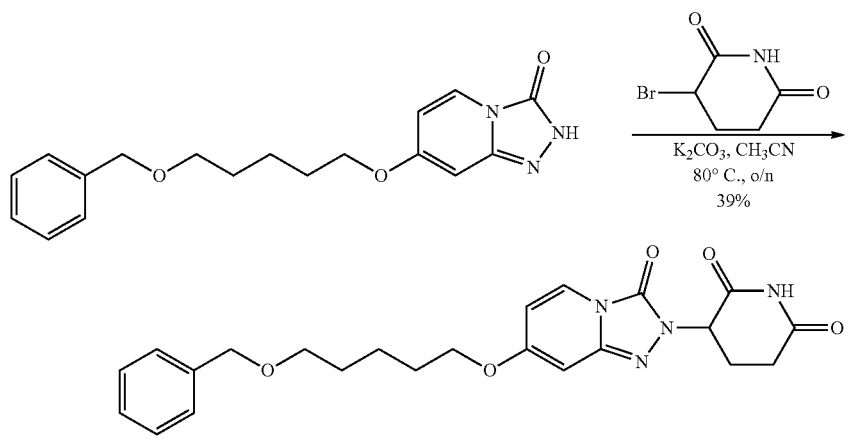

The solution of 7-(5-(benzyloxy)pentyloxy)-[1,2,4]triazolo[4,3-a]pyridin-3(2H)-one (300 mg, 0.9 mmol), 3-bromopiperidine-2,6-dione (438 mg, 2.3 mmol) and $K_2CO_3$ (253 mg, 1.8 mmol) in acetonitrale (10 mL) was stirred at 80° C. overnight. When it was cooled to room temperature, water (10 mL) was added. The resultant mixture was extracted by ethyl acetate (10 mL×3) and the combined organic layers were washed by brine (10 mL×3), dried over anhydrous sodium sulfate, filtered and concentrated. The residue was purified by Prep-TLC (DCM/MeOH=20/1) to give 3-(7-(5-(benzyloxy)pentyloxy)-3-oxo-[1,2,4]triazolo[4,3-a]pyridin-2(3H)-yl)piperidine-2,6-dione (157 mg, 39% yield) as a white solid.

LC-MS (Agilent LCMS 1200-6120, Column: Waters X-Bridge C18 (50 mm×4.6 mm×3.5 µm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min.) Purity is 99.45%, Rt=1.836 min. MS Calcd.: 438.19; MS Found: 439.3 $[M+H]^+$.

Step 5: Synthesis of 3-(7-(5-iodopentyloxy)-3-oxo-[1,2,4]triazolo[4,3-a]pyridin-2(3H)-yl)piperidine-2,6-dione

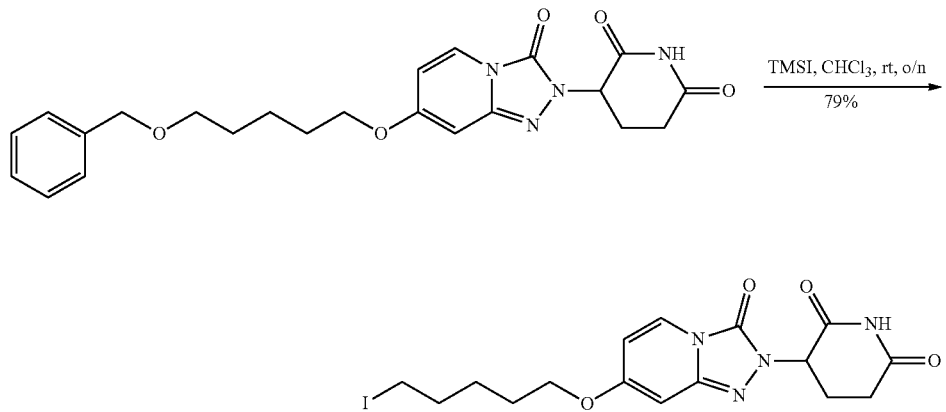

To a solution of 3-(7-(5-(benzyloxy)pentyloxy)-3-oxo-[1,2,4]triazolo[4,3-a]pyridin-2(3H)-yl)piperidine-2,6-dione (157 mg, 0.4 mmol) in CHCl₃ (5 mL) was added TMSI (143 mg, 0.7 mmol), and the mixture was stirred at room temperature overnight. Then the mixture was washed by sat. NaHSO₃ (5 mL×2), washed by brine (5 mL×2), dried over anhydrous sodium sulfate, filtered and concentrated. The residue was purified by Prep-TLC (DCM/MeOH=15/1) to give 3-(7-(5-iodopentyloxy)-3-oxo-[1,2,4]triazolo[4,3-a]pyridin-2(3H)-yl)piperidine-2,6-dione (130 mg, 79% yield) as a white solid.

LCMS (Agilent LCMS 1200-6120, Column: Waters X-Bridge C18 (50 mm×4.6 mm×3.5 μm); Column Temperature: 40° C.: Flow Rate: 2.0 mL/min: Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min.) Purity is 100%, Rt=1.754 min. MS Calcd.: 458.05; MS Found: 459.1 [M+H]⁺.

Step 6: Synthesis of N-((1r,3r)-3-(3-chloro-4-cyanophenoxy)-2,2,4,4-tetramethylcyclobutyl)-6-(4-(5-(2-(2,6-dioxopiperidin-3-yl)-3-oxo-2,3-dihydro-[1,2,4]triazolo[4,3-a]pyridin-7-yloxy)pentyl)piperazin-1-yl)nicotinamide

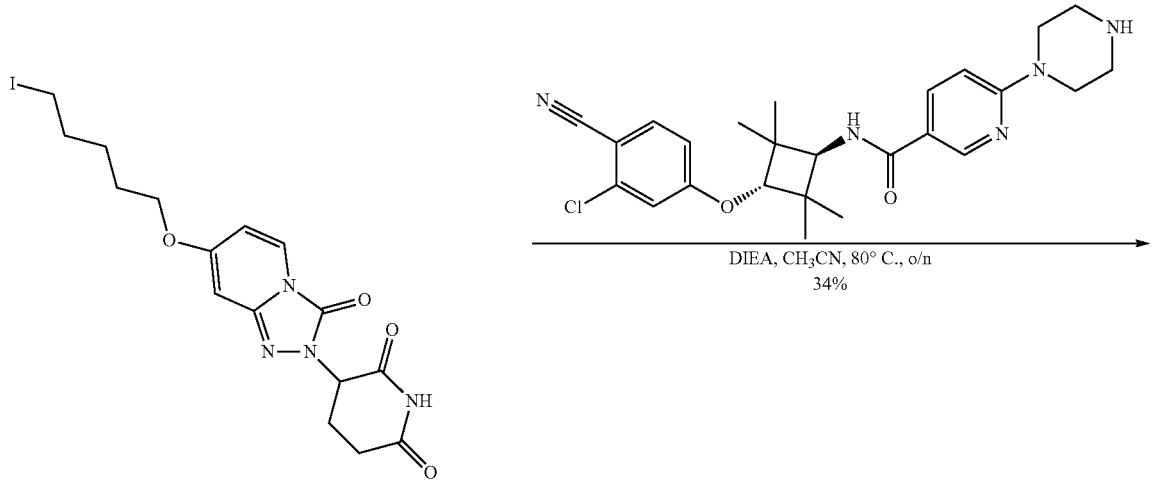

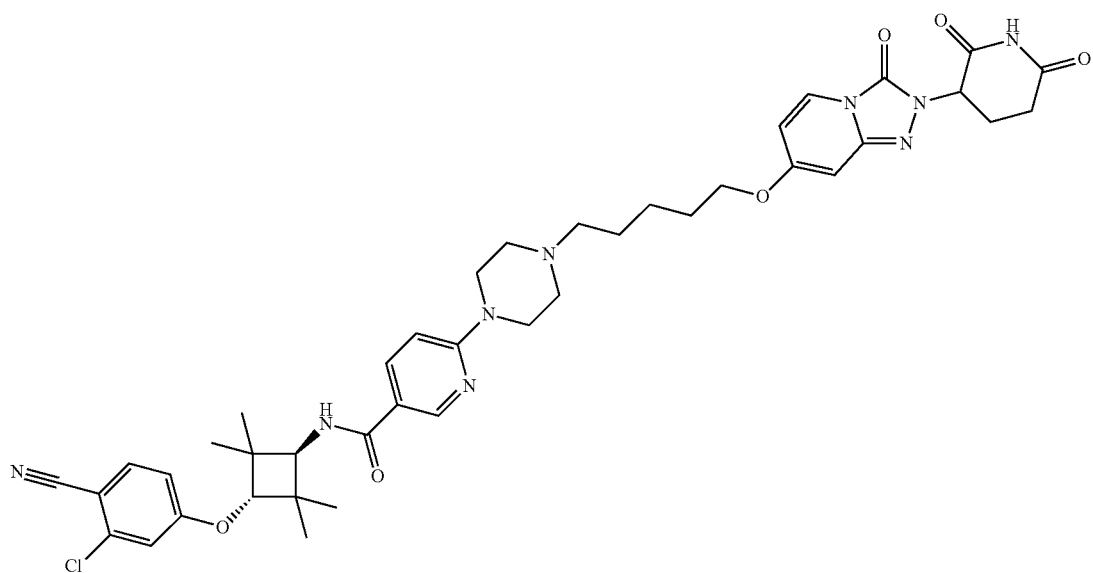

A solution of 3-(7-(5-iodopentyloxy)-3-oxo-[1,2,4]triazolo[4,3-a]pyridin-2(3H)-yl)piperidine-2,6-dione (85 mg, 0.2 mmol), N-((1r,3r)-3-(3-chloro-4-cyanophenoxy)-2,2,4,4-tetramethylcyclobutyl)-6-(piperazin-1-yl)nicotinamide (87 mg, 0.2 mmol), and ethyldiisopropylamine (72 mg, 0.6 mmol) in acetonitrile (5 mL) was stirred at 80° C. overnight. When it was cooled to room temperature, water (5 mL) was added and the mixture was extracted by ethyl acetate (5 mL×3) and the combined organic layers were washed by brine (5 mL×3), dried over anhydrous sodium sulfate, filtered and concentrated. The residue was purified by Prep-HPLC to give N-((1r,3r)-3-(3-chloro-4-cyanophenoxy)-2,2,4,4-tetramethylcyclobutyl)-6-(4-(5-(2-(2,6-dioxopiperidin-3-yl)-3-oxo-2,3-dihydro-[1,2,4]triazolo[4,3-a]pyridin-7-yloxy)pentyl)piperazin-1-yl)nicotinamide (50 mg, 34% yield) as a white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 3.0 min, then under this condition for 1.0 min, finally changed to 95% [water+10 mM NH$_4$HCO$_3$] and 5% [CH$_3$CN] in 0.1 min and under this condition for 0.7 min.) Purity is 100%, Rt=2.877 min; MS Calcd.: 797.34; MS Found: 798.3 [M+H]$^+$.

HPLC (Agilent HPLC 1200, Column: Waters X-Bridge C18 (150 mm×4.6 mm×3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min.) Purity is 93.85%, Rt=9.967 min.

$^1$H NMR (400 MHz, DMSO-d$_6$) δ 1.12 (6H, s), 1.21 (6H, s), 1.43-1.47 (2H, m), 1.49-1.53 (2H, m), 1.73-1.78 (2H, m), 2.13-2.17 (1H, m), 2.32 (2H, t, J=7.2 Hz), 2.43-2.47 (5H, m), 2.61-2.62 (1H, m), 2.87-2.93 (1H, m), 3.59 (4H, s), 4.01-4.07 (3H, m), 4.30 (1H, s), 5.28 (1H, dd, J=12.4, 5.2 Hz), 6.35 (1H, dd, J=8.0, 2.4 Hz), 6.52 (1H, d, J=1.6 Hz), 6.86 (1H, d, J=8.8 Hz), 7.00 (1H, dd, J=8.8, 2.4 Hz), 7.21 (1H, d, J=2.4 Hz), 7.63 (1H, d, J=9.2 Hz), 7.80 (1H, d, J=8.0 Hz), 7.90 (0H, d, J=8.8 Hz), 7.95 (1H, dd, J=9.2, 2.4 Hz), 8.62 (1H, d, J=2.4 Hz), 11.09 (1H, s).

Chemical Formula: C$_{41}$H$_{48}$ClN$_9$O$_6$, Molecular Weight: 798.33.

Total H count from HNMR data: 48.

Exemplary Synthesis of Exemplary Compound 49

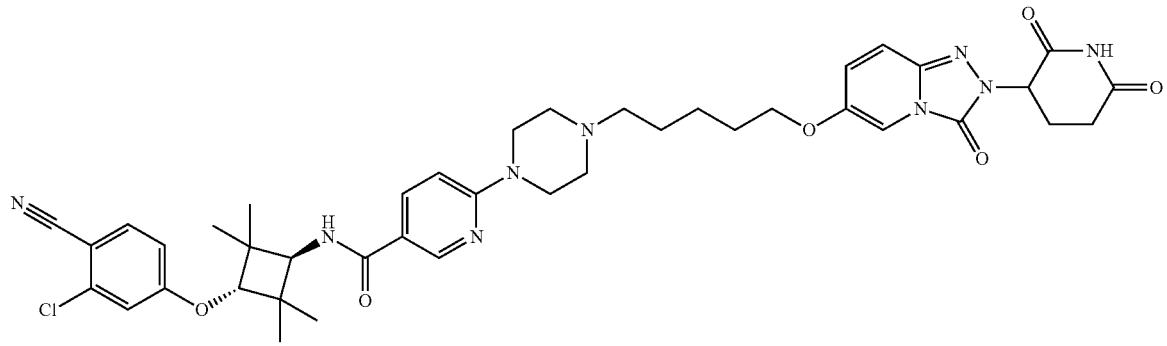 [SMILES: CC1(C)[C@H](NC(=O)c2ccc(N3CCN(CCCCCOc4ccc5nn(C6CCC(=O)NC6=O)c(=O)n5c4)CC3)nc2)C(C)(C)[C@H]1Oc1ccc(C#N)c(Cl)c1]

N-((1r,3r)-3-(3-chloro-4-cyanophenoxy)-2,2,4,4-tetramethylcyclobutyl)-6-(4-(5-((2-(2,6-dioxopiperidin-3-yl)-3-oxo-2,3-dihydro-[1,2,4]triazolo[4,3-a]pyridin-6-yl)oxy)pentyl)piperazin-1-yl)nicotinamide Synthetic Scheme

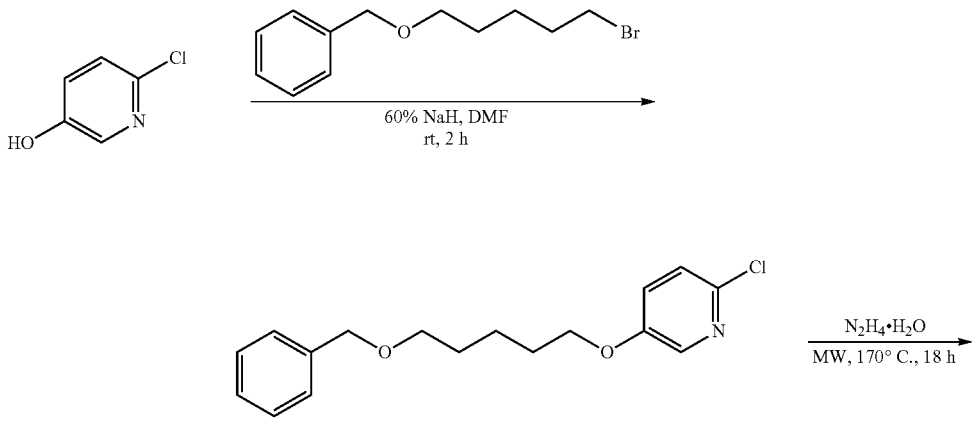

Step 1: Synthesis of
5-(5-(benzyloxy)pentyloxy)-2-chloropyridine

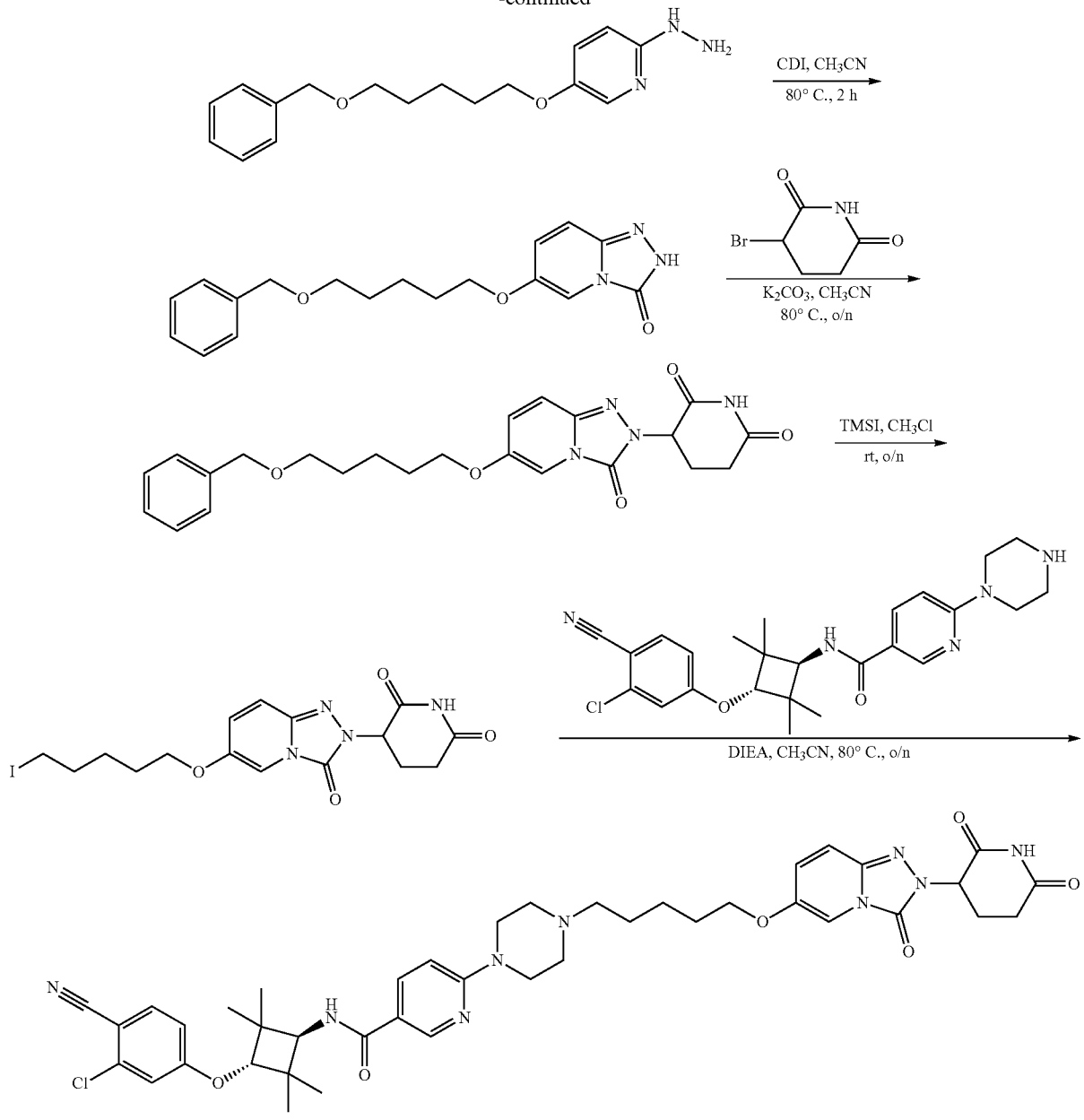

To a solution of 6-chloropyridin-3-ol (1.0 g, 7.7 mmol) in DMF (10 mL) was added sodium hydride (60% dispersed in mineral oil, 371 mg, 9.3 mmol) at 0° C., and the mixture was stirred at room temperature for 30 min. Then ((5-bromopentyloxy)methyl)benzene (2.0 g, 7.7 mmol) was added to the reaction and the resulted mixture was stirred at room temperature for 2 h. When the reaction was completed (monitored by TLC), water (30 mL) was added. The resultant mixture was extracted by ethyl acetate (10 mL×3) and the combined organic layers were washed by brine (10 mL×3), dried over anhydrous sodium sulfate, filtered and concentrated. The residue (1.6 g, 68% yield) was directly used to the next step without further purification as a brown solid.

Step 2: Synthesis of 5-(5-(benzyloxy)pentyloxy)-2-hydrazinylpyridine

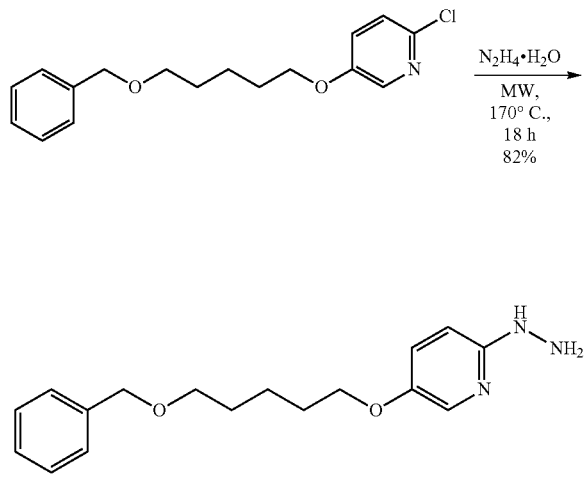

To a microwave glass vial was added 5-(5-(benzyloxy)pentyloxy)-2-chloropyridine (1.6 g, 5.2 mmol) and hydrazine monohydrate (20 mL), and the mixture was stirred under microwave conditions at 170° C. for 18 h. When it was cooled to room temperature, water (20 mL) was added to the reaction. The resultant mixture was extracted by ethyl acetate (10 mL×3) and the combined organic layers were washed by brine (15 mL×3), dried over anhydrous sodium sulfate, filtered and concentrated in vacuo. The residue (1.3 g, 82% yield) was directly used to the next step without further purification as brown oil.

Step 3: Synthesis of 6-(5-(benzyloxy)pentyloxy)-[1,2,4]triazolo[4,3-a]pyridin-3(2H)-one

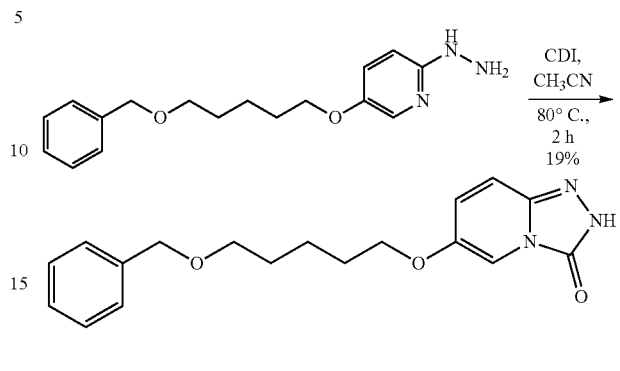

To a solution of 5-(5-(benzyloxy)pentyloxy)-2-hydrazinylpyridine (1.3 g, 4.4 mmol) in acetonitrile (30 mL) was added CDI (1.1 g, 6.7 mmol), and the mixture was stirred at 80° C. for 2 h. When it was cooled to room temperature, water (20 mL) was added to the reaction. The resultant mixture was extracted by ethyl acetate (10 mL×3) and the combined organic layers were washed by brine (15 mL×3), dried over anhydrous sodium sulfate, filtered and concentrated in vacuo. The residue was purified by column chromatography on silica (DCM/MeOH=20/1) to give 6-(5-(benzyloxy)pentyloxy)-[1,2,4]triazolo[4,3-a]pyridin-3(2H)-one (280 mg, 19% yield) as a white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min.) Purity is 98.98%, Rt=1.728 min. MS Calcd.: 327.16; MS Found: 328.1 $[M+H]^+$.

Step 4: Synthesis of 3-(6-(5-(benzyloxy)pentyloxy)-3-oxo-[1,2,4]triazolo[4,3-a]pyridin-2(3H)-yl)piperidine-2,6-dione

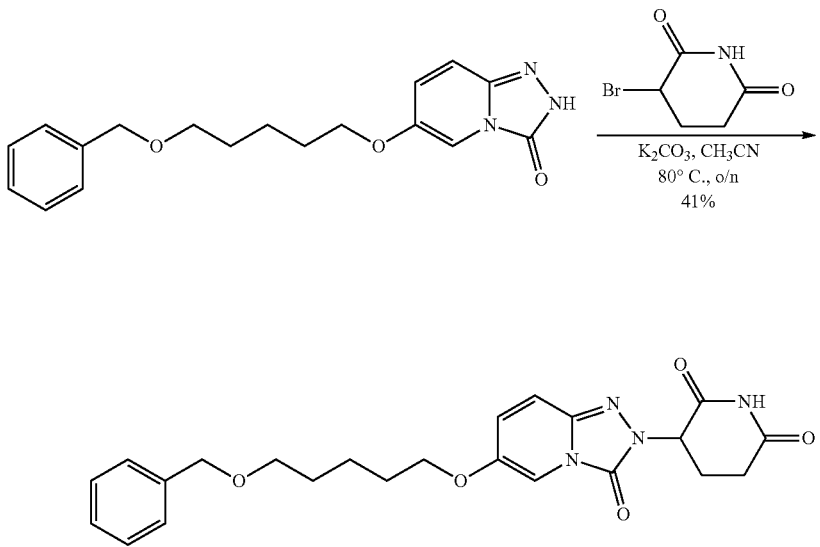

The solution of 6-(5-(benzyloxy)pentyloxy)-[1,2,4]triazolo[4,3-a]pyridin-3(2H)-one (280 mg, 0.9 mmol), 3-bromopiperidine-2,6-dione (438 mg, 2.3 mmol) and K₂CO₃ (253 mg, 1.8 mmol) in acetonitrile (10 mL) was stirred at 80° C. overnight. When it was cooled to room temperature, water (10 mL) was added. The resultant mixture was extracted by ethyl acetate (10 mL×3) and the combined organic layers were washed by brine (10 mL×3), dried over anhydrous sodium sulfate, filtered and concentrated. The residue was purified by Prep-TLC (DCM/MeOH=20/1) to give 3-(6-(5-(benzyloxy)pentyloxy)-3-oxo-[1,2,4]triazolo[4,3-a]pyridin-2(3H)-yl)piperidine-2,6-dione (155 mg, 41% yield) as a white solid.

LC-MS (Agilent LCMS 1200-6120, Column: Waters X-Bridge C18 (50 mm×4.6 mm×3.5 m); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min.) Purity is 85.76%, Rt=1.675 min. MS Calcd.: 438.19; MS Found: 439.2 [M+H]⁺.

Step 5: Synthesis of 3-(6-(5-iodopentyloxy)-3-oxo-[1,2,4]triazolo[4,3-a]pyridin-2(3H)-yl)piperidine-2,6-dione

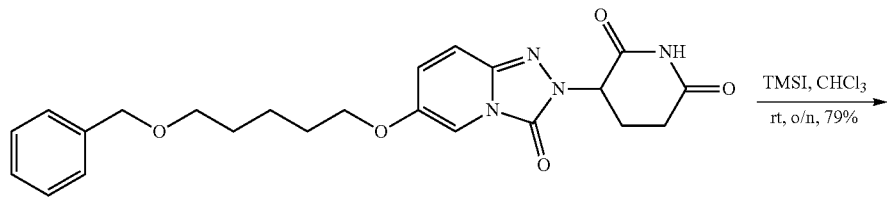

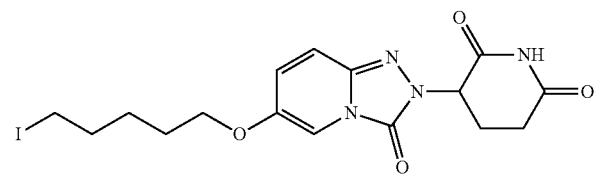

To a solution of 3-(6-(5-(benzyloxy)pentyloxy)-3-oxo-[1,2,4]triazolo[4,3-a]pyridin-2(3H)-yl)piperidine-2,6-dione (155 mg, 0.4 mmol) in CHCl₃ (5 mL) was added TMSI (143 mg, 0.7 mmol), and the mixture was stirred at room temperature overnight. Then the mixture was washed by sat. NaHSO₃ (5 mL×2), washed by brine (5 mL×2), dried over anhydrous sodium sulfate, filtered and concentrated. The residue was purified by Prep-TLC (DCM/MeOH=15/1) to give 3-(7-(5-iodopentyloxy)-3-oxo-[1,2,4]triazolo[4,3-a]pyridin-2(3H)-yl)piperidine-2,6-dione (130 mg, 79% yield) as a white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min.) Purity is 95.44%, Rt=1.706 min. MS Calcd.: 458.05; MS Found: 459.1 [M+H]⁺.

Step 6: Synthesis of N-((1r,3r)-3-(3-chloro-4-cyanophenoxy)-2,2,4,4-tetramethylcyclobutyl)-6-(4-(5-(2-(2,6-dioxopiperidin-3-yl)-3-oxo-2,3-dihydro-[1,2,4]triazolo[4,3-a]pyridin-6-yloxy)pentyl)piperazin-1-yl)nicotinamide

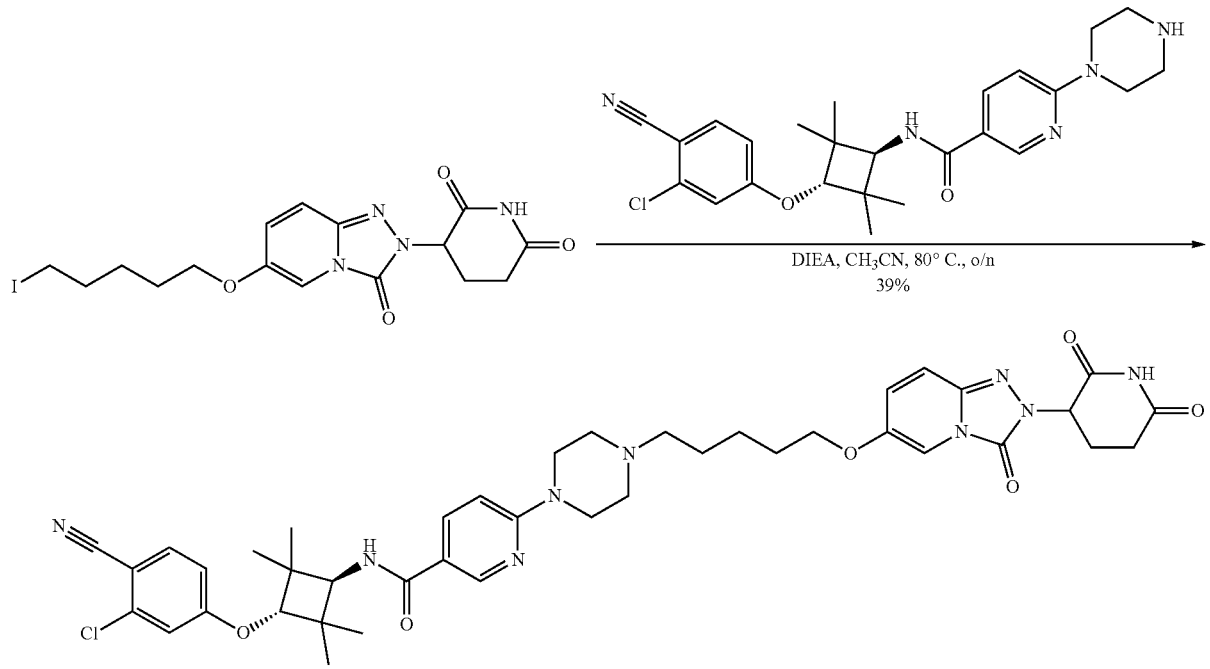

A solution of 3-(6-(5-iodopentyloxy)-3-oxo-[1,2,4]triazolo[4,3-a]pyridin-2(3H)-yl)piperidine-2,6-dione (85 mg, 0.2 mmol), N-((1r,3r)-3-(3-chloro-4-cyanophenoxy)-2,2,4,4-tetramethylcyclobutyl)-6-(piperazin-1-yl)nicotinamide (87 mg, 0.2 mmol), and ethyldiisopropylamine (72 mg, 0.6 mmol) in acetonitrile (5 mL) was stirred at 80° C. overnight. When it was cooled to room temperature, water (5 mL) was added and the mixture was extracted by ethyl acetate (5 mL×3) and the combined organic layers were washed by brine (5 mL×3), dried over anhydrous sodium sulfate, filtered, and concentrated. The residue was purified by Prep-HPLC to give N-((1r,3r)-3-(3-chloro-4-cyanophenoxy)-2,2,4,4-tetramethylcyclobutyl)-6-(4-(5-(2-(2,6-dioxopiperidin-3-yl)-3-oxo-2,3-dihydro-[1,2,4]triazolo[4,3-a]pyridin-6-yloxy)pentyl)piperazin-1-yl)nicotinamide (58 mg, 39% yield) as a white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min.) Purity is 100%, Rt=2.890 min; MS Calcd.: 797.34; MS Found: 798.3 $[M+H]^+$.

HPLC (Agilent HPLC 1200, Column: Waters X-Bridge C18 (150 mm×4.6 mm×3.5 μm): Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100/6 [$CH_3CN$] in 10 min, then under this condition for 5 min, finally changed to 95% [water+10 mM $NH_4HCO_3$] and 5% [$CH_3CN$] in 0.1 min and under this condition for 5 min.) Purity is 93.46%, Rt=10.027 min.

$^1$H NMR (400 MHz, DMSO-$d_6$) δ 1.12 (6H, s), 1.21 (6H, s), 1.44-1.48 (2H, m), 1.52-1.58 (2H, m), 1.74-1.79 (2H, m), 2.15-2.19 (1H, m), 2.30 (2H, t, J=7.2 Hz), 2.43-2.50 (4H, m), 2.51-2.67 (2H, m), 2.86-2.95 (1H, m), 3.60 (4H, s), 3.97 (2H, t, J=6.4 Hz), 4.05 (1H, d, J=9.2 Hz), 4.30 (1H, s), 5.38 (1H, dd, J=5.2, 12.8 Hz), 6.86 (1H, d, J=9.2 Hz), 7.00 (1H, dd, J=8.4, 2.4 Hz), 7.10 (1H, dd, J=10.0, 2.0 Hz), 7.21 (1H, d, J=2.4 Hz), 7.25 (1H, d, J=10.0 Hz), 7.36 (1H, s), 7.62 (1H, d, J=9.2 Hz), 7.90 (1H, d, J=8.8 Hz), 7.95 (1H, dd, J=9.2, 2.4 Hz), 8.62 (1H, d, J=2.4 Hz), 11.10 (1H, s).

Chemical Formula: $C_{41}H_{48}CN_9O_6$, Molecular Weight: 798.33.

Total H count from HNMR data: 48.

Exemplary Synthesis of Exemplary Compound 50

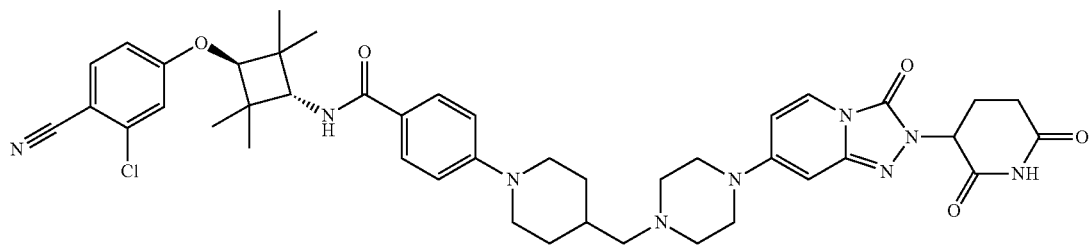 [SMILES: CC1(C)[C@H](NC(=O)c2ccc(N3CCC(CN4CCN(c5ccn6c(=O)n(C7CCC(=O)NC7=O)nc6c5)CC4)CC3)cc2)C(C)(C)[C@H]1Oc1ccc(C#N)c(Cl)c1]

N-((1r,3r)-3-(3-chloro-4-cyanophenoxy)-2,2,4,4-tetramethylcyclobutyl)-4-(4-((4-(2-(2,6-dioxopiperidin-3-yl)-3-oxo-2,3-dihydro-[1,2,4]triazolo[4,3-a]pyridin-7-yl)piperazin-1-yl)methyl)piperidin-1-yl)benzamide
Synthetic Scheme
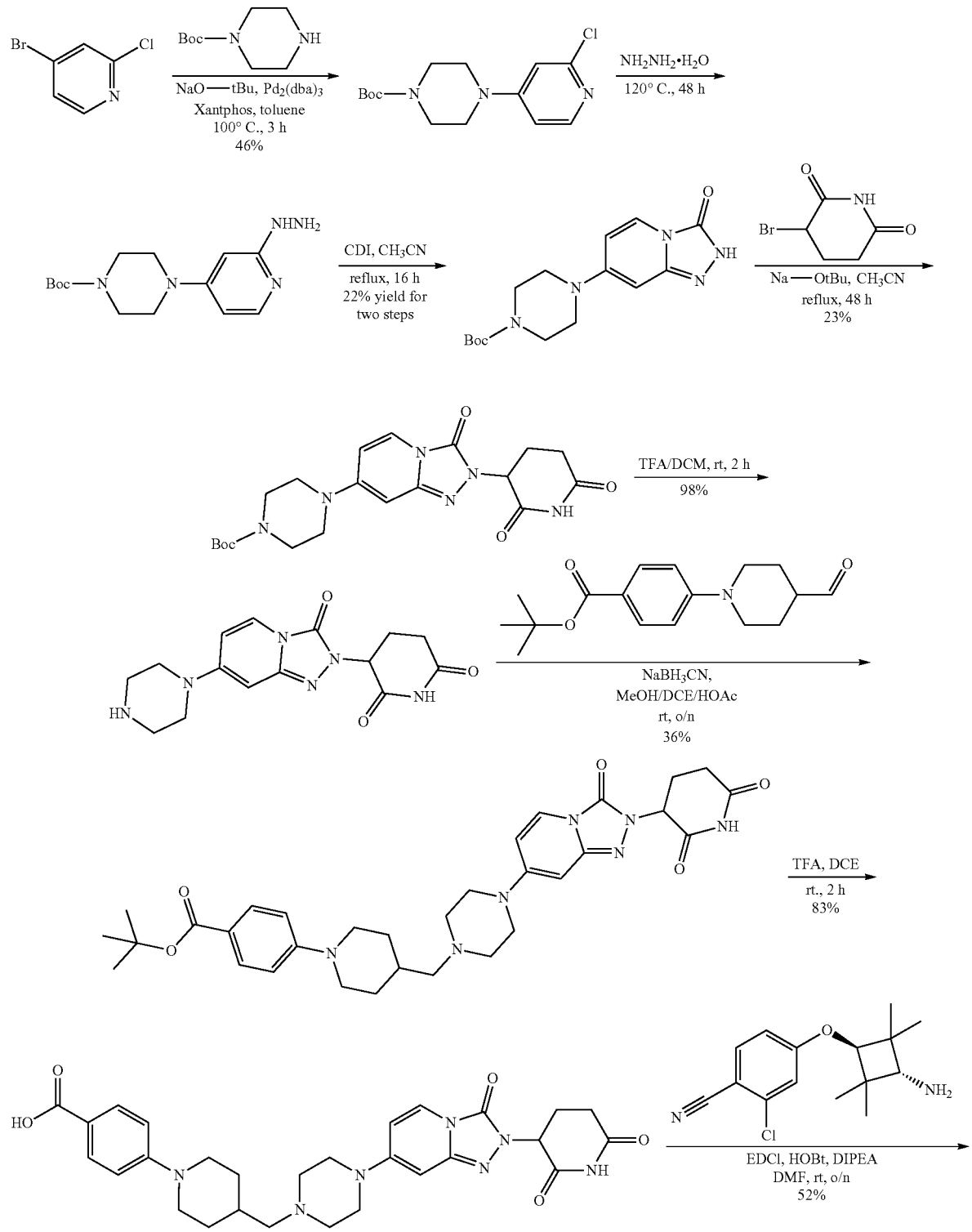

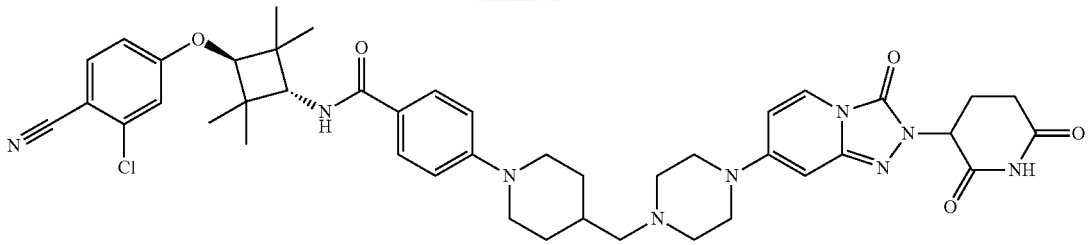 [SMILES: CC1(C)[C@H](NC(=O)c2ccc(N3CCC(CN4CCN(c5ccn6c(=O)n(C7CCC(=O)NC7=O)nc6c5)CC4)CC3)cc2)C(C)(C)[C@H]1Oc1ccc(C#N)c(Cl)c1]

Step 1: Synthesis of tert-butyl 4-(2-chloropyridin-4-yl)piperazine-1-carboxylate

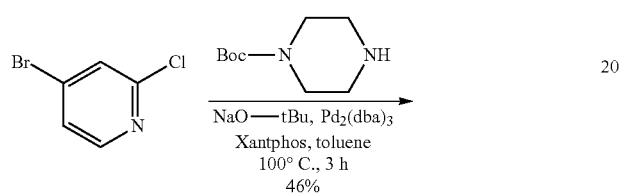

To a solution of 4-bromo-2-chloropyridine (5.8 g, 30.2 mmol) in dry toluene (150 mL) was added sodium tert-butoxide (4.3 g, 45.0 mmol), Pd$_2$(dba)$_3$ (0.55 g, 0.60 mmol), Xantphos (1.0 g, 1.80 mmol) and tert-butyl piperazine-1-carboxylate (5.6 g, 30.2 mmol). The reaction mixture was stirred at 100° C. for 3 h under nitrogen and then cooled to rt. The organic layer was washed with water and brine and then dried over anhydrous sodium sulfate, filtered, and concentrated. The residue was purified by silica gel chromatography column (PE/EA=8:1) to give tert-butyl 4-(2-chloropyridin-4-yl)piperazine-1-carboxylate (3.6 g, 46%) as a yellow solid.

$^1$H NMR (400 MHz, DMSO-d$_6$) δ 1.42 (9H, s), 3.38-3.41 (8H, m), 6.83-6.86 (2H, m), 7.96 (1H, d, J=6.0 Hz).

Chemical Formula: C$_{14}$H$_{20}$ClN$_3$O$_2$, Molecular Weight: 297.78.

Total H count from HNMR data: 20.

Step 2: Synthesis of tert-butyl 4-(2-hydrazinylpyridin-4-yl)piperazine-1-carboxylate

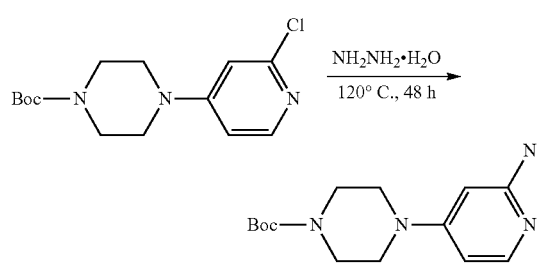

To a solution of tert-butyl 4-(2-chloropyridin-4-yl)piperazine-1-carboxylate (5.0 g, 16.8 mmol) in hydrazine monohydrate (98%, 40 mL), was stirred at 120° C. for 48 h under nitrogen. Water (100 mL) was added to the mixture. The resultant mixture was extracted by ethyl acetate (50 mL×3), washed by brine (100 mL), dried over anhydrous sodium sulfate, filtered, and concentrated in vacuo. The residue (4.8 g, 30% purity) was directly used to the next step without further purification as a brown solid.

Step 3: Synthesis of tert-butyl 4-(3-oxo-2,3-dihydro-[1,2,4]triazolo[4,3-a]pyridin-7-yl)piperazine-1-carboxylate

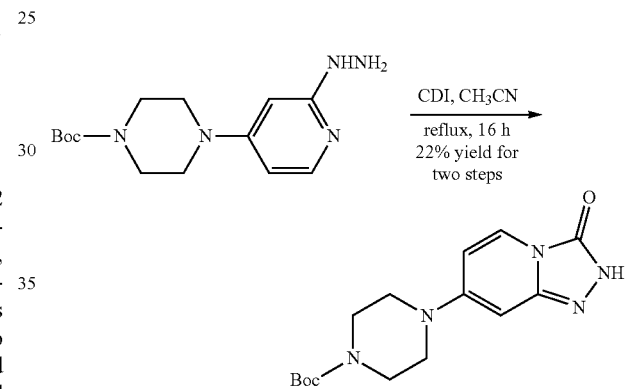

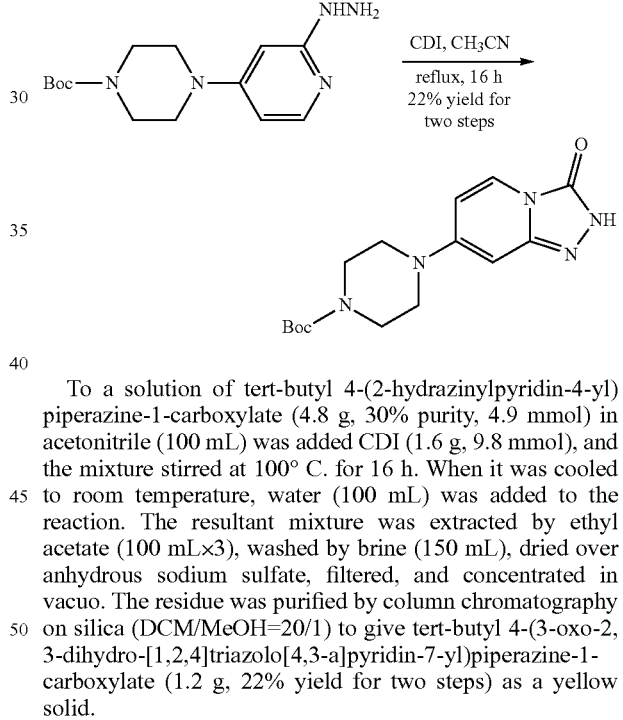

To a solution of tert-butyl 4-(2-hydrazinylpyridin-4-yl)piperazine-1-carboxylate (4.8 g, 30% purity, 4.9 mmol) in acetonitrile (100 mL) was added CDI (1.6 g, 9.8 mmol), and the mixture stirred at 100° C. for 16 h. When it was cooled to room temperature, water (100 mL) was added to the reaction. The resultant mixture was extracted by ethyl acetate (100 mL×3), washed by brine (150 mL), dried over anhydrous sodium sulfate, filtered, and concentrated in vacuo. The residue was purified by column chromatography on silica (DCM/MeOH=20/1) to give tert-butyl 4-(3-oxo-2,3-dihydro-[1,2,4]triazolo[4,3-a]pyridin-7-yl)piperazine-1-carboxylate (1.2 g, 22% yield for two steps) as a yellow solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM AcONH$_4$) water/CH$_3$CN=900/100 (v/v)] and 10% [(total 10 mM AcONH$_4$) water/CH$_3$CN=100/900 (v/v)] to 10% [(total 10 mM AcONH$_4$) water/CH$_3$CN=900/100 (v/v)] and 90% [(total 10 mM AcONH$_4$) water/CH$_3$CN=100/900 (v/v)] in 1.6 min, then under this condition for 2.4 min, finally changed to 90% [(total 10 mM AcONH$_4$) water/CH$_3$CN=900/100 (v/v)] and 10% [(total 10 mM AcONH$_4$) water/CH; CN=100/900 (v/v)] in 0.1 min and under this condition for 0.7 min). Purity is 99.11%, Rt=1.418 min; MS Calcd.: 319.7; MS Found: 320.2 [M+H]$^+$.

$^1$H NMR (400 MHz, DMSO-d$^6$) δ 1.42 (9H, s), 3.21-3.23 (4H, m), 3.42-3.43 (4H, m), 6.13 (1H, d, J=1.6 Hz), 6.60 (1H, dd, J=8.0, 2.0 Hz), 7.65 (1H, d, J=8.0 Hz), 11.90 (1H, s).

Chemical Formula: $C_{15}H_{21}N_5O_3$, Molecular Weight: 319.36

Total H count from HNMR data: 21.

Step 4: Synthesis of tert-butyl 4-(2-(2,6-dioxopiperidin-3-yl)-3-oxo-2,3-dihydro-[1,2,4]triazolo[4,3-a]pyridin-7-yl)piperazine-1-carboxylate

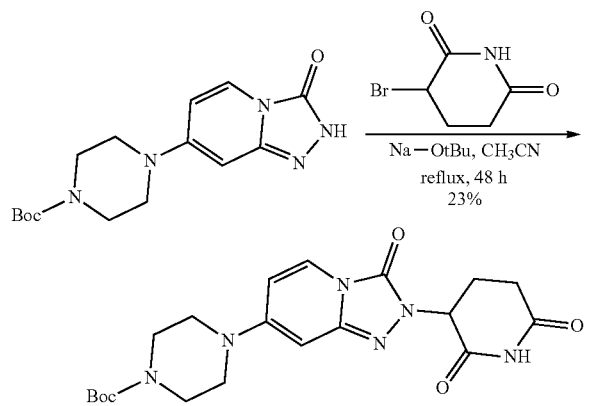

The solution of tert-butyl 4-(3-oxo-2,3-dihydro-[1,2,4]triazolo[4,3-a]pyridin-7-yl)piperazine-1-carboxylate (320 mg, 1.0 mmol), 3-bromopiperidine-2,6-dione (390 mg, 2.0 mmol) and sodium tert-butoxide (120 mg, 1.2 mmol) in acetonitrale (20 mL) was stirred at 100° C. overnight. When it was cooled to room temperature, water (20 mL) was added. The resultant mixture was extracted by ethyl acetate (20 mL×3), washed by brine (30 mL), dried over anhydrous sodium sulfate, filtered and concentrated. The residue was purified by Prep-TLC (DCM/MeOH=20/1) to give tert-butyl 4-(2-(2,6-dioxopiperidin-3-yl)-3-oxo-2,3-dihydro-[1,2,4]triazolo[4,3-a]pyridin-7-yl)piperazine-1-carboxylate (100 mg, 23% yield) as a yellow solid.

$^1$H NMR (400 MHz, DMSO-d$_6$) δ 1.47 (9H, s), 2.16-2.20 (1H, m), 2.47-2.50 (1H, m), 2.66-2.70 (1H, m), 2.90-2.99 (1H, m), 3.31-3.33 (4H, m), 3.47-3.49 (4H, m), 5.27-5.31 (1H, m), 6.20 (1H, d, J=1.2 Hz), 6.73 (1H, dd, J=7.6, 2.0 Hz), 7.80 (1H, d, J=8.0 Hz), 11.11 (1H, s).

Chemical Formula: $C_{20}H_{26}N_6O_5$, Molecular Weight: 430.46.

Total H count from HNMR data: 26.

Step 5: Synthesis of 3-(3-oxo-7-(piperazin-1-yl)-[1,2,4]triazolo[4,3-a]pyridin-2(3H)-yl)piperidine-2,6-dione

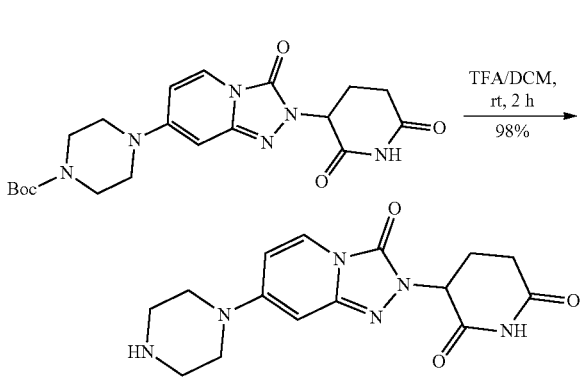

To a solution of tert-butyl 4-(2-(2,6-dioxopiperidin-3-yl)-3-oxo-2,3-dihydro-[1,2,4]triazolo[4,3-a]pyridin-7-yl)piperazine-1-carboxylate (0.40 g, 0.93 mmol) in dichloromethane (20 mL) was added TFA (8 mL), then stirred at room temperature for 2 h and concentrated in vacuo to give 3-(3-oxo-7-(piperazin-1-yl)-[1,2,4]triazolo[4,3-a]pyridin-2(3H)-yl)piperidine-2,6-dione (0.30 g, 98%) as a yellow solid, which was used to the next step without further purification.

Step 6: Synthesis of tert-butyl 4-(4-((4-(2-(2,6-dioxopiperidin-3-yl)-3-oxo-2,3-dihydro-[1,2,4]triazolo[4,3-a]pyridin-7-yl)piperazin-1-yl)methyl)piperidin-1-yl)benzoate

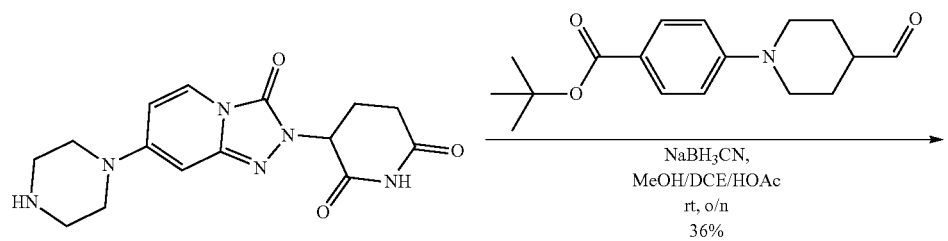

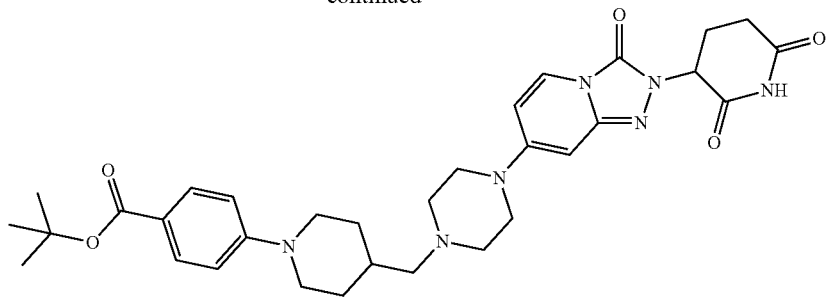

To a solution of 3-(3-oxo-7-(piperazin-1-yl)-[1,2,4]triazolo[4,3-a]pyridin-2(3H)-yl)piperidine-2,6-dione (0.30 g, 0.91 mmol) in dry methanol/1,2-dichloroethane/HOAc (20 mL/4 mL/0.1 mL) was added tert-butyl 4-(4-formylpiperidin-1-yl)benzoate (0.26 g, 0.91 mmol). The mixture was left to stir for 30 min under $N_2$ gas. Then sodium cyanoborohydride (0.11 g, 1.82 mmol) was added and the reaction mixture was left to stir for 16 h at room temperature. The solvent was removed and the residue partitioned between dichloromethane and water, washed with brine, dried over anhydrous sodium sulfate, filtered, and concentrated in vacuo to give crude product. The residue was purified by prep-TLC to give compound tert-butyl 4-(4-((4-(2-(2,6-dioxopiperidin-3-yl)-3-oxo-2,3-dihydro-[1,2,4]triazolo[4,3-a]pyridin-7-yl)piperazin-1-yl)methyl)piperidin-1-yl)benzoate (0.20 g, 36%) as a yellow solid.

LC-MS (Agilent LCMS 1200-6120, Column: Waters X-Bridge C18 (50 mm*4.6 mm*3.5 μm); Column Temperature: 40° C.; Flow Rate: 2.0 m/min; Mobile Phase: from 90% [(total 10 mM $AcONH_4$) water/$CH_3CN$=900/100 (v/v)] and 10% [(total 10 mM $AcONH_4$) water/$CH_3CN$=100/900 (v/v)] to 10% [(total 10 mM $AcONH_4$) water/$CH_3CN$=900/100 (v/v)] and 90% [(total 10 mM $AcONH_4$) water/$CH_3CN$=100/900 (v/v)] in 1.6 min, then under this condition for 2.4 min, finally changed to 90% [(total 10 mM $AcONH_4$) water/$CH_3CN$=900/100 (v/v)] and 10% [(total 10 mM $AcONH_4$) water/$CH_3CN$=100/900 (v/v)] in 0.1 min and under this condition for 0.7 min). Purity is 87.07%, Rt=2.195 min.; MS Calcd.: 603.3: MS Found: 604.4 $[M+H]^+$.

Step 7: Synthesis of 4-(4-((4-(2-(2,6-dioxopiperidin-3-yl)-3-oxo-2,3-dihydro-[1,2,4]triazolo[4,3-a]pyridin-7-yl)piperazin-1-yl)methyl)piperidin-1-yl)benzoic acid

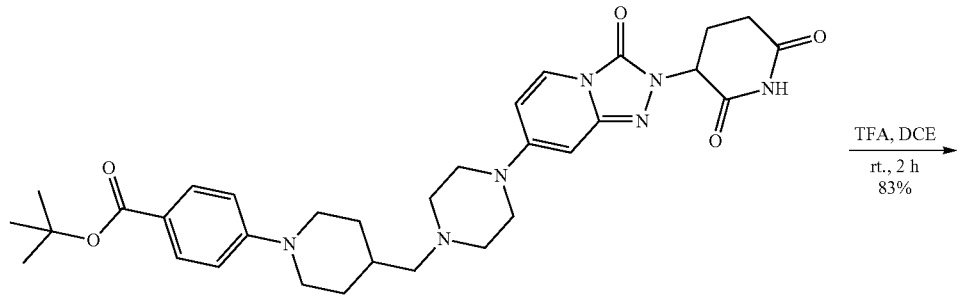

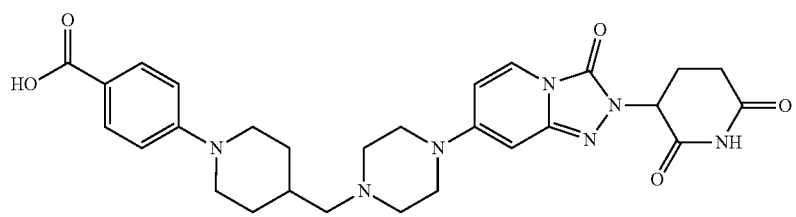

To a solution of tert-butyl 4-(4-((4-(2-(2,6-dioxopiperidin-3-yl)-3-oxo-2,3-dihydro-[1,2,4]triazolo[4,3-a]pyridin-7-yl)piperazin-1-yl)methyl)piperidin-1-yl)benzoate (0.10 g, 0.16 mmol) in dichloromethane (10 mL) was added TFA (5 mL), then stirred at room temperature for 2 h, then concentrated in vacuo to give 4-(4-((4-(2-(2,6-dioxopiperidin-3-yl)-3-oxo-2,3-dihydro-[1,2,4]triazolo[4,3-a]pyridin-7-yl)piperazin-1-yl)methyl)piperidin-1-yl)benzoic acid (0.075 g, 83%) as a yellow solid, which was used to the next step without further purification.

Step 8: Synthesis of N-((1r,3r)-3-(3-chloro-4-cyanophenoxy)-2,2,4,4-tetramethylcyclobutyl)-4-(4-((4-(2-(2,6-dioxopiperidin-3-yl)-3-oxo-2,3-dihydro-[1,2,4]triazolo[4,3-a]pyridin-7-yl)piperazin-1-yl)methyl)piperidin-1-yl)benzamide

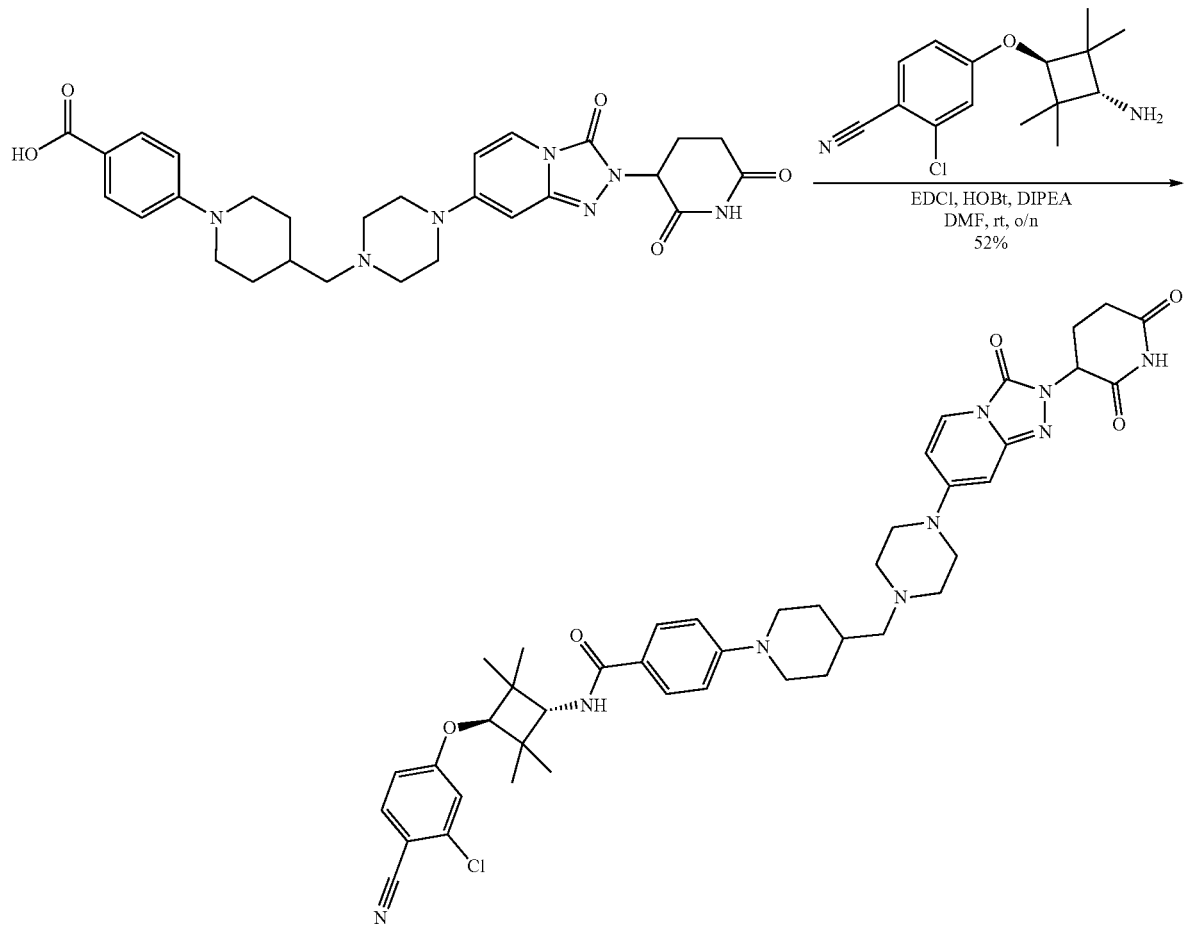

A solution of 4-(4-((4-(2-(2,6-dioxopiperidin-3-yl)-3-oxo-2,3-dihydro-[1,2,4]triazolo[4,3-a]pyridin-7-yl)piperazin-1-yl)methyl)piperidin-1-yl)benzoic acid (75 mg, 0.14 mmol), 1-(3-dimethylaminopropyl)-3-ethylcarbodiimide hydrochloride (EDCI) (39 mg, 0.21 mmol), 1-hydroxybenzotriazole hydrate (HOBt) (28 mg, 0.21 mmol) and ethyldiisopropylamine (88 mg, 0.69 mmol) in DMF (5 mL) was stirred for 30 min, and then 4-((1r,3r)-3-amino-2,2,4,4-tetramethylcyclobutoxy)-2-chlorobenzonitrile (38 mg, 0.14 mmol) was added. The mixture was stirred at room temperature overnight and water (10 mL) was added. The aqueous layer was extracted by dichloromethane (20 mL×2). The combined organic layer was washed by brine (10 mL×2), dried over anhydrous sodium sulfate, filtered, and concentrated in vacuo. The residue was purified by prep-HPLC to give N-((1r,3r)-3-(3-chloro-4-cyanophenoxy)-2,2,4,4-tetramethylcyclobutyl)-4-(4-((4-(2-(2,6-dioxopiperidin-3-yl)-3-oxo-2,3-dihydro-[1,2,4]triazolo[4,3-a]pyridin-7-yl)piperazin-1-yl)methyl)piperidin-1-yl)benzamide (57 mg, 52%) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0%

[water+10 mM NH$_4$HCO$_3$] and 100% [CH$_3$CN] in 3.0 min, then under this condition for 1.0 min, finally changed to 95% [water+10 mM NH$_4$HCO$_3$] and 5% [CH$_3$CN] in 0.1 min and under this condition for 0.7 min). Purity is 98.22%, Rt=3.022 min; MS Calcd.: 807.4; MS Found: 808.3 [M+H]$^+$.

HPLC (Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity is 99.00%, Rt=10.305 min.

$^1$H NMR (400 MHz, DMSO-d$_6$) δ 1.13 (6H, s), 1.22 (6H, s), 1.79-1.81 (3H, m), 2.09-2.15 (1H, m), 2.19-2.21 (2H, m), 2.49-2.50 (7H, m), 2.60-2.67 (1H, m), 2.76-2.92 (3H, m), 3.22-3.26 (4H, m), 3.86 (2H, d, J=12.8 Hz), 4.05 (1H, d, J=9.2 Hz), 4.32 (1H, s), 5.23 (1H, dd, J=12.4, 5.2 Hz), 6.12 (1H, s), 6.70 (1H, dd, J=8.0, 1.6 Hz), 6.95 (2H, d, J=9.2 Hz), 7.00 (1H, dd, J=8.8, 2.4 Hz), 7.21 (1H, d, J=2.4 Hz), 7.48 (1H, d, J=8.8 Hz), 7.72 (3H, t, J=8.4 Hz), 7.91 (1H, d, J=8.8 Hz), 11.04 (1H, s).

Chemical Formula: C$_{43}$H$_{50}$ClN$_9$O$_5$, Molecular Weight: 808.37.

Total H count from HNMR data: 50.

General Synthetic Scheme C-3

Synthesis of Building Block N-((1r,3r)-3-(3-chloro-4-cyanophenoxy)-2,2,4,4-tetramethylcyclobutyl)-4-(4-formylpiperidin-1-yl)benzamide

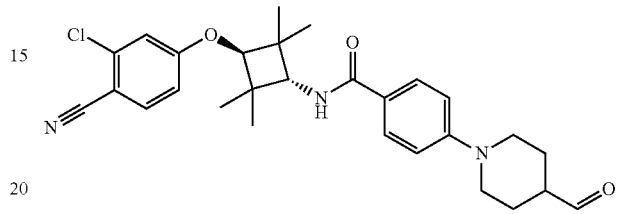

Synthetic Scheme

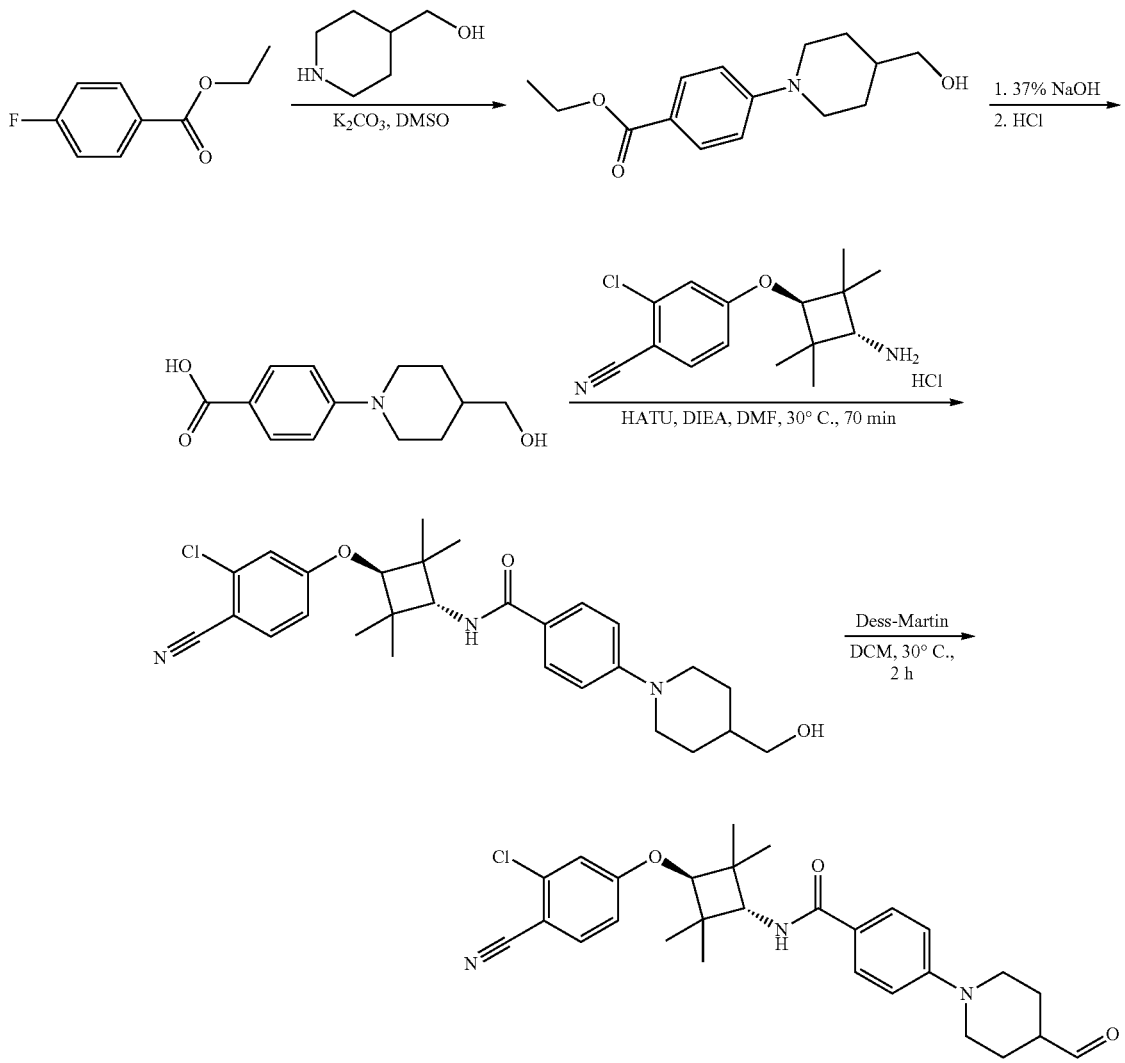

Step 1: Synthesis of Ethyl 4-(4-(hydroxymethyl)piperidin-1-yl)benzoate

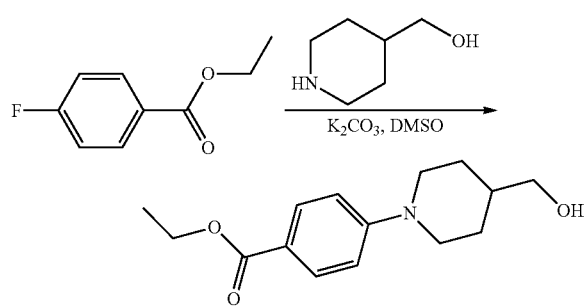

To a solution of ethyl 4-fluorobenzoate (27 g, 0.16 mol) in DMSO (500 mL) was added K₂CO₃ (44 g, 0.32 mol) and piperidin-4-ylmethanol (32 g, 0.19 mol) at 25° C. The resulting solution was stirred at 100° C. for 12 h. The reaction was diluted with H₂O (600 mL). The resulting mixture was extracted with EtOAc (200 mL×3). The combined organic layers were dried over anhydrous sodium sulfate and concentration. The crude product was slurry in PE/MTBE=1:1 to afford ethyl 4-(4-(hydroxymethyl)piperidin-1-yl)benzoate (30 g, 71% yield) as a white solid, which was used into next step without further purification.

Chemical Formula: $C_{15}H_{21}NO_3$; Molecular Weight: 263.34.

$^1$H NMR (400 MHz, DMSO-d₆): δ 7.91 (d, J=8.8 Hz, 2H), 6.87 (d, J=8.8 Hz, 2H), 4.30-4.35 (m, 2H), 3.90 (d, J=12.8 Hz, 2H), 3.54 (d, J=6.4 Hz, 2H), 2.82-2.89 (m, 2H), 1.85 (d, J=12.8 Hz, 2H), 1.71-1.77 (m, 1H), 1.35-1.54 (m, 6H).

Total H count from $^1$H NMR data: 21

Step 2: Synthesis of 4-(4-(Hydroxymethyl)piperidin-1-yl)benzoic acid

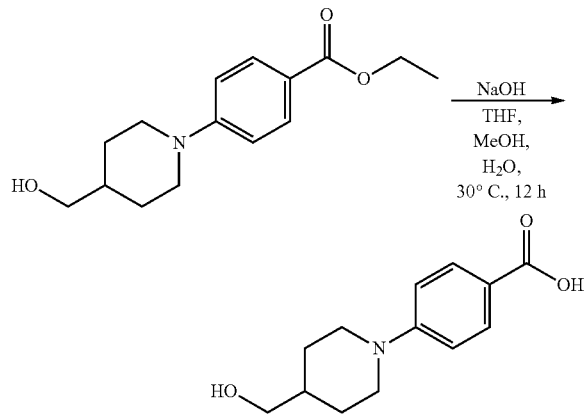

To a solution of ethyl 4-[4-(hydroxymethyl)-1-piperidyl]benzoate (52 g, 197.47 mmol, 1 eq) in tetrahydrofuran (250 mL), methanol (250 mL) and water (250 mL) was added sodium hydroxide (31.6 g, 0.79 mmol, 4 eq). The mixture was stirred at 30° C. for 12 hours. Thin layer chromatography (petroleum ether: ethyl acetate=1:1) showed the reaction was completed. The mixture was adjusted to pH 3~4 with hydrochloric acid (2 M) and filtered. The filter cake was dried in vacuum. The residue was triturated with ethyl acetate (500 mL) to give 4-[4-(hydroxymethyl)-1-piperidyl]benzoic acid (35 g, 148.76 mmol, 75% yield) as a white solid.

$^1$H NMR: (400 MHz, DMSO-d₆) δ: 12.19 (s, 1H), 7.74 (d, J=8.8 Hz, 2H), 6.93 (d, J=8.8 Hz, 2H), 4.48 (br t, J=5.2 Hz, 1H), 3.90 (d, J=12.8 Hz, 2H), 3.27 (br t, J=5.2 Hz, 2H), 2.86-2.72 (m, 2H), 1.72 (d, J=12.8 Hz, 2H), 1.66-1.51 (m, 1H), 1.17 (dq, J=4.0, 12.0 Hz, 2H)

Chemical Formula: $C_{13}H_{17}NO_3$, Molecular Weight: 235.28.

Total H count from HNMR data: 17.

Step 3: Synthesis of N-[3-(3-chloro-4-cyano-phenoxy)-2,2,4,4-tetramethyl-cyclobutyl]-4-[4-(hydroxymethyl)-1-piperidyl]benzamide

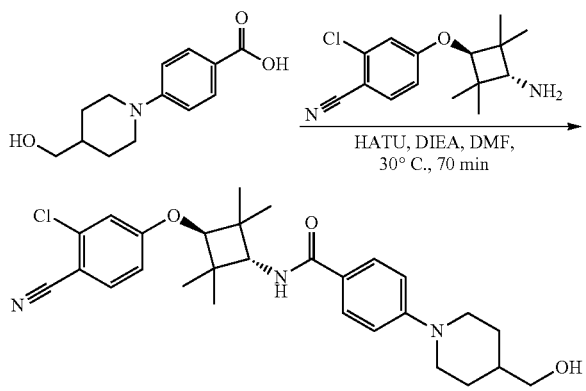

To a solution of 4-[4-(hydroxymethyl)-1-piperidyl]benzoic acid (38 g, 161.51 mmol, 1 eq) and 4-(3-amino-2,2,4,4-tetramethyl-cyclobutoxy)-2-chloro-benzonitrile (50.9 g, 161.51 mmol, 1 eq, hydrochloride) in dimethylformamide (800 mL) was added diisopropylethylamine (83.5 g, 646.04 mmol, 112 mL, 4 eq). The mixture was stirred at 30° C. for 10 min, and then o-(7-azabenzotriazol-1-yl)-n,n,n',n'-tetramethyluronium hexafluorophosphate (64.48 g, 169.59 mmol, 1.05 eq) was added. The mixture was stirred at 30° C. for 1 hour. LCMS showed the reaction was completed and desired MS can be detected. The mixture was poured into water (4 L) and filtered. The filter cake was concentrated and triturated with methanol (500 mL×2) to give N-[3-(3-chloro-4-cyano-phenoxy)-2,2,4,4-tetramethyl-cyclobutyl]-4-[4-(hydroxymethyl)-1-piperidyl]benzamide (72 g, 137.89 mmol, 85% yield, 95% purity) as a white solid.

LCMS: MS (ESI) m z: 496.1 [M+1]⁺

$^1$H NMR: (400 MHz, DMSO-d₆) δ: 7.90 (d, J=8.8 Hz, 1H), 7.73 (d, J=8.8 Hz, 2H), 7.48 (d, J=9.2 Hz, 1H), 7.20 (d, J=2.4 Hz, 1H), 7.00 (dd, J=2.4, 8.8 Hz, 1H), 6.95 (d, J=8.8 Hz, 2H), 4.48 (t, J=5.2 Hz, 1H), 4.31 (s, 1H), 4.05 (d, J=9.2 Hz, 1H), 3.86 (d, J=12.8 Hz, 2H), 3.27 (t, J=5.6 Hz, 2H), 2.80-2.70 (m, 2H), 1.73 (d, J=11.2 Hz, 2H), 1.63-1.52 (m, 1H), 1.27-1.15 (m, 8H), 1.12 (s, 6H).

Chemical Formula: $C_{28}H_{34}ClN_3O_3$, Molecular Weight: 496.04.

Total H count from HNMR data: 34.

Step 4: Synthesis of N-[3-(3-chloro-4-cyano-phenoxy)-2,2,4,4-tetramethyl-cyclobutyl]-4-(4-formyl-1-piperidyl)benzamide

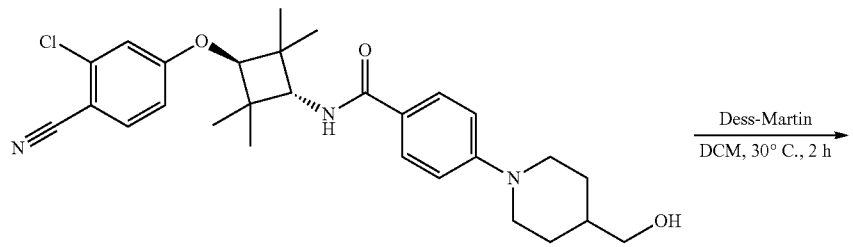

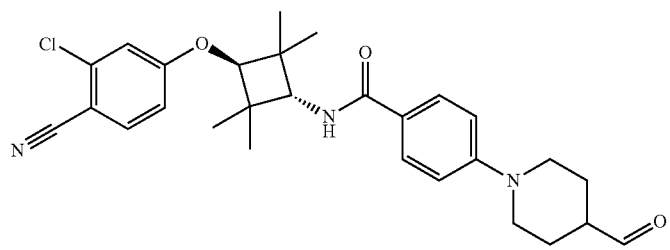 [SMILES: CC1(C)[C@H](NC(=O)c2ccc(N3CCC(C=O)CC3)cc2)C(C)(C)[C@H]1Oc1ccc(C#N)c(Cl)c1]

To a solution of N-[3-(3-chloro-4-cyano-phenoxy)-2,2,4,4-tetramethyl-cyclobutyl]-4-[4-(hydroxymethyl)-1-piperidyl]benzamide (65 g, 131.04 mmol, 1 eq) in dichloromethane (700 mL) was added Dess-Martin reagent (76.70 g, 180.83 mmol, 1.38 eq). The mixture was stirred at 30° C. for 2 hours. Thin layer chromatography (dichloromethane:methanol=1:1) showed the reaction was completed. The reaction was adjusted to pH 8~9 with saturated sodium bicarbonate. The mixture was diluted with water (3 L) and extracted with dichloromethane (1.5 L×3). The combined organic phase was washed with saturated brine (1.5 L×2), dried with anhydrous sodium sulfate, filtered and concentrated in vacuum. The residue was purified by silica gel chromatography (dichloromethane:methanol=100:0 to 50:1) to give N-[3-(3-chloro-4-cyano-phenoxy)-2,2,4,4-tetramethyl-cyclobutyl]-4-(4-formyl-1-piperidyl)benzamide (34.6 g, 67.94 mmol, 51% yield, 97% purity) as a white solid.

$^1$H NMR: (400 MHz, DMSO-$d_6$) δ: 9.63 (s, 1H), 7.90 (d, J=8.8 Hz, 1H), 7.74 (d, J=8.8 Hz, 2H), 7.49 (d, J=9.2 Hz, 1H), 7.20 (d, J=2.4 Hz, 1H), 7.03-6.94 (m, 3H), 4.32 (s, 1H), 4.05 (d, J=9.2 Hz, 1H), 3.76 (td, J=3.6, 12.8 Hz, 2H), 3.01-2.92 (m, 2H), 2.62-2.55 (m, 1H), 2.62-2.55 (m, 1H), 1.92 (dd, J=3.6, 12.8 Hz, 2H), 1.62-1.48 (m, 2H), 1.21 (s, 6H), 1.12 (s, 6H).

Chemical Formula: $C_{28}H_{32}ClN_3O_3$, Molecular Weight: 494.02.

Total H count from HNMR data: 32.

General Synthetic Scheme C-4

Synthesis of Building Block N-((1r,3r)-3-(3-chloro-4-cyanophenoxy)-2,2,4,4-tetramethylcyclobutyl)-4-(4-(2-oxoethyl)piperidin-1-yl)benzamide

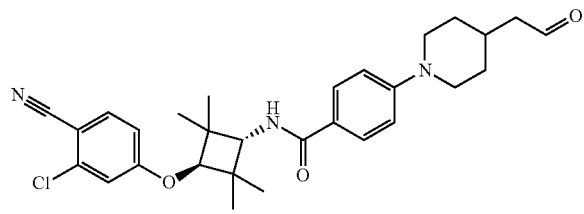 [SMILES: CC1(C)[C@H](NC(=O)c2ccc(N3CCC(CC=O)CC3)cc2)C(C)(C)[C@H]1Oc1ccc(C#N)c(Cl)c1]

Synthetic Scheme

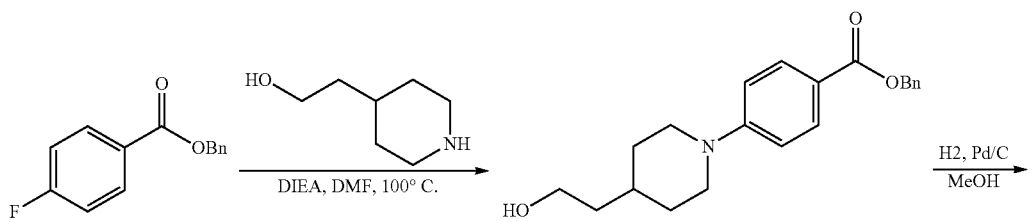

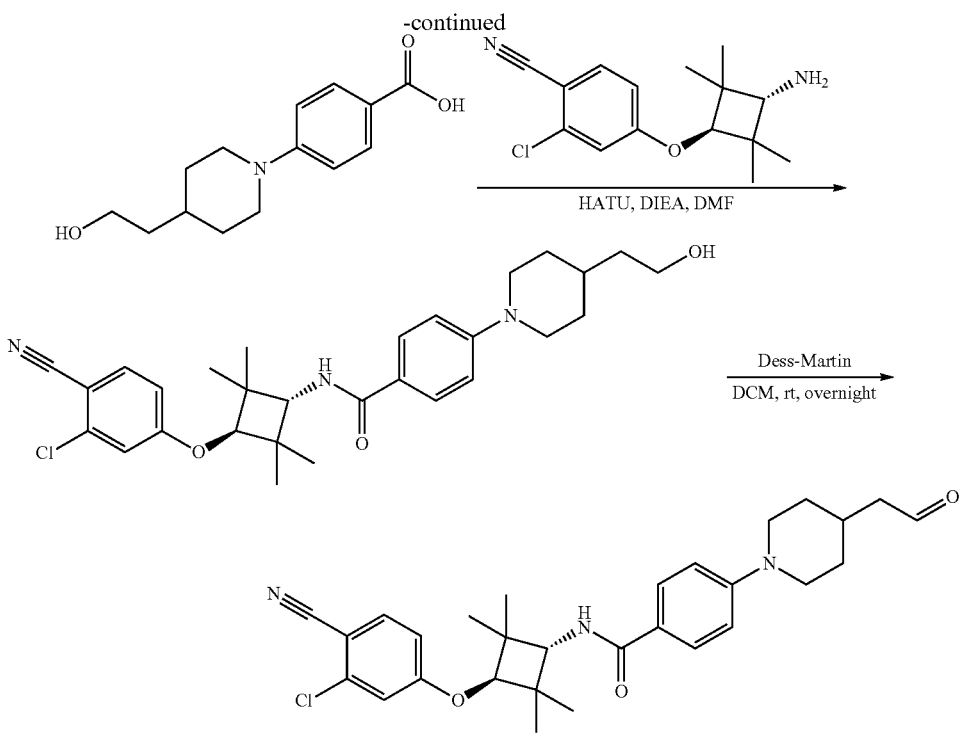

Step 1: Synthesis of benzyl 4-[4-(2-hydroxyethyl)piperidin-1-yl]benzoate

Step 2: Synthesis of 4-[4-(2-hydroxyethyl)piperidin-1-yl]benzoic acid

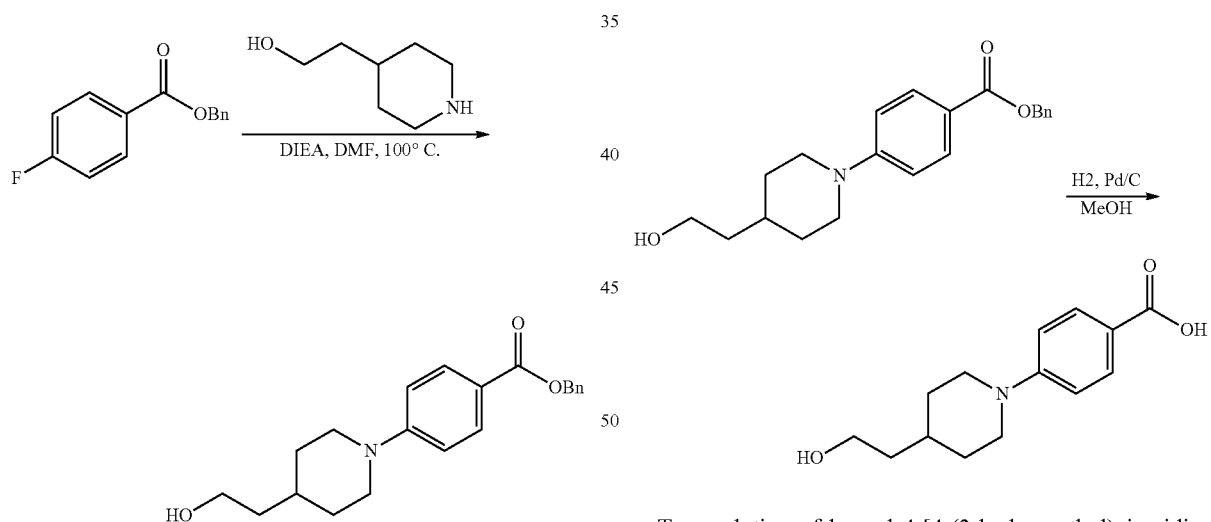

Into a 100-mL round-bottom flask, was placed benzyl 4-fluorobenzoate (2.3 g, 10.0 mmol, 1.0 equiv), N,N-dimethylformamide (30.0 mL), 2-(piperidin-4-yl)ethan-1-ol (1.3 g, 10.0 mmol, 1.0 equiv), N,N-Diisopropylethylamine (3.87 g, 29.9 mmol, 4.0 equiv). The resulting solution was stirred for 12 h at 90° C. The resulting mixture was concentrated under vacuum. The residue was applied onto a silica gel column with ethyl acetate/petroleum ether (1/1). This resulted in 2.1 g (62%) of benzyl 4-[4-(2-hydroxyethyl) piperidin-1-yl]benzoate as a yellow solid.

LC-MS (ES$^+$): 340.25 m/z [MH$^+$], $t_R$=1.20 min, (1.90 minute run).

To a solution of benzyl 4-[4-(2-hydroxyethyl)piperidin-1-yl]benzoate (500 mg, 1.47 mmol, 1.00 equiv) in 20.0 mL methyl alcohol (30.0 mL) was added Pd/C (10%, 300 mg) under nitrogen atmosphere in a 100.0 mL round bottom flask. The flask was then vacuumed and flushed with hydrogen. The reaction mixture was hydrogenated at room temperature for 12 hours under hydrogen atmosphere using a hydrogen balloon, then filtered through a Celite pad and concentrated under reduced pressure. This resulted in 300.0 mg (82.0%) of 4-[4-(2-hydroxyethyl)piperidin-1-yl]benzoic acid as a yellow solid.

LC-MS (ES$^+$): 250.00 m/z [MH$^+$], $t_R$=0.74 min, (2.00 minute run).

Step 3: Synthesis of 4-[4-(2-hydroxyethyl)piperidin-1-yl]-N-[(1r,3r)-3-(3-chloro-4-cyanophenoxy)-2,2,4,4-tetramethylcyclobutyl]benzamide

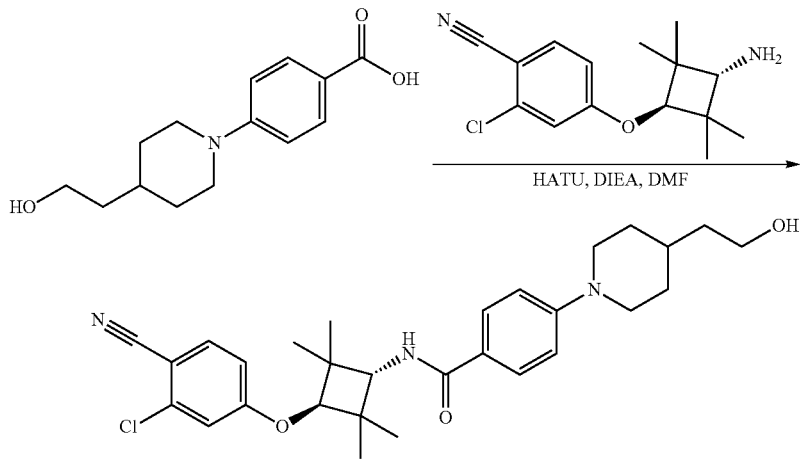

Into a 100-mL round-bottom flask, was placed 4-[4-(2-hydroxyethyl)piperidin-1-yl]benzoic acid (300.0 mg, 1.2 mmol, 2.0 equiv), N,N-dimethylformamide (10.0 g, 136.8 mmol, 227.0 equiv), N,N,N',N'-Tetramethyl-O-(7-azabenzotriazol-1-yl)uronium hexafluorophospate (686 mg, 1.8 mmol, 3.0 equiv), 2-chloro-4-[(1r,3r)-3-amino-2,2,4,4-tetramethylcyclobutoxy]benzonitrile hydrochloride (190.0 mg, 0.6 mmol, 1.0 equiv), N,N-Diisopropylethylamine (466.0 mg, 3.6 mmol, 6.0 equiv). The resulting solution was stirred for 1 h at room temperature. The reaction was then quenched by the addition of 60 mL of water. The resulting solution was extracted with 3×30 mL of ethyl acetate and the organic layers combined and dried over anhydrous sodium sulfate and concentrated under vacuum. The residue was applied onto a silica gel column with ethyl acetate/petroleum ether (1:1). This resulted in 250.0 mg (81%) of 4-[4-(2-hydroxyethyl)piperidin-1-yl]-N-[(1r,3r)-3-(3-chloro-4-cyanophenoxy)-2,2,4,4-tetramethylcyclobutyl]benzamide as a yellow solid.

LC-MS (ES$^+$): 510.25 m/z [MH$^+$], $t_R$=1.35 min, (1.90 minute run).

Step 4: Synthesis of 4-[4-(2-oxoethyl)piperidin-1-yl]-N-[(1r,3r)-3-(3-chloro-4-cyanophenoxy)-2,2,4,4-tetramethylcyclobutyl]benzamide

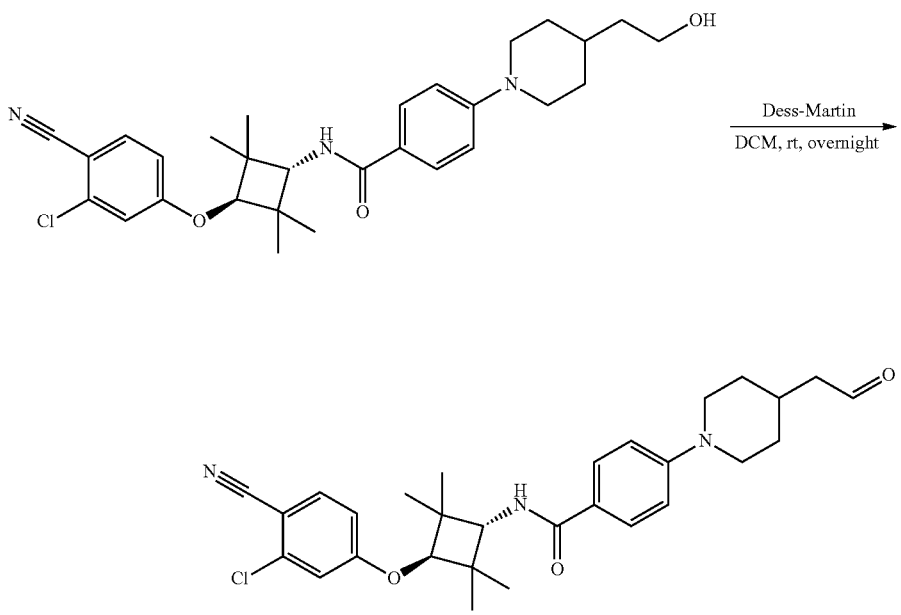

Into a 100-mL round-bottom flask, was placed 4-[4-(2-hydroxyethyl)piperidin-1-yl]-N-[(1r,3r)-3-(3-chloro-4-cyanophenoxy)-2,2,4,4-tetramethylcyclobutyl]benzamide (200.0 mg, 0.4 mmol, 1.0 equiv), dichloromethane (20.0 mL), Dess-Martin (249.0 mg, 0.60 mmol, 1.5 equiv). The resulting solution was stirred for 4 h at room temperature. The resulting solution was extracted with of ethyl acetate and the organic layers combined and concentrated under vacuum. The residue was applied onto a silica gel column with ethyl acetate/petroleum ether (1:1). This resulted in 80.0 mg (40%) of 4-[4-(2-oxoethyl)piperidin-1-yl]-N-[(1r,3r)-3-(3-chloro-4-cyanophenoxy)-2,2,4,4-tetramethylcyclobutyl]benzamide as a yellow solid.

LC-MS (ES$^+$): 508.20 m/z [MH$^+$], $t_R$=1.19 min, (2.00 minute run).

Exemplary Synthesis of Exemplary Compound 51

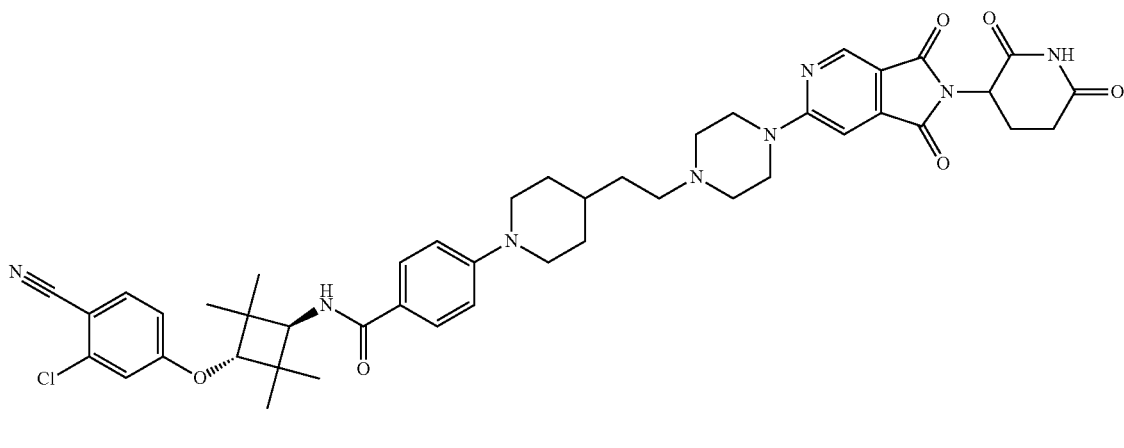 [SMILES: CC1(C)[C@H](NC(=O)c2ccc(N3CCC(CCN4CCN(c5cc6c(cn5)C(=O)N(C5CCC(=O)NC5=O)C6=O)CC4)CC3)cc2)C(C)(C)[C@H]1Oc1ccc(C#N)c(Cl)c1]

rac-N-((1r,3r)-3-(3-chloro-4-cyanophenoxy)-2,2,4,4-tetramethylcyclobutyl)-4-(4-(2-(4-(2-(2,6-dioxopiperidin-3-yl)-1,3-dioxo-2,3-dihydro-1H-pyrrolo[3,4-c]pyridin-6-yl)piperazin-1-yl)ethyl)piperidin-1-yl)benzamide Synthetic Scheme

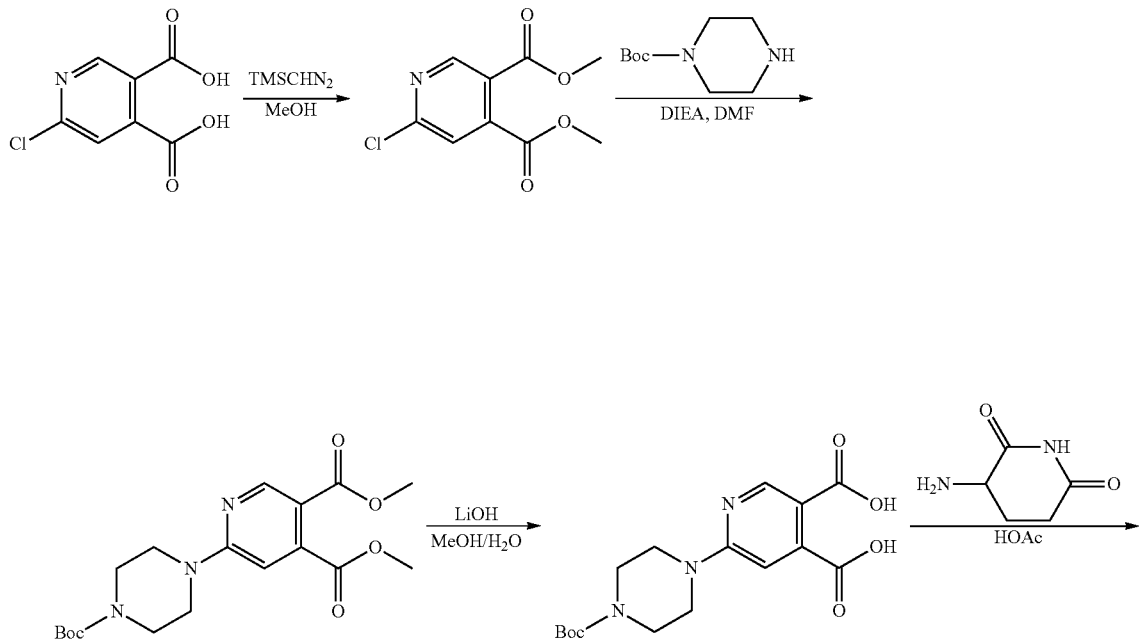

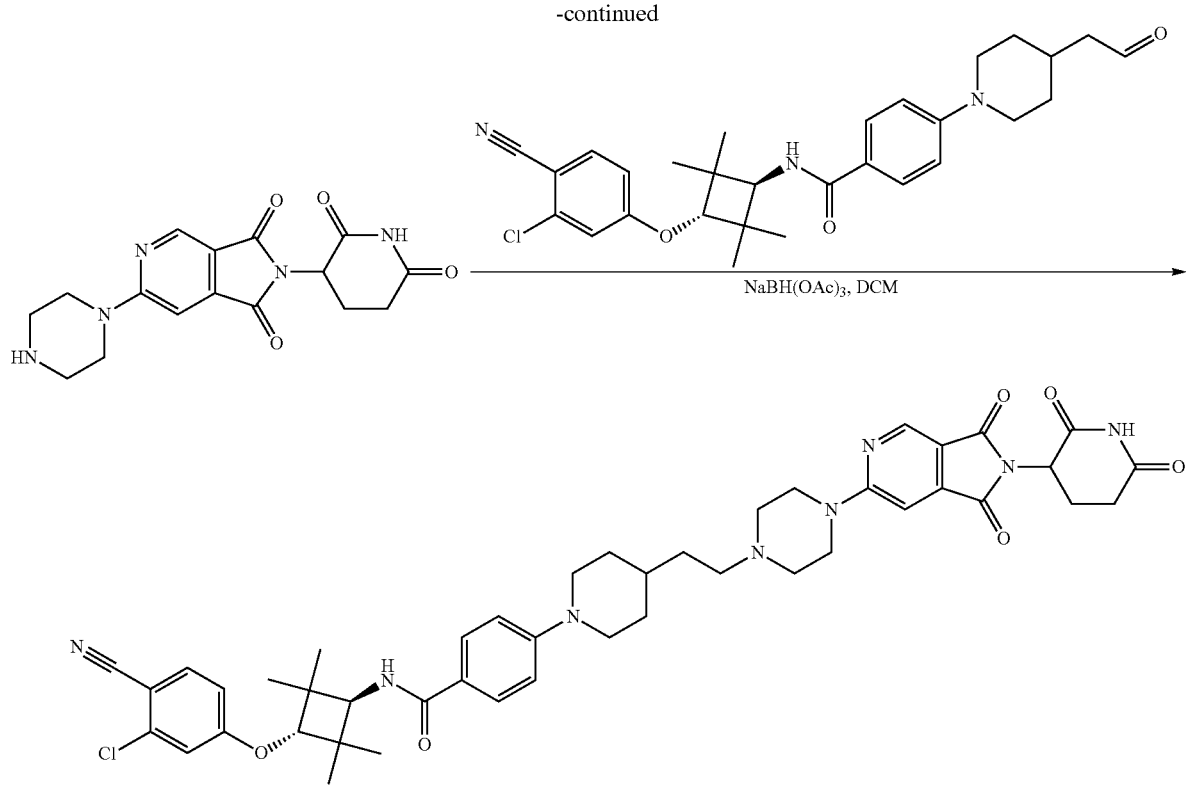

Step 1: Synthesis of 3,4-dimethyl 6-chloropyridine-3,4-dicarboxylate

LC-MS (ES⁺): 230.10 m/z [MH⁺], $t_R$=1.01 min, (1.90 minute run).

Step 2: Synthesis of 3,4-dimethyl 6-[4-[(tert-butoxy)carbonyl]piperazin-1-yl]pyridine-3,4-dicarboxylate

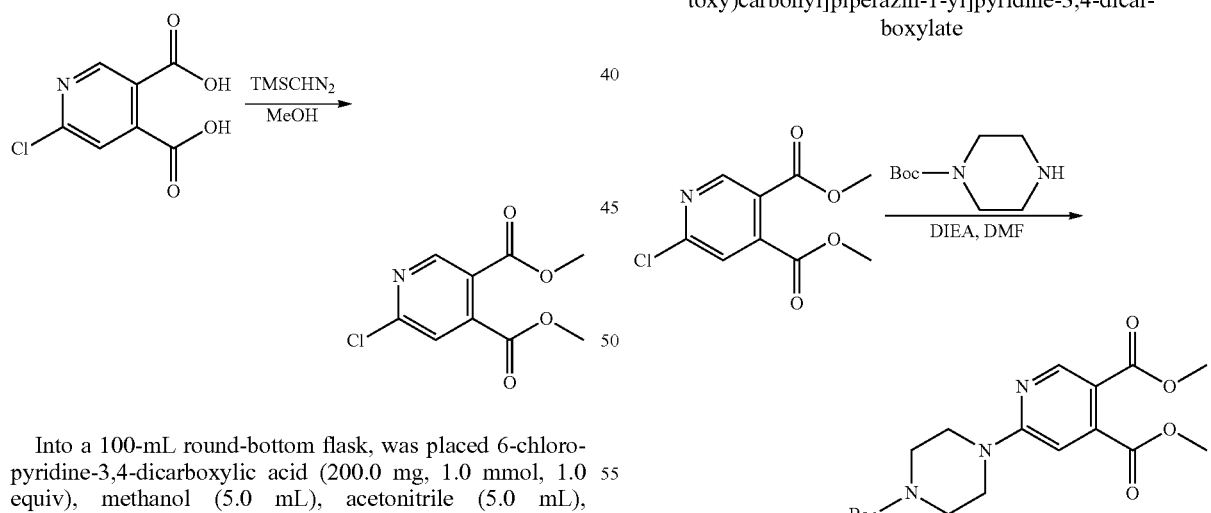

Into a 100-mL round-bottom flask, was placed 6-chloropyridine-3,4-dicarboxylic acid (200.0 mg, 1.0 mmol, 1.0 equiv), methanol (5.0 mL), acetonitrile (5.0 mL), TMSCHN2 (2.0 mL), N,N-Diisopropylethylamine (516.0 mg, 4.0 mmol, 4.0 equiv). The resulting solution was stirred for 2 h at room temperature. The reaction was then quenched by the addition of water (30 mL). The resulting solution was extracted with ethyl acetate (20.0 mL×3) and the organic layers combined and concentrated under vacuum. The residue was applied onto a silica gel column with ethyl acetate/petroleum ether (1:1). The resulting mixture was concentrated under vacuum. This resulted in 220 mg (96%) of 3,4-dimethyl 6-chloropyridine-3,4-dicarboxylate as a yellow solid.

Into a 100-mL round-bottom flask, was placed 3,4-dimethyl 6-chloropyridine-3,4-dicarboxylate (200.0 mg, 0.9 mmol, 1.0 equiv), N,N-dimethylformamide (5.0 mL), tert-butyl piperazine-1-carboxylate (325.0 mg, 1.7 mmol, 2.0 equiv), N,N-Diisopropylethylamine (450.0 mg, 3.5 mmol, 4.0 equiv). The resulting solution was stirred for 2 h at 100° C. The reaction was then quenched by the addition of water (80 mL). The resulting solution was extracted with ethyl acetate (30.0 mL×3) and the organic layers combined and concentrated under vacuum. The residue was applied onto a silica gel column with ethyl acetate/petroleum ether (1:3). This resulted in 320.0 mg (97%) of 3,4-dimethyl 6-[4-[(tert-butoxy)carbonyl]piperazin-1-yl]pyridine-3,4-dicarboxylate as a yellow solid.

LC-MS (ES+): 380.10 m/z [MH+], $t_R$=1.19 min, (2.0 minute run).

Step 3: Synthesis of 6-[4-[(tert-butoxy)carbonyl]piperazin-1-yl]pyridine-3,4-dicarboxylic acid

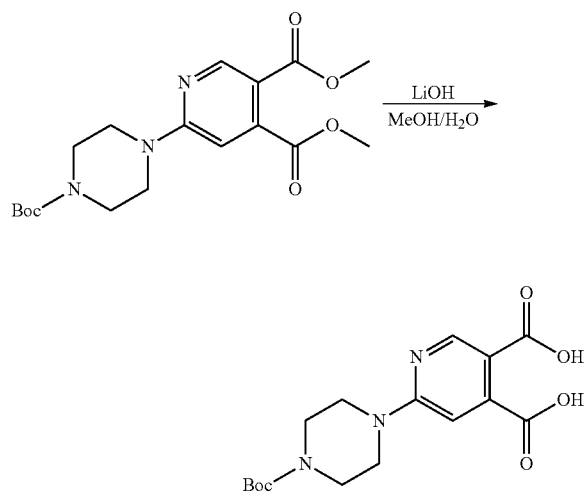

Into a 100-mL round-bottom flask, was placed 3,4-dimethyl 6-[4-[(tert-butoxy)carbonyl]piperazin-1-yl]pyridine-3,4-dicarboxylate (320.0 mg, 0.8 mmol, 1.0 equiv), methanol (10.0 mL), water (5 mL), lithium hydroxide (96 mg, 4 mmol, 5 equiv). The resulting solution was stirred for 5 h at room temperature. The resulting mixture was concentrated under vacuum. This resulted in 300.0 mg (101%) of 6-[4-[(tert-butoxy)carbonyl]piperazin-1-yl]pyridine-3,4-dicarboxylic acid as a white solid.

LC-MS (ES+): 296.20 m/z [MH+], $t_R$=0.52 min, (1.90 minute run).

Step 4: Synthesis of 3-[1,3-dioxo-6-(piperazin-1-yl)-1H,2H,3H-pyrrolo[3,4-c]pyridin-2-yl]piperidine-2,6-dione

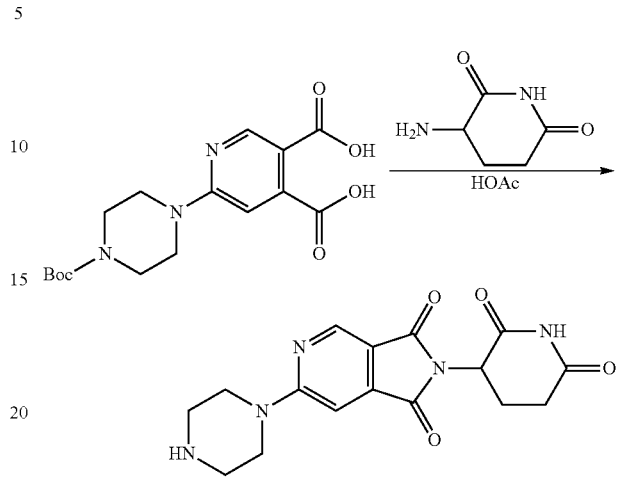

Into a 100-mL round-bottom flask, was placed 6-[4-[(tert-butoxy)carbonyl]piperazin-1-yl]pyridine-3,4-dicarboxylic acid (300.0 mg, 0.8 mmol, 1.0 equiv), acetic acid (20.0 mL), 3-aminopiperidine-2,6-dione (218 mg, 1.7 mmol, 2.0 equiv). The resulting solution was stirred for 2 h at 130° C. The reaction was then quenched by the addition of water (30 mL). The resulting solution was extracted with ethyl acetate (30 mL×3) and the organic layers combined and dried in an oven under reduced pressure, and concentrated under vacuum. The residue was applied onto a silica gel column with dichloromethane/methanol (3:1). This resulted in 60.0 mg (20%) of 3-[1,3-dioxo-6-(piperazin-1-yl)-1H,2H,3H-pyrrolo[3,4-c]pyridin-2-yl]piperidine-2,6-dione as a yellow solid.

LC-MS (ES+): 344.20 m/z [MH+], $t_R$=0.66 min, (1.90 minute run).

Step 5: Synthesis of 4-[4-(2-[4-[2-(2,6-dioxopiperidin-3-yl)-1,3-dioxo-1H,2H,3H-pyrrolo[3,4-c]pyridin-6-yl]piperazin-1-yl]ethyl)piperidin-1-yl]-N-[(1r,3r)-3-(3-chloro-4-cyanophenoxy)-Z,2,4,4-tetramethylcyclobutyl]benzamide

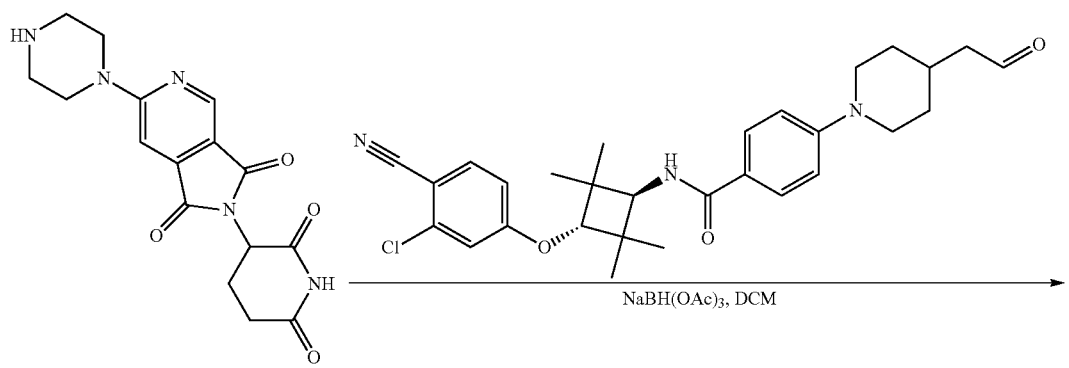

-continued

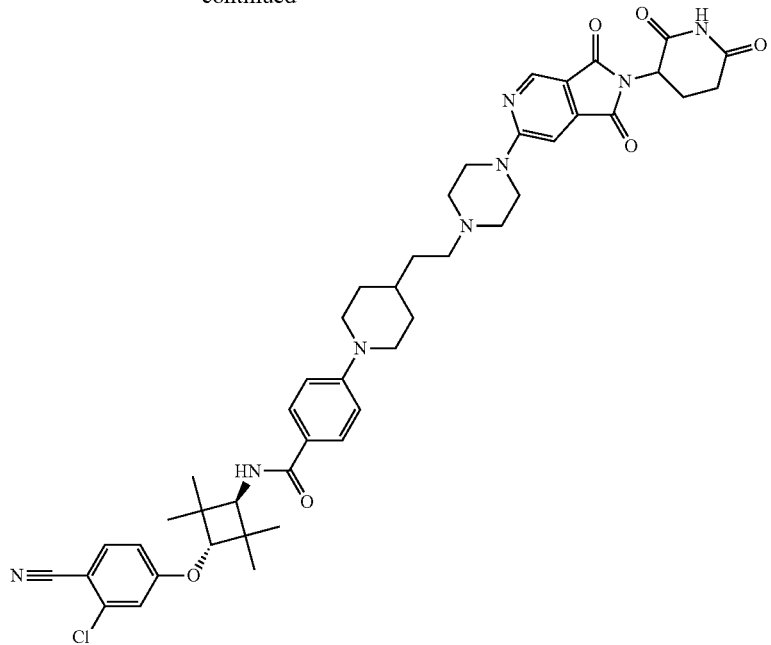

Into a 100-mL round-bottom flask, was placed 3-[1,3-dioxo-6-(piperazin-1-yl)-1H,2H,3H-pyrrolo[3,4-c]pyridin-2-yl]piperidine-2,6-dione hydrochloride (60.0 mg, 0.2 mmol, 1.0 equiv), dichloromethane (10 mL), 4-[4-(2-oxoethyl)piperidin-1-yl]-N-[(1r,3r)-3-(3-chloro-4-cyanophenoxy)-2,2,4,4-tetramethylcyclobutyl]benzamide (80.0 mg, 0.1 mmol, 1.0 equiv), Sodium triacetoxyborohydride (110.0 mg, 3.0 equiv). The resulting solution was stirred for 4 h at room temperature. The reaction was then quenched by the addition of 40 mL of water. The resulting solution was extracted with dichloromethane (20 mL×3) and the organic layers combined and concentrated under vacuum. The crude product (4.0 mL) was purified by Prep-HPLC with the following conditions: Column, Sunfire Prep C18 OBD Column, 10 um, 19*250 mm; mobile phase, Water (0.1% formic acid) and acetonitrile (30.0% acetonitrile up to 52.0% in 8 min); Detector, UV 254 nm. 5.0 mL product was obtained.

This resulted in 50.5 mg (38.2%) of 4-[4-(2-[4-[2-(2,6-dioxopiperidin-3-yl)-1,3-dioxo-1H,2H,3H-pyrrolo[3,4-c]pyridin-6-yl]piperazin-1-yl]ethyl)piperidin-1-yl]-N-[(1r,3r)-3-(3-chloro-4-cyanophenoxy)-2,2,4,4-tetramethylcyclobutyl]benzamide as a yellow solid.

1H NMR (300 MHz, DMSO-d6) δ 11.07 (s, 1H), 8.57 (s, 1H), 7.87 (d, J=8.7 Hz, 1H), 7.70 (d, J=8.6 Hz, 2H), 7.44 (d, J=9.1 Hz, 1H), 7.29 (s, 1H), 7.17 (d, J=2.2 Hz, 1H), 7.02-6.87 (m, 3H), 5.07 (dd, J=12.8, 5.3 Hz, 1H), 4.29 (s, 1H), 4.02 (d, J=9.1 Hz, 1H), 3.28 (s, 5H), 2.59-2.41 (m, 9H), 2.00 (t, J=11.3 Hz, 1H), 1.73 (d, J=12.8 Hz, 2H), 1.45 (s, 3H), 1.14 (d, J=27.2 Hz, 14H).

LC-MS (ES+): 835.25 m/z [MH+], $t_R$=2.56 min, (4.80 minute run).

Exemplary Synthesis of Exemplary Compound 52

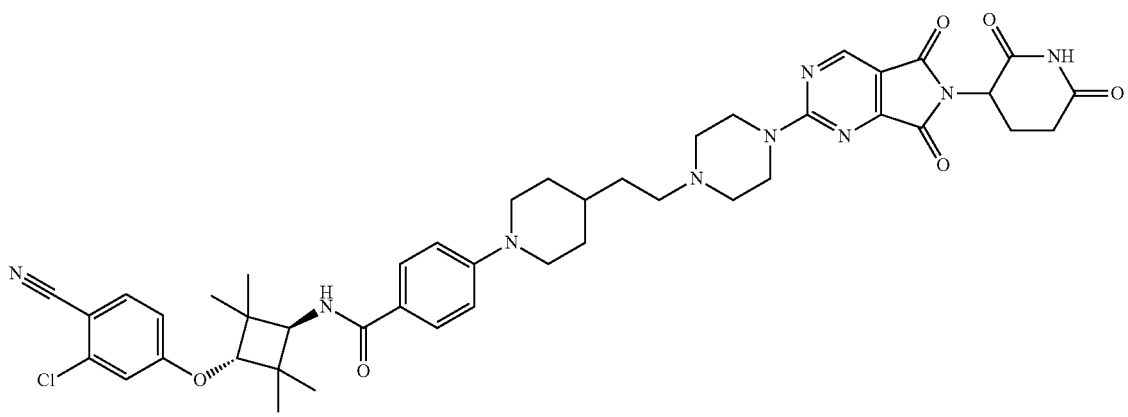 [SMILES: CC1(C)[C@H](NC(=O)c2ccc(N3CCC(CCN4CCN(c5ncc6c(n5)C(=O)N(C5CCC(=O)NC5=O)C6=O)CC4)CC3)cc2)C(C)(C)[C@H]1Oc1ccc(C#N)c(Cl)c1]

(rac)-N-((1r,3r)-3-(3-chloro-4-cyanophenoxy)-2,2,4,4-tetramethylcyclobutyl)-4-(4-(2-(4-(6-(2,6-dioxopiperidin-3-yl)-5,7-dioxo-6,7-dihydro-5H-pyrrolo[3,4-d]pyrimidin-2-yl)piperazin-1-yl)ethyl)piperidin-1-yl)benzamide
Synthetic Scheme
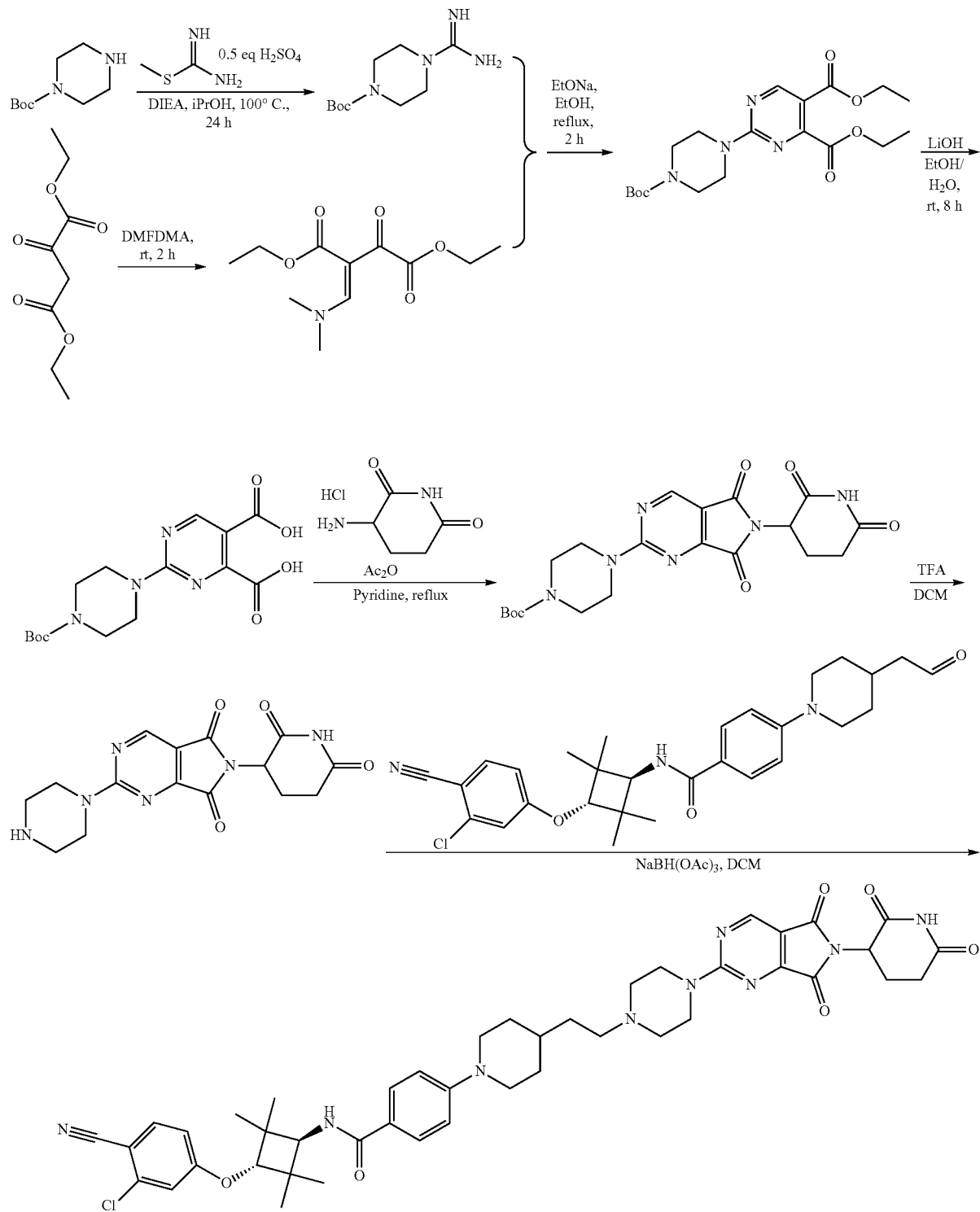

Step 1: Synthesis of tert-butyl 4-carbamimidoylpiperazine-1-carboxylate

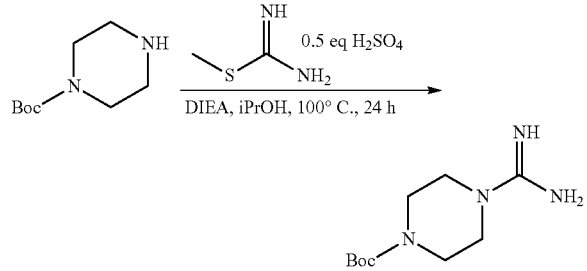

Into a 250-mL round-bottom flask, was placed tert-butyl piperazine-1-carboxylate (10 g, 53.69 mmol, 1.00 equiv), i-propanol (150 mL), (methylsulfanyl)methanimidamide (7.4 g, 82.09 mmol, 1.00 equiv), DIEA (25 mL, 3.00 equiv). The resulting solution was stirred for 24 h at 100° C. in an oil bath. The resulting mixture was concentrated under vacuum. The resulting solution was diluted with acetonitrile (150 mL), then stirred for 30 min. The solids were collected by filtration. This resulted in 11.5 g (94%) of tert-butyl 4-carbamimidoylpiperazine-1-carboxylate as a white solid.

Step 2: Synthesis of 1,4-diethyl (2Z)-2-[(dimethylamino)methylidene]-3-oxobutanedioate

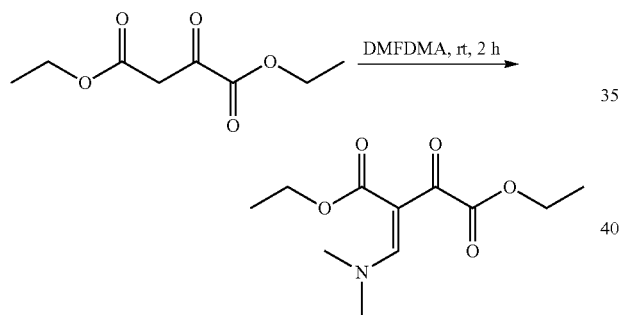

Into a 250-mL round-bottom flask, was placed 1,4-diethyl 2-oxobutanedioate (10 g, 53.14 mmol, 1.00 equiv), DMFDMA (12.65 g, 106.30 mmol, 2.00 equiv) at 0° C. The resulting solution was stirred for 2 h at room temperature. The residue was applied onto a silica gel column with ethyl acetate/petroleum ether (7/3). This resulted in 2.79 g (22%) of 1,4-diethyl (2Z)-2-[(dimethylamino)methylidene]-3-oxobutanedioate as yellow oil.

LC-MS (ES$^+$): m/z 243.95 [MH+], $t_R$=0.64 min, (1.90 minute run).

Step 3: Synthesis of 4,5-diethyl 2-[4-[(tert-butoxy)carbonyl]piperazin-1-yl]pyrimidine-4,5-dicarboxylate

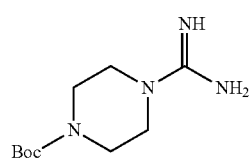

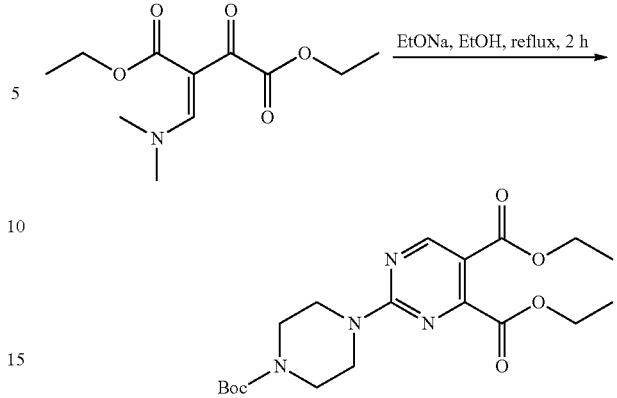

Into a 250-mL round-bottom flask, was placed tert-butyl 4-carbamimidoylpiperazine-1-carboxylate (1.0 g, 4.38 mmol, 1.00 equiv), ethanol (20 mL), 1,4-diethyl (2Z)-2-[(dimethylamino)methylidene]-3-oxobutanedioate (1.065 g, 4.38 mmol, 1.00 equiv), EtONa (596 mg, 8.76 mmol, 1.00 equiv). The resulting solution was stirred for 2 h at 75° C. in an oil bath. The resulting mixture was concentrated under vacuum. The resulting solution was extracted with ethyl acetate (100 mL) and the organic layers combined. The resulting mixture was washed with brine (100 mL). The mixture was dried over anhydrous sodium sulfate. The residue was applied onto a silica gel column with ethyl acetate/petroleum ether (1/5). This resulted in 873.0 mg (49%) of 4,5-diethyl 2-[4-[(tert-butoxy)carbonyl]piperazin-1-yl]pyrimidine-4,5-dicarboxylate as light yellow oil.

LC-MS (ES$^+$): m/z 409.20 [MH$^+$], $t_R$=1.19 min, (1.90 minute run).

Step 4: Synthesis of 2-[4-[(tert-butoxy)carbonyl]piperazin-1-yl]pyrimidine-4,5-dicarboxylic acid

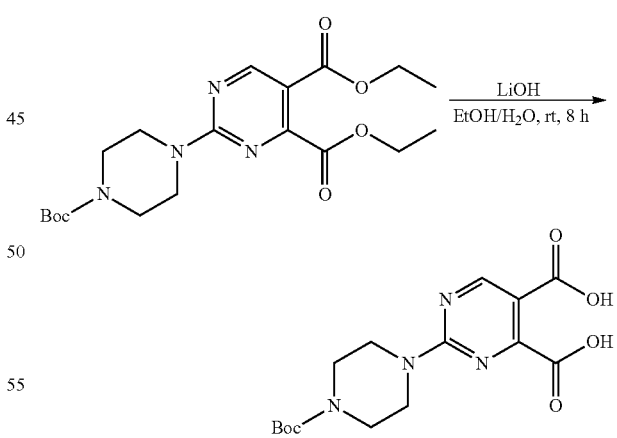

Into a 100-mL round-bottom flask, was placed 4,5-diethyl 2-[4-[(tert-butoxy)carbonyl]piperazin-1-yl]pyrimidine-4,5-dicarboxylate (873.0 mg, 2.14 mmol, 1.00 equiv), ethanol/water (5/2) (14 mL), lithium hydroxide (256.7 mg, 10.72 mmol, 5.00 equiv). The resulting solution was stirred for 8 h at room temperature. The resulting mixture was concentrated under vacuum. This resulted in 1.02 g (crude) of 2-[4-[(tert-butoxy)carbonyl]piperazin-1-yl]pyrimidine-4,5-dicarboxylic acid as a white solid.

LC-MS (ES+): m/z 352.45 [MH+], $t_R$=0.73 min, (1.90 minute run).

Step 5: Synthesis of tert-butyl 4-[6-(2,6-dioxopiperidin-3-yl)-5,7-dioxo-5H,6H,7H-pyrrolo[3,4-d]pyrimidin-2-yl]piperazine-1-carboxylate

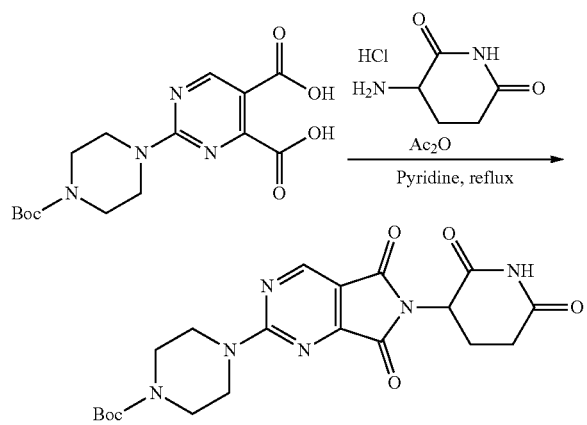

Into a 100-mL round-bottom flask, was placed 2-[4-[(tert-butoxy)carbonyl]piperazin-1-yl]pyrimidine-4,5-dicarboxylic acid (735.0 mg, 2.09 mmol, 1.00 equiv). This was followed by the addition of acetic anhydride (10 mL), after stirred 2 h at 130° C., concentrated under vacuum. To this was added pyridine (10 mL), 3-aminopiperidine-2,6-dione hydrochloride (445.0 mg, 2.70 mmol, 1.30 equiv). The resulting solution was stirred overnight at 120° C. in an oil bath. The resulting mixture was concentrated under vacuum. The resulting solution was diluted with dichloromethane (100 mL). The solids were filtered out. The residue was applied onto a silica gel column with ethyl acetate/petroleum ether (7/3). This resulted in 243.0 mg (26%) of tert-butyl 4-[6-(2,6-dioxopiperidin-3-yl)-5,7-dioxo-5H,6H,7H-pyrrolo[3,4-d]pyrimidin-2-yl]piperazine-1-carboxylate as brown oil.

LC-MS (ES+): m/z 467.10 [M Na+], $t_R$=1.10 min, (2.00 minute run).

Step 6: Synthesis of 3-[5,7-dioxo-2-(piperazin-1-yl)-5H,6H,7H-pyrrolo[3,4-d]pyrimidin-6-yl]piperidine-2,6-dione

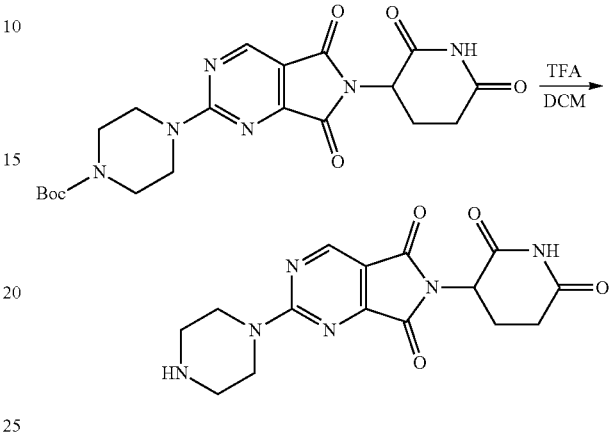

Into a 50-mL round-bottom flask, was placed tert-butyl 4-[6-(2,6-dioxopiperidin-3-yl)-5,7-dioxo-5H,6H,7H-pyrrolo[3,4-d]pyrimidin-2-yl]piperazine-1-carboxylate (243.0 mg, 0.55 mmol, 1.00 equiv), dichloromethane (5.0 mL), trifluoroacetic acid (2.0 mL). The resulting solution was stirred for 2 h at room temperature. The resulting mixture was concentrated under vacuum. This resulted in 320.0 mg (crude) of 3-[5,7-dioxo-2-(piperazin-1-yl)-5H,6H,7H-pyrrolo[3,4-d]pyrimidin-6-yl]piperidine-2,6-dione as brown oil.

LC-MS (ES+): m/z 345.25 [MH+], $t_R$=0.61 min, (1.90 minute run).

Step 7: Synthesis of 4-[4-(2-[4-[6-(2,6-dioxopiperidin-3-yl)-5,7-dioxo-5H,6H,7H-pyrrolo[3,4-d]pyrimidin-2-yl]piperazin-1-yl]ethyl)piperidin-1-yl]-N-[(1r,3r)-3-(3-chloro-4-cyanophenoxy)-2,2,4,4-tetramethylcyclobutyl]benzamide

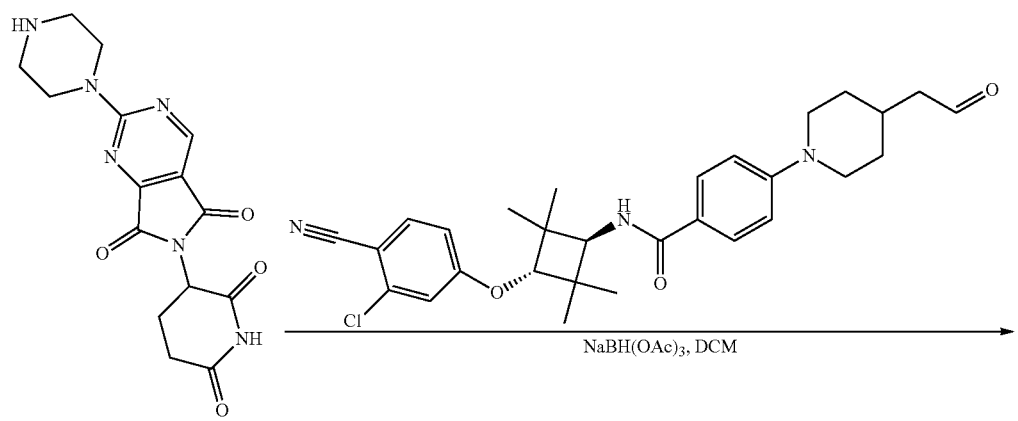

-continued

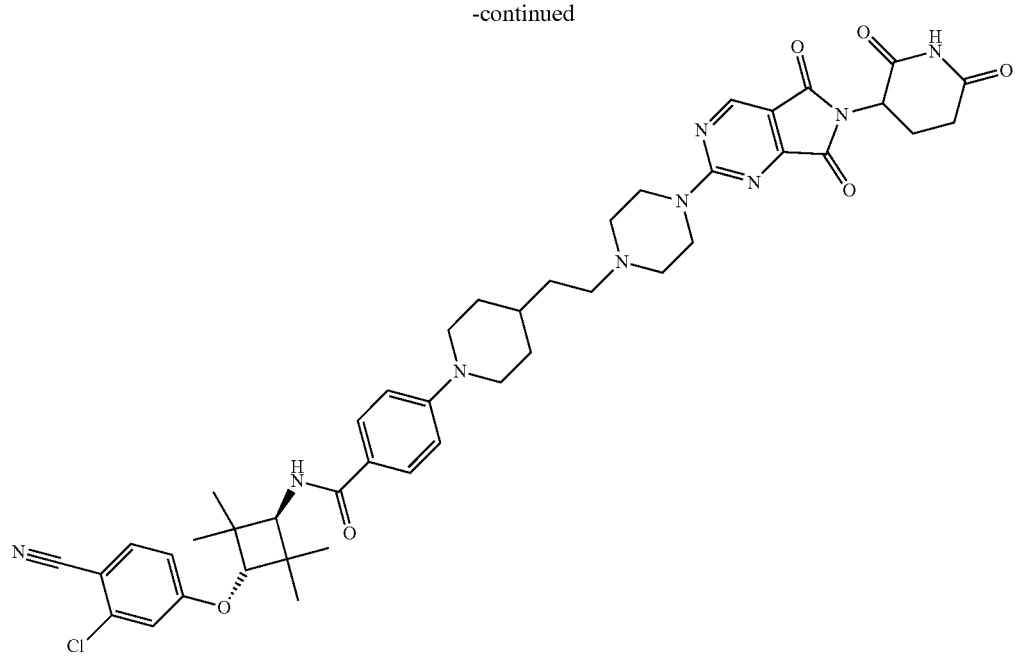

Into a 100-mL round-bottom flask, was placed 4-[4-(2-oxoethyl)piperidin-1-yl]-N-[(1r,3r)-3-(3-chloro-4-cyanophenoxy)-2,2,4,4-tetramethylcyclobutyl]benzamide (90 mg, 0.18 mmol, 1.00 equiv), dichloromethane (10 mL), 3-[5,7-dioxo-2-(piperazin-1-yl)-5H,6H,7H-pyrrolo[3,4-d]pyrimidin-6-yl]piperidine-2,6-dione (61.24 mg, 0.18 mmol, 1.00 equiv). This was followed by the addition of DIEA (0.5 mL), after stirred at 30° C. for 1 h. To this was added NaBH(OAc)$_3$ (122.89 mg, 0.58 mmol, 3.00 equiv). The resulting solution was stirred for 5 h at 30° C. in an oil bath. The resulting solution was extracted with dichloromethane (150 mL) and the organic layers combined. The resulting mixture was washed with brine (50 mL). The mixture was dried over anhydrous sodium sulfate and concentrated under vacuum. The crude product was purified by Prep-HPLC with the following conditions: Column, XBridge Prep C18 OBD Column, 5 um, 19*150 mm: mobile phase, water (10 mmol/L bicarbonate amine) and acetonitrile (30.0% acetonitrile up to 51.0% in 8 min); Detector, UV 254 nm. This resulted in 50 mg (34%) of 4-[4-(2-[4-[6-(2,6-dioxopiperidin-3-yl)-5,7-dioxo-5H,6H,7H-pyrrolo[3,4-d]pyrimidin-2-yl]piperazin-1-yl]ethyl)piperidin-1-yl]-N-[(1r,3r)-3-(3-chloro-4-cyanophenoxy)-2,2,4,4-tetramethylcyclobutyl]benzamide as a yellow solid.

$^1$H NMR (400 MHz, d6-DMSO): δ11.12 (s, 1H), 8.90 (s, 1H), 7.91-7.89 (d, J=8.4 Hz, 1H), 7.74-7.72 (d, J=7.6 Hz, 2H), 7.49-7.47 (d, J=8.8 Hz, 1H), 7.20 (s, 1H), 6.99-6.94 (m, 3H), 5.16-5.13 (m, 1H), 4.32 (s, 1H), 4.06-3.83 (m, 7H), 2.88-2.57 (m, 5H), 2.39-2.33 (m, 2H), 2.07-2.01 (m, 1H), 1.78-1.75 (m, 2H), 1.54-1.35 (m, 3H), 1.21 (m, 8H), 1.12 (s, 6H); LC-MS (ES$^+$): m/z 836.45/838.45 [MH$^+$], t$_R$=2.17 min, (2.95 minute run).

Chemical formula: $C_{44}H_{50}ClN_9O_6$ [835.36/837.36].

Total H count from HNMR data: 50.

D. Exemplary Synthetic Schemes for Exemplary BRaf Targeting Moiety Based Compounds General Synthetic Approach The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/ILMs/VLMs/CLMs/LLMs.

With PTMs and ULMs (e.g. ILMs, VLMs, CLMs, and/or ILMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

General Synthetic Scheme D-1

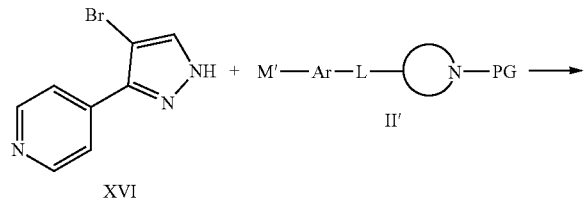

XVI

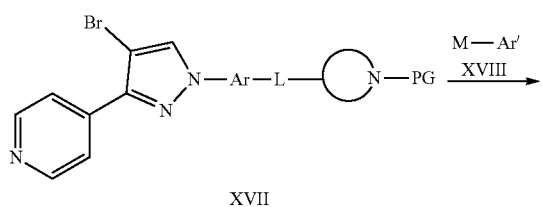

XVII

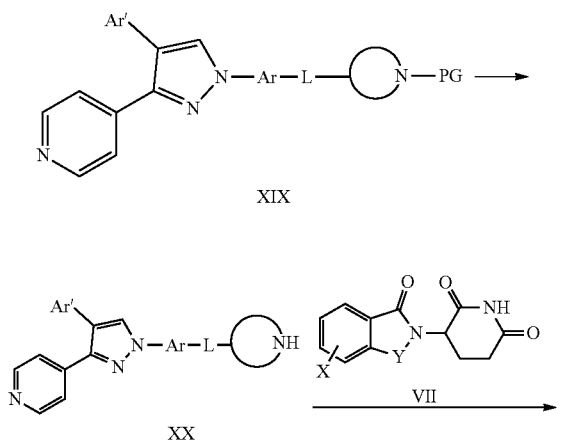

XIX

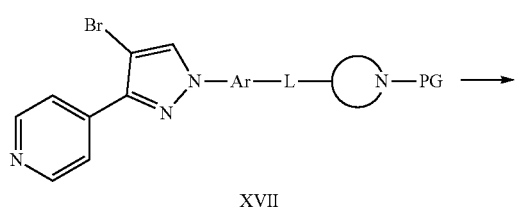

XX

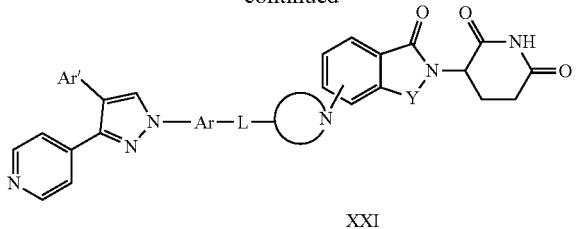

XXI

A compound of formula XVI may be reacted with a reagent II' (commercially available or readily prepared using standard reaction techniques known to one skilled in the art) under Chan-Lam cross-coupling conditions, e.g. copper (II) acetate, pyridine or diethylamine or triethylamine, 100° C., to produce a compound of formula XVII. M' represents a boronic acid or boronic ester; Ar represents an aromatic or heteroaromatic ring system; L represents an optional linker, represents a primary or secondary amine, optionally cyclized into a 4 to 8 membered heterocyclic ring, wherein PG represents a suitable protecting group, including but not limited to t-butoxycarbonyl or benzyl. Compounds of formula XVII may be may be reacted with a reagent XVIII under palladium-catalyzed cross-coupling conditions, e.g. [1,1'-bis(diphenylphosphino)ferrocene]dichloropalladium, tri-tert-butylphosphine tetrafluoroborate, cesium fluoride, 1,4-dioxane, 90° C., to produce a compound of formula XIX. M represents a functional group capable of undergoing palladium-catalyzed transmetallation, e.g. a boronic acid, boronic ester, or trialkylstannane and Ar' represents an aromatic or heteroaromatic ring system with optional substituents. A compound of formula XIX may then be converted to a compound of formula XX by treatment with a reagent suitable for the removal of PG, e.g. hydrogen chloride in 1,4-dioxane or methanol when PG is t-butyl. A compound of formula XX may also be reacted with a compound of formula VII to provide compounds of formula XXI, wherein X is a suitable leaving group such as fluorine or chlorine, Y is C=O, the aromatic ring of VII may have further optional substituents, and reaction conditions are those for a nucleophilic aromatic substitution, e.g. triethylamine, DMSO, 80° C. In cases where the group Ar' contains optional substituents, e.g. a ketone, these may undergo further functionalization, e.g. by treatment with hydroxylamine hydrochloride and pyridine at room temperature, to provide further compounds of formula XXI.

General Synthetic Scheme D-2

XVII

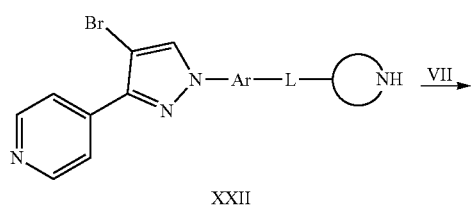

XXII

-continued

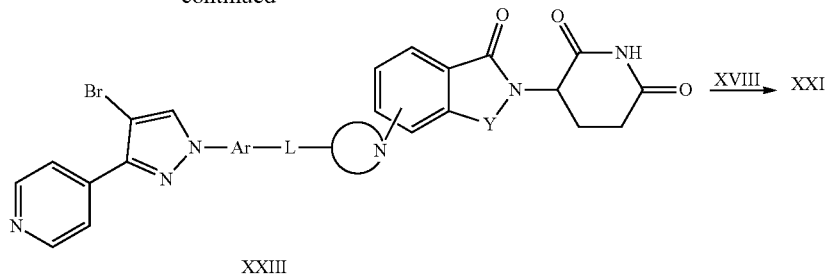

XXIII

Alternatively, a compound of formula XVII may be converted to a compound of formula XXII by using conditions analogous to those for the conversion of XIX to XX in Scheme 5. A compound of formula XXII may then be treated with a compound of formula VII as defined in Scheme 5 to produce a compound of formula XXIII. The compound of formula XXIII may then be treated with a reagent XVIII as defined in Scheme 5 to produce a compound of formula XXI. In cases where the group Ar' contains optional substituents, e.g. a ketone, these may undergo further functionalization, e.g. by treatment with hydroxylamine hydrochloride and pyridine at room temperature, to provide further compounds of formula XXI.

Exemplary Synthesis of Exemplary Compound 42

(E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenyl)piperazin-1-yl)-4-methylisoindoline-1,3-dione

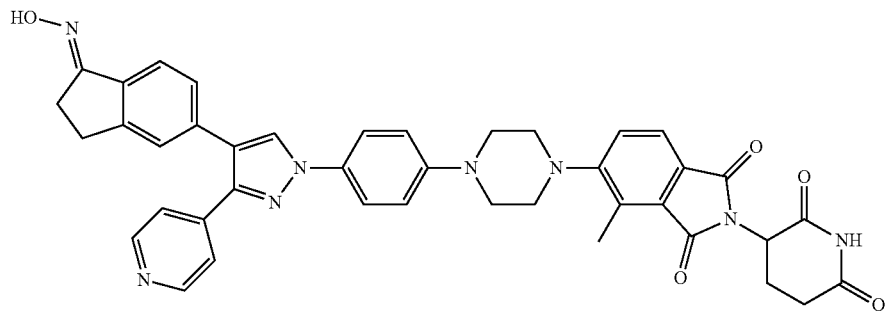 [SMILES: Cc1c(N2CCN(c3ccc(-n4cc(-c5ccc6c(c5)CC/C6=N\O)c(-c5ccncc5)n4)cc3)CC2)ccc2c1C(=O)N(C1CCC(=O)NC1=O)C2=O]

Step A: 2-(2,6-dioxopiperidin-3-yl)-4-methyl-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione

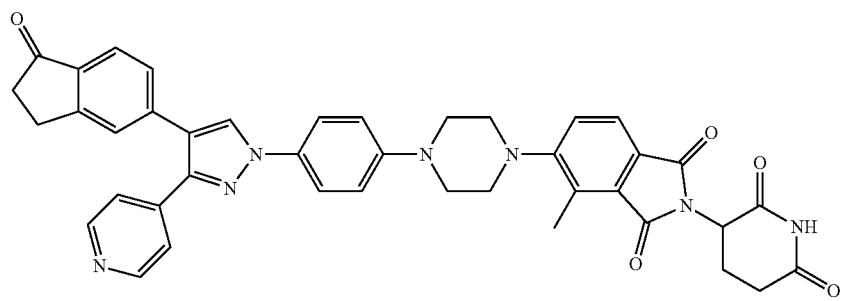 [SMILES: Cc1c(N2CCN(c3ccc(-n4cc(-c5ccc6c(c5)CCC6=O)c(-c5ccncc5)n4)cc3)CC2)ccc2c1C(=O)N(C1CCC(=O)NC1=O)C2=O]

To a solution of 4-chloro-2-(2,6-dioxopiperidin-3-yl)-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione (100 mg, 0.14 mmol) in 1,4-dioxane 10 mL and H2O 1 mL were added methylboronic acid (33.6 mg, 0.56 mmol), Pd(aMPhos)Cl$_2$ (9.9 mg, 0.014 mmol), and CsF (85.12 mg, 0.56 mmol). The resulting solution was irradiated at 90° C. with MW for 2 h. After cooling to rt, it was diluted with EA (50 mL), and the mixture was washed with brine (3×20 mL). The organic phase was dried over Na$_2$SO$_4$, filtered and concentrated under reduced pressure. The residue was purified by prep-TLC to afford 2-(2,6-dioxopiperidin-3-yl)-4-methyl-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione (70 mg, 72.1% yield). LCMS (ES$^+$): m/z 706.3 [M+H]$^+$.

Step B: (E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenyl)piperazin-1-yl)-4-methylisoindoline-1,3-dione

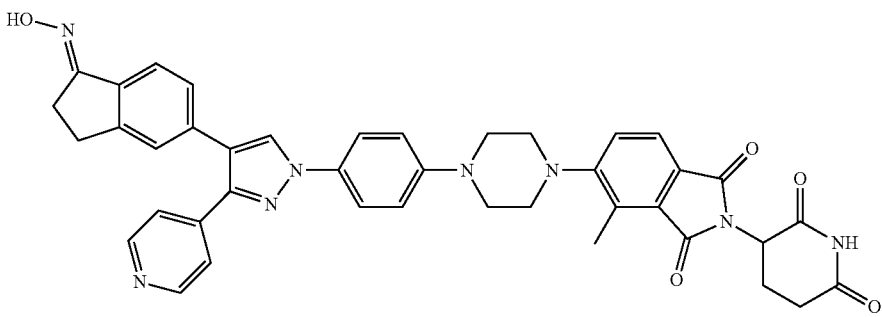 [SMILES: Cc1c(N2CCN(c3ccc(-n4cc(-c5ccc6c(c5)CC/C6=N\O)c(-c5ccncc5)n4)cc3)CC2)ccc2c1C(=O)N(C1CCC(=O)NC1=O)C2=O]

To a solution of 2-(2,6-dioxopiperidin-3-yl)-4-methyl-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione (70 mg, 0.10 mmol) in acetonitrile 3 mL and pyridine 3 mL was added hydroxylamine hydrochloride (69.5 mg, 1.0 mmol). The mixture was stirred at 40° C. for 20 min. Then it was diluted with DCM (20 mL), and the mixture was washed with brine (10 mL). The organic phase was concentrated and purified by prep-TLC to afford (E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenyl)piperazin-1-yl)-4-methylisoindoline-1,3-dione (19.6 mg, 27.8% yield) as yellow solid.

$^1$H NMR (400 MHz, DMSO-d$_6$): δ 11.09 (s, 1H), 10.89 (s, 1H), 8.72 (s, 1H), 8.58-8.57 (m, 2H), 7.83 (d, J=8.0 Hz, 2H), 7.73 (d, J=7.6 Hz, 1H), 7.56 (d, J=7.6 Hz, 1H), 7.50-7.41 (m, 4H), 7.23-7.17 (m, 3H), 5.13-5.09 (m, 1H), 3.61-3.42 (m, 8H), 3.04-2.97 (m, 2H), 2.93-2.82 (m, 3H), 2.62-2.56 (m, 5H), 2.08-2.00 (m, 1H); LCMS (ES$^+$): m/z 721.3 [M+H]$^+$.

Exemplary Compound 41 may be prepared by a procedure analogous to that described for Exemplary Compound 42.

E. Exemplary Synthetic Schemes for Exemplary BRD4 Binding Moiety Based Compounds Exemplar Synthesis of Exemplary Compound 45: 2-((S)-4-(4-chlorophenyl)-2,3,9-trimethyl-6H-thieno[3,2-f][1,2,4]triazolo[4,3-a][1,4]diazepin-6-yl)-N-(4-(2-(2-(2-(2-((3-(2,6-dioxopiperidin-3-yl)-2-methyl-4-oxo-3,4-dihydroquinazolin-7-yl)oxy)ethoxy)ethoxy)ethoxy)ethoxy)phenyl)acetamide

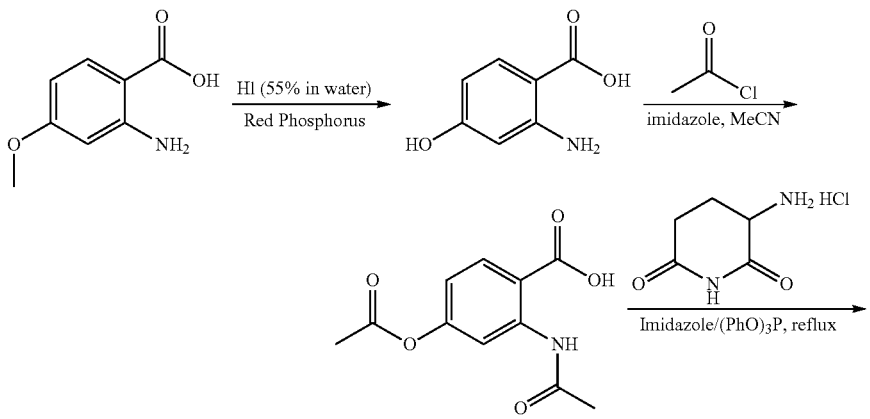

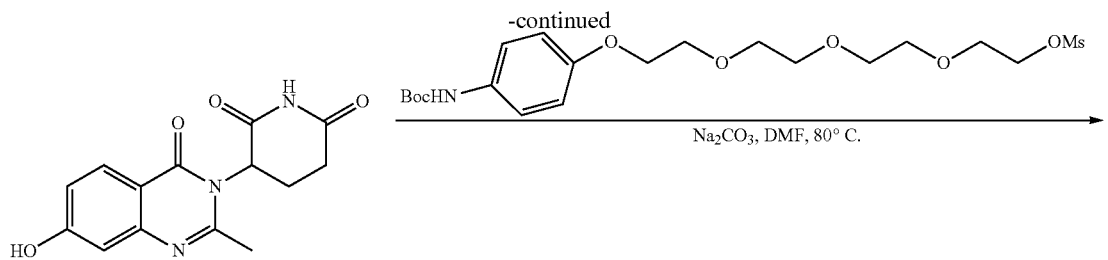

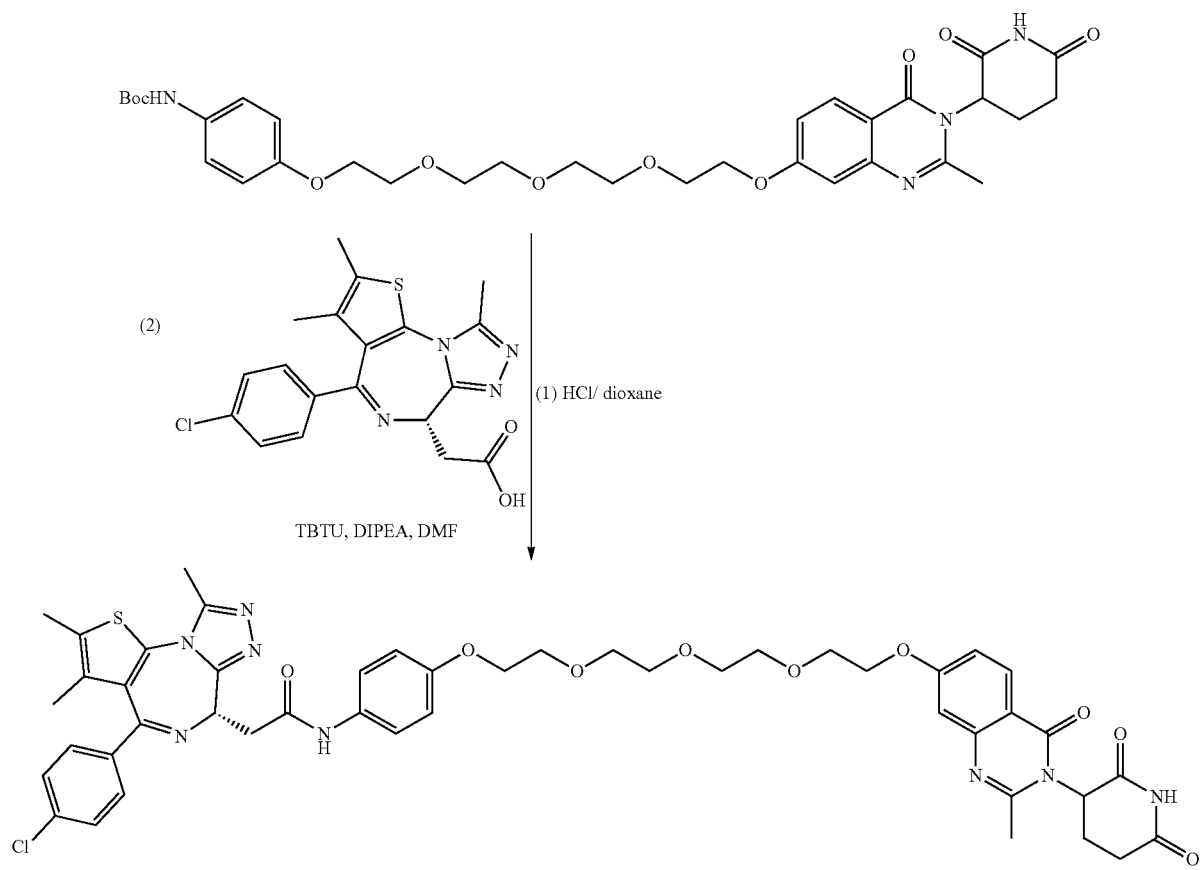

Step 1: Preparation of 2-amino-4-hydroxybenzoic acid

A mixture of 2-amino-4-methoxybenzoic acid (1.0 g, 5.98 mmol), red phosphorus (556 mg, 17.94 mmol) and 55% hydroiodic acid (10 mL) was heated at 100° C. for 14 h in a sealed tube. The reaction mixture was poured into ice water. The pH of the solution was adjusted to 6-7 by sodium carbonate. The solution was extracted with ethyl acetate (20 mL×3). The combined organic phases were dried over anhydrous sodium sulfate, filtered and concentrated in vacuum to afford crude 2-amino-4-hydroxybenzoic acid (400 mg, 44% yield) which was used in the next step without further purification. $^1$HNMR (400 MHz, DMSO-$d_6$): δ 7.53-7.55 (m, 1H), 6.12 (s, 1H), 5.99-6.02 (m, 1H).

Step 2: Preparation of 2-acetamido-4-acetoxybenzoic acid

To a mixture of 2-amino-4-hydroxybenzoic acid (400 mg, 2.61 mmol) and imidazole (888 mg, 10.06 mmol) in acetonitrile (20 mL) was added acetyl chloride (789 mg, 10.06 mmol) dropwise at 0° C. The solution was stirred at rt for 10 h and then quenched by water (40 mL). The mixture was extracted with ethyl acetate (20 mL×3). The combined organic layers were washed with brine, dried over anhydrous sodium sulfate and filtered. Volatiles were evaporated in vacuum and the residue was purified by column chromatography (ethyl acetate/petroleum ether=2:1) to afford 2-acetamido-4-acetoxybenzoic acid (350 mg, 57% yield). $^1$HNMR (400 MHz, DMSO-$d_6$): δ 11.19 (s, 1H), 8.30 (s, 1H), 8.01-8.03 (m, 1H), 6.92-6.95 (m, 1H), 2.30 (s, 3H), 2.15 (s, 3H).

Step 3: Preparation of 3-(7-hydroxy-2-methyl-4-oxoquinazolin-3(4H)-yl)piperidine-2,6-dione To a mixture of 2-acetamido-4-acetoxybenzoic acid (400 mg, 1.69 mmol), 3-aminopiperidine-2,6-dione hydrochloride (333 mg, 2.02 mmol), triphenyl phosphite (2.0 mL) in acetonitrile (10 mL) was added imidazole (383 mg, 5.63 mmol). The reaction solution was heated to reflux for 10 h. The solution was evaporated under reduced pressure and the residue was re-crystallized (20% ethyl acetate in hexane) to afford 3-(7-Hydroxy-2-methyl-4-oxoquinazolin-3(4H)-yl)piperidine-2,6-dione (110 mg, 19% yield). $^1$HNMR (400 MHz, DMSO-d$^6$): δ 10.94 (s, 1H), 10.51 (s, 1H), 7.84-7.86 (m, 1H), 6.92-6.94 (m, 1H), 6.85 (s, 1H), 5.16-5.20 (m, 1H), 2.73-2.85 (m, 1H), 2.58-2.63 (m, 5H), 2.13-2.15 (m, 1H).

Step 4: Preparation of tert-butyl (4-(2-(2-(2-(2-((3-(2,6-dioxopiperidin-3-yl)-2-methyl-4-oxo-3,4-dihydroquinazolin-7-yl)oxy)ethoxy)ethoxy)ethoxy)ethoxy)phenyl)carbamate To a mixture of 3-(7-hydroxy-2-methyl-4-oxoquinazolin-3(4H)-yl)piperidine-2,6-dione (161 mg, 0.348 mmol) and 2-(2-(2-(2-(4-(((tert-butoxycarbonyl)amino)phenoxy)ethoxy)ethoxy)ethoxy)ethyl methanesulfonate (100 mg, 0.348 mmol, prepared according to procedures of similar intermediate described in US 2015/0291562) in DMF (5.0 mL) was added sodium carbonate (74 mg, 0.696 mmol). The mixture was stirred at 80° C. for 6 h. The resulting mixture was cooled to rt. Ethyl acetate (30 mL) was added and the organic layer was washed with water and brine. The organic layer was dried over anhydrous sodium sulfate, filtered and evaporated under reduced pressure. The residue was purification by preparative TLC to afford tert-butyl (4-(2-(2-(2-(2-((3-(2,6-dioxopiperidin-3-yl)-2-methyl-4-oxo-3,4-dihydroquinazolin-7-yl)oxy)ethoxy)ethoxy)ethoxy)ethoxy)phenyl)carbamate (55.4 mg, 24% yield). $^1$HNMR (400 MHz, DMSO-d$^6$): δ 10.98 (s, 1H), 9.08 (s, 1H), 7.91-7.93 (m, 1H), 7.32-7.34 (m, 2H), 7.07-7.09 (m, 2H), 6.82-6.84 (m, 2H), 5.20-5.24 (m, 1H), 4.24 (s, 2H), 3.99 (m, 2H), 3.79 (m, 2H), 3.70-3.71 (m, 2H), 3.56-3.60 (m, 8H), 2.79-2.87 (m, 1H), 2.57-2.70 (m, 5H), 2.17-2.18 (m, 1H), 1.47 (s, 9H). LC-MS: (ES$^+$): m/z 655.3 [M+H]$^+$.

Step 5: Preparation of 2-((S)-4-(4-chlorophenyl)-2,3,9-trimethyl-6H-thieno[3,2-f][1,2,4]triazolo[4,3-a][1,4]diazepin-6-yl)-N-(4-(2-(2-(2-(2-((3-(2,6-dioxopiperidin-3-yl)-2-methyl-4-oxo-3,4-dihydroquinazolin-7-yl)oxy)ethoxy)ethoxy)ethoxy)ethoxy)phenyl)acetamide Exemplary Compound 45

To a pre-mixed solution containing (S)-2-(4-(4-chlorophenyl)-2,3,9-trimethyl-6H-thieno[3,2-f][1,2,4]triazolo[4,3-a][1,4]diazepin-6-yl)acetic acid (6.11 mg, 0.01525 mmol) in DMF (2.00 ml), TBTU (7.34 mg, 0.02287 mmol) and DIPEA (7.96 µL, 0.04575 mmol) was added 3-(7-(2-(2-(2-(2-(4-aminophenoxy)ethoxy)ethoxy)ethoxy)ethoxy)-2-methyl-4-oxoquinazolin-3(4H)-yl)piperidine-2,6-dione (8.46 mg, 0.01525 mmol, prepared by treating the product from step 4 with HCl in dioxane) and the mixture was left to stir for 2 h. The mixture was diluted with ethyl acetate and water. The organic layer was washed with sodium bicarbonate, water (3×) and brine. The resulting solution was filtered through a thin pad of silica gel and then concentrated in vacuo to give a crude solid. This material was purified by silica gel chromatography on a Teledyne Combiflash ISCO eluting with MeOH/DCM (0:100 to 7:93) to yield 2-((S)-4-(4-chlorophenyl)-2,3,9-trimethyl-6H-thieno[3,2-f][1,2,4]triazolo[4,3-a][1,4]diazepin-6-yl)-N-(4-(2-(2-(2-(2-((3-(2,6-dioxopiperidin-3-yl)-2-methyl-4-oxo-3,4-dihydroquinazolin-7-yl)oxy)ethoxy)ethoxy)ethoxy)ethoxy)phenyl)acetamide (10.1 mg, 0.01077 mmol, 71.1% yield). $^1$H NMR (400 MHz, methanol-d$_4$) ☐ 8.55 (s, 1H), 7.96-8.00 (m, 1H), 7.36-7.50 (m, 6H), 7.03-7.09 (m, 2H), 6.87 (dd, J=3.03, 9.10 Hz, 2H), 5.22 (td, J=5.40, 10.91 Hz, 1H), 4.70-4.74 (m, 1H), 4.22 (d, J=3.33 Hz, 2H), 4.10 (d, J=4.30 Hz, 2H), 3.85-3.91 (m, 2H), 3.79-3.84 (m, 2H), 3.64-3.71 (m, 7H), 3.55-3.64 (m, 2H), 3.42-3.50 (m, 2H), 2.71 (s, 3H), 2.66 (d, J=3.33 Hz, 2H), 2.44 (d, J=3.33 Hz, 3H), 1.89 (s, 3H), 1.68 (d, J=3.33 Hz, 2H), 1.29 (br. s., 3H). LC/MS (ES$^+$): m/z 937.19/939.19 [M+H]$^+$.

Exemplar Synthesis of Exemplary Compound 44: 2-((S)-4-(4-chlorophenyl)-2,3,9-trimethyl-6H-thieno[3,2-f][1,2,4]triazolo[4,3-a][1,4]diazepin-6-yl)-N-(4-(2-(2-(2-(2-((3-(2,6-dioxopiperidin-3-yl)-2-methyl-4-oxo-3,4-dihydroquinazolin-8-yl)oxy)ethoxy)ethoxy)ethoxy)ethoxy)phenyl)acetamide

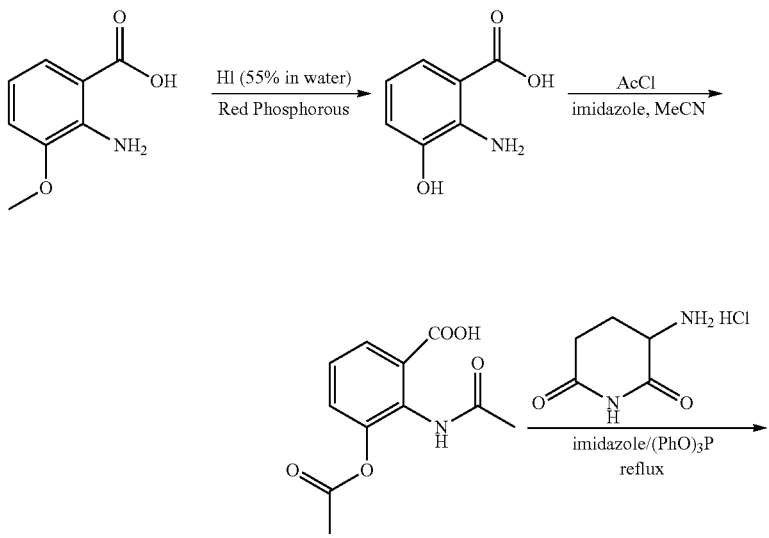

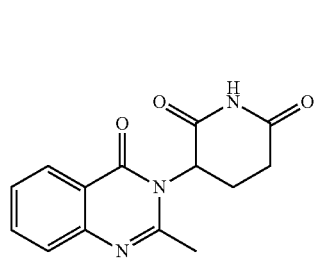
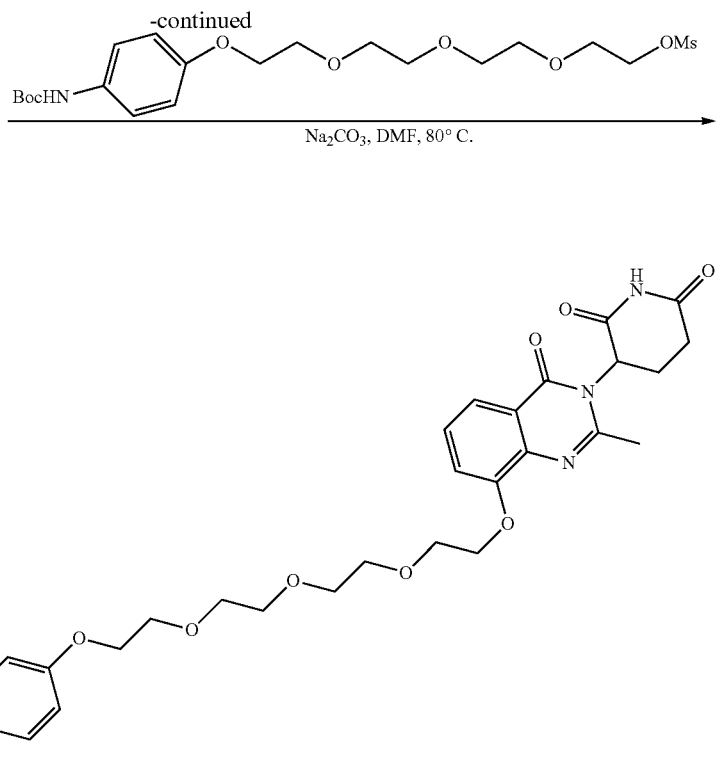

This molecule was synthesized using the same method as described in Example 1. The key intermediate was prepared according the scheme listed above. ¹H NMR (400 MHz, methanol-d₄) □ 8.55 (s, 1H), 7.96-8.00 (m, 1H), 7.36-7.50 (m, 6H), 7.03-7.09 (m, 2H), 6.87 (dd, J=3.03, 9.10 Hz, 2H), 5.22 (td, J=5.40, 10.91 Hz, 1H), 4.70-4.74 (m, 1H), 4.22 (d, J=3.33 Hz, 2H), 4.10 (d, J=4.30 Hz, 2H), 3.85-3.91 (m, 2H), 3.79-3.84 (m, 2H), 3.64-3.71 (m, 7H), 3.55-3.64 (m, 2H), 3.42-3.50 (m, 2H), 2.71 (s, 3H), 2.66 (d, J=3.33 Hz, 2H), 2.44 (d, J=3.33 Hz, 3H), 1.89 (s, 3H), 1.68 (d, J=3.33 Hz, 2H), 1.29 (br. s., 3H). LCMS (ES⁺): m/z 937.19/939.19 [M+H]⁺.

Exemplary Synthesis of Exemplar Compound 43: 2-((S)-4-(4-chlorophenyl)-2,3,9-trimethyl-6H-thieno[3,2-f][1,2,4]triazolo[4,3-a][1,4]diazepin-6-yl)-N-(4-(2-(2-(2-(2-((1-oxo-2-((S)-6-oxopiperidin-3-yl)isoindolin-4-yl)amino)ethoxy)ethoxy)ethoxy)ethoxy)phenyl)acetamide

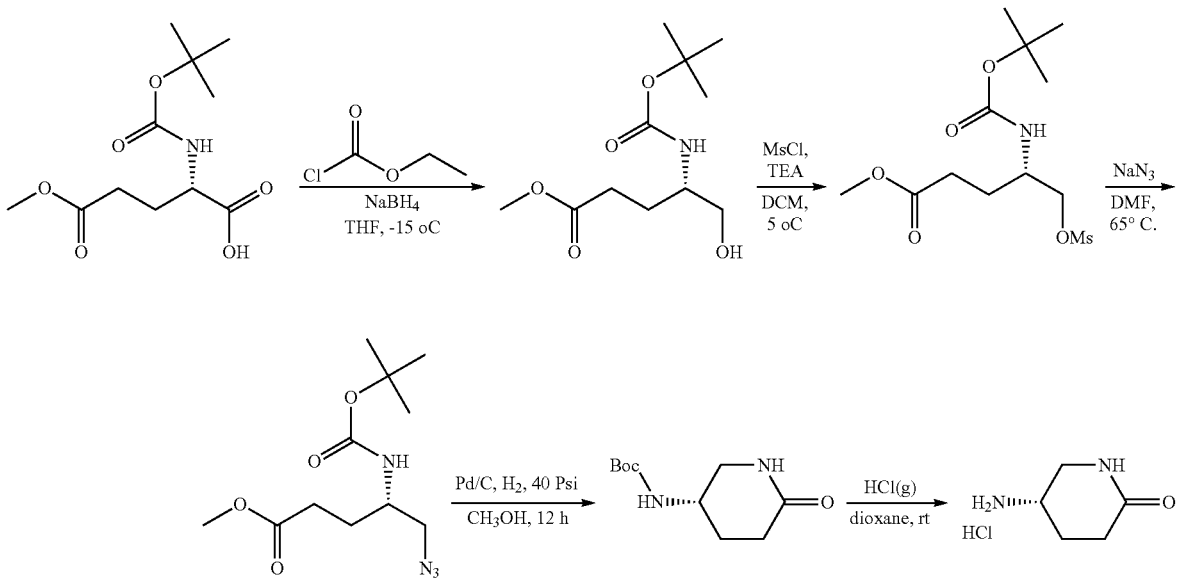

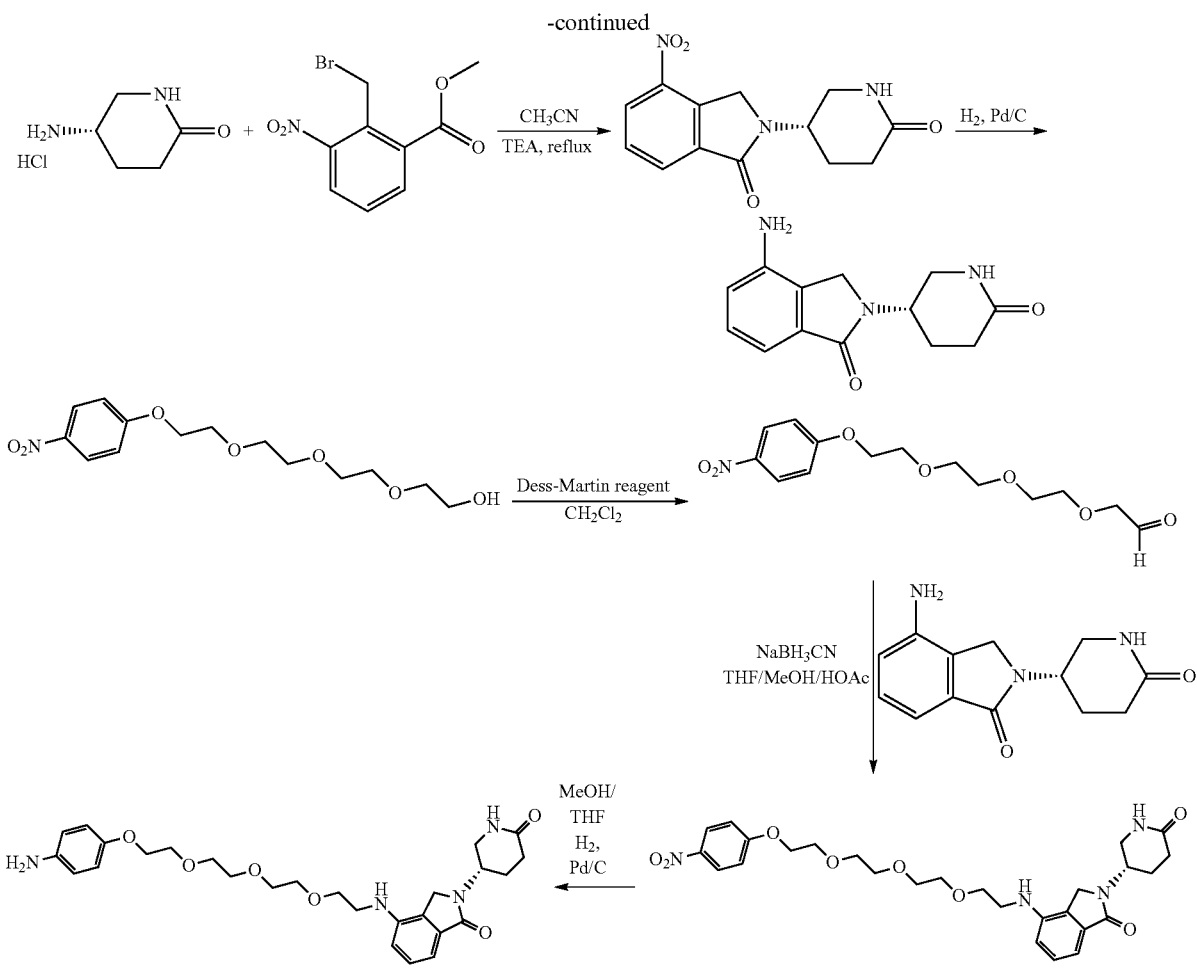

The key intermediate for the preparation of this compound was synthesized according the scheme listed above. The final step of amide coupling was carried out under the same condition as described in Example 1. $^1$H NMR (400 MHz, CDCl$_3$) d 9.03 (s, 1H), 7.45 (dd, J=8.71, 13.21 Hz, 4H), 7.31-7.37 (m, 3H), 7.24 (d, J=7.24 Hz, 1H), 6.84 (d, J=9.00 Hz, 2H), 6.78 (d, J=8.02 Hz, 1H), 6.75 (br. s., 1H), 4.66-4.73 (m, 2H), 4.20 (d, J=2.74 Hz, 1H), 4.07-4.12 (m, 2H), 3.80-3.90 (m, 3H), 3.64-3.77 (m, 10H), 3.52-3.58 (m, 1H), 3.35-3.42 (m, 3H), 2.68 (br. s., 3H), 2.52-2.59 (m, 2H), 2.41 (s, 3H), 2.02-2.08 (m, 2H), 1.69 (s, 3H), 1.26 (s, 3H). LC-MS (ES$^+$): m/z 895.22/897.22 [M+H]$^+$.

Protein Level Control

This description also provides methods for the control of protein levels with a cell. This is based on the use of compounds as described herein, which are known to interact with a specific target protein such that degradation of a target protein in vivo will result in the control of the amount of protein in a biological system, prerferably to a particular therapeutic benefit.

The following examples are used to assist in describing the present invention, but should not be seen as limiting the present invention in any way.

Exemplary Embodiments of the Present Disclosure

The present disclosure encompasses the following specific embodiments. These following embodiments may include all of the features recited in a proceeding embodiment, as specified. Where applicable, the following embodiments may also include the features recited in any proceeding embodiment inclusively or in the alternative.

An aspect of the present disclosure provides a cereblon E3 ubiquitin ligase binding compound having a chemical structure selected from:

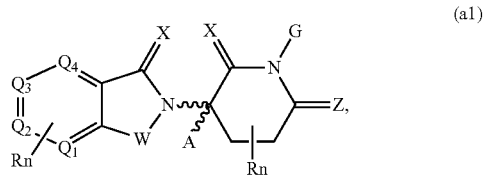

(a1)

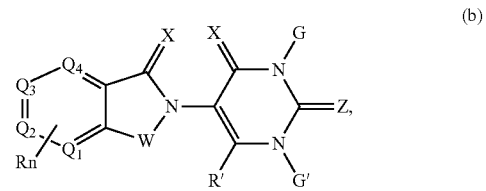

(b)

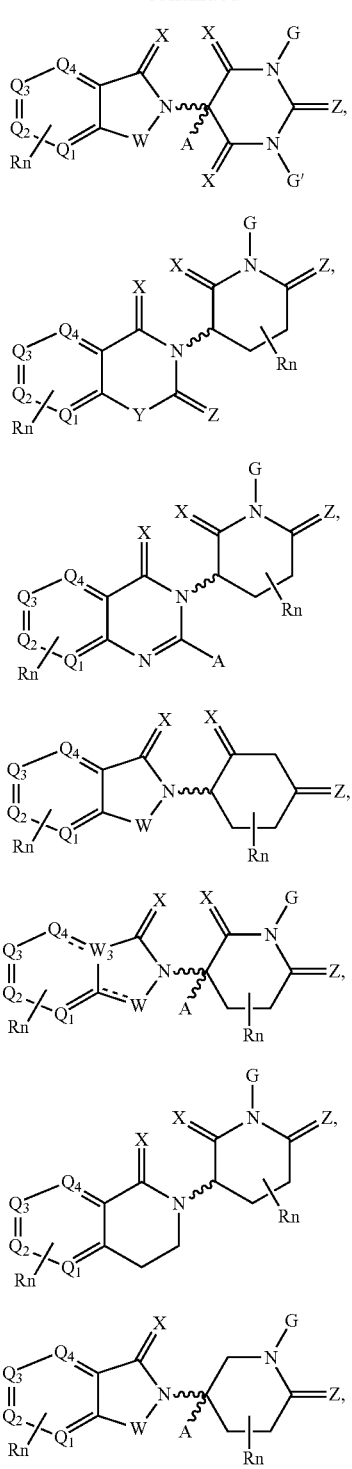

(c)
(d1)
(e)
(f)
(a2)
(d2)
(a3)

wherein:

W is selected from the group consisting of $CH_2$, CHR, C=O, $SO_2$, NH, N, optionally substituted cyclopropyl group, optionally substituted cyclobutyl group, and N-alkyl;

$W_3$ is selected from C or N;

each X is independently selected from the group consisting of O, S, and $H_2$;

Y is selected from the group consisting of $CH_2$, —C=CR'NH, N-alkyl, N-aryl, N-hetaryl, N-cycloalkyl, N-heterocyclyl, O, and S;

Z is selected from the group consisting of O, S, and $H_2$;

G and G' are independently selected from the group consisting of H, alkyl (linear, branched, optionally substituted), OH, R'OCOOR, R'OCONRR", $CH_2$-heterocyclyl optionally substituted with R', and benzyl optionally substituted with R';

$Q_1$, $Q_2$, $Q_3$, and $Q_4$ represent a carbon C substituted with a group independently selected from R', N or N-oxide;

A is independently selected from the group H, alkyl (linear, branched, optionally substituted), cycloalkyl, Cl and F;

R comprises —CONR'R", —OR', —NR'R", —SR', —$SO_2$R', —$SO_2$NR'R", —CR'R"—, —CR'NR'R"—, (—CR'O)$_{n'}$R", -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —$CF_3$, —CN, —$NR'SO_2$NR'R", —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R')R", —$SF_5$ and —$OCF_3$;

R' and R" are independently selected from the group consisting of a bond, H, alkyl, cycloalkyl, aryl, heteroaryl, heterocyclic, —C(=O)R, heterocyclyl, each of which is optionally substituted;

n' integer from 1-10;

⎓ represents a single bond or a double bond;

∿∿∿ represents a bond that may be stereospecific ((R) or (S)) or non-stereospecific; and Rn comprises 1-4 independent functional groups, optionally substituted linear or branched alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted aryl (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted

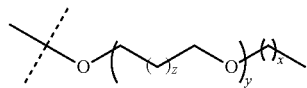

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted

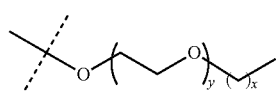

(e.g., optionally substituted with one or more halogen, alkyl, haloalky, fluoroalkyl, cycloalkyl (e.g., a C3-C6 cycloalkyl), or aryl (e.g., C5-C7 aryl)), or atoms; and each of x, y, and z are independently 0, 1, 2, 3, 4, 5, or 6, n is an integer from 1-10 (e.g., 1-4).

Another aspect of the present disclosure provides a bifunctional compound having the chemical structure:

CLM-L-PTM, or a pharmaceutically acceptable salt, enantiomer, stereoisomer, solvate, polymorph or prodrug thereof, wherein:
the PTM is a small molecule comprising a protein targeting moiety;
the L is a bond or a chemical linking moiety covalently coupling the CLM and the PTM; and
the CLM is a small molecule cereblon E3 ubiquitin ligase binding moiety of claim 1, wherein when n is 2, 3, or 4, then at least one of R. or W is modified to be covalently joined to the linker group (L) or a PTM.

In any aspect or embodiment described herein, the CLM is linked to the PTM, the chemical linker group (L), or a combination thereof via W, X, $R^1$, $R^2$, $R^3$, $R^4$, R', $Q_1$, $Q_2$, $Q_3$, $Q_4$, and $Q_5$.

In any aspect or embodiment described herein, the PTM is a moiety that binds BRD4, BRaf, Estrogen Receptor (ER), or Androgen Receptor (AR).

In any aspect or embodiment described herein, the compound may further comprise a second E3 ubiquitin ligase binding moiety coupled through a linker group.

In any aspect or embodiment described herein, the second E3 ubiquitin ligase binding moiety binds or targets an E3 ubiquitin ligase selected from the group consisting of Von Hippel-Lindau (VLM), cereblon (CLM), mouse double-minute homolog2 (MLM), and inhibitors of apoptosis proteins (ILM).

In any aspect or embodiment described herein, the CLM is represented by a chemical structure selected from the group consisting of:

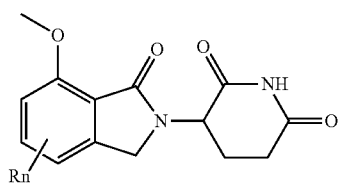

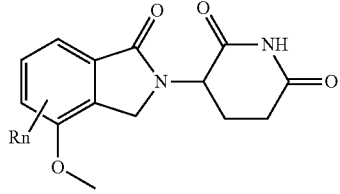

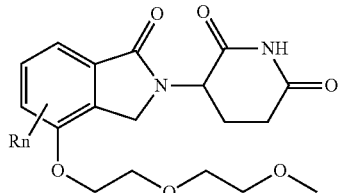

-continued

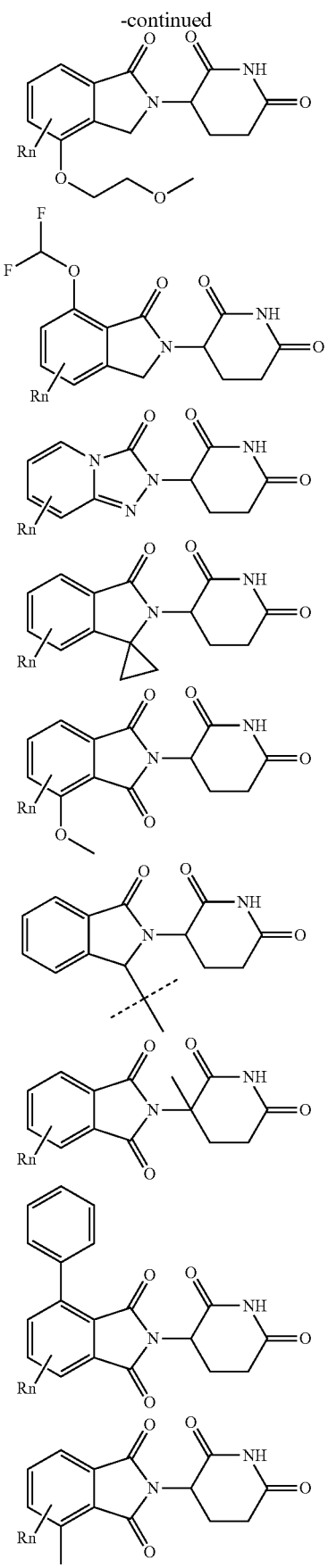

-continued

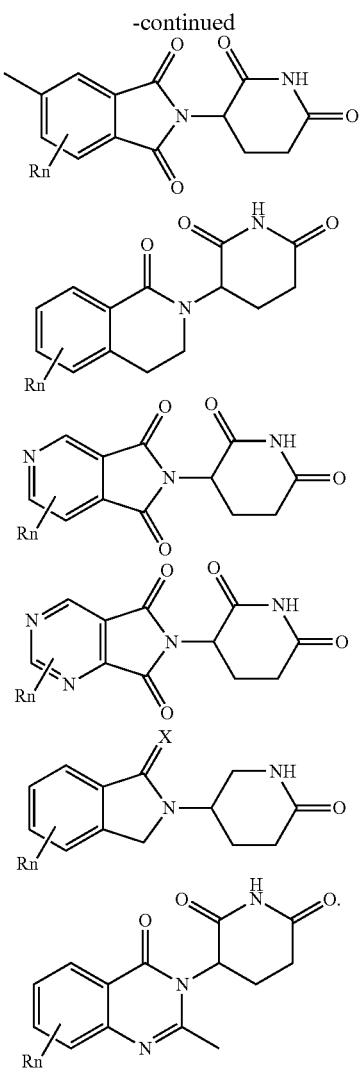

In any aspect or embodiment described herein, the linker (L) comprises a chemical structural unit represented by the formula:

-(A$^L$)q- wherein:
(A$^L$)$_q$ is a group which is connected to at least one of the CLM, the PTM, or a combination thereof,
q is an integer greater than or equal to 1;
each A$^L$ is independently selected from the group consisting of, a bond, CR$^{L1}$R$^{L2}$, O, S, SO, SO$_2$, NR$^{L3}$, SO$_2$NR$^{L3}$, SONR$^{L3}$, CONR$^{L3}$, NR$^{L3}$CONR$^{L4}$, NR$^{L3}$SO$_2$NR$^{L4}$, CO, CR$^{L1}$=CR$^{L2}$, C≡C, SiR$^{L1}$R$^{L2}$, P(O)R$^{L1}$, P(O)OR$^{L1}$, NR$^{L3}$C(=NCN)NR$^{L4}$, NR$^{L3}$C(=NCN), NR$^{L3}$C(=CNO$_2$)NR$^{L4}$, C$_{3-11}$cycloalkyl optionally substituted with 0-6 R$^{L1}$ and/or R$^{L2}$ groups, C$_{3-11}$heteocyclyl optionally substituted with 0-6 R$^{L1}$ and/or R$^{L2}$ groups, aryl optionally substituted with 0-6 R$^{L1}$ and/or R$^{L2}$ groups, heteroaryl optionally substituted with 0-6 R$^{L1}$ and/or R$^{L2}$ groups, where R$^{L1}$ or R$^{L2}$, each independently are optionally linked to other groups to form cycloalkyl and/or heterocyclyl moiety, optionally substituted with 0-4 R$^{L5}$ groups; and
R$^{L1}$, R$^{L2}$, R$^{L3}$, R$^{L4}$ and R$^{L5}$ are, each independently, H, halo, C$_{1-8}$alkyl, OC$_{1-8}$alkyl, SC$_{1-8}$alkyl, NHC$_{1-8}$alkyl, N(C$_{1-8}$alkyl)$_2$, C$_{3-11}$cycloalkyl, aryl, heteroaryl, C$_{3-11}$heterocyclyl, OC$_{1-8}$cycloalkyl, SC$_{1-8}$cycloalkyl, NHC$_{1-8}$cycloalkyl, N(C$_{1-8}$cycloalkyl)$_2$, N(C$_{1-8}$cycloalkyl)(C$_{1-8}$alkyl), OH, NH$_2$, SH, SO$_2$C$_{1-8}$alkyl, P(O)(OC$_{1-8}$alkyl)(C$_{1-8}$alkyl), P(O)(OC$_{1-8}$alkyl)$_2$, CC—C$_{1-8}$alkyl, CCH, CH=CH(C$_{1-8}$alkyl), C(C$_{1-8}$alkyl)=CH(C$_{1-8}$alkyl), C(C$_{1-8}$alkyl)=C(C$_{1-8}$alkyl)$_2$, Si(OH)$_3$, Si(C$_{1-8}$alkyl)$_3$, Si(OH)(C$_{1-8}$alkyl)$_2$, COC$_{1-8}$alkyl, CO$_2$H, halogen, CN, CF$_3$, CHF$_2$, CH$_2$F, NO$_2$, SF$_5$, SO$_2$NHC$_{1-8}$alkyl, SO$_2$N(C$_{1-8}$alkyl)$_2$, SONHC$_{1-8}$alkyl, SON(C$_{1-8}$alkyl)$_2$, CONHC$_{1-8}$alkyl, CON(C$_{1-8}$alkyl)$_2$, N(C$_{1-8}$alkyl)CONH(C$_{1-8}$alkyl), N(C$_{1-8}$alkyl)CON(C$_{1-8}$alkyl)$_2$, NHCONH(C$_{1-8}$alkyl), NHCON(C$_{1-8}$alkyl)$_2$, NHCONH$_2$, N(C$_{1-8}$alkyl)SO$_2$NH(C$_{1-8}$alkyl), N(C$_{1-8}$alkyl) SO$_2$N(C$_{1-8}$alkyl)$_2$, NH SO$_2$NH(C$_{1-8}$alkyl), NH SO$_2$N(C$_{1-8}$alkyl)$_2$, NH SO$_2$NH$_2$.

In any aspect or embodiment described herein, the A$^L$ is selected from the group consisting of:

—N(R)—(CH2)$_m$-O(CH2)$_n$-O(CH2)$_o$-O(CH2)$_p$-O(CH2)$_q$ -O(CH2)$_r$-OCH2-,

—O—(CH2)$_m$-O(CH2)$_n$-O(CH2)$_o$-O(CH2)$_p$-O(CH2)$_q$-O(CH2)$_r$-OCH2-,

—O—(CH2)$_m$-O(CH2)$_n$-O(CH2)$_o$-O(CH2)$_p$-O(CH2)$_q$-O(CH2)$_r$-O—;

—N(R)—(CH2)$_m$-O(CH2)$_n$-O(CH2)$_o$-O(CH2)$_p$-O(CH2)$_q$ -O(CH2)$_r$-O—;

—(CH2)$_m$-O(CH2)$_n$-O(CH2)$_o$-O(CH2)$_p$-O(CH2)$_q$-O(CH2)$_r$-O—;

—(CH2)$_m$-O(CH2)$_n$-O(CH2)$_o$-O(CH2)$_p$-O(CH2)$_q$-O(CH2)$_r$-OCH2-;

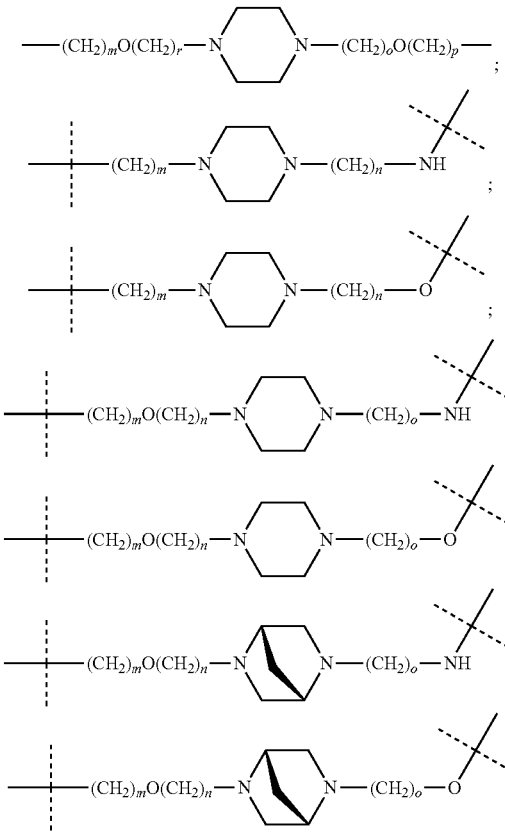

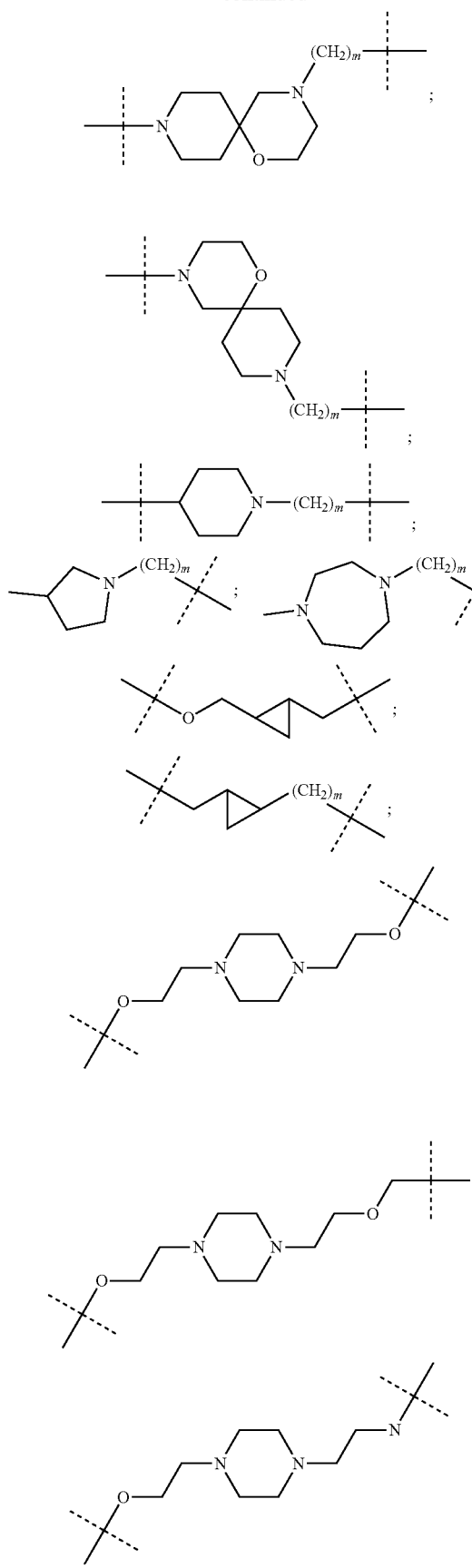
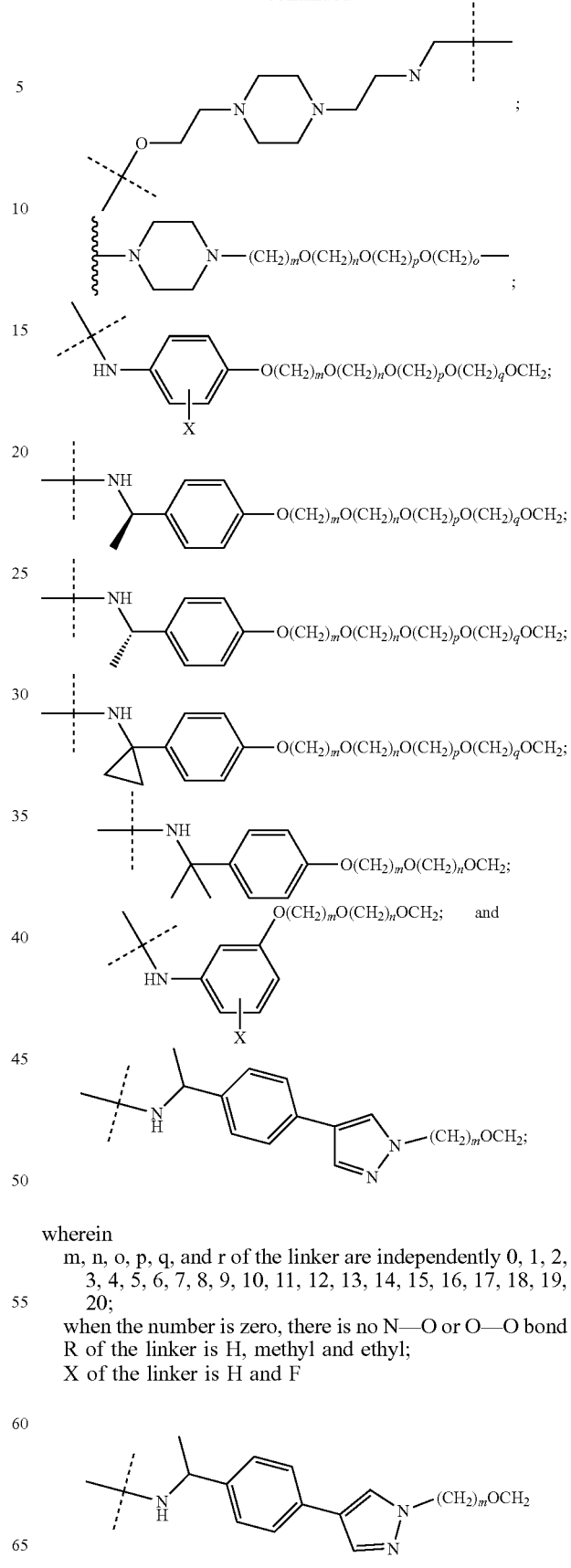
wherein
m, n, o, p, q, and r of the linker are independently 0, 1, 2, 3, 4, 5, 6, 7, 8, 9, 10, 11, 12, 13, 14, 15, 16, 17, 18, 19, 20;
when the number is zero, there is no N—O or O—O bond
R of the linker is H, methyl and ethyl;
X of the linker is H and F

491 492
where m of the linker can be 2, 3, 4, 5;
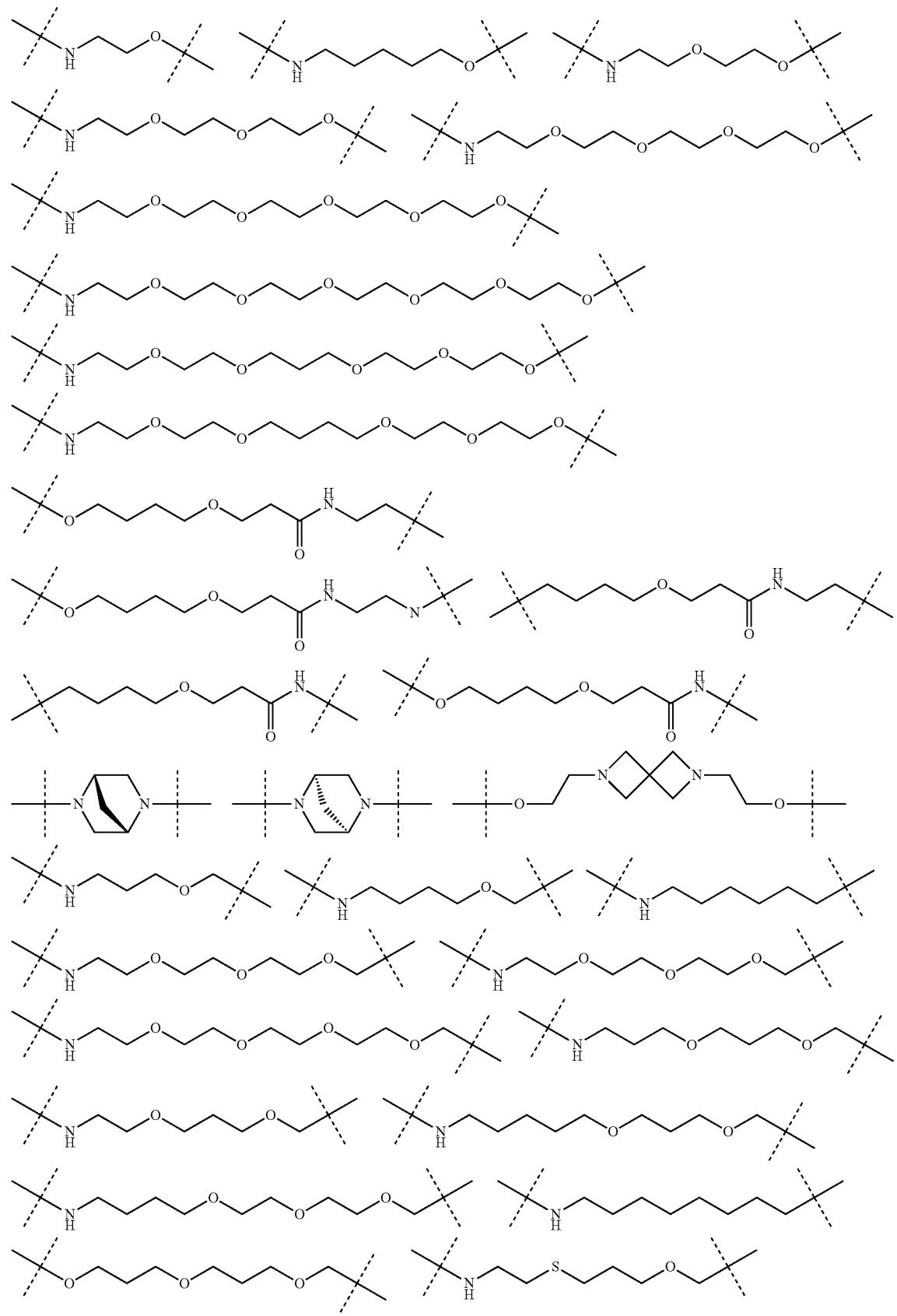

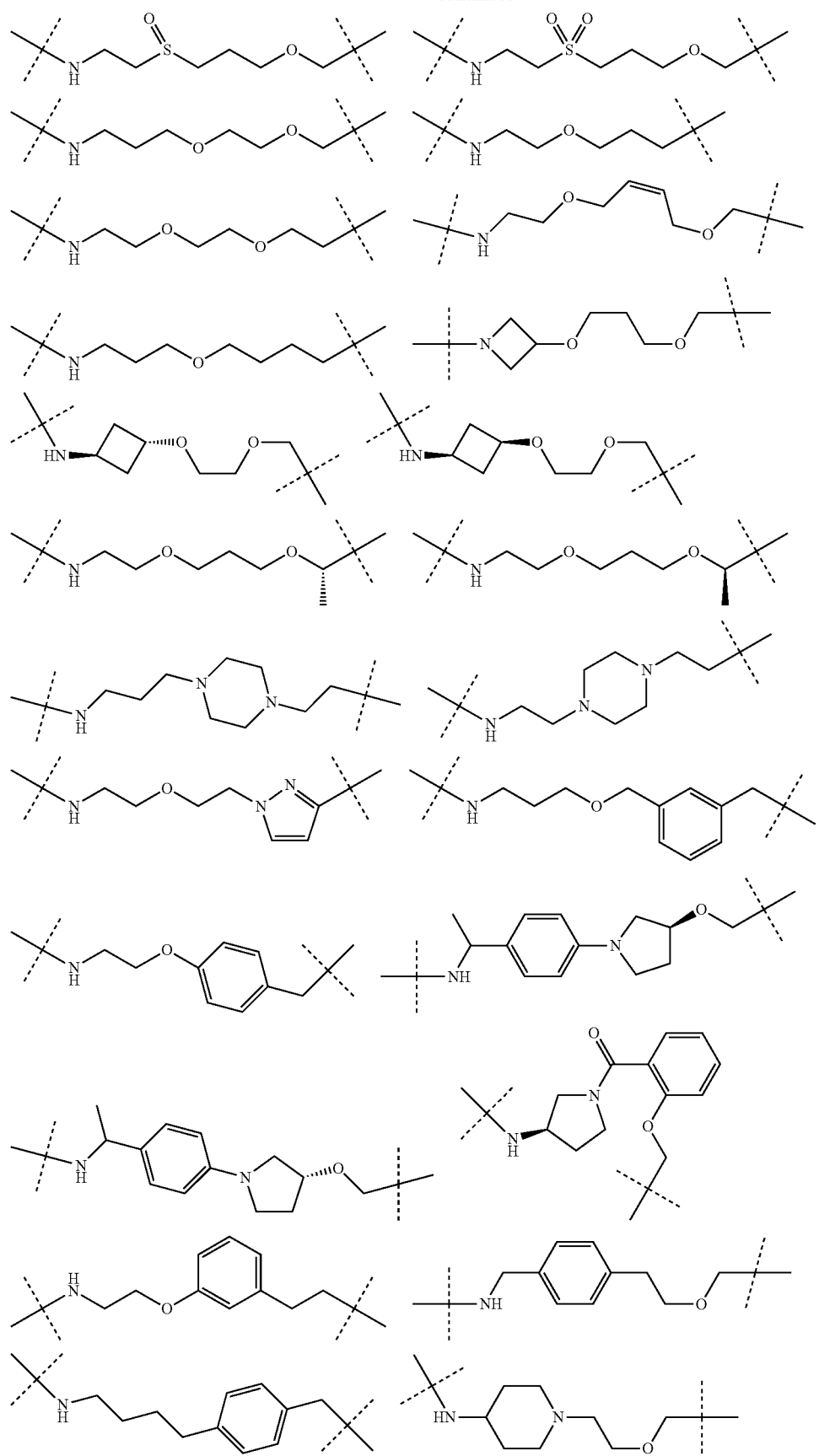

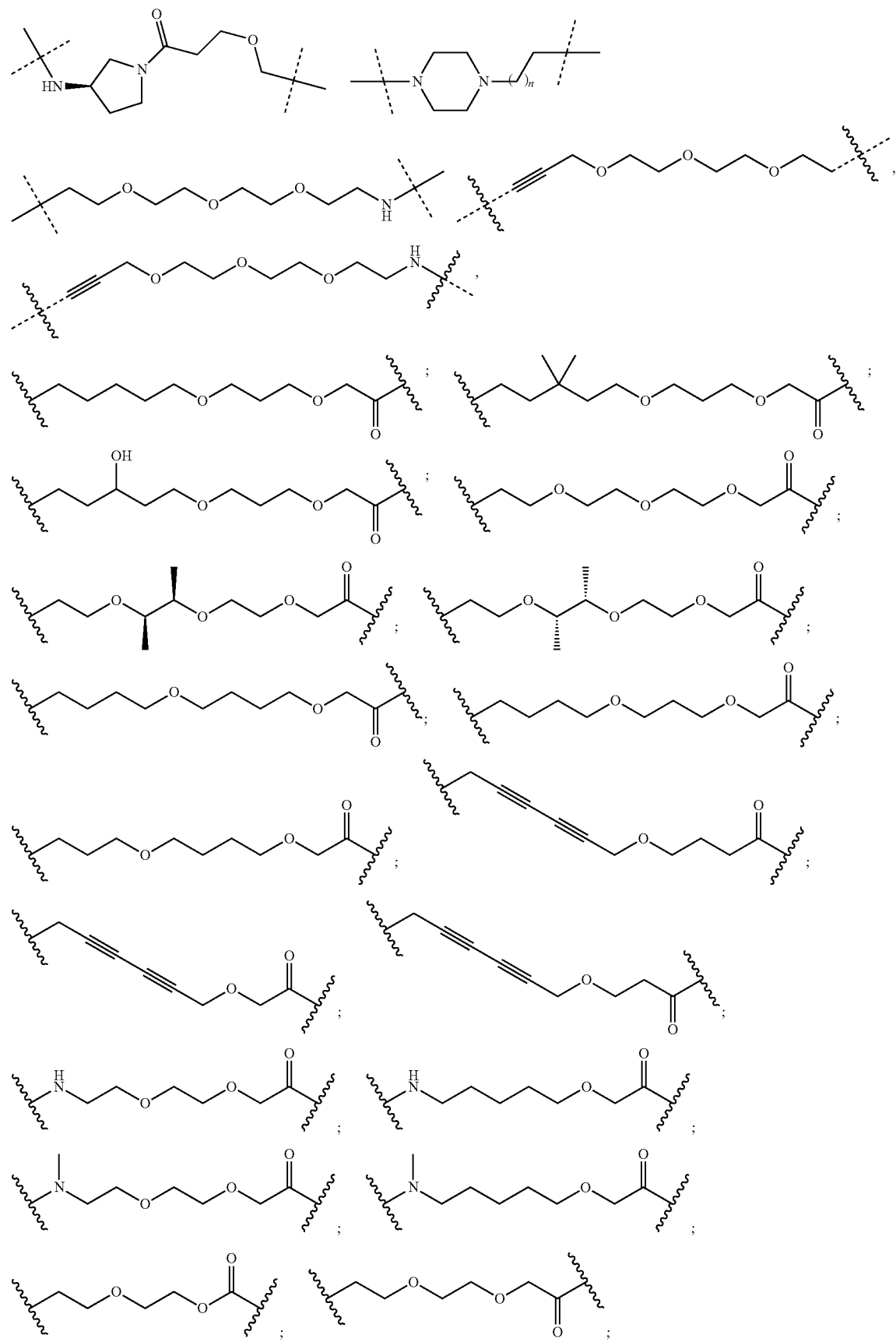

-continued
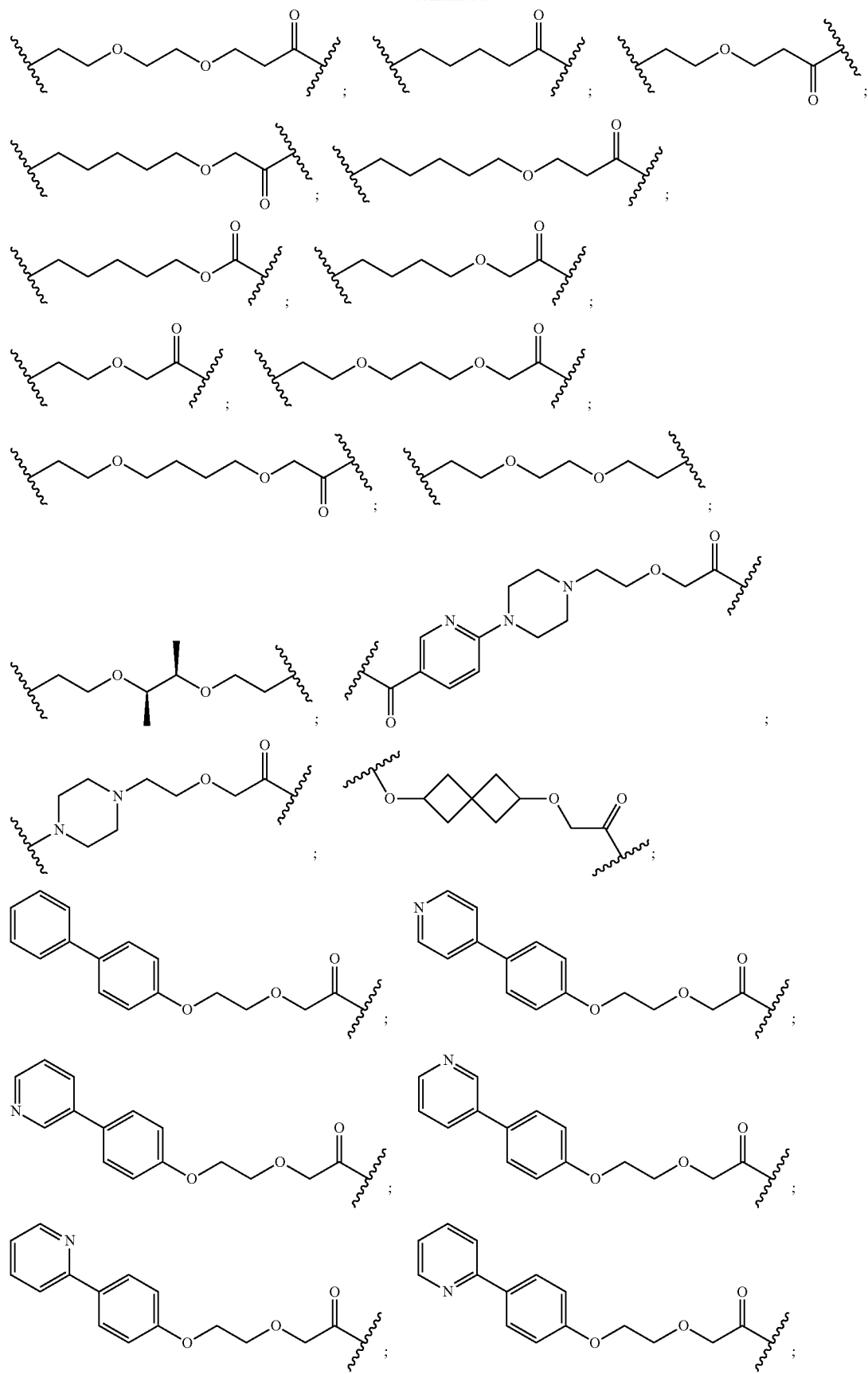

499
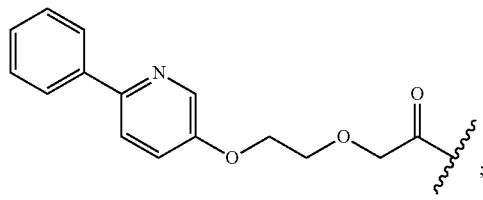
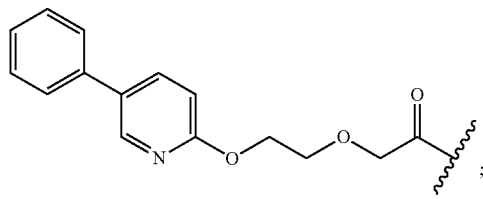
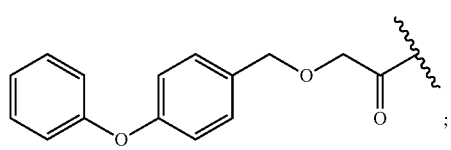
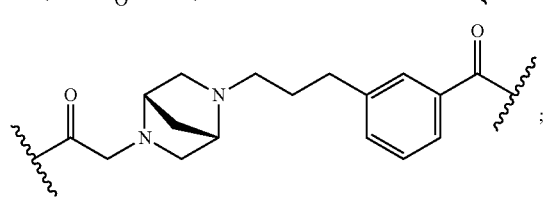
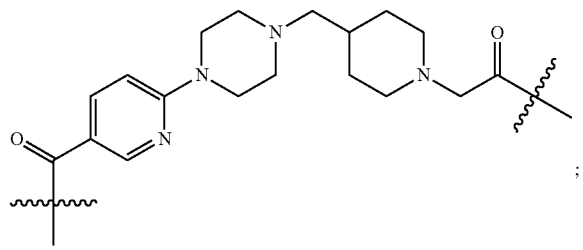
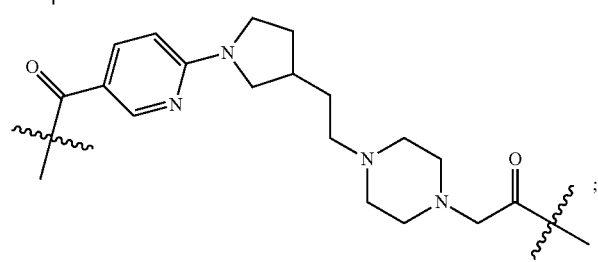
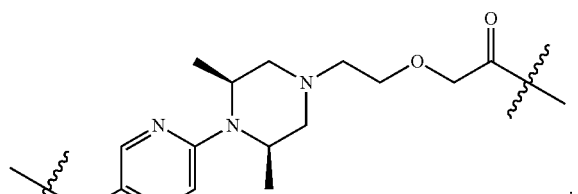
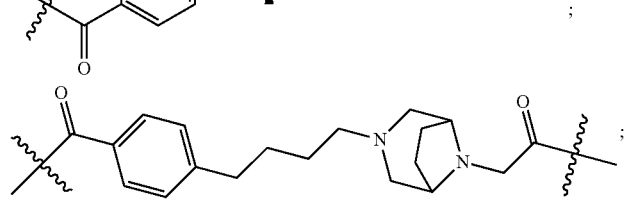
500
-continued
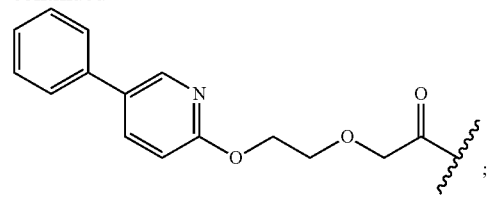
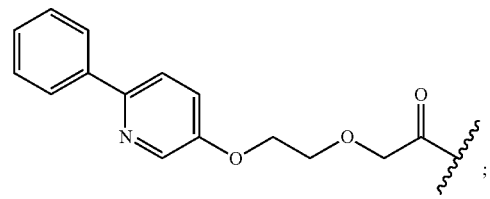
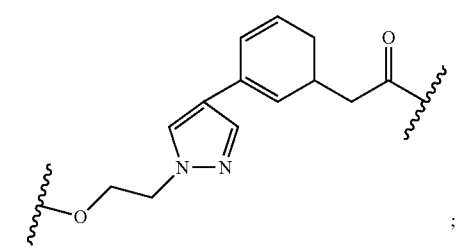
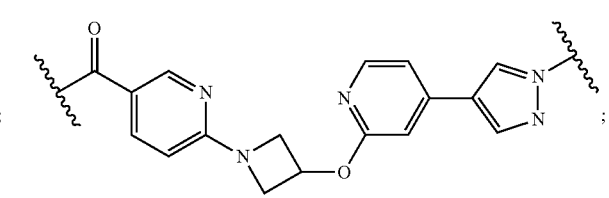

-continued
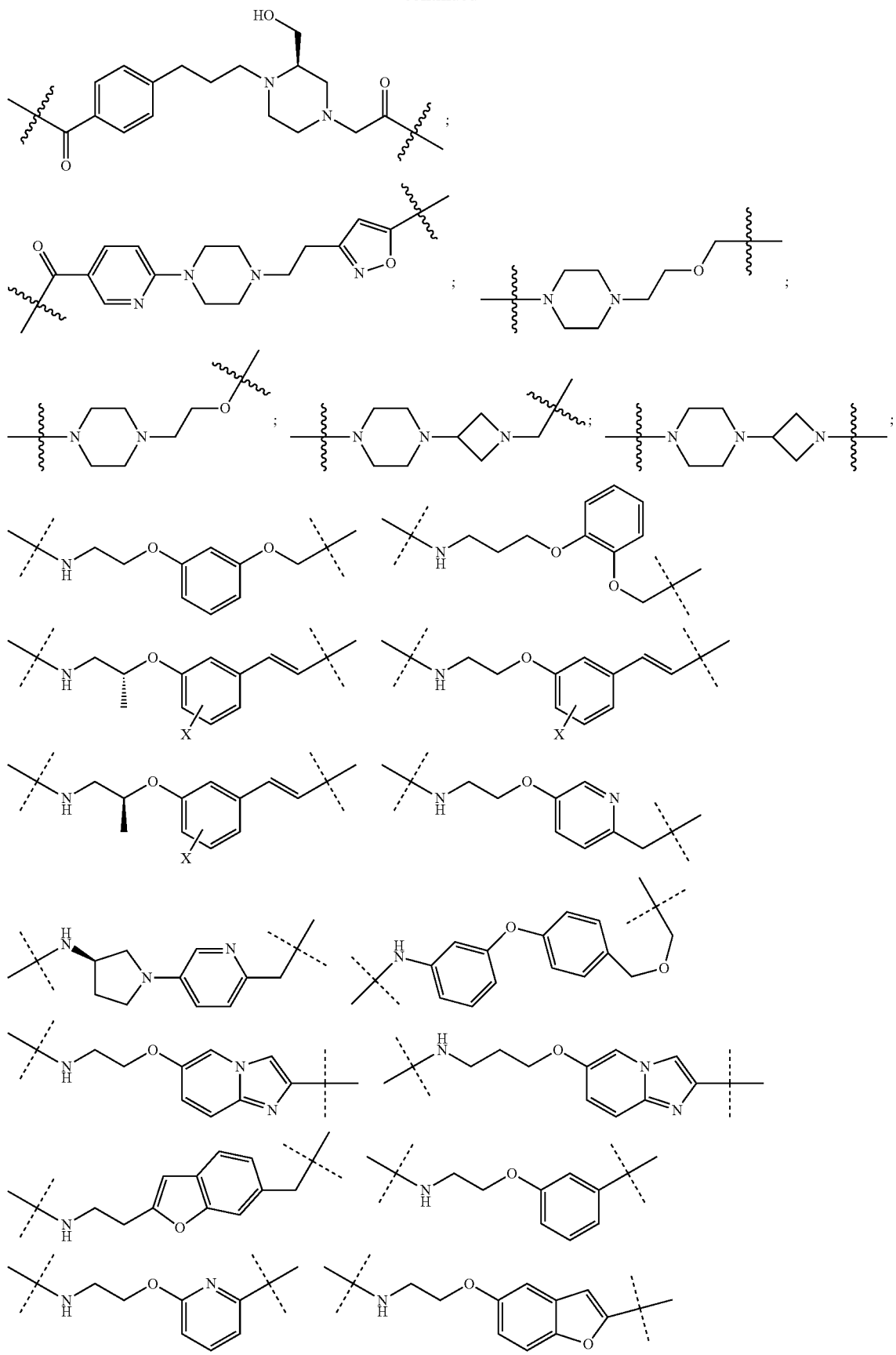

503 504
-continued
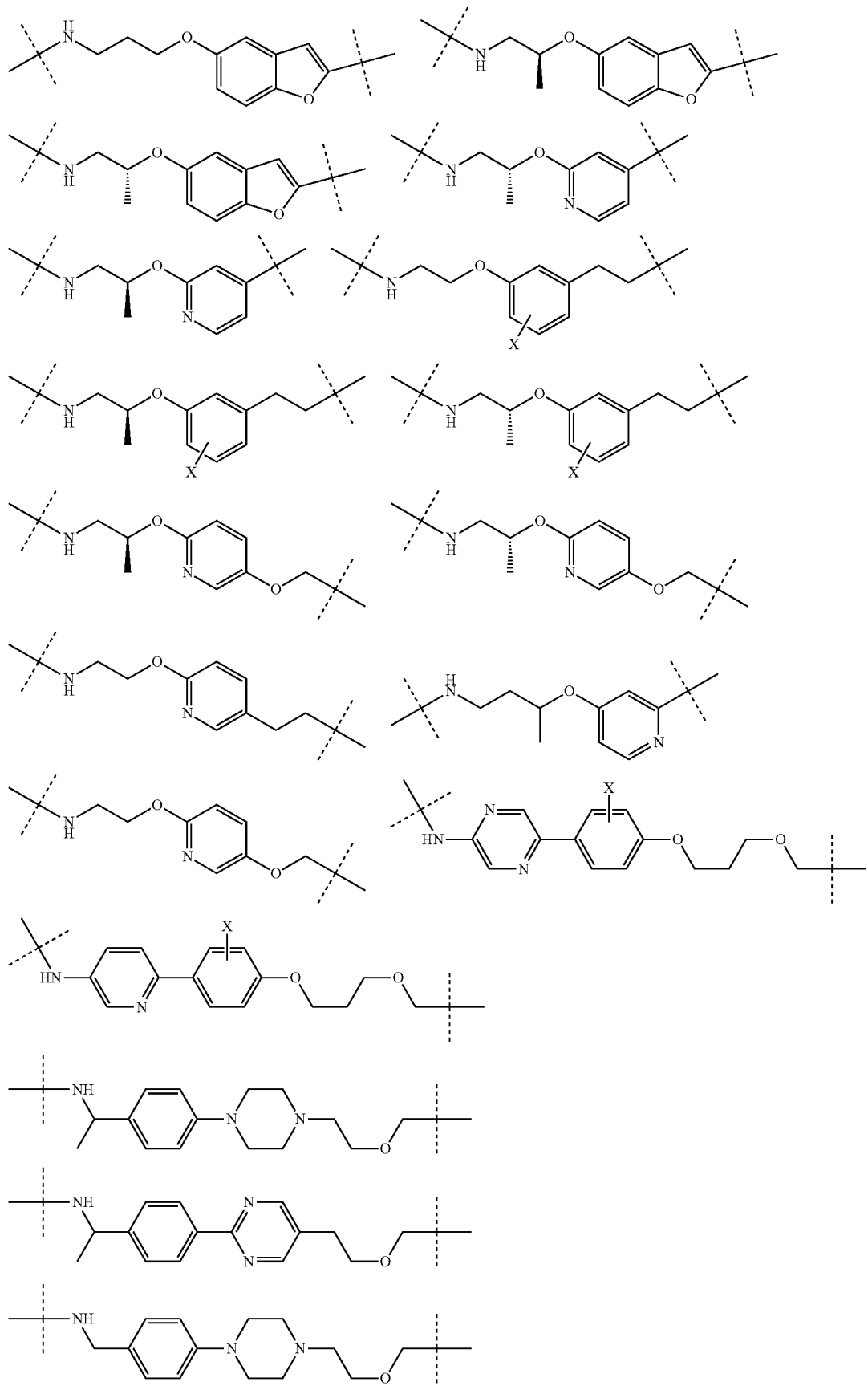

-continued
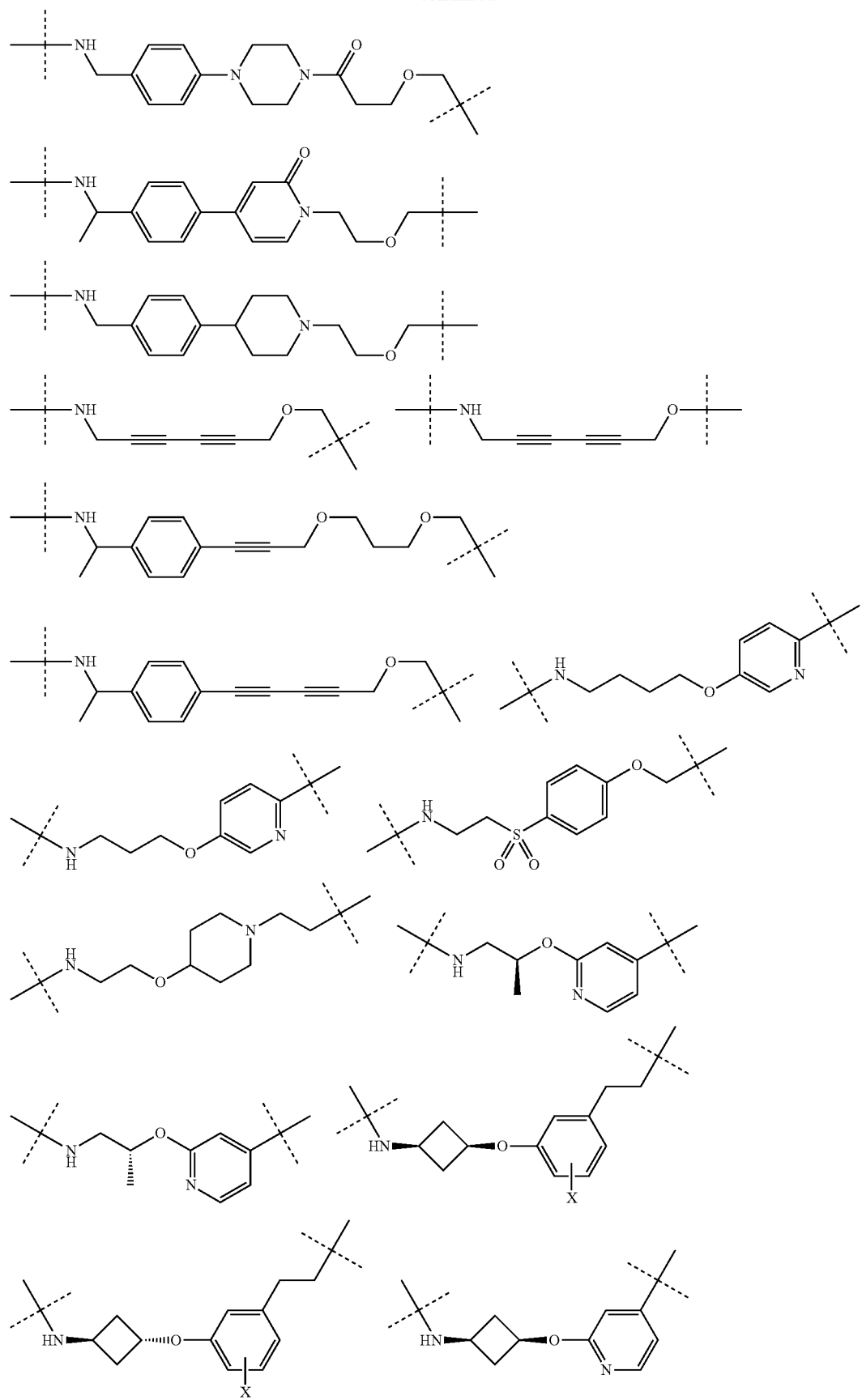

507 508
-continued
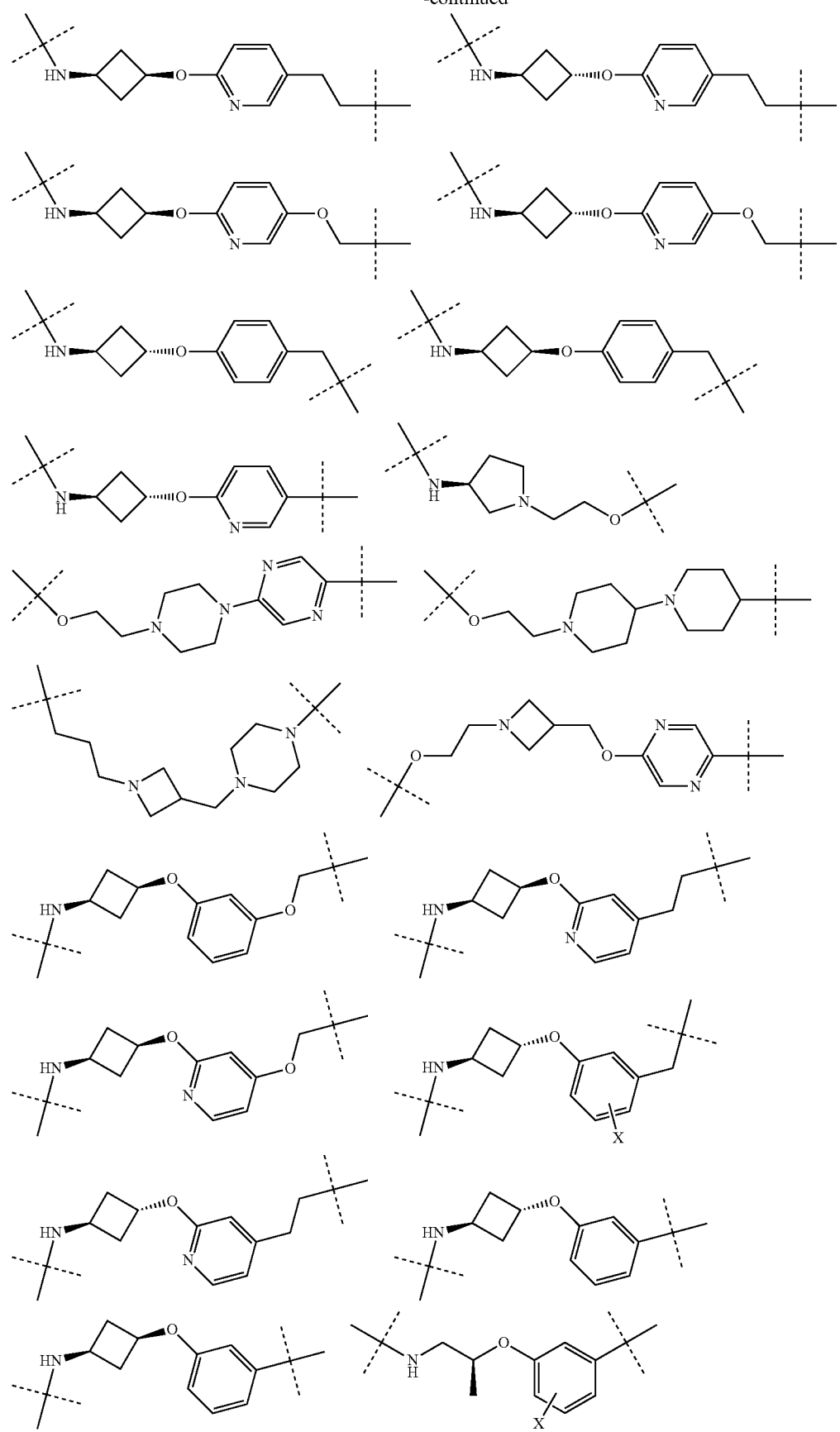

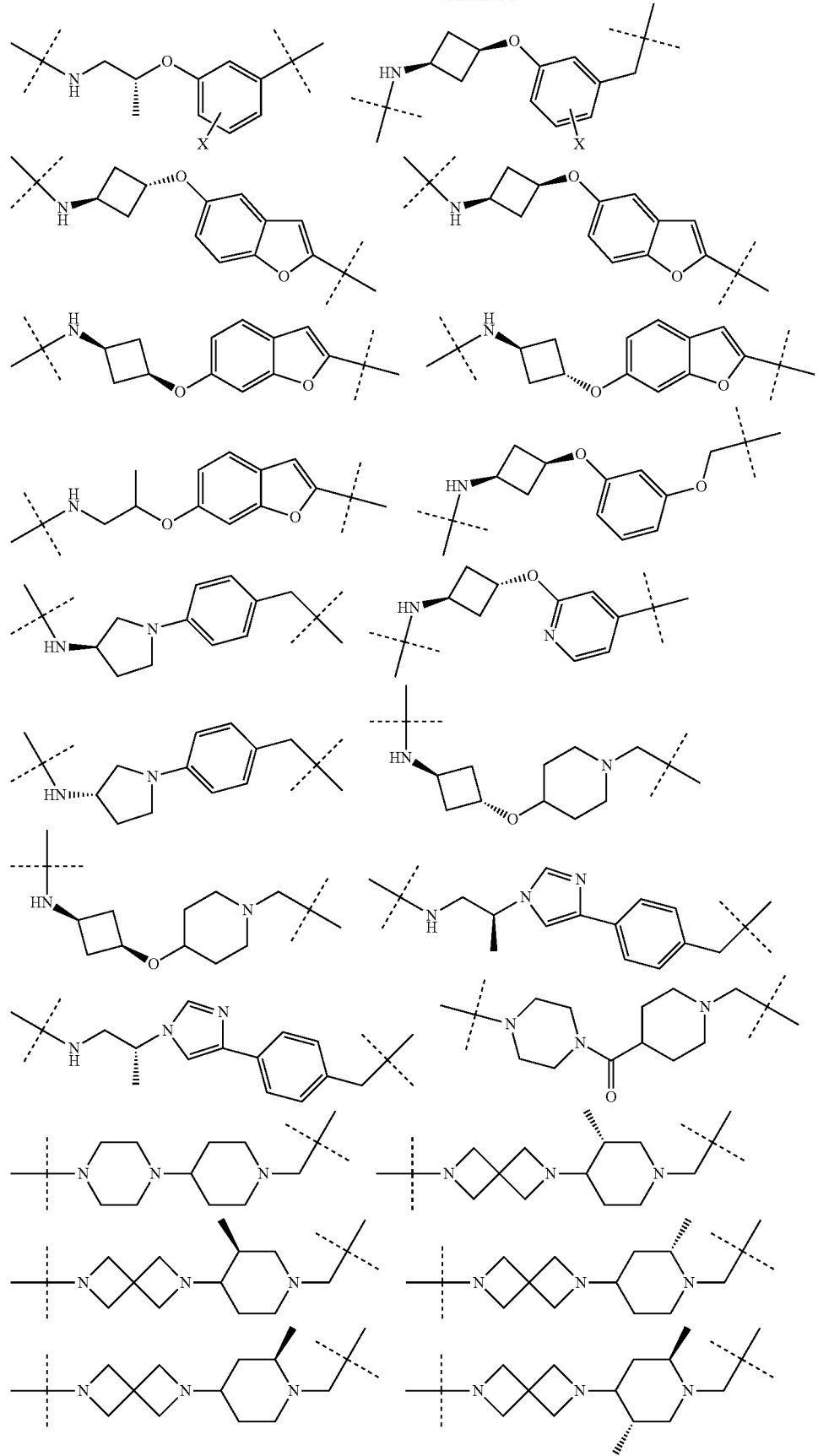

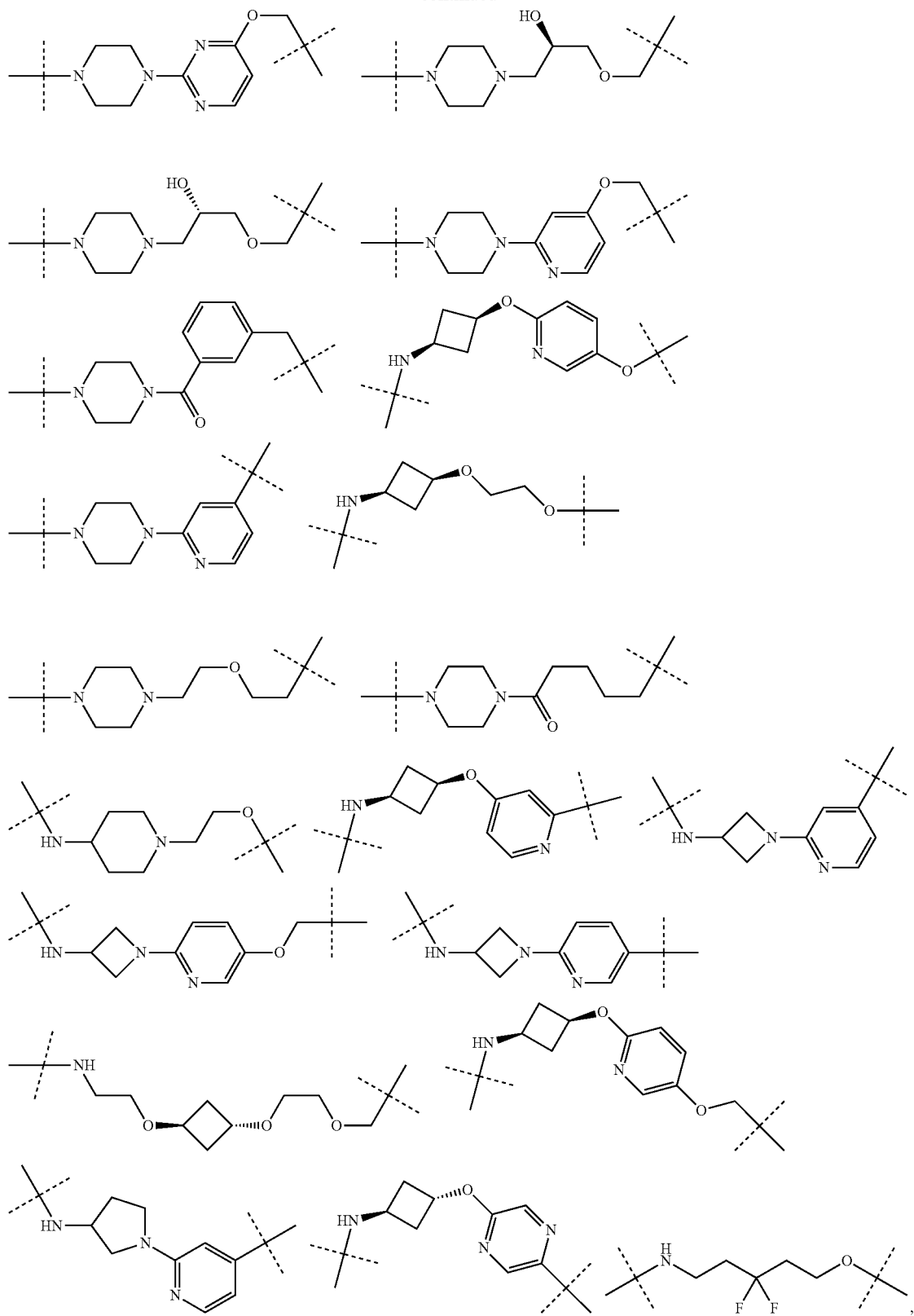
X = H, F where each n and m of the linker can independently be 0, 1, 2, 3, 4, 5, 6, 7, 8, 9, 10, 11, 12, 13, 14, 15, 16, 17, 18, 19, 20.
In any aspect or embodiment described herein, the $A^L$ is selected from the group consisting of:
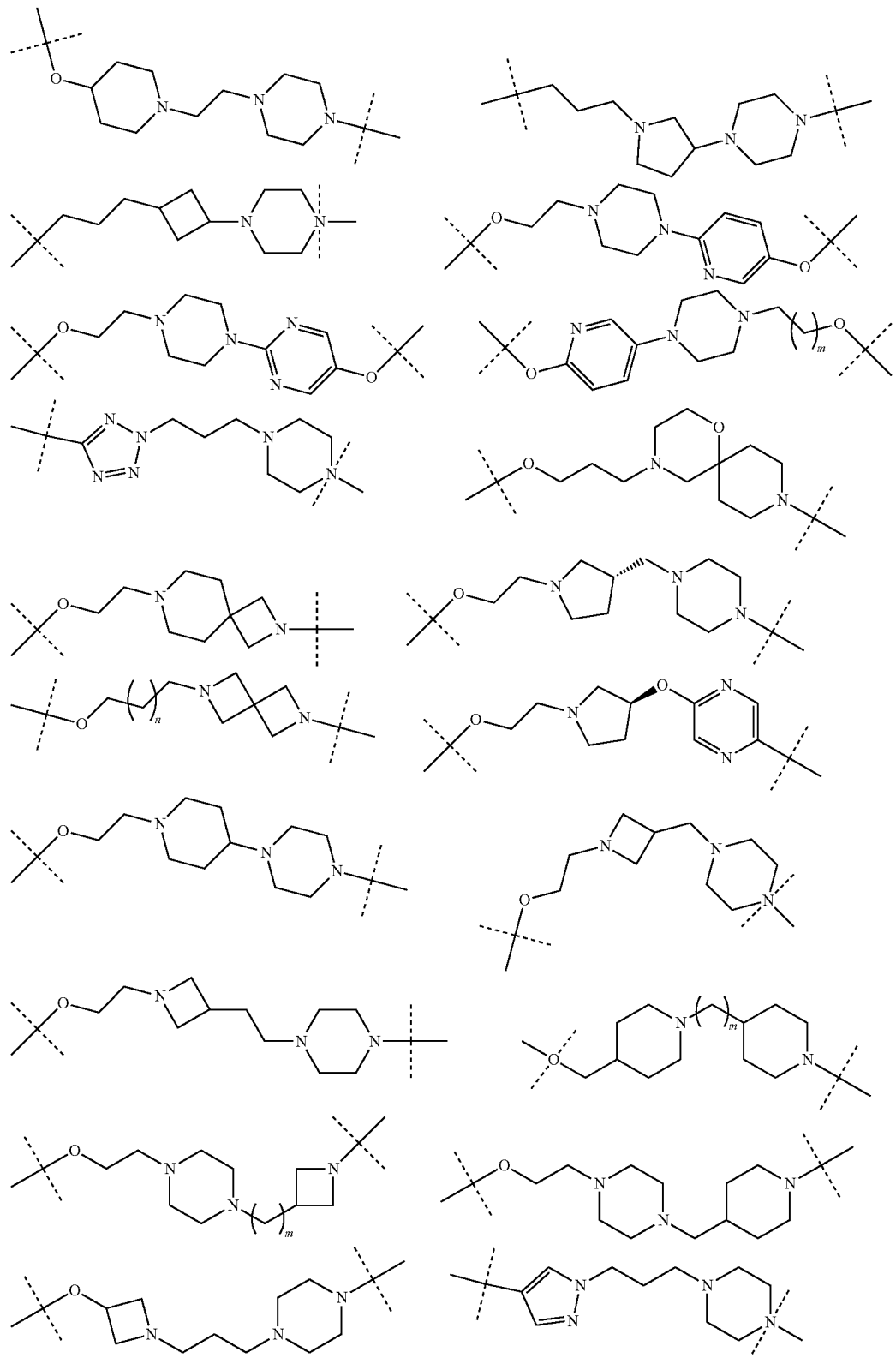

515
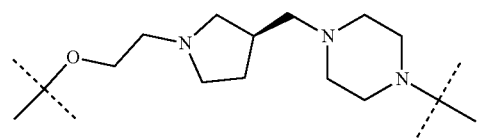
516
-continued
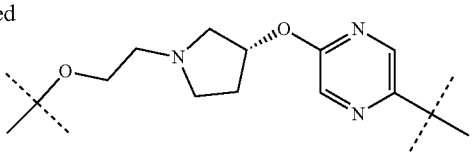
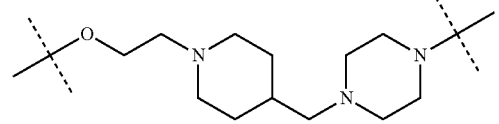
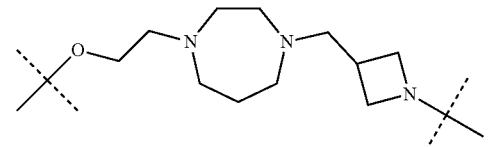
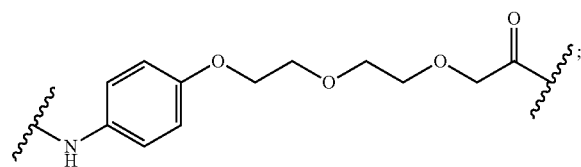
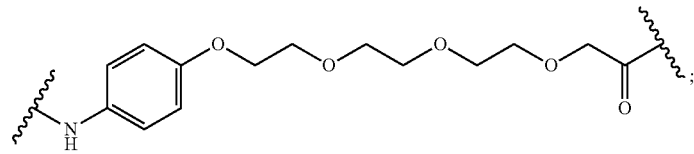
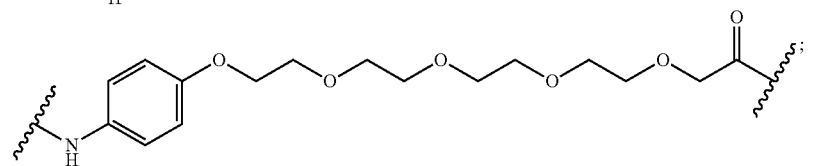
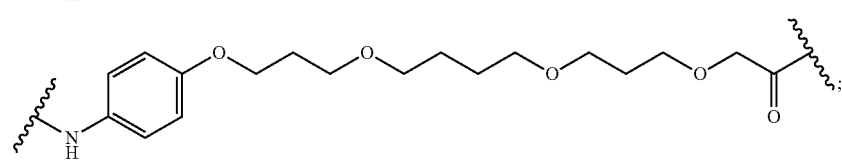
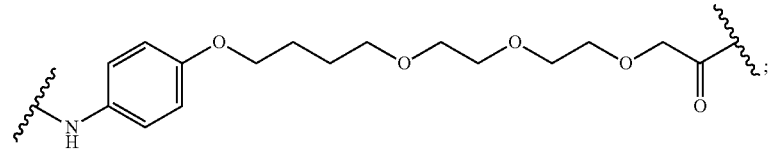
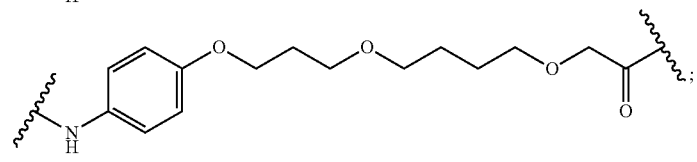
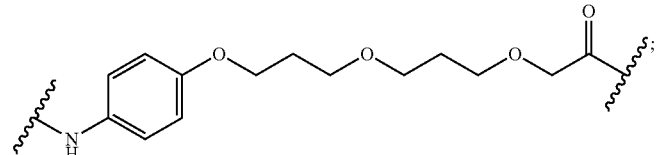
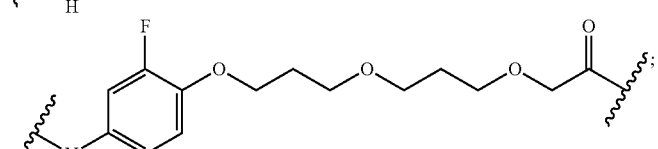
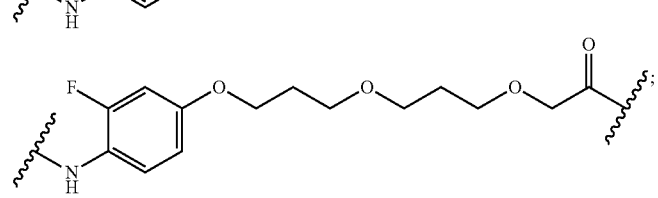

-continued
517
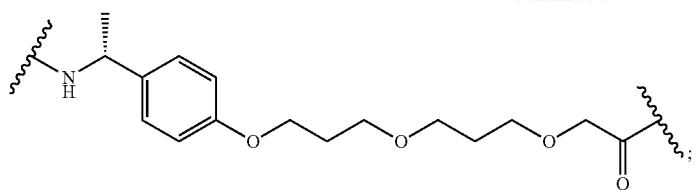
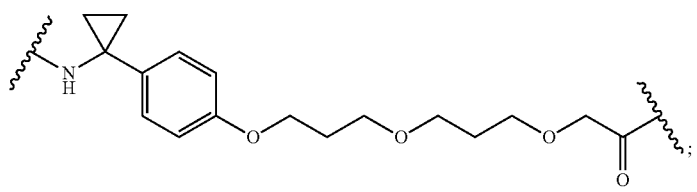
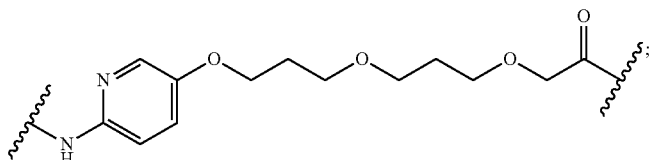
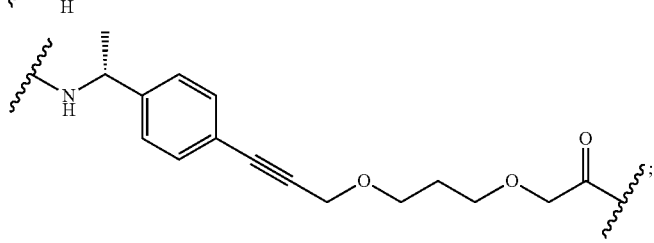
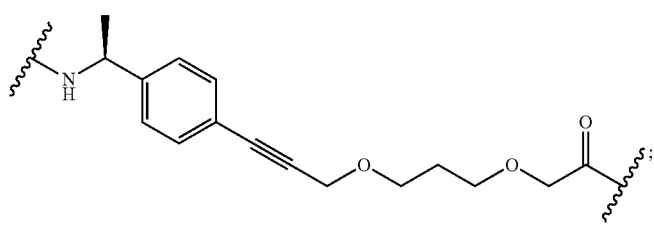
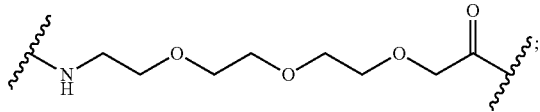
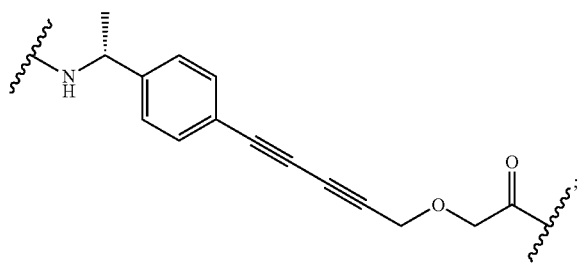
518
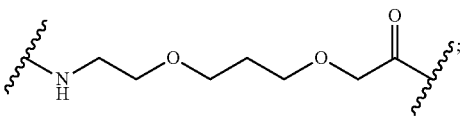
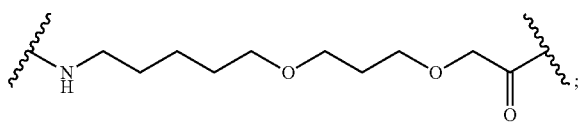
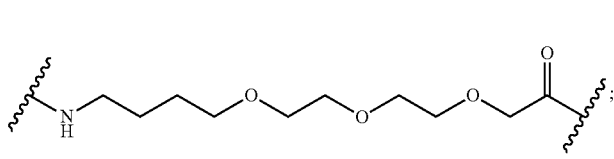
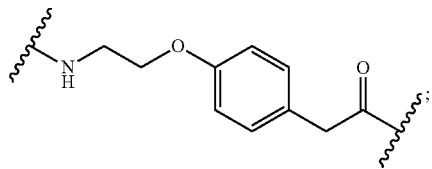

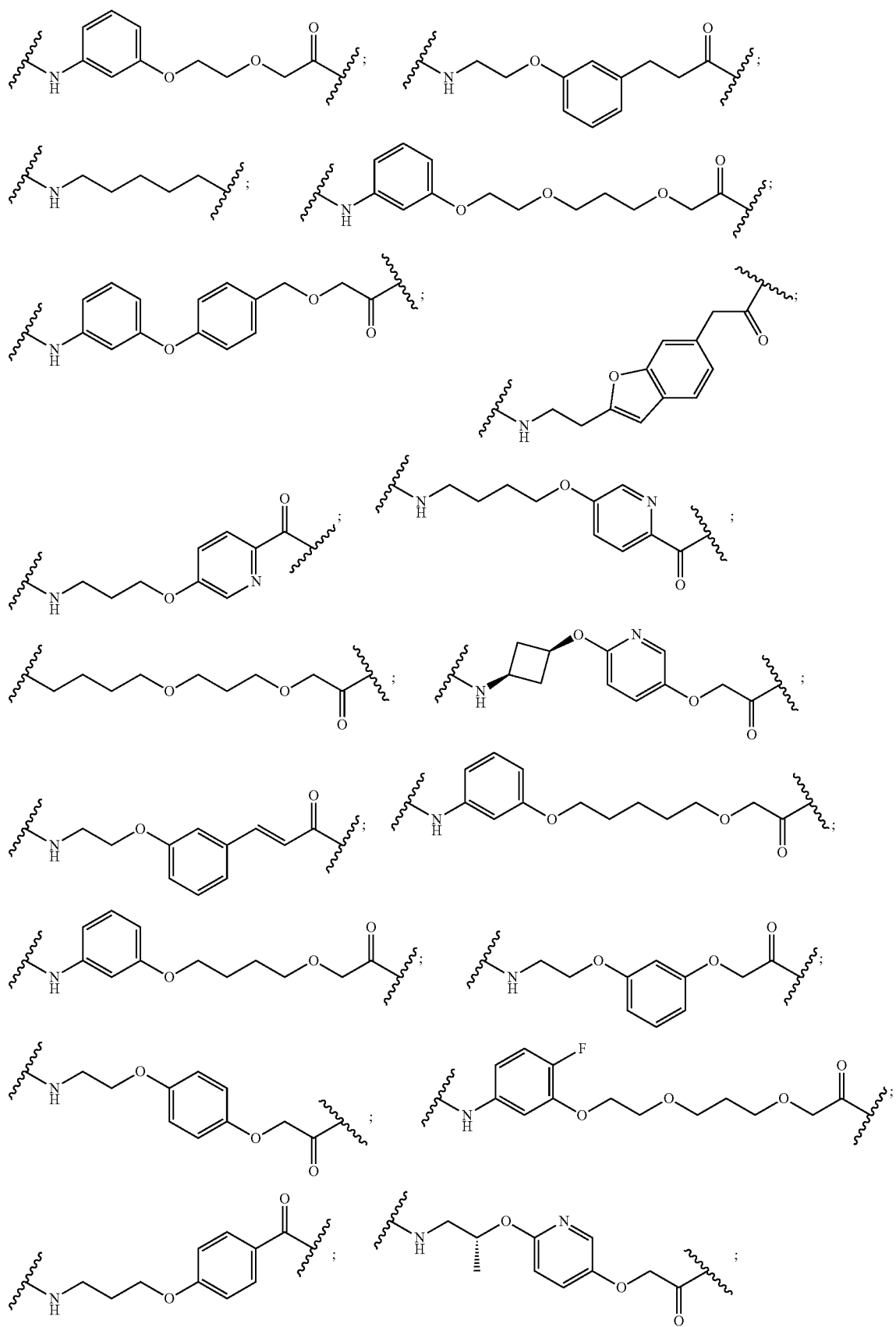

521
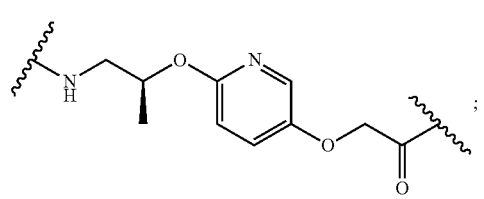
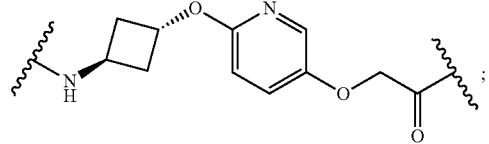
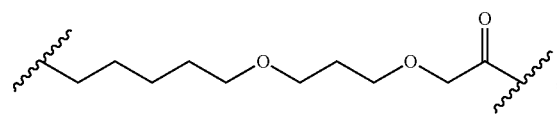
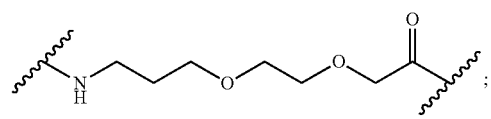
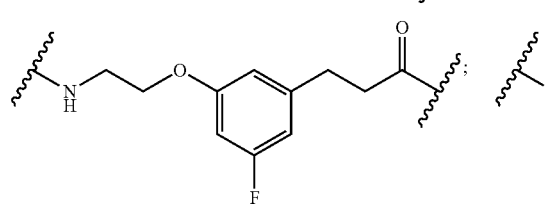
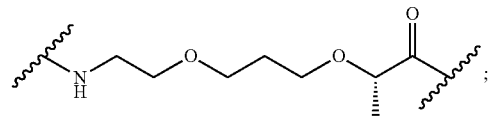
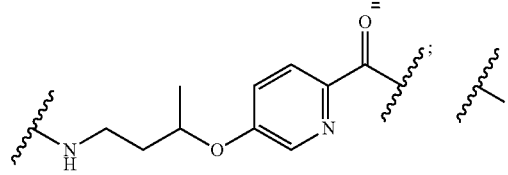
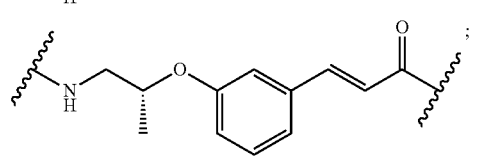
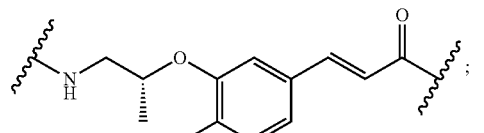
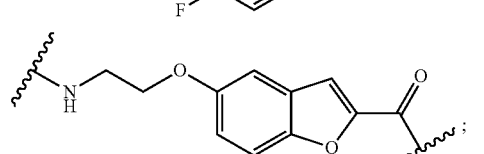
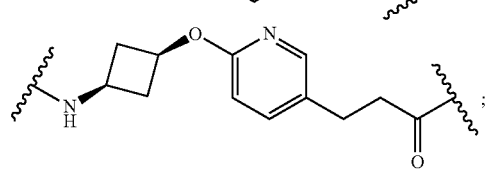
-continued
522
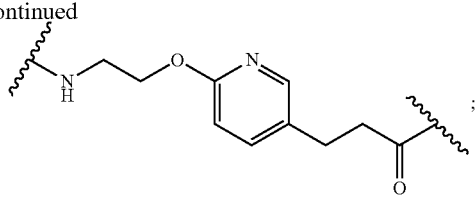
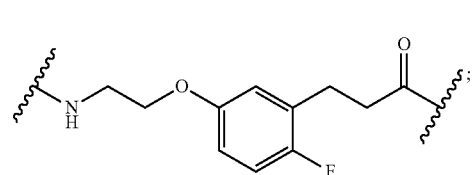
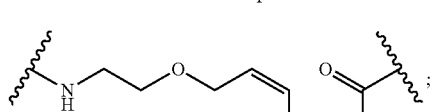
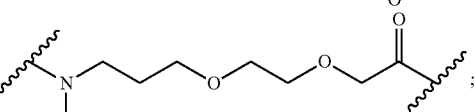
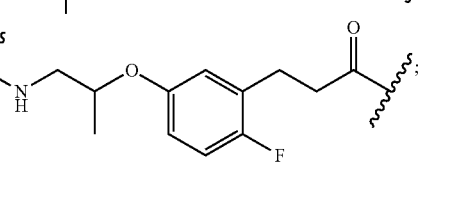
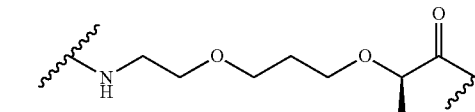
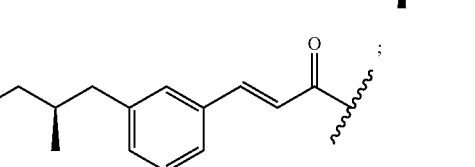
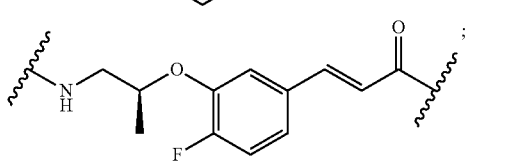
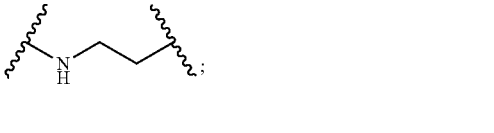
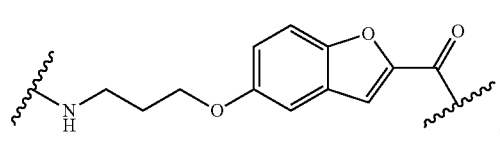
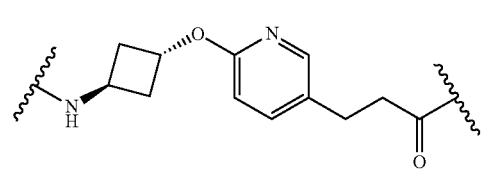

-continued
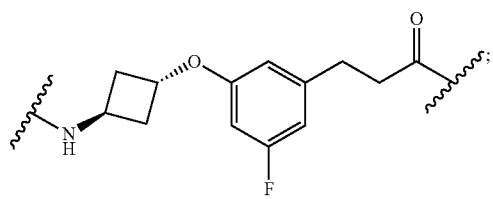
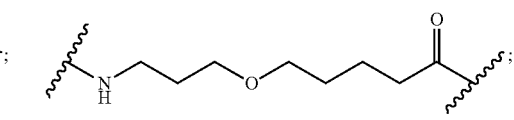
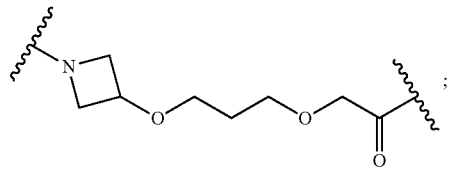
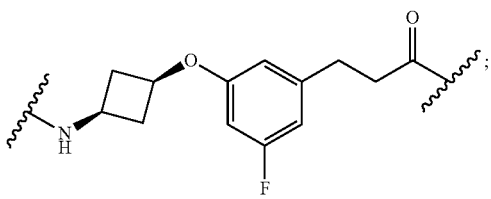
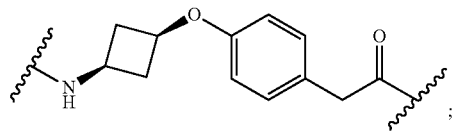
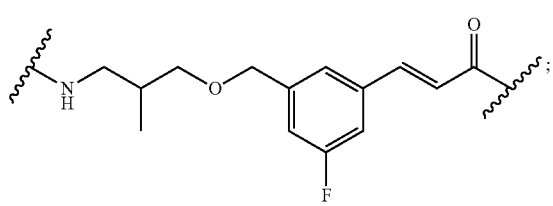
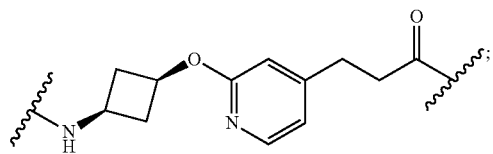
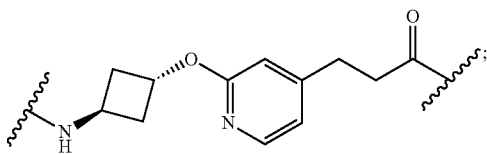
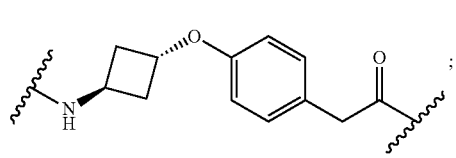
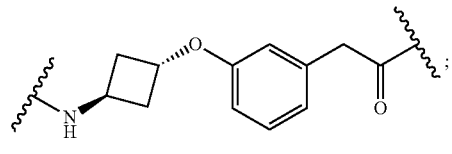
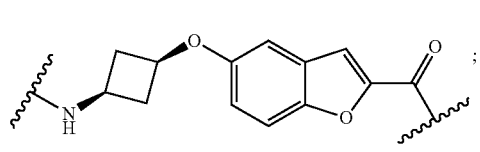
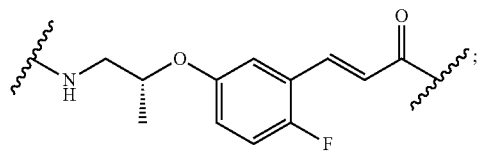
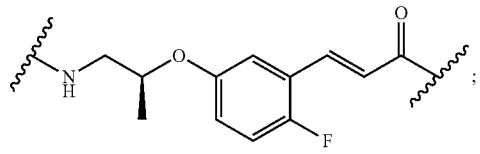
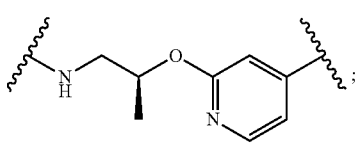
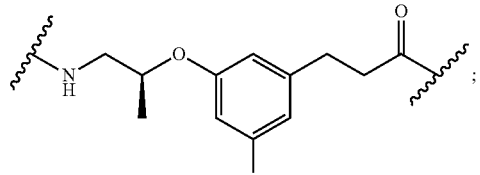
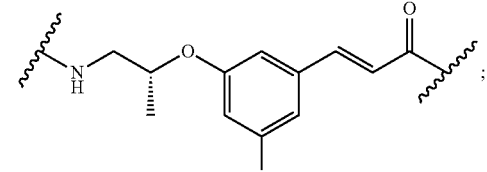
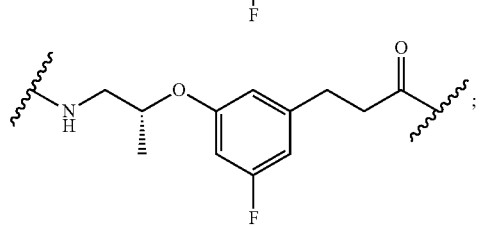
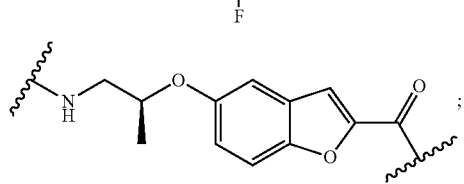

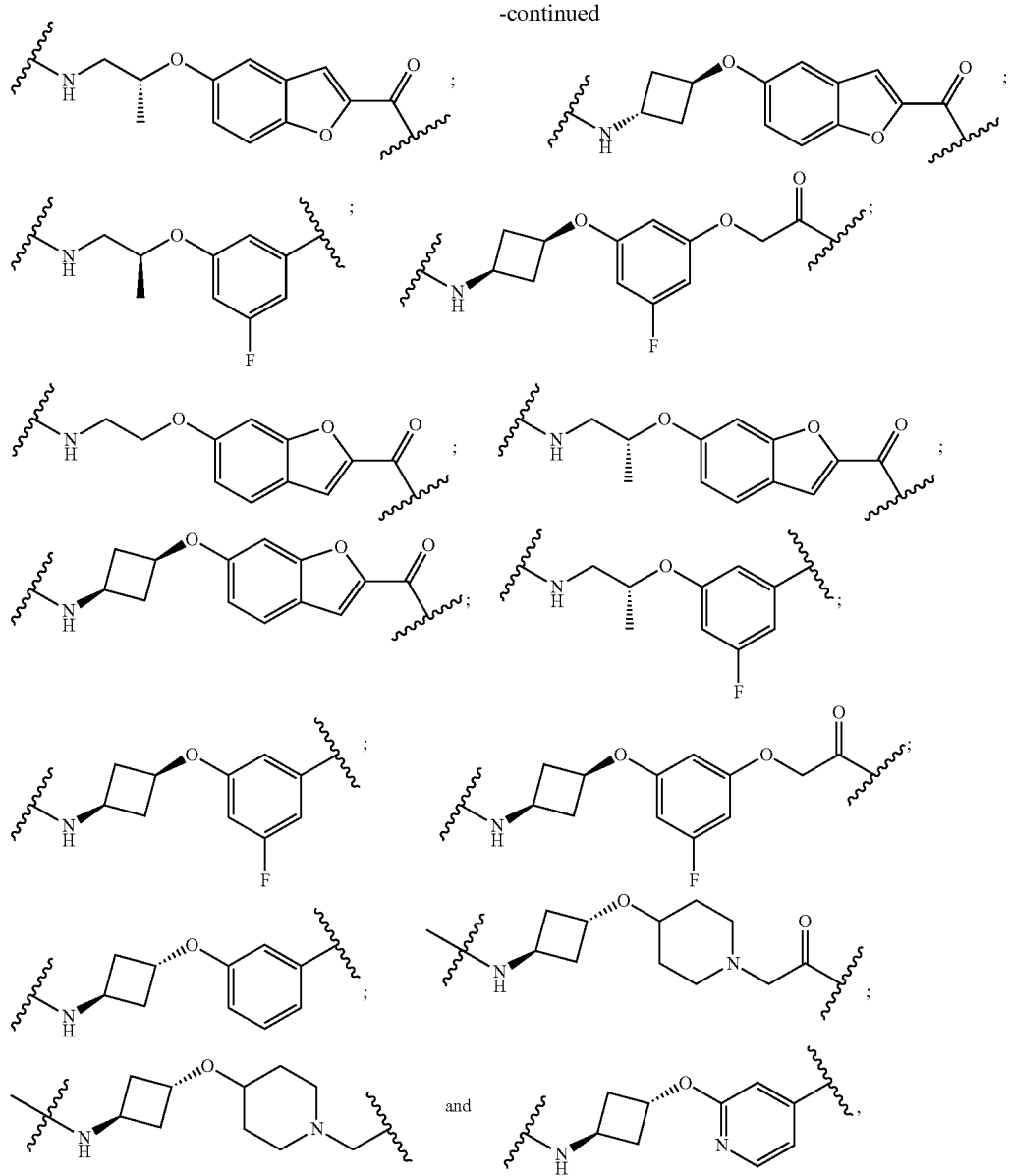
wherein each m and n is independently selected from 0, 1, 2, 3, 4, 5, 6, 7, 8, 9, 10, 11, 12, 13, 14, 15, 16, 17, 18, 19, 20.
In any aspect or embodiment described herein, the $A^L$ is selected from the group consisting of:
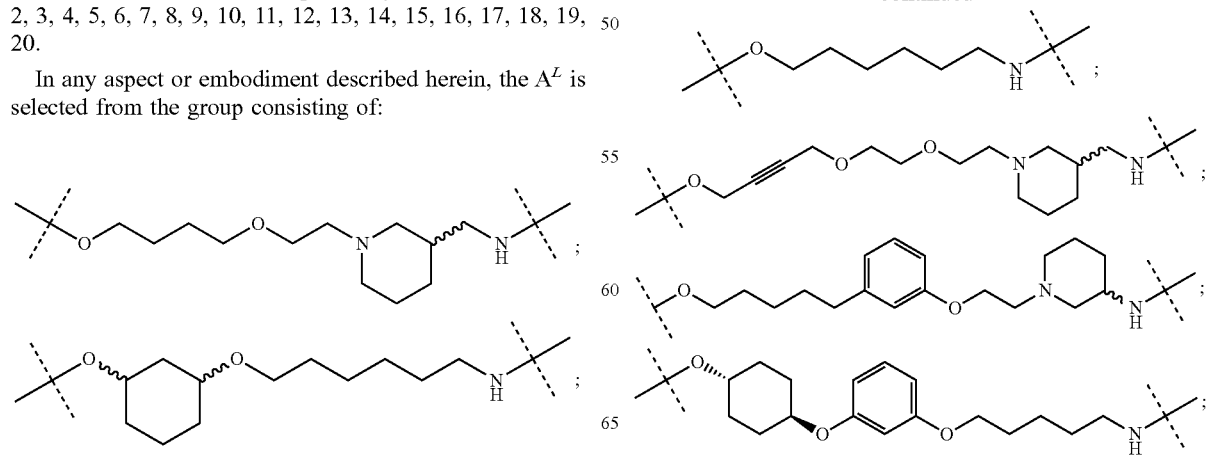

527
-continued
528
-continued
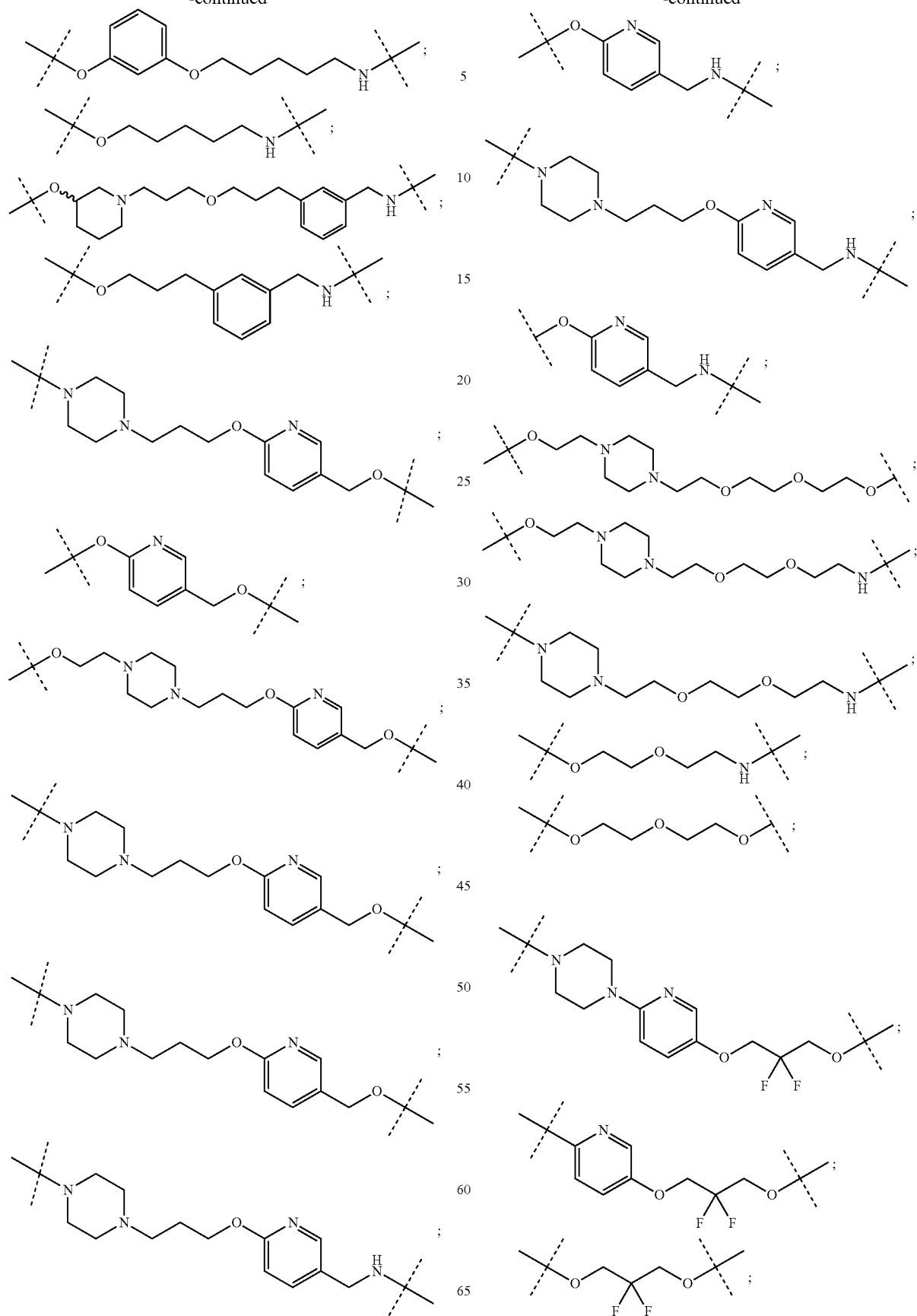

529
-continued
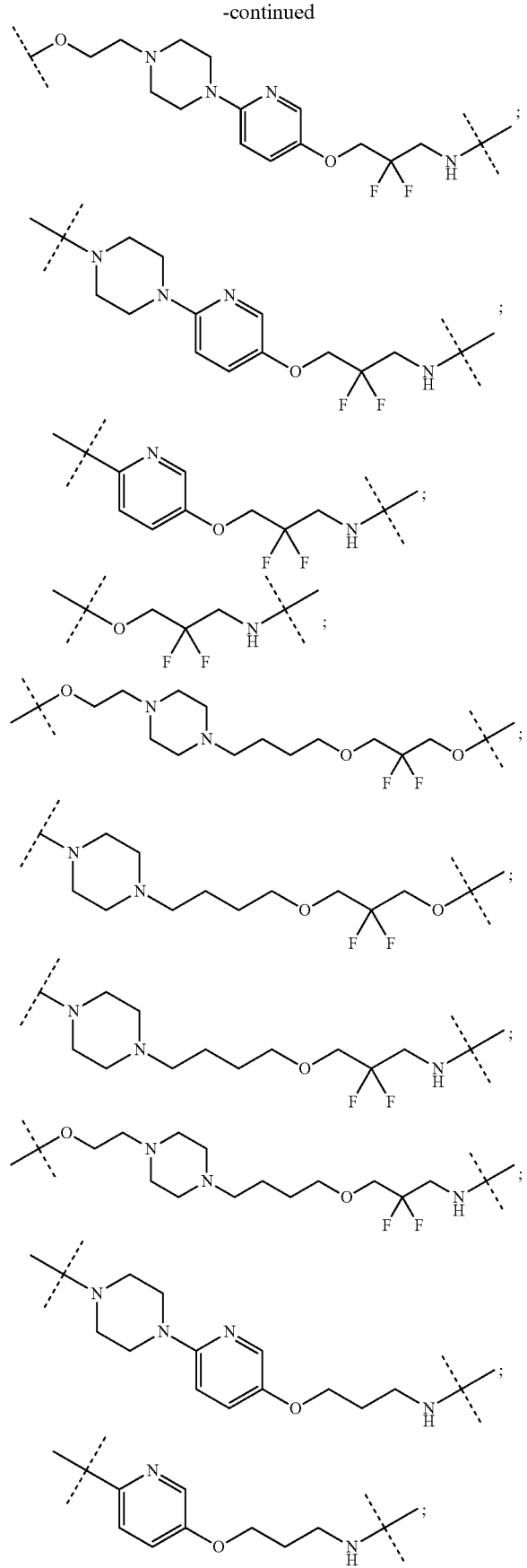
530
-continued
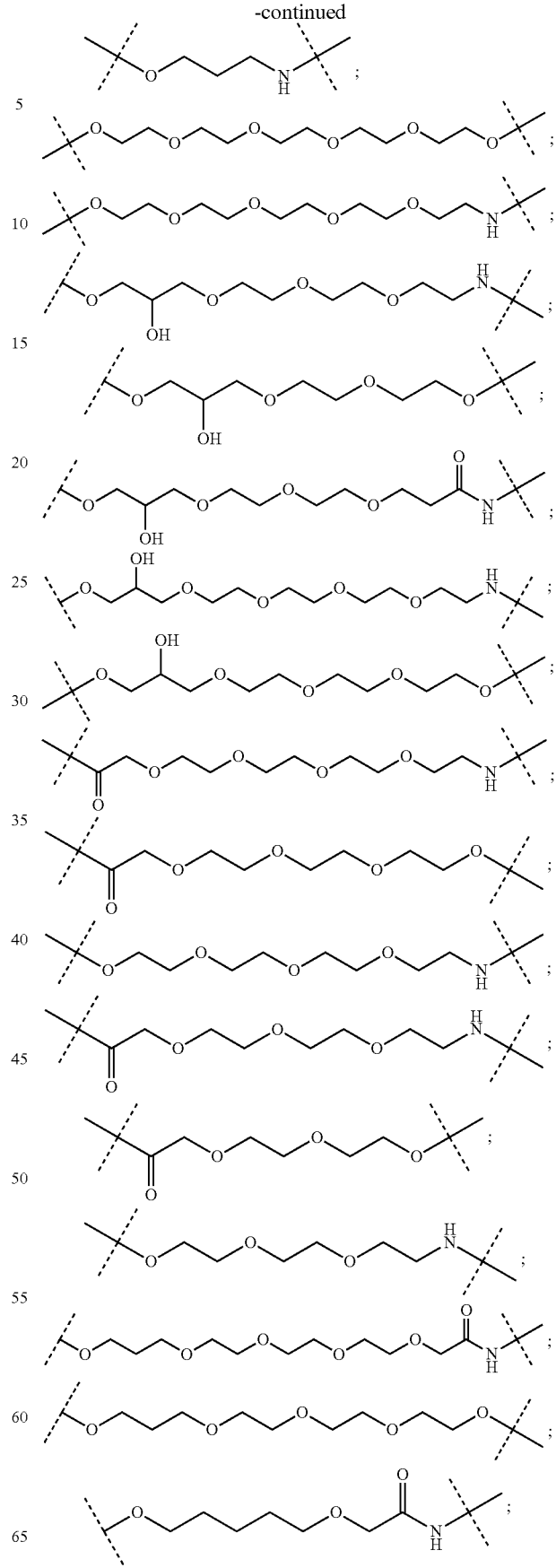

531
-continued
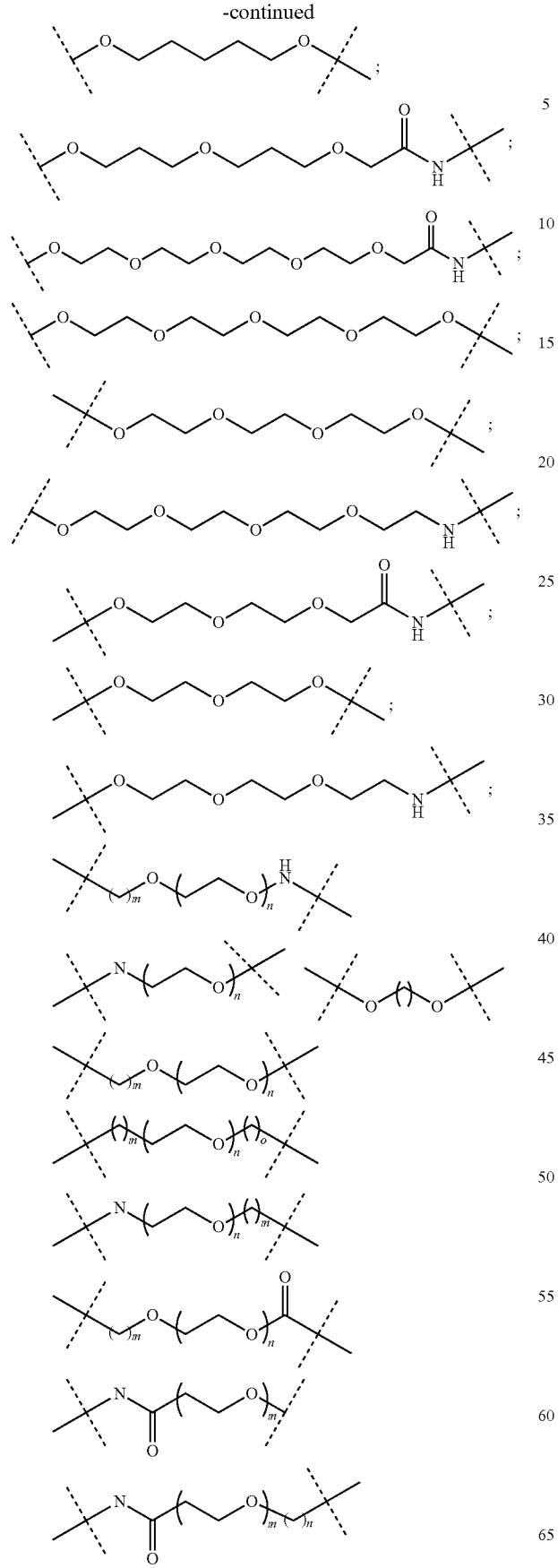
532
-continued
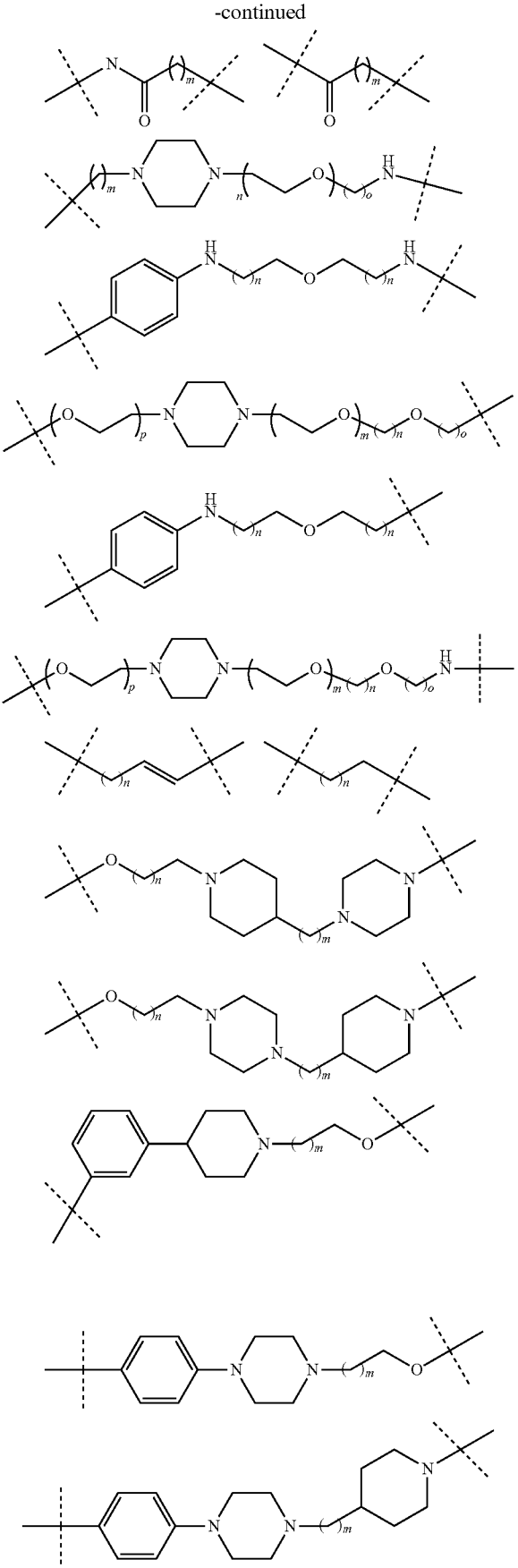

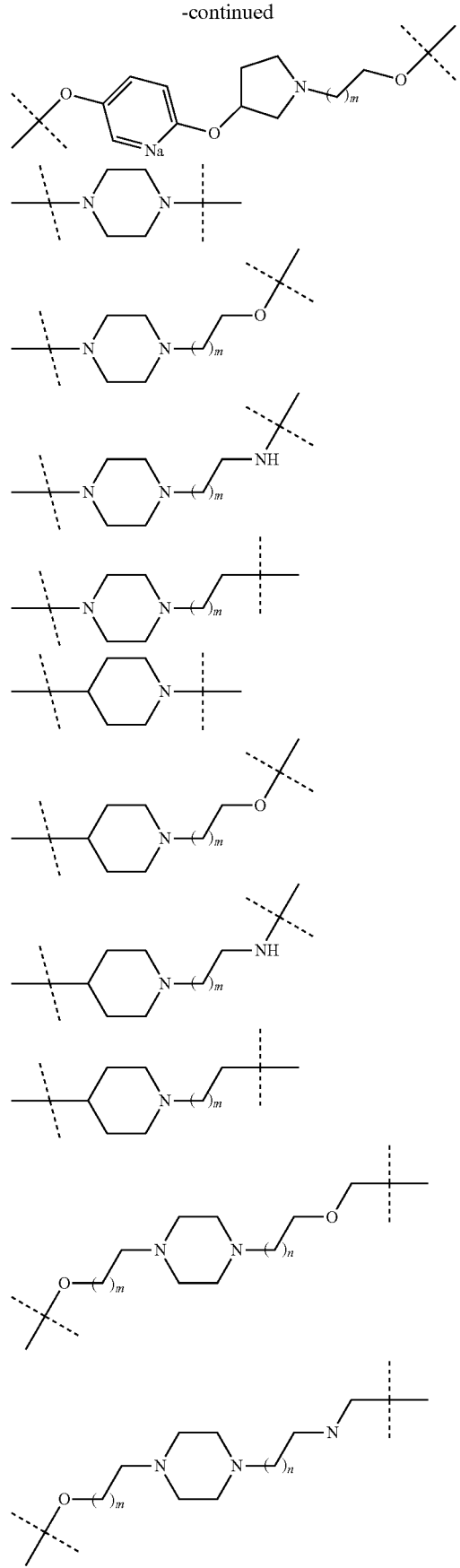
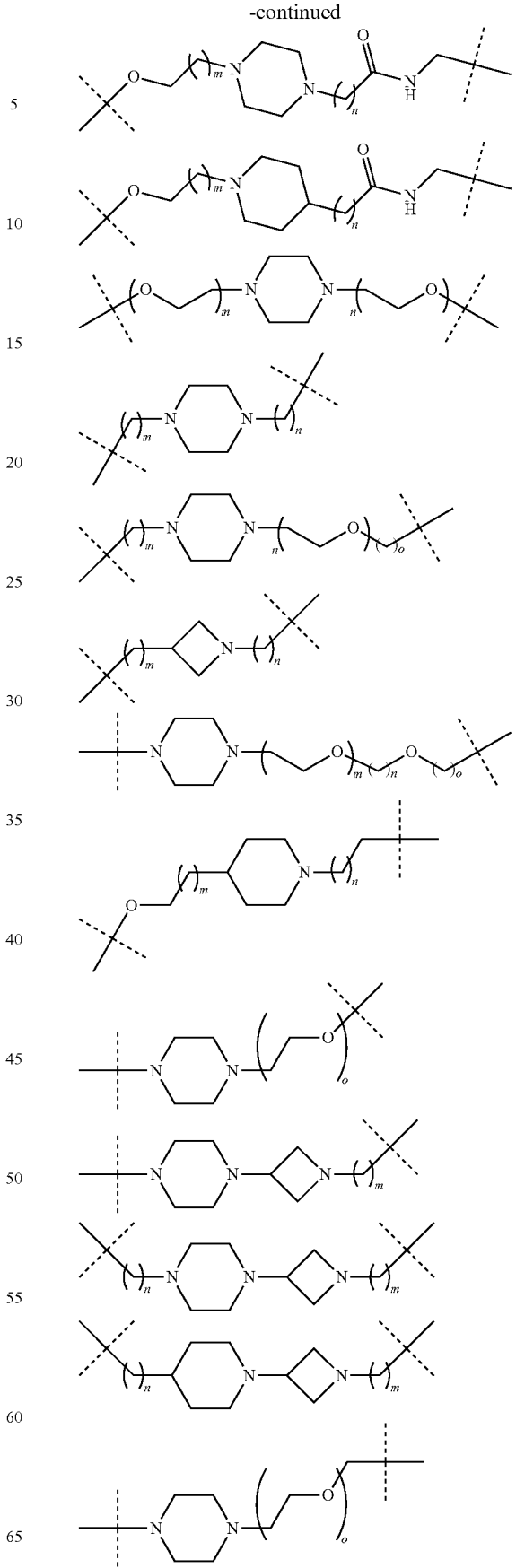

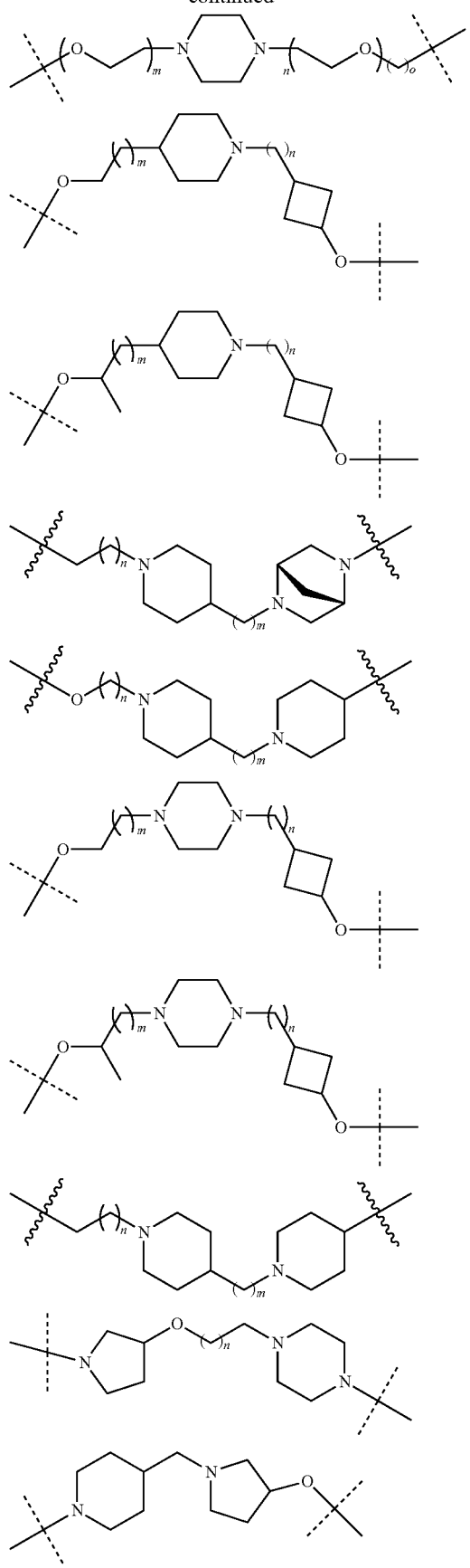
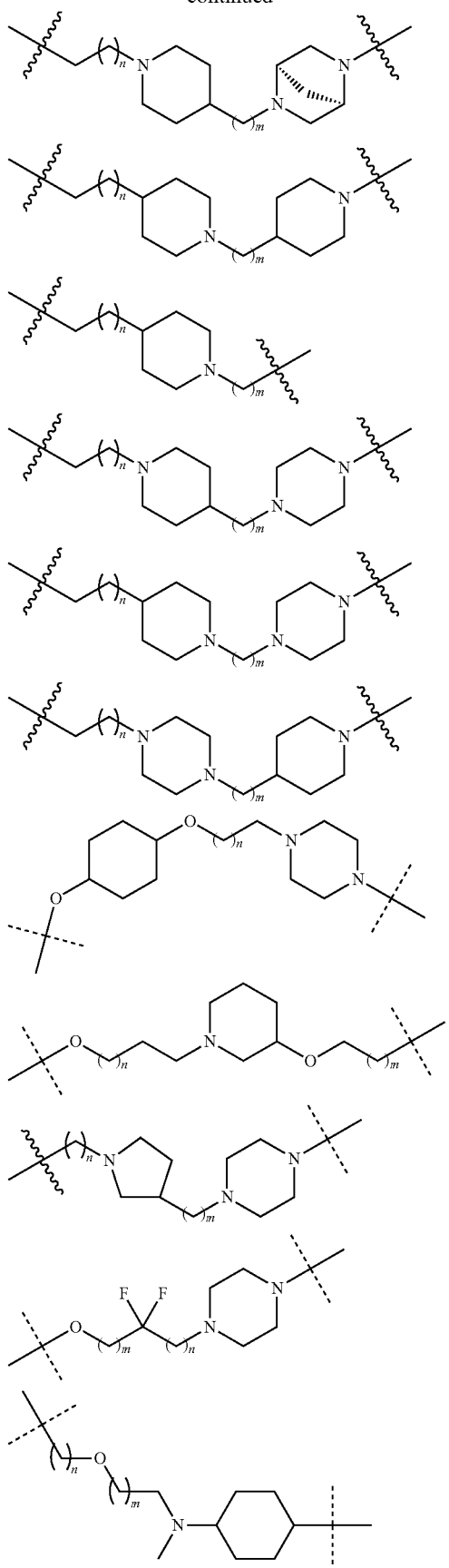

537
-continued
538
-continued
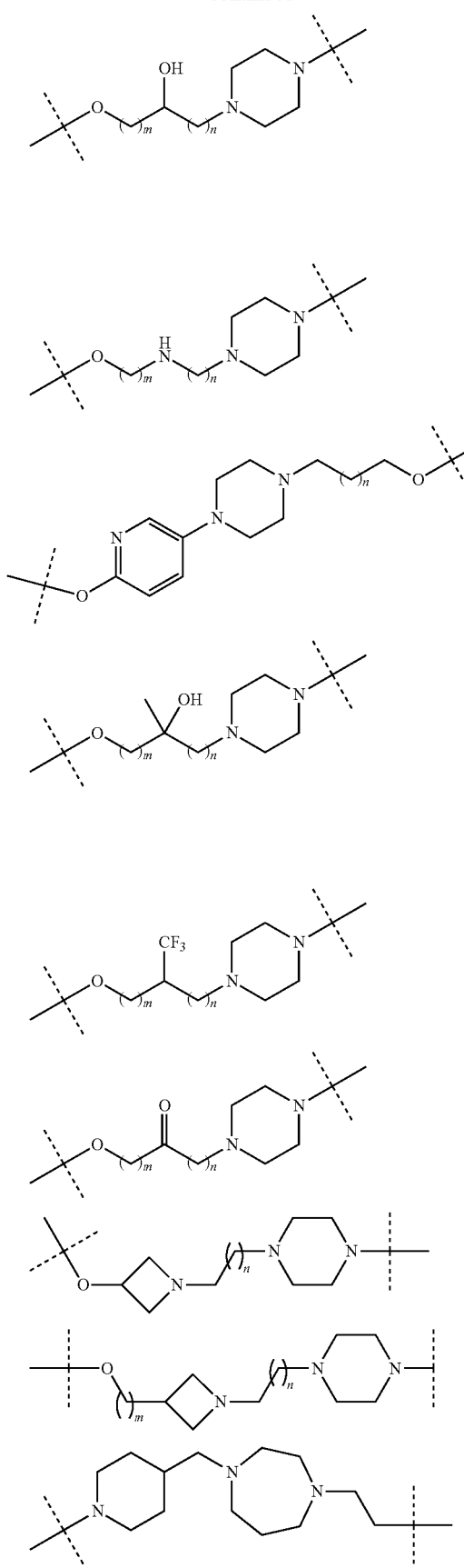
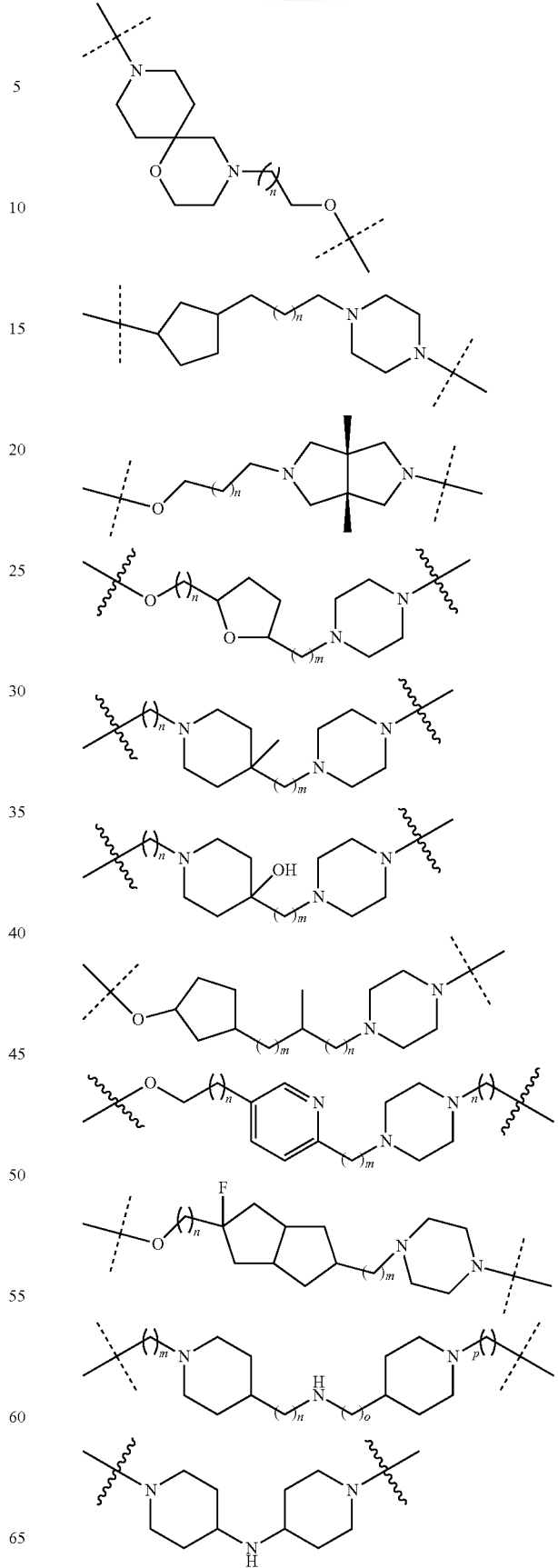

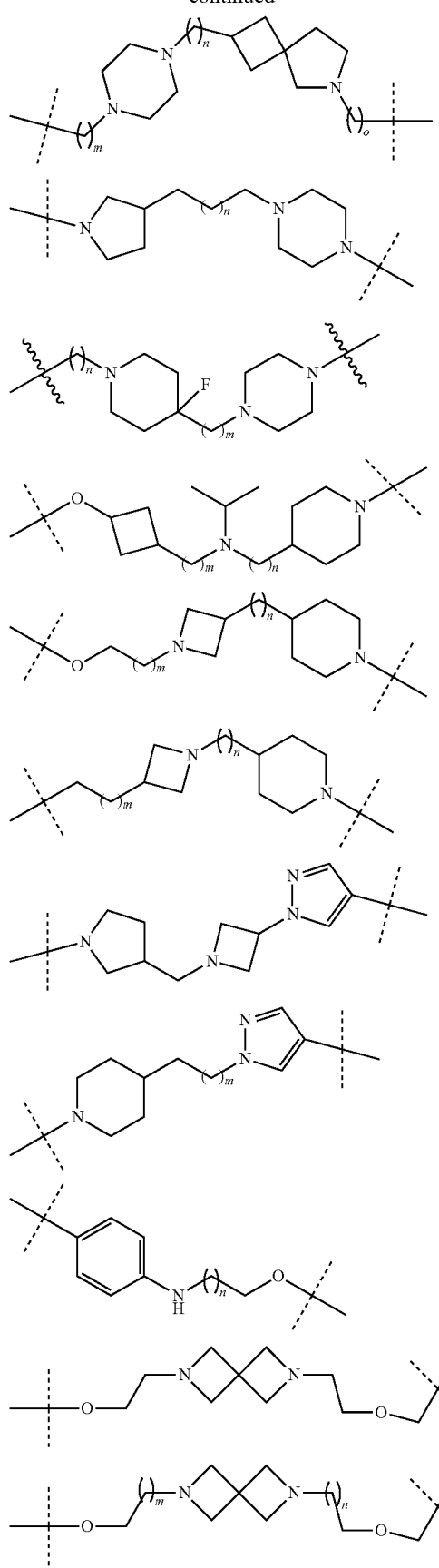
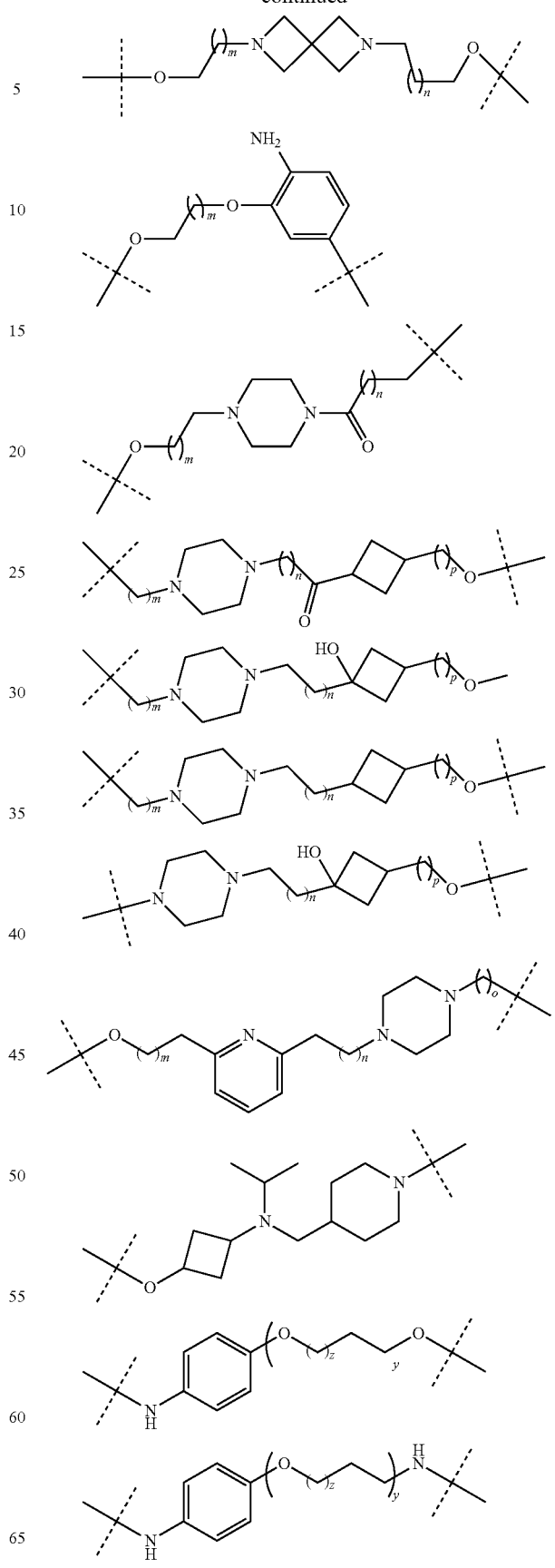

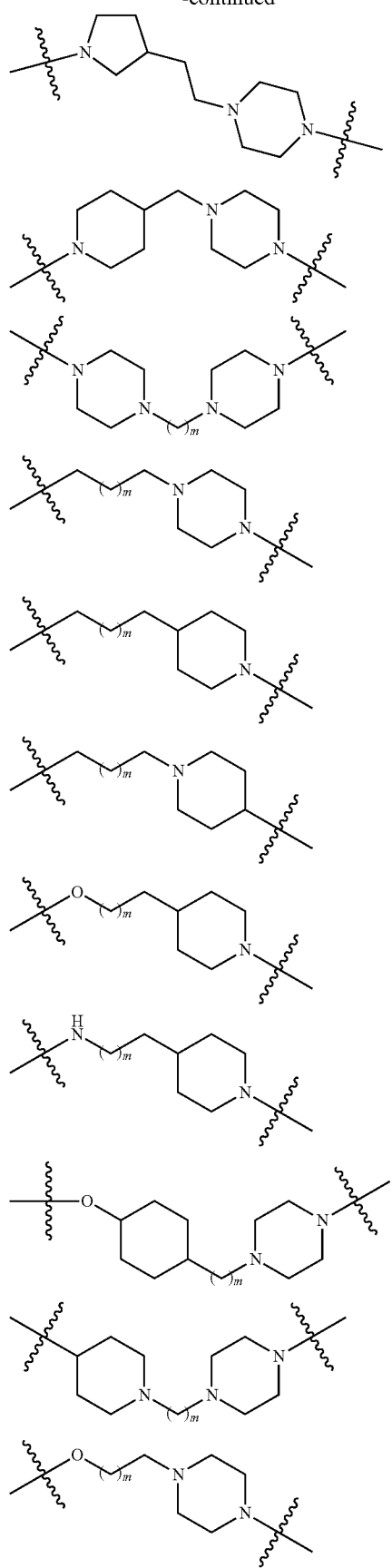
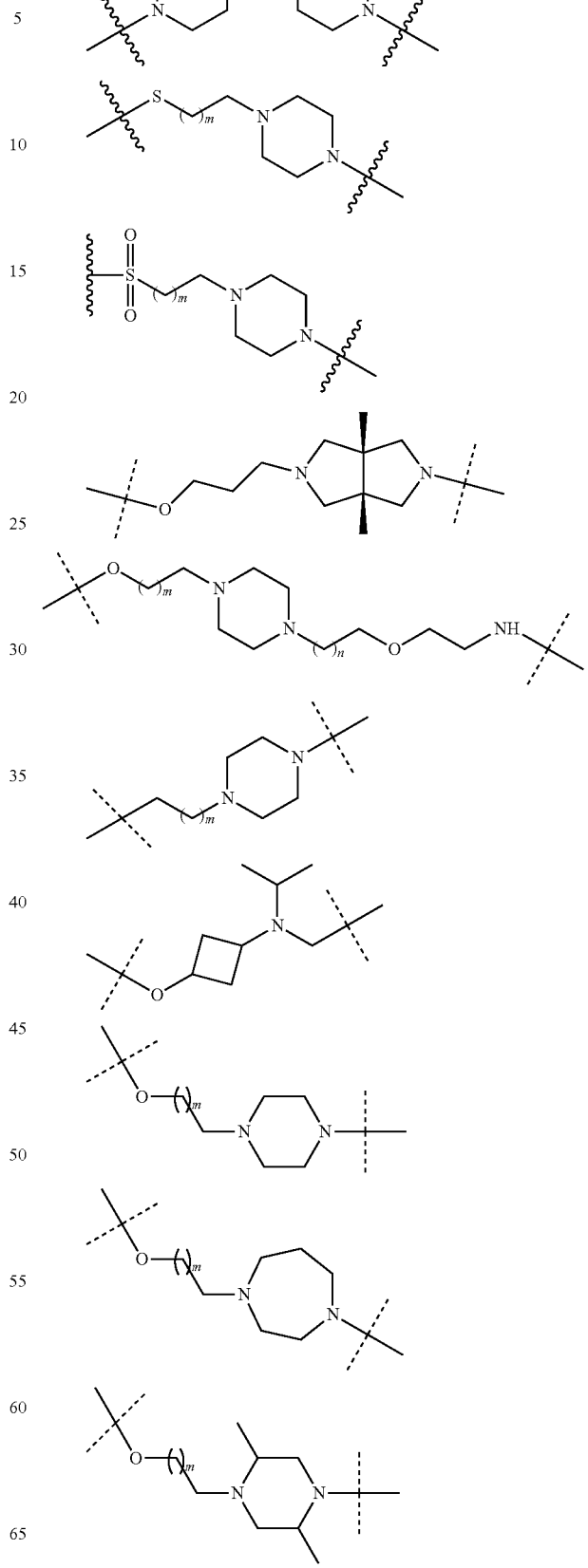

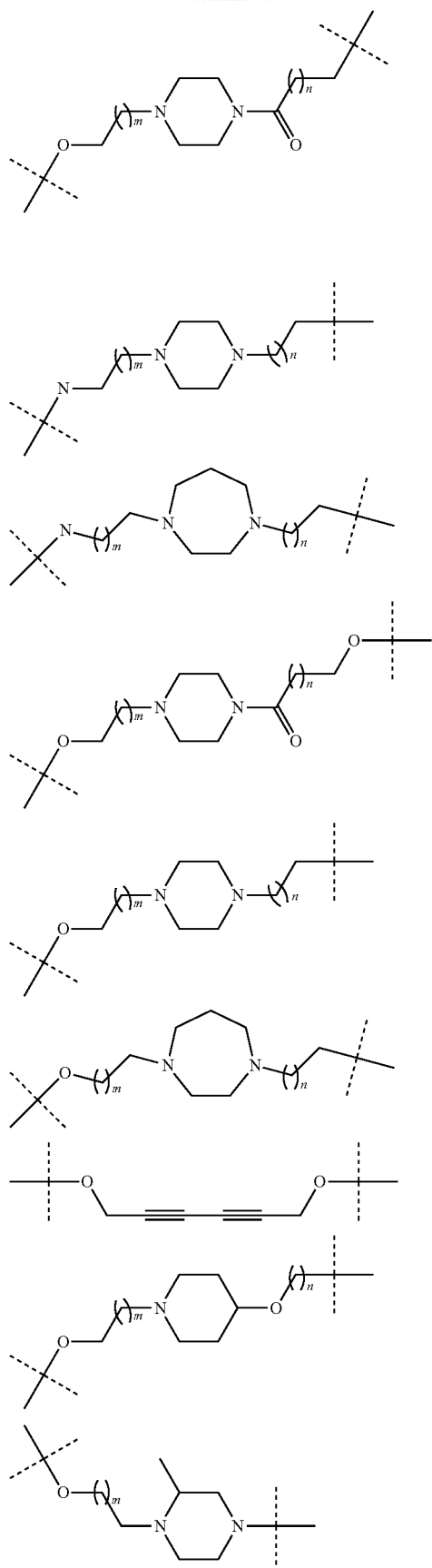
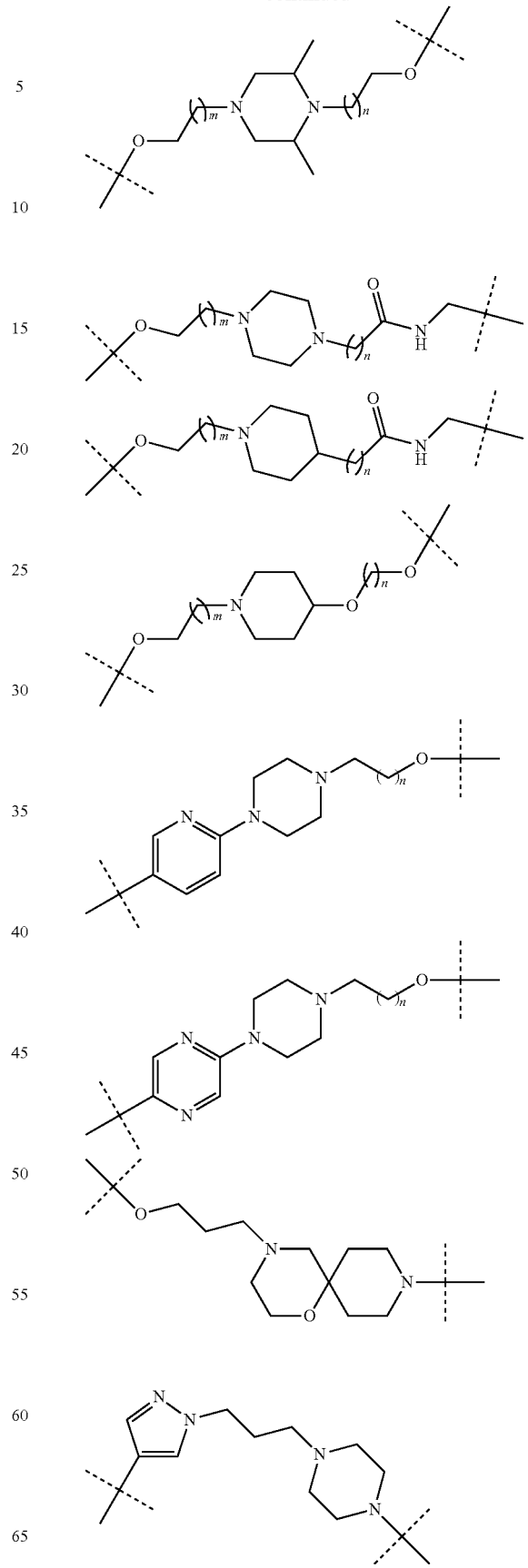

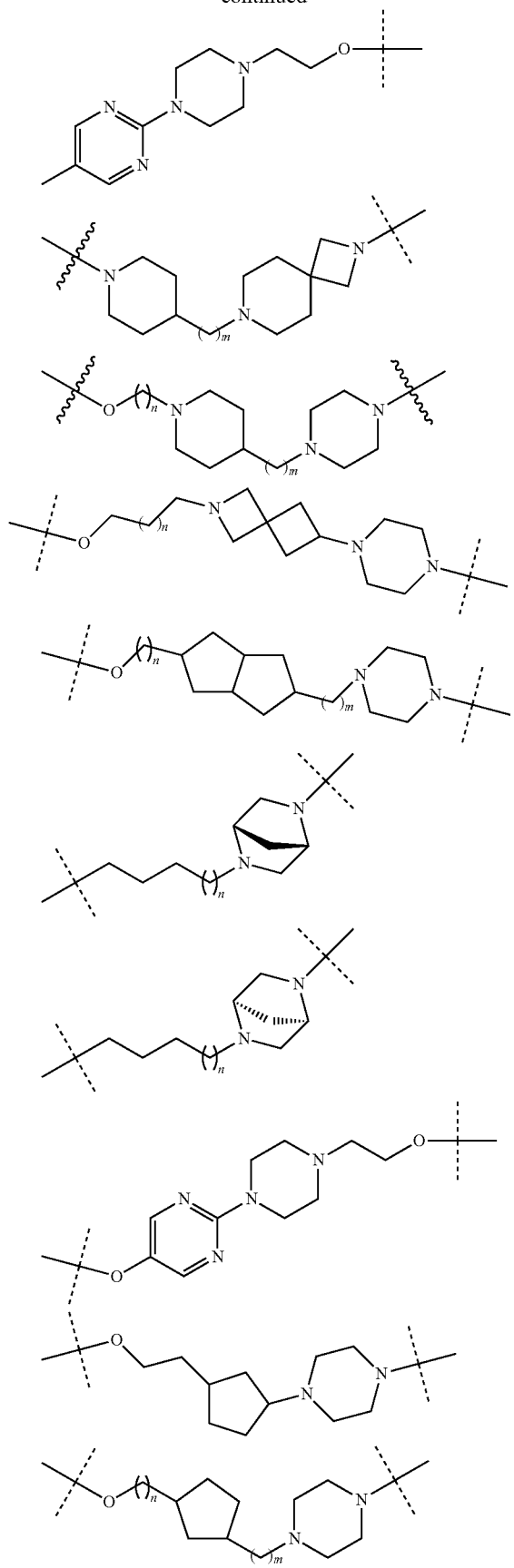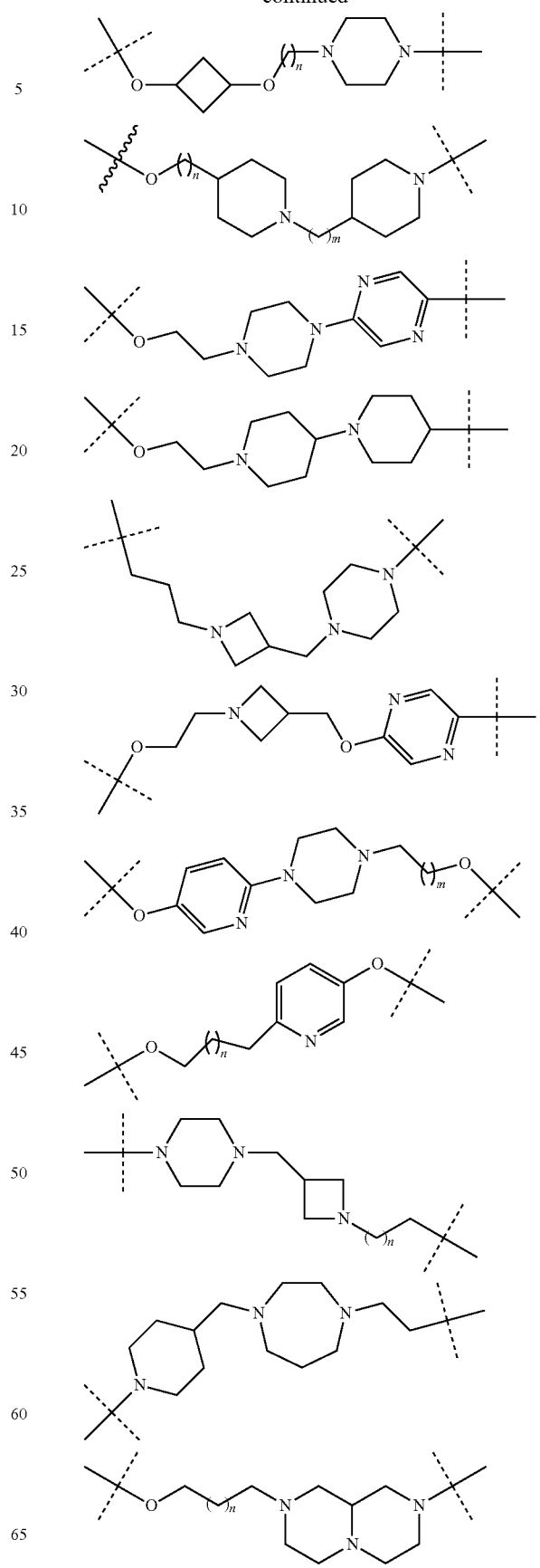

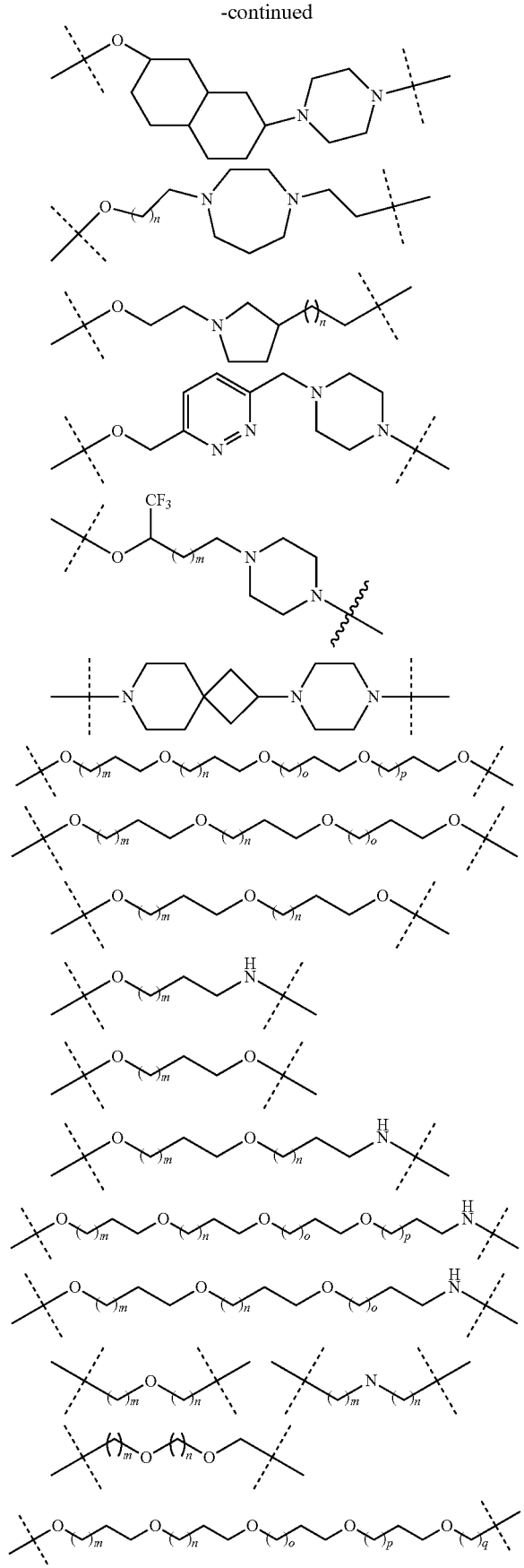
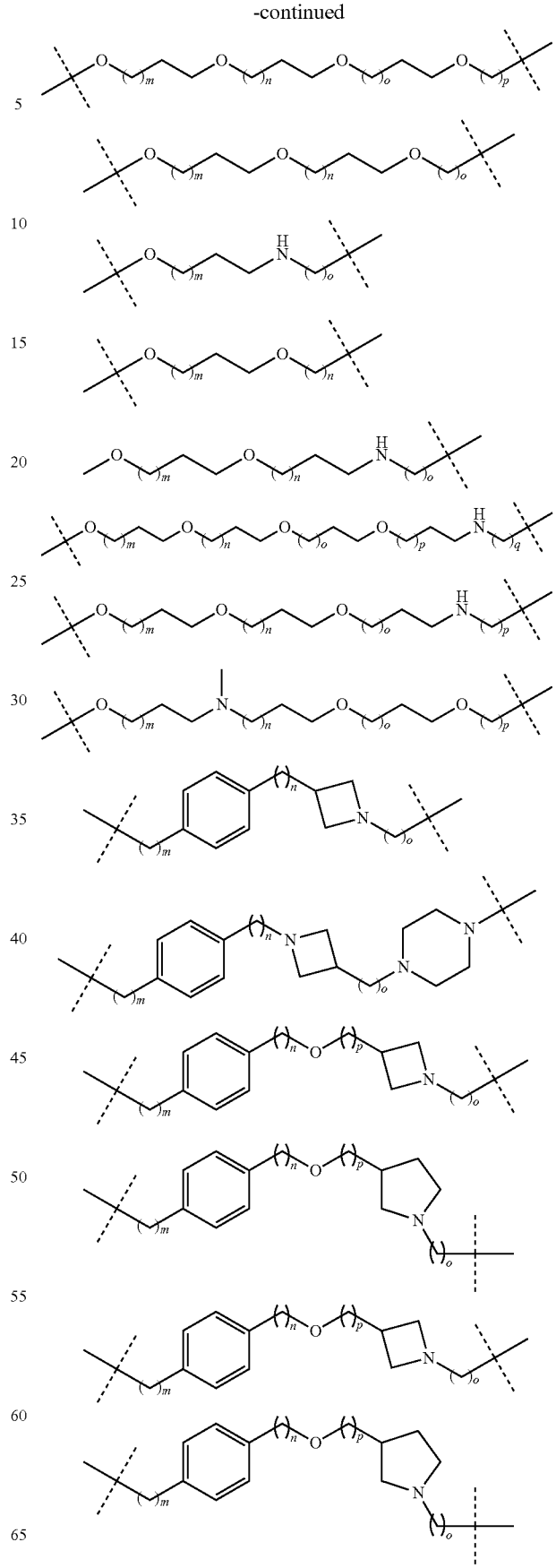

549
-continued
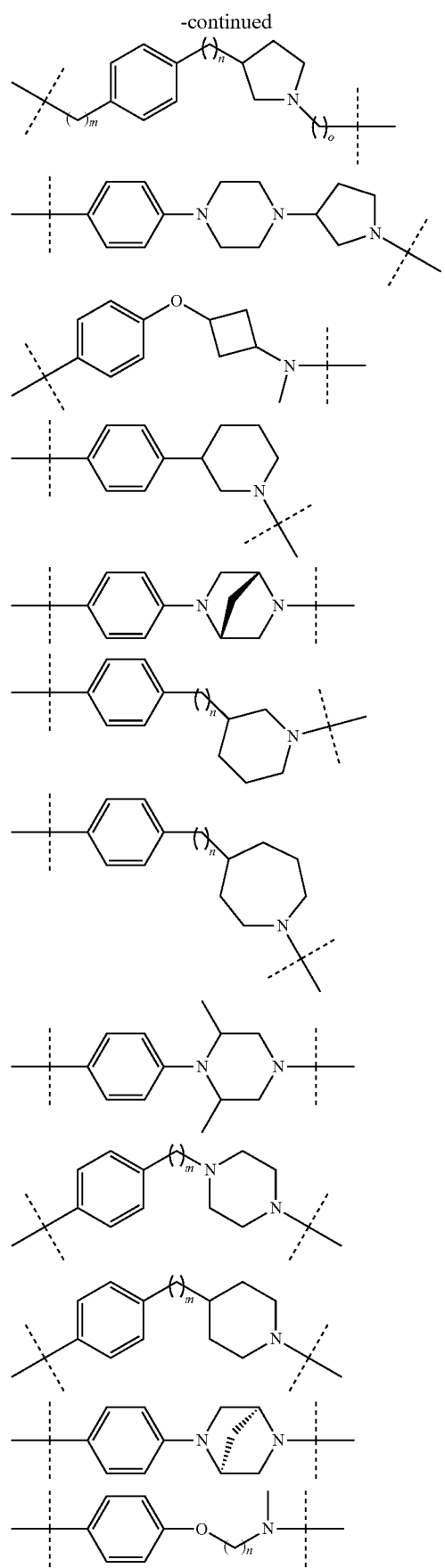
550
-continued
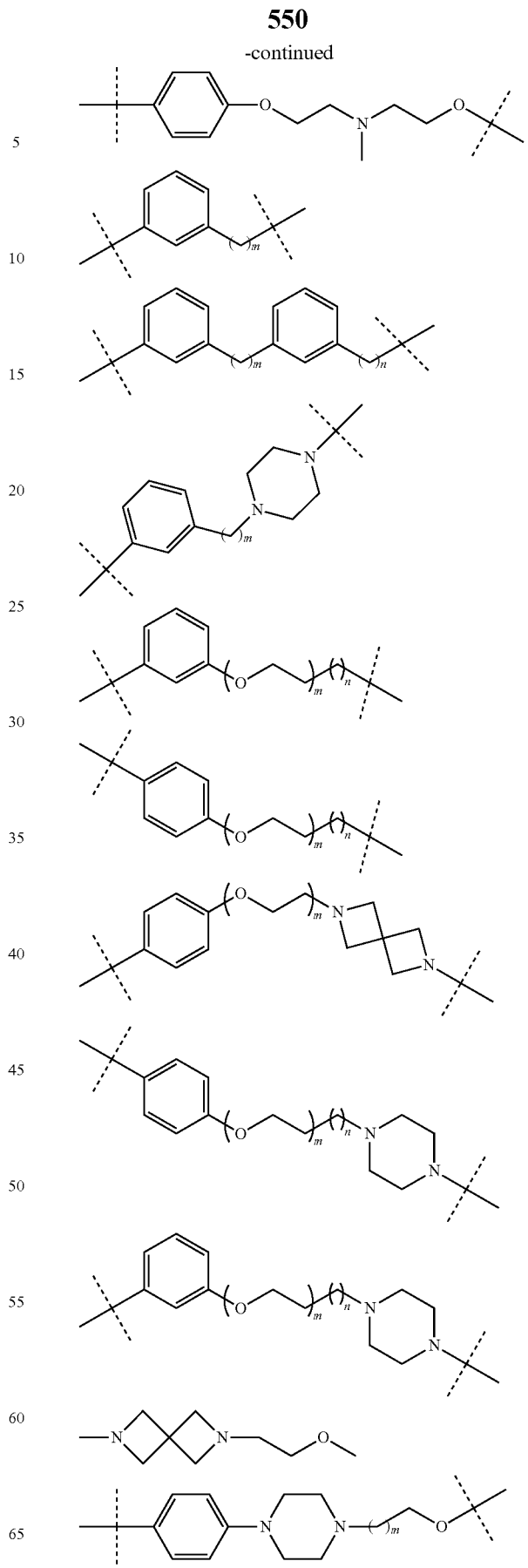

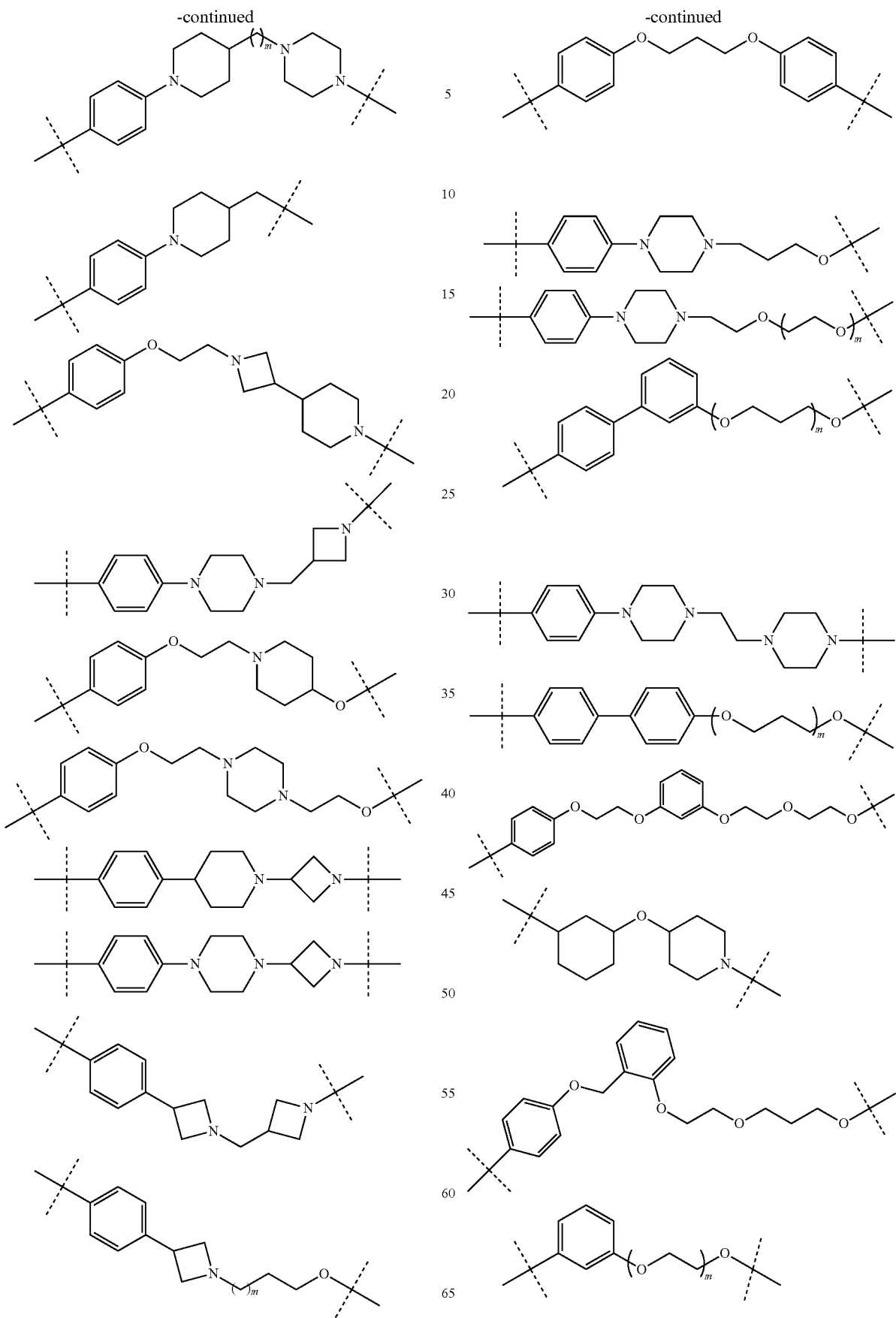

553 554
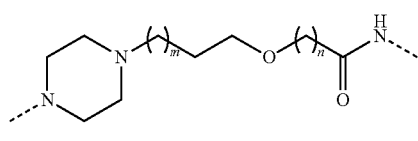 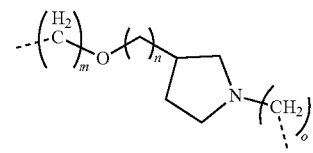 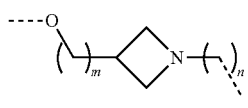
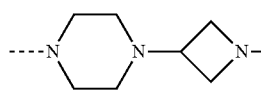 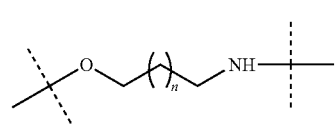 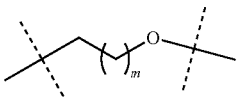
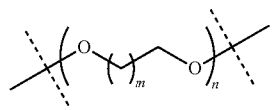 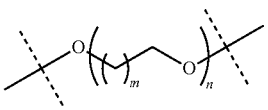 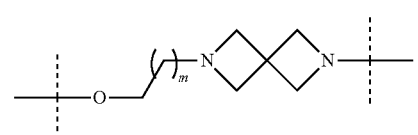
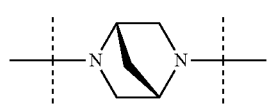 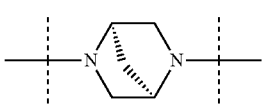 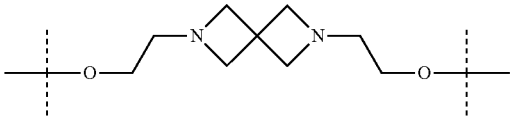
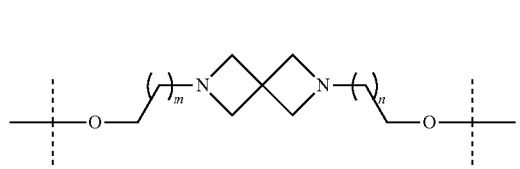 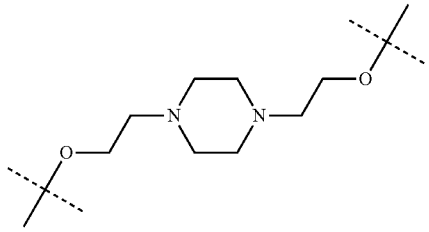
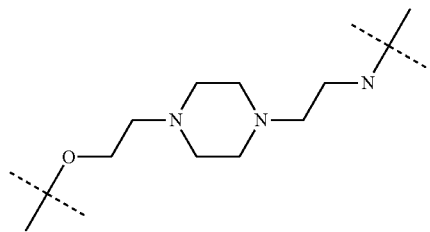 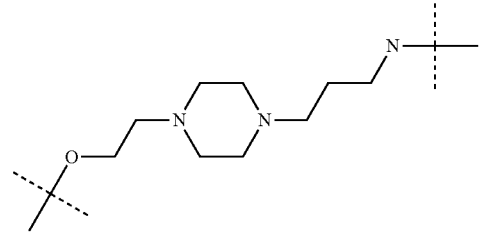
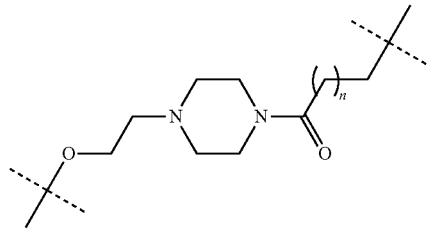 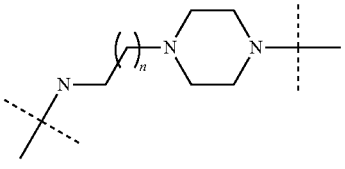
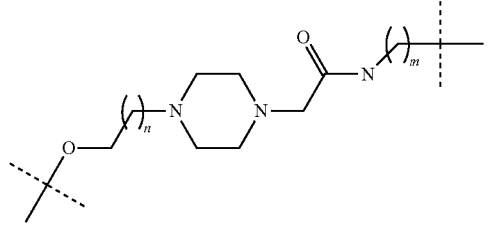 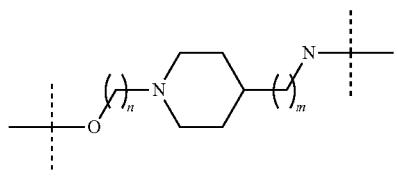
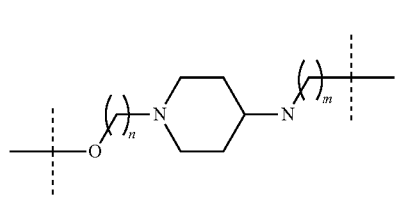 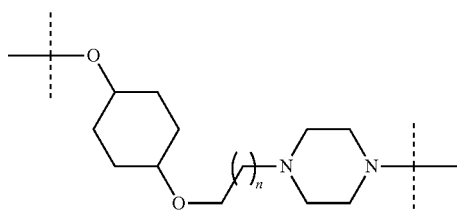

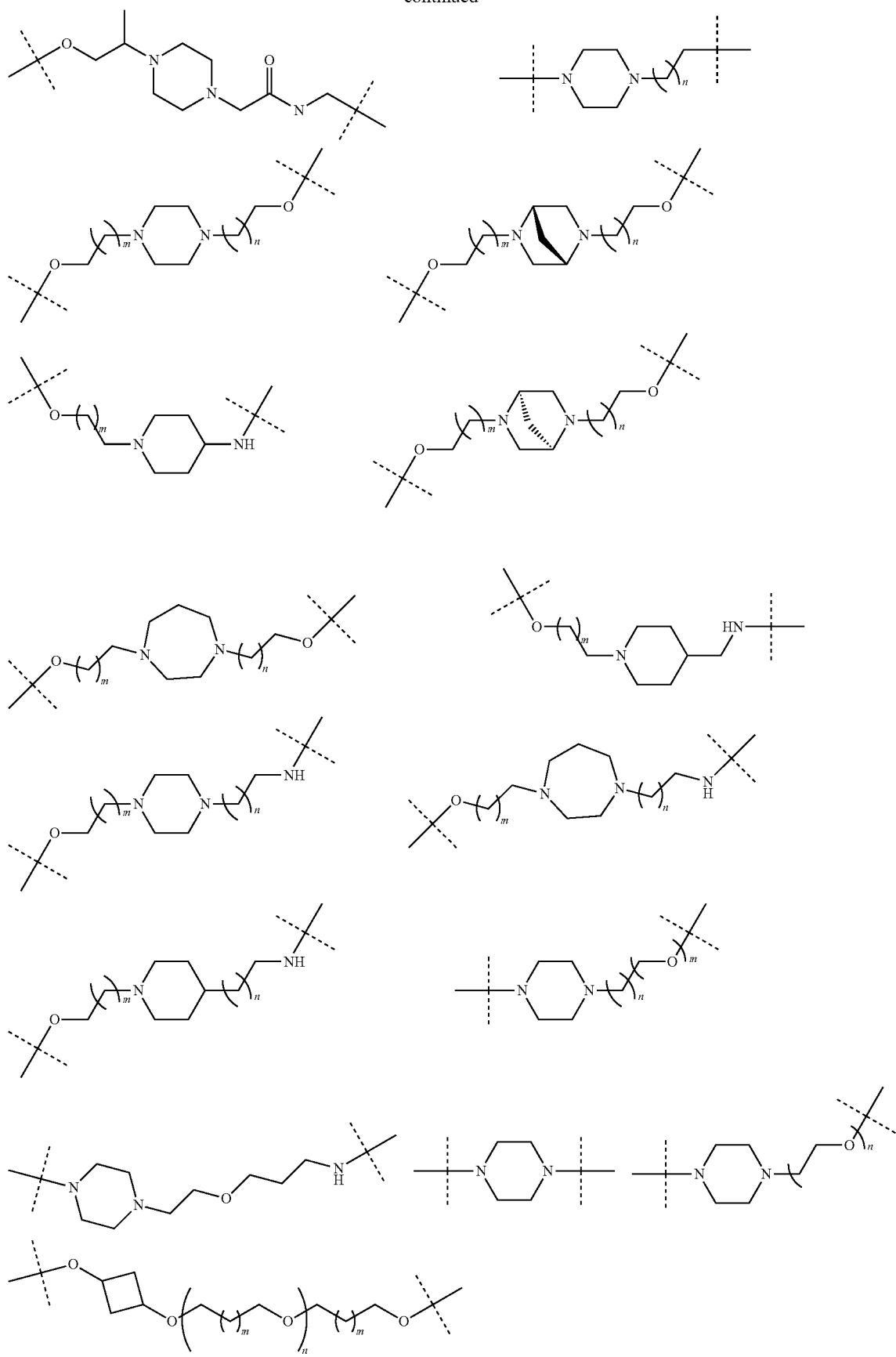

-continued
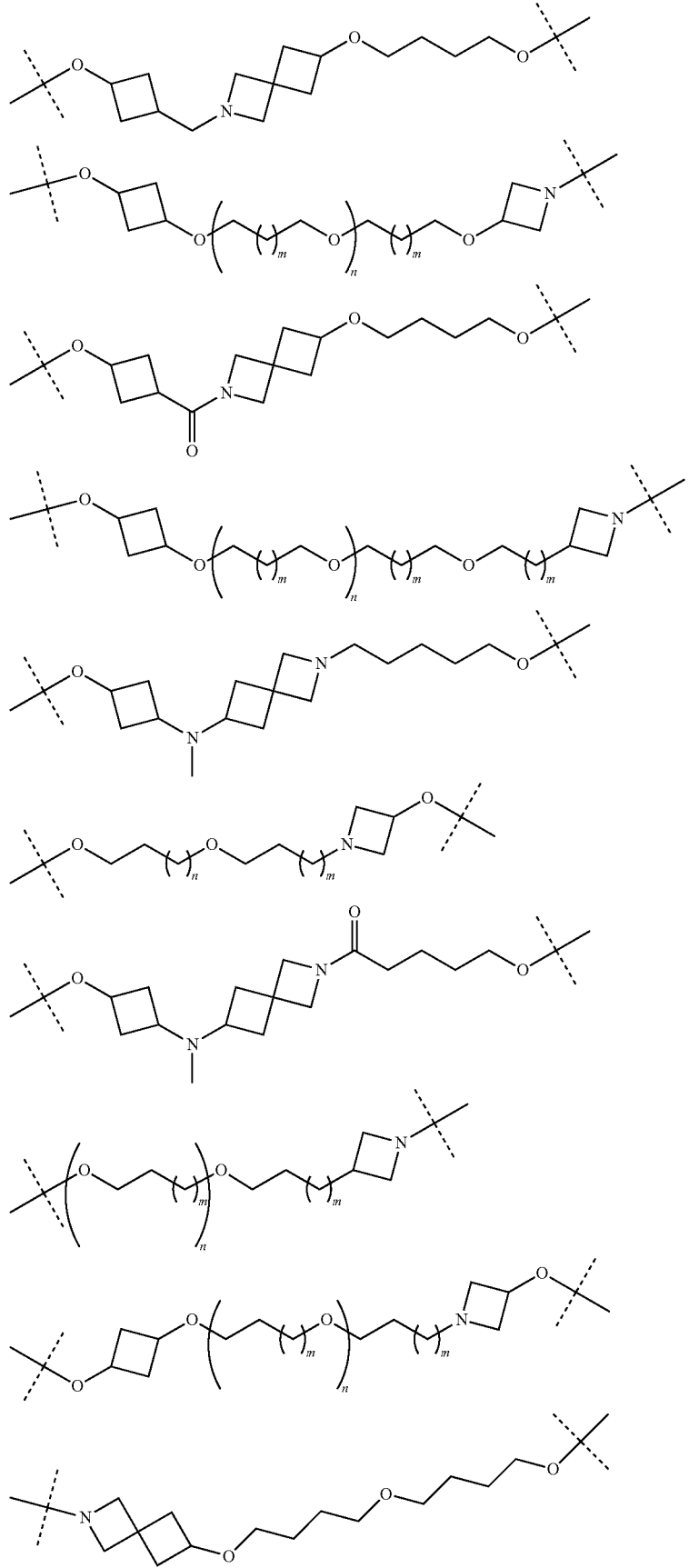

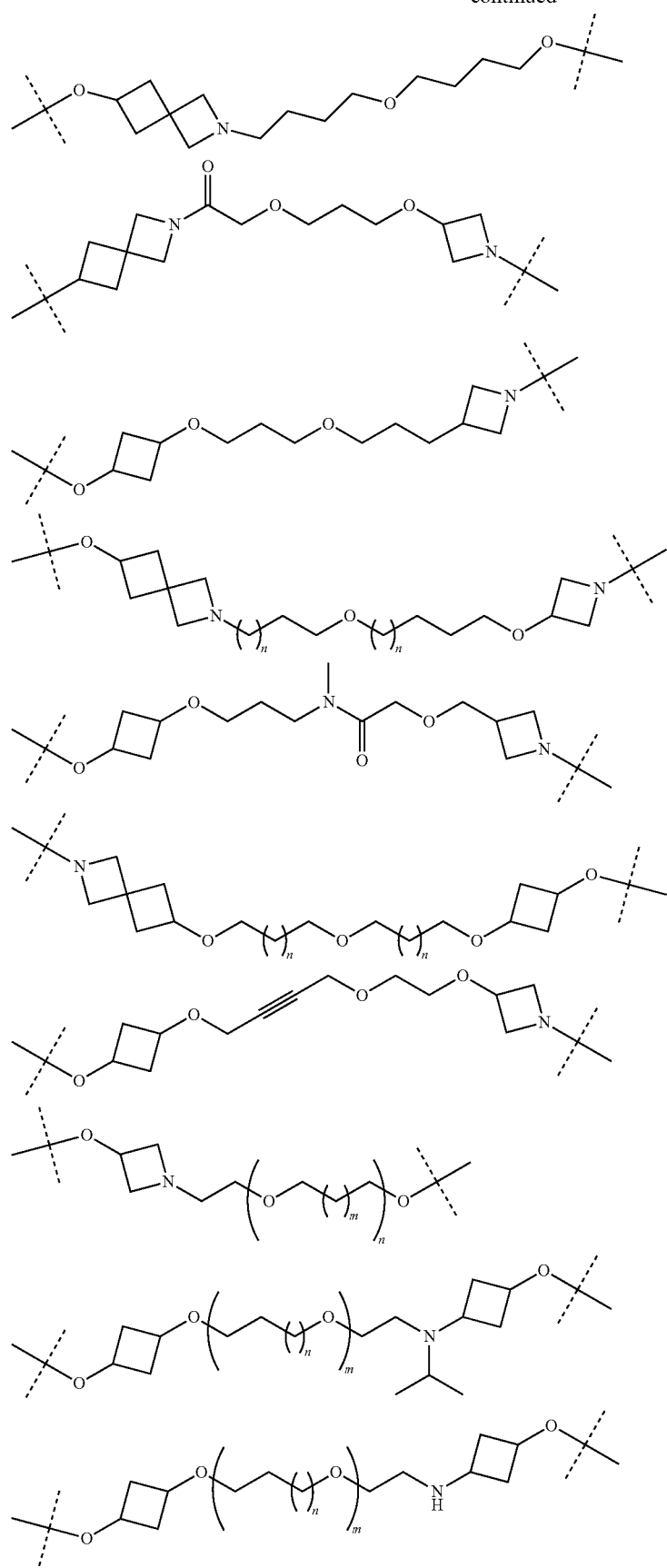

-continued
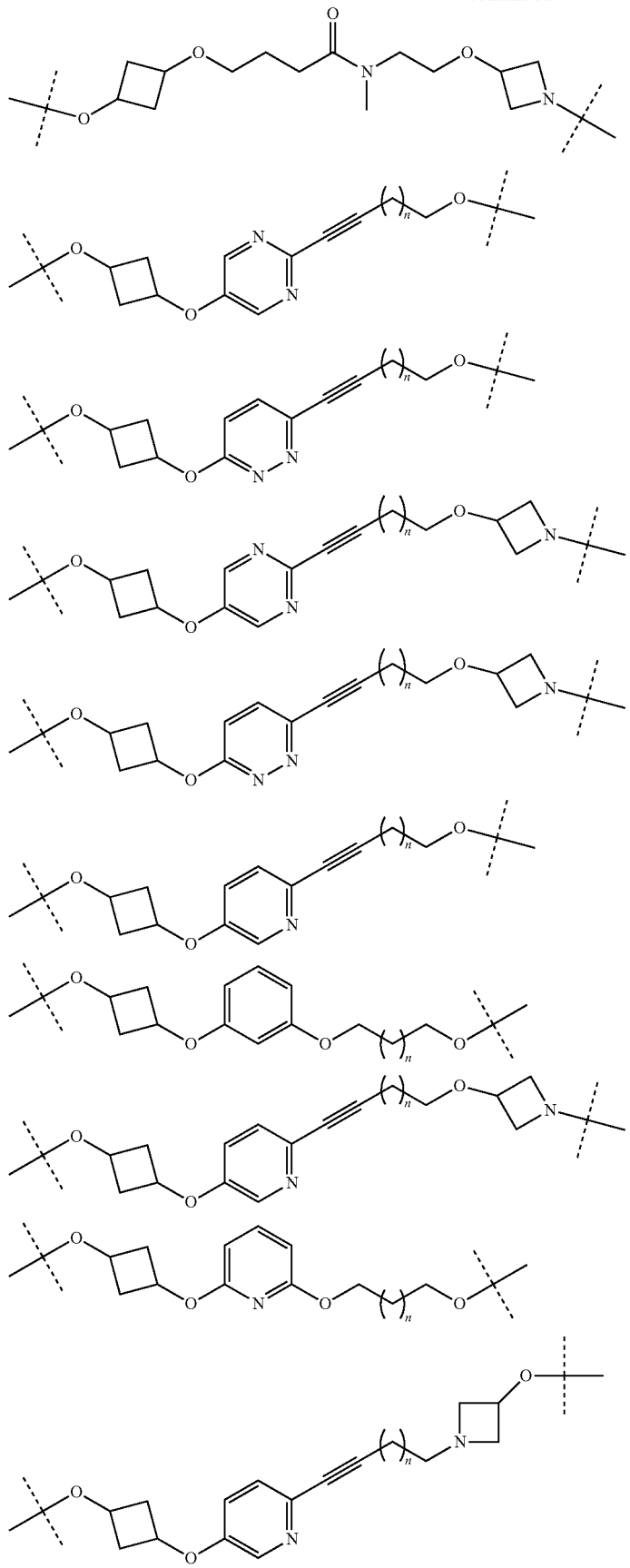

-continued
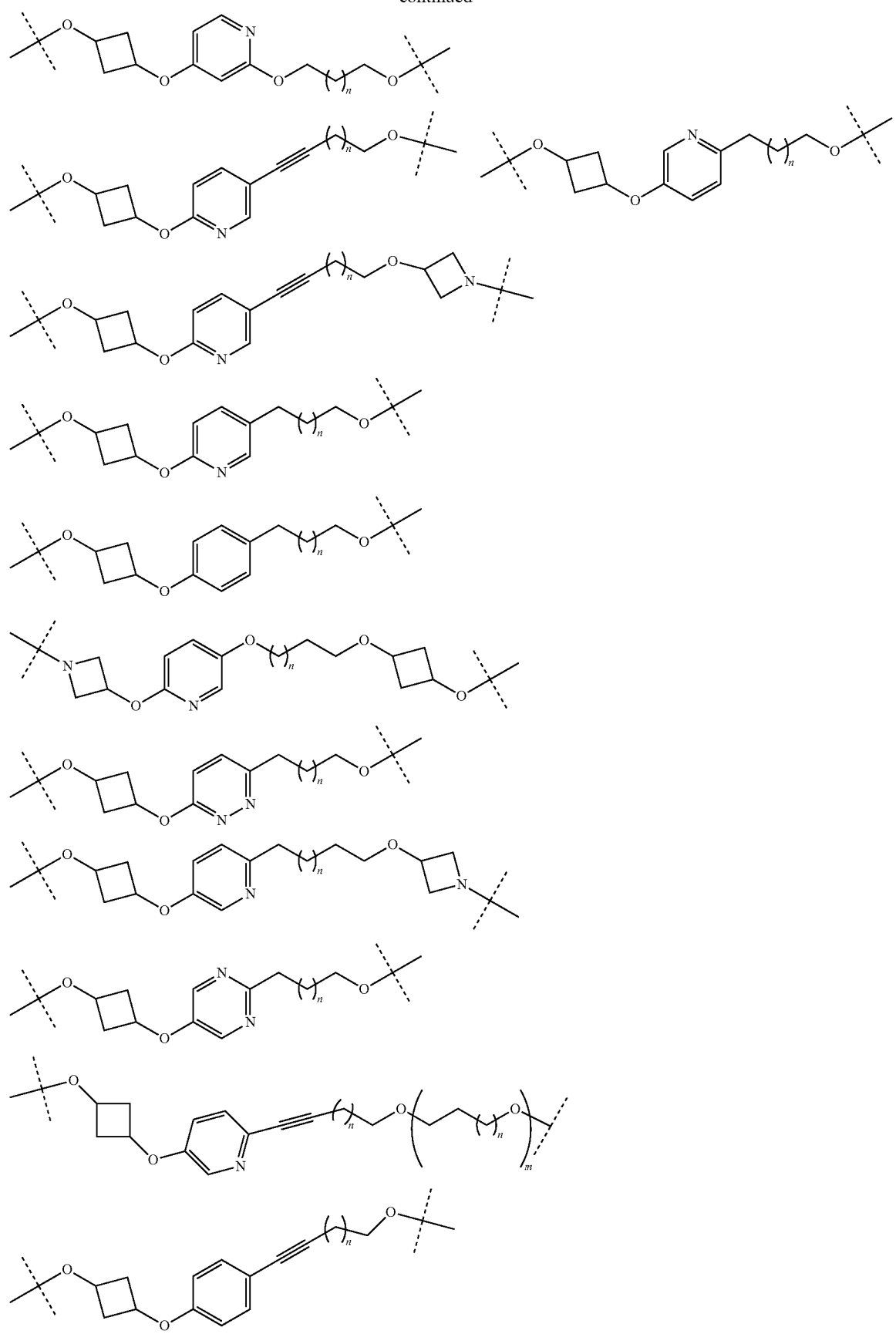

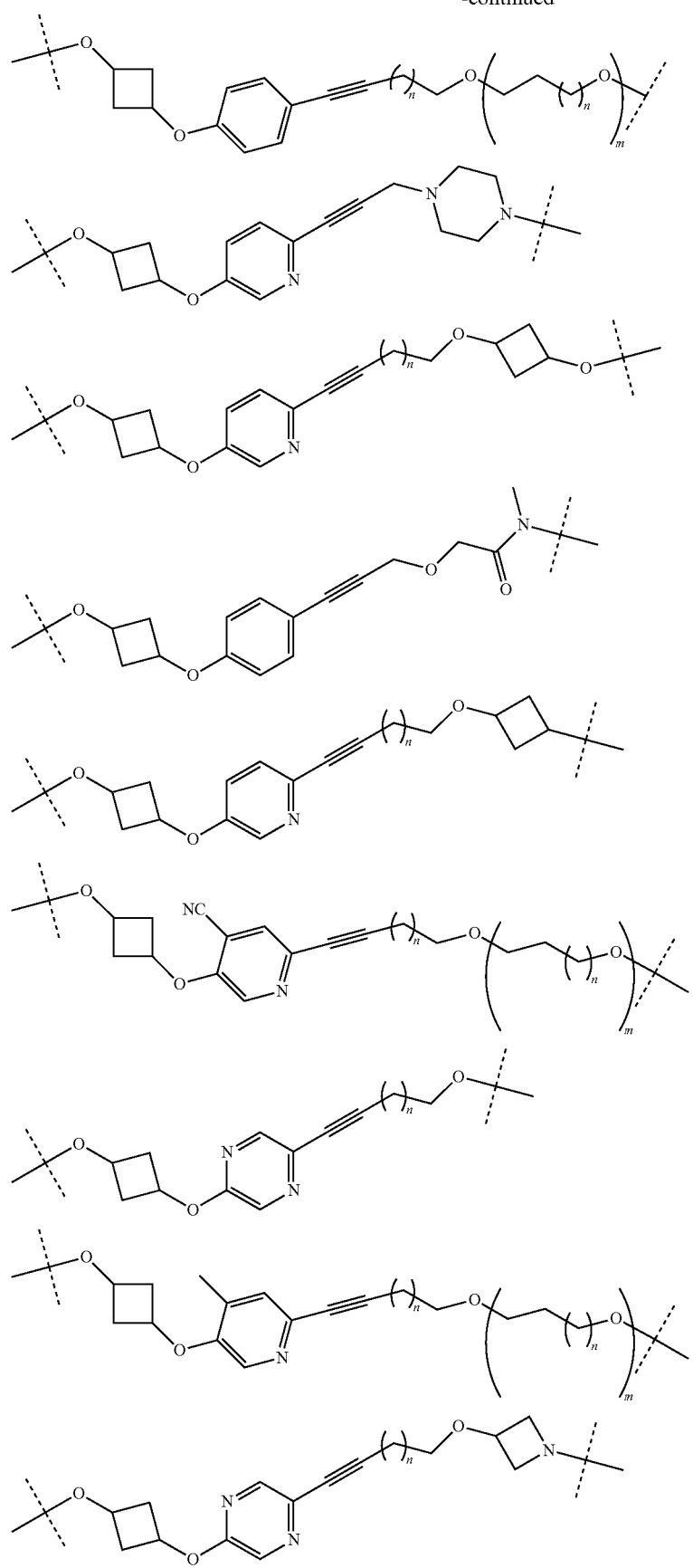

-continued
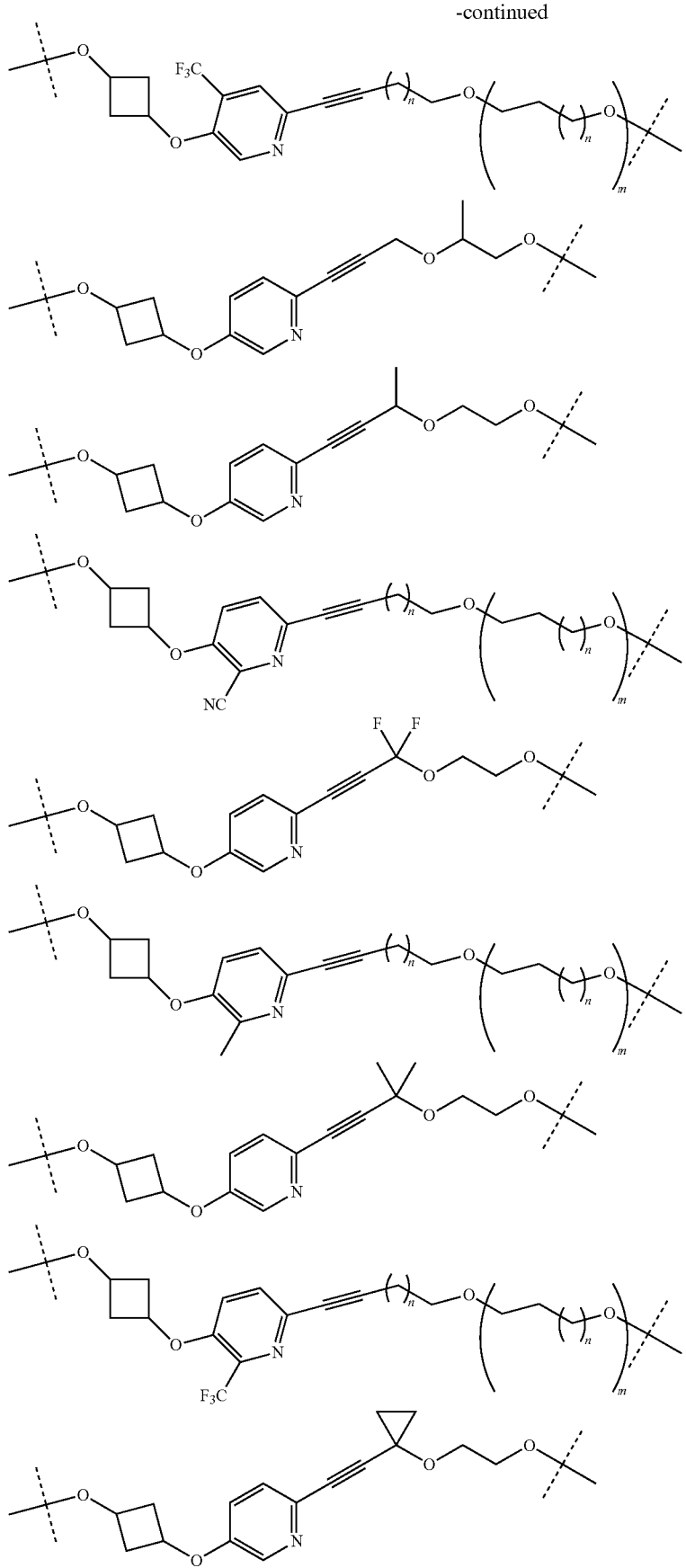

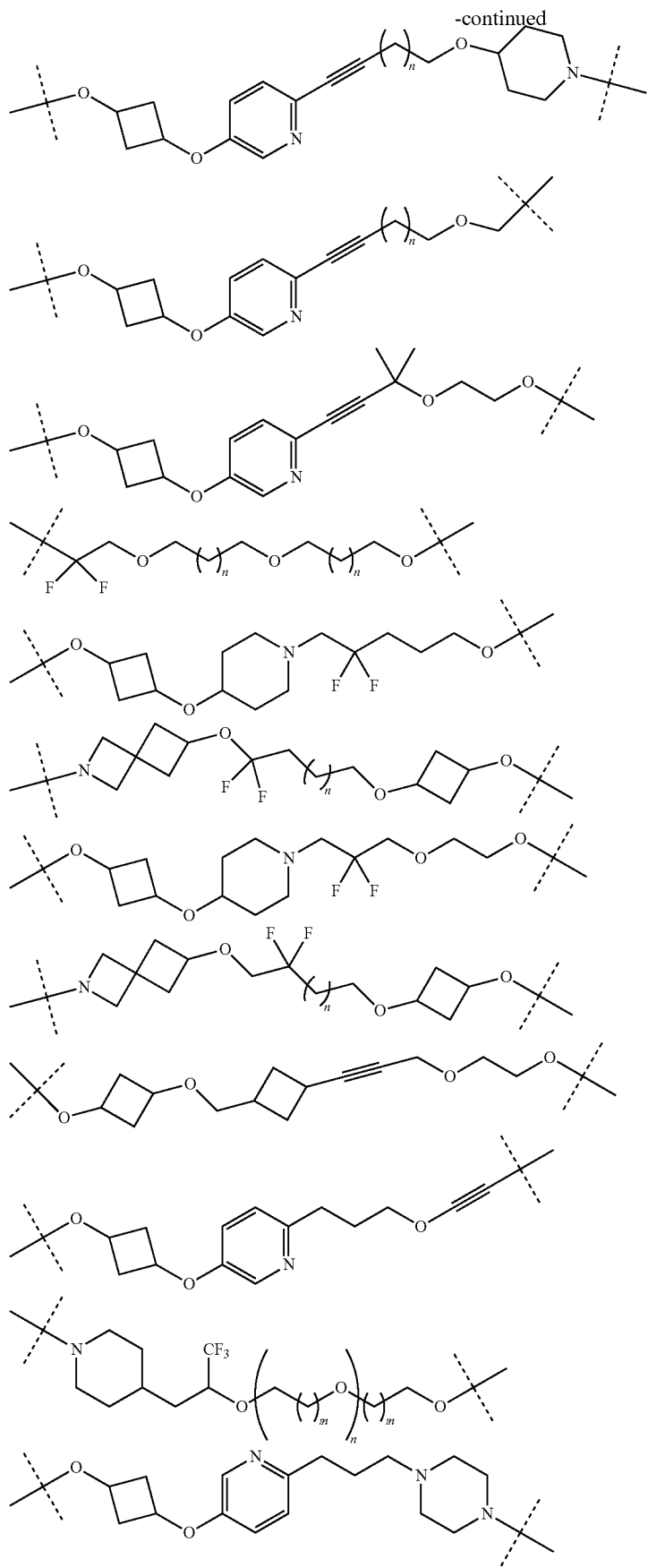

-continued
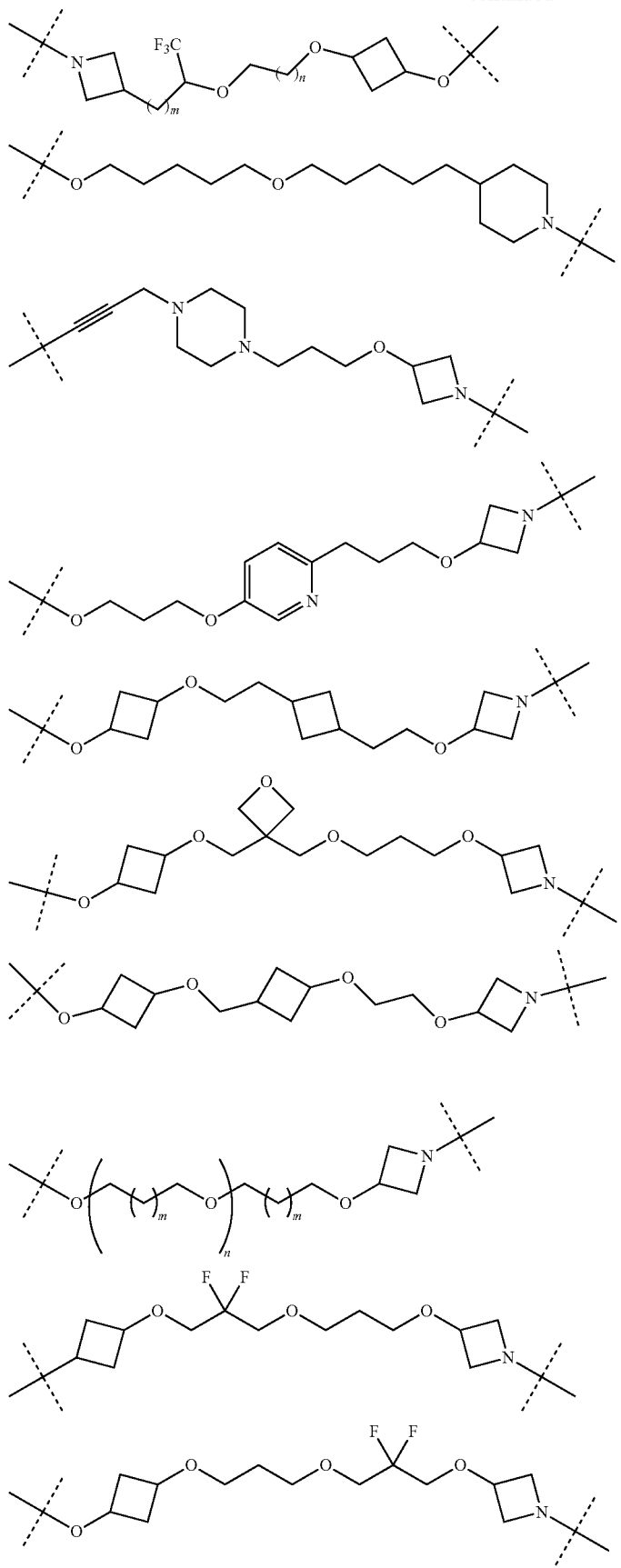

-continued
573 574
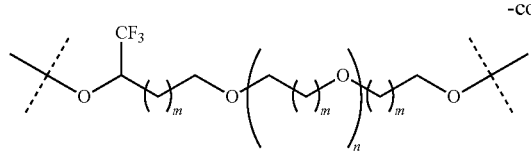 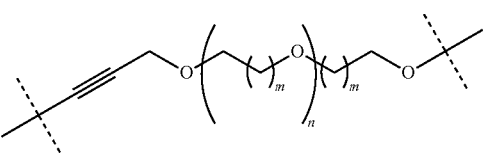
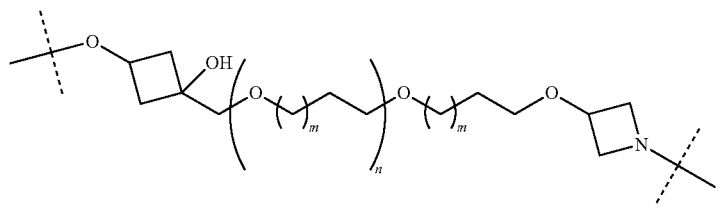
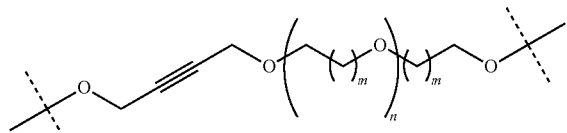
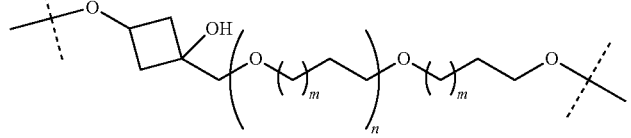
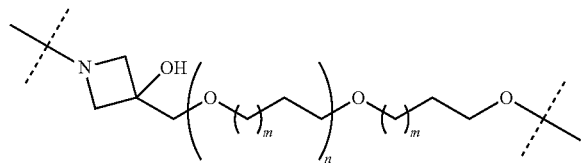
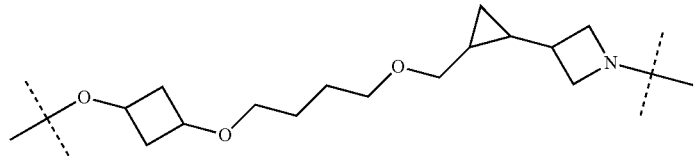
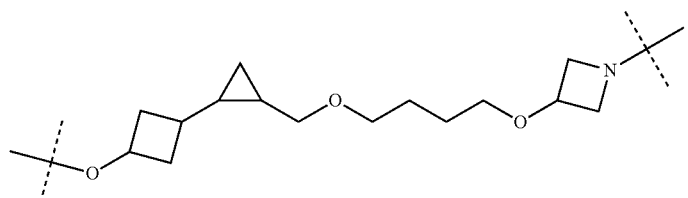
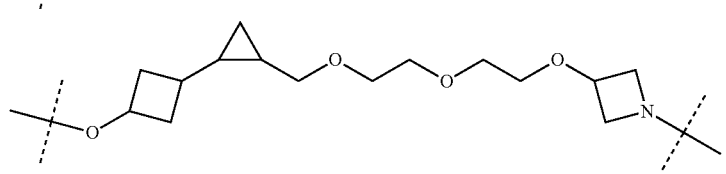
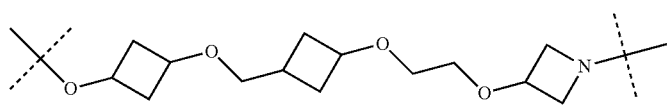
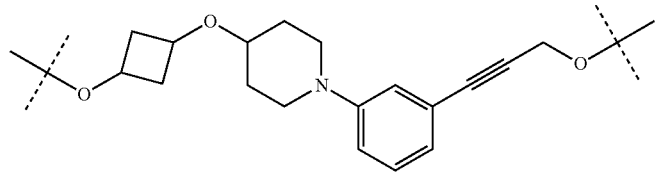

-continued
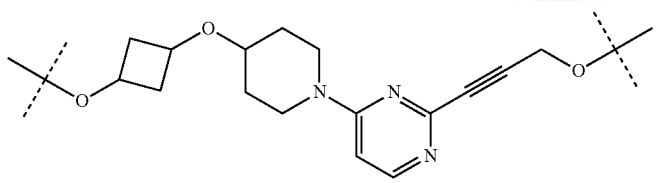
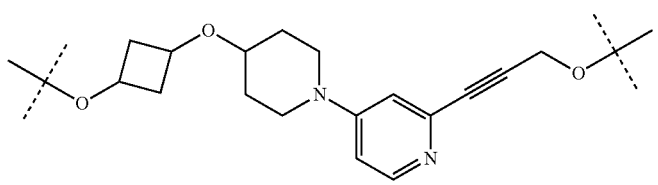
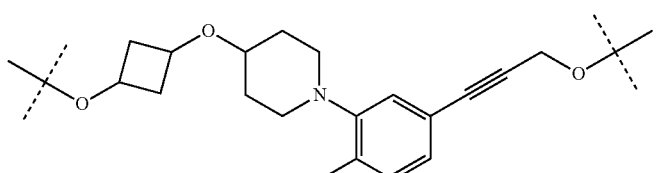
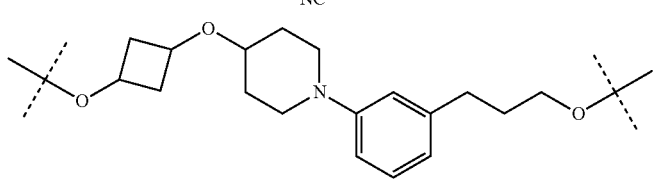
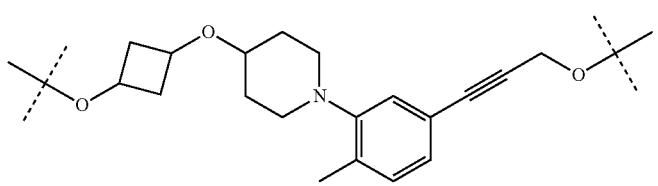
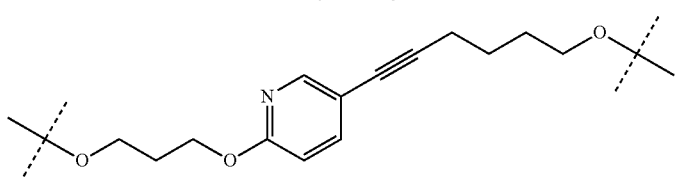
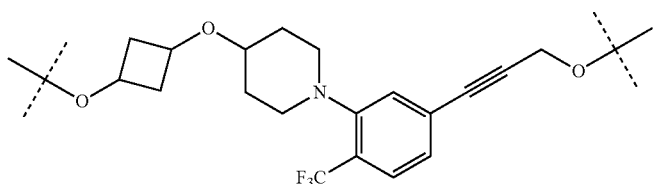
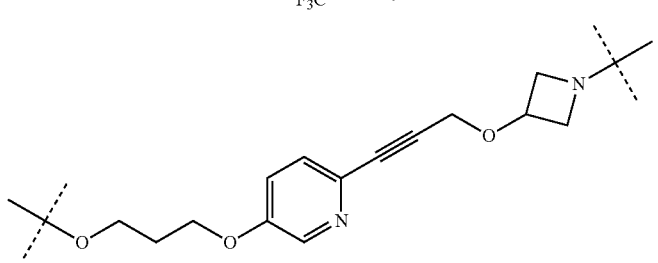
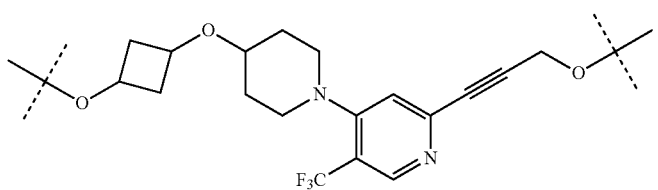

-continued
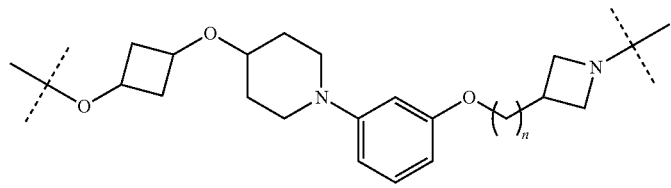
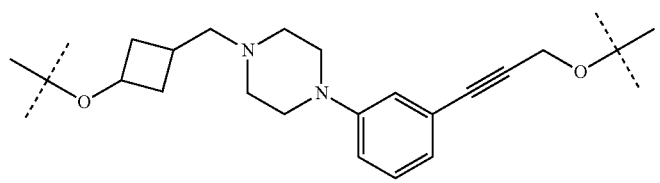
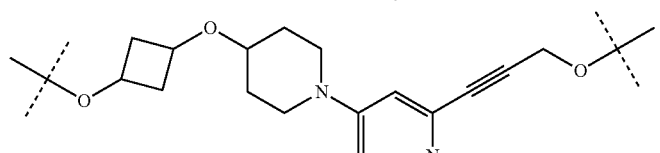
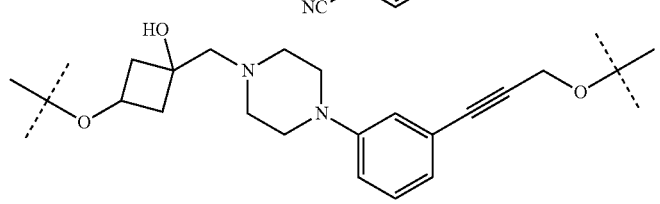
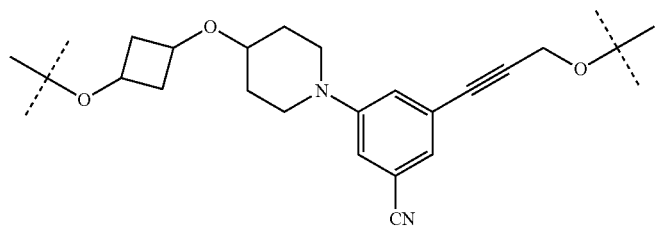
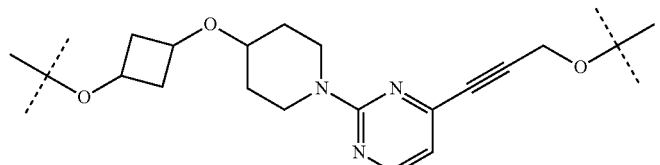
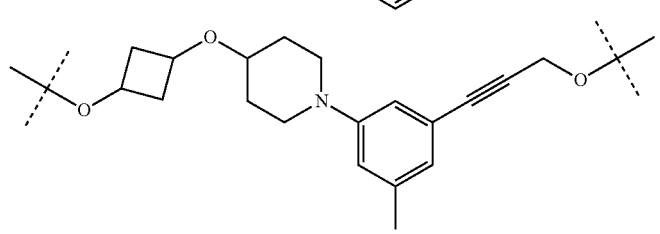
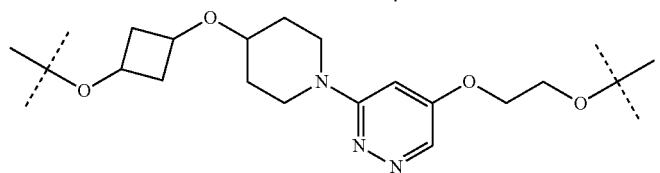

-continued
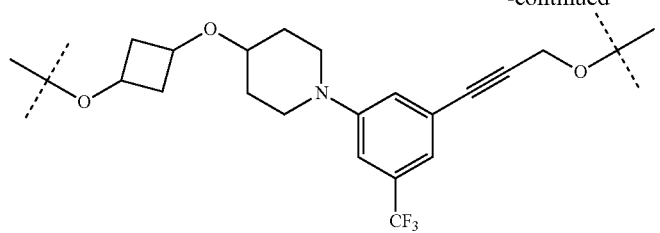
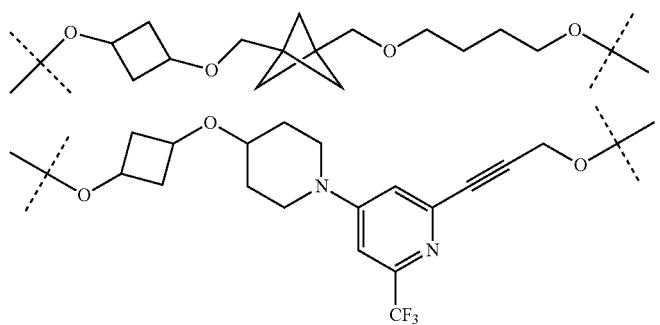
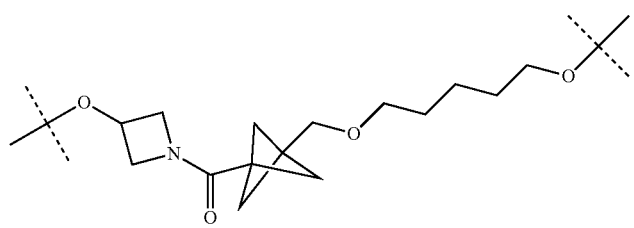
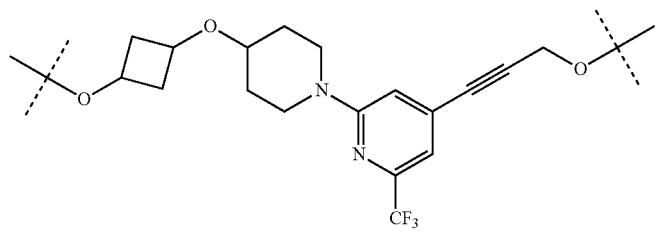
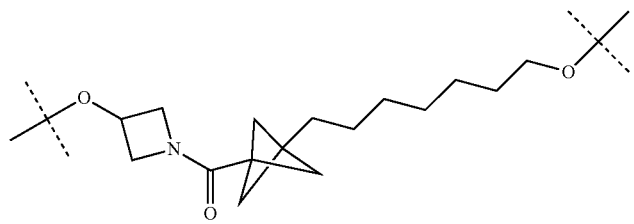
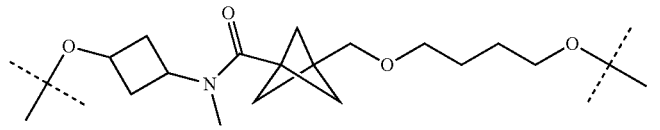
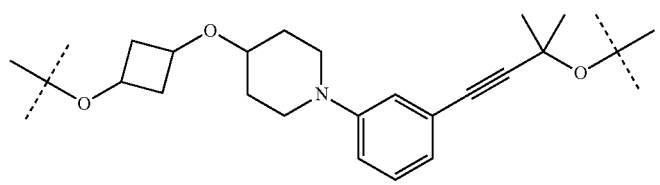
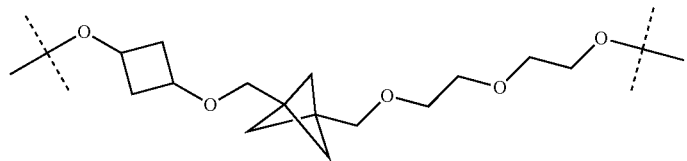

-continued
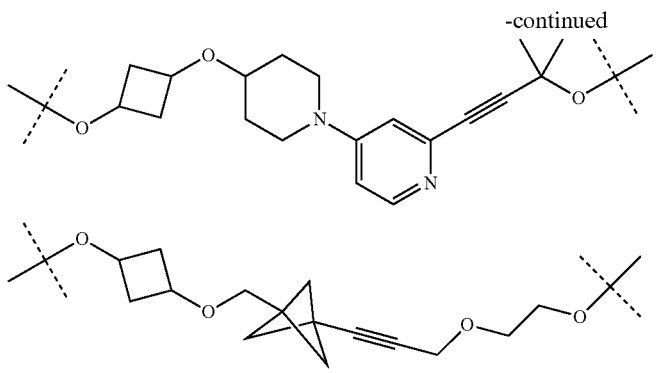
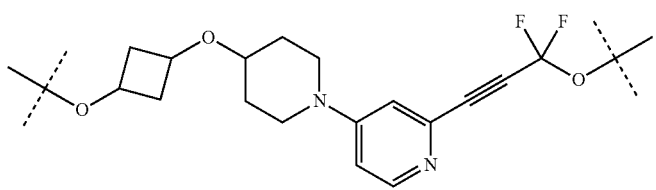
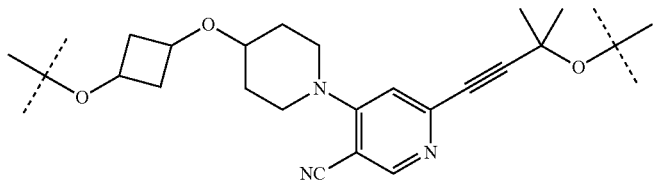
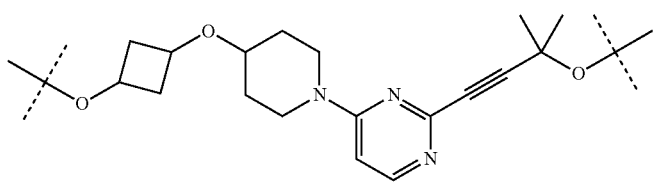
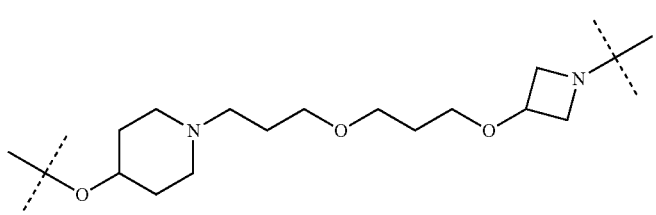
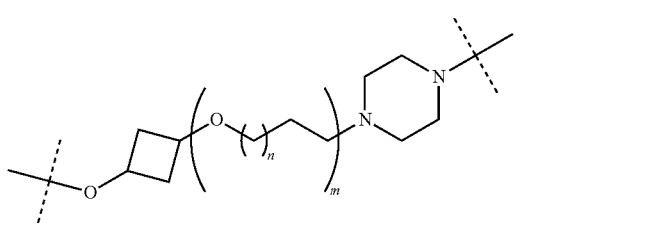
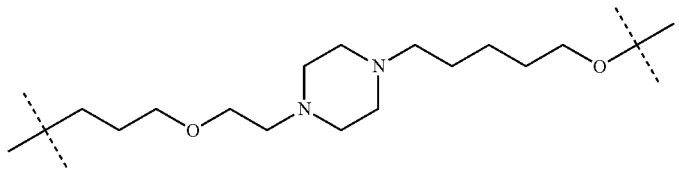

583 584
-continued
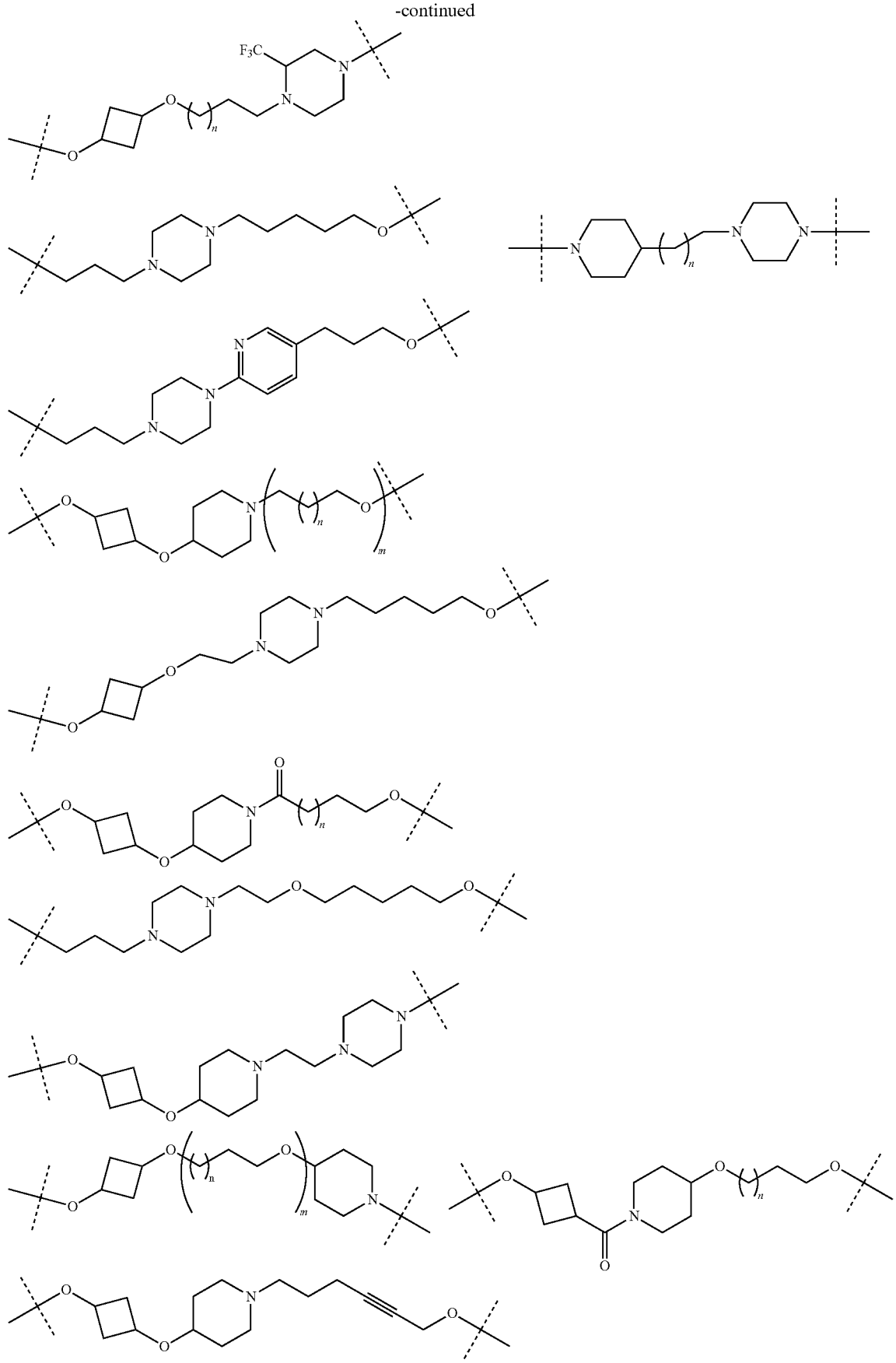

-continued
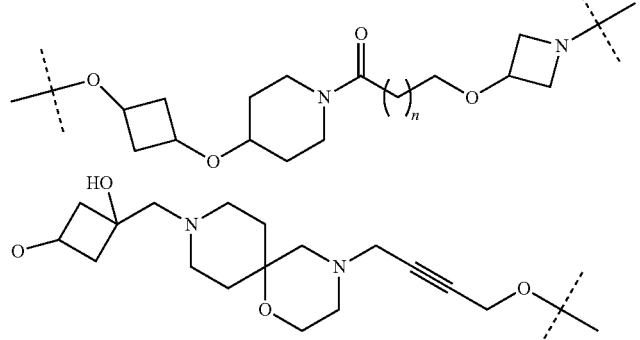
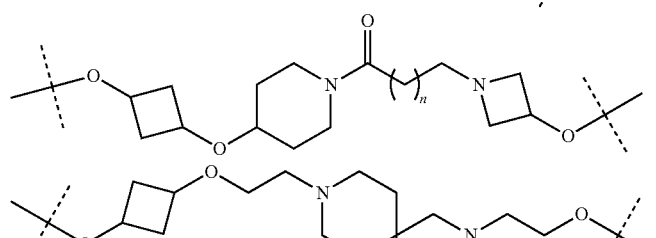
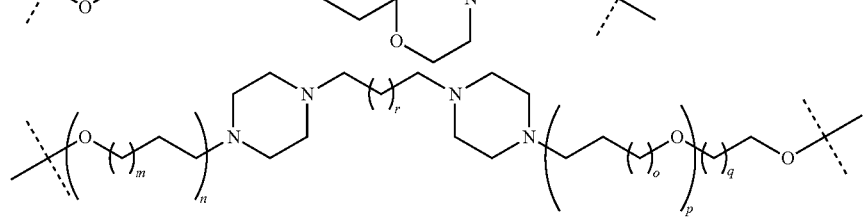
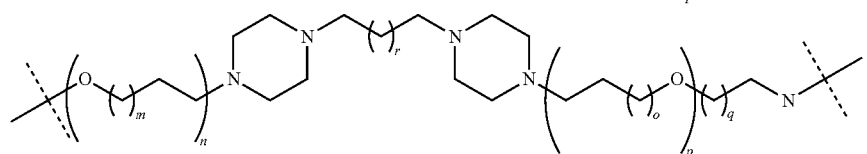
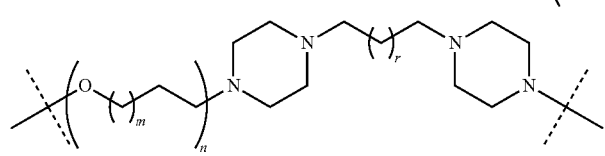
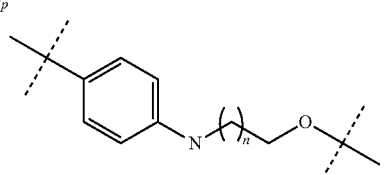
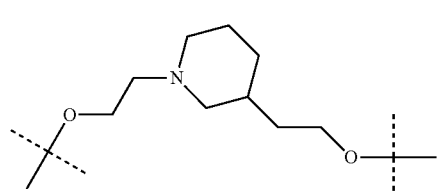
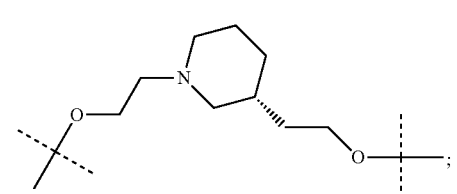
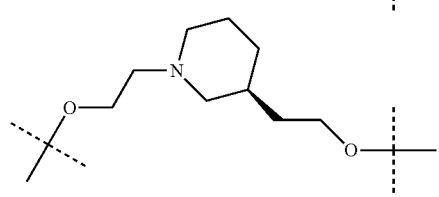
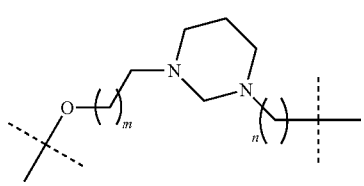
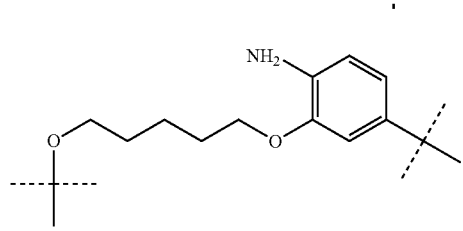
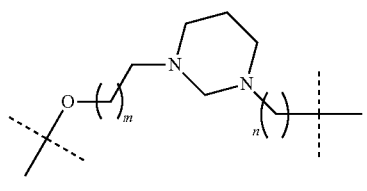

-continued
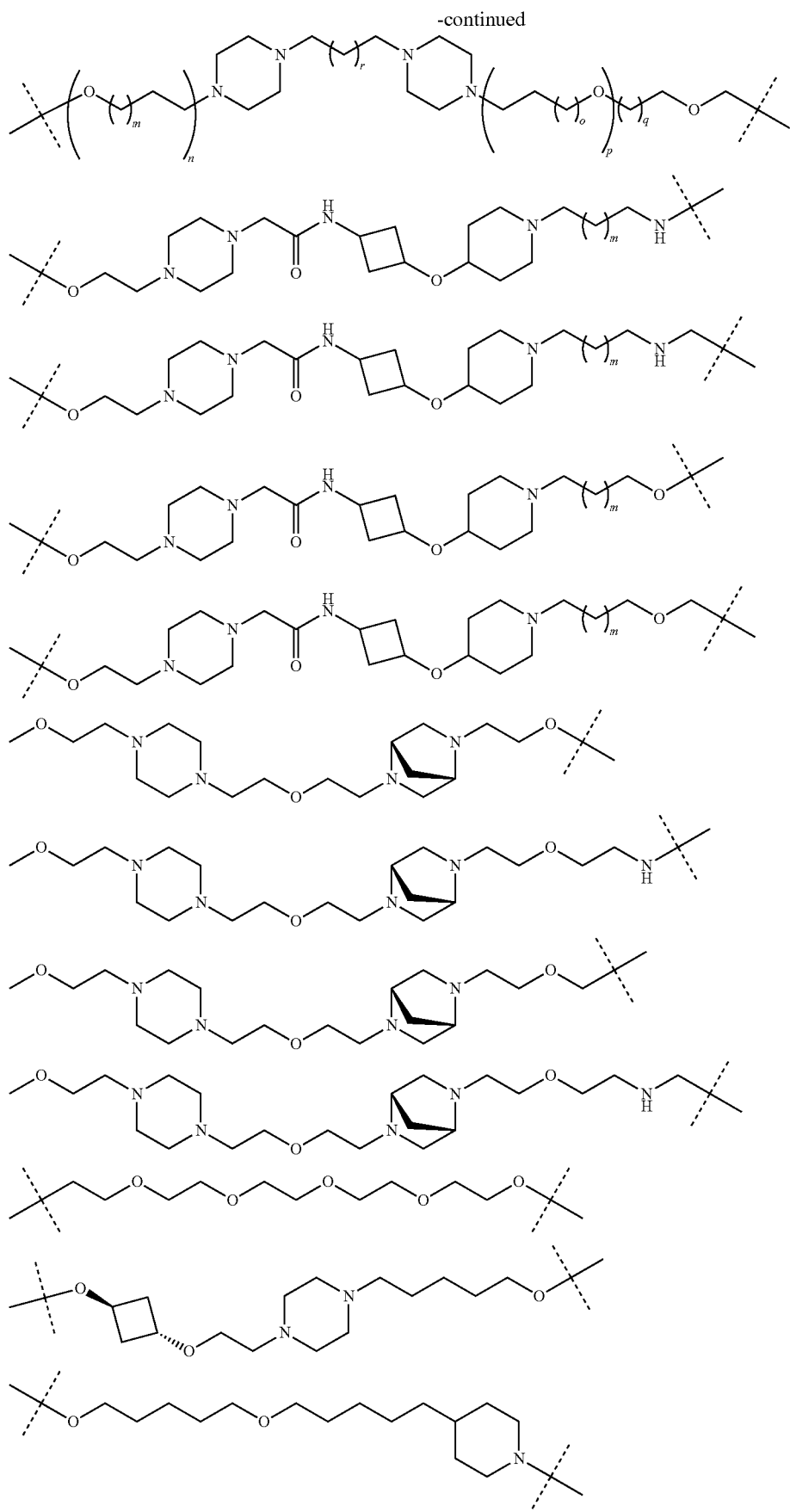

-continued
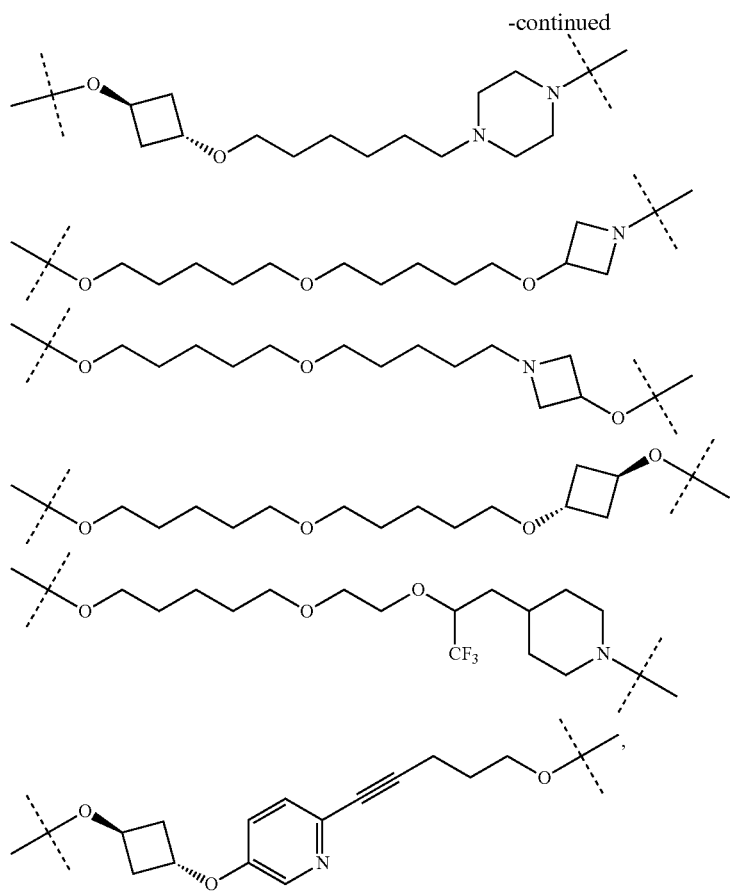
wherein each m, n, o, p, q, and r is independently 0, 1, 2, 3, 4, 5, 6, 7, 8, 9, 10, 11, 12, 13, 14, 15, 16, 17, 18, 19, or 20.
In any aspect or embodiment described herein, the $A^L$ is selected from the group consisting of:
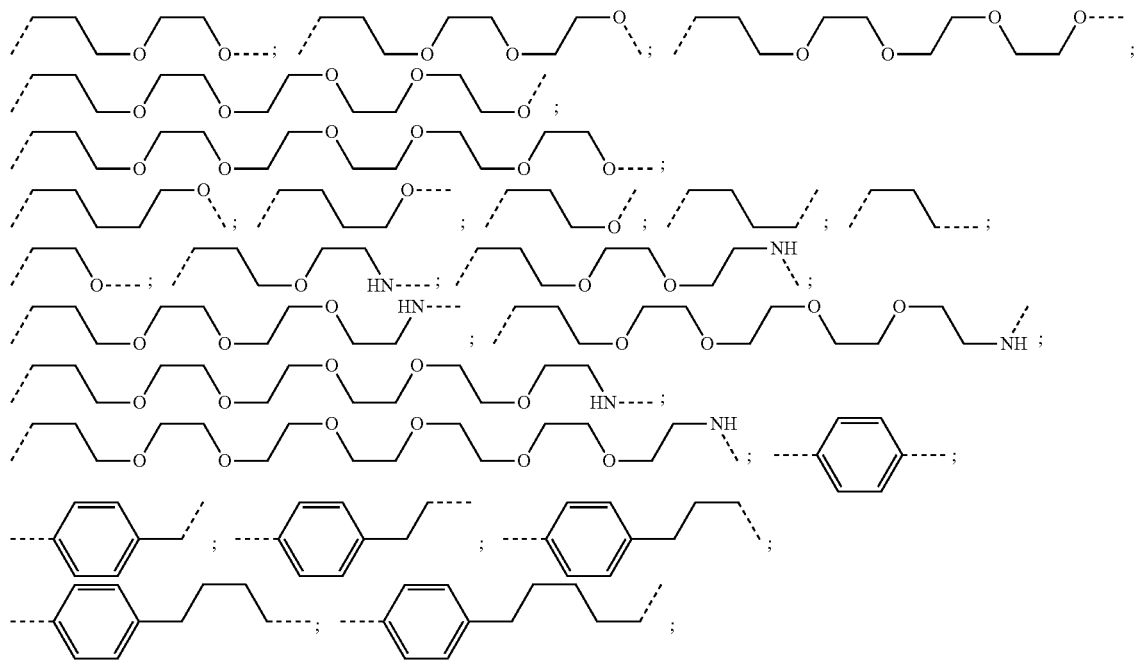

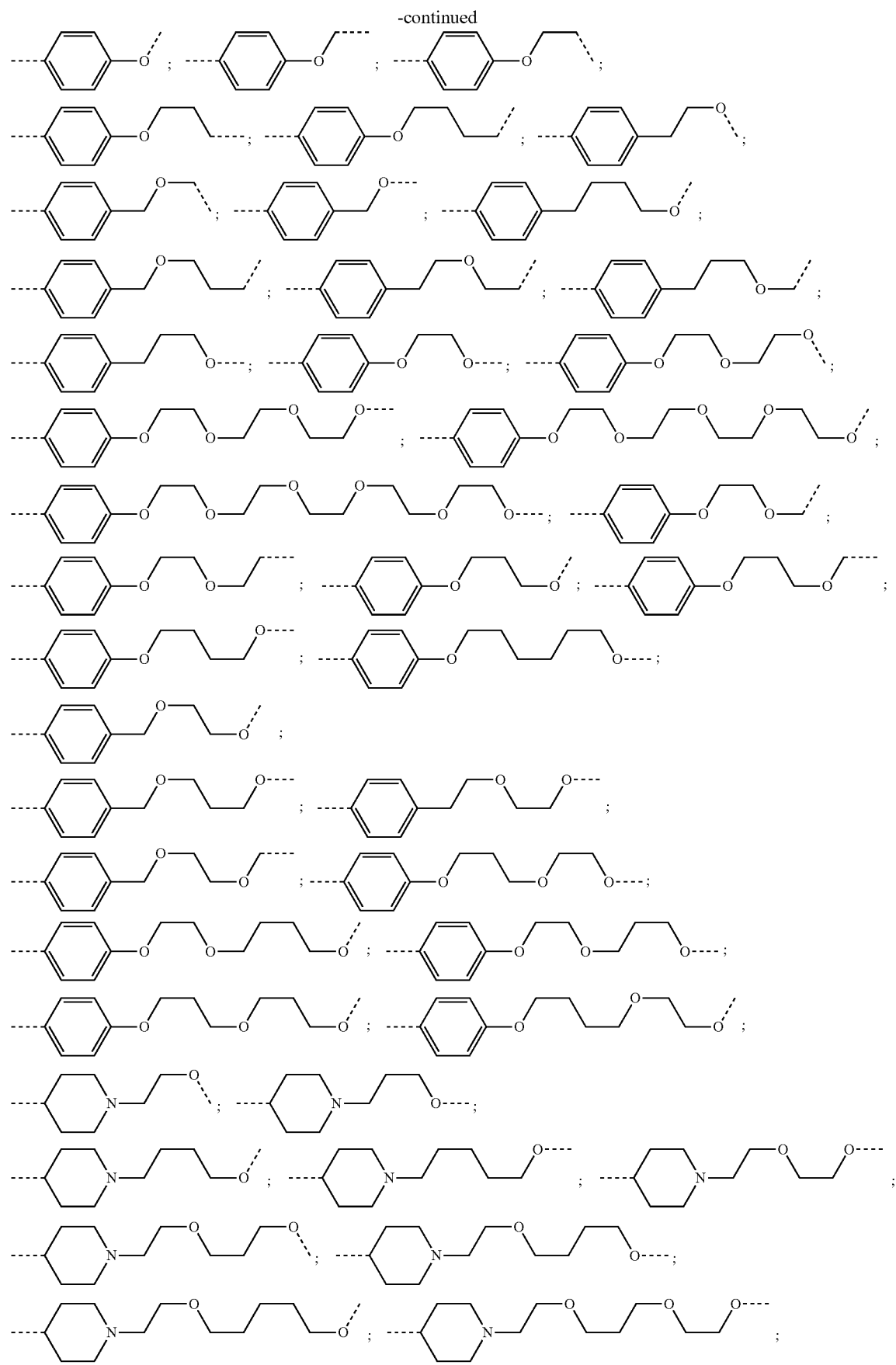

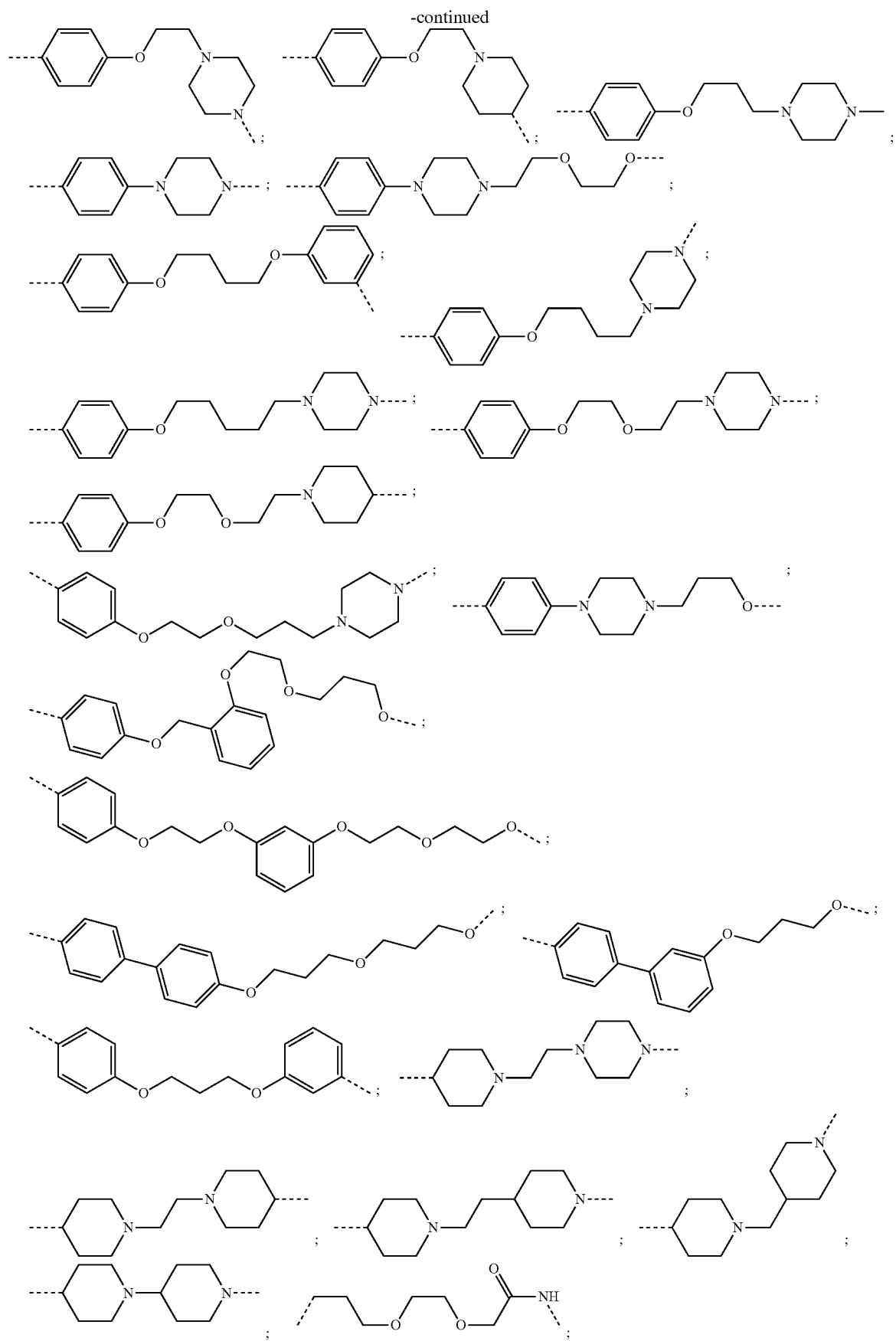

595 596
-continued
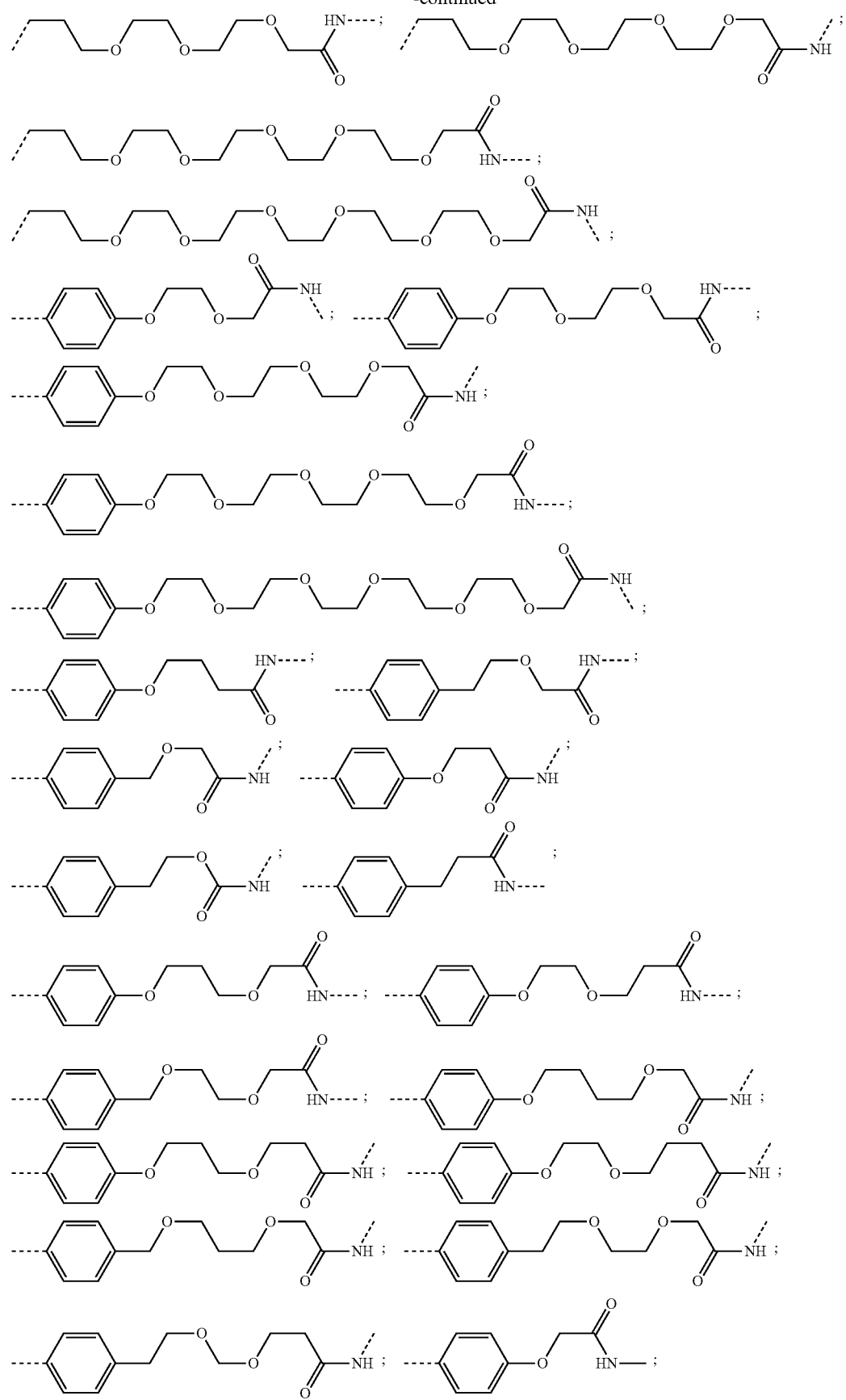

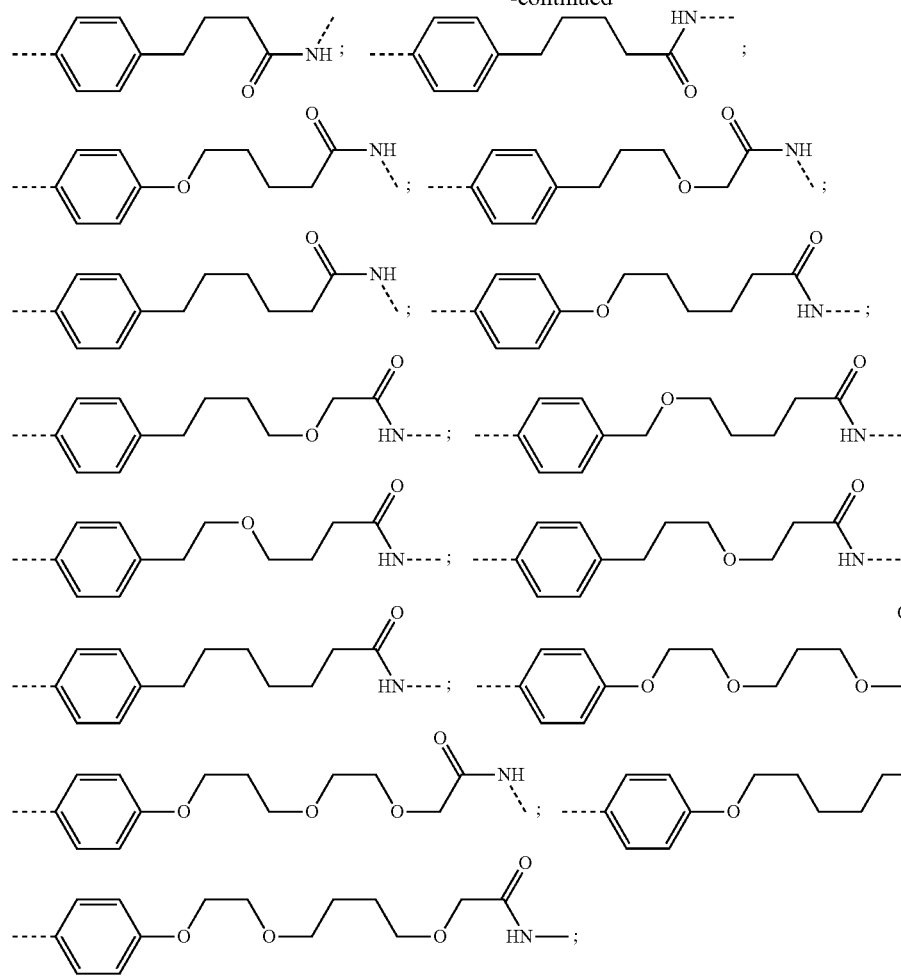

599
-continued
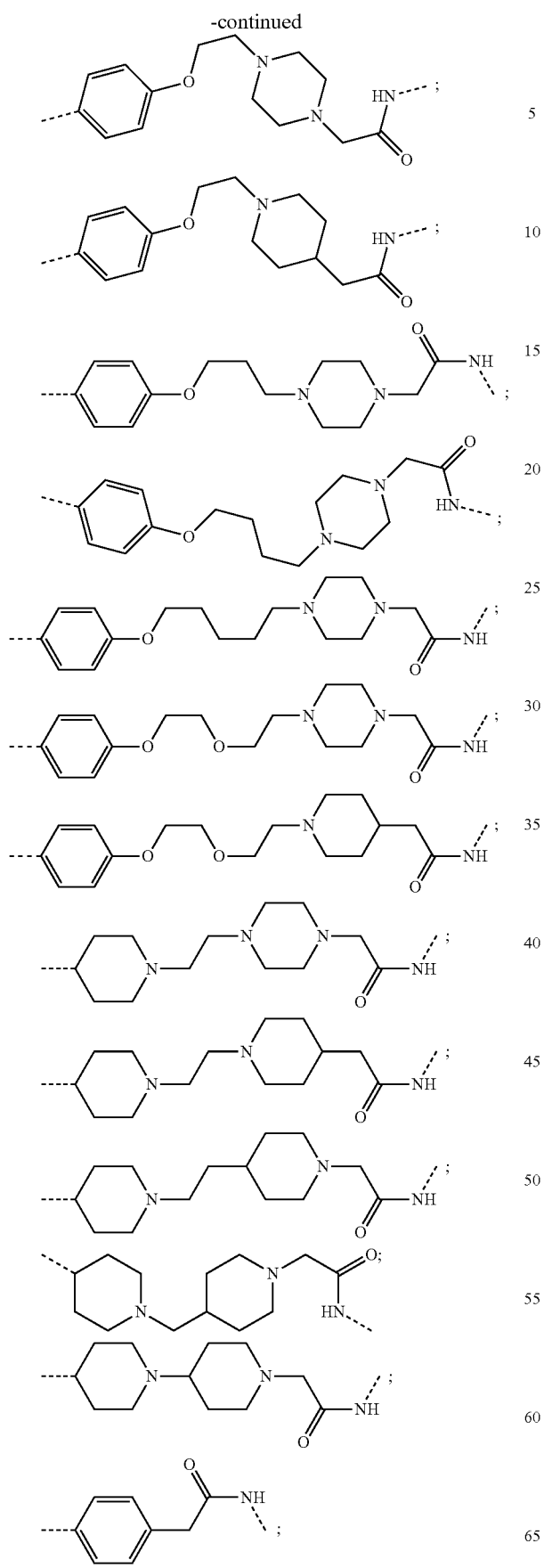
600
-continued
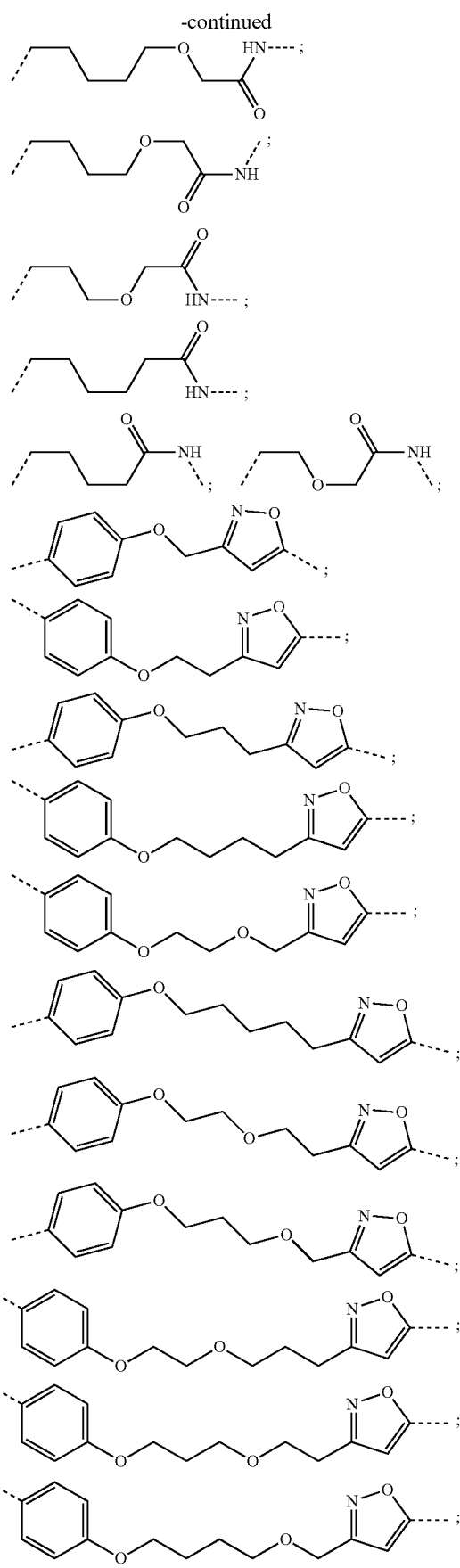

601
-continued
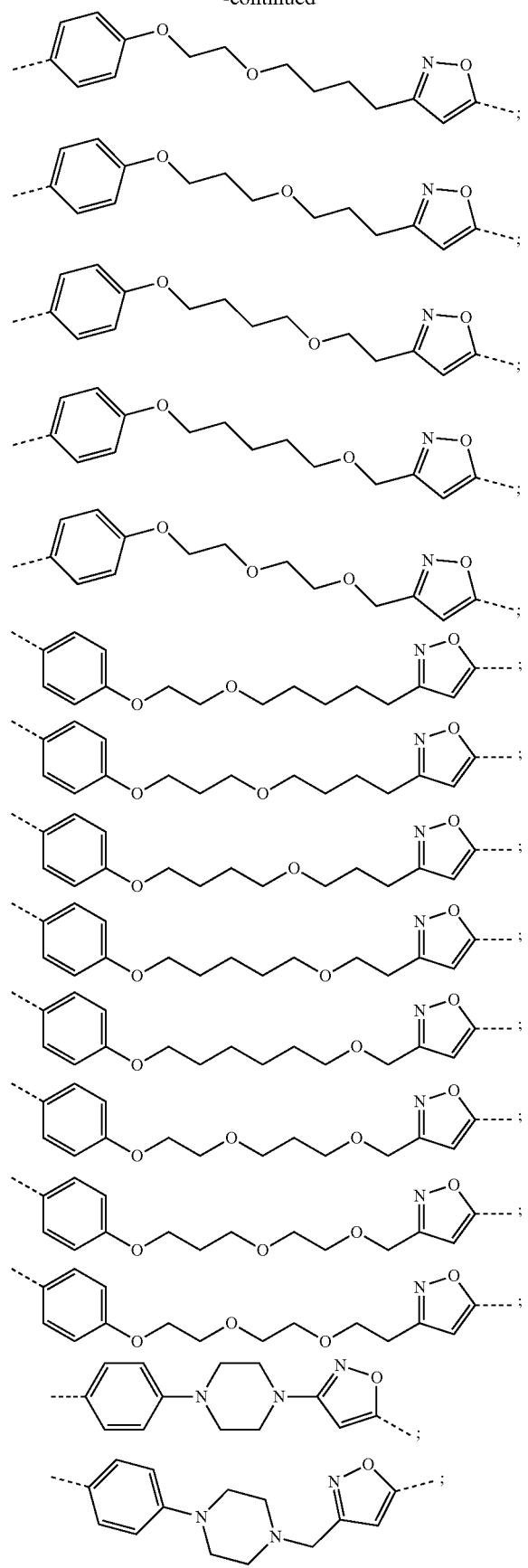
602
-continued
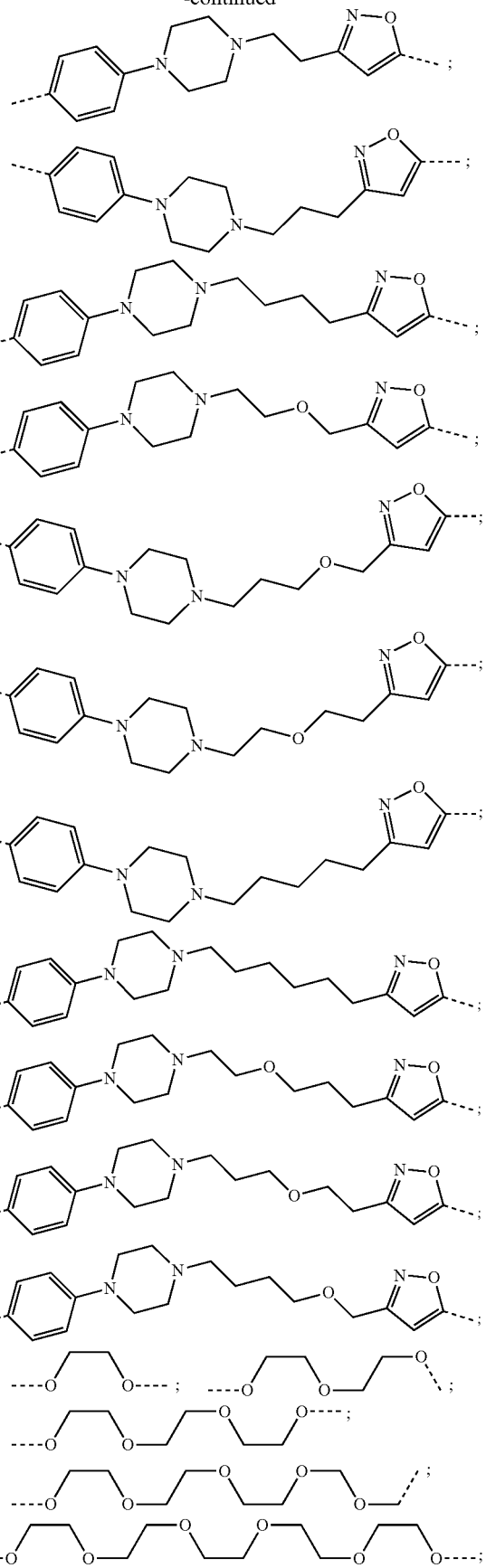

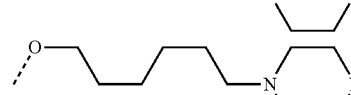

605
-continued
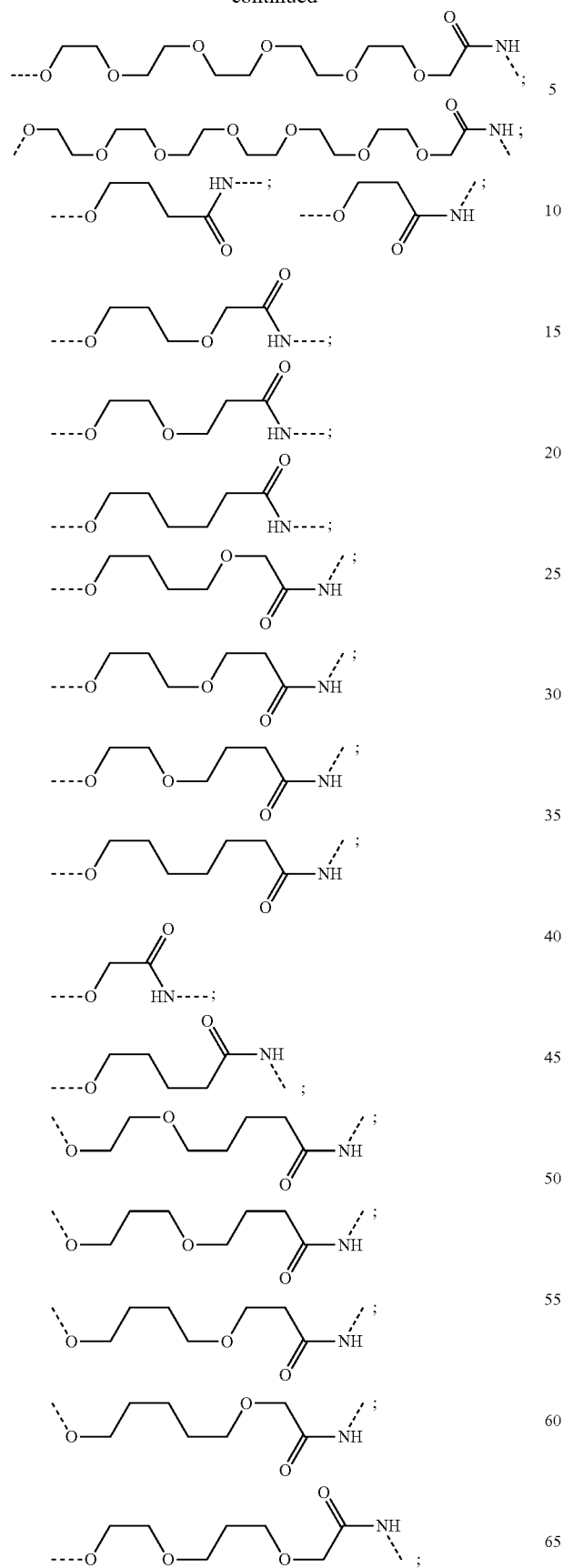
606
-continued
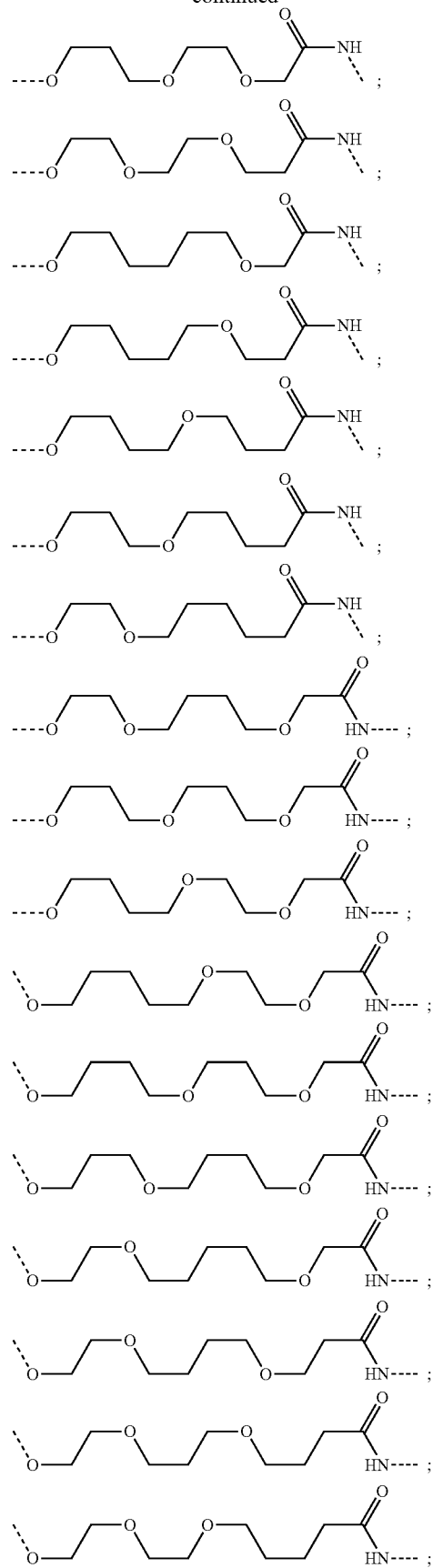

607
-continued
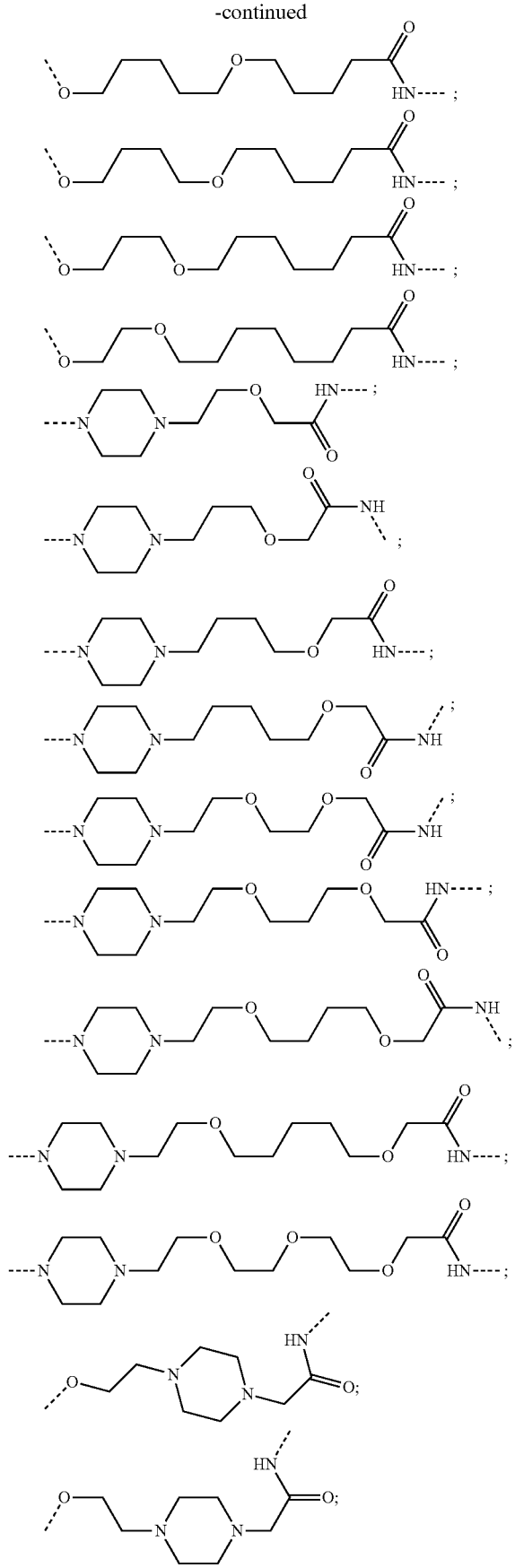
608
-continued
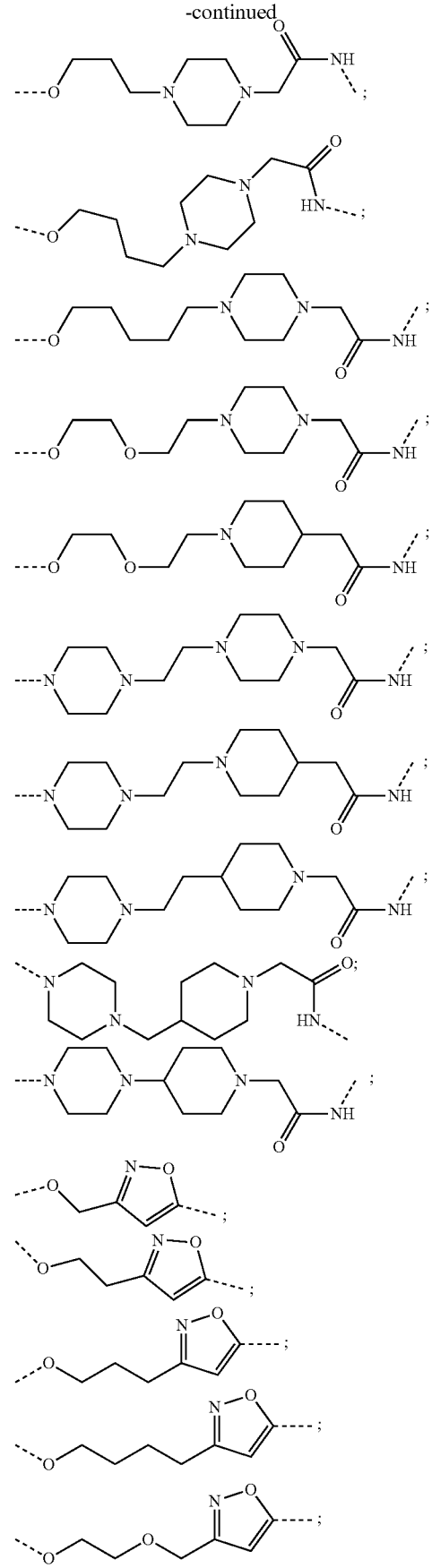

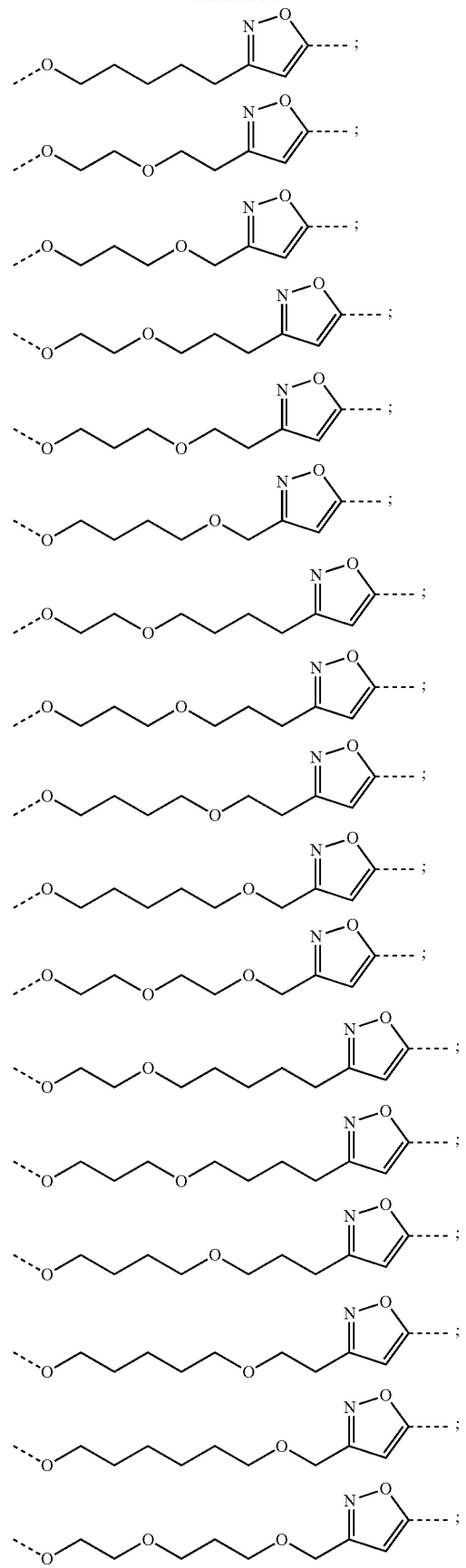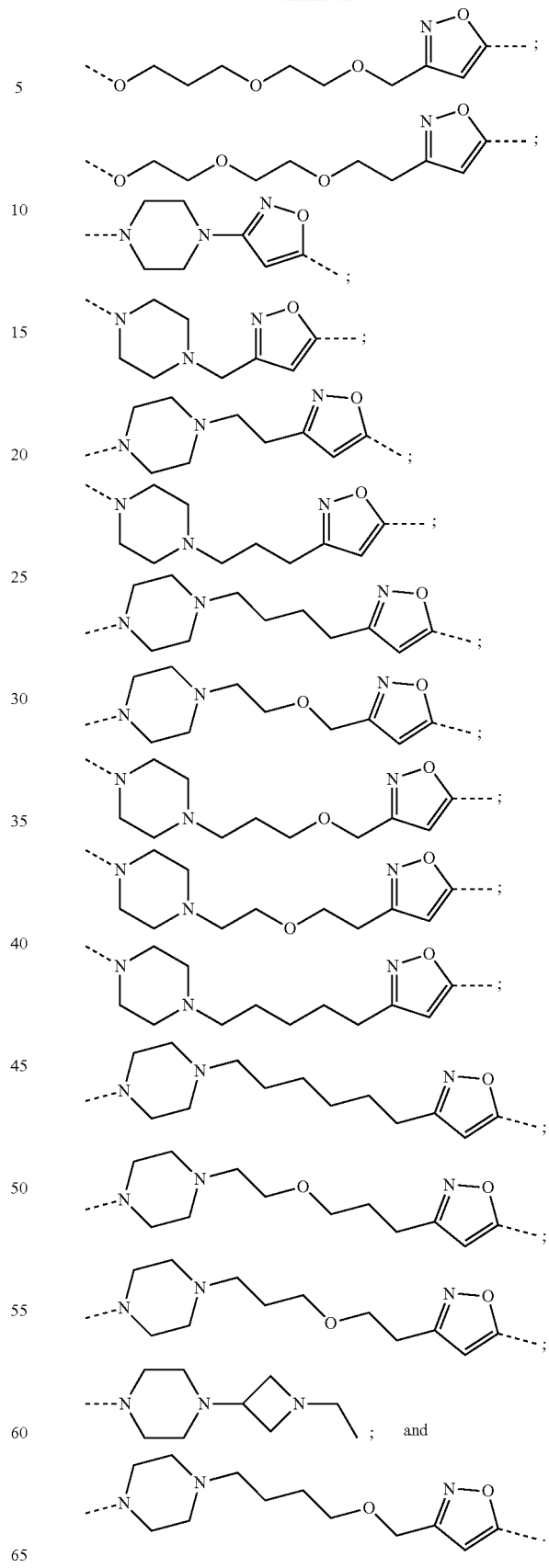

In any aspect or embodiment described herein, the $A^L$ is selected from:
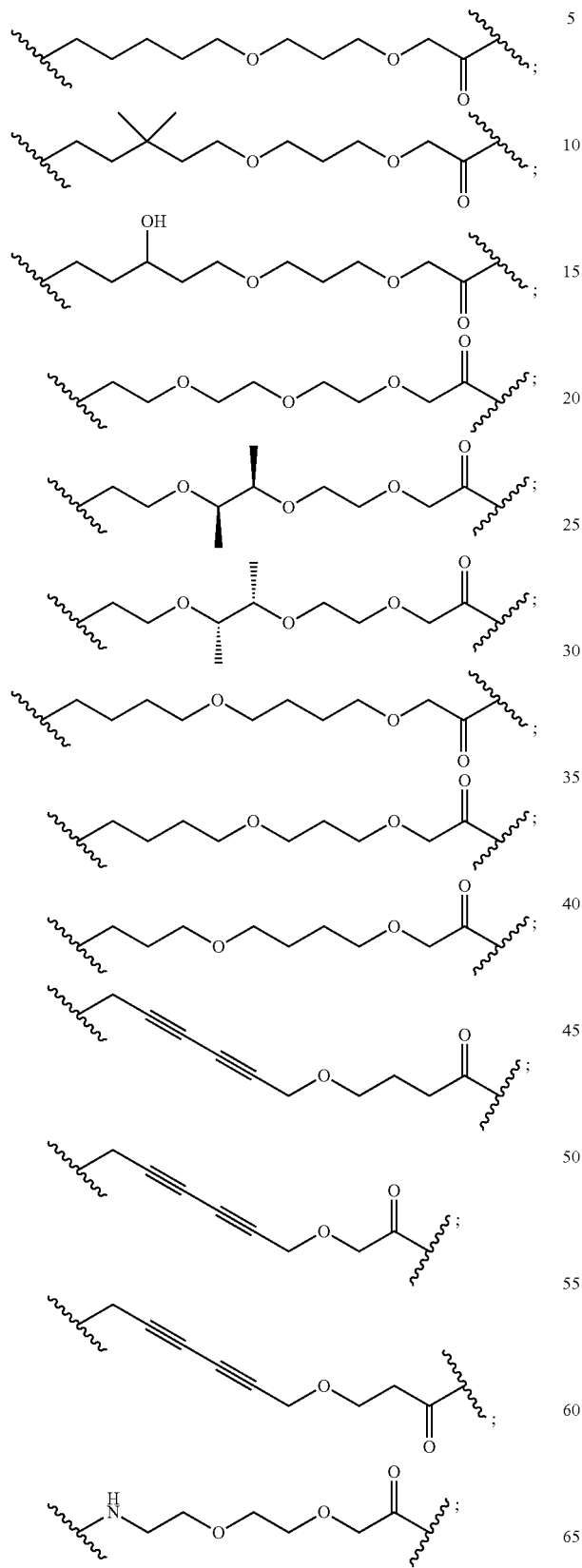
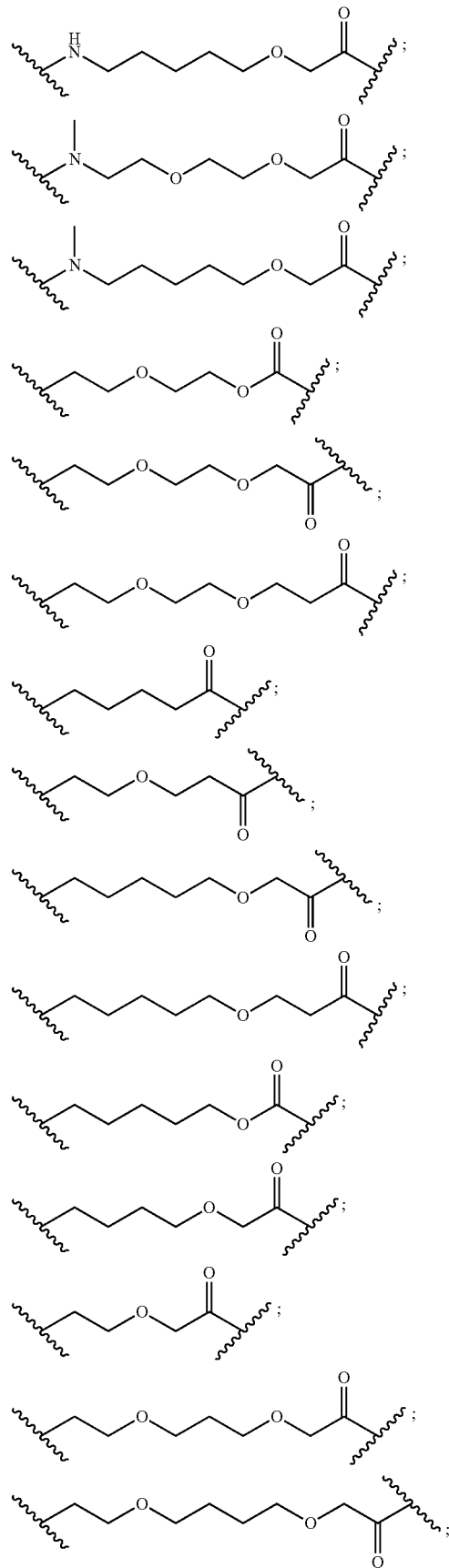

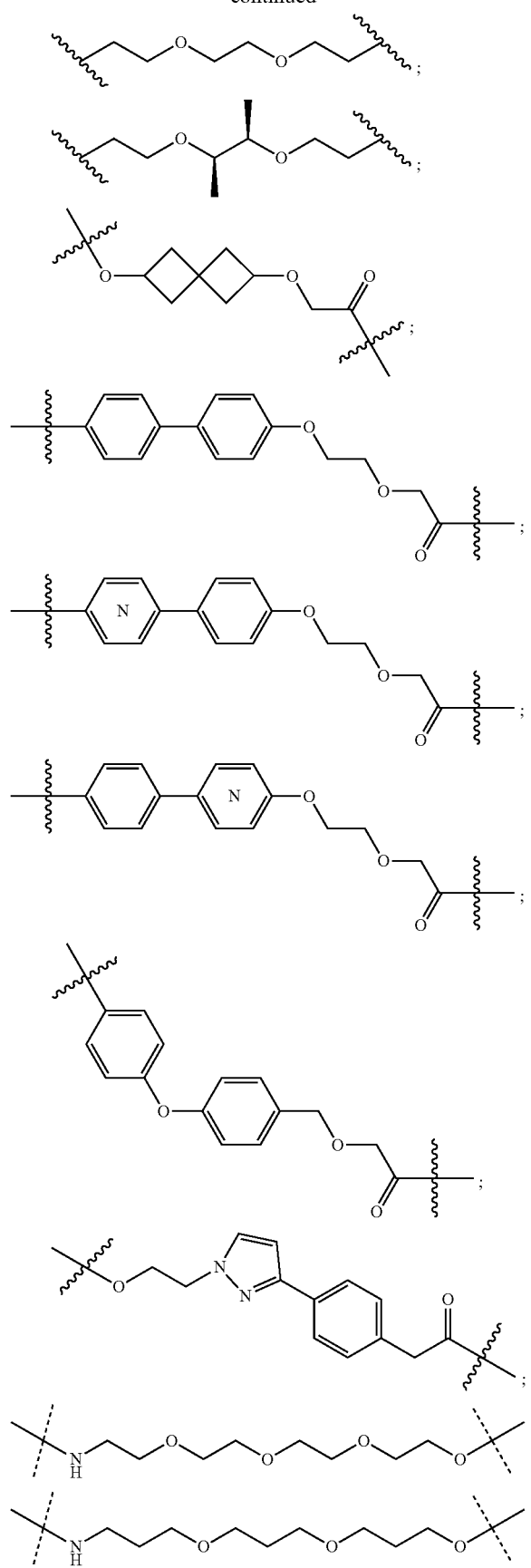
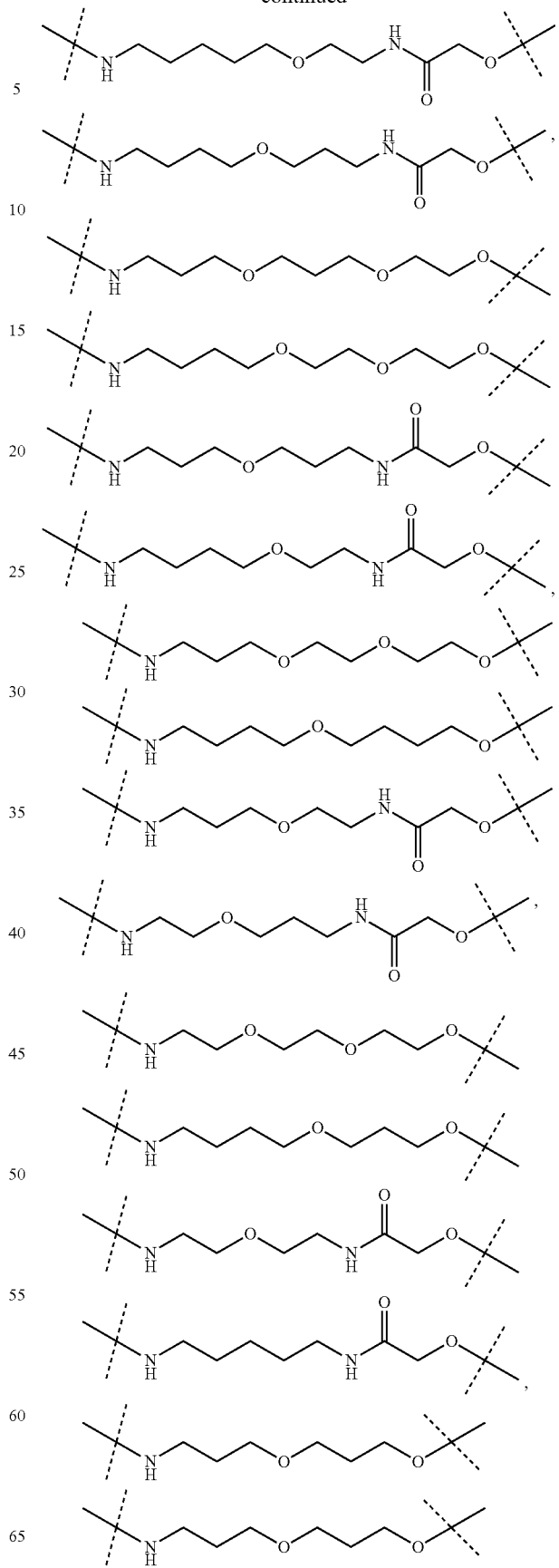

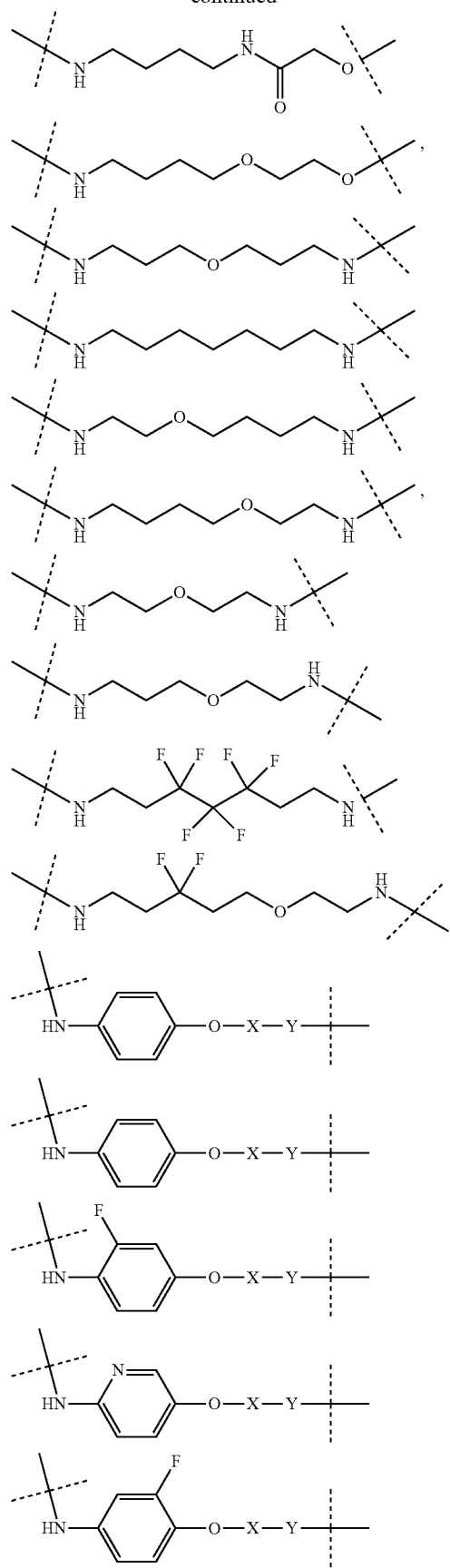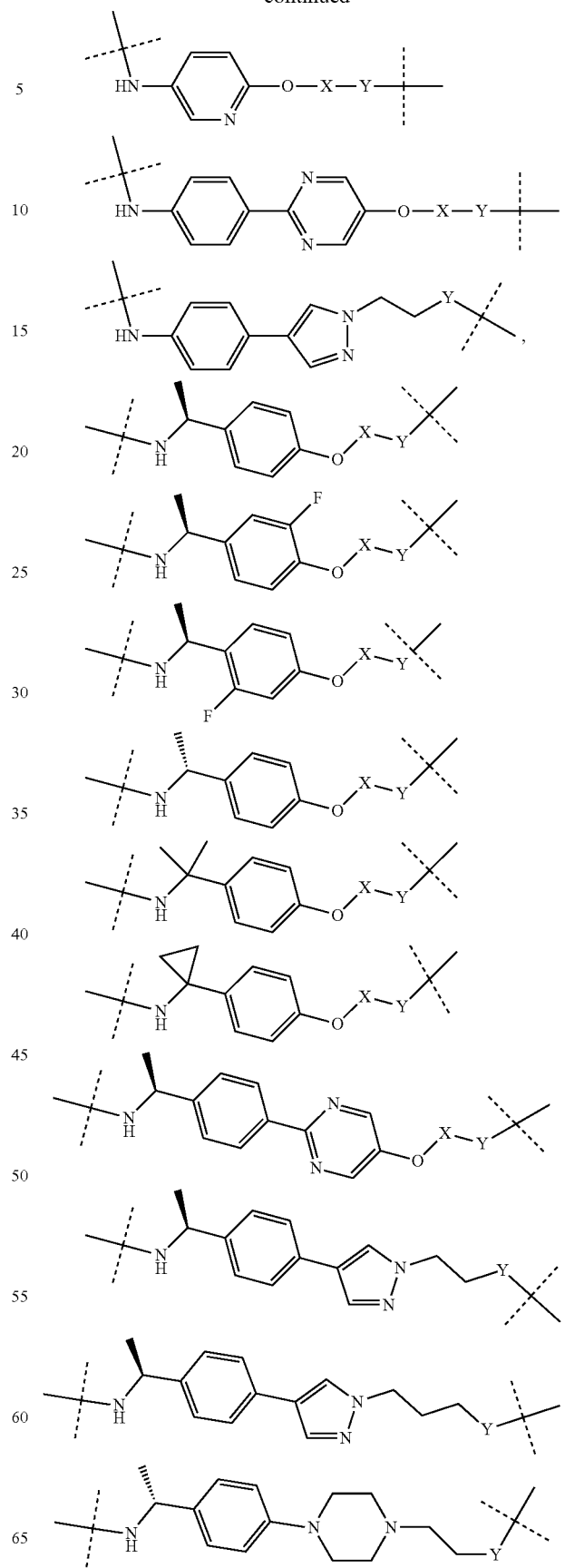

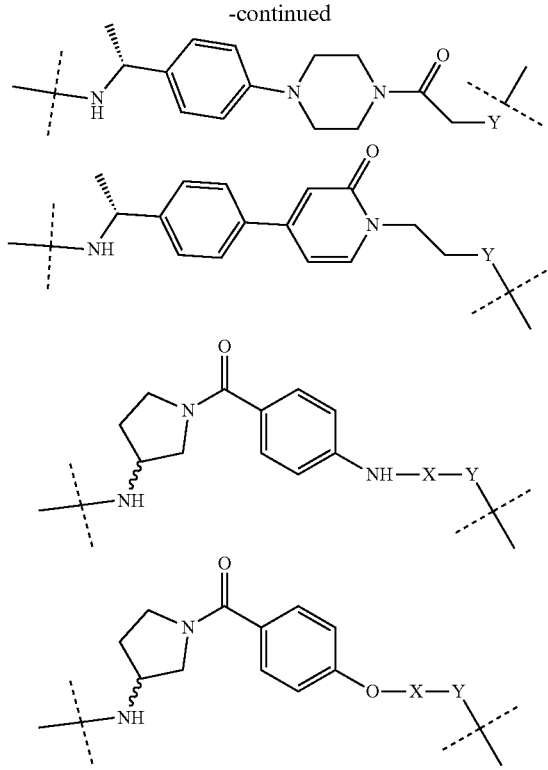

wherein:
'X" in above structures can be linear chain with atoms ranging from 2 to 14, and the mentioned chain can contain heteroatoms such as oxygen; and
"Y" in above structures can be O, N, S(O)$_n$ (n=0, 1, 2).

In any aspect or embodiment described herein, the linker (L) comprises a structure selected from:

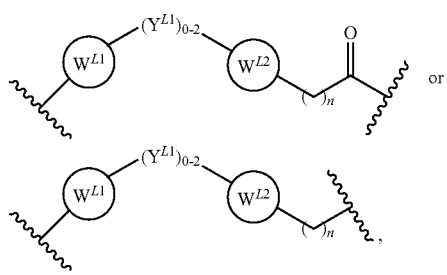

wherein:
$W^{L1}$ and $W^{L2}$ are each independently absent, a 4-8 membered ring with 0-4 heteroatoms, optionally substituted with $R^Q$, each $R^Q$ is independently a H, halo, OH, CN, CF$_3$, C$_{1-6}$ alkyl (linear, branched, optionally substituted), C$_1$-C$_6$ alkoxy (linear, branched, optionally substituted), or 2 $R^Q$ groups taken together with the atom they are attached to, form a 4-8 membered ring system containing 0-4 heteroatoms;
$Y^{L1}$ is each independently a bond, C$_1$-C$_6$ alkyl (linear, branched, optionally substituted) and optionally one or more C atoms are replaced with O; or C$_1$-C$_6$ alkoxy (linear, branched, optionally substituted);
n is 0-10; and
a dashed line indicates the attachment point to the PTM or CLM moieties.

In any aspect or embodiment described herein, the linker comprises a structure selected from:

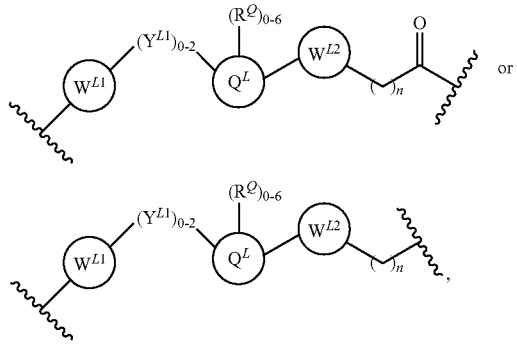

wherein:
$W^{L1}$ and $W^{L2}$ are each independently absent, aryl, heteroaryl, cyclic, heterocyclic, C$_{1-6}$ alkyl and optionally one or more C atoms are replaced with O, C$_{1-6}$ alkene and optionally one or more C atoms are replaced with O, C$_{1-6}$ alkyne and optionally one or more C atoms are replaced with O, bicyclic, biaryl, biheteroaryl, or biheterocyclic, each optionally substituted with $R^Q$, each $R^Q$ is independently a H, halo, OH, CN, CF$_3$, hydroxyl, nitro, C≡CH, C$_{2-6}$ alkenyl, C$_{2-6}$ alkynyl, C$_1$-C$_6$ alkyl (linear, branched, optionally substituted), C$_1$-C$_6$ alkoxy (linear, branched, optionally substituted), OC$_{1-3}$alkyl (optionally substituted by 1 or more —F), OH, NH$_2$, NR$^{Y1}$R$^{Y2}$, CN, or 2 $R^Q$ groups taken together with the atom they are attached to, form a 4-8 membered ring system containing 0-4 heteroatoms;
$Y^{L1}$ is each independently a bond, NR$^{YL1}$, O, S, NR$^{YL2}$, CR$^{YL1}$R$^{YL2}$, C=O, C=S, SO, SO$_2$, C$_1$-C$_6$ alkyl (linear, branched, optionally substituted) and optionally one or more C atoms are replaced with O; C$_1$-C$_6$ alkoxy (linear, branched, optionally substituted);
$Q^L$ is a 3-6 membered alicyclic or aromatic ring with 0-4 heteroatoms, optionally bridged, optionally substituted with 0-6 $R^Q$, each $R^Q$ is independently H, C$_{1-6}$ alkyl (linear, branched, optionally substituted by 1 or more halo, C$_{1-6}$ alkoxyl), or 2 $R^Q$ groups taken together with the atom they are attached to, form a 3-8 membered ring system containing 0-2 heteroatoms);
$R^{YL1}$, $R^{YL2}$ are each independently H, OH, C$_{1-6}$ alkyl (linear, branched, optionally substituted by 1 or more halo, C$_{1-6}$ alkoxyl), or R$^1$, R$^2$ together with the atom they are attached to, form a 3-8 membered ring system containing 0-2 heteroatoms);
n is 0-10; and
a dashed line indicates the attachment point to the PTM or CLM moieties.

In any aspect or embodiment described herein, the linker (L) is a polyethylenoxy group optionally substituted with aryl or phenyl comprising from 1 to 10 ethylene glycol units.

In any aspect or embodiment described herein, the PTM is an estrogen receptor (ER) binding moiety represented by the chemical structure:

PTM-I

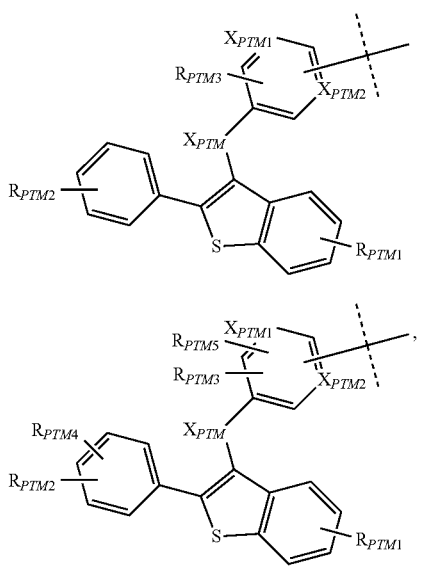

PTM-II wherein:

$X_{PTM}$ is O or C=O;

each of $X_{PTM1}$ and $X_{PTM2}$ is independently selected from N or CH;

$R_{PTM1}$ is independently selected from OH, O(CO)$R_{PTM}$, O-lower alkyl, wherein $R_{PTM}$ is an alkyl or aryl group in the ester;

$R_{PTM2}$ and $R_{PTM4}$ are independently selected from H, OH, halogen, CN, $CF_3$, $SO_2$-alkyl, O-lower alkyl;

$R_{PTM3}$ and $R_{PTM5}$ are independently selected from H, halogen;

PTM-I has at least one $R_{PTM2}$ and at least one $R_{PTM3}$ on each respective rings; and the

indicates the site of attachment of at least one of the linker, the CLM, a CLM', or a combination thereof.

In any aspect or embodiment described herein, the PTM is an estrogen receptor (ER) binding moiety represented by the chemical structure:

Formula ($I_{PTM}$)

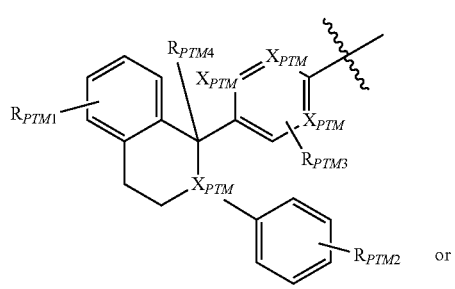

or

Formula ($II_{PTM}$)

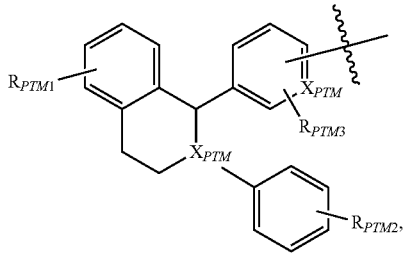

wherein:

each $X_{PTM}$ is independently CH, N;

 indicates the site of attachment of at least one of the linker (L), the CLM, a CLM', ULM, an ILM, a VLM, MLM, a ULM', a ILM', a VLM', a MLM', or a combination thereof;

each $R_{PTM1}$ is independently OH, halogen, alkoxy, methoxy, ethoxy, O(CO)$R_{PTM}$, wherein the substitution can be a mono-, di- or tri-substitution and the $R_{PTM}$ is alkyl or cycloalkyl group with 1 to 6 carbons or aryl groups;

each $R_{PTM2}$ is independently H, halogen, CN, $CF_3$, liner or branched alkyl, alkoxy, methoxy, ethoxy, wherein the substitution can be mono- or di-substitution;

each $R_{PTM3}$ is independently H, halogen, wherein the substitution can be mono- or di-substitution; and $R_{PTM4}$ is a H, alkyl, methyl, ethyl.

In any aspect or embodiment described herein, the PTM is an androgen receptor (AR) binding moiety (ABM) represented by a structure selected from the group consisting of:

ABM-a

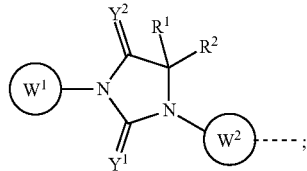

ABM-b

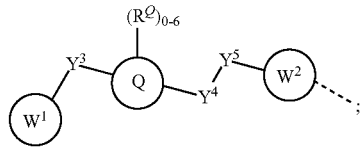

ABM-c

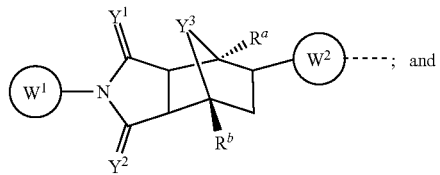

; and

ABM-d

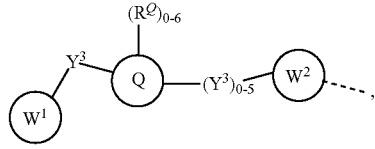

wherein:

$W^1$ is aryl, heteroaryl, bicyclic, or biheterocyclic, each independently substituted by 1 or more H, halo, hydroxyl, nitro, CN, C≡CH, C$_{1-6}$ alkyl (linear, branched, optionally substituted; for example, optionally substituted by 1 or more halo, C$_{1-6}$ alkoxyl), C$_{1-6}$ alkoxyl (linear, branched, optionally substituted; for example, optionally substituted by 1 or more halo), C$_{2-6}$ alkenyl, C$_{2-6}$ alkynyl, or CF$_3$;

Y$^1$, Y$^2$ are each independently NR$^{Y1}$, O, S, SO2, heteroaryl, or aryl;

Y$^3$, Y$^4$, Y$^5$ are each independently a bond, O, NR$^{Y2}$, CR$^{Y1}$R$^{Y2}$, C=O, C=S, SO, SO$_2$, heteroaryl, or aryl;

Q is a 3-6 membered ring with 0-4 heteroatoms, optionally substituted with 0-6 R$^Q$, each R$^Q$, is independently H, C$_{1-6}$ alkyl (linear, branched, optionally substituted, for example, optionally substituted by 1 or more halo, C$_{1-6}$ alkoxyl), halogen, C$_{1-6}$ alkoxy, or 2 R$^Q$ groups taken together with the atom they are attached to, form a 3-8 membered ring system containing 0-2 heteroatoms);

R$^1$, R$^2$, R$^a$, R$^b$, R$^{Y1}$, R$^{Y2}$ are each independently H, C$_{1-6}$ alkyl (linear, branched, optionally substituted; for example, optionally substituted by 1 or more halo, C$_{1-6}$ alkoxyl), halogen, C$_{1-6}$ alkoxy, cyclic, heterocyclic or R$^1$, R$^2$ together with the atom they are attached to, form a 3-8 membered ring system containing 0-2 heteroatoms);

W$^2$ is a bond, C$_{1-6}$ alkyl, C$_{1-6}$ heteroalkyl, O, aryl, heteroaryl, alicyclic, heterocyclic, biheterocyclic, biaryl, or biheteroaryl, each optionally substituted by 1-10 R$^{W2}$;

each R$^{W2}$ is independently H, halo, C$_{1-6}$ alkyl (linear or branched optionally substituted; for example, optionally substituted by 1 or more F), —OR$^{W2A}$, C$_{3-6}$ cycloalkyl, C$_{4-6}$ cycloheteroalkyl, C$_{1-6}$ alkyl (optionally substituted), heterocyclic (optionally substituted), aryl (optionally substituted), or heteroaryl (optionally substituted), bicyclic hereoaryl or aryl, OC$_{1-3}$alkyl (optionally substituted; for example, optionally substituted by 1 or more —F), OH, NH$_2$, NR$^{Y1}$R$^{Y2}$, CN;

R$^{W2A}$ is H, C$_{1-6}$ alkyl (linear, branched), or C$_{1-6}$ heteroalkyl (linear, branched), each optionally substituted by a cycloalkyl, cycloheteroalkyl, aryl, heterocyclic, heteroaryl, halo, or OC$_{1-3}$alkyl; and the dashed line indicates the site of attachment of at least one of the linker, the CLM, a CLM', or a combination thereof.

In any aspect or embodiment described herein, the PTM is a BET/BRD4 targeting moiety comprising a group according to the chemical structure PTM-a:

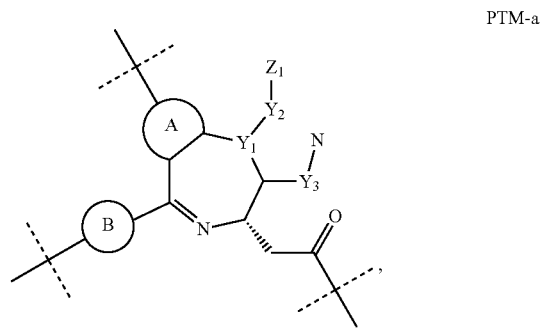

PTM-a wherein:
Y$_1$, Y$_2$ and Y$_3$ are independently selected from the group of carbon, nitrogen or oxygen and together with the atoms to form an aromatic fused ring.

A and B are independently selected from the group of a 5-membered aromatic ring, a 6-membered aromatic ring, a heteroaromatic ring, a carbocyclic, a thiophene a pyrrole ring, a pyridine, a pyrimidine, a pyrazine, a pyrazole ring each optionally substituted with alkyl, alkoxy, halogen, an aromatic and a heteroaromatic ring; wherein ring A is fused to the central azepine (Y1=C) or diazepine (Y1=N) moiety; and Z1 is selected from the group of methyl or analkyl group, and wherein the dashed line indicates the site of attachment of at least one of the linker, the CLM, a CLM', or a combination thereof.

In any aspect or embodiment described herein, the PTM is a BRaf targeting moiety that is represented by at least one of chemical structures PTM-Ia, PTM-Ib, PTM-IIa, PTM-IIb, PTM-IIIa, PTM-IIIb, PTM-IVa, PTM-IVb:

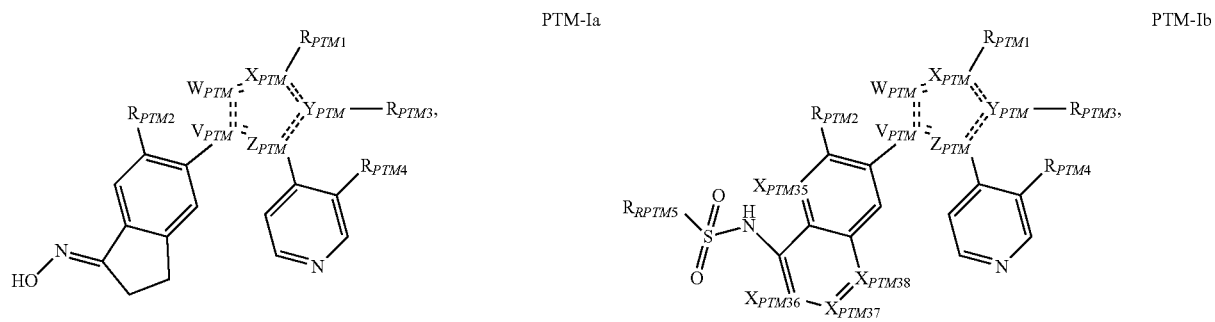

-continued

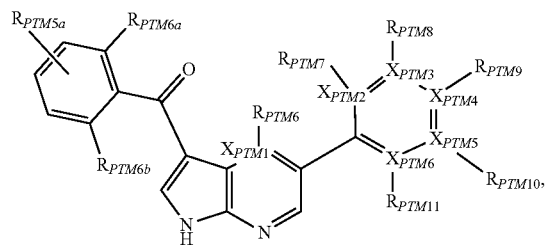
PTM-IIa

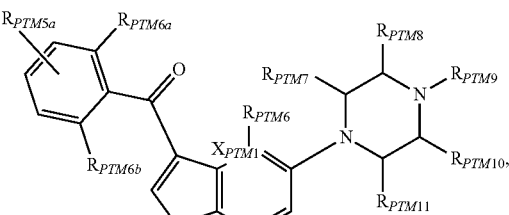
PTM-IIb

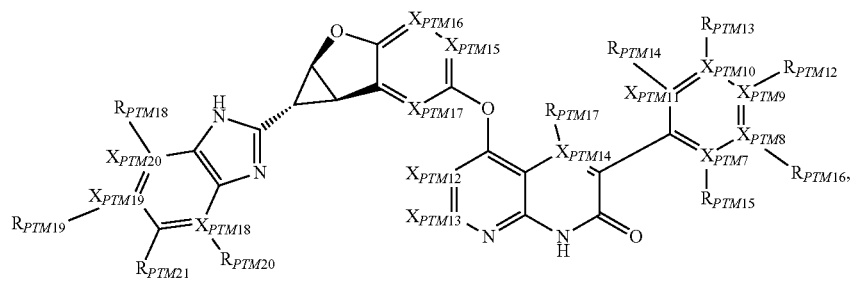
PTM-III

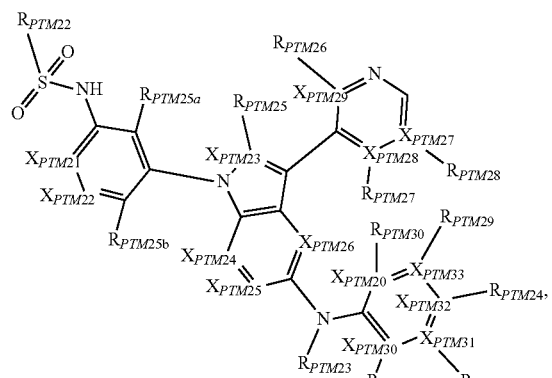
PTM-IVa

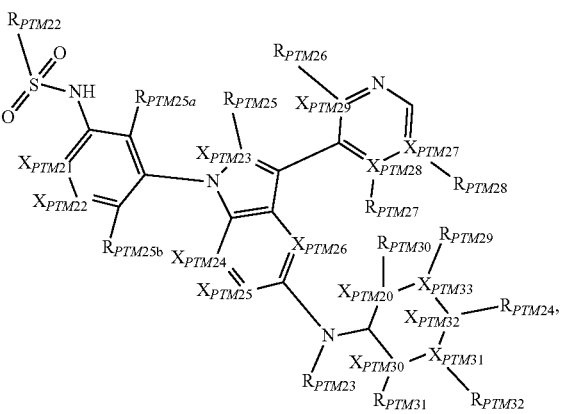
PTM-IVb wherein;
double dotted bonds are aromaric bonds;
$V_{PTM}, W_{PTM}, X_{PTM}, Y_{PTM}, Z_{PTM}$ is one of the following combinations: C, CH, N, N, C; C, N, N, CH, C; C, O, C, CH, C; C, S, C, CH, C; C, CH, C, O, C; C, CH, C, S, C; C, CH, N, CH, C; N, CH, C, CH, C; C, CH, C, CH, N; N, N, C, CH, C; N, CH, C, N, C; C, CH, C, N, N; C, N, C, CH, N; C, N, C, N, C; and C, N, N, N, C;
$R_{PTM1}$ is covalently joined to a ULM, a chemical linker group (L), a CLM, an ILM, a VLM, MLM, a ULM', a CLM', a ILM', a VLM', a MLM', or combination thereof;
$R_{PTM2}$ is hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;
$R_{PTM3}$ is absent, hydrogen, aryl, methyl, ethyl, other alkyl, cyclic alkyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;
$R_{PTM4}$ is hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

each of $R_{PTM5}$ and $R_{PTM22}$ is independently selected from the group consisting of

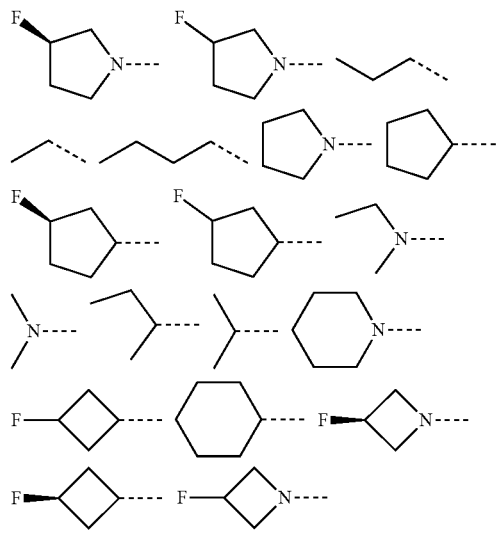

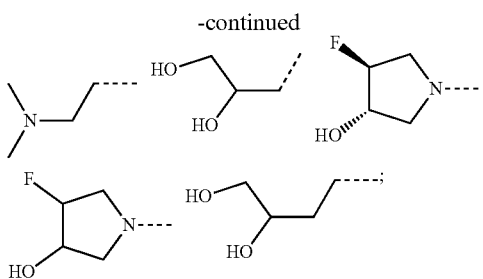

$X_{PTM1}, X_{PTM2}, X_{PTM3}, X_{PTM4}, X_{PTM5}, X_{PTM6}, X_{PTM7}, X_{PTM8}, X_{PTM9}, X_{PTM10}, X_{PTM11}, X_{PTM12}, X_{PTM13}, X_{PTM14}, X_{PTM15}, X_{PTM16}, X_{PTM17}, X_{PTM18}, X_{PTM19}, X_{PTM20}, X_{PTM21}, X_{PTM22}, X_{PTM23}, X_{PTM24}, X_{PTM25}, X_{PTM26}, X_{PTM27}, X_{PTM28}, X_{PTM29}, X_{PTM30}, X_{PTM31}, X_{PTM32}, X_{PTM33}, X_{PTM34}, X_{PTM35}, X_{PTM36}, X_{PTM37}, X_{PTM38}$ are independently selected from CH or N;

$R_{PTM5a}$ is selected from the group consisting of: H, optionally substituted amide (e.g., optionally substituted with an alkyl, methyl, ethyl, propyl, or butyl group), optionally substituted amine,

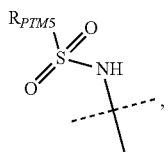

—NHC(O)$R_{PTM5}$;

$R_{PTM6a}$ and $R_{PTM6b}$ are each independently selected from hydrogen, halogen, or $C_1$-$C_6$ alkyl (linear, branched, optionally substituted);

$R_{PTM6}$ is either of the following groups: absent, hydrogen, halogen, aryl, methyl, ethyl, OCH$_3$, NHCH$_3$ or M1-CH$_2$—CH$_2$-M2, wherein M1 is CH$_2$, O and NH, and M2 is hydrogen, alkyl, cyclic alkyl, aryl or heterocycle.

$R_{PTM7}$ is absent, hydrogen, halogen, aryl, methyl, ethyl, OCH$_3$, NHCH$_3$ or M1-CH$_2$—CH$_2$-M2, wherein M1 is CH$_2$, O and NH, and M2 is hydrogen, alkyl, cyclic alkyl, aryl or heterocycle.

$R_{PTM8}$, $R_{PTM9}$ or $R_{PTM10}$ are independently selected from the group consisting of absent, hydrogen, halogen, aryl, heteroaryl, alkyl, cycloalkyl, heterocycle, methyl, ethyl, OCH$_3$, NHCH$_3$ or M1-CH$_2$—CH$_2$-M2, wherein M1 is CH$_2$, O and NH, and M2 is hydrogen, alkyl, cyclic alkyl, aryl or heterocycle;

$R_{PTM11}$ is absent, hydrogen, halogen, methyl, ethyl, OCH$_3$, NHCH$_3$ or M1-CH$_2$—CH$_2$-M2 in which M1, wherein CH$_2$, O and NH, and M2 is hydrogen, alkyl, cyclic alkyl, aryl or heterocycle;

$R_{PTM12}$, $R_{PTM13}$, $R_{PTM14}$, $R_{PTM15}$, $R_{PTM16}$, $R_{PTM17}$, $R_{PTM18}$, $R_{PTM19}$ are independently selected from the group consisting of absent, hydrogen, halogen, aryl, heteroaryl, cycloalkyl, heterocycle, methyl, ethyl, other alkyl, OCH$_3$, NHCH$_3$ or M1-CH$_2$—CH$_2$-M2, wherein M1 is CH$_2$, O and NH, and M2 is hydrogen, alkyl, cyclic alkyl, aryl or heterocycle;

$R_{PTM20}$ is a small group containing less than four non-hydrogen atoms;

$R_{PTM21}$ is selected from the group consisting of trifluoromethyl, chloro, bromo, fluoro, methyl, ethyl, propyl, isopropyl, tert-butyl, butyl, iso-butyl, cyclopropyl, cyclobutyl, cyclopentyl, cyclohexyl, OCH$_3$, NHCH$_3$, dimethylamino or M1-CH$_2$—CH$_2$-M2, wherein M1 is CH$_2$, O or NH, and M2 is hydrogen, alkyl, cyclic alkyl, aryl or heterocycle;

$R_{PTM25a}$ and $R_{PTM25b}$ are each independently selected from hydrogen, halogen, or $C_1$-$C_6$ alkyl (linear, branched, optionally substituted);

$R_{PTM23}$, $R_{PTM24}$, $R_{PTM28}$, $R_{PTM29}$, $R_{PTM30}$, $R_{PTM31}$, $R_{PTM32}$ are independently selected from the group consisting of absent, bond, hydrogen, halogen, aryl (optionally substituted), heteroaryl (optionally substituted), cycloalkyl (optionally substituted), heterocycle (optionally substituted), methyl, ethyl (optionally substituted), other alkyl (linear, branched, optionally substituted), OCH$_3$, NHCH$_3$ or M1-CH$_2$—CH$_2$-M2, wherein M1 is CH$_2$, O and NH, and M2 is hydrogen, alkyl (linear, branched, optionally substituted), cyclic alkyl (optionally substituted), aryl (optionally substituted) or heterocycle (optionally substituted);

$R_{PTM25}$ is selected from absent, hydrogen, halogen, $C_1$-$C_6$ alkyl (linear, branched, optionally substituted), OCH$_3$, NHCH$_3$ or SCH$_3$;

$R_{PTM26}$ is selected from absent, hydrogen, halogen, $C_1$-$C_6$ alkyl (linear, branched, optionally substituted), OCH$_3$, NHCH$_3$ or SCH$_3$;

$R_{PTM27}$ is selected from the group consisting of absent, hydrogen, halogen, $C_1$-$C_6$ alkyl (linear, branched, optionally substituted), OCH$_3$, NHCH$_3$ or SCH$_3$; and at least one of $R_{PTM8}$, $R_{PTM9}$ or $R_{PTM10}$, $R_{PTM12}$, $R_{PTM13}$, $R_{PTM16}$, $R_{PTM24}$, $R_{PTM29}$, and $R_{PTM32}$ is modified to be covalently joined to a ULM, a chemical linker group (L), a CLM, an ILM, a VLM, MLM, a ULM', a CLM', a ILM', a VLM', a MLM', or combination thereof.

In any aspect or embodiment described herein, when $R_{PTM9}$ is the covalently joined position, $R_{PTM7}$ and $R_{PTM8}$ are connected together via a covalent bond in a way to form a bicyclic group with the ring to which $R_{PTM7}$ and $R_{PTM8}$ are attached.

In any aspect or embodiment described herein, when $R_{PTM8}$ is the covalently joined position, $R_{PTM9}$ and $R_{PTM10}$ are connected together via a covalent bond in a way to form a bicyclic group with the ring to which $R_{PTM9}$ and $R_{PTM10}$ are attached.

In any aspect or embodiment described herein, when RPTM10 is the covalently joined position, RPTM8 and RPTM9 are connected together via a covalent bond in a way to form a bicyclic group with the ring to which RPTM8 and RPTM9 are attached.

In any aspect or embodiment described herein, when $R_{PTM12}$ is the covalently joined position, $R_{PTM13}$ and $R_{PTM14}$ are connected together via a covalent bond in a way to form a bicyclic group with the ring to which $R_{PTM13}$ and $R_{PTM14}$ are attached, and/or $R_{PTM15}$ and $R_{PTM16}$ are connected together via a covalent bond in a way to form a bicyclic group with the ring to which $R_{PTM15}$ and $R_{PTM16}$ are attached.

In any aspect or embodiment described herein, when $R_{PTM13}$ is the covalently joined position, $R_{PTM12}$ and $R_{PTM16}$ are connected together via a covalent bond in a way to form a bicyclic group with the ring to which $R_{PTM12}$ and $R_{PTM16}$ are attached, and/or $R_{PTM15}$ and $R_{PTM16}$ are connected together via a covalent bond in a way to form a bicyclic group with the ring to which $R_{PTM15}$ and $R_{PTM16}$ are attached.

In any aspect or embodiment described herein, when $R_{PTM16}$ is the covalently joined position, $R_{PTM12}$ and $R_{PTM13}$ are connected together via a covalent bond in a way to form a bicyclic group with the ring to which $R_{PTM12}$ and $R_{PTM13}$ are attached, and/or $R_{PTM13}$ and $R_{PTM14}$ are connected together via a covalent bond in a way to form a bicyclic group with the ring to which $R_{PTM13}$ and $R_{PTM14}$ are attached.

In any aspect or embodiment described herein, when $R_{PTM24}$ is the covalently joined position, $R_{PTM31}$ and $R_{PTM32}$ are connected together via a covalent bond in a way to form a bicyclic group with the ring to which $R_{PTM31}$ and $R_{PTM32}$ are attached, or $R_{PTM29}$ and $R_{PTM30}$ are connected together via a covalent bond in a way to form a bicyclic group with the ring to which $R_{PTM29}$ and $R_{PTM30}$ are attached.

In any aspect or embodiment described herein, when $R_{PTM29}$ is the covalently joined position, $R_{PTM24}$ and $R_{PTM32}$ are connected together via a covalent bond in a way to form a bicyclic group with the ring to which $R_{PTM24}$ and $R_{PTM32}$ are attached, and/or $R_{PTM31}$ and $R_{PTM32}$ are connected together via a covalent bond in a way to form a bicyclic group with the ring to which $R_{PTM31}$ and $R_{PTM32}$ are attached.

In any aspect or embodiment described herein, when $R_{PTM32}$ is the covalently joined position, $R_{PTM24}$ and $R_{PTM29}$ are connected together via a covalent bond in a way to form a bicyclic group with the ring to which $R_{PTM24}$ and $R_{PTM29}$ are attached, and/or $R_{PTM29}$ and $R_{PTM30}$ are connected together via a covalent bond in a way to form a bicyclic group with the ring to which $R_{PTM29}$ and $R_{PTM30}$ are attached.

In any aspect or embodiment described herein, the PTM has a structure selected from the group consisting of:

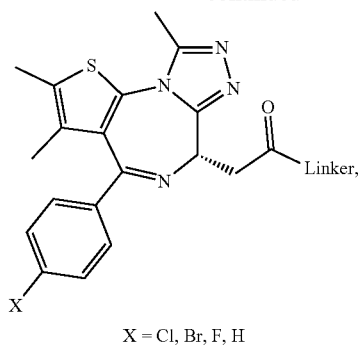

X = Cl, Br, F, H

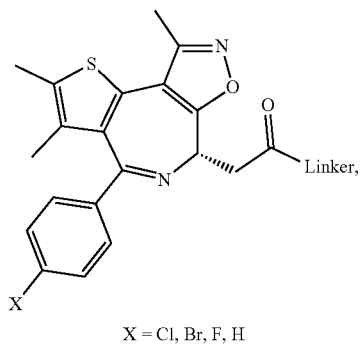

X = Cl, Br, F, H

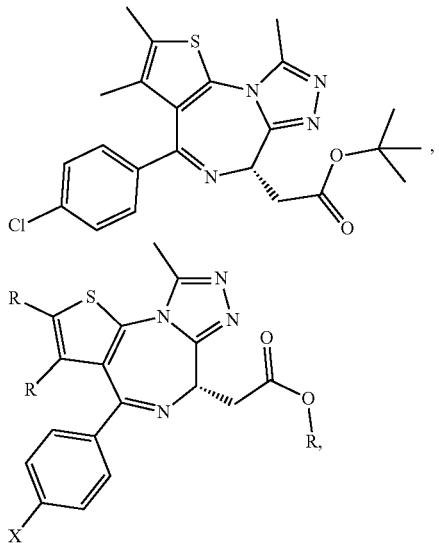

X = Cl, Br, F, H, bond, or a chemical moiety coupling the CLM to the PTM

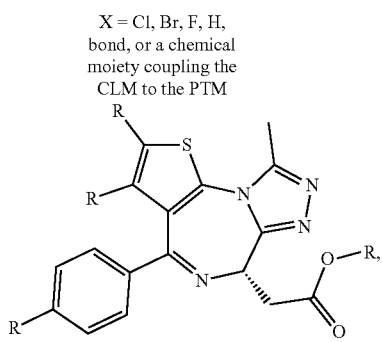

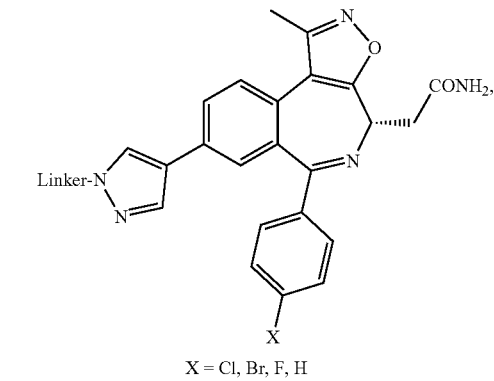

X = Cl, Br, F, H

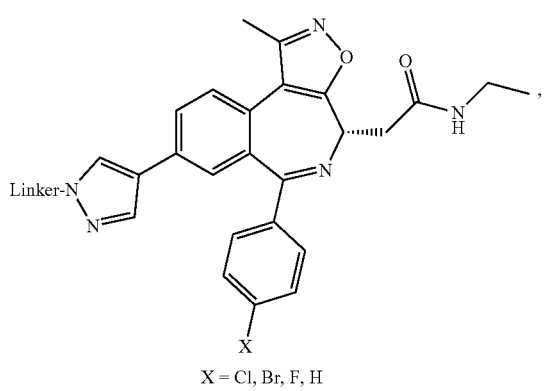

X = Cl, Br, F, H

629
-continued
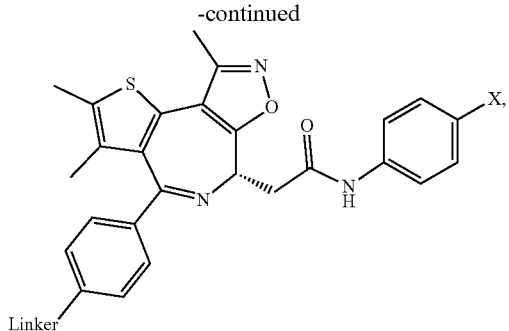
Linker
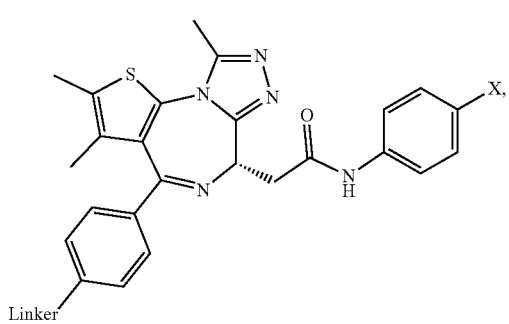
Linker
X = H, F
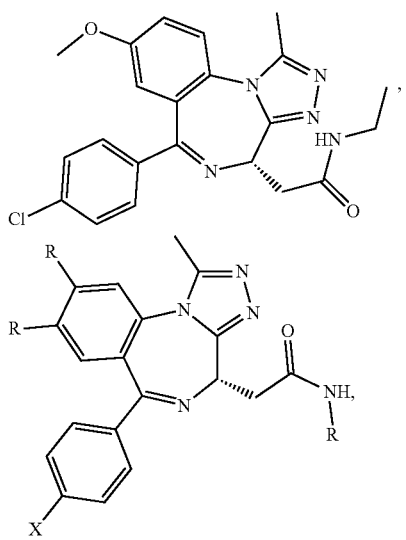
X = Cl, Br, F, H, bond, or a chemical moiety coupling the CLM to the PTM
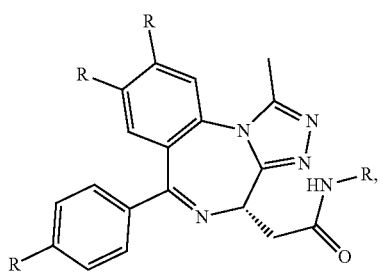
630
-continued
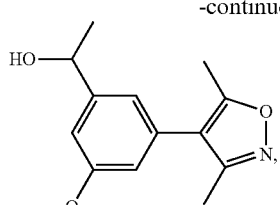
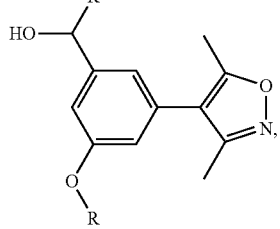
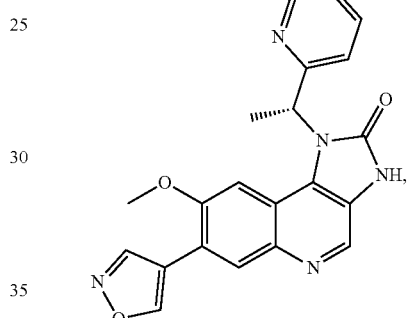
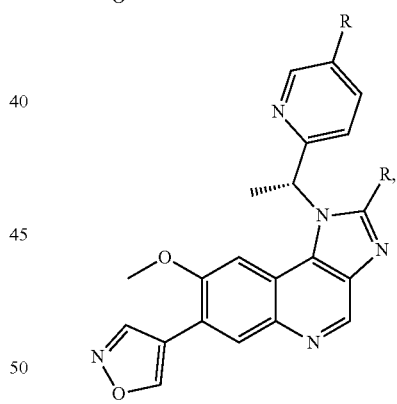
Linker
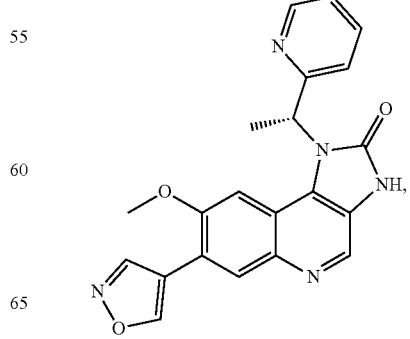

631
-continued
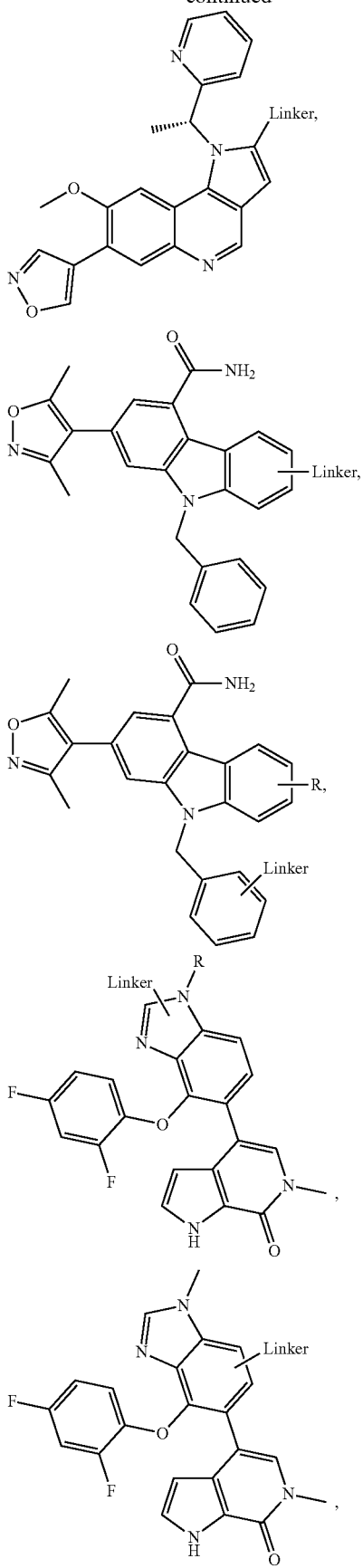
632
-continued
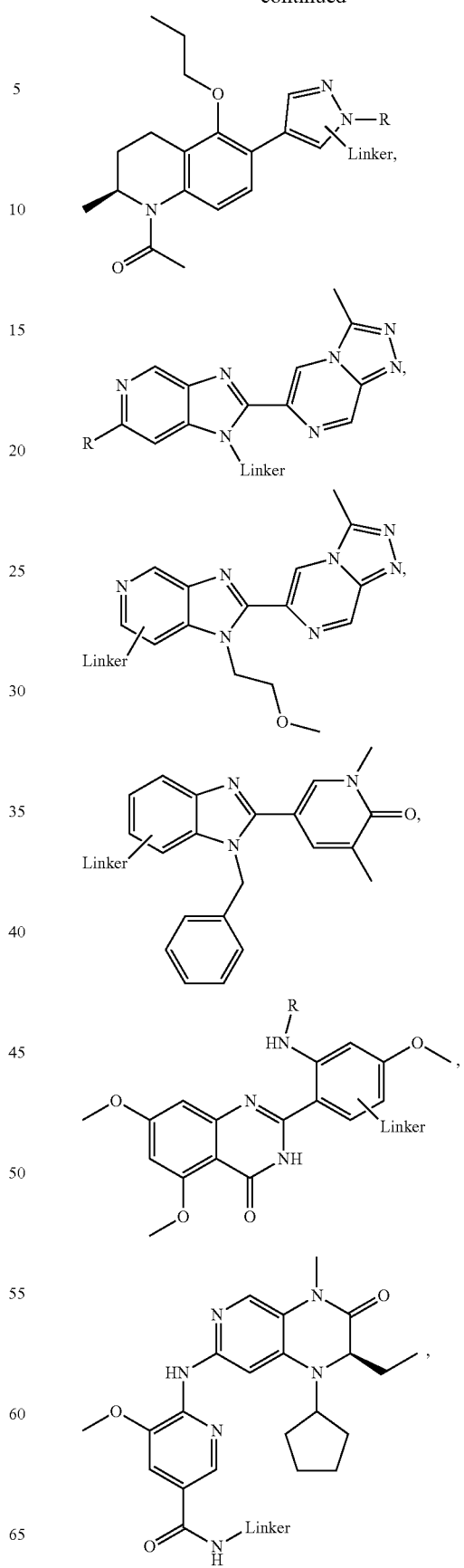

633
-continued
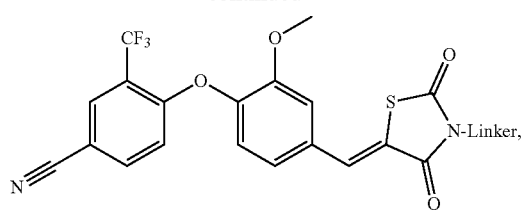
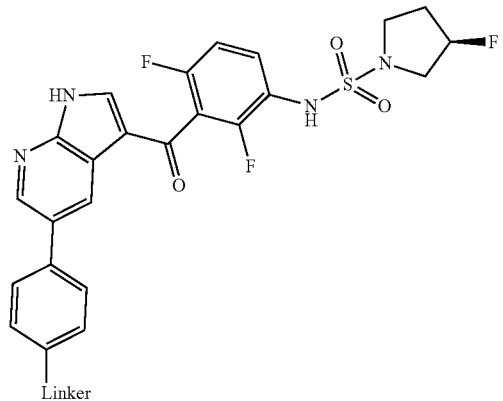
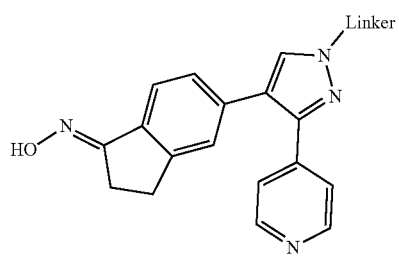
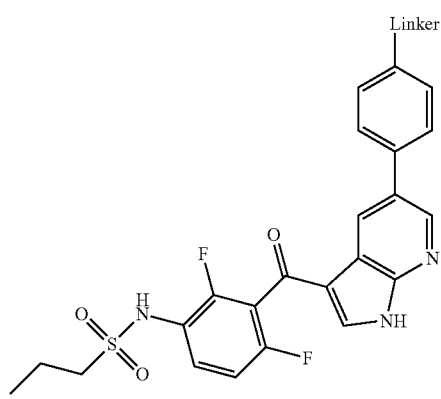
634
-continued
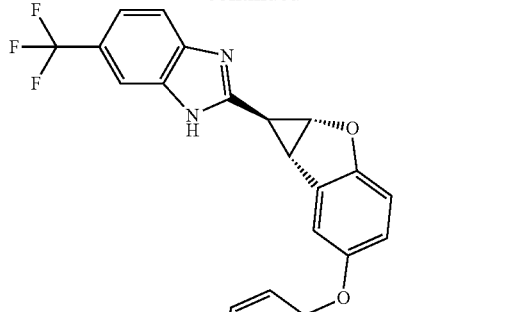
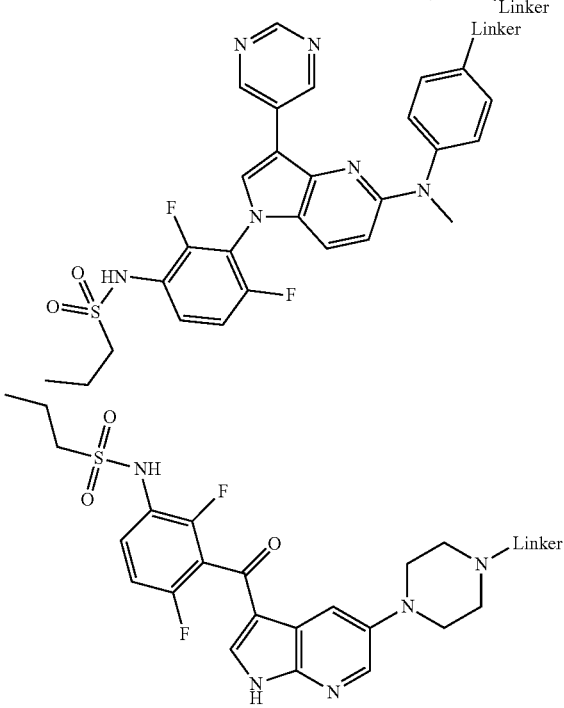
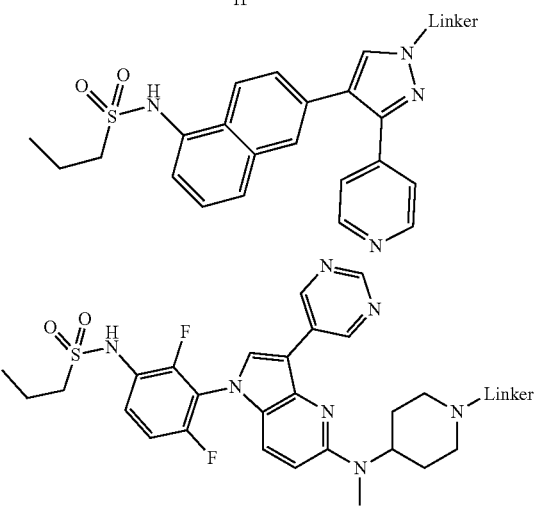

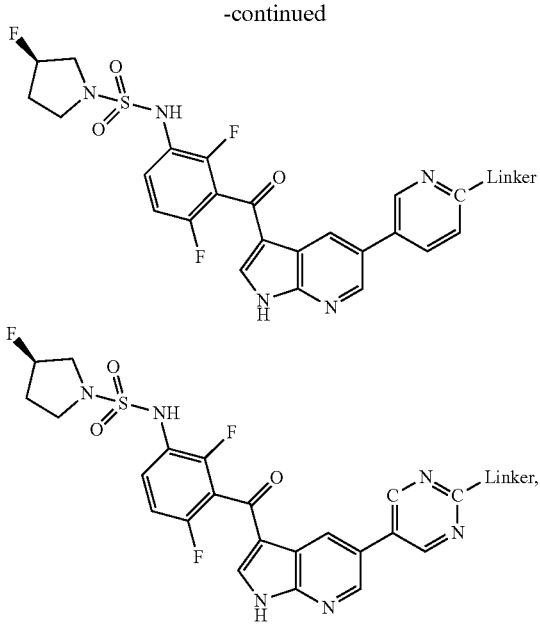

wherein:
R is H, a lower alkyl, a bond, or a chemical moiety coupling the CLM to the PTM; and
Linker is a bond or a chemical linker moiety coupling the CLM to the PTM, including pharmaceutically acceptable salt forms thereof.

In any aspect or embodiment described herein, the compound is selected from the group consisting of compounds 1-52.

A further aspect of the present disclosure provides a composition comprising an effective amount of a bifunctional compound of the present disclosure, and a pharmaceutically acceptable carrier.

In any aspect or embodiment described herein, the composition further comprises at least one of additional bioactive agent or another bifunctional compound of the present disclosure.

In any aspect or embodiment described herein, the additional bioactive agent is anti-cancer agent, an anti-neurodegenerative agent, an antimicrobial agent, an antiviral agent, an anti-HIV agent, or an antifungal agent.

An additional aspect of the present disclosure provides a composition comprising an effective amount of at least one compound of the present disclosure and a pharmaceutically acceptable carrier, additive, and/or excipient for treating a disease or disorder in a subject, the method comprising administering the composition to a subject in need thereof, wherein the compound is effective in treating or ameliorating at least one symptom of the disease or disorder.

In any aspect or embodiment described herein, the disease or disorder is associated with the accumulation and/or aggregation of the target protein.

In any aspect or embodiment described herein, the disease or disorder is selected from the group consisting of asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

In any aspect or embodiment described herein, the disease or disorder is selected from the group consisting of Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barre syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

In any aspect or embodiment described herein, the disease or disorder is selected from the group consisting of aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alstrom syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dub6 syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/ Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia, familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Kennedy's syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alstrom syndrome), Vrolik disease, Waardenburg syndrome, Warburg Sjo Fledelius Syndrome, Weissenbacher-Zweymuller syndrome, Wolf-Hirschhorn syndrome, Wolff Periodic disease, Weissenbacher-Zweymuller syndrome and Xeroderma pigmentosum.

In any aspect or embodiment described herein, the composition further comprises an additional bioactive agent.

In any aspect or embodiment described herein, the additional bioactive agent is at least one of an anti-cancer agent, an anti-neurodegenerative agent, an antimicrobial agent, an antiviral agent, an anti-HIV agent, an antifungal agent, or a combination thereof.

In any aspect or embodiment described herein, the anti-cancer agent is selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(But) 6, Azgly 10] (pyro-Glu-His-Trp-Ser-Tyr-D-Ser(But)-Leu-Arg-Pro-Azgly-NH$_2$ acetate [$C_{59}H_{84}N_{18}Oi_4$-($C_2H_4O_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunoubicin, diethylstilbestrol, epirubicin, fludarabine, fludrocortisone, fluoxymesterone, flutamide, gleevac, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-0-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

An additional aspect of the present disclosure provides a method for inducing degradation of a target protein in a cell comprising administering an effective amount of a compound of the present disclosure to the cell, wherein the compound effectuates degradation of the target protein.

Another aspect of the present disclosure provides a composition comprising an effective amount of a compound of the present disclosure for use in a method for treating cancer, said method comprising administering the composition to a patient in need thereof, wherein the composition is effectuates for the treatment or alleviation of at least one symptom of cancer in the patient.

In any aspect or embodiment described herein, the cancer is squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; multiple myeloma, sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor or teratocarcinomas, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

EXAMPLES

A. Protein Degradation Bioassays:

The following bioassays evaluate the level of protein degradation observed in various cell types using representative compounds disclosed herein.

In each bioassay, cells were treated with varying amounts of compounds encompassed by the present disclosure. The degradation of the following proteins may be evaluated: estrogen receptor α (ERα), bromodomain-containing protein 4 (BRD4), androgen receptor (AR), and BRaf protein.

1. ERE Luciferase Assay for Compounds in Table 5.

T47D-KBluc cells (ATCC® #CRL_2865, T47D human breast cancer cells stably transfected with estrogen responsive element/promoter/luciferase reporter gene) were seeded into 96-well white opaque plates in RPMI growth medium supplemented with 10% fetal bovine serum (FBS) and allowed to adhere overnight in a 37° C. humidified incubator. The following day, cells were treated with PROTACs in a 12-point concentration curve (top final concentration of 300 nM with subsequent concentrations being 3-fold less with 2 pM being the lowest concentration in the assay). Each PROTAC was tested independently in two experiments on 96-well plates. After 24 hours, media was removed and lysis buffer was added to the wells. Following lysis, Bright-Glo™ Luciferase Assay Substrate (Promega, Madison WI) was added and the luciferase activity was measured using a Cytation 3 plate reader (BioTek™, Winooski, VT). Each compound was assayed in duplicate and the activity was calculated as IC50 using GraphPad Prism software (San Diego, CA).

2. Estrogen Receptor-Alpha (ERα) Degradation Assay in MCF-7 Cells Using Western Blot Method for Table 5.

The exemplary novel ERα degraders were assessed for their activity in degrading ERα in MCF-7 cells via western blot. The assay was carried out in the presence of 10% FBS or high percentage of human or mouse serum. Protocols of the western blot assay are described below.

MCF7 cells were grown in DMEM/F12 with 10% FBS and seeded at 24,000 cells per well in 100 µl into 96-well clear tissue culture plates. The following day, the cells were treated with PROTACs in a 7-point concentration curve with 100 nM being the top concentration and serial dilutions to make the other concentrations (30 nM, 10 nM, 3 nM, 1 nM, and 0.3 nM). At all concentrations, 0.01% DMSO is the final concentration in the well. The following day, the plates are aspirated, washed with 50 µl of cold PBS. The cells are lysed with 50 µl/well 4° C. Cell Lysis Buffer (Catalog #9803; Cell Signaling Technology, Danvers, MA) (20 mM Tris-HCL (pH 7.5), 150 mM NaCl, 1 mM $Na_2EDTA$, 1 mM EGTA, 1% Triton, 2.5 mM sodium pyrophosphate, 1 mM B-glycerophosphate, 1 mM sodium vanadate, 1 ug/ml leupeptin). Lysates were clarified at 16,000×g for 10 minutes, and 2 µg of protein was subjected to SDS-PAGE analysis and followed by immunoblotting according to standard protocols. The antibodies used were ERα (Cell Signaling Technologies Catalog #8644), and Tubulin (Sigma Catalog #T9026; St. Louis, MO). Detection reagents were Clarity Western ECL substrate (Bio-Rad Catalog #170-5060; Hercules, CA).

Alternatively, MCF7 cells were grown in DMEM/F12 with 10% FBS and seeded at 24,000 cells per well in 500 µl in 24-well clear tissue culture plates. The following day, the cells were treated with PROTACs in a 5-point concentration curve (100 nM, 33 nM, 11 nM, 3.7 nM, and 1.2 nM) in the presence of 0.01% DMSO. After 72 hours, the wells are aspirated and washed with 500 µl of PBS. The cells are lysed with 100 µl/well 4° C. Cell Lysis Buffer (Catalog #9803; Cell Signaling Technology, Danvers, MA) (20 mM Tris-HCL (pH 7.5), 150 mM NaCl, 1 mM $Na_2EDTA$, 1 mM EGTA, 1% Triton, 2.5 mM sodium pyrophosphate, 1 mM B-glycerophosphate, 1 mM sodium vanadate, 1 ug/ml leupeptin). Lysates were clarified at 16,000×g for 10 minutes, and 2 µg of protein was subjected to SDS-PAGE analysis and followed by immunoblotting according to standard protocols. The antibodies used were ERα (Cell Signaling Technologies Catalog #8644), and Tubulin (Sigma Catalog #T9026; St. Louis, MO). Detection reagents were Clarity Western ECL substrate (Bio-Rad Catalog #170-5060; Hercules, CA).

3. Estrogen Receptor-Alpha (ERα) Degradation Assay Using In-Cell Western™ Assay for Table 5.

Degradation of ERα by claimed compounds were determined in MCF7 cells using an In-Cell Western™ assay. Briefly, MCF7 cells were plated in 96-well plates (2000 cells per well in 100 µl media) and incubated at 37° C. under an atmosphere of 5% $CO_2$ in a humidified incubator overnight. One-hundred (100) µl of media containing test compound (at 2× concentration) was added to the appropriate wells to provide 11 serially decreasing concentrations (top final concentration, 1 µM then 3-fold less for the next 10 concentrations); a vehicle control (DMSO) was also added for each compound. For each experiment, all compounds were assayed in duplicate plates. Cells were then incubated for 3 or 5 days in the above-mentioned environment. The assay was terminated by removal of media, a single wash with ice-cold PBS and the addition of 50 µl paraformaldehyde (PFA: 4% in PBS). After 15 minutes in PFA at room temperature, the cells were permeabilized in Tris-phosphate-buffered saline with Tween (0.1%) (TBST) supplemented with Triton X-100 (0.5%) for 15 minutes. Cells were then blocked in BSA (TBST with BSA, 3%) for one hour. Primary antibodies for the detection of ERα (rabbit monoclonal, 1:1000, Cell Signaling Technology Catalog #8644) and tubulin (mouse monoclonal, 1:5000, Sigma Catalog #T6074) in TBST with BSA (3%) were added. The cells were incubated overnight at 4° C. The cells were then washed thrice with TBST at room temperature and then incubated with anti-rabbit and anti-mouse fluorescently-labelled secondary antibodies (IRDye®; LI-COR; Lincoln, NE) in LI-COR blocking buffer (Catalog #927-50000) for one hour at room temperature. Following 3 washes with TBST, the buffer was removed and the plates were read on an Odyssey® infrared imaging system (LI-COR®; Lincoln, NE) at 700 nm and 800 nm. Using commercial software (ImageStudio™; LI-COR, Lincoln, NE), the staining intensity for ERα and tubulin in each well was quantified and exported for analysis. For each data point, ERα intensity was normalized to tubulin intensity and for each compound all normalized intensity values were normalized to the vehicle control. $DC_{50}$ and $D_{max}$ values were determined following a 4-parameter $IC_{50}$ curve fit using ACAS dose response module (McNeil & Co Inc.).

4. AR ELISA Assay Protocol for Table 6

Compounds were evaluated in this assay in LNCaP and/or VCaP cells utilizing similar protocols. The protocols used with VCaP cells are described below. The androgen receptor ELISA assay was performed using PathScani AR Sandwich ELISA (Cell Signaling Catalog #12850) according to the following assay steps:

VCaP cells were seeded at 40,000 cells/well at a volume of 100 µL/well in VCaP assay medium [Phenol red free RPMI (Gibco Cat #11835-030); 5% Charcoal Stripped (Dextran treated) FBS (Omega Scientific, Cat #FB-04); 1% penstrep (Life Technologies, Gibco Cat #: 10378-016)] in Corning 3904 plates. The cells were incubated for a minimum of 3 days. Cells were dosed with PROTACs diluted in 0.01% DMSO and the drug treatment was allowed for 5 hours.

AR ELISA (Cell Signaling) was performed as follows: 1× Cell Signaling Cell lysis buffer was made (Catalogue #9803; comes with the kit). Media from the treated wells is aspirated, and 100 µL 1× cell lysis buffer/well is added. The cells were placed on a shaker for 10 minutes at 4° C. Twenty microliters of lysate was transferred to 100 µl of Diluent in ELISA plate (0.15 µg/ml-0.075 µg/ml). The lysate-diluent mixture was shaken for 30 minutes at 37° C. Allow mouse AR antibody, anti-mouse antibody, TMB, and STOP solution to come to room temperature. The 1× ELISA buffer included in kit was made and loaded in the reservoir. Media from the plates was discarded, the ELISA plate tapped hard on paper towel, and washed 4×200 µl ELISA wash buffer using a plate washer.

One-hundred (100) µL/well of mouse AR detection Ab was added; the plates were covered and shaken at 37° C. for 1 hour; media was discarded from the plates, the plates were tapped on a paper towel, washed 4× with 200 µL ELISA wash buffer with a plate washer.

One-hundred (100) µL/well of anti-mouse—HRP conjugated Ab (comes with the kit) was added; the plates were covered and shaken at 37° C. for 30 minutes; the TMB reagent was allowed to come to room temperature; the media was discard from the plate, the plates were tapped on paper towel, washed 4× with 200 μL of ELISA wash buffer; the plates were tapped the plates on paper towel. One-hundred (100) μL of TMB was added and the plates shaken for 2 minutes—while watching for color development. One-hundred (100) μL Stop solution was added when light blue color developed. Plates were shaken and read at 450 nM.

Progression of prostate cancer in patients treated with anti-androgen therapy usually involves one of several mechanisms of enhanced Androgen Receptor (AR) signaling, including increased intratumoral androgen synthesis, increased AR expression and AR mutations. PROTACs (PROteolysis TArgeting Chimera), which use bi-functional molecules that simultaneously bind a target of choice and an E3 ligase, cause ubiquitination via induced proximity and degradation of the targeted, pathological protein. As opposed to traditional target inhibition, which is a competitive process, degradation is a progressive process. As such, it is less susceptible to increases in endogenous ligand, target expression, or mutations in the target. Thus, this technology appears to be ideal for addressing the mechanisms of AR resistance in patients with prostate cancer. Data was analyzed and plotted using GraphPad Prism software.

5. BRaf Protein In Vitro Degradation Assay (A375 Cells) of Table 7

A375 cells were cultured in ATCC DMEM+10% FBS in 12 well plates, and treated with indicated compound from Tables 1-41 or 0.1% DMSO vehicle control for 16 hours. Cells were harvested in Cell Signaling lysis buffer (Cat #9803) with the addition of Roche protease inhibitor tablets (Cat #11873580001), and lysates clarified by microcentrifugation. Proteins were separated by SDS-PAGE, and transferred onto nitrocellulose membranes using an Invitrogen iBlot system. Immunoblotting was performed for BRaf (Santa Cruz Cat #9002), CRAF (BD Cat #610151), and pErk (Cell Signaling Cat #9106). GAPDH (Cell Signaling Cat #2118) was used as a loading control. Quantification was carried out using the BioRad Image Lab 5 software.

6. BRaf In-Cell Western Cellular Degradation Assay (A375 Cells) of Table 7

A375 cells were cultured in ATCC DMEM+10% FBS in 96-well plates, and treated with indicated compounds from Tables-43 or 0.1% DMSO vehicle control for 72 hours. Cells were washed with PBS 1×, and affixed to plate using 4% PFA in phosphate buffered saline for 15 minutes; washed 1× and permeabilized using 0.1% Triton-X-100 in PBS for 5 minutes; washed 1× and blocked with LICOR blocker (Cat. #927-50000) for 1 hour. Cells were then incubated with B-Raf antibody (Santa Cruz Cat #9002, Santa Cruz Cat #528) and tubulin antibody (Sigma #T6074) in LICOR blocker for 18 hours. Cells were washed 3× prior to adding secondary antibodies (LICOR cat #926-32210 and 926-68071) and incubated for 1 hour. Cells were washed 3× and imaged using LICOR Odyssey Software.

7. BRD4 Western Protocol for Table 8

22Rv-1 or VCaP cells were purchased from ATCC and cultured in Dulbecco's Modified Eagle's Medium (ATCC), supplemented with 10% FBS (ATCC) and Penicillin/Streptomycin (Life Technologies). DMSO control and compound treatments (0.003 μM, 0.01 μM, 0.03 μM and 0.1 μM) were performed in 12-well plates for 16 hours. Cells were harvested, and lysed in RIPA buffer (50 mM Tris pH8, 150 mM NaCl, 1% Tx-100, 0.1% SDS, 0.5% sodium deoxycholate) supplemented with protease and phosphatase inhibitors. Lysates were clarified at 16,000 g for 10 minutes, and protein concentration was determined. Equal amount of protein (20 μg) was subjected to SDS-PAGE analysis and followed by immunoblotting according to standard protocols. The antibodies used were BRD4 (Cell Signaling #13440), and Actin (Sigma #5441). Detection reagents were Clarity Western ECL substrate (Bio-rad #170-5060).

TABLE 1
Exemplary Estrogen Receptor PROTACs

| Ex. # | Chemical Structure | Name | General Synthetic Method |
|---|---|---|---|
| 1 | 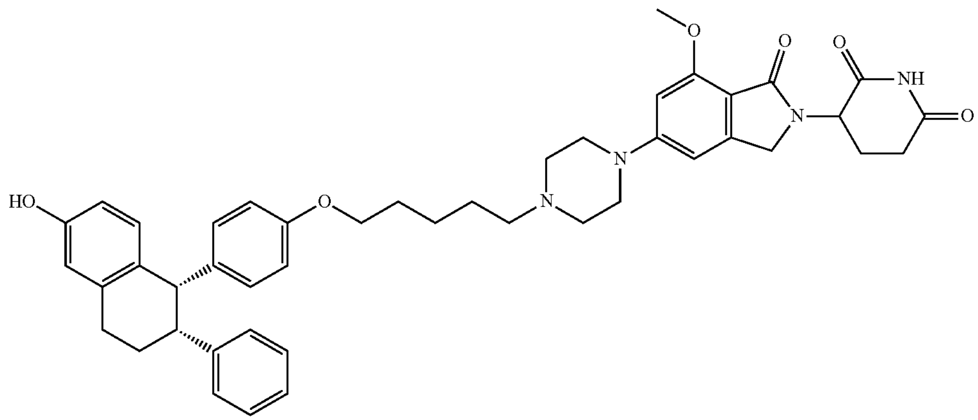 [SMILES: COc1cc(N2CCN(CCCCCOc3ccc([C@H]4c5ccc(O)cc5CC[C@H]4c4ccccc4)cc3)CC2)cc2c1C(=O)N(C1CCC(=O)NC1=O)C2] | 3-{5-[4-(5-{4-[(1S,2R)-6-hydroxy-2-phenyl-1,2,3,4-tetrahydronaphthalen-1-yl]phenoxy}pentyl)piperazin-1-yl]-7-methoxy-1-oxo-2,3-dihydro-1H-isoindol-2-yl}piperidine-2,6-dione | A-2, A-8 |
| 2 | 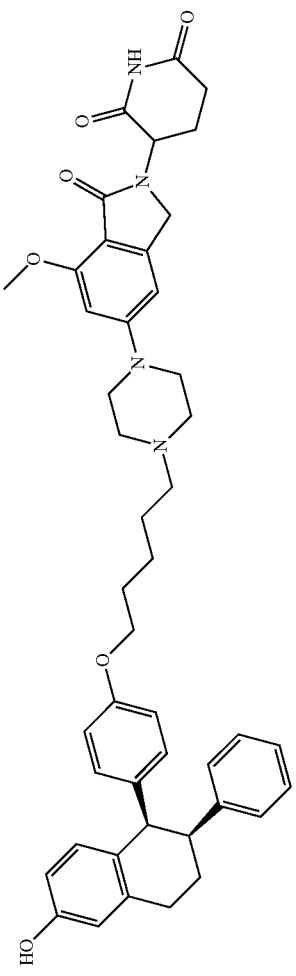 | 3-(5-(4-(5-(4-((1R,2S)-6-hydroxy-2-phenyl-1,2,3,4-tetrahydronaphthalen-1-yl)phenoxy)pentyl)piperazin-1-yl)-7-methoxy-1-oxoisoindolin-2-yl)piperidine-2,6-dione | A-2, A-8 Exp. Procedure included |

TABLE 1-continued

Exemplary Estrogen Receptor PROTACs

| Ex. # | Chemical Structure | Name | General Synthetic Method |
|---|---|---|---|
| 3 | 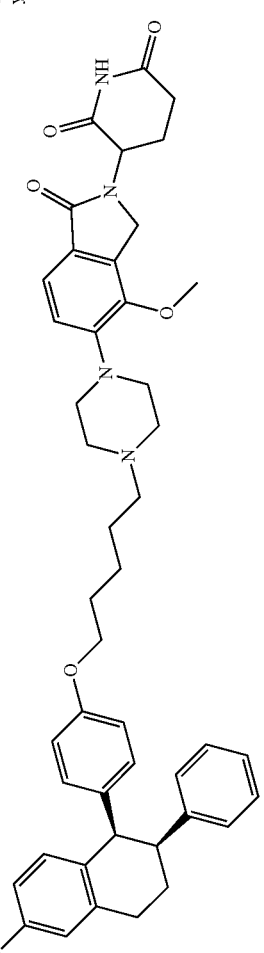 | 3-[5-[4-[5-[4-[(1R,2S)-6-hydroxy-2-phenyl-tetralin-1-yl]phenoxy]pentyl]piperazin-1-yl]-4-methoxy-1-oxo-isoindolin-2-yl]piperidine-2,6-dione | A-4, A-8 Exp. Procedure included |
| 4 | 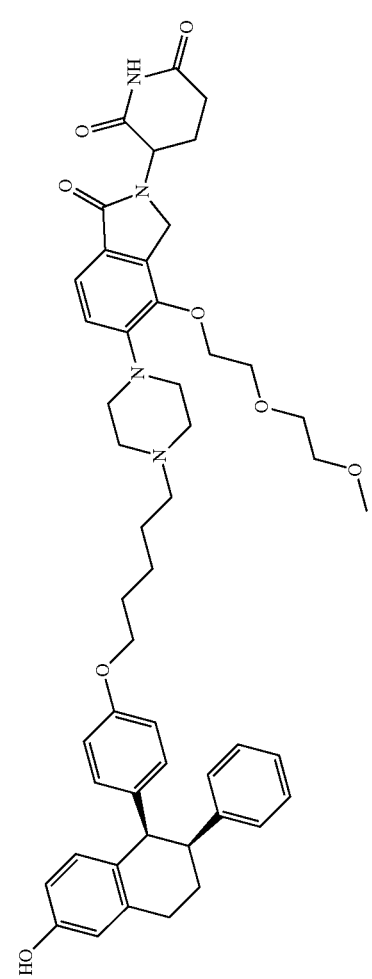 | 3-[5-[4-[5-[4-[(1R,2S)-6-hydroxy-2-phenyl-tetralin-1-yl]phenoxy]pentyl]piperazin-1-yl]-4-[2-(2-methoxyethoxy)ethoxy]-1-oxo-isoindolin-2-yl]piperidine-2,6-dione | A-4, A-5, A-8 |

TABLE 1-continued

Exemplary Estrogen Receptor PROTACs

| Ex. # | Chemical Structure | Name | General Synthetic Method |
|---|---|---|---|
| 5 | 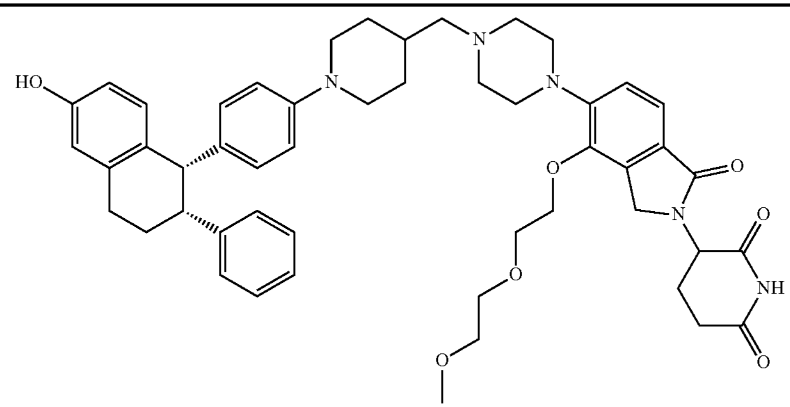 | 3-(5-{4-[(1-{4-[(1S,2R)-6-hydroxy-2-phenyl-1,2,3,4-tetrahydronaphthalen-1-yl]phenyl}piperidin-4-yl)methyl]piperazin-1-yl}-4-[2-(2-methoxyethoxy)ethoxy]-1-oxo-2,3-dihydro-1H-isoindol-2-yl)piperidine-2,6-dione | A-4, A-5, A-12 |
| 6 | 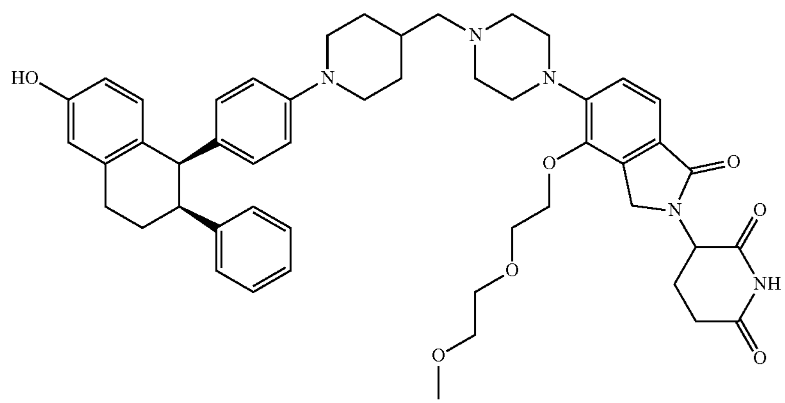 [SMILES: COCCOCCOc1c(N2CCN(CC3CCN(c4ccc([C@@H]5c6ccc(O)cc6CC[C@@H]5c5ccccc5)cc4)CC3)CC2)ccc2c1CN(C1CCC(=O)NC1=O)C2=O] | 3-(5-{4-[(1-{4-[(1R,2S)-6-hydroxy-2-phenyl-1,2,3,4-tetrahydronaphthalen-1-yl]phenyl}piperidin-4-yl)methyl]piperazin-1-yl}-4-[2-(2-methoxyethoxy)ethoxy]-1-oxo-2,3-dihydro-1H-isoindol-2-yl)piperidine-2,6-dione | A-4, A-5, A-12 |

TABLE 1-continued

Exemplary Estrogen Receptor PROTACs

| Ex. # | Chemical Structure | Name | General Synthetic Method |
|---|---|---|---|
| 7 | 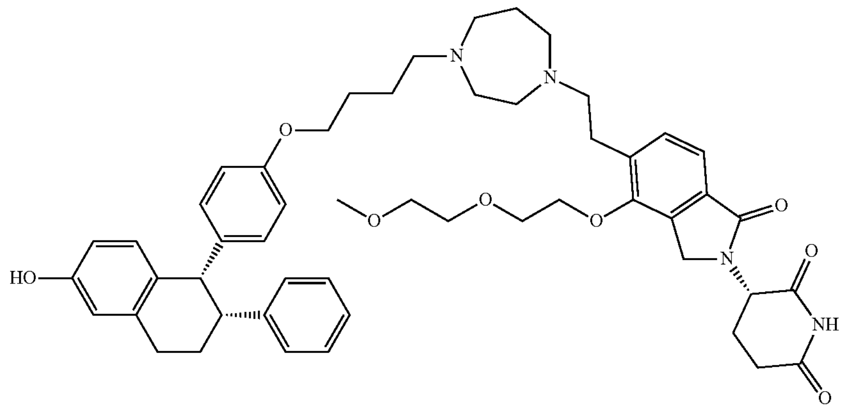 [SMILES: COCCOCCOc1c(CCN2CCCN(CCCCOc3ccc([C@H]4c5ccc(O)cc5CC[C@H]4c4ccccc4)cc3)CC2)ccc2c1CN([C@H]1CCC(=O)NC1=O)C2=O] | (3S)-3-(5-{2-[4-(4-{4-[(1S,2R)-6-hydroxy-2-phenyl-1,2,3,4-tetrahydronaphthalen-1-yl]phenoxy}butyl)-1,4-diazepan-1-yl]ethyl}-4-[2-(2-methoxyethoxy)ethoxy]-1-oxo-2,3-dihydro-1H-isoindol-2-yl)piperidine-2,6-dione | A-5, A-9 |
| 8 | 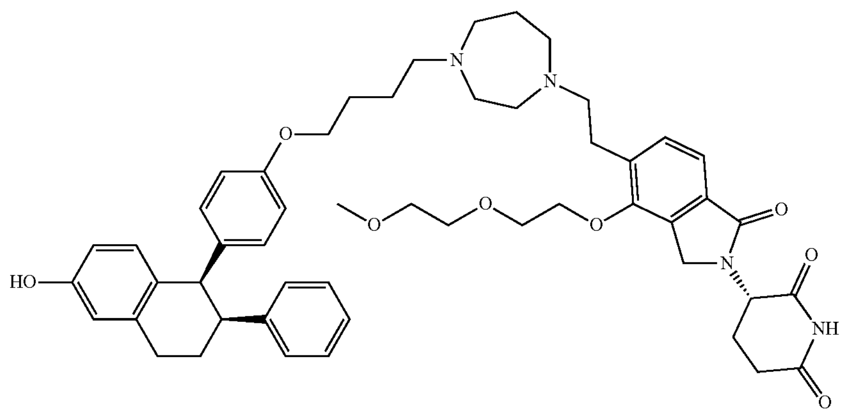 [SMILES: COCCOCCOc1c(CCN2CCCN(CCCCOc3ccc([C@@H]4c5ccc(O)cc5CC[C@@H]4c4ccccc4)cc3)CC2)ccc2c1CN([C@H]1CCC(=O)NC1=O)C2=O] | (3S)-3-[5-[2-[4-(4-{4-[(1R,2S)-6-hydroxy-2-phenyl-tetralin-1-yl]phenoxy]butyl]-1,4-diazepan-1-yl]ethyl]-4-[2-(2-methoxyethoxy)ethoxy]-1-oxo-isoindolin-2-yl]piperidine-2,6-dione | A-5, A-9 |

TABLE 1-continued

Exemplary Estrogen Receptor PROTACs

| Ex. # | Chemical Structure | Name | General Synthetic Method |
|---|---|---|---|
| 9 | 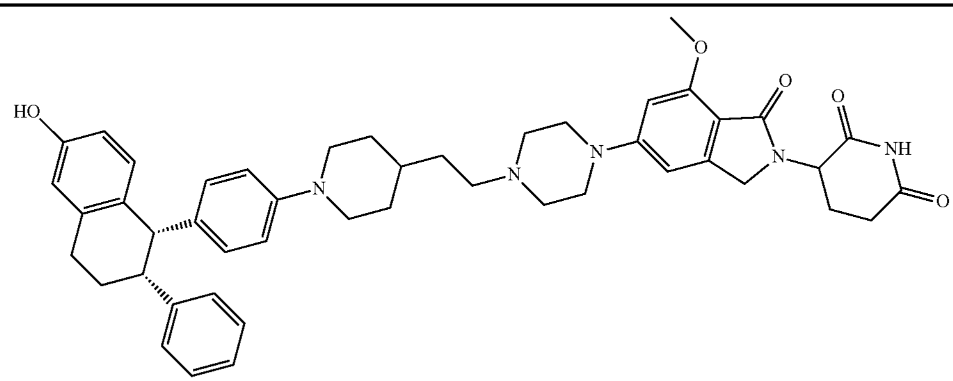 | 3-(5-{4-[2-(1-{4-[(1S,2R)-6-hydroxy-2-phenyl-1,2,3,4-tetrahydronaphthalen-1-yl]phenyl}piperidin-4-yl)ethyl]piperazin-1-yl}-7-methoxy-1-oxo-2,3-dihydro-1H-isoindol-2-yl)piperidine-2,6-dione | A-2, A-13 |
| 10 | 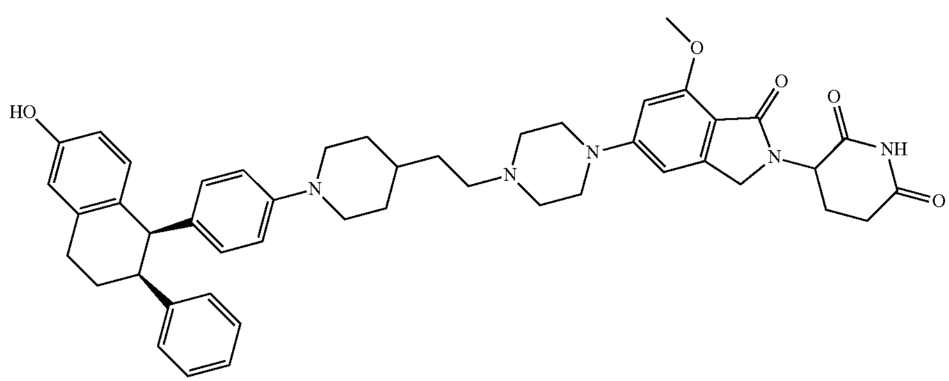 [SMILES: COc1cc(N2CCN(CCC3CCN(c4ccc([C@@H]5c6ccc(O)cc6CC[C@@H]5c5ccccc5)cc4)CC3)CC2)cc2c1C(=O)N(C1CCC(=O)NC1=O)C2] | 3-[5-[4-[2-[1-[4-[(1R,2S)-6-hydroxy-2-phenyl-tetralin-1-yl]phenyl]-4-piperidyl]ethyl]piperazin-1-yl]-7-methoxy-1-oxo-isoindolin-2-yl]piperidine-2,6-dione | A-2, A-13 |

TABLE 1-continued

Exemplary Estrogen Receptor PROTACs

| Ex. # | Chemical Structure | Name | General Synthetic Method |
|---|---|---|---|
| 11 | 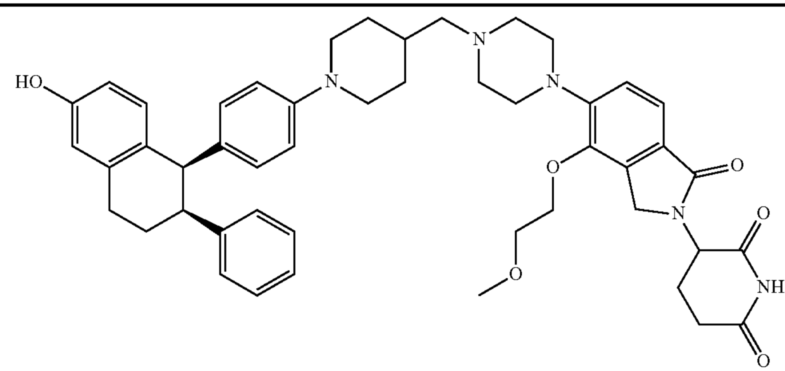 | 3-[5-[4-[[1-[4-[(1R,2S)-6-hydroxy-2-phenyl-tetralin-1-yl]phenyl]-4-piperidyl]methyl]piperazin-1-yl]-4-(2-methoxyethoxy)-1-oxo-isoindolin-2-yl]piperidine-2,6-dione | A-4, A-12 |
| 12 | 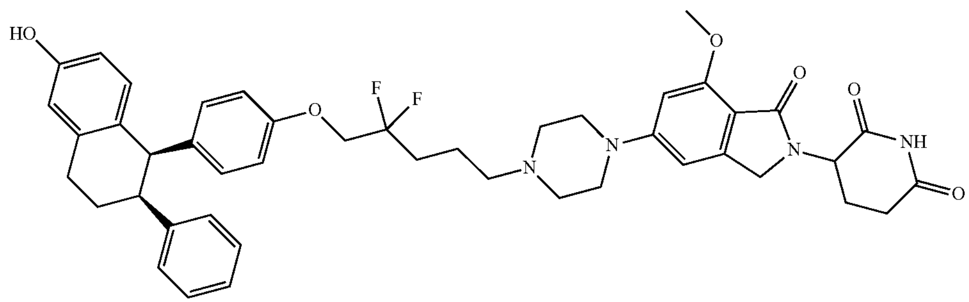 [SMILES: COc1cc(N2CCN(CCCC(F)(F)COc3ccc([C@@H]4c5ccc(O)cc5CC[C@@H]4c4ccccc4)cc3)CC2)cc2c1C(=O)N(C1CCC(=O)NC1=O)C2] | 3-[5-[4-[4,4-difluoro-5-[4-[(1R,2S)-6-hydroxy-2-phenyl-tetralin-1-yl]phenoxy]pentyl]piperazin-1-yl]-7-methoxy-1-oxo-isoindolin-2-yl]piperidine-2,6-dione | A-2, A-10 |
| 13 | 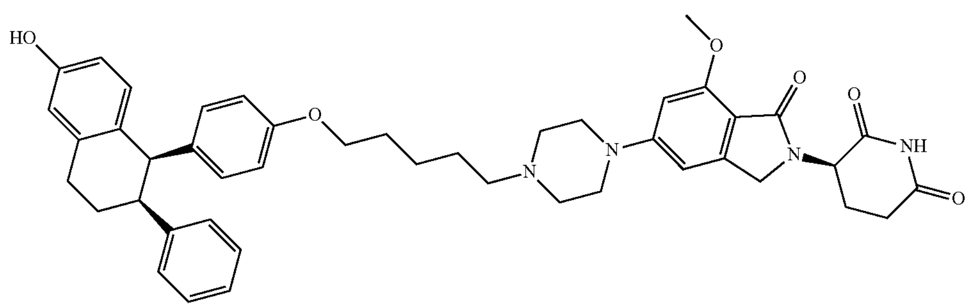 [SMILES: COc1cc(N2CCN(CCCCCOc3ccc([C@@H]4c5ccc(O)cc5CC[C@@H]4c4ccccc4)cc3)CC2)cc2c1C(=O)N([C@@H]1CCC(=O)NC1=O)C2] | (3R)-3-[5-[4-[5-[4-[(1R,2S)-6-hydroxy-2-phenyl-tetralin-1-yl]phenoxy]pentyl]piperazin-1-yl]-7-methoxy-1-oxo-isoindolin-2-yl]piperidine-2,6-dione | A-2, A-8 |

TABLE 1-continued

Exemplary Estrogen Receptor PROTACs

| Ex. # | Chemical Structure | Name | General Synthetic Method |
|---|---|---|---|
| 14 | 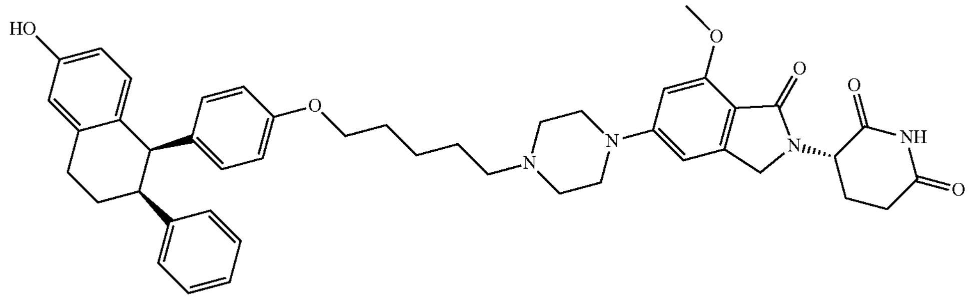 [SMILES: COc1cc(N2CCN(CCCCCOc3ccc([C@@H]4c5ccc(O)cc5CC[C@@H]4c4ccccc4)cc3)CC2)cc2c1C(=O)N([C@H]1CCC(=O)NC1=O)C2] | (3S)-3-[5-[4-[5-[4-[(1R,2S)-6-hydroxy-2-phenyl-tetralin-1-yl]phenoxy]pentyl]piperazin-1-yl]-7-methoxy-1-oxo-isoindolin-2-yl]piperidine-2,6-dione | A-2, A-8 |
| 15 | 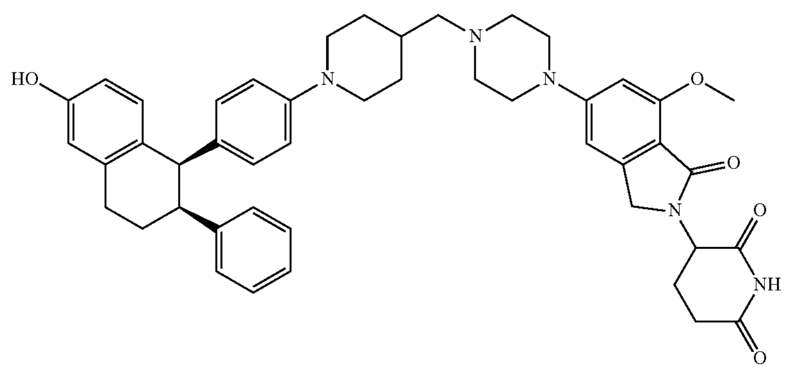 [SMILES: COc1cc(N2CCN(CC3CCN(c4ccc([C@@H]5c6ccc(O)cc6CC[C@@H]5c5ccccc5)cc4)CC3)CC2)cc2c1C(=O)N(C1CCC(=O)NC1=O)C2] | 3-[5-[4-[[1-[4-[(1R,2S)-6-hydroxy-2-phenyl-tetralin-1-yl]phenyl]-4-piperidyl]methyl]piperazin-1-yl]-7-methoxy-1-oxo-isoindolin-2-yl]piperidine-2,6-dione | A-2, A-12 |
| 16 | 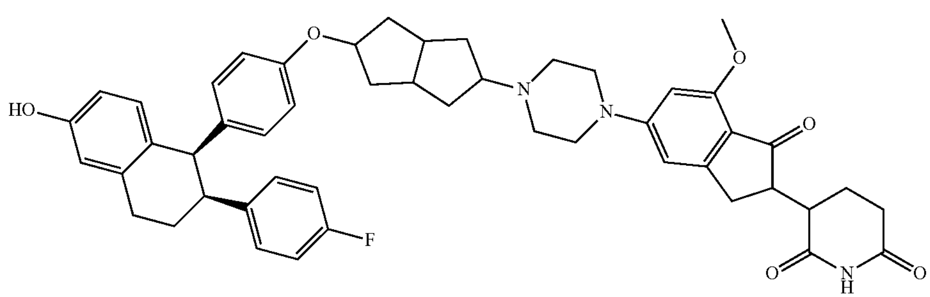 [SMILES: COc1cc(N2CCN(C3CC4CC(Oc5ccc([C@@H]6c7ccc(O)cc7CC[C@@H]6c6ccc(F)cc6)cc5)CC4C3)CC2)cc2c1C(=O)C(C1CCC(=O)NC1=O)C2] | 3-[5-[4-[(1R,2S)-2-(4-fluorophenyl)-6-hydroxy-tetralin-1-yl]phenoxy]-1,2,3,3a,4,5,6,6a-octahydropentalen-2-yl]piperazin-1-yl]-7-methoxy-1-oxo-isoindolin-2-yl]piperidine-2,6-dione | A-2, A-11 |

TABLE 1-continued

Exemplary Estrogen Receptor PROTACs

| Ex. # | Chemical Structure | Name | General Synthetic Method |
|---|---|---|---|
| 17 | 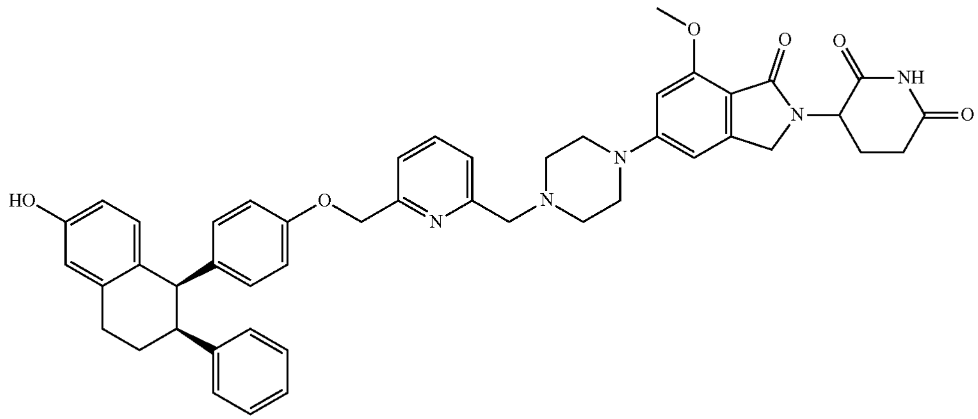 [SMILES: COc1cc(N2CCN(Cc3cccc(COc4ccc([C@@H]5c6ccc(O)cc6CC[C@@H]5c5ccccc5)cc4)n3)CC2)cc2c1C(=O)N(C1CCC(=O)NC1=O)C2] | 3-[5-[4-[[6-[[4-[(1R,2S)-6-hydroxy-2-phenyl-tetralin-1-yl]phenoxy]methyl]-2-pyridyl]methyl]piperazin-1-yl]-7-methoxy-1-oxo-isoindolin-2-yl]piperidine-2,6-dione | A-16 |
| 18 | 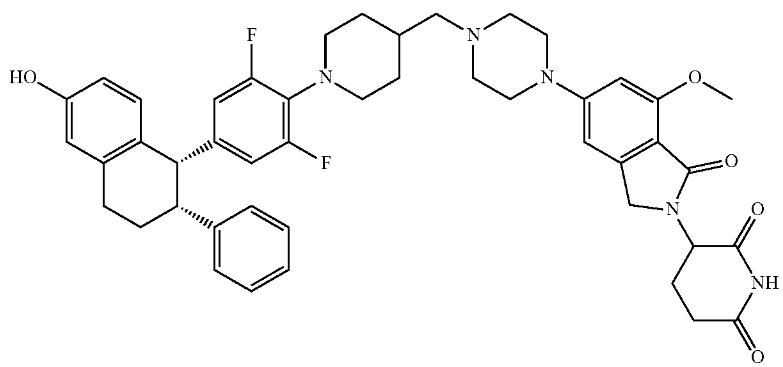 [SMILES: COc1cc(N2CCN(CC3CCN(c4c(F)cc([C@H]5c6ccc(O)cc6CC[C@H]5c5ccccc5)cc4F)CC3)CC2)cc2c1C(=O)N(C1CCC(=O)NC1=O)C2] | 3-(5-{4-[(1-{2,6-difluoro-4-[(1S,2R)-6-hydroxy-2-phenyl-1,2,3,4-tetrahydronaphthalen-1-yl]phenyl}piperidin-4-yl)methyl]piperazin-1-yl}-7-methoxy-1-oxo-2,3-dihydro-1H-isoindol-2-yl)piperidine-2,6-dione | A-1, A-2 |

TABLE 1-continued

Exemplary Estrogen Receptor PROTACs

| Ex. # | Chemical Structure | Name | General Synthetic Method |
|---|---|---|---|
| 19 | 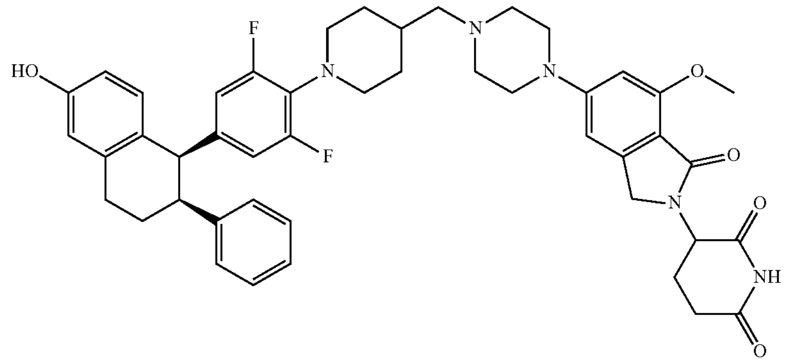 [SMILES: COc1cc(N2CCN(CC3CCN(c4c(F)cc([C@@H]5c6ccc(O)cc6CC[C@@H]5c5ccccc5)cc4F)CC3)CC2)cc2c1C(=O)N(C1CCC(=O)NC1=O)C2] | 3-(5-(4-((1-(2,6-difluoro-4-((1R,2S)-6-hydroxy-2-phenyl-1,2,3,4-tetrahydronaphthalen-1-yl)phenyl)piperidin-4-yl)methyl)piperazin-1-yl)-7-methoxy-1-oxoisoindolin-2-yl)piperidine-2,6-dione | A-1, A-2, A-8 |
| 20 | 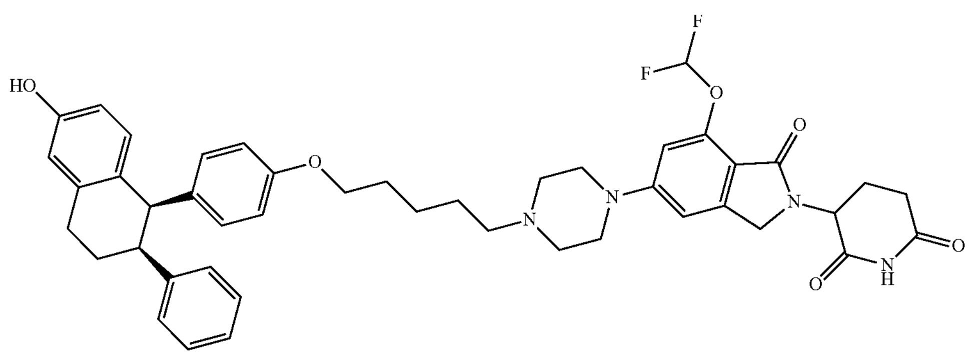 [SMILES: O=C1CCC(N2Cc3cc(N4CCN(CCCCCOc5ccc([C@@H]6c7ccc(O)cc7CC[C@@H]6c6ccccc6)cc5)CC4)cc(OC(F)F)c3C2=O)C(=O)N1] | 3-[7-(difluoromethoxy)-5-[4-[5-[4-[(1R,2S)-6-hydroxy-2-phenyl-tetralin-1-yl]phenoxy]pentyl]piperazin-1-yl]-1-oxo-isoindolin-2-yl]piperidine-2,6-dione | A-3, A-8 |

TABLE 1-continued

Exemplary Estrogen Receptor PROTACs

| Ex. # | Chemical Structure | Name | General Synthetic Method |
|---|---|---|---|
| 21 | 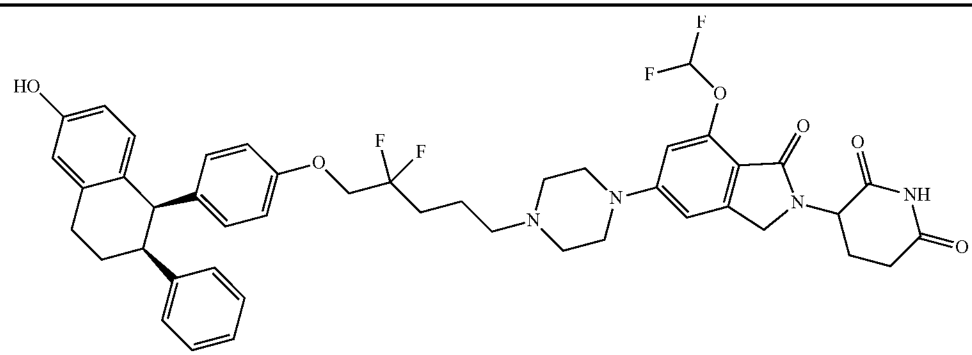 | 3-[5-[4-[4,4-difluoro-5-[4-[(1R,2S)-6-hydroxy-2-phenyl-tetralin-1-yl]phenoxy]pentyl]piperazin-1-yl]-7-(difluoromethoxy)-1-oxo-isoindolin-2-yl]piperidine-2,6-dione | A-6, A-10 |
| 22 | 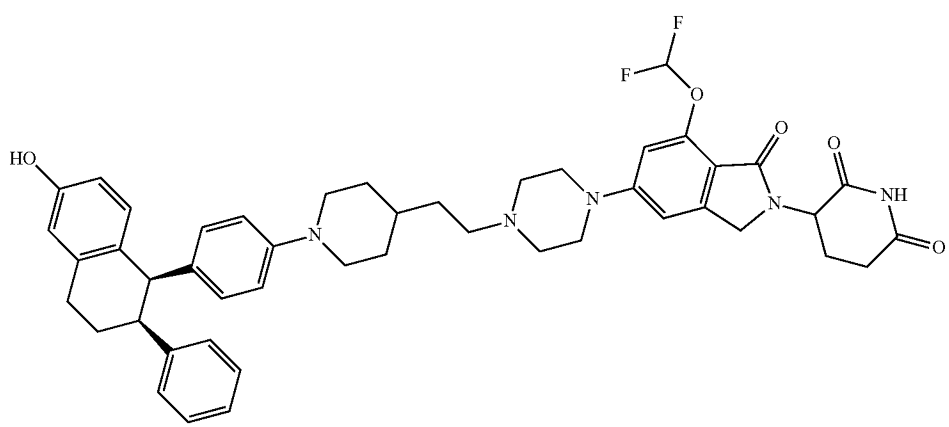 [SMILES: O=C1CCC(N2Cc3cc(N4CCN(CCC5CCN(c6ccc([C@@H]7c8ccc(O)cc8CC[C@@H]7c7ccccc7)cc6)CC5)CC4)cc(OC(F)F)c3C2=O)C(=O)N1] | 3-[7-(difluoromethoxy)-5-[4-[2-[1-[4-[(1R,2S)-6-hydroxy-2-phenyl-tetralin-1-yl]phenyl]-4-piperidyl]ethyl]piperazin-1-yl]-1-oxo-isoindolin-2-yl]piperidine-2,6-dione | A-2, A-13 |

TABLE 1-continued

Exemplary Estrogen Receptor PROTACs

| Ex. # | Chemical Structure | Name | General Synthetic Method |
|---|---|---|---|
| 23 | 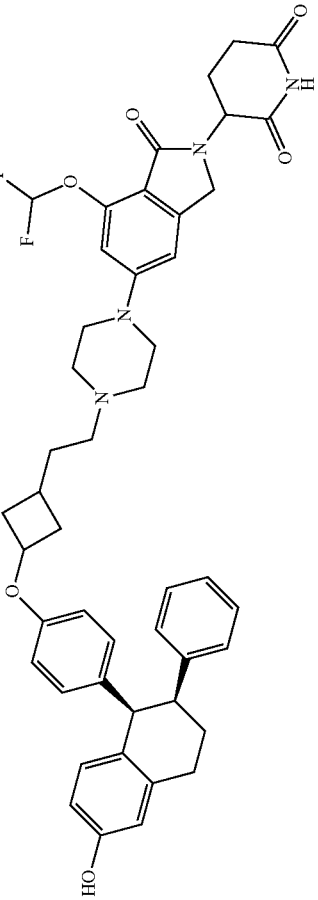 | 3-[7-(difluoromethoxy)-5-[4-[2-[3-[4-[(1R,2S)-6-hydroxy-2-phenyl-tetralin-1-yl]phenoxy]cyclobutyl]piperazin-1-yl]ethyl]piperazin-1-yl]-1-oxo-isoindolin-2-yl]piperidine-2,6-dione | A-3, A-14 |
| 24 | 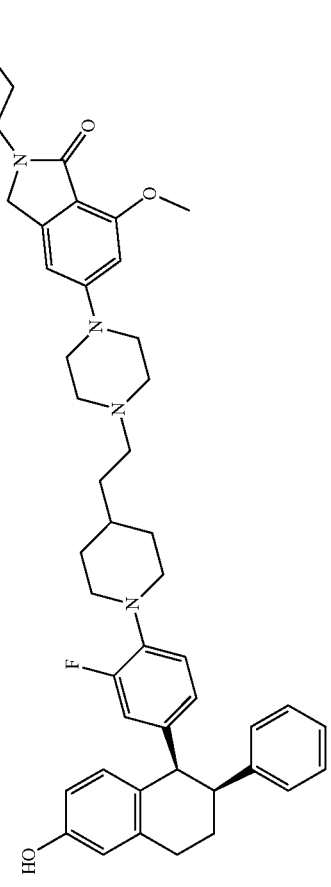 | 3-[5-[4-[2-[1-[2-fluoro-4-[(1R,2S)-6-hydroxy-2-phenyl-tetralin-1-yl]phenyl]-4-piperidyl]ethyl]piperazin-1-yl]-7-methoxy-1-oxo-isoindolin-2-yl]piperidine-2,6-dione | A-2, A-12 |

TABLE 1-continued

Exemplary Estrogen Receptor PROTACs

| Ex. # | Chemical Structure | Name | General Synthetic Method |
|---|---|---|---|
| 25 | 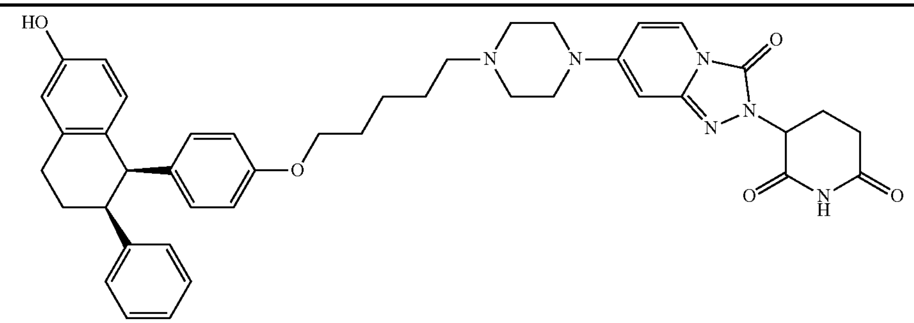 | 3-{7-[4-(5-{4-[(1R,2S)-6-hydroxy-2-phenyl-1,2,3,4-tetrahydronaphthalen-1-yl]phenoxy}pentyl)piperazin-1-yl]-3-oxo-2H,3H-[1,2,4]triazolo[4,3-a]pyridin-2-yl}piperidine-2,6-dione | A-7, A-8 |
| 26 | 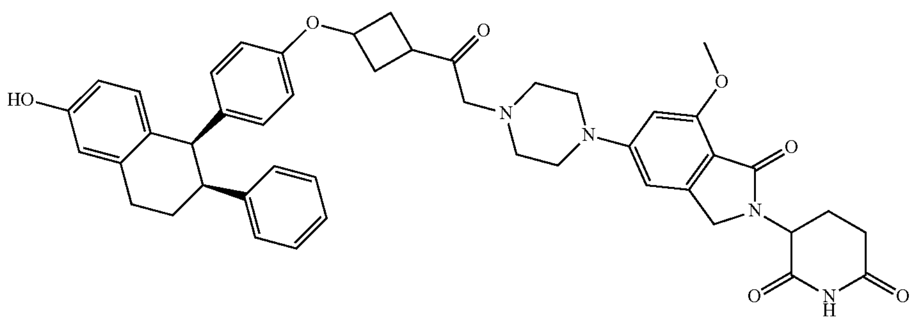 [SMILES: COc1cc(N2CCN(CC(=O)C3CC(Oc4ccc([C@@H]5c6ccc(O)cc6CC[C@@H]5c5ccccc5)cc4)C3)CC2)cc2c1C(=O)N(C1CCC(=O)NC1=O)C2] | 3-{5-[4-{3-[4-{(1R,2S)-6-hydroxy-2-phenyl-tetralin-1-yl]phenoxy}piperazin-1-yl]-2-oxo-ethyl]piperazin-1-yl}-7-methoxy-1-oxo-isoindolin-2-yl]piperidine-2,6-dione | A-17 |
| 27 | 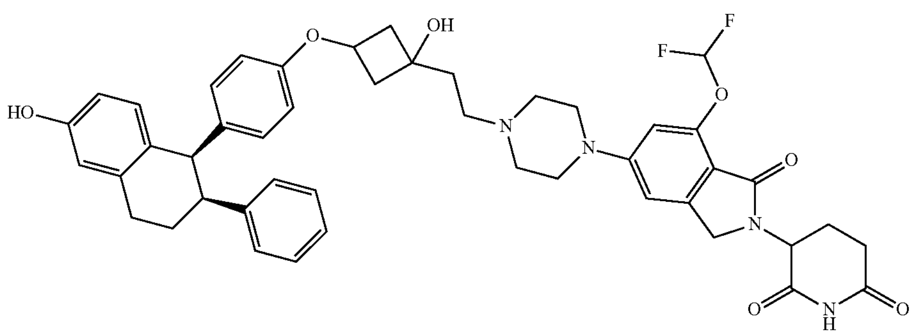 [SMILES: O=C1CCC(N2Cc3cc(N4CCN(CCC5(O)CC(Oc6ccc([C@@H]7c8ccc(O)cc8CC[C@@H]7c7ccccc7)cc6)C5)CC4)cc(OC(F)F)c3C2=O)C(=O)N1] | 3-{7-(difluoromethoxy)-5-[4-{2-[1-hydroxy-3-[4-{(1R,2S)-6-hydroxy-2-phenyl-tetralin-1-yl]phenoxy}cyclobutyl]ethyl]piperazin-1-yl]-1-oxo-isoindolin-2-yl]piperidine-2,6-dione | A-3, A-15 |

TABLE 1-continued

Exemplary Estrogen Receptor PROTACs

| Ex. # | Chemical Structure | Name | General Synthetic Method |
|---|---|---|---|
| 28 | 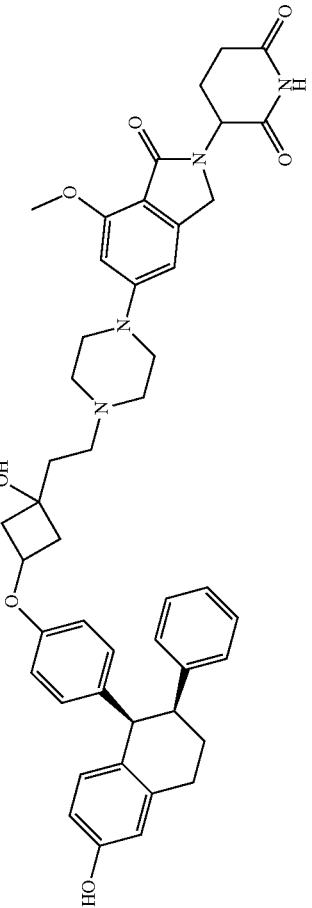 | 3-[5-[4-[2-[1-hydroxy-3-[4-[((1R,2S)-6-hydroxy-2-phenyl-tetralin-1-yl]phenoxy]cyclobutyl]ethyl]piperazin-1-yl]-7-methoxy-1-oxo-isoindolin-2-yl]piperidine-2,6-dione | A-2, A-15 |
| 29 | 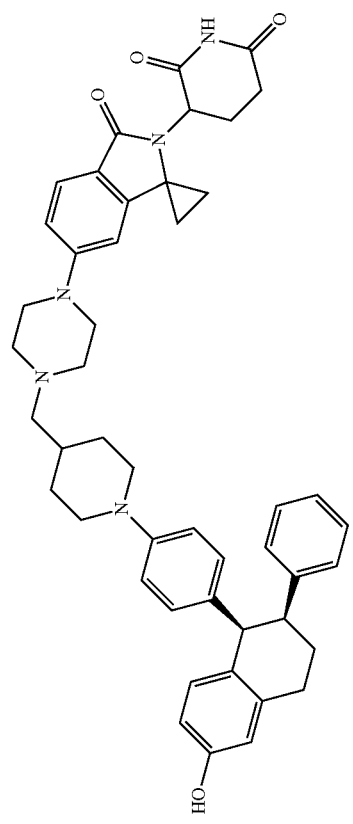 | 3-(6'-{4-[(1-{4-[((1R,2S)-6-hydroxy-2-phenyl-1,2,3,4-tetrahydronaphthalen-1-yl]phenyl}piperidin-4-yl)methyl]piperazin-1-yl}methyl]piperazin-1-yl]-3'-oxo-2',3'-dihydrospiro[cyclopropane-1,1'-isoindole]-2-yl)piperidine-2,6-dione | A-6, A-12 |

TABLE 1-continued
Exemplary Estrogen Receptor PROTACs
| Ex. # | Chemical Structure | Name | General Synthetic Method |
|---|---|---|---|
| 30 | 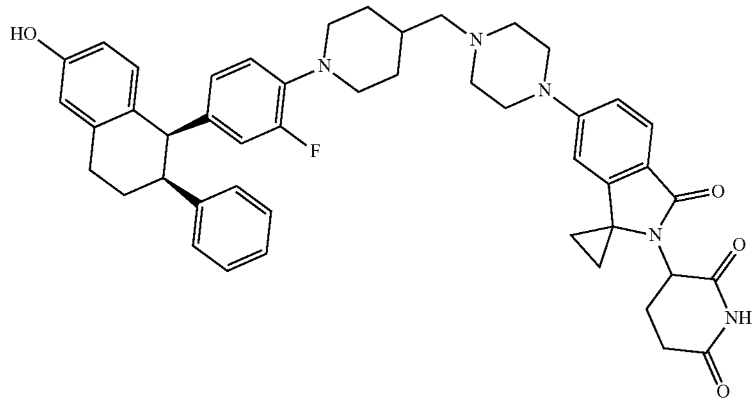 [SMILES: O=C1CCC(N2C(=O)c3ccc(N4CCN(CC5CCN(c6ccc([C@@H]7c8ccc(O)cc8CC[C@@H]7c7ccccc7)cc6F)CC5)CC4)cc3C23CC3)C(=O)N1] | 3-[6-[4-[[1-[2-fluoro-4-[(1R,2S)-6-hydroxy-2-phenyl-tetralin-1-yl]phenyl]-4-piperidyl]methyl]piperazin-1-yl]-3'-oxo-spiro[cyclopropane-1,1'-isoindoline]-2'-yl]piperidine-2,6-dione | A-6, A-12 |
| 31 | 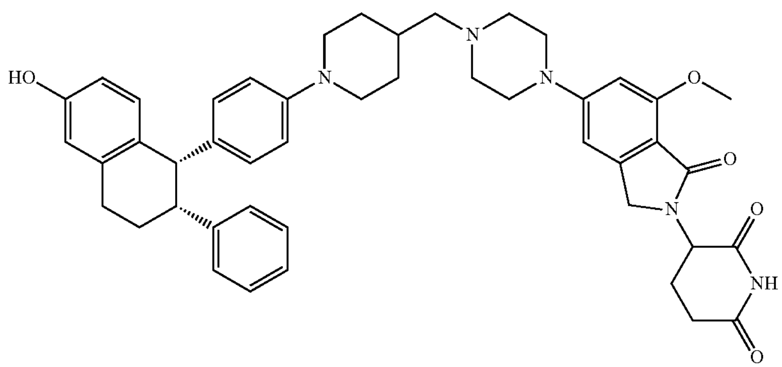 [SMILES: COc1cc(N2CCN(CC3CCN(c4ccc([C@H]5c6ccc(O)cc6CC[C@H]5c5ccccc5)cc4)CC3)CC2)cc2c1C(=O)N(C1CCC(=O)NC1=O)C2] | | A-1, A-2 |
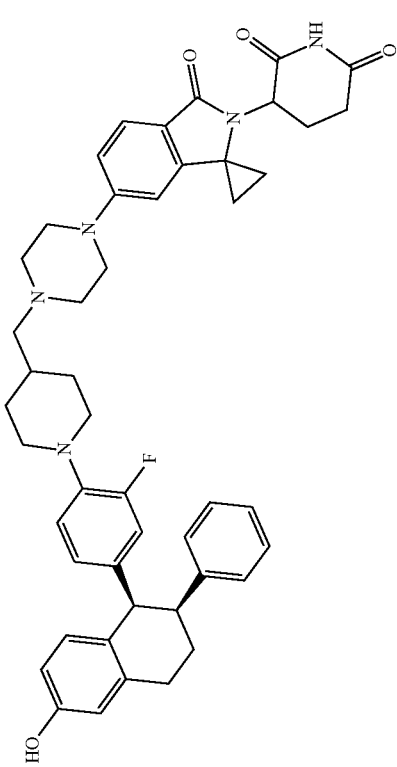

TABLE 2

Exemplary Androgen Receptor PROTACs

| Ex. # | Chemical Structure | Name | General Method |
|---|---|---|---|
| 32 | 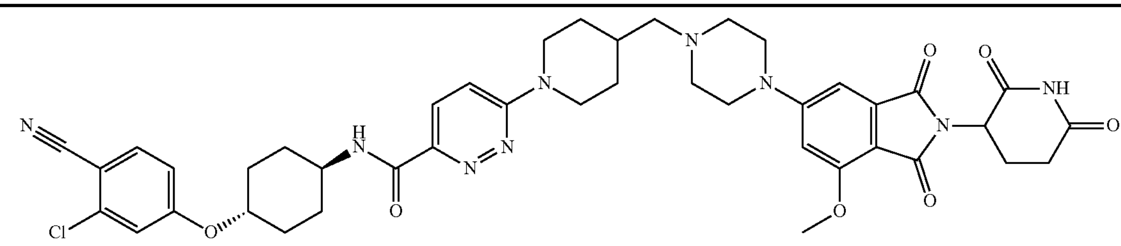 | rac-N-((1r,4r)-4-(3-chloro-4-cyanophenoxy)cyclohexyl)-6-(4-((4-(2-(2,6-dioxopiperidin-3-yl)-7-methoxy-1,3-dioxoisoindolin-5-yl)piperazin-1-yl)methyl)piperidin-1-yl)pyridazine-3-carboxamide | Exp. procedure provided |
| 33 | 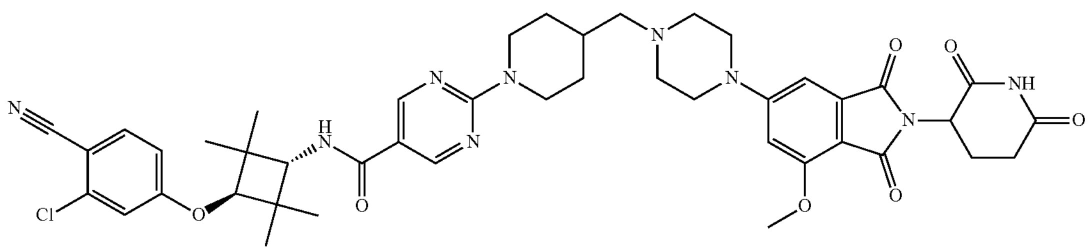 [SMILES: COc1cc(N2CCN(CC3CCN(c4ncc(C(=O)N[C@H]5C(C)(C)[C@H](Oc6ccc(C#N)c(Cl)c6)C5(C)C)cn4)CC3)CC2)cc2c1C(=O)N(C1CCC(=O)NC1=O)C2=O] | rac-N-((1r,3r)-3-(3-chloro-4-cyanophenoxy)-2,2,4,4-tetramethylcyclobutyl)-2-(4-((4-(2-(2,6-dioxopiperidin-3-yl)-7-methoxy-1,3-dioxoisoindolin-5-yl)piperazin-1-yl)methyl)piperidin-1-yl)pyrimidine-5-carboxamide | B-1, B-2 |
| 34 | 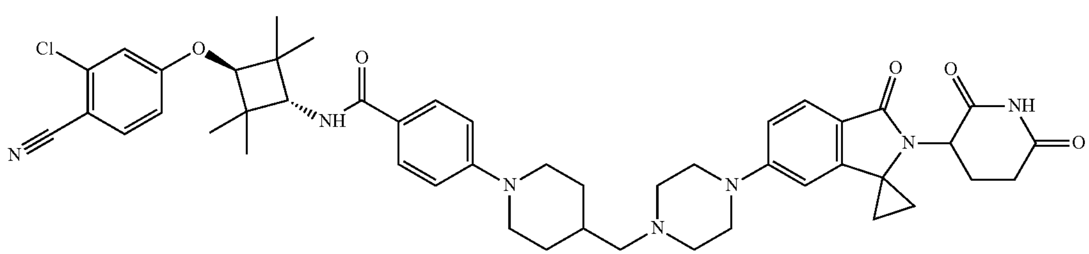 [SMILES: CC1(C)[C@H](NC(=O)c2ccc(N3CCC(CN4CCN(c5ccc6c(c5)C5(CC5)N(C5CCC(=O)NC5=O)C6=O)CC4)CC3)cc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-4-(4-((4-(2'-(2,6-dioxopiperidin-3-yl)-3'-oxospiro[cyclopropane-1,1'-isoindolin]-6-yl)piperazin-1-yl)methyl)piperidin-1-yl)benzamide | Synthesis described in detail |
| 35 | 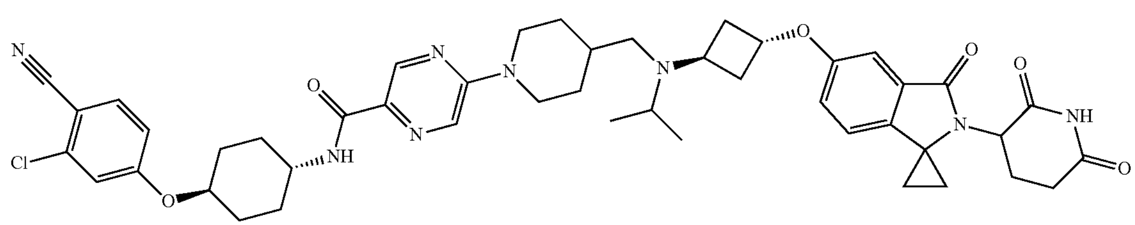 [SMILES: CC(C)N(CC1CCN(c2cnc(C(=O)N[C@H]3CC[C@H](Oc4ccc(C#N)c(Cl)c4)CC3)cn2)CC1)[C@H]1C[C@H](Oc2ccc3c(c2)C(=O)N(C2CCC(=O)NC2=O)C32CC2)C1] | rac-N-((1r,4r)-4-(3-chloro-4-cyanophenoxy)cyclohexyl)-5-(4-(((1r,3r)-3-((2'-(2,6-dioxopiperidin-3-yl)-3'-oxospiro[cyclopropane-1,1'-isoindolin]-5-yl)oxy)cyclobutyl)(isopropyl)amino)methyl)piperidin-1-yl)pyrazine-2-carboxamide | Synthesized following the route described for Ex. Comp. 34 |

TABLE 2-continued

Exemplary Androgen Receptor PROTACs

| Ex. # | Chemical Structure | Name | General Method |
|---|---|---|---|
| 36 | 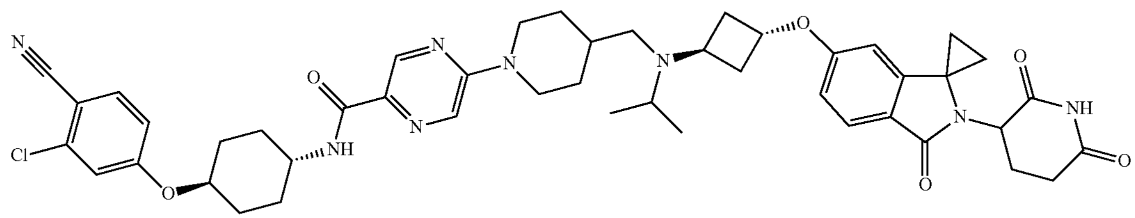 [SMILES: CC(C)N(CC1CCN(c2cnc(C(=O)N[C@H]3CC[C@H](Oc4ccc(C#N)c(Cl)c4)CC3)cn2)CC1)[C@H]1C[C@H](Oc2ccc3c(c2)C2(CC2)N(C2CCC(=O)NC2=O)C3=O)C1] | rac-N-((1r,4r)-4-(3-chloro-4-cyanophenoxy)cyclohexyl)-5-(4-((((1r,3r)-3-((2'-(2,6-dioxopiperidin-3-yl)-3'-oxospiro[cyclopropane-1,1'-isoindolin]-6-yl)oxy)cyclobutyl)(isopropyl)amino)methyl)piperidin-1-yl)pyrazine-2-carboxamide | Synthesized following the route described for Ex. Comp. 34 |
| 37 | 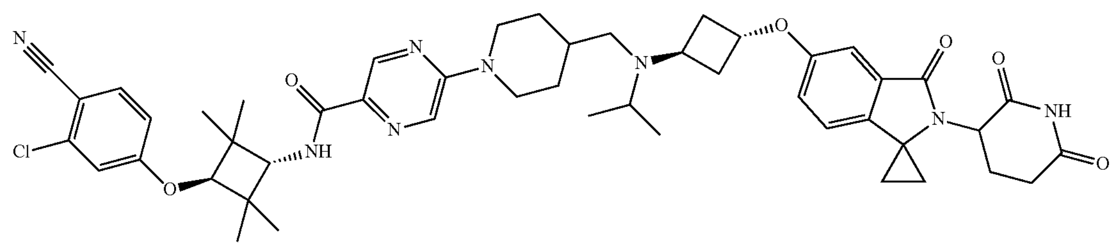 [SMILES: CC(C)N(CC1CCN(c2cnc(C(=O)N[C@H]3C(C)(C)[C@H](Oc4ccc(C#N)c(Cl)c4)C3(C)C)cn2)CC1)[C@H]1C[C@H](Oc2ccc3c(c2)C(=O)N(C2CCC(=O)NC2=O)C32CC2)C1] | rac-N-((1r,3r)-3-(3-chloro-4-cyanophenoxy)-2,2,4,4-tetramethylcyclobutyl)-5-(4-((((1r,3r)-3-((2'-(2,6-dioxopiperidin-3-yl)-3'-oxospiro[cyclopropane-1,1'-isoindolin]-5'-yl)oxy)cyclobutyl)(isopropyl)amino)methyl)piperidin-1-yl)pyrazine-2-carboxamide | Synthesized following the route described for Ex. Comp. 34 |
| 38 | 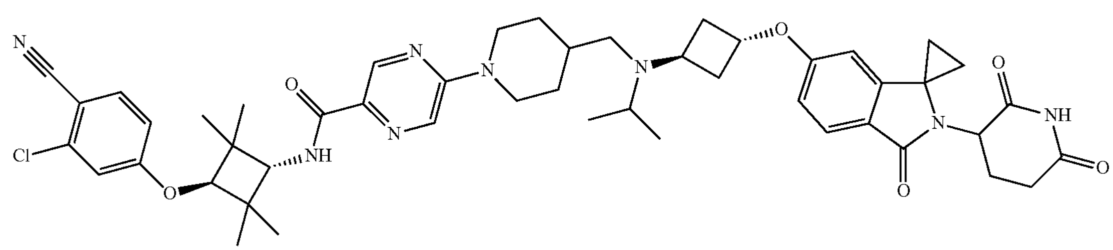 [SMILES: CC(C)N(CC1CCN(c2cnc(C(=O)N[C@H]3C(C)(C)[C@H](Oc4ccc(C#N)c(Cl)c4)C3(C)C)cn2)CC1)[C@H]1C[C@H](Oc2ccc3c(c2)C2(CC2)N(C2CCC(=O)NC2=O)C3=O)C1] | rac-N-((1r,3r)-3-(3-chloro-4-cyanophenoxy)-2,2,4,4-tetramethylcyclobutyl)-5-(4-((((1r,3r)-3-((2'-(2,6-dioxopiperidin-3-yl)-3'-oxospiro[cyclopropane-1,1'-isoindolin]-6-yl)oxy)cyclobutyl)(isopropyl)amino)methyl)piperidin-1-yl)pyrazine-2-carboxamide | Synthesized following the route described for Ex. Comp. 34 |

TABLE 2-continued

Exemplary Androgen Receptor PROTACs

| Ex. # | Chemical Structure | Name | General Method |
|---|---|---|---|
| 46 | 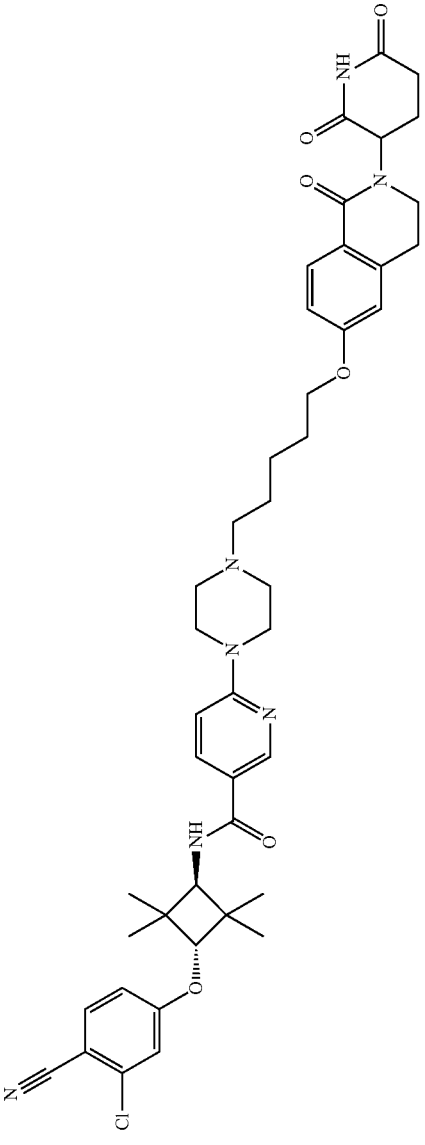 | rac-N-((1r,3r)-3-(3-chloro-4-cyanophenoxy)-2,2,4,4-tetramethylcyclobutyl)-6-(4-(5-((2-(2,6-dioxopiperidin-3-yl)-1-oxo-1,2,3,4-tetrahydroisoquinolin-6-yl)oxy)pentyl)piperazin-1-yl)nicotinamide | C-1 and Exp. procedure provided as well |
| 47 | 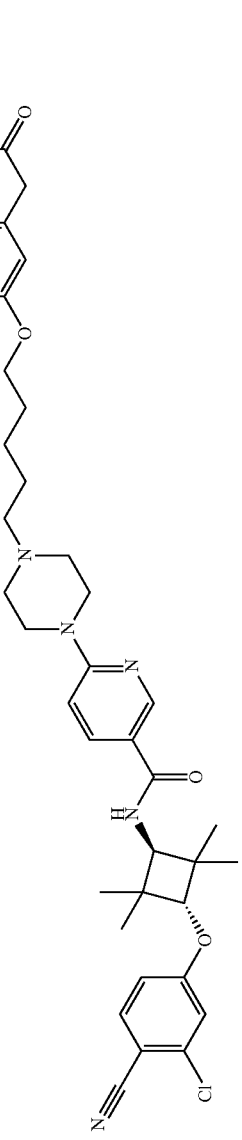 | rac-N-((1r,3r)-3-(3-chloro-4-cyanophenoxy)-2,2,4,4-tetramethylcyclobutyl)-6-(4-(5-((2-(2,6-dioxopiperidin-3-yl)-1,3-dioxo-1,2,3,4-tetrahydroisoquinolin-6-yl)oxy)pentyl)piperazin-1-yl)nicotinamide | C-1 and Exp. procedure provided as well |

TABLE 2-continued

Exemplary Androgen Receptor PROTACs

| Ex. # | Chemical Structure | Name | General Method |
|---|---|---|---|
| 48 | 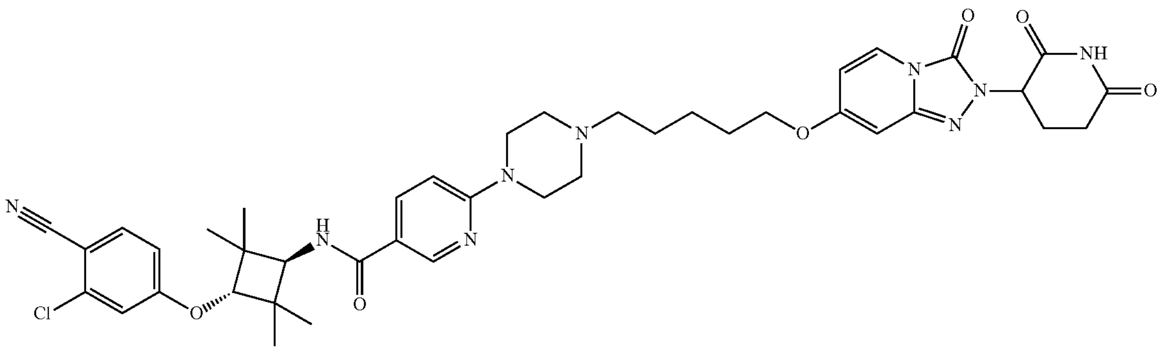 [SMILES: CC1(C)[C@H](NC(=O)c2ccc(N3CCN(CCCCCOc4ccn5c(=O)n(C6CCC(=O)NC6=O)nc5c4)CC3)nc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-6-(4-(5-((2-(2,6-dioxopiperidin-3-yl)-3-oxo-2,3-dihydro-[1,2,4]triazolo[4,3-a]pyridin-7-yl)oxy)pentyl)piperazin-1-yl)nicotinamide | Exp procedure provided |
| 49 | 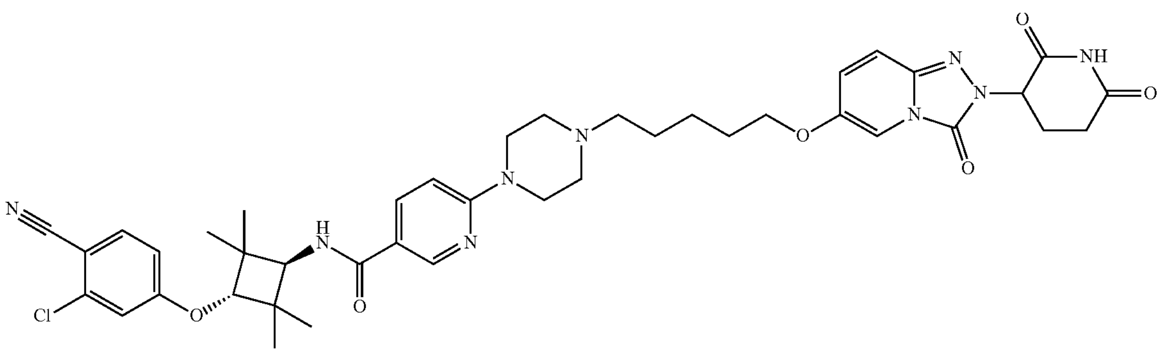 [SMILES: CC1(C)[C@H](NC(=O)c2ccc(N3CCN(CCCCCOc4ccc5nn(C6CCC(=O)NC6=O)c(=O)n5c4)CC3)nc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-6-(4-(5-((2-(2,6-dioxopiperidin-3-yl)-3-oxo-2,3-dihydro-[1,2,4]triazolo[4,3-a]pyridin-6-yl)oxy)pentyl)piperazin-1-yl)nicotinamide | Exp procedure provided |
| 50 | 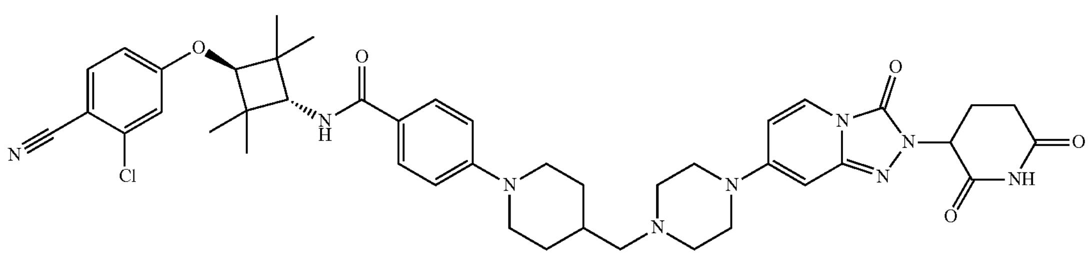 [SMILES: CC1(C)[C@H](NC(=O)c2ccc(N3CCC(CN4CCN(c5ccn6c(=O)n(C7CCC(=O)NC7=O)nc6c5)CC4)CC3)cc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-4-(4-((4-(2-(2,6-dioxopiperidin-3-yl)-3-oxo-2,3-dihydro-[1,2,4]triazolo[4,3-a]pyridin-7-yl)piperazin-1-yl)methyl)piperidin-1-yl)benzamide | Exp procedure provided |

TABLE 2-continued

Exemplary Androgen Receptor PROTACs

| Ex. # | Chemical Structure | Name | General Method |
|---|---|---|---|
| 51 | 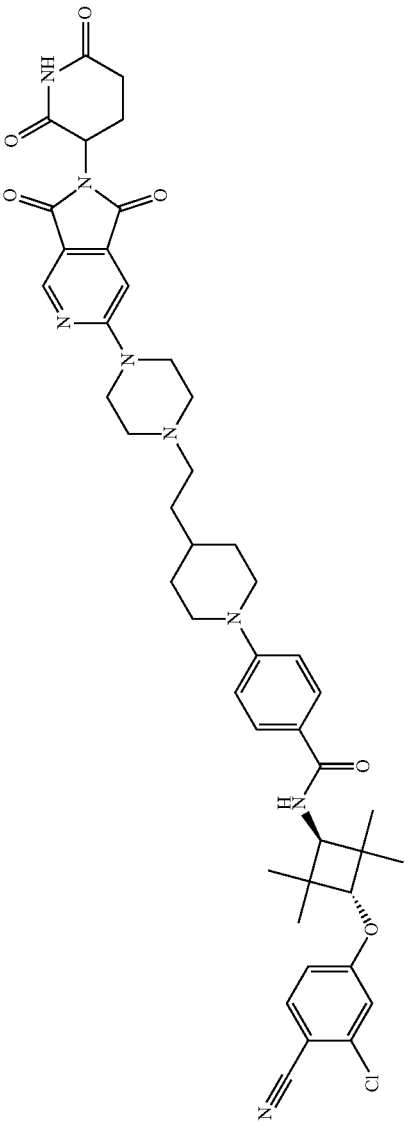 | N-((1r,3r)-3-(3-chloro-4-cyanophenoxy)-2,2,4,4-tetramethylcyclobutyl)-4-(4-(2-(4-(2-(2,6-dioxopiperidin-3-yl)-1,3-dioxo-2,3-dihydro-1H-pyrrolo[3,4-c]pyridin-6-yl)piperazin-1-yl)ethyl)piperidin-1-yl)benzamide | C-3, C-4 and Exp procedure provided |
| 52 | 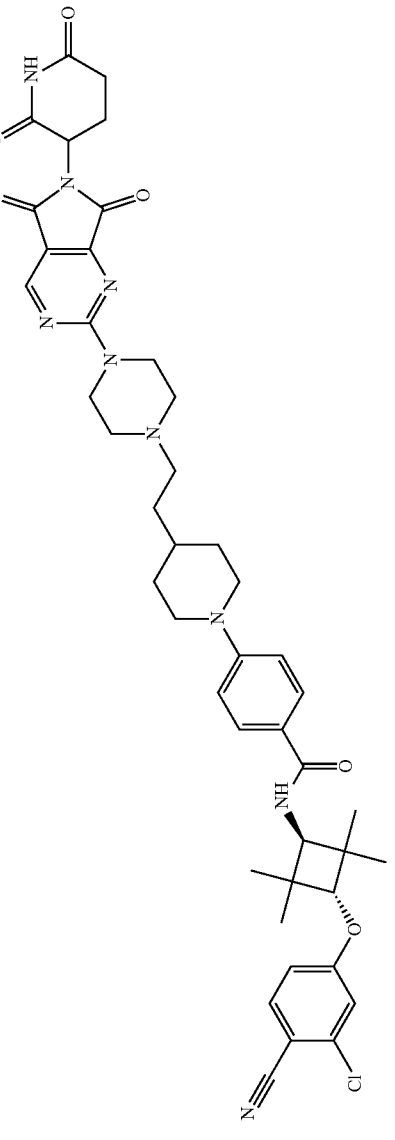 | N-((1r,3r)-3-(3-chloro-4-cyanophenoxy)-2,2,4,4-tetramethylcyclobutyl)-4-(4-(2-(4-(6-(2,6-dioxopiperidin-3-yl)-5,7-dioxo-6,7-dihydro-5H-pyrrolo[3,4-d]pyrimidin-2-yl)piperazin-1-yl)ethyl)piperidin-1-yl)benzamide | C-3, c-4 and exp procedure provided |

TABLE 3

Exemplary BRaf PROTACs

| Ex. # | Chemical Structure | Name | Synthetic Scheme |
|---|---|---|---|
| 39 | 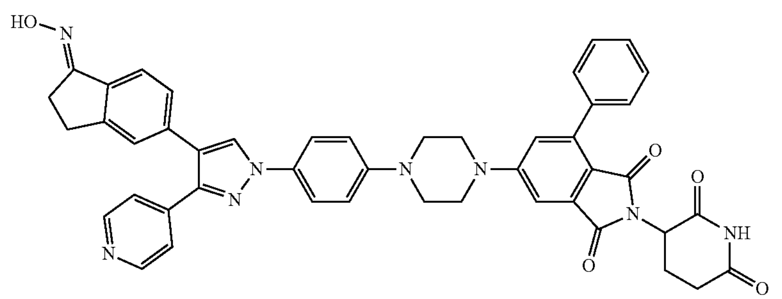 [SMILES: O=C1CCC(N2C(=O)c3cc(N4CCN(c5ccc(-n6cc(-c7ccc8c(c7)CC/C8=N\O)c(-c7ccncc7)n6)cc5)CC4)cc(-c4ccccc4)c3C2=O)C(=O)N1] | (E)-2-(2,6-dioxopiperidin-3-yl)-6-(4-(4-(4-(1-(hydroxyimino)-2,3-dihydro-1H-inden-5-yl)-3-(pyridin-4-yl)-1H-pyrazol-1-yl)phenyl)piperazin-1-yl)-4-phenylisoindoline-1,3-dione | D-1 |
| 40 | 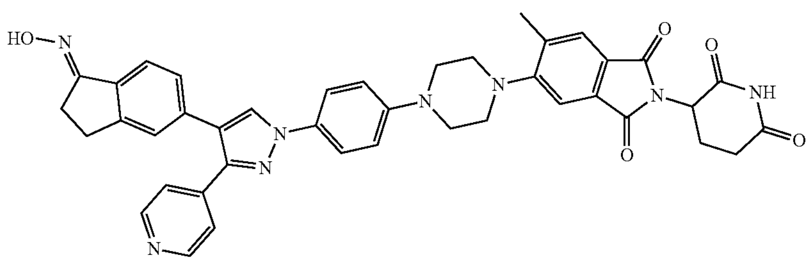 [SMILES: Cc1cc2c(cc1N1CCN(c3ccc(-n4cc(-c5ccc6c(c5)CC/C6=N\O)c(-c5ccncc5)n4)cc3)CC1)C(=O)N(C1CCC(=O)NC1=O)C2=O] | (E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenyl)pipeiazin-1-yl)-6-methylisoindoline-1,3-dione | D-1 |
| 41 | 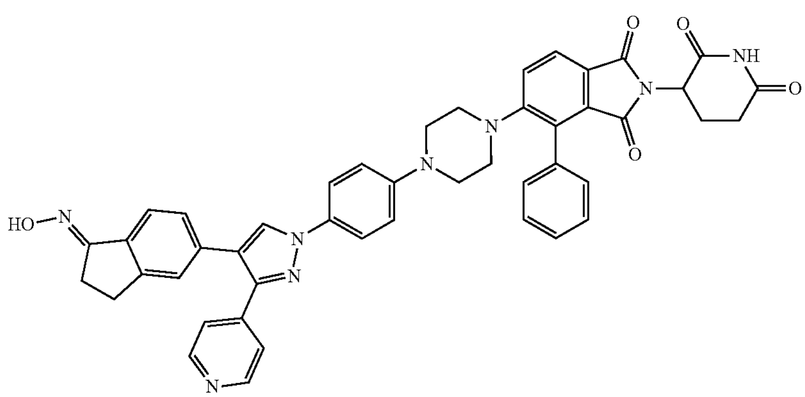 [SMILES: O=C1CCC(N2C(=O)c3ccc(N4CCN(c5ccc(-n6cc(-c7ccc8c(c7)CC/C8=N\O)c(-c7ccncc7)n6)cc5)CC4)c(-c4ccccc4)c3C2=O)C(=O)N1] | (E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenyl)piperazin-1-yl)-4-phenylisoindoline-1,3-dione | Custom synthesis provided |
| 42 | 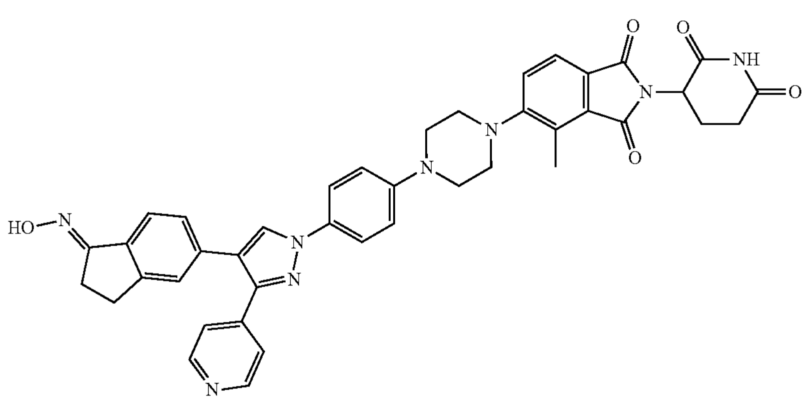 [SMILES: Cc1c(N2CCN(c3ccc(-n4cc(-c5ccc6c(c5)CC/C6=N\O)c(-c5ccncc5)n4)cc3)CC2)ccc2c1C(=O)N(C1CCC(=O)NC1=O)C2=O] | (E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenyl)piperazin-1-yl)-4-methylisoindoline-1,3-dione | Custom synthesis provided |

TABLE 4

Exemplary BRD4 PROTACs

| Ex. # | Chemical Structure | Name |
|---|---|---|
| 43 | 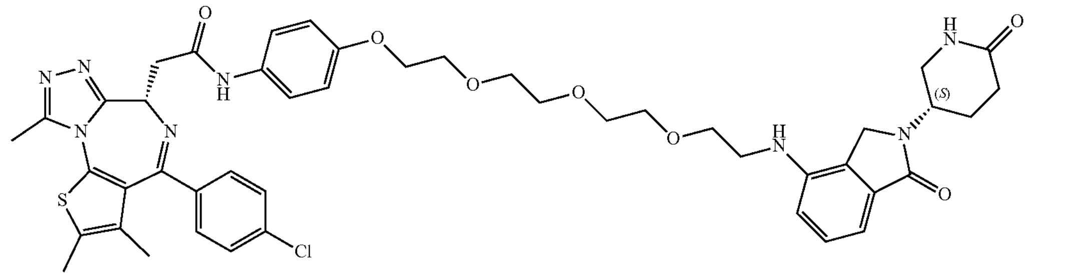 | 2-((R)-4-(4-chlorophenyl)-2,3,9-trimethyl-6H-thieno[3,2-f][1,2,4]triazolo[4,3-a][1,4]diazepin-6-yl)-N-(4-(2-(2-(2-(2-((R)-1-oxo-2-((R)-6-oxopiperidin-3-yl)isoindolin-4-yl)amino)ethoxy)ethoxy)ethoxy)ethoxy)phenyl)acetamide |
| 44 | 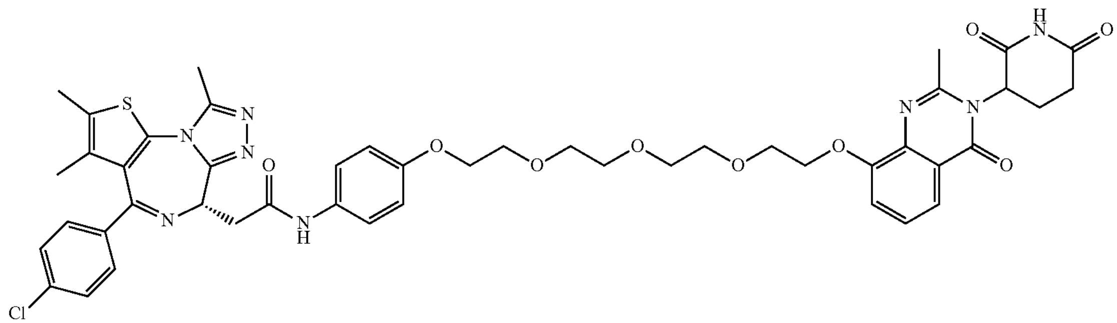 [SMILES: Cc1sc2c(c1C)C(c1ccc(Cl)cc1)=N[C@@H](CC(=O)Nc1ccc(OCCOCCOCCOCCOc3cccc4c(=O)n(C5CCC(=O)NC5=O)c(C)nc34)cc1)c1nnc(C)n1-2] | 2-((R)-4-(4-chlorophenyl)-2,3,9-trimethyl-6H-thieno[3,2-f][1,2,4]triazolo[4,3-a][1,4]diazepin-6-yl)-N-(4-(2-(2-(2-(3-(2,6-dioxopiperidin-3-yl)-2-methyl-4-oxo-3,4-dihydroquinazolin-8-yl)oxy)ethoxy)ethoxy)ethoxy)phenyl)acetamide |
| 45 | 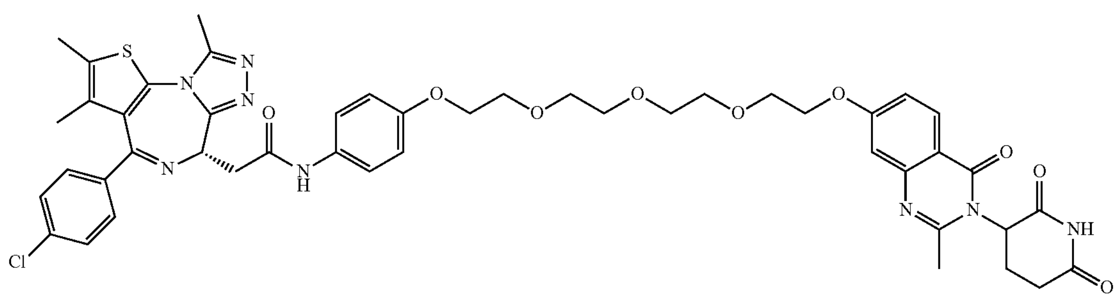 [SMILES: Cc1sc2c(c1C)C(c1ccc(Cl)cc1)=N[C@@H](CC(=O)Nc1ccc(OCCOCCOCCOCCOc3ccc4c(=O)n(C5CCC(=O)NC5=O)c(C)nc4c3)cc1)c1nnc(C)n1-2] | 2-((R)-4-(4-chlorophenyl)-2,3,9-trimethyl-6H-thieno[3,2-f][1,2,4]triazolo[4,3-a][1,4]diazepin-6-yl)-N-(4-(2-(2-(2-(3-(2,6-dioxopiperidin-3-yl)-2-methyl-4-oxo-3,4-dihydroquinazolin-7-yl)oxy)ethoxy)ethoxy)ethoxy)phenyl)acetamide |

TABLE 5

Characterization of Exemplary Estrogen Receptor PROTACs

| Ex. # | Observed [M + H]/Z | Target Engagement IC$_{50}$ (nM) | ER DC$_{50}$* | ER D$_{max}$* | NMR |
|---|---|---|---|---|---|
| 1 | 743.58 | 58.2 | C | B | |
| 2 | 743.58 | 0.79 | B | A | δ 10.93 (s, 1H), 10.56-10.43 (m, 1H), 9.18-9.13 (m, 1H), 7.16-7.13 (m, 3H), 6.84-6.83 (d, J = 6.4 Hz, 2H), 6.69 (s, 1H), 6.62-6.61 (m, 2H), 6.55-6.52 (m, 3H), 6.28-6.26 (d, J = 8.4 Hz, 2H), 4.99-4.97 (m, 1H), 4.29-4.25 (m, 1H), 4.23-4.18 (m, 1H), 4.17-4.15 (m, 1H), 4.06-4.00 (m, 2H), 3.85-3.83 (m, 5H), 3.56-3.53 (m, 1H), 3.34-3.33 (m, 4H), 3.10-3.02 (m, 4H), 3.00-2.85 (m, 2H), 2.60-2.58 (m, 3H), 2.16-2.08 (m, 1H), 1.91-1.88 (m, 1H), 1.76-1.69 (m, 5H), 1.43-1.41 (m, 2H). (DMSO-d6, 400 MHz) |
| 3 | 743.57 | 1.35 | A | A | δ: 10.96 (s, 1H), 9.12 (s, 1H), 7.39 (d, J = 8.0 Hz, 1H), 7.25-6.98 (m, 4H), 6.83 (d, J = 6.8 Hz, 2H), 6.72-6.43 (m, 5H), 6.26 (d, J = 8.6 Hz, 2H), 5.06 (dd, J = 5.0, 13.2 Hz, 1H), 4.56-4.11 (m, 3H), 3.94-3.70 (m, 5H), 3.30-3.25 (m, 1H), 3.21-2.77 (m, 8H), 2.64-2.55 (m, 5H), 2.46-2.26 (m, 2H), 2.16-1.94 (m, 2H), 1.80-1.22 (m, 7H). (DMSO-d6, 400 MHz) |
| 4 | 831.65 | 1.42 | A | A | δ 10.98 (s, 1H), 9.13 (s, 1H), 8.14 (s, 1H), 7.40 (d, J = 8.8 Hz, 1H), 7.17-7.07 (m, 4H), 6.83-6.82 (m, 2H), 6.65-6.60 (m, 2H), 6.54-6.47 (m, 3H), 6.27-6.29 (m, 2H), 5.07 (dd, J = 5.2, 13.2 Hz, 1H), 4.44-4.40 (m, 1H), 4.29-4.17 (m, 4H), 3.81 (t, J = 6.4 Hz, 2H), 3.62-3.60 (m, 3H), 3.53-3.51 (m, 3H), 3.43-3.41 (m, 4H), 3.24-3.17 (m, 6H), 2.97-2.88 (m, 4H), 2.78-2.74 (m, 3H), 2.61-2.56 (m, 2H), 2.44-2.37 (m, 2H), 2.10-1.97 (m, 2H), 1.71-1.53 (m, 5H), 1.41-1.38 (m, 2H). (DMSO-d6, 400 MHz) |
| 5 | 842.66 | >300 | | C | |
| 6 | 842.67 | 2.18 | | C | |
| 7 | 859.68 | 102 | D | B | |
| 8 | 859.68 | 0.34 | B | B | δ 10.99 (s, 1H), 9.12 (s, 1H), 8.16 (s, 1H), 7.36 (s, 2H), 7.17-7.10 (m, 3H), 6.83 (d, J = 6.8 Hz, 2H), 6.66-6.59 (m, 2H), 6.52 (d, J = 8.8 Hz, 2H), 6.50-6.46 (m, 1H), 6.26 (d, J = 8.4 Hz, 2H), 5.10 (dd, J = 5.2, 13.2 Hz, 1H), 4.59 (d, J = 17.2 Hz, 1H), 4.41 (d, J = 17.2 Hz, 1H), 4.22-4.16 (m, 3H), 3.82 (t, J = 6.0 Hz, 2H), 3.73-3.67 (m, 2H), 3.60-3.55 (m, 2H), 3.48-3.42 (m, 2H), 3.37-3.35 (m, 2H), 3.22 (s, 3H), 3.03-2.82 (m, 6H), 2.82-2.69 (m, 10H), 2.63-2.61 (m, 1H), 2.42-2.36 (m, 1H), 2.15-2.04 (m, 1H), 2.03-1.95 (m, 1H), 1.81-1.69 (m, 3H), 1.66-1.60 (m, 2H), 1.58-1.50 (m, 2H). (DMSO-d6, 400 MHz) |
| 9 | 768.61 | >300 | D | B | |
| 10 | 768.61 | 0.86 | B | A | δ 10.90 (s, 1H), 8.28 (s, 1H), 7.19-7.07 (m, 3H), 6.83 (d, J = 6.4 Hz, 2H), 6.64 (d, J = 8.4 Hz, 1H), 6.59 (s, 2H), 6.52 (d, J = 8.8 Hz, 2H), 6.49-6.44 (m, 2H), 6.19 (d, J = 8.8 Hz, 2H), 5.02-4.91 (m, 1H), 4.96 (dd, J = 5.2, 13.2 Hz, 1H), 4.26-4.19 (m, 1H), 4.14-4.06 (m, 2H), 3.82 (s, 3H), 3.55-3.45 (m, 2H), 3.30-3.10 (m, 12H), 2.98-2.85 (m, 3H), 2.59-2.53 (m, 1H), 2.44-2.41 (m, 1H), 2.38-2.35 (m, 2H), 2.13-2.03 (m, 1H), 1.95-1.87 (m, 1H), 1.75-1.65 (m, 3H), 1.48-1.33 (m, 3H), 1.26-1.12 (m, 2H). (DMSO-d6, 400 MHz) |
| 11 | 798.63 | 2 | B | B | δ 10.95 (s, 1H), 9.09 (s, 1H), 7.38 (d, J = 8.03 Hz, 1H), 7.14 (m, 4H), 6.83 (d, J = 6.53 Hz, 2H), 6.64-6.59 (m, 2H), 6.56-6.45 (m, 3H), 6.19 (d, J = 8.66 Hz, 2H), 5.06 (dd, J = 12.99, 5.08 Hz, 1H), 4.36-4.27 (m, 1H), 4.19-4.18 (m, 4H), 3.55-3.53 (m, 4H), 3.26 (s, 3H), 3.11 (s, 4H), 2.96 (d, J = 5.9 Hz, 2H), 2.69-2.57 (m, 1H), 2.32-2.31 (m, 1H), 2.19 (d, J = 6.65 Hz, 4H), 2.14-2.04 (m, 3H), 1.98-1.89 (m, 2H), 11.56 (m, 6H), 1.29-1.01 (m, 3H). (DMSO-d6, 400 MHz) |
| 12 | 779.56 | 1 | A | A | 10.91 (br s, 1H), 8.20 (s, 1H), 7.19-7.09 (m, 3H), 6.84 (br d, J = 6.9 Hz, 2H), 6.67-6.58 (m, 5H), 6.54-6.43 (m, 2H), 6.30 (d, J = 8.5 Hz, 2H), 4.97 (dd, J = 5.1, 13.2 Hz, 1H), 4.27-4.07 (m, 5H), 3.83 (s, 3H), 3.39-3.28 (m, 5H), 3.04-2.85 (m, 4H), 2.59 (br s, 3H), 2.43-2.22 (m, 4H), 2.15-1.88 (m, 4H), 1.82-1.56 (m, 4H). (DMSO-d6, 400 MHz) |
| 13 | 743.58 | 0.37 | A | A | δ 10.91 (s, 1H), 9.13 (s, 1H), 8.14 (s, 1H), 7.18-7.07 (m, 3H), 6.82 (d, J = 6.8 Hz, 2H), 6.69-6.58 (m, 3H), 6.55-6.47 (m, 4H), 6.26 (d, J = 8.8 Hz, 2H), 4.96 (dd, J = 5.2, 13.2 Hz, 1H), 4.29-4.06 (m, 3H), 3.85-3.78 (m, 5H), 3.30-3.28 (m, 4H), 3.04-2.80 (m, 3H), 2.60-2.52 (m, 6H), 2.45-2.34 (m, 3H), 2.17-1.99 (m, 1H), 1.97-1.82 (m, 1H), 1.76-1.58 (m, 3H), 1.56-1.45 (m, 2H), 1.43-1.29 (m, 2H). (DMSO-d6, 400 MHz) |
| 14 | 743.58 | 0.49 | A | A | δ 10.91 (s, 1H), 9.13 (s, 1H), 8.14 (s, 1H), 7.18-7.08 (m, 3H), 6.82 (d, J = 6.8 Hz, 2H), 6.66-6.58 (m, 3H), 6.55-6.47 (m, 4H), 6.26 (d, J = 8.8 Hz, 2H), 4.96 (dd, J = 5.2, 13.2 Hz, 1H), 4.28-4.10 (m, 3H), 3.85-3.78 (m, 5H), 3.30-3.28 (m, 4H), 3.05-2.80 (m, 3H), 2.58-2.51 (m, 6H), 2.38-2.33 (m, 2H), 2.32-2.24 (m, 1H), 2.18-2.00 (m, 1H), 1.97-1.86 (m, 1H), 1.74-1.58 (m, 3H), 1.55-1.44 (m, 2H), 1.43-1.34 (m, 2H). (DMSO-d6, 400 MHz) |
| 15 | 754.60 | 1.7 | A | A | δ 10.91 (s, 1H), 8.23 (s, 2H), 7.17-7.09 (m, 3H), 6.83 (d, J = 6.8 Hz, 2H), 6.64 (d, J = 8.4 Hz, 1H), 6.59 (s, 2H), 6.53 (d, J = 8.8 Hz, 2H), 6.49-6.45 (m, 2H), 6.20 (d, J = 8.8 Hz, 2H), 4.96 (dd, J = 5.0, 13.2 Hz, 1H), 4.25-4.19 (m, 1H), 4.14-4.06 (m, 1H), 4.15-4.06 (m, 1H), 3.84-3.80 (m, 3H), 3.51 (d, J = 9.2 Hz, 7H), 3.28 (s, 4H), 2.98-2.83 (m, 1H), 3.03-2.82 (m, 2H), 2.58 (s, 1H), 2.32-2.26 (m, 1H), 2.22-2.04 (m, 4H), 1.94-1.87 (m, 1H), 1.80-1.55 (m, 5H), 1.21-1.11 (m, 2H). (DMSO-d6, 400 MHz) |

TABLE 5-continued

Characterization of Exemplary Estrogen Receptor PROTACs

| Ex. # | Observed [M + H]/Z | Target Engagement IC$_{50}$ (nM) | ER DC$_{50}$* | ER D$_{max}$* | NMR |
|---|---|---|---|---|---|
| 16 | 799.6 | 0.82 | A | B | δ 10.90 (s, 1H), 9.13 (s, 1H), 8.14 (s, 1H), 7.01-6.92 (m, 2H), 6.87-6.79 (m, 2H), 6.65 (d, J = 8.4 Hz, 1H), 6.60 (s, 2H), 6.55 (d, J = 8.8 Hz, 2H), 6.51-6.44 (m, 2H), 6.26 (d, J = 8.4 Hz, 2H), 4.96 (dd, J = 5.4, 13.4 Hz, 1H), 4.75 (t, J = 4.8 Hz, 1H), 4.27-4.06 (m, 3H), 3.85-3.80 (m, 3H), 3.29-3.25 (m, 6H), 2.99-2.84 (m, 3H), 2.54 (d, J = 4.4 Hz, 8H), 2.19-1.86 (m, 4H), 1.85-1.58 (m, 5H), 1.24-1.07 (m, 2H). (DMSO-d6, 400 MHz) |
| 17 | 778.57 | 1.5 | B | B | δ 10.91 (s, 1H), 9.14 (s, 1H), 7.85 (br s, 1H), 7.48-7.34 (m, 2H), 7.18-7.10 (m, 3H), 6.83 (br d, J = 6.7 Hz, 2H), 6.69-6.60 (m, 5H), 6.54-6.47 (m, 2H), 6.30 (d, J = 8.5 Hz, 2H), 5.08-4.94 (m, 3H), 4.28-4.17 (m, 2H), 4.16-4.08 (m, 1H), 3.84 (s, 4H), 3.66 (br s, 1H), 3.04-2.83 (m, 4H), 2.82-2.71 (m, 1H), 2.68 (br s, 1H), 2.63-2.54 (m, 2H), 2.48-2.26 (m, 2H), 2.15-2.03 (m, 1H), 1.97-1.88 (m, 1H), 1.71 (br d, J = 7.5 Hz, 1H). (DMSO-d6, 400 MHz) |
| 18 | 790.59 | 17.5 | B | B | |
| 19 | 790.58 | 4.5 | B | A | δ 10.89 (s, 1H), 8.19 (s, 1H), 7.22-7.16 (m, 3H), 6.90 (br d, J = 6.8 Hz, 2H), 6.68 (d, J = 8.4 Hz, 1H), 6.61 (br d, J = 9.2 Hz, 2H), 6.54-6.50 (m, 1H), 6.47 (s, 1H), 5.87 (d, J = 11.2 Hz, 2H), 4.95 (dd, J = 5.2, 13.2 Hz, 1H), 4.25-4.20 (m, 2H), 4.13-4.07 (m, 1H), 3.82 (s, 3H), 3.27-3.25 (m, 6H), 3.03-2.83 (m, 9H), 2.19 (br d, J = 7.2 Hz, 3H), 2.07-1.89 (m, 3H), 1.76-1.58 (m, 5H), 1.16 (br d, J = 9.2 Hz, 2H). (DMSO-d6, 400 MHz) |
| 20 | 779.6 | 1.2 | B | B | δ 10.96 (s, 1H), 8.20 (s, 1H), 7.62-7.20 (m, 1H), 7.18-7.05 (m, 3H), 6.94 (s, 1H), 6.82 (d, J = 6.4 Hz, 2H), 6.71 (s, 1H), 6.67-6.58 (m, 2H), 6.56-6.43 (m, 3H), 6.26 (d, J = 8.8 Hz, 2H), 5.00 (dd, J = 5.2, 13.2 Hz, 1H), 4.37-4.29 (m, 1H), 4.26-4.14 (m, 2H), 3.81 (t, J = 6.4 Hz, 2H), 3.31-3.27 (m, 5H), 3.04-2.82 (m, 3H), 2.64-2.52 (m, 2H), 2.48-2.42 (m, 3H), 2.41-2.25 (m, 3H), 2.17-2.02 (m, 1H), 2.00-1.90 (m, 1H), 1.75-1.59 (m, 3H), 1.53-1.43 (m, 2H), 1.42-1.32 (m, 2H). (DMSO-d6, 400 MHz) |
| 21 | 815.6 | 2.5 | B | B | δ 10.98 (s, 1H), 8.15 (s, 1H), 7.68-7.34 (m, 1H), 7.21-7.05 (m, 3H), 6.95 (s, 1H), 6.84 (d, J = 7.2 Hz, 2H), 6.73 (s, 1H), 6.68-6.58 (m, 4H), 6.50 (d, J = 8.2 Hz, 1H), 6.31 (d, J = 8.4 Hz, 2H), 5.02 (dd, J = 4.8, 13.2 Hz, 1H), 4.42-4.27 (m, 1H), 4.27-4.04 (m, 4H), 3.31 (s, 4H), 3.03-2.78 (m, 3H), 2.68-2.55 (m, 1H), 2.48 (s, 6H), 2.41-2.32 (m, 3H), 2.16-1.90 (m, 4H), 1.72 (m, 1H), 1.63 (m, 2H). (DMSO-d6, 400 MHz) |
| 22 | 804.6 | 4.4 | B | A | δ 10.97 (s, 1H), 8.19 (s, 1H), 7.68-7.20 (m, 1H), 7.18-7.07 (m, 3H), 6.94 (s, 1H), 6.83 (d, J = 6.4 Hz, 2H), 6.71 (s, 1H), 6.66-6.57 (m, 2H), 6.55-6.43 (m, 3H), 6.19 (d, J = 8.4 Hz, 2H), 5.00 (dd, J = 5.0, 13.2 Hz, 1H), 4.38-4.28 (m, 1H), 4.26-4.17 (m, 1H), 4.12 (d, J = 4.6 Hz, 1H), 3.30 (s, 9H), 3.01-2.78 (m, 4H), 2.71-2.55 (m, 2H), 2.44-2.26 (m, 5H), 2.16-2.03 (m, 1H), 2.02-1.89 (m, 1H), 1.79-1.62 (m, 3H), 1.40 (m, 3H), 1.27-1.06 (m, 2H). (DMSO-d6, 400 MHz) |
| 23 | 791.6 | 1.8 | B | B | δ 10.96 (s, 1H), 9.12 (s, 1H), 8.16 (s, 1H), 7.63-7.20 (m, 1H), 7.18-7.06 (m, 3H), 6.94 (s, 1H), 6.81 (d, J = 6.4 Hz, 2H), 6.71 (s, 1H), 6.67-6.58 (m, 2H), 6.51-6.37 (m, 3H), 6.24 (d, J = 8.4 Hz, 2H), 5.00 (dd, J = 5.2, 13.2 Hz, 1H), 4.71-4.60 (m, 1H), 4.40-4.29 (m, 1H), 4.26-4.13 (m, 2H), 3.32-3.27 (m, 9H), 3.04-2.80 (m, 3H), 2.63-2.54 (m, 2H), 2.42-2.31 (m, 1H), 2.30-2.19 (m, 3H), 2.13-2.03 (m, 4H), 2.02-1.91 (m, 1H), 1.74-1.51 (m, 3H). (DMSO-d6, 400 MHz) |
| 24 | 786.6 | 0.7 | B | A | δ 10.89 (s, 1H), 9.17 (s, 1H), 8.32 (s, 1H), 7.21-7.10 (m, 3H), 6.86 (d, J = 6.4 Hz, 2H), 6.68-6.58 (m, 4H), 6.52-6.44 (m, 2H), 6.08 (d, J = 8.0 Hz, 1H), 5.97 (d, J = 14.2 Hz, 1H), 4.95 (dd, J = 5.2, 13.2 Hz, 1H), 4.28-4.16 (m, 2H), 4.14-4.05 (m, 1H), 3.83 (s, 3H), 3.18 (s, 2H), 2.99-2.85 (m, 3H), 2.54-2.52 (m, 13H), 2.12-1.86 (m, 3H), 1.71 (d, J = 10.8 Hz, 3H), 1.48-1.19 (m, 6H). (DMSO-d6, 400 MHz) |
| 25 | 715.6 | 0.5 | | C | |
| 26 | 769.6 | 0.7 | A | A | δ 10.90 (s, 1H), 9.16 (s, 1H), 7.19-7.09 (m, 3H), 6.82 (br d, J = 6.6 Hz, 2H), 6.68-6.57 (m, 3H), 6.53-6.40 (m, 4H), 6.29-6.23 (m, 2H), 4.96 (dd, J = 5.1, 13.3 Hz, 1H), 4.53 (quin, J = 7.3 Hz, 1H), 4.31-4.01 (m, 3H), 3.83 (s, 3H), 3.63 (br s, 1H), 3.33-3.23 (m, 11H), 3.10 (td, J = 8.8, 17.4 Hz, 1H), 3.03-2.79 (m, 3H), 2.55 (br s, 2H), 2.46-2.25 (m, 2H), 2.16-2.00 (m, 3H), 1.99-1.87 (m, 1H), 1.70 (br d, J = 6.0 Hz, 1H). (DMSO-d6, 400 MHz) |
| 27 | 807.6 | 0.5 | A | B | δ 10.96 (s, 1H), 9.13 (br s, 1H), 8.20-7.39 (m, 1H), 7.22-7.08 (m, 3H), 6.97-6.93 (m, 1H), 6.81 (br d, J = 7.7 Hz, 2H), 6.73-6.69 (m, 1H), 6.67-6.62 (m, 1H), 6.60 (d, J = 2.3 Hz, 1H), 6.50-6.38 (m, 3H), 6.27-6.21 (m, 2H), 5.00 (br dd, J = 5.1, 13.2 Hz, 1H), 4.65 (br t, J = 5.8 Hz, 1H), 4.37-4.30 (m, 1H), 4.25-4.18 (m, 1H), 4.16 (br d, J = 4.9 Hz, 1H), 3.28-3.25 (m, 6H), 3.02-2.81 (m, 3H), 2.61-2.53 (m, 4H), 2.45-2.37 (m, 4H), 2.12-1.90 (m, 5H), 1.76-1.64 (m, 3H). (DMSO-d6, 400 MHz) |

TABLE 5-continued

Characterization of Exemplary Estrogen Receptor PROTACs

| Ex. # | Observed [M + H]/Z | Target Engagement $IC_{50}$ (nM) | ER $DC_{50}$* | ER $D_{max}$* | NMR |
|---|---|---|---|---|---|
| 28 | 771.6 | 0.3 | A | A | δ 10.91 (s, 1H), 9.13 (s, 1H), 8.14 (s, 1H), 7.18-7.08 (m, 3H), 6.81 (br d, J = 7.7 Hz, 2H), 6.66-6.59 (m, 3H), 6.51-6.39 (m, 4H), 6.27-6.22 (m, 2H), 4.96 (br dd, J = 5.1, 12.9 Hz, 1H), 4.65 (br t, J = 6.3 Hz, 1H), 4.26-4.19 (m, 1H), 4.16 (br d, J = 4.6 Hz, 1H), 4.13-4.07 (m, 1H), 3.84-3.80 (m, 3H), 3.29-3.23 (m, 5H), 3.00-2.84 (m, 3H), 2.62-2.52 (m, 8H), 2.35 (br s, 2H), 2.09-1.88 (m, 4H), 1.78-1.66 (m, 3H). (DMSO-d6, 400 MHz) |
| 29 | 750.6 | 2.4 | | C | |
| 30 | 768.6 | 2.1 | B | B | δ 10.87 (s, 1H), 9.20 (s, 1H), 8.26 (s, 1H), 7.46 (d, J = 8.8 Hz, 1H), 7.24-7.07 (m, 3H), 6.99 (d, J = 8.8 Hz, 1H), 6.86 (d, J = 6.8 Hz, 2H), 6.75-6.56 (m, 4H), 6.50 (d, J = 8.0 Hz, 1H), 6.09 (d, J = 8.0 Hz, 1H), 5.97 (d, J = 14.4 Hz, 1H), 4.18 (d, J = 4.4 Hz, 1H), 3.89 (s, 1H), 3.35-3.23 (m, 8H), 3.19 (d, J = 6.8 Hz, 3H), 3.05-2.84 (m, 2H), 2.76-2.60 (m, 2H), 2.54 (s, 3H), 2.20 (d, J = 6.8 Hz, 2H), 2.06 (dd, J = 6.0, 12.0 Hz, 1H), 1.83 (s, 1H), 1.75 (d, J = 12.0 Hz, 3H), 1.62 (s, 1H), 1.54-1.44 (m, 2H), 1.44-1.29 (m, 2H), 1.21 (d, J = 10.0 Hz, 2H). (DMSO-d6, 400 MHz) |
| 31 | | | | C | |

*ER $DC_{50}$ (nM) A < 1; 1 <= B < 10; 10 <= C < 100; D >= 100
**ER $D_{max}$ (%) A >= 75; 50 <= B < 75; C < 50

TABLE 6

Characterization of Exemplary Androgen Receptor PROTACs

| Ex. # | m/z observed | AR $DC_{50}$* | AR $D_{max}$** | NMR |
|---|---|---|---|---|
| 32 | 824.54 | A | | |
| 33 | 852.58 | A | | |
| 34 | 832.61 | | C | 1H NMR (400 MHz, d6-DMSO): δ 10.88 (s, 1H), 8.22 (s, 1H), 7.91 (d, J = 8.8 Hz, 1H), 7.74 (d, J = 8.8 Hz, 2H), 7.53-7.45 (m, 2H), 7.21 (d, J = 2.4 Hz, 1H), 6.99 (dd, J = 9.2, 17.6 Hz, 4H), 6.73 (s, 1H), 4.33 (s, 1H), 4.06 (d, J = 9.2 Hz, 1H), 3.86 (d, J = 12.4 Hz, 3H), 3.32-3.29 (m, 9H), 2.80 (t, J = 12.0 Hz, 3H), 2.59-2.54 (m, 4H), 2.22 (d, J = 6.8 Hz, 2H), 1.81 (d, J = 10.3 Hz, 4H), 1.55-1.47 (m, 2H), 1.45-1.31 (m, 2H), 1.25-1.17 (s, 8H), 1.13 (s, 6H) |
| 35 | 849.6 | | C | |
| 36 | 849.61 | | C | |
| 37 | 877.64 | | C | |
| 38 | 877.64 | | C | |
| 46 | 810.3 | A | A | ¹H NMR (400 MHz, DMSO-d₆) δ 1.12 (6H, s), 1.21 (6H, s), 1.43-1.54 (4H, m), 1.74-1.78 (2H, m), 1.88-1.91 (1H, m), 2.30-2.44 (8H, m), 2.90-2.97 (3H, m), 3.42-3.59 (7H, m), 4.03-4.07 (3H, m), 4.30 (1H, s), 6.86-6.91 (3H, m), 6.99-7.02 (1H, m), 7.22 (1H, d, J = 2.4 Hz), 7.64 (1H, d, J = 8.8 Hz), 7.79 (1H, d, J = 8.8 Hz), 7.90-7.97 (2H, m), 8.62 (1H, d, J = 2.0 Hz), 10.90 (1H, s). |
| 47 | 824.3 | B | B | ¹H NMR (400 MHz, DMSO-d⁶) δ 1.12 (6H, s), 1.21 (6H, s), 1.37-1.58 (4H, m), 1.73-1.81 (2H, m), 1.86-1.91 (1H, m), 2.40-2.46 (2H, m), 2.82-2.91(1H, m), 3.30-3.35 (4H, m), 3.55-3.65 (4H, m), 4.03-4.30 (6H, m), 5.54-5.63 (1H, m), 6.87 (1H, d, J = 9.6 Hz), 6.96-7.07 (3H, m), 7.21 (1H, d, J = 2.4 Hz), 7.63 (1H, d, J = 9.6 Hz), 7.90-8.04 (3H, m), 8.62 (1H, d, J = 2.4 Hz), 10.93 (1H, s). |
| 48 | 798.6 | A | B | ¹H NMR (400 MHz, DMSO-d₆) δ 1.12 (6H, s), 1.21 (6H, s), 1.43-1.47 (2H, m), 1.49-1.53 (2H, m), 1.73-1.78 (2H, m), 2.13-2.17 (1H, m), 2.32 (2H, t, J = 7.2 Hz), 2.43-2.47 (5H, m), 2.61-2.62 (1H, m), 2.87-2.93 (1H, m), 3.59 (4H, s), 4.01-4.07 (3H, m), 4.30 (1H, s), 5.28 (1H, dd, J = 12.4, 5.2 Hz), 6.35 (1H, dd, J = 8.0, 2.4 Hz), 6.52 (1H, d, J = 1.6 Hz), 6.86 (1H, d, J = 8.8 Hz), 7.00 (1H, dd, J = 8.8, 2.4 Hz), 7.21 (1H, d, J = 2.4 Hz), 7.63 (1H, d, J = 9.2 Hz), 7.80 (1H, d, J = 8.0 Hz), 7.90 (1H, d, J = 8.8 Hz), 7.95 (1H, dd, J = 9.2, 2.4 Hz), 8.62 (1H, d, J = 2.4 Hz), 11.09 (1H, s). |
| 49 | 798.6 | A | A | ¹H NMR (400 MHz, DMSO-d₆) δ 1.12 (6H, s), 1.21 (6H, s), 1.44-1.48 (2H, m), 1.52-1.58 (2H, m), 1.74-1.79 (2H, m), 2.15-2.19 (1H, m), 2.30 (2H, t, J = 7.2 Hz), 2.43-2.50 (4H, m), 2.51-2.67 (2H, m), 2.86-2.95 (1H, m), 3.60 (4H, s), 3.97 (2H, t, J = 6.4 Hz), 4.05 (1H, d, J = 9.2 Hz), 4.30 (1H, s), 5.38 (1H, dd, J = 5.2, 12.8 Hz), 6.86 (1H, d, J = 9.2 Hz), 7.00 (1H, dd, J = 8.4, 2.4 Hz), 7.10 (1H, dd, J = 10.0, 2.0 Hz), 7.21 (1H, d, J = 2.4 Hz), 7.25 (1H, d, J = 10.0 Hz), 7.36 (1H, s), 7.62 (1H, d, J = 9.2 Hz), 7.90 (1H, d, J = 8.8 Hz), 7.95 (1H, dd, J = 9.2, 2.4 Hz), 8.62 (1H, d, J = 2.4 Hz), 11.10 (1H, s). |
| 50 | 808.6 | A | A | ¹H NMR (400 MHz, DMSO-d⁶) δ 1.13 (6H, s), 1.22 (6H, s), 1.79-1.81 (3H, m), 2.09-2.15 (1H, m), 2.19-2.21 (1H, m), 2.49-2.50 (7H, m), 2.60-2.67 (1H, m), 2.76-2.92 (3H, m), 3.22-3.26 (4H, m), 3.86 (2H, d, J = 12.8 Hz), 4.05 (1H, d, J = 9.2 Hz), 4.32 (1H, s), 5.23 (1H, dd, J = 12.4, 5.2 Hz), 6.12 (1H, s), 6.70 (1H, dd, J = 8.0, 1.6 Hz), 6.95 (2H, d, J = 9.2 Hz), 7.00 (1H, dd, J = 8.8, 2.4 Hz), |

TABLE 6-continued

Characterization of Exemplary Androgen Receptor PROTACs

| Ex. # | m/z observed | AR DC$_{50}$* | AR D$_{max}$** | NMR |
|---|---|---|---|---|
| | | | | 7.21 (1H, d, J = 2.4 Hz), 7.48 (1H, d, J = 8.8 Hz), 7.72 (3H, t, J = 8.4 Hz), 7.91 (1H, d, J = 8.8 Hz), 11.04 (1H, s). |
| 51 | 835.59 | A | A | 1H NMR (300 MHz, DMSO-d6) δ 11.07 (s, 1H), 8.57 (s, 1H), 7.87 (d, J = 8.7 Hz, 1H), 7.70 (d, J = 8.6 Hz, 2H), 7.44 (d, J = 9.1 Hz, 1H), 7.29 (s, 1H), 7.17 (d, J = 2.2 Hz, 1H), 7.02-6.87 (m, 3H), 5.07 (dd, J = 12.8, 5.3 Hz, 1H), 4.29 (s, 1H), 4.02 (d, J = 9.1 Hz, 1H), 3.88-3.70 (m, 5H), 3.29 (br s, 5H), 2.95-2.65 (m, 3H), 2.59-2.41 (m, 6H), 2.00 (m, 1H), 1.73 (d, J = 12.8 Hz, 2H), 1.45 (br, 3H), 1.17 (s, 6H), 1.09 (s, 6H) |
| 52 | 836.59 | A | B | $^1$H NMR (400 MHz, d6-DMSO): δ 11.12 (s, 1H), 8.90 (s, 1H), 7.91-7.89 (d, J = 8.4 Hz, 1H), 7.74-7.72 (d, J = 7.6 Hz, 2H), 7.49-7.47 (d, J = 8.8 Hz, 1H), 7.20 (s, 1H), 6.99-6.94 (m, 3H), 5.16-5.13 (m, 1H), 4.32 (s, 1H), 4.06-3.83 (m, 7H), 2.88-2.57 (m, 5H), 2.39-2.33 (m, 2H), 2.07-2.01 (m, 1H), 1.78-1.75 (m, 2H), 1.54-1.35 (m, 3H), 1.21 (m, 8H), 1.12 (s, 6H) |

*AR DC$_{50}$ (nM) A < 1; 1 <= B < 10; 10 <= C < 100; D >= 100
**AR D$_{max}$ (%) A >= 75; 50 <= B < 75; C < 50

TABLE 7

Characterization of Exemplary BRaf PROTACs

| Ex. # | BRaf DC$_{50}$* | BRaf D$_{max}$** | MH+ | NMR Transcript |
|---|---|---|---|---|
| 39 | C | B | 783.51 | 1H NMR (400 MHz, DMSO-d6): δ 11.03 (s, 1H), 10.87 (s, 1H), 8.72 (s, 1H), 8.57 (m, 2H), 7.83 (d, J = 8.4 Hz, 2H), 7.62-7.60 (m, 2H), 7.56 (d, J = 8.4 Hz, 2H), 7.50-7.41 (m, 6H), 7.22 (d, J = 8.0 Hz, 2H), 7.17-7.15(m, 3H), 5.07-5.03 (m, 1H), 3.73 (m, 8H), 3.01 (s, 2H), 2.83-2.81 (m, 3H), 2.67 (s, 2H), 2.03-2.00 (m, 1H) |
| 40 | C | A | 721.48 | 1H NMR (400 MHz, DMSO-d6): δ 11.15 (bs, 1H), 8.72 (s, 1H), 8.72 (s, 1H), 8.57 (d, J = 5.6 Hz, 2H), 7.83 (d, J = 8.8 Hz, 2H), 7.77 (s, 1H), 7.49-7.57 (m, 4H), 7.41 (s, 1H), 7.17-7.30 (m, 3H), 5.09-5.13 (m, 1H), 3.20-3.35 (m, 8H), 2.80-3.12 (m, 6H), 2.52-2.75 (m, 3H), 1.90-2.12 (m, 2H) |
| 41 | C | A | 783.51 | 1H NMR (400 MHz, DMSO-d6): δ 11.04 (s, 1H), 10.88 (s, 1H), 8.69 (s, 1H), 8.57 (d, J = 4.8 Hz, 2H), 7.87 (d, J = 8.4 Hz, 1H), 7.76 (d, J = 8.8 Hz, 2H), 7.40-7.56 (m, 10H), 7.22 (d, J = 4.8 Hz, 1H), 7.03 (d, J = 9.2 Hz, 2H), 5.00-5.05 (m, 1H), 3.02 (m, 9H), 2.83 (t, J = 6.8 Hz, 2H), 1.99-2.01 (m, 3H) |
| 42 | C | B | 721.48 | 1H NMR (400 MHz, DMSO-d6): δ 11.09 (s, 1H), 10.89 (s, 1H), 8.72 (s, 1H), 8.58-8.57 (m, 2H), 7.83 (d, J = 8.0 Hz, 2H), 7.73 (d, J = 7.6 Hz, 1H), 7.56 (d, J = 7.6 Hz, 1H), 7.50-7.41 (m, 4H), 7.23-7.17 (m, 3H), 5.13-5.09 (m, 1H), 3.61-3.42 (m, 8H), 3.04-2.97 (m, 2H), 2.93-2.82 (m, 3H), 2.62-2.56 (m, 5H), 2.08-2.00 (m, 1H) |

*BRaf DC$_{50}$ (nM) A < 1; 1 <= B < 10; 10 <= C < 100; D >= 100
**BRaf D$_{max}$ (%) A >= 75; 50 <= B < 75; C < 50

TABLE 8

Characterization of Exemplary BRD4 PROTACs

| Ex. # | BRD4 DC$_{50}$* | BRD4 D$_{max}$** | Observed [M + H]+ | NMR |
|---|---|---|---|---|
| 43 | D | B | 895.22 | $^1$H NMR (400 MHz, CHLOROFORM-d) d 9.03 (s, 1H), 7.45 (dd, J = 8.71, 13.21 Hz, 4H), 7.31-7.37 (m, 3H), 7.24 (d, J = 7.24 Hz, 1H), 6.84 (d, J = 9.00 Hz, 2H), 6.78 (d, J = 8.02 Hz, 1H), 6.75 (br. s., 1H), 4.66-4.73 (m, 2H), 4.20 (d, J = 2.74 Hz, 1H), 4.07-4.12 (m, 2H), 3.80-3.90 (m, 3H), 3.64-3.77 (m, 10H), 3.52-3.58 (m, 1H), 3.35-3.42 (m, 3H), 2.68 (br. s., 3H), 2.52-2.59 (m, 2H), 2.41 (s, 3H), 2.02-2.08 (m, 2H), 1.69 (s, 3H), 1.26 (s, 3H). |
| 44 | D | C | 937.19 | 1H NMR (400 MHz, METHANOL-d4) d 7.60-7.65 (m, 1H), 7.30-7.47 (m, 8H), 6.82-6.87 (m, 2H), 5.24 (dd, J = 5.67, 10.76 Hz, 1H), 4.69 (ddd, J = 2.84, 5.62, 8.56 Hz, 1H), 4.26-4.31 (m, 2H), 4.02-4.07 (m, 2H), 3.91-3.96 (m, 2H), 3.77-3.81 (m, 2H), 3.70-3.74 (m, 2H), 3.63-3.69 (m, 6H), 3.53-3.61 (m, 1H), 3.43-3.49 (m, 2H), 2.81 (dt, J = 4.60, 14.33 Hz, 2H), 2.70 (s, 6H), 2.43 (s, 3H), 2.13-2.20 (m, 1H), 1.68 (s, 2H), 1.26-1.29 (m, 2H). |

TABLE 8-continued

Characterization of Exemplary BRD4 PROTACs

| Ex. # | BRD4 DC$_{50}$* | BRD4 D$_{max}$** | Observed [M + H]+ | NMR |
|---|---|---|---|---|
| 45 | C | A | 937.19 | $^1$H NMR (400 MHz, METHANOL-d4) d 8.55 (s, 1H), 7.96-8.00 (m, 1H), 7.36-7.50 (m, 6H), 7.03-7.09 (m, 2H), 6.87 (dd, J = 3.03, 9.10 Hz, 2H), 5.22 (td, J = 5.40, 10.91 Hz, 1H), 4.70-4.74 (m, 1H), 4.22 (d, J = 3.33 Hz, 2H), 4.10 (d, J = 4.30 Hz, 2H), 3.85-3.91 (m, 2H), 3.79-3.84 (m, 2H), 3.64-3.71 (m, 7H), 3.55-3.64 (m, 2H), 3.42-3.50 (m, 2H), 2.71 (s, 3H), 2.66 (d, J = 3.33 Hz, 2H), 2.44 (d, J = 3.33 Hz, 3H), 1.89 (s, 3H), 1.68 (d, J = 3.33 Hz, 2H), 1.29 (br. s., 3H). |

*BRD4 DC$_{50}$ (nM) A < 1; 1 <= B < 10; 10 <= C < 100; D >= 100
**BRD4 D$_{max}$ (%) A >= 75; 50 <= B < 75; C < 50

5. INDUSTRIAL APPLICABILITY

A novel bifunctional molecule, which contains a BRD4 or an androgen receptor recruiting moiety and an E3 Ligase Cereblon recruiting moiety, through PROTAC technology is described. The bifunctional molecules of the present disclosure actively degrades BRD4, leading to significant and persistent downstream MYC suppression and robust cellular proliferation suppression and apoptosis induction. PROTAC mediated protein degradation provides a promising strategy in targeting the "undruggable" pathological proteins by traditional approaches.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the invention described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

What is claimed is:

1. A compound selected from the group consisting of:

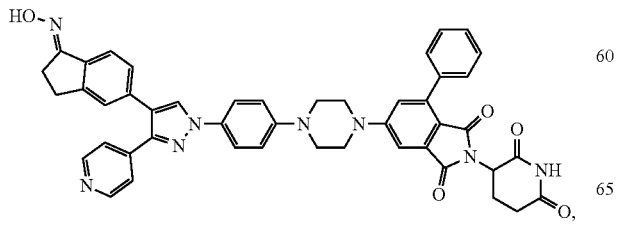

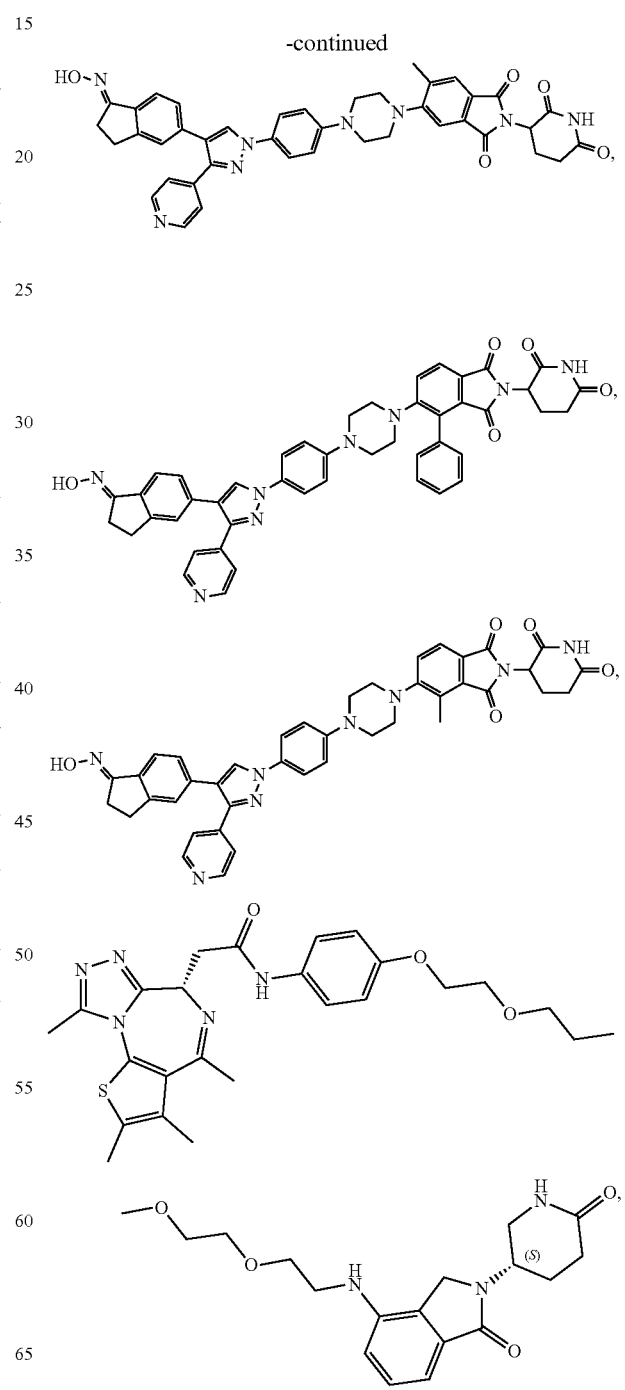

697
-continued
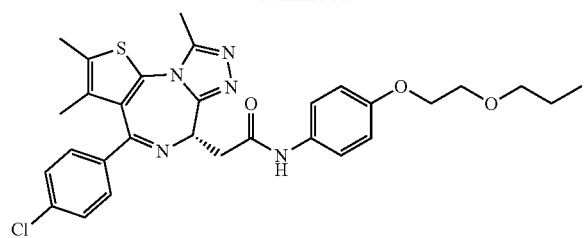
698
-continued
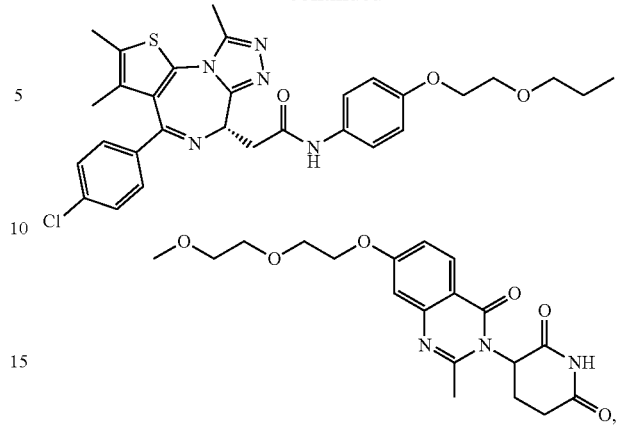
or a pharmaceutically acceptable salt thereof.
* * * * *

UNITED STATES PATENT AND TRADEMARK OFFICE
CERTIFICATE OF CORRECTION

PATENT NO. : 12,239,711 B2
APPLICATION NO. : 17/571018
DATED : March 4, 2025
INVENTOR(S) : Andrew P. Crew et al.

Page 1 of 1

It is certified that error appears in the above-identified patent and that said Letters Patent is hereby corrected as shown below:

In the Claims

In Claim 1, Column 696, Lines 50-70, please replace the structure with:

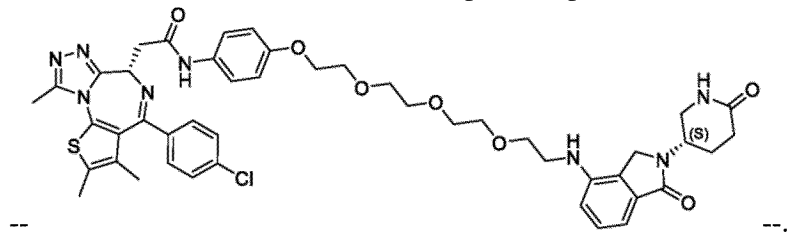

--                                    --.

In Claim 1, Column 697, Lines 1-20, please replace the structure with:

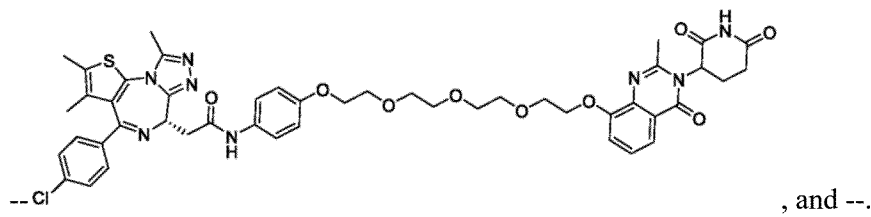

-- Cl                                  , and --.

In Claim 1, Column 698, Lines 1-20, please replace the structure with:

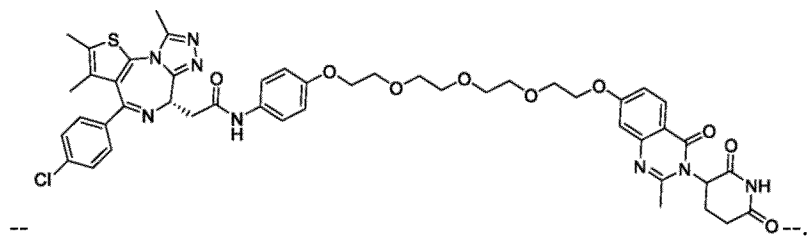

--                                    --.

Signed and Sealed this
Twenty-second Day of July, 2025

Coke Morgan Stewart
*Acting Director of the United States Patent and Trademark Office*